US008119663B2

(12) United States Patent
Heimbach et al.

(10) Patent No.: US 8,119,663 B2
(45) Date of Patent: Feb. 21, 2012

(54) HETEROARYL-SUBSTITUTED PIPERIDINES

(75) Inventors: Dirk Heimbach, Düsseldorf (DE); Susanne Röhrig, Hilden (DE); Dirk Schneider, Wuppertal (DE); Ulrich Rester, Wuppertal (DE); Eckhard Bender, Langenfeld (DE); Mark Meininghaus, Wuppertal (DE); Katja Zimmermann, Düsseldorf (DE); Dmitry Zubov, Remscheid (DE); Anja Buchmüller, Essen (DE); Georges Von Degenfeld, Leverkusen (DE); Christoph Gerdes, Leverkusen (DE); Michael Gerisch, Wuppertal (DE); Mark Jean Gnoth, Mettmann (DE); Yolanda Cancho Grande, Leverkusen (DE); Mario Jeske, Solingen (DE); Kersten Matthias Gericke, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 503 days.

(21) Appl. No.: 12/323,454

(22) Filed: Nov. 25, 2008

(65) Prior Publication Data
US 2009/0306139 A1 Dec. 10, 2009

(30) Foreign Application Priority Data

Nov. 30, 2007 (DE) .......................... 10 2007 057 718
Feb. 20, 2008 (DE) .......................... 10 2008 010 221

(51) Int. Cl.
*A61K 31/445* (2006.01)
*C07D 401/00* (2006.01)

(52) U.S. Cl. ........................................ 514/326; 546/209
(58) Field of Classification Search .................. 514/326; 546/209
See application file for complete search history.

(56) References Cited

U.S. PATENT DOCUMENTS

| 5,767,144 | A | 6/1998 | Winn et al. |
| 2001/0044454 | A1 | 11/2001 | Nantermet et al. |
| 2006/0004049 | A1 | 1/2006 | Yao et al. |
| 2008/0003214 | A1 | 1/2008 | Cezanne et al. |

FOREIGN PATENT DOCUMENTS

| WO | WO 97/36873 | * | 10/1997 |
| WO | WO-03/039440 A2 | | 5/2003 |
| WO | 2006002349 | | 1/2006 |
| WO | 2006002350 | | 1/2006 |
| WO | WO-2006/012226 A2 | | 2/2006 |
| WO | WO-2006/020598 A2 | | 2/2006 |
| WO | WO-2007/038138 A2 | | 4/2007 |
| WO | 2007089683 | | 9/2007 |
| WO | WO-2007/101270 A1 | | 9/2007 |
| WO | WO-2007/130898 A1 | | 11/2007 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Golub et al. Science (1999), vol. 286 531-537.*
Lala et al. Cancer and Metastasis Reviews (1998), 17(1), 91-106.*
A. Mochizuki et al.: "Design, Synthesis, and Biological Activity of Piperidine Diamine Derivatives as Factor Xa Inhibitor," Bioorganic & Medicinal Chemistry Letters 18, Elsevier, 2008, pp. 783-787.
T-K H. Vu et al.: "Molecular Cloning of a Functional Thrombin Receptor Reveals a Novel Proteolytic Mechanism of Receptor Activation," Cell, vol. 64, Mar. 22, 1991, pp. 1057-1068.
D. L. Bhatt et al.: "Scientific and Therapeutic Advances in Antiplatelet Therapy," Nature Reviews Drug Discovery, vol. 2, Jan. 2003, pp. 15-28.
M. L. Khan et al.: "Protease-Activated Receptors 1 and 4 Mediate Activation of Human Platelets by Thrombin," The Journal of Clinical Investigation, vol. 103, No. 6, Mar. 1999, pp. 879-887.
C. K. Derian et al.: "Blockade of the Thrombin Receptor Protease-Activated Receptor-1 with a Small-Molecule Antagonist Prevents Thrombus Formation and Vascular Occlusion in Nonhuman Primates," The Journal of Pharmacology and Experimental Therapeutics, vol. 304, No. 2, 2003, pp. 855-861.
R. P. Dellinger et al.: "Surviving Sepsis Campaign Guidelines for Management of Severe Sepsis and Septic Shock," Critical Care Medicine, vol. 32, No. 3, 2004, pp. 858-873.
U.S. Appl. No. 12/788,529, filed May 27, 2010.
U.S. Appl. No. 12/788,641, filed May 27, 2010.
J.C. Barrow et al., "Discovery and Initial Structure-Activity Relationships of Trisubstituted Ureas as Thrombin Receptor (PAR-1) Antagonists," Bioorganic & Medicinal Chemistry Letters, 11: 2691-2696 (2001).
Chackalamannil, Samuel: "Thrombin receptor (protease activated receptor-1) antagonists as potent antithrombotic agents with strong antiplatelet effects", Journal of Medicinal Chemistry, 49(10): 5389-5403 ( Sep. 7, 2006).
Diaz, J. L. et al., "Fast efficient access to a family of multifunctional 1,3,5-trisubstituted piperidines", Synthetic Communications, 38: 2799-2813 (Jan. 2008).
McAtee J. J. et al., "Development of potent and selective small-molecule human Urotensin-II antagonists," Bioorganic and Medicinal Chemistry Letters, 18: 3500-3503 (2008).
Morissette et al., High-throughput cyrstallization: polymorphs, salts ,co-crystals, and solvates of pharmaceuitical solids, Advanced Drug Delivery Reviews, 56: 275-300 (2004).
Vippagunta et al., abstract, Vippagunta, Sudha R. "Crystalline Solids." Advanced Drug Delivery Reviews 48 (2001):3-26.
Golub et al., "Molecular classification of cancer: class discovery and class prediction by gene expression monitoring," Science, vol. 286: 531-537 (1999).
Lala et al., "Role of nitric oxide in tumor progression: lessons from experimental tumors," Cancer and Matastasis Reviews, 17(1), 91-106 (1998).

* cited by examiner

*Primary Examiner* — Rebecca Anderson
*Assistant Examiner* — Samantha Shterengarts

(57) ABSTRACT

The invention relates to novel heteroaryl-substituted piperidines, to processes for their preparation, to their use for the treatment and/or prophylaxis of diseases and to their use for preparing medicaments for the treatment and/or prophylaxis of diseases, in particular of cardiovascular diseases and tumor diseases.

8 Claims, No Drawings

HETEROARYL-SUBSTITUTED PIPERIDINES

RELATED APPLICATIONS/PATENTS AND INCORPORATION BY REFERENCE

This application claims priority to German Patent Application Number 102007057718.6 filed Nov. 30, 2007, and German Patent Application Number 102008010221.0 filed Feb. 20, 2008, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The invention relates to novel heteroaryl-substituted piperidines, to processes for their preparation, to their use for the treatment and/or prophylaxis of diseases and to their use for preparing medicaments for the treatment and/or prophylaxis of diseases, in particular of cardiovascular diseases and tumour diseases.

Thrombocytes (blood platelets) are an essential factor both in physiological haemostasis and in thromboembolic disorders. In particular in the arterial system, platelets are of central importance in the complex interaction between blood components and the wall of the vessel. Unwanted platelet activation may, by formation of platelet-rich thrombi, result in thromboembolic disorders and thrombotic complications with life-threatening states.

One of the most potent platelet activators is the blood coagulation protease thrombin, which is formed at injured blood vessel walls and which, in addition to fibrin formation, leads to the activation of platelets, endothelial cells and mesenchymal cells (Vu TKH, Hung DT, Wheaton VI, Coughlin SR, *Cell* 1991, 64, 1057-1068). In platelets in vitro and in animal models, thrombin inhibitors inhibit platelet aggregation and the formation of platelet-rich thrombi. In man, arterial thromboses can be prevented or treated successfully with inhibitors of platelet function and thrombin inhibitors (Bhatt D L, Topol E J, *Nat. Rev. Drug Discov.* 2003, 2, 15-28). Accordingly, there is a high probability that antagonists of thrombin action on platelets reduce the formation of thrombi and the occurrence of clinical sequelae such as myocardial infeaction and stroke. Other cellular actions of thrombin, for example on endothelial and smooth-muscle cells of vessels, leukocytes and fibroblasts, are possibly responsible for inflammatory and proliferative disorders.

At least some of the cellular effects of thrombin are mediated via a family of G-protein-coupled receptors (Protease Activated Receptors, PARs) whose prototype is the PAR-1 receptor. PAR-1 is activated by binding of thrombin and proteolytic cleavage of its extracellular N-terminus. The proteolysis exposes a new N-terminus having the amino acid sequence SFLLRN which, as agonist ("tethered ligand") leads to intramolecular receptor activation and transmission of intracellular signals. Peptides derived from the tethered-ligand sequence can be used as agonists of the receptor and, on platelets, lead to activation and aggregation. Other proteases are likewise capable of activating PAR-1, these proteases include, for example, plasmin, factor VIIa, factor Xa, trypsin, activated protein C (aPC), tryptase, cathepsin G, proteinase 3, granzyme A, elastase and matrix metalloprotease 1 (MMP-1).

In contrast to the inhibition of protease activity of thrombin with direct thrombin inhibitors, a blockade of PAR-1 should result in an inhibition of platelet activation without reduction of the coagulability of the blood (anticoagulation).

Antibodies and other selective PAR-1 antagonists inhibit the thrombin-induced aggregation of platelets in vitro at low to medium thrombin concentrations (Kahn M L, Nakanishi-Matsui M, Shapiro MJ, Ishihara H, Coughlin SR, *J. Clin. Invest.* 1999, 103, 879-887). A further thrombin receptor with possible significance for the pathophysiology of thrombotic processes, PAR-4, was identified on human and animal platelets. In experimental throm-boses in animals having a PAR expression pattern similar to humans, PAR-1 antagonists reduced the formation of platelet-rich thrombi (Derian C K, Damiano B P, Addo M F, Darrow AL, D'Andrea MR, Nedelman M, Zhang H-C, Maryanoff BE, Andrade-Gordon P, *J. Pharmacol. Exp. Ther.* 2003, 304, 855-861).

In recent years, a large number of substances have been examined for their platelet function-inhibiting action; however, in practice, only a few platelet function inhibitors have proved themselves. Accordingly, there is a need for pharmaceuticals which specifically inhibit an increased platelet reaction without significantly increasing the risk of bleeding, thus reducing the risk of thromboembolic complications.

Effects of thrombin which are mediated via the receptor PAR-1 influence the progression of the disease during and after coronary artery bypass graft (CABG) and other surgical interventions and in particular surgical interventions with extracorporeal circulation (for example heart-lung machine). During the course of the operation, there may be bleeding complications owing to pre- or intraoperative medication with coagulation-inhibiting and/or platelet-inhibiting substances. For this reason, for example, medication with clopidogrel has to be interrupted several days prior to a CABG. Moreover, as already mentioned, a disseminated intravascular coagulation or consumption coagulopathy (DIC) may develop (for example owing to the extended contact between blood and synthetic surfaces during extracorporeal circulation or blood transfusions), which in turn can lead to bleeding complications. As the disorder progresses, there is frequently a restenosis of the venous or arterial bypasses grafted (which may even result in occlusion) owing to thrombosis, intimafibrosis, arteriosclerosis, angina pectoris, myocardial infarction, heart failure, arrhythmias, transitory ischaemic attack (TIA) and/or stroke.

In man, the receptor PAR-1 is also expressed in other cells including, for example, endothelial cells, smooth muscle cells and tumour cells. Malignant tumour disorders (cancer) have a high incidence and are generally associated with high mortality. Current therapies achieve full remission in only a fraction of patients and are typically associated with severe side effects. Accordingly, there is a high demand for more effective and safer therapies. The PAR-1 receptor contributes to cancer generation, growth, invasiveness and metastasis. Moreover, PAR-1 expressed on endothelial cells transmits signals resulting in vascular growth ("angiogenesis"), a process which is vital for allowing a tumour to grow larger than about 1 mm$^3$. Angiogenesis also contributes to the generation or worsening of other disorders including, for example, haematopoetic cancer disorders, macular degeneration, which leads to blindness, and diabetic retinopathy, inflammatory disorders, such as rheumatoid arthritis and colitis.

Sepsis (or septicaemia) is a frequent disorder with high mortality. Initial symptoms of sepsis are typically unspecific (for example fever, reduced general state of health); however, during further progress there may be a general activation of the coagulation system ("disseminated intravascular coagulation" or "consumption coagulopathy" (DIC)) with the formation of microthrombi in various organs and secondary bleeding complications. DIC may also occur independently of a sepsis, for example during surgical interventions or associated with tumour disorders.

Therapy of sepsis consists, firstly, in the consequent elimination of the infectious cause, for example by operative focal reconstruction and antibiosis. Secondly, it consists in temporary intensive medical support of the affected organ systems. Therapies of various stages of this disease have been described, for example, in the following publication (Dellinger et al., *Crit. Care Med.* 2004, 32, 858-873). There are no proven effective therapies for DIC.

Accordingly, it is an object of the present invention to provide novel PAR-1 antagonists for the treatment of disorders such as, for example, cardiovascular disorders and thromboembolic disorders, and also tumour disorders in humans and animals. WO 2006/012226, WO 2006/020598, WO 2007/038138, WO 2007/130898, WO 2007/101270 and US 2006/0004049 describe structurally similar piperidines as 11-β HSD1 inhibitors for the treatment of inter alia diabetes, thromboembolic disorders and stroke.

The invention provides compounds of the formula

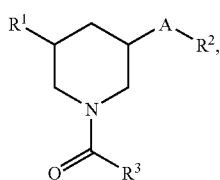

(I)

in which
A represents a group of the formula

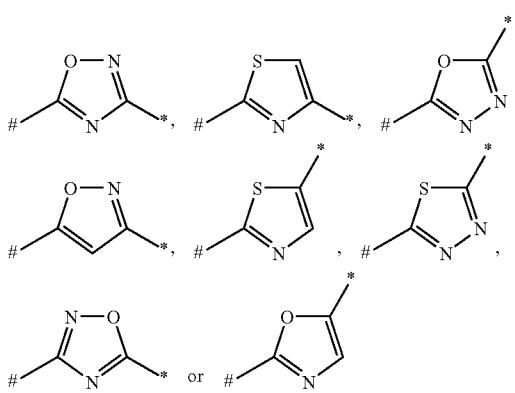

where
# is the point of attachment to the piperidine ring,
and
* is the point of attachment to $R^2$
$R^1$ represents phenyl,
where phenyl may be substituted by 1 to 3 substituents independently of one another selected from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy, $C_1$-$C_4$-alkoxycarbonyl and $C_3$-$C_6$-cycloalkyl,
where $C_2$-$C_4$-alkoxy may be substituted by a substituent selected from the group consisting of methoxy and ethoxy,
and
where cycloalkyl may be substituted by 1 to 3 substituents independently of one another selected from the group consisting of halogen and $C_1$-$C_4$-alkyl,
$R^2$ represents hydrogen, trifluoromethyl, aminomethyl, $C_1$-$C_6$-alkyl, $C_2$-$C_6$-alkenyl, $C_1$-$C_4$-alkoxycarbonyl, $C_3$-$C_6$-cycloalkyl, cyclopentenyl, 4- to 6-membered heterocyclyl, phenyl, 1,3-benzodioxolyl, 5- or 6-membered heteroaryl or pyridylaminocarbonyl,
where cycloalkyl, heterocyclyl, phenyl and heteroaryl may be substituted by 1 to 3 substituents independently of one another selected from the group consisting of halogen, cyano, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino, $C_1$-$C_4$-alkoxycarbonylamino, $C_3$-$C_6$-cycloalkyl, 4- to 6-membered heterocyclyl, phenyl and 5- or 6-membered heteroaryl,
where alkylamino may be substituted by a substituent selected from the group consisting of $C_1$-$C_4$-alkoxy and $C_1$-$C_6$-alkylamino,
and
where $C_1$-$C_4$-alkyl may be substituted by a substituent selected from the group consisting of halogen, hydroxyl, amino, aminocarbonyl, $C_1$-$C_4$-alkoxy, $C_1$-$C_6$-alkylamino, $C_1$-$C_4$-alkylthio, $C_1$-$C_4$-alkylcarbonyl, $C_1$-$C_4$-alkylcarbonyloxy, $C_1$-$C_4$-alkylsulphonyl, $C_1$-$C_4$-alkoxycarbonyl, $C_1$-$C_4$-alkoxycarbonylamino, $C_3$-$C_6$-cycloalkyl, $C_3$-$C_6$-cycloalkylamino, 4- to 6-membered heterocyclyl, phenyl, phenoxy, 5- or 6-membered heteroaryl and 5- or 6-membered heteroarylthio,
where cycloalkyl, heterocyclyl, phenyl, phenoxy, heteroaryl and heteroarylthio may be substituted by 1 to 3 substituents independently of one another selected from the group consisting of halogen, cyano, hydroxymethyl, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_3$-$C_6$-cycloalkyl, 4- to 6-membered heterocyclyl, phenyl and 5- or 6-membered heteroaryl,
$R^3$ represents $C_1$-$C_6$-alkyl, $C_1$-$C_6$-alkoxy, $C_1$-$C_6$-alkylamino, $C_3$-$C_7$-cycloalkyl, 4- to 6-membered heterocyclyl, phenyl or 5- or 6-membered heteroaryl,
where alkyl, $C_2$-$C_6$-alkoxy and alkylamino may be substituted by a substituent selected from the group consisting of hydroxyl, amino, cyano and $C_1$-$C_4$-alkoxy,
and
where cycloalkyl, heterocyclyl, phenyl and heteroaryl may be substituted by 1 to 3 substituents independently of one another selected from the group consisting of halogen, cyano, nitro, oxo, hydroxyl, amino, aminomethyl, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl and $C_1$-$C_4$-alkylaminocarbonyl,
and their salts, their solvates and the solvates of their salts.

Compounds according to the invention are the compounds of the formula (I) and their salts, solvates and solvates of the salts, the compounds, comprised by formula (I), of the formulae mentioned below and their salts, solvates and solvates of the salts and the compounds comprised by the formula (I), mentioned below as embodiments and their salts, solvates and solvates of the salts if the compounds, comprised by the formula (I), mentioned below are not already salts, solvates and solvates of the salts.

Depending on their structure, the compounds according to the invention can exist in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform constituents in a known manner.

If the compounds according to the invention can be present in tautomeric forms, the present invention comprises all tautomeric forms.

In the context of the present invention, preferred salts are physiologically acceptable salts of the compounds according to the invention. The invention also comprises salts which for their part are not suitable for pharmaceutical applications, but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates are those forms of the compounds according to the invention which, in solid or liquid state, form a complex by coordination with solvent molecules. Hydrates are a specific form of the solvates where the coordination is with water.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the context of the present invention, unless specified otherwise, the substituents have the following meanings:

Alkyl per se and "Alk" and "alkyl" in alkoxy, alkylamino, alkylthio, alkylcarbonyl, alkoxycarbonyl, alkoxycarbonylamino, alkylaminocarbonyl, alkylcarbonylamino, alkylcarbonyloxy and alkylsulphonyl represents a straight-chain or branched alkyl radical having 1 to 6 carbon atoms, by way of example and by way of preference methyl, ethyl, n-propyl, isopropyl, n-butyl, tert-butyl, n-pentyl and n-hexyl.

Alkenyl represents a straight-chain or branched alkenyl radical having 2 to 6 carbon atoms. Preference is given to a straight-chain or branched alkenyl radical having 2 to 4, particularly preferably 2 or 3, carbon atoms. The following radicals may be mentioned by way of example and by way of preference: vinyl, allyl, n-prop-1-en-1-yl and n-but-2-en-1-yl.

By way of example and by way of preference, allkoxy represents methoxy, ethoxy, n-propoxy, isopropoxy, n-butoxy, tert-butoxy, n-pentoxy and n-hexoxy.

Alkylamino represents an alkylamino radical having one or two (independently selected) alkyl substituents, by way of example and by way of preference methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-alkylamino represents, by way of example, a monoalkylamino radical having 1 to 4 carbon atoms or represents a dialkylamino radical having in each case 1 to 4 carbon atoms per alkyl substituent.

By way of example and by way of preference, alkylthio represents methylthio, ethylthio, n-propylthio, isopropylthio, n-butylthio, tert-butylthio, n-pentylthio and n-hexylthio.

By way of example and by way of preference, alkylcarbonyl represents methylcarbonyl, ethyl-carbonyl, n-propylcarbonyl, isopropylcarbonyl, n-butylcarbonyl and tert-butylcarbonyl.

By way of example and by way of preference, alkoxycarbonyl represents methoxycarbonyl, ethoxycarbonyl, n-propoxycarbonyl, isopropoxycarbonyl, n-butoxycarbonyl, tert-butoxycarbonyl, n-pentoxycarbonyl and n-hexoxycarbonyl.

By way of example and by way of preference, alkoxycarbonylamino represents methoxycarbonylamino, ethoxycarbonylamino, n-propoxycarbonylamino, isopropoxycarbonylamino, n-butoxycarbonylamino and tert-butoxycarbonylamino.

Alkylaminocarbonyl represents an alkylaminocarbonyl radical having one or two (independently selected) alkyl substituents, by way of example and by way of preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl represents, by way of example, a monoalkylaminocarbonyl radical having 1 to 4 carbon atoms or represents a dialkylamino-carbonyl radical having in each case 1 to 4 carbon atoms per alkyl substituent.

By way of example and by way of preference, alkylcarbonylamino represents methylcarbonylamino, ethylcarbonylamino, n-propylcarbonylamino, isopropylcarbonylamino, n-butylcarbonylamino and tert-butylcarbonylamino.

By way of example and by way of preference, alkylcarbonyloxy represents methylcarbonyloxy, ethylcarbonyloxy, n-propylcarbonyloxy, isopropylcarbonyloxy, n-butylcarbonyloxy and tert-butylcarbonyloxy.

By way of example and by way of preference, alkylsulphonyl represents methylsulphonyl, ethylsulphonyl, n-propylsulphonyl, isopropylsulphonyl, n-butylsulphonyl, tert-butylsulphonyl, n-pentylsulphonyl and n-hexylsulphonyl.

Cycloalkyl represents a monocyclic cycloalkyl group having generally 3 to 7, preferably 5 or 6, carbon atoms; cycloalkyl groups which may be mentioned by way of example and by way of preference are cyclopropyl, cyclobutyl, cyclopentyl, cyclohexyl and cycloheptyl.

Cycloalkylamino represents a monocyclic cycloalkylamino group having generally 3 to 6, preferably 3 or 4, carbon atoms; cycloalkylamino groups which may be mentioned by way of example and by way of preference are cyclopropylamino, cyclobutylamino, cyclopentylamino and cyclohexylamino.

Heterocyclyl represents a monocyclic heterocyclic radical having 5 or 6 ring atoms and up to 3, preferably up to 2, heteroatoms and/or hetero groups from the group consisting of N, O, S, SO, $SO_2$, where a nitrogen atom may also form an N-oxide. The heterocyclyl radicals can be saturated or partially unsaturated. Preference is given to 5- or 6-membered monocyclic saturated heterocyclyl radicals having up to two heteroatoms from the group consisting of O, N and S, by way of example and by way of preference pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, 1,2,5,6-tetrahydropyridin-3-yl, 1,2,5,6-tetrahydropyridin-4-yl, thiopyranyl, morpholin-1-yl, morpholin-2-yl, morpholin-3-yl, piperazin-1-yl, piperazin-2-yl.

Heteroaryl represents an aromatic monocyclic radical having generally 5 or 6 ring atoms and up to 4 heteroatoms from the group consisting of S, O and N, where a nitrogen atom may also form an N-oxide, by way of example and by way of preference thienyl, furyl, pyrrolyl, thiazolyl, oxazolyl, isoxazolyl, oxadiazolyl, pyrazolyl, imidazolyl, pyridyl, pyrimidyl, pyridazinyl, pyrazinyl.

Heteroarylthio represents an aromatic monocyclic heteroarylthio radical having generally 5 or 6 ring atoms and up to 4 heteroatoms from the group consisting of S, O and N, where a nitrogen atom may also form an N-oxide, by way of example and by way of preference thienylthio, furylthio, pyrrolylthio, thiazolylthio, oxazolylthio, isoxazolylthio, oxadiazolylthio, pyrazolylthio, imidazolylthio, pyridylthio, pyrimidylthio, pyridazinylthio, pyrazinylthio.

Halogen represents fluorine, chlorine, bromine and iodine, preferably fluorine and chlorine.

In the formula of the group which may represent A, the end point of the line marked by # or * does not represent a carbon atom or a $CH_2$ group, but is part of the bond to the atom to which A is attached.

Preference is given to compounds of the formula (I) in which
A represents a group of the formula

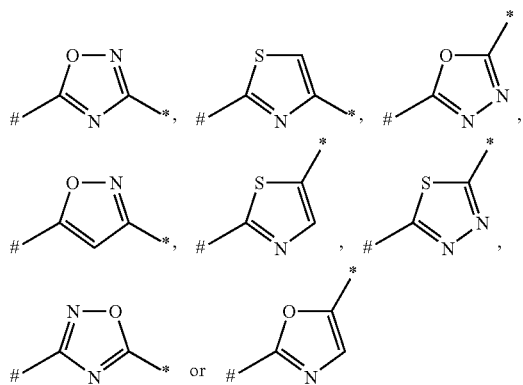

where
# is the point of attachment to the piperidine ring, and
* is the point of attachment to $R^2$ $R^1$ represents phenyl,
where phenyl is substituted by 1 to 3 substituents independently of one another selected from the group consisting of trifluoromethyl, trifluoromethoxy, methylsulphonyl, $C_1$-$C_4$-alkyl and $C_1$-$C_4$-alkoxy, $R^2$ represents hydrogen, trifluoromethyl, aminomethyl, $C_1$-$C_6$-alkyl, $C_3$-$C_6$-alkenyl, methoxycarbonyl, ethoxycarbonyl, $C_3$-$C_6$-cycloalkyl, cyclopentenyl, 4- to 6-membered heterocyclyl, phenyl, 1,3-benzodioxolyl, 5- or 6-membered heteroaryl or pyridylaminocarbonyl,
where cycloalkyl, heterocyclyl, phenyl and heteroaryl may be substituted by 1 to 3 substituents independently of one another selected from the group consisting of halogen, cyano, amino, trifluoromethyl, trifluoromethoxy, methyl, ethyl, methoxy, ethoxy, ethylamino, tert-butoxycarbonylamino and 4- to 6-membered heterocyclyl,
where ethylamino may be substituted by a substituent selected from the group consisting of methoxy and dimethylamino,
and
where methyl and ethyl may be substituted by a substituent selected from the group consisting of halogen, hydroxyl, amino, aminocarbonyl, $C_1$-$C_4$-alkoxy, $C_1$-$C_4$-alkylamino, $C_1$-$C_4$-alkylthio, methylcarbonyl, ethylcarbonyl, methylcarbonyloxy, ethylcarbonyloxy, $C_1$-$C_4$-alkylsulphonyl, methoxycarbonyl, ethoxycarbonyl, tert-butoxycarbonylamino, cyclopropyl, cyclopropylamino, 4- to 6-membered heterocyclyl, phenyl, phenoxy, 5- or 6-membered heteroaryl and 5- or 6-membered heteroarylthio,
where heterocyclyl, phenyl, phenoxy, heteroaryl and heteroarylthio may be substituted by 1 to 3 substituents independently of one another selected from the group consisting of halogen, cyano, hydroxymethyl, trifluoromethyl, trifluoromethoxy, methyl, ethyl, methoxy and ethoxy, $R^3$ represents $C_1$-$C_6$-alkyl, $C_1$-$C_6$-alkylamino, $C_3$-$C_7$-cycloalkyl, 4- to 6-membered heterocyclyl, phenyl or 5- or 6-membered heteroaryl,
where alkyl and alkylamino may be substituted by a substituent selected from the group consisting of hydroxyl, amino, methoxy and ethoxy,
and
where cycloalkyl, heterocyclyl, phenyl and heteroaryl may be substituted by 1 to 3 substituents independently of one another selected from the group consisting of halogen, cyano, oxo, hydroxyl, amino, aminomethyl, trifluoromethyl, trifluoromethoxy, methyl, ethyl, methoxy, ethoxy and dimethylamino, and their salts, their solvates and the solvates of their salts.

Preference is also given to compounds of the formula (I) in which
A represents a group of the formula

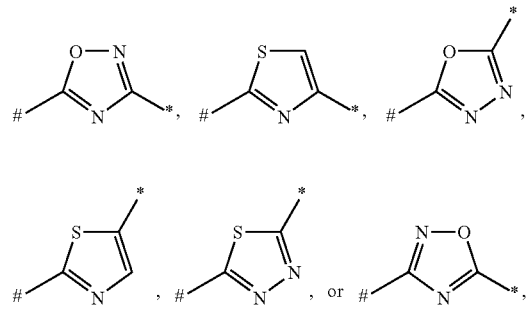

where
# is the point of attachment to the piperidine ring,
and
* is the point of attachment to $R^2$ $R^1$ represents phenyl,
where phenyl is substituted by 1 or 2 substituents independently of one another selected from the group consisting of trifluoromethyl, trifluoromethoxy, methyl, ethyl, isopropyl and methoxy, $R^2$ represents methyl, ethyl, isopropyl, n-propyl, tert-butyl, methoxycarbonyl, ethoxycarbonyl, cyclopropyl, cyclobutyl, azetidinyl, oxetanyl, pyrrolidinyl, tetrahydropyridinyl, phenyl, 1,3-benzodioxolyl, thienyl, furanyl, pyrrolyl, thiazolyl, isoxazolyl, imidazolyl, triazolyl, pyridyl, pyrimidinyl or pyrazinyl,
where azetidinyl, oxetanyl, pyrrolidinyl, tetrahydropyridinyl, phenyl, thienyl, furanyl, pyrrolyl, thiazolyl, isoxazolyl, imidazolyl, triazolyl, pyridyl, pyrimidinyl and pyrazinyl may be substituted by 1 to 2 substituents independently of one another selected from the group consisting of halogen, trifluoromethyl, trifluoromethoxy, methyl, ethyl, methoxy, ethoxy and ethylamino,
where ethylamino may be substituted by a substituent selected from the group consisting of methoxy and dimethylamino,
and
where methyl and ethyl may be substituted by a substituent selected from the group consisting of hydroxyl, amino, methoxy, ethoxy, isopropoxy, dialkylamino, methylsulphonyl, cyclopropylamino, morpholinyl, phenyl and phenoxy,
where phenyl may be substituted by 1 or 2 substituents independently of one another selected from the group consisting of halogen, hydroxymethyl, trifluoromethyl, trifluoromethoxy, methyl, ethyl, methoxy and ethoxy, $R^3$ represents tert-butyl, N-methyl-N-ethylamino, methoxyalkylamino, cyclopropyl, cyclopentyl, azetidinyl, 3,3-difluoroazetidinyl, 3-hydroxyazetidinyl, 3-methylazetidinyl, 3-methoxyazetidinyl, 3-dimethylaminoazetidinyl, pyrroldinyl, 3,3-difluoropyrroldin-1-yl, 3-hydroxypyrroldin-1-yl, 3-aminopyrroldin-1-yl, 4,4-difluoropiperidin-1-yl, 4-hydroxypiperidin-1-yl, 4-aminopiperidin-1-yl, 4-cyanopiperidin-1-yl, 3-methoxypiperidin-1-yl, thiazolidinyl, morpholin-4-yl, 2,2-dimethylmorpholin-4-yl, 2-oxopiperazin-1-yl or 3-oxo-4-methylpiperazin-1-yl,
and their salts, their solvates and the solvates of their salts.

Preference is also given to compounds of the formula (I) in which
A represents a group of the formula

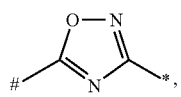

where
# is the point of attachment to the piperidine ring,
and
* is the point of attachment to $R^2$ $R^1$ represents phenyl,
where phenyl is substituted by 1 or 2 substituents independently of one another selected from the group consisting of trifluoromethyl, trifluoromethoxy, methyl and ethyl, $R^2$ represents methyl, ethyl or isopropyl,
where methyl and ethyl may be substituted by a substituent methoxy, $R^3$ represents 3-hydroxyazetidinyl, 3-hydroxypyrroldin-1-yl, 4-hydroxypiperidin-1-yl, 4-cyanopiperidin-1-yl or morpholin-4-yl,
and their salts, their solvates and the solvates of their salts.

Preference is also given to compounds of the formula (I) in which
A represents a group of the formula

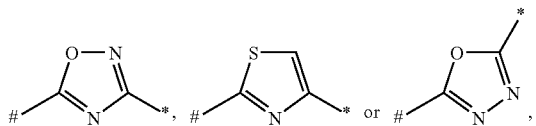

where
# is the point of attachment to the piperidine ring,
and
* is the point of attachment to $R^2$, $R^1$ represents phenyl,
where phenyl may be substituted by 1 to 3 substituents independently of one another selected from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_4$-alkoxycarbonyl and $C_3$-$C_6$-cycloalkyl,
where $C_2$-$C_4$-alkoxy may be substituted by a substituent selected from the group consisting of methoxy and ethoxy,
and
where cycloalkyl may be substituted by 1 to 3 substituents independently of one another selected from the group consisting of halogen and $C_1$-$C_4$-alkyl, $R^2$ represents hydrogen, aminomethyl, $C_1$-$C_6$-alkyl, $C_1$-$C_4$-alkoxycarbonyl, $C_3$-$C_6$-cycloalkyl, 4- to 6-membered heterocyclyl, phenyl, 1,3-benzodioxolyl or 5- or 6-membered heteroaryl,
where cycloalkyl, heterocyclyl, phenyl and heteroaryl may be substituted by 1 to 3 substituents independently of one another selected from the group consisting of halogen, cyano, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino, $C_3$-$C_6$-cycloalkyl, 4- to 6-membered heterocyclyl, phenyl and 5- or 6-membered heteroaryl,
where alkylamino may be substituted by a substituent selected from the group consisting of $C_1$-$C_4$-alkoxy and $C_1$-$C_6$-alkylamino,
and
where $C_1$-$C_2$-alkyl may be substituted by a substituent selected from the group consisting of $C_1$-$C_4$-alkylsulphonyl, $C_1$-$C_4$-alkoxycarbonylamino, $C_3$-$C_6$-cycloalkyl, 4- to 6-membered heterocyclyl, phenyl, phenoxy and 5- or 6-membered heteroaryl,
where cycloalkyl, heterocyclyl, phenyl, phenoxy and heteroaryl may be substituted by 1 to 3 substituents independently of one another selected from the group consisting of halogen, cyano, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_3$-$C_6$-cycloalkyl, 4- to 6-membered heterocyclyl, phenyl and 5- or 6-membered heteroaryl, $R^3$ represents $C_1$-$C_6$-alkyl, $C_1$-$C_6$-alkoxy, $C_1$-$C_6$-alkylamino, $C_3$-$C_7$-cycloalkyl, 4- to 6-membered heterocyclyl, phenyl or 5- or 6-membered heteroaryl, where alkyl, $C_2$-$C_6$-alkoxy and alkylamino may be substituted by a substituent selected from the group consisting of hydroxyl, cyano and $C_1$-$C_4$-alkoxy, and where cycloalkyl, heterocyclyl, phenyl and heteroaryl may be substituted by 1 to 3 substituents independently of one another selected from the group consisting of halogen, cyano, nitro, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl and $C_1$-$C_4$-alkylaminocarbonyl, and their salts, their solvates and the solvates of their salts.

Preference is also given to compounds of the formula (I) in which

A represents a group of the formula

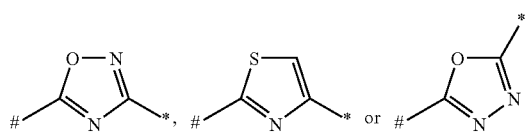

where # is the point of attachment to the piperidine ring, and

*is the point of attachment to $R^2$, $R^1$ represents phenyl, where phenyl is substituted by 1 to 3 substituents independently of one another selected from the group consisting of trifluoromethyl, trifluoromethoxy, $C_1$-$C_4$-alkyl and $C_1$-$C_4$-alkoxy, $R^2$ represents hydrogen, aminomethyl, $C_1$-$C_4$-alkyl, methoxycarbonyl, ethoxycarbonyl, 4- to 6-membered heterocyclyl, phenyl, 1,3-benzodioxolyl or 5- or 6-membered heteroaryl, where heterocyclyl, phenyl and heteroaryl may be substituted by 1 to 3 substituents independently of one another selected from the group consisting of halogen, cyano, trifluoromethyl, trifluoromethoxy, methyl, ethyl, methoxy, ethoxy, ethylamino and 4- to 6-membered heterocyclyl, where ethylamino may be substituted by a substituent selected from the group consisting of methoxy and dimethylamino, and where methyl may be substituted by a substituent selected from the group consisting of methylsulphonyl, ethylsulphonyl, tert-butoxycarbonylamino, 4- to 6-membered heterocyclyl, phenyl, phenoxy and 5- or 6-membered heteroaryl, where heterocyclyl, phenyl, phenoxy and heteroaryl may be substituted by 1 to 3 substituents independently of one another selected from the group consisting of halogen, cyano, trifluoromethyl, trifluoromethoxy, methyl, ethyl, methoxy and ethoxy, $R^3$ represents $C_1$-$C_6$-alkyl, $C_1$-$C_6$-alkylamino, $C_3$-$C_7$-cycloalkyl, 4- to 6-membered heterocyclyl, phenyl or 5- or 6-membered heteroaryl, where alkylamino may be substituted by a substituent selected from the group consisting of hydroxyl, methoxy and ethoxy, and where cycloalkyl, heterocyclyl, phenyl and heteroaryl may be substituted by 1 to 3 substituents independently of one another selected from the group consisting of halogen, cyano, oxo, hydroxyl, amino, trifluoromethyl, trifluoromethoxy, methyl, ethyl, methoxy and ethoxy, and their salts, their solvates and the solvates of their salts.

Preference is also given to compounds of the formula (I) in which

A represents a group of the formula

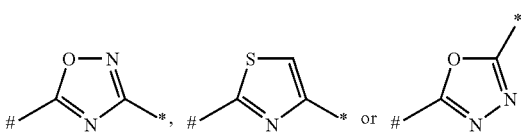

where # is the point of attachment to the piperidine ring, and

* is the point of attachment to $R^2$, $R^1$ represents phenyl, where phenyl is substituted by a substituent selected from the group consisting of trifluoromethyl, trifluoromethoxy, ethyl, isopropyl and methoxy, $R^2$ represents hydrogen, aminomethyl, methyl, n-propyl, tert-butyl, methoxycarbonyl, ethoxycarbonyl, tetrahydropyridinyl, phenyl, 1,3-benzodioxolyl, thiazolyl, isoxazolyl, pyridyl or pyrazinyl, where tetrahydropyridinyl, phenyl, thiazolyl, isoxazolyl, pyridyl and pyrazinyl may be substituted by 1 to 3 substituents independently of one another selected from the group consisting of halogen, trifluoromethyl, trifluoromethoxy, methyl, ethyl, methoxy, ethoxy, ethylamino and morpholinyl, where ethylamino may be substituted by a substituent selected from the group consisting of methoxy and dimethylamino, and where methyl may be substituted by a substituent selected from the group consisting of methylsulphonyl, tert-butoxycarbonylamino, morpholinyl, phenyl and phenoxy, where morpholinyl, phenyl and phenoxy may be substituted by 1 to 3 substituents independently of one another selected from the group consisting of halogen, trifluoromethyl, trifluoromethoxy, methyl, ethyl, methoxy and ethoxy, $R^3$ represents tert-butyl, N-methyl-N-ethylamino, methoxyalkylamino, cyclopentyl, pyrroldinyl, 4-hydroxypiperidin-1-yl, 4-cyanopiperidin-1-yl or morpholinyl, and their salts, their solvates and the solvates of their salts.

Preference is also given to compounds of the formula (I) in which
A represents a group of the formula

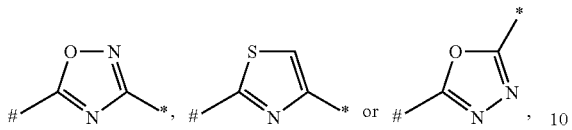

where
\# is the point of attachment to the piperidine ring,
and
* is the point of attachment to $R^2$,
$R^1$ represents phenyl,
where phenyl is substituted by a substituent selected from the group consisting of trifluoromethyl, trifluoromethoxy, ethyl, isopropyl and methoxy,
$R^2$ represents hydrogen, aminomethyl, methyl, n-propyl, tert-butyl, methoxycarbonyl, ethoxycarbonyl, tetrahydropyridinyl, phenyl, 1,3-benzodioxolyl, thiazolyl, isoxazolyl, pyridyl or pyrazinyl,
where tetrahydropyridinyl, phenyl, thiazolyl, isoxazolyl, pyridyl and pyrazinyl may be substituted by 1 to 3 substituents independently of one another selected from the group consisting of halogen, trifluoromethyl, trifluoromethoxy, methyl, ethyl, methoxy, ethoxy, ethylamino and morpholinyl,
where ethylamino may be substituted by a substituent selected from the group consisting of methoxy and dimethylamino,
and
where methyl may be substituted by a substituent selected from the group consisting of methylsulphonyl, tert-butoxycarbonylamino, morpholinyl, phenyl and phenoxy,
where morpholinyl, phenyl and phenoxy may be substituted by 1 to 3 substituents independently of one another selected from the group consisting of halogen, trifluoromethyl, trifluoromethoxy, methyl, ethyl, methoxy and ethoxy,
$R^3$ represents tert-butyl, N-methyl-N-ethylamino, methoxyalkylamino, cyclopentyl or morpholinyl,
and their salts, their solvates and the solvates of their salts.

Preference is also given to compounds of the formula (I) in which the substituents -$R^1$ and -A-$R^2$ are in the cis-position to one another.

Preference is also given to compounds of the formula (I) in which
A represents a group of the formula

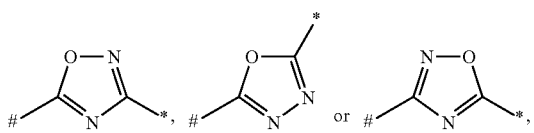

where
\# is the point of attachment to the piperidine ring,
and
* is the point of attachment to $R^2$.

Preference is also given to compounds of the formula (I) in which
A represents a group of the formula

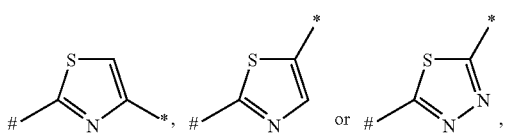

where
\# is the point of attachment to the piperidine ring,
and
* is the point of attachment to $R^2$.

Preference is also given to compounds of the formula (I) in which
A represents a group of the formula

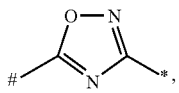

where
\# is the point of attachment to the piperidine ring,
and
* is the point of attachment to $R^2$.

Preference is also given to compounds of the formula (I) in which
A represents a group of the formula

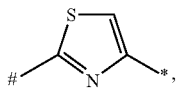

where
\# is the point of attachment to the piperidine ring,
and
* is the point of attachment to $R^2$.

Preference is also given to compounds of the formula (I) in which
A represents a group of the formula

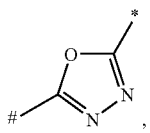

where
\# is the point of attachment to the piperidine ring,
and
* is the point of attachment to $R^2$.

Preference is also given to compounds of the formula (I) in which
A represents a group of the formula

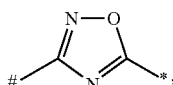
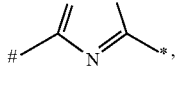

where

\# is the point of attachment to the piperidine ring, and

\* is the point of attachment to $R^2$.

Preference is also given to compounds of the formula (I) in which $R^1$ represents phenyl, where phenyl is substituted in the para-position to the point of attachment to the piperidine ring, by a substituent selected from the group consisting of trifluoromethyl, trifluoromethoxy and ethyl.

Preference is also given to compounds of the formula (I) in which $R^2$ represents methyl, ethyl or isopropyl, where methyl and ethyl may be substituted by a methoxy substituent.

Preference is also given to compounds of the formula (I) in which $R^2$ represents methyl, ethyl or isopropyl.

Preference is also given to compounds of the formula (I) in which $R^2$ represents 2-methoxyeth-1-yl.

Preference is also given to compounds of the formula (I) in which $R^3$ represents 3-hydroxyazetidinyl, 3-hydroxypyrrolidin-1-yl, 4-hydroxypiperidin-1-yl, 4-cyanopiperidin-1-yl or morpholin-4-yl.

Preference is also given to compounds of the formula (I) in which $R^3$ represents morpholin-4-yl.

Preference is also given to compounds of the formula (I) in which $R^3$ represents 4-hydroxypiperidin-1-yl.

The individual radical definitions specified in the respective combinations or preferred combinations of radicals are, independently of the respective combinations of radicals given, also replaced by radical definitions of other combinations.

Very particular preference is given to combinations of two or more of the preferred ranges mentioned above.

The invention furthermore provides a process for preparing the compounds of the formula (I), or its salts, its solvates or the solvates of its salts, where either

[A] compounds of the formula

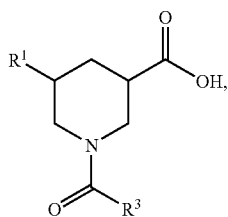

(II)

in which $R^1$ and $R^3$ have the meaning given above are reacted with compounds of the formula

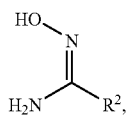

(III)

in which $R^2$ has the meaning given above or

[B] compounds of the formula

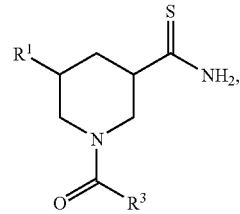

(X)

in which $R^1$ and $R^3$ have the meaning given above
are reacted with compounds of the formula

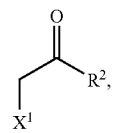

(XI)

in which $R^2$ has the meaning given above and $X^1$ represents bromine or chlorine, or

[C] compounds of the formula (II) are reacted with compounds of the formula $R^2CONHNH_2$ (XVI), in which $R^2$ has the meaning given above in the presence of phosphoryl chloride or thionyl chloride or

[D] compounds of the formula (II) are, in the first step, reacted with compounds of the formula $R^2COCH_2NH_2$ (XVII), in which $R^2$ has the meaning given above, in the presence of phosphoryl chloride or thionyl chloride, and, in the second step, with Lawesson reagent or

[E] compounds of the formula (II) are reacted with compounds of the formula (XVII) in the presence of phosphoryl chloride or thionyl chloride or

[F] compounds of the formula (II) are, in the first step, reacted with compounds of the formula (XVI) in the presence of phosphoryl chloride or thionyl chloride and, in the second step, reacted with Lawesson reagent or

[G] compounds of the formula

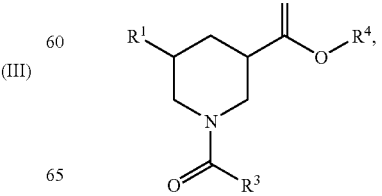

(IV)

in which
R¹ and R³ have the meaning given above and
R⁴ represents methyl or ethyl,
are reacted with compounds of the formula

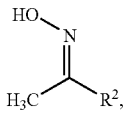

(XVIII)

in which
R² has the meaning given above
in the presence of butyllithium
or
[H] compounds of the formula

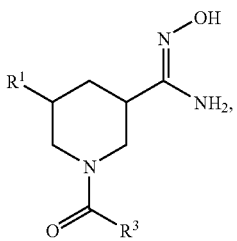

(XIX)

in which
R¹ and R³ have the meaning given above
are reacted with compounds of the formula

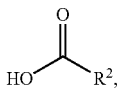

(XX)

in which
R² has the meaning given above
or
[J] compounds of the formula

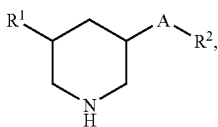

(XXI)

in which
A, R¹ and R² have the meaning given above
are, in the first step, reacted with 4-nitrophenyl chloroformate
and, in the second step, with compounds of the formula

   R³—H   (XXII), in which
R³ has the meaning given above.

The reaction according to process [A] is generally carried out in inert solvents, in the presence of a dehydrating agent, if appropriate in the presence of a base, preferably in a temperature range of from room temperature to reflux of the solvents at atmospheric pressure.

Inert solvents are, for example, halogenated hydrocarbons, such as methylene chloride, trichloromethane or 1,2-dichloroethane, ethers, such as dioxane, tetrahydrofuran or 1,2-dimethoxyethane, or other solvents, such as acetone, dimethylformamide, dimethylacetamide, 2-butanone or acetonitrile. It is also possible to use mixture of the solvents. Preference is given to dimethylformamide or a mixture of dioxane and dimethylformamide.

Suitable dehydrating agents in this context are, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexyl-carbodiimide-N'-propyloxymethyl-polystyrene (PS-carbodiimide), or carbonyl compounds, such as carbonyldiimidazole, or 1,2-oxazolium compounds, such as 2-ethyl-5-phenyl-1,2-oxazolium 3-sulphate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxa-zolidinyl)phosphoryl chloride or benzotriazolyloxy-tri(dimethylamino)phosphonium hexa-fluorophosphate, or O-(benzotriazol-1-yl)-N,N,N',N'-tetramethyluronium hexa-fluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N'-hydroxysuccinimide, or mixtures of these, with bases.

Bases are, for example, alkali metal carbonates, such as, for example, sodium carbonate or potassium carbonate, or sodium bicarbonate or potassium bicarbonate, or organic bases, such as trialkylamines, for example triethylamine, N-methylmorpholine, N-methyl-piperidine, 4-dimethylaminopyridine or diisopropylethylamine; preference is given to diisopropylethylamine.

Preferably, the condensation is carried out with HATU in the presence of diisopropyl-ethylamine or alternatively only with carbonyldiimidazole.

The compounds of the formula (III) are known or can be synthesized by known processes from the appropriate starting materials.

The reaction according to process [B] is generally carried out in inert solvents, preferably in a temperature range of from 50° C. to reflux of the solvents at atmospheric pressure.

Inert solvents are, for example, dimethylformamide, dimethylacetamide, 2-butanone or acetonitrile. Preference is given to dimethylformamide.

The compounds of the formula (XI) are known or can be synthesized by known processes from the appropriate starting materials.

The reaction according to process [C] is generally carried out in phosphoryl chloride as solvent or with thionyl chloride in an inert solvent, preferably in a temperature range of from room temperature to reflux of the solvent at atmospheric pressure.

Inert solvents are, for example, halogenated hydrocarbons, such as methylene chloride, tri-chloromethane or 1,2-dichloroethane; preference is given to methylene chloride.

The compounds of the formula (XVI) are known or can be synthesized by known processes from the appropriate starting materials.

The reaction of the first step according to process [D] is generally carried out in inert solvents, where the reaction with phosphoryl chloride can also be carried out in phosphoryl chloride as solvent, preferably in a temperature range of from room temperature to reflux of the solvents at atmospheric pressure.

Inert solvents are, for example, halogenated hydrocarbons, such as methylene chloride, trichloromethane or 1,2-dichloroethane, or dioxane; preference is given to methylene chloride.

The reaction of the second step according to process [D] is carried out as described for the conversion of the compounds of the formula (XII) into compounds of the formula (X).

The compounds of the formula (XVII) are known or can be synthesized by known processes from the appropriate starting materials.

The reaction according to process [E] is carried out as described for the first step of the process [D].

The reaction of the first step according to process [F] is generally carried out in inert solvents, where the reaction with phosphoryl chloride can also be carried out in phosphoryl chloride as solvent, preferably in a temperature range of from room temperature to reflux of the solvents at atmospheric pressure.

Inert solvents are, for example, halogenated hydrocarbons, such as methylene chloride, trichloromethane or 1,2-dichloroethane, or dioxane; preference is given to dioxane.

The reaction of the second step according to process [F] is carried out as described for the conversion of the compounds of the formula (XII) into compounds of the formula (X).

The reaction according to process [G] is generally carried out in inert solvents, preferably in a temperature range of from −10° C. to room temperature at atmospheric pressure.

Inert solvents are, for example, ethers, such as tetrahydrofuran; preference is given to tetrahydrofuran.

The butyllithium used can be n-butyllithium, sec-butyllithium or tert-butyllithium; preference is given to n-butyllithium.

The compounds of the formula (XVIII) are known or can be synthesized by known processes from the appropriate starting materials.

The reaction according to process [H] is carried out as described for process [A].

The compounds of the formula (XX) are known or can be synthesized by known processes from the appropriate starting materials.

The reaction of the first step according to process [J] is generally carried out in inert solvents, in the presence of a base, preferably in a temperature range of from 0° C. to 50° C. at atmospheric pressure.

Inert solvents are, for example, halogenated hydrocarbons, such as methylene chloride, trichloromethane, carbon tetrachloride or 1,2-dichloroethane; preference is given to methylene chloride.

Bases are, for example, organic bases, such as trialkylamines, for example triethylamine, N-methylmorpholine, N-methylpiperidine, 4-dimethylaminopyridine or diisopropyl-ethylamine; preference is given to triethylamine.

The reaction of the second step according to process [J] is generally carried out in inert solvents, in the presence of a base, if appropriate in a microwave oven, preferably in a temperature range of from 50° C. to 200° C. at atmospheric pressure to 5 bar.

Inert solvents are, for example, dimethyl sulphoxide, dimethylformamide or N-methylpyrrolidone; preference is given to dimethylformamide.

Bases are, for example, alkali metal carbonates, such as, for example, sodium carbonate or potassium carbonate; preference is given to potassium carbonate.

The compounds of the formula (XXI) are known or can be prepared by the general processes [A] to [H], where during the reaction the free amino group is protected by protective groups known to the person skilled in the art. Preference is given to a tert-butoxycarbonyl protective group.

The compounds of the formula (XXII) are known or can be synthesized by known processes from the appropriate starting materials.

The compounds of the formula (II) are known or and can be prepared by reacting compounds of the formula

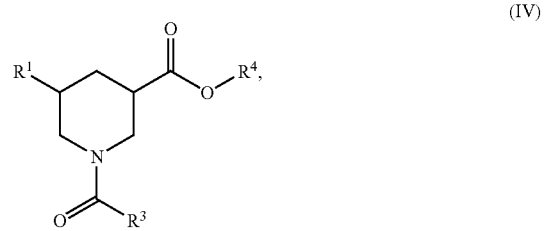

(IV)

in which
$R^1$ and $R^3$ have the meaning given above and
$R^4$ represents methyl or ethyl,
with a base.

The reaction is generally carried out in inert solvents, in the presence of a base, preferably in a temperature range of from room temperature to reflux of the solvents at atmospheric pressure.

Inert solvents are, for example, halogenated hydrocarbons, such as methylene chloride, trichloromethane, carbon tetrachloride or 1,2-dichloroethane, ethers, such as diethyl ether, methyl tert-butyl ether, 1,2-dimethoxyethane, dioxane or tetrahydrofuran, or other solvents, such as dimethylformamide, dimethylacetamide, acetonitrile or pyridine, or mixtures of solvents, or mixtures of solvent with water; preference is given to a mixture of tetrahydrofuran and water.

Bases are, for example, alkali metal hydroxides, such as sodium hydroxide, lithium hydroxide or potassium hydroxide, or alkali metal carbonates, such as caesium carbonate, sodium carbonate or potassium carbonate; preference is given to lithium hydroxide.

The compounds of the formula (IV) are known or and can be prepared by reacting compounds of the formula

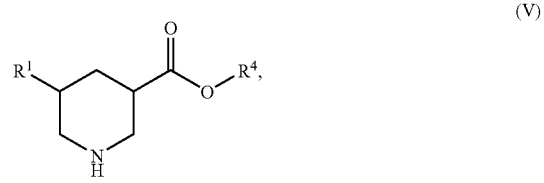

(V)

in which
$R^1$ and $R^4$ have the meaning given above
with compounds of the formula

(VI)

in which
$R^3$ has the meaning given above and
$X^2$ represents halogen, preferably bromine or chlorine, or hydroxyl.

If $X^2$ represents halogen, the reaction is generally carried out in inert solvents, if appropriate in the presence of a base, preferably in a temperature range of from −30° C. to 50° C. at atmospheric pressure.

Inert solvents are, for example, tetrahydrofuran, methylene chloride, pyridine, dioxane or dimethylformamide; preference is given to methylene chloride.

Bases are, for example, triethylamine, diisopropylethylamine or N-methylmorpholine; preference is given to triethylamine or diisopropylethylamine.

If $X^2$ represents hydroxyl, the reaction is generally carried out in inert solvents, in the presence of a dehydrating agent, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is also possible to use mixtures of the solvents. Particular preference is given to dichloromethane or dimethylformamide.

Suitable dehydrating agents in this context are, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexyl-carbodiimide-N'-propyloxymethyl-polystyrene (PS-carbodiimide), or carbonyl compounds, such as carbonyldiimidazole, or 1,2-oxazolium compounds, such as 2-ethyl-5-phenyl-1,2-oxazolium 3-sulphate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxa-zolidinyl)phosphoryl chloride or benzotriazolyloxy-tri(dimethylamino)phosphonium hexa-fluorophosphate, or O-(benzotriazol-1-yl)-N,N,N',N'-tetramethyluronium hexa-fluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N'-hydroxysuccinimide, or mixtures of these, with bases.

Bases are, for example, alkali metal carbonates, such as, for example, sodium carbonate or potassium carbonate, or sodium bicarbonate or potassium bicarbonate, or organic bases, such as trialkylamines, for example triethylamine, N-methylmorpholine, N-methyl-piperidine, 4-dimethylaminopyridine or diisopropylethylamine.

Preferably, the condensation is carried out with HATU or with EDC in the presence of HOBt.

The compounds of the formula (VI) are known or can be synthesized by known processes from the appropriate starting materials.

In an alternative process, the compounds of the formula (IV) can be prepared by reacting compounds of the formula (V) in the first step with 4-nitrophenyl chloroformate and, in the second step, with compounds of the formula (XXII).

The reactions of the first and the second step are carried out as described under process [J].

The compounds of the formula (V) are known or and can be prepared by hydrogenating compounds of the formula

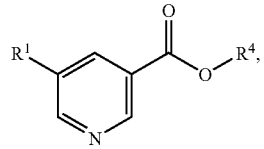

(VII)

in which
$R^1$ and $R^4$ have the meaning given above.

The hydrogenation is generally carried out using a reducing agent in inert solvents, if appropriate with addition of acid such as mineral acids and carboxylic acids, preferably acetic acid, preferably in a temperature range of from room temperature to reflux of the solvents and in a pressure range of from atmospheric pressure to 100 bar, preferably at 50-80 bar.

Preferred reducing agents are hydrogen with palladium on activated carbon, with rhodium on activated carbon, with ruthenium on activated carbon or catalysts thereof, or hydrogen with palladium on alumina or with rhodium on alumina; preference is given to hydrogen with palladium on activated carbon or with rhodium on activated carbon.

Inert solvents are, for example, alcohols, such as methanol, ethanol, n-propanol, isopropanol, n-butanol or tert-butanol; preference is given to methanol or ethanol.

The compounds of the formula (VII) are known or and can be prepared by reacting compounds of the formula

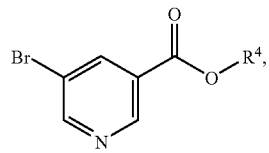

(VIII)

in which
$R^4$ has the meaning given above
with compounds of the formula

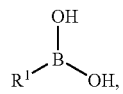

(IX)

in which
$R^1$ has the meaning given above.

The reaction is generally carried out in inert solvents, in the presence of a catalyst, if appropriate in the presence of an additive, preferably in a temperature range of from room temperature to reflux of the solvent at atmospheric pressure.

Inert solvents are, for example, ethers, such as dioxane, tetrahydrofuran or 1,2-dimethoxyethane, hydrocarbons, such as benzene, xylene or toluene, or other solvents, such as nitrobenzene, dimethylformamide, dimethylacetamide, dimethyl sulphoxide or N-methylpyrrolidone, if appropriate, some water is added to these solvents. Preference is given to toluene with water or to a mixture of 1,2-dimethoxyethane, dimethylformamide and water.

Catalysts are, for example, palladium catalysts customary for Suzuki reaction conditions; preference is given to catalysts such as, for example, dichlorobis(triphenylphosphine) palladium, tetrakistriphenylphosphinepalladium(0), palladium(II) acetate or bis(diphenylphosphaneferrocenyl) palladium-(II) chloride.

Additives are, for example, potassium acetate, caesium carbonate, potassium carbonate or sodium carbonate, barium hydroxide, potassium tert-butoxide, caesium fluoride, potassium fluoride or potassium phosphate; preference is given to potassium fluoride or sodium carbonate.

The compounds of the formulae (VIII) and (IX) are known or can be synthesized by known processes from the appropriate starting materials.

The compounds of the formula (X) are known or and can be prepared by reacting compounds of the formula

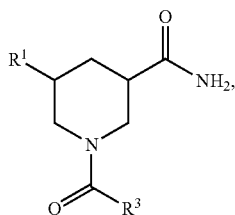

(XII)

in which
R$^1$ and R$^3$ have the meaning given above
with Lawesson reagent (2,4-bis[4-methoxyphenyl] 1,3-dithia-2,4-diphosphetane 2,4-disulphide).

The reaction is generally carried out in inert solvents, preferably in a temperature range of from room temperature to reflux of the solvents at atmospheric pressure.

Inert solvents are, for example, ethers, such as dioxane, tetrahydrofuran or 1,2-dimethoxyethane, hydrocarbons, such as benzene, xylene or toluene, or halogenated hydrocarbons, such as methylene chloride, trichloromethane, carbon tetrachloride or 1,2-dichloroethane. Preference is given to dioxane.

The compounds of the formula (XII) are known or and can be prepared by reacting compounds of the formula

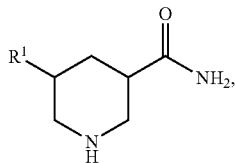

(XIII)

in which
R$^1$ has the meaning given above
with compounds of the formula (VI).

The reaction is carried out under the reaction conditions given for the reaction of compounds of the formula (V) with compounds of the formula (VI).

The compounds of the formula (XIII) are known or and can be prepared by hydrogenating compounds of the formula

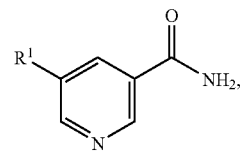

(XIV)

in which
R$^1$ has the meaning given above.

The hydrogenation is carried out under the reaction conditions given for the hydrogenation of compounds of the formula (VII).

The compounds of the formula (XIV) are known or and can be prepared by reacting the compound of the formula (XV)

Br
R$^1$
O
NH$_2$,
N with compounds of the formula (IX).

The reaction is carried out under the reaction conditions given for the reaction of compounds of the formula (VIII) with compounds of the formula (IX).

The compound of the formula (XV) is known or can be synthesized by known processes from the appropriate starting materials.

The compounds of the formula (XIX) are known or and can be prepared from compounds of the formula (XII), as described in Example 83A and Example 84A.

The preparation of the compounds of the formula (I) can be illustrated by the synthesis—schemes below.

Scheme 1:

-continued
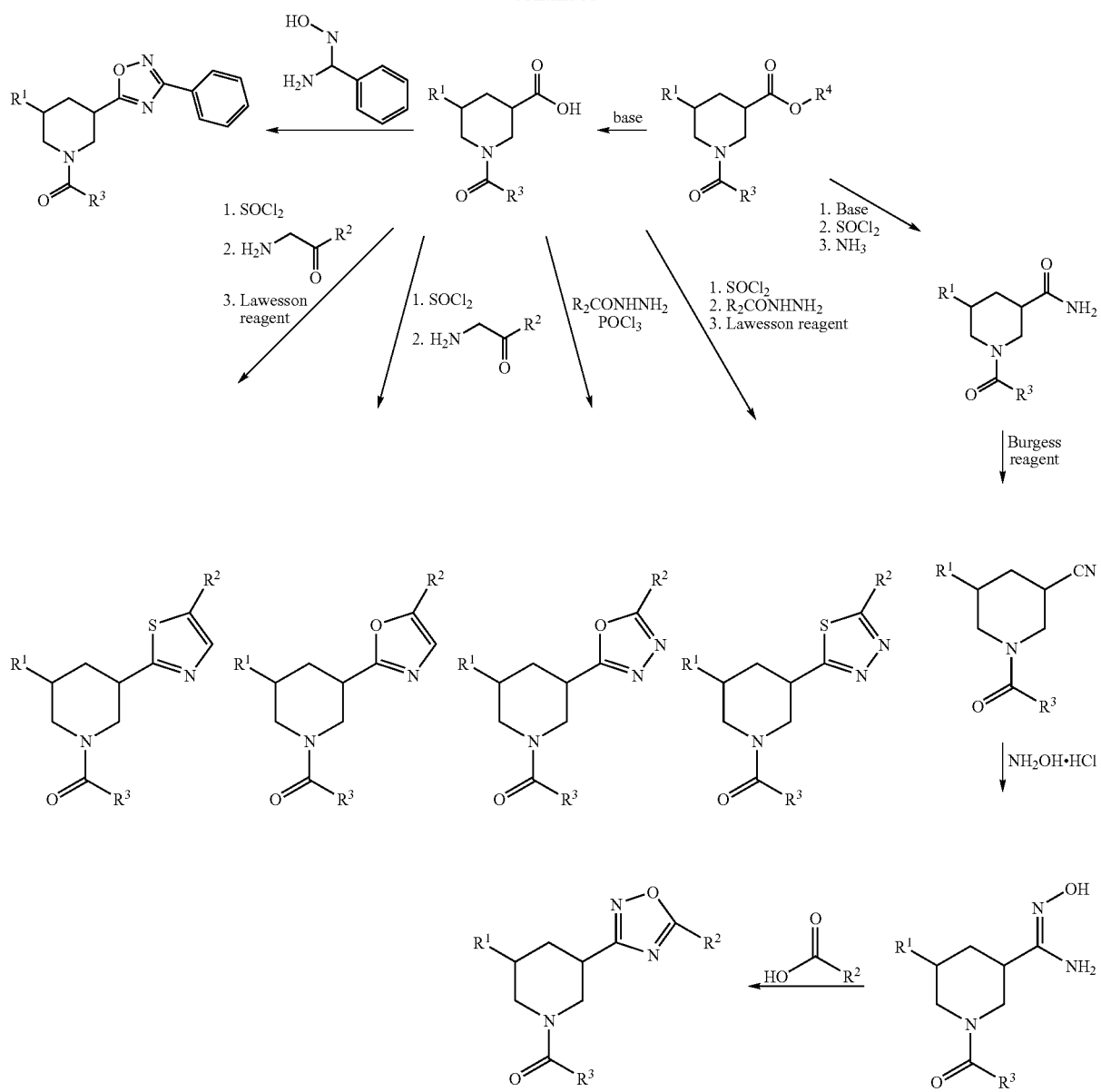
Scheme 2:
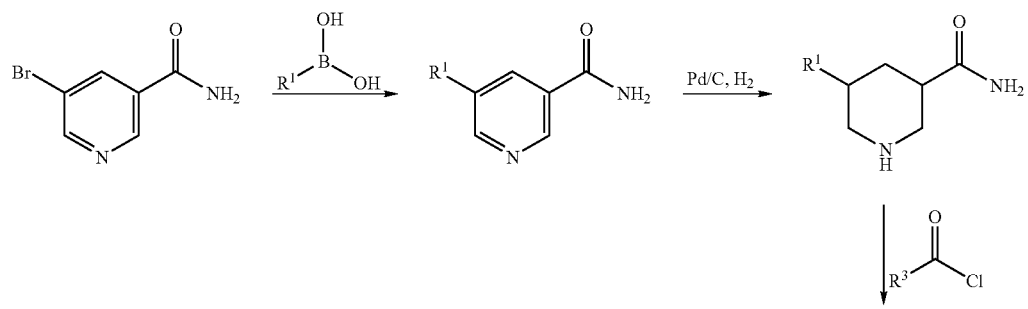

-continued

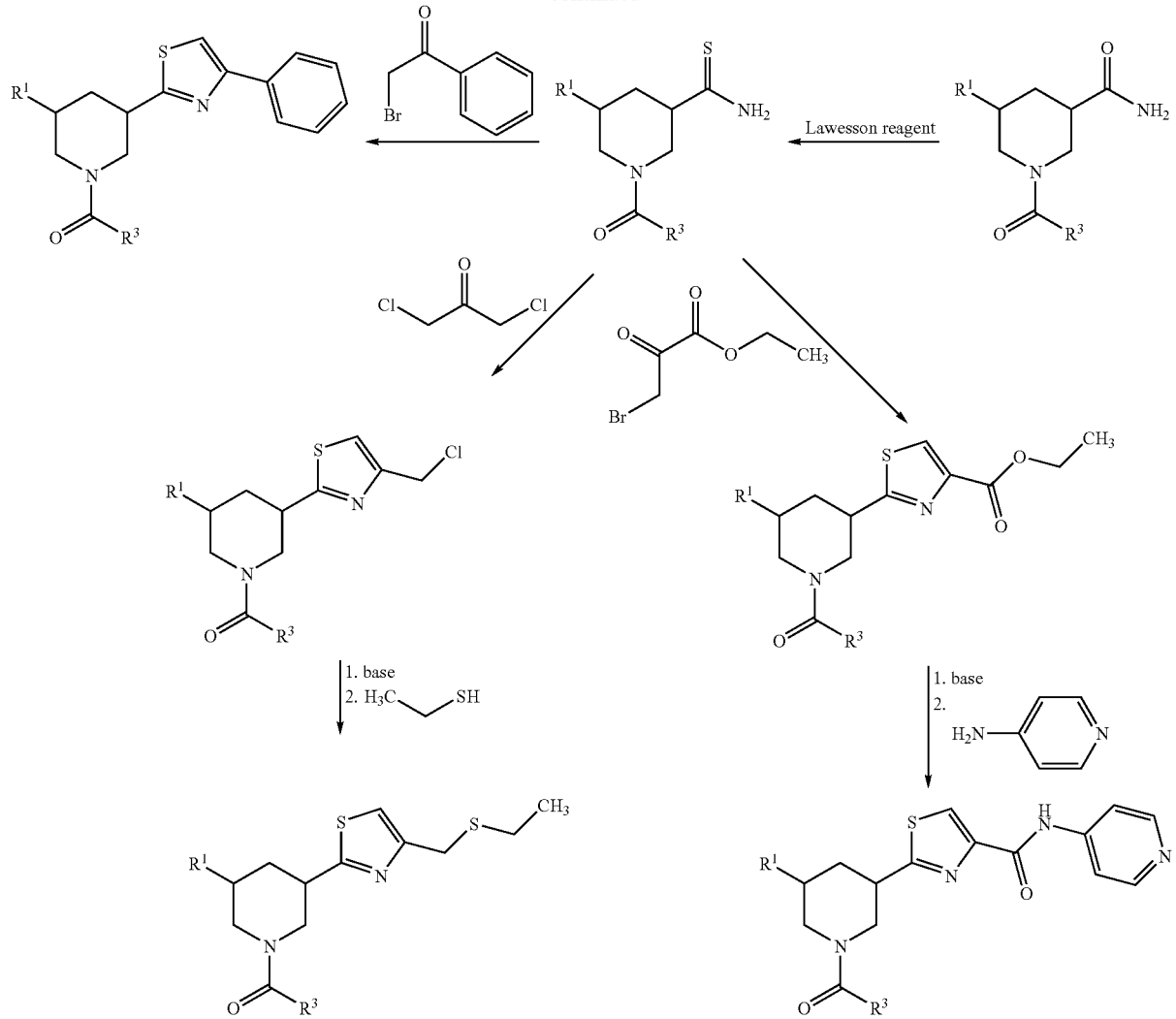

The compounds according to the invention have an unforeseeable useful spectrum of pharmacological and pharmacokinetic activity. They are selective antagonists of the PAR-1 receptor acting in particular as platelet aggregation inhibitors, as inhibitors of endothelium proliferation and as inhibitors of tumour growth.

Accordingly, they are suitable for use as medicaments for the treatment and/or prophylaxis of diseases in man and animals.

The present invention furthermore provides the use of the compounds according to the invention for the treatment and/or prophylaxis of disorders, preferably of thromboembolic disorders and/or thromboembolic complications.

"Thromboembolic disorders" in the sence of the present invention include in particular disorders such as ST-segment elevation myocardial infarction (STEMI) and non-ST-segment elevation myocardial infarction (non-STEMI), stabile angina pectoris, unstabile angina pectoris, reocclusions and restenoses after coronary interventions such as angioplasty, stent implantations or aortocoronary bypass, peripheral arterial occlusion diseases, pulmonary embolisms, deep venous thromboses and renal vein thromboses, transitory ischaemic attacks and also thrombotic and thromboembolic stroke. Accordingly, the substances are also suitable for the prevention and treatment of cardiogenic thromboembolisms, such as, for example, brain ischaemias, stroke and systemic thromboembolisms and ischaemias, in patients with acute, intermittent or persistent cardial arrhythmias, such as, for example, atrial fibrillation, and those undergoing cardioversion, furthermore in patients with heart valve disorders or with intravasal objects, such as, for example, artificial heart valves, catheters, intraaortic balloon counterpulsation and pacemaker probes.

Thromboembolic complications are furthermore encountered in connection with microangiopathic haemolytic anaemias, extracorporeal circulation, such as, for example, haemodialysis, haemofiltration, ventricular assist devices and artifical hearts, and also heart valve prostheses.

Moreover, the compounds according to the invention are also used for influencing wound healing, for the prophylaxis and/or treatment of atherosclerotic vascular disorders and inflammatory disorders, such as rheumatic disorders of the locomotive system, coronary heart diseases, of heart failure, of hypertension, of inflammatory disorders, such as, for example, asthma, COPD, inflammatory pulmonary disorders, glomerulonephritis and inflammatory intestinal disorders, and additionally also for the prophylaxis and/or treatment of Alzheimer's disease, autoimmune disorders, Crohn's disease and ulcerative colitis.

Moreover, the compounds according to the invention can be used for inhibiting tumour growth and the formation of metastases, for microangiopathies, age-related macular degeneration, diabetic retinopathy, diabetic nephropathy and other microvascular disorders, and also for the prevention and treatment of thromboembolic complications, such as, for example, venous thromboembolisms, for tumour patients, in particular those undergoing major surgical interventions or chemo- or radiotherapy.

The compounds according to the invention are furthermore suitable for the treatment of cancer. Cancerous disorders include inter alia: carcinomas (including breast cancer, hepatocellular carcinomas, lung cancer, colorectal cancer, cancer of the colon and melanomas), lymphomas (for example non-Hodgkin's lymphomas and mycosis fungoides), leukaemias, sarcomas, mesotheliomas, brain cancer (for example gliomas), germinomas (for example testicular cancer and ovarian cancer), choriocarcinomas, renal cancer, cancer of the pancreas, thyroid cancer, head and neck cancer, endometrial cancer, cancer of the cervix, cancer of the bladder, stomach cancer and multiple myeloma.

Moreover, PAR-1 expressed on endothelial cells mediates signals resulting in vascular growth ("angiogenesis"), a process which is vital for allowing a tumour to grow larger than about 1 mm$^3$. Induction of angiogenesis is also relevant for other disorders; these include disorders of the rheumatic type (for example rheumatoid arthritis), pulmonary disorders (for example pulmonary fibrosis, pulmonary hypertension, in particular pulmonary arterial hypertension, disorders characterized by pulmonary occlusion), arteriosclerosis, plaque rupture, diabetic retinopathy and wet macular degeneration.

In addition, the compounds according to the invention are suitable for the treatment of sepsis. Sepsis (or septicaemia) is a frequent disorder with high mortality. Initial symptoms of sepsis are typically unspecific (for example fever, reduced general state of health); however, during further progress there may be a general activation of the coagulation system ("disseminated intravascular coagulation" or "consumption coagulopathy"; hereinbelow referred to as "DIC") with the formation of microthrombi in various organs and secondary bleeding complications. Moreover, there may be endothelial damage with increased permeability of the vessels and diffusion of fluid and proteins into the extravasal space. As the disorder worsens, there may be organ dysfunction or organ failure (for example kidney failure, liver failure, respiratory failure, deficits of the central nervous system and heart/circulatory failure) and even multi-organ failure. In principle, this may affect any organ; the most frequently encountered organ dysfunctions and organ failures are those of the lung, the kidney, the cardiovascular system, the coagulation system, the central nervous system, the endocrine glands and the liver. Sepsis may be associated with an "acute respiratory distress syndrome" (hereinbelow referred to as ARDS). ARDS may also occur independently of sepsis. "Septic shock" is the occurence of treatment-requiring hypotension which facilitates further organ damage and is associated with a worsening of the prognosis.

Pathogens can be bacteria (gram-negative and gram-positive), fungi, viruses and/or eukaryotes. Site of entry or primary infection can be pneumonia, an infection of the urinary tract or peritonitis, for example. The infection can be associated with bacteriaemia, but this is not necessarily the case.

Sepsis is defined as the presence of an infection and a "systemic inflammatory response syndrome" (hereinbelow referred to as "SIRS"). SIRS occurs during infections, but also during other states such as injuries, burns, shock, surgical interventions, ischaemia, pancreatitis, reanimation or tumours. The definition of ACCP/SCCM Consensus Conference Committee of 1992 (*Crit. Care Med.* 1992, 20, 864-874) describes the symptoms required for the diagnosis "SIRS" and measurement parameters (inter alia a change in body temperature, increased heart rate, breathing difficulties and changes in the blood picture). The later (2001) SCCM/ESICM/ACCP/ATS/SIS International Sepsis Definitions Conference essentially kept the criteria, but fine-tuned details (Levy et al., *Crit. Care Med.* 2003, 31, 1250-1256).

DIC and SIRS may occur during sepsis, but also as a result of surgical interventions, tumour disorders or other injuries. In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin, fibrinogen) and platelets, which reduces the coagulability of the blood and may result in heavy bleeding.

In addition, the compounds according to the invention can also be used for preventing coagulation ex vivo, for example for preserving blood and plasma products, for cleaning/pretreating catheters and other medical auxiliaries and instruments, including extracorporeal circulation, for coating synthetic surfaces of medical auxiliaries and instruments used in vivo or ex vivo or for platelet-containing biological samples.

The present invention furthermore provides the use of the compounds according to the invention for coating medical instruments and implants, for example catheters, prostheses, stents or artificial heart valves. Here, the compounds according to the invention can be firmly attached to the surface or, for local action, be released over a certain period of time from a carrier coating into the immediate surroundings.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, which involves the use of a therapeutically effective amount of a compound according to the invention.

The present invention furthermore provides medicaments comprising a compound according to the invention and one or more further active compounds, in particular for the treatment and/or prophylaxis of the disorders mentioned above. Active compounds suitable for combinations are, by way of example and by way of preference:

calcium channel blockers, for example amlodipine besilate (for example Norvasc®), felodipine, diltiazem, verapamil, nifedipine, nicardipine, nisoldipine and bepridil;
iomerizine;
statins, for example atorvastatin, fluvastatin, lovastatin, pitavastatin, pravastatin, rosuvastatin and simvastatin;
cholesterol resorption inhibitors, for example ezetimibe and AZD4121;
cholesteryl ester transfer protein ("CETP") inhibitors, for example torcetrapib;
low-molecular weight heparins, for example dalteparin sodium, ardeparin, certoparin, enoxaparin, parnaparin, tinzaparin, reviparin and nadroparin;

other anticoagulants, for example warfarin, marcumar, fondaparinux;

antiarrhythmics, for example dofetilide, ibutilide, metoprolol, metoprolol tartrate, propranolol, atenolol, ajmaline, disopyramide, prajmaline, procainamide, quinidine, sparteine, aprindine, lidocaine, mexiletine, tocamide, encamide, flecamide, lorcamide, moricizine, propafenone, acebutolol, pindolol, amiodarone, bretylium tosylate, bunaftine, sotalol, adenosine, atropine and digoxin;

alpha-adrenergic agonists, for example doxazosin mesylate, terazoson and prazosin;

beta-adrenergic blockers, for example carvedilol, propranolol, timolol, nadolol, atenolol, metoprolol, bisoprolol, nebivolol, betaxolol, acebutolol and bisoprolol;

aldosterone antagonists, for example eplerenone and spironolactone;

angiotensin-converting enzyme inhibitors ("ACE inhibitors"), for example moexipril, quinapril hydrochloride, ramipril, lisinopril, benazepril hydrochloride, enalapril, captopril, spirapril, perindopril, fosinopril and trandolapril;

angiotensin II receptor blockers ("ARBs"), for example olmesartan-medoxomil, candesartan, valsartan, telmisartan, irbesartan, losartan and eprosartan;

endothelin antagonists, for example tezosentan, bosentan and sitaxsentan-sodium;

inhibitors of neutral endopeptidase, for example candoxatril and ecadotril;

phosphodiesterase inhibitors, for example milrinone, theophylline, vinpocetine, EHNA (erythro-9-(2-hydroxy-3-nonyl)adenine), sildenafil, vardenafil and tadalafil;

fibrinolytics, for example reteplase, alteplase and tenecteplase;

GP IIb/IIIa antagonists, for example integrillin, abciximab and tirofiban;

direct thrombin inhibitors, for example AZD0837, argatroban, bivalirudin and dabigatran;

indirect thrombin inhibitors, for example odiparcil;

direct and indirect factor Xa inhibitors, for example fondaparinux-sodium, apixaban, razaxaban, rivaroxaban (BAY 59-7939), KFA-1982, DX-9065a, AVE3247, otamixaban (XRP0673), AVE6324, SAR377142, idraparinux, SSR126517, DB-772d, DT-831j, YM-150, 813893, LY517717 and DU-1766;

direct and indirect factor Xa/IIa inhibitors, for example enoxaparin-sodium, AVE5026, SSR128428, SSR128429 and BIBT-986 (Tanogitran);

lipoprotein-associated phospholipase A2 ("LpPLA2") modulators;

diuretics, for example chlorthalidone, ethacrynic acid, furosemide, amiloride, chlorothiazide, hydrochlorothiazide, methylclothiazide and benzthiazide;

nitrates, for example isosorbide 5-mononitrate;

thromboxane antagonists, for example seratrodast, picotamide and ramatroban;

platelet aggregation inhibitors, for example clopidogrel, tiklopidin, cilostazol, aspirin, abciximab, limaprost, eptifibatide and CT-50547;

cyclooxygenase inhibitors, for example meloxicam, rofecoxib and celecoxib;

B-type natriuretic peptides, for example nesiritide and ularitide;

NV1FGF modulators, for example XRP0038;

HT1B/5-HT2A antagonists, for example SL65.0472;

guanylate cyclase activators, for example ataciguat (HMR1766) and HMR1069;

e-NOS transcription enhancers, for example AVE9488 and AVE3085;

antiatherogenic substances, for example AGI-1067:

CPU inhibitors, for example AZD9684;

renin inhibitors, for example aliskirin and VNP489;

inhibitors of adenosine diphosphate-induced platelet aggregation, for example clopidogrel, tiklopidin, prasugrel and AZD6140;

NHE-1 inhibitors, for example AVE4454 and AVE4890.

antibiotic therapy: various antibiotics or antifungal medicament combinations are suitable, either as calculated therapy (before a microbial assessment has been made) or as specific therapy; fluid therapy, for example crystalloid or colloidal fluids; vasopressors, for example norepinephrine, dopamine or vasopressin; inotropic therapy, for example dobutamine; corticosteroids, for example hydrocortisone, or fludrocortisone; recombinant human activated protein C, Xigris; blood products, for example erythrocyte concentrates, platelet concentrates, erythropoietin or fresh frozen plasma; assisted ventilation in sepsis-induced acute lung injury (ALI) or acute respiratory distress syndrome (ARDS), for example permissive hypercapnia, low tidal volumes; sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium; glucose control, for example insulin, glucose; renal replacement therapies, for example continuous venovenous haemofiltration or intermittent haemodialysis. Low-dose dopamine for renal protection; anticoagulants, for example for thrombosis prophylaxis or for renal replacement therapies, for example unfractionated heparins, low-molecular weight heparins, heparinoids, hirudin, bivalirudin or argatroban; bicarbonate therapy; stress ulcer prophylaxis, for example H2 receptor inhibitors, antacids.

Medicaments for proliferative disorders: uracil, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, methotrexate, 5-fluorouracil, floxuridine, cytarabine, 6-mercaptopurine, 6-thioguanine, fludarabine phosphate, pentostatin, vinblastine, vincristine, vindesine, bleomycin, dactinomycin, daunorubicin, doxorubicin, epirubicin, idarubicin, paclitaxel, mithramycin, deoxycoformycin, mitomycin-C, L-asparaginase, interferons, etoposide, teniposide, 17.alpha.-ethynylestradiol, diethylstilbestrol, testosterone, prednisone, fluoxymesterone, dromostanolone propionate, testolactone, megestrol acetate, tamoxifen, methylprednisolone, methyltestosterone, prednisolone, triamcinolone, chlorotrianisene, hydroxyprogesterone, aminoglutethimide, estranrustine, medroxyprogesterone acetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), Iressa (gefmitib, Zdl839), XELODA® (capecitabine), Tarceva® (erlotinib), Azacitidine (5-azacytidine; 5-AzaC), temozolomide (Temodar®), gemcitabine (e.g. GEMZAR® (gemcitabine HCl)), vasostatin or a combination of two or more of the above.

The present invention furthermore provides a method for preventing the coagulation of blood in vitro, in particular in banked blood or biological samples containing platelets, which method is characterized in that an anticoagulatory effective amount of the compound according to the invention is added.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

The compounds according to the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

The present invention further provides medicaments comprising at least one compound according to the invention, preferably together with one or more inert nontoxic pharmaceutically suitable auxiliaries, and their use for the purposes mentioned above.

It has generally proved advantageous to administer on parenteral administration amounts of about 5 to 250 mg every 24 hours to achieve effective results. On oral administration the amount is about 5 to 100 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentage data in the following tests and examples are, unless indicated otherwise, percentages by weight; parts are parts by weight. Solvent ratios, dilution ratios and concentration data for the liquid/liquid solutions are in each case based on volume. "w/v" means "weight/volume". Thus, for example, "10% w/v" means: 100 ml of solution or suspension comprise 10 g of substance.

A) EXAMPLES

Abbreviations

CDI carbonyldiimidazole
d days(s), doublet (in NMR)
TLC thin-layer chromatography
DCI direct chemical ionization (in MS)
dd doublet of doublets (in NMR)
DMAP 4-dimethylaminopyridine
DMF N,N-dimethylformamide
DMSO dimethyl sulphoxide
eq. equivalent(s)
ESI electrospray ionization (in MS)
h hours(s)
HATU O-(7-azabenzotriazol-1-yl)-N,N,N',N'-tetramethyluronium hexafluorophosphate
HPLC high-pressure, high-performance liquid chromatography
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
PYBOP benzotriazol-1-yloxy-tris(pyrrolidino)phosphonium hexafluorophosphate
RP reversed phase (in HPLC)
RT room temperature
$R_t$ retention time (in HPLC)
s singlet (in NMR)
THF tetrahydrofuran HPLC Methods Method 1A: Instrument: HP 1100 with DAD detection; column: Kromasil 100 RP-18, 60 mm×2.1 mm, 3.5 µm; mobile phase A: 5 ml of perchloric acid (70% strength)/l of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 2A: Instrument: HP 1100 with DAD detection; column: Kromasil 100 RP-18, 60 mm×2.1 mm, 3.5 µm; mobile phase A: 5 ml of perchloric acid (70% strength)/l of water, mobile phase B: acetonitrile; gradient: 0 min 2% B→0.5 min 2% B→4.5 min 90% B→9 min 0% B→9.2 min 2% B→10 min 2% B; flow rate: 0.75 ml/min; column temperature: 30° C.; UV detection: 210 nm.

Method 3A: Instrument: HP 1100 with DAD detection; column: Kromasil 100 RP-18, 60 mm×2.1 mm, 3.5 µm; mobile phase A: 5 ml of perchloric acid (70% strength)/l of water, mobile phase B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Method 4A: Phase: Kromasil 100, C18, 5 µm, 250 mm×4 mm; mobile phase: water/acetonitrile 50:50; flow rate: 1 ml/min; T: 40° C.; UV: 210 nm.

LC-MS Methods:

Method 1B: MS instrument type: Micromass ZQ; HPLC instrument type: HP 1100 Series; UV DAD; column: Phenomenex Gemini 3μ, 30 mm×3.0 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2B: Instrument: Micromass QuattroPremier with Waters HPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+ 0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 3B: MS instrument type: Micromass ZQ; HPLC instrument type: Waters Alliance 2795; column: Phenomenex Synergi 2.5μ MAX-RP 100A Mercury, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4B: MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 5B: Instrument: Micromass Quattro Micro MS with HPLC Agilent Serie 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A→5.00 min 100% A; oven: 50° C.; flow rate: 2 ml/min; UV detection: 210 nm.

Method 6B: Instrument: Micromass Quattro LCZ with HPLC Agilent Serie 1100; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 7B: Instrument: Micromass Quattro LCZ with HPLC Agilent Serie 1100; column: Phenomenex Onyx Monolithic C18, 100 mm×3 mm. mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 8B: Instrument: Micromass Platform LCZ with HPLC Agilent Serie 1100; column: Thermo HyPURITY Aquastar 3μ 50 mm×2.1 mm; mobile phase A: 1 l of water+ 0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 9B: Instrument: Waters ACQUITY SQD UPLC System; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 10B: Instrument MS: Waters ZQ 2000; Instrument HPLC: Agilent 1100, 2-column system, autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Preparative Separation of Diastereomers:

Method 1C: Phase: Kromasil 100 C18, 5 μm 250 mm×20 mm, mobile phase: 0.2% strength aqueous trifluoroacetic acid/acetonitrile 47:53; flow rate: 25 ml/min, temperature: 23° C.; UV detection: 210 nm.

Method 2C: Phase: Xbrdge C18, 5 μm OBD 19 mm×150 mm, mobile phase: acetonitrile/0.2% strength trifluoroacetic acid 50:50; flow rate: 25 ml/min, temperature: RT; UV detection: 210 nm.

Method 3C: Phase: Kromasil 100 C18, 5 μm 250 mm×20 mm, mobile phase: acetonitrile/0.2% strength trifluoroacetic acid 50:50; flow rate: 25 ml/min, temperature: RT; UV detection: 210 nm.

Method 4C: Phase: Kromasil 100 C18, 5 μm 250 mm×20 mm, mobile phase: acetonitrile/0.2% strength trifluoroacetic acid 57:43; flow rate: 25 ml/min, temperature: RT; UV detection: 210 nm.

Method 5C: Phase: Kromasil 100 C18, 5 μm 250 mm×20 mm, mobile phase: water:acetonitrile 25:75; flow rate: 25 ml/min, temperature: 35° C.; UV detection: 220 nm.

Method 6C: Phase: Kromasil 100 C18, 5 μm 250 mm×20 mm, mobile phase: acetonitrile/water 35:65; flow rate: 25 ml/min, temperature: 30° C.; UV detection: 210 nm.

Method 7C: Phase: Sunfire C18, 5 μm 150 mm×19 mm, mobile phase: water/acetonitrile 50:50; flow rate: 25 ml/min, temperature: 24° C.; UV detection: 225 nm.

Method 8C: Phase: Kromasil 100 C18, 5 μm 250 mm×20 mm, mobile phase: water/acetonitrile 50:50; flow rate: 25 ml/min, temperature: 40° C.; UV detection: 210 nm.

Method 9C: Phase: Kromasil 100 C18, 5 μm 250 mm×20 mm, mobile phase: water/acetonitrile 35:65; flow rate: 25 ml/min, temperature: 30° C.; UV detection: 210 nm.

Method 10C: Phase: Sunfire C18, 5 μm 150 mm×30 mm, mobile phase: water/acetonitrile 50:50; flow rate: 56 ml/min, temperature: 30° C.; UV detection: 210 nm.

Method 11C: Phase: Xbrdge C18, 5 μm OBD 19 mm×150 mm, mobile phase: acetonitrile/0.1% ammonia solution 55:45; flow rate: 25 ml/min, temperature: 28° C.; UV detection: 210 nm.

Method 12C: Phase: Sunfire C18, 5 μm OBD 19 mm×150 mm, mobile phase: acetonitrile/water 42:58; flow rate: 25 ml/min, temperature: 45° C.; UV detection: 210 nm.

Method 13C: Phase: Sunfire C18, 5 μm OBD 19 mm×150 mm, mobile phase: acetonitrile/water 38:62; flow rate: 25 ml/min, temperature: 40° C.; UV detection: 210 nm.

Method 14C: Phase: Sunfire C18, 5 μm OBD 19 mm×150 mm, mobile phase: water/acetonitrile 52:48; flow rate: 25 ml/min, temperature: 40° C.; UV detection: 210 nm.

Method 15C: Phase: Sunfire C18, 5 μm OBD 19 mm×150 mm, mobile phase: water/acetonitrile 95:5; flow rate: 25 ml/min, temperature: 40° C.; UV detection: 210 nm.

Preparative Separation of Enantiomers:

Method 1D: Phase: Daicel Chiralcel OD-H, 5 μm 250 mm×20 mm, mobile phase: isopropanol/isohexane 40:60; flow rate: 15 ml/min, temperature: 24° C.; UV detection: 230 nm.

Method 2D: Phase: Daicel Chiralpak AD-H, 5 µm 250 mm×20 mm; mobile phase: isopropanol/isohexane 20:80; flow rate: 20 ml/min; temperature: 25° C.; UV detection: 260 nm.

Method 3D: Phase: Daicel Chiralcel OD-H, 5 µm 250 mm×20 mm, mobile phase: ethanol/isohexane 30:70; flow rate: 15 ml/min, temperature: 25° C.; UV detection: 230 nm.

Method 4D: Phase: Daicel Chiralcel OD-H, 5 µm 250 mm×20 mm, mobile phase: isopropanol/isohexane 40:60; flow rate: 18 ml/min, temperature: 25° C.; UV detection: 230 nm.

Method 5D: Phase: Daicel Chiralpak AD-H, 5 µm 250 mm×20 mm; mobile phase: isopropanol/isohexane 50:50; flow rate: 20 ml/min; temperature: 24° C.; UV detection: 260 nm.

Method 6D: Phase: Daicel Chiralpak AD-H, 5 µm 250 mm×20 mm, mobile phase: isopropanol/isohexane 50:50; flow rate: 18 ml/min; T: 24° C.; UV detection: 230 nm.

Method 7D: Phase: Daicel Chiralcel OD-H, 5 µm 250 mm×20 mm, mobile phase: isopropanol/isohexane 30:70; flow rate: 18 ml/min, temperature: 24° C.; UV detection: 230 nm.

Method 8D: Phase: Daicel Chiralpak AD-H, 5 µm 250 mm×20 mm, mobile phase: isohexane/ethanol 25:75; flow rate: 15 ml/min, temperature: 40° C.; UV detection: 220 nm.

Method 9D: Phase: Daicel Chiralpak AD-H, 5 µm 250 mm×20 mm, mobile phase: ethanol 100%; flow rate: 12 ml/min, temperature: 40° C.; UV detection: 220 nm.

Method 10D: Phase: Daicel Chiralpak AD-H, 5 µm 250 mm×20 mm, mobile phase: isohexane/isopropanol 40:60; flow rate: 15 ml/min, temperature: 40° C.; UV detection: 220 nm.

Method 11D: Phase: Daicel Chiralpak AD-H, 5 µm 250 mm×20 mm, mobile phase: ethanol 100%; flow rate: 15 ml/min, temperature: 40° C.; UV detection: 220 nm.

Method 12D: Phase: Daicel Chiralpak AD-H, 5 µm 250 mm×20 mm, mobile phase: isohexane/isopropanol 30:70; flow rate: 15 ml/min, temperature: 40° C.; UV detection: 220 nm.

Method 13D: Phase: Daicel Chiralpak AD-H, 5 µm 250 mm×20 mm, mobile phase: isohexane/ethanol 30:70; flow rate: 15 ml/min, temperature: 40° C.; UV detection: 220 nm.

Method 14D: Phase: Daicel Chiralpak AS-H, 5 µm 250 mm×20 mm, mobile phase: isohexane/ethanol 50:50; flow rate: 15 ml/min, temperature: 40° C.; UV detection: 220 nm.

Method 15D: Phase: Daicel Chiralpak AS-H, 5 µm 250 mm×20 mm, mobile phase: isohexane/ethanol 70:30; flow rate: 15 ml/min, temperature: 40° C.; UV detection: 220 nm.

Method 16D: Phase: Daicel Chiralpak AD-H, 5 µm 250 mm×20 mm, mobile phase: isohexane/isopropanol 50:50; flow rate: 15 ml/min, temperature: 40° C.; UV detection: 220 nm.

Method 17D: Phase: Daicel Chiralpak OD-H, 5 µm 250 mm×20 mm, mobile phase: isohexane/isopropanol 40:60; flow rate: 15 ml/min, temperature: 24° C.; UV detection: 230 nm.

Method 18D: Phase: Daicel Chiralpak OJ-H, 5 µm 250 mm×20 mm, mobile phase: isohexane/ethanol 60:40; flow rate: 20 ml/min; temperature: 28° C.; UV detection: 230 nm.

Method 19D: Phase: Daicel Chiralpak AS-H, 5 µm 250 mm×20 mm, mobile phase: isohexane/isopropanol 50:50; flow rate: 20 ml/min, temperature: 24° C.; UV detection: 230 nm.

Method 20D: Phase: Daicel Chiralpak AD-H, 5 µm 250 mm×20 mm, mobile phase: ethanol/heptane 50:50; flow rate: 25 ml/min, temperature: 40° C.; UV detection: 220 nm.

Method 21D: Phase: Daicel Chiralpak AD-H, 5 µm 250 mm×20 mm; mobile phase: isohexane/isopropanol 30:70; flow rate: 15 ml/min; temperature: 30° C.; UV detection: 220 nm.

Method 22D: Phase: Daicel Chiralpak AD-H, 5 µm 250 mm×20 mm; mobile phase: isohexane/isopropanol 50:50; flow rate: 25 ml/min; temperature: 40° C.; UV detection: 220 nm.

Method 23D: Phase: Daicel Chiralpak AD-H, 5 µm 250 mm×20 mm; mobile phase: isohexane/ethanol 50:50; flow rate: 18 ml/min; temperature: 24° C.; UV detection: 230 nm.

Method 24D: Phase: Daicel Chiralpak AD-H, 5 µm 250 mm×20 mm, mobile phase: isohexane/isopropanol 50:50; flow rate: 25 ml/min, temperature: 50° C.; UV detection: 210 nm.

Method 25D: Phase: Daicel Chiralpak AD-H, 5 µm 250 mm×20 mm, mobile phase: isohexane/ethanol 50:50; flow rate: 20 ml/min, temperature: 40° C.; UV detection: 220 nm.

Analytic Separation of Enantiomers:

Method 1E: Phase: Daicel Chiralcel OD-H, 5 µm 250 mm×4.6 mm, mobile phase: isopropanol/isohexane 50:50; flow rate: 1 ml/min, temperature: 40° C.; UV detection: 220 nm.

Method 2E: Phase: Daicel Chiralpak AD-H, 5 µm 250 mm×4 mm; mobile phase: isopropanol/isohexane: 20:80; flow rate: 1 ml/min; temperature: 24° C.; UV detection: 230 nm.

Method 3E: Phase: Daicel Chiralcel OD-H, 5 µm 250 mm×4 mm, mobile phase: ethanol/isohexane 30:70; flow rate: 1 ml/min, temperature: 24° C.; UV detection: 230 nm.

Method 4E: Phase: Daicel Chiralpak AD-H, 5 µm 250 mm×4 mm; mobile phase: isopropanol/isohexane: 50:50; flow rate: 1 ml/min; temperature: 24° C.; UV detection: 230 nm.

Method 5E: Phase: Daicel Chiralpak AD-H, 5 µm 250 mm×4 mm; mobile phase: isopropanol/isohexane: 50:50; flow rate: 1 ml/min; temperature: 24° C.; UV detection: 230 nm.

Method 6E: Phase: Daicel Chiralpak AD-H, 5 µm 250 mm×4.6 mm; mobile phase: isohexane/ethanol+0.2% diethylamine 25:75; flow rate: 1 ml/min; temperature: 40° C.; UV detection: 220 nm.

Method 7E: Phase: Daicel Chiralpak AD-H, 5 µm 250 mm×4.6 mm; mobile phase: ethanol 100%; flow rate: 1 ml/min; temperature: 40° C.; UV detection: 220 nm.

Method 8E: Phase: Daicel Chiralpak AD-H, 5 µm 250 mm×4.6 mm; mobile phase: isohexane/isopropanol+0.2% diethylamine 40:60; flow rate: 1 ml/min; temperature: 40° C.; UV detection: 235 nm.

Method 9E: Phase: Daicel Chiralpak AD-H, 5 µm 250 mm×4.6 mm; mobile phase: isohexane/isopropanol 30:70; flow rate: 1 ml/min; temperature: 45° C.; UV detection: 220 nm.

Method 10E: Phase: Daicel Chiralpak AD-H, 5 µm 250 mm×4.6 mm; mobile phase: isohexane/ethanol 30:70; flow rate: 1 ml/min; temperature: 45° C.; UV detection: 220 nm.

Method 11E: Phase: Daicel Chiralpak AS-H, 5 µm 250 mm×4.6 mm; mobile phase: isohexane/ethanol 50:50; flow rate: 1 ml/min; temperature: 40° C.; UV detection: 220 nm.

Method 12E: Phase: Daicel Chiralpak AS-H, 5 µm 250 mm×4.6 mm; mobile phase: isohexane/ethanol 70:30; flow rate: 1 ml/min; temperature: 40° C.; UV detection: 220 nm.

Method 13E: Phase: Daicel Chiralpak OD-H, 5 µm 250 mm×4.0 mm; mobile phase: isohexane/isopropanol 50:50; flow rate: 1 ml/min; temperature: 40° C.; UV detection: 230 nm.

Method 14E: Phase: Daicel Chiralpak OJ-H, 5 μm 250 mm×4.0 mm; mobile phase: isohexane/ethanol 50:50; flow rate: 1 ml/min; temperature: 40° C.; UV detection: 230 nm.

Method 15E: Phase: Daicel Chiralpak AS-H, 5 μm 250 mm×4.0 mm; mobile phase: isohexane/isopropanol 50:50; flow rate: 1 ml/min; temperature: 40° C.; UV detection: 230 nm.

Method 16E: Phase: Daicel Chiralpak AD-H, 5 μm 250 mm×4.6 mm; mobile phase: isohexane/isopropanol 50:50; flow rate: 1 ml/min; temperature: 40° C.; UV detection: 220 nm.

Method 17E: Phase: Daicel Chiralpak AS-H, 5 μm 250 mm×4.6 mm; mobile phase: isohexane/ethanol 60:40; flow rate: 1 ml/min; temperature: 40° C.; UV detection: 220 nm.

Method 18E: Phase: Daicel Chiralpak AD-H, 5 μm 250 mm×4.6 mm; mobile phase: isohexane/isopropanol 30:70; flow rate: 1 ml/min; temperature: 40° C.; UV detection: 220 nm.

Method 19E: Phase: Daicel Chiralpak AS-H, 5 μm 250 mm×4.6 mm; mobile phase: isohexane/ethanol 30:70; flow rate: 1 ml/min; temperature: 40° C.; UV detection: 220 nm.

Method 20E: Phase: Daicel Chiralpak AD-H, 5 μm 250 mm×4 mm; mobile phase: isohexane/ethanol 50:50; flow rate: 1 ml/min; temperature: 24° C.; UV detection: 230 nm.

Method 21E: Phase: Daicel Chiralpak AD-H, 5 μm 250 mm×4.6 mm; mobile phase: isohexane/ethanol 50:50; flow rate: 1 ml/min; temperature: 40° C.; UV detection: 220 nm.

GC-MS Methods:

Method 1F: Instrument: Micromass GCT, GC6890; column: Restek RTX-35, 15 m×200 μm×0.33 μm; constant flow rate with helium: 0.88 ml/min; oven: 70° C.; inlet: 250° C.; gradient: 70° C., 30° C./min→310° C. (maintained for 3 min).

The microwave reactor used was a "single mode" instrument of the Emrys™ Optimizer type.

Starting Materials

General Method 1A: Suzuki Coupling

Under argon and at RT, tetrakis(triphenylphosphine)palladium (0.02 eq.), a solution of the appropriate arylboronic acid (1.2 eq.) in ethanol (0.5 ml/mmol) and a solution of potassium fluoride (2.0 eq.) in water (0.2 ml/mmol) are added to a mixture of the appropriate bromopyridine in toluene (1.8 ml/mmol). The reaction mixture is stirred under reflux for a number of hours until the conversion is substantially complete. After addition of ethyl acetate and phase separation, the organic phase is washed once with water and once with saturated aqueous sodium chloride solution, dried (magnesium sulphate), filtered and concentrated under reduced pressure. The crude product is purified by flash chromatography (silica gel-60, mobile phase: dichloromethane/methanol mixtures).

General Method 2A: Hydrogenation of the Pyridine

Palladium on activated carbon (moistened with about 50% water, 0.3 g/mmol) is added to a solution of the pyridine in ethanol (9 ml/mmol), and the mixture is hydrogenated in a 50 bar hydrogen atmosphere at 60° C. overnight. The catalyst is then filtered off over a filter layer and washed repeatedly with ethanol. The combined filtrates are concentrated under reduced pressure.

General Method 3A: Reaction with Carbamoyl Chlorides or Carbonyl Chlorides

Under argon and at 0° C., N,N-diisopropylethylamine (1.2 eq.) and the appropriate carbamoyl chloride or carbonyl chloride (1.2 eq.) are added dropwise to a solution of the piperidine in dichloromethane (2.5 ml/mmol). The reaction mixture is stirred at RT. After addition of water and phase separation, the organic phase is washed three times with water and once with saturated aqueous sodium chloride solution, dried (sodium sulphate), filtered and concentrated under reduced pressure.

General Method 4A: Hydrolysis

At RT, lithium hydroxide (2 eq.) is added to a solution of the appropriate ester in a mixture of tetrahydrofuran/water (3:1, 12.5 ml/mmol). The reaction mixture is stirred at 60° C. and then adjusted to pH 1 using aqueous 1 N hydrochloric acid solution. After addition of water/ethyl acetate, the aqueous phase is extracted three times with ethyl acetate. The combined organic phases are dried (sodium sulphate), filtered and concentrated under reduced pressure.

General Method 5A: N'-Hydroxyimidamide Formation

At RT, hydroxylammonium chloride (1.5 eq.) and triethylamine (1.2 eq.) are added to a solution of the appropriate nitrile (1.0 eq) in ethanol (1.2 ml/mmol). The reaction mixture is stirred at room temperature overnight. For work-up, the ethanol is removed under reduced pressure, saturated aqueous sodium bicarbonate solution is added and the reaction mixture is extracted with ethyl acetate. The organic phase is dried over sodium sulphate and concentrated. The residue is reacted without further purification.

General Method 6A: N'-Hydroxyimidamide Formation

At RT, hydroxylammonium chloride (1.08 eq.) and sodium hydroxide (0.12 eq.) are added to a solution of the appropriate nitrile (1.0 eq) in a mixture of ethanol (1.9 ml/mmol) and water (0.5 ml/mmol). The reaction mixture is stirred at room temperature for 16 h. For work-up, the reaction mixture is concentrated under reduced pressure, dichloromethane is added and the mixture is filtered. The filtrate is concentrated under reduced pressure and the residue is reacted without further purification.

General Method 7A: Reaction with Carbonyl Chlorides

Under argon and at 0° C., triethylamine (1.5 eq.) and the appropriate carbonyl chloride (2.0 eq.) are added dropwise to a solution of the piperidine in dichloromethane (4 ml/mmol). The reaction mixture is allowed to warm slowly to RT. After addition of water and phase separation, the organic phase is twice washed with water, dried over sodium sulphate, filtered and concentrated under reduced pressure. If the purity of the crude product is insufficient, the substance is purified by preparative HPLC.

General Method 8A: Urea Formation

At RT, the appropriate amine (2.0-3.0 eq.) and potassium carbonate (1.0 eq.) are added to a solution of the nitrophenylcarbamate (1.0 eq.) in dimethylformamide (10 ml/mmol), and the mixture is stirred in 15 ml portions in a single-mode microwave (Emrys Optimizer) at 150° C. for 0.5-1 h. The reaction solution is filtered and the filtrate is purified by preparative HPLC.

General Method 9A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For work-up, the methanol is removed under reduced pressure, water is added to the residue and the mixture is acidified (pH 1) using aqueous 1 N hydrochloric acid solution. The mixture is extracted with ethyl acetate and the organic phase is dried with magnesium sulphate, filtered and concentrated under reduced pressure.

General Method 10A: Thioamide Formation

Lawesson reagent (2,4-bis[4-methoxyphenyl] 1,3-dithia-2,4-diphosphetane 2,4-disulphide) (0.6 eq.) is added to a solution of the appropriate acid (1.0 eq.) in dioxane (5.6 ml/mmol). The reaction mixture is stirred at 60° C. for 30 minutes. After addition of saturated aqueous sodium bicarbonate solution and removal of the dioxane, the residue is extracted with ethyl acetate. The combined organic phases are washed with a saturated aqueous sodium bicarbonate solution, dried over magnesium sulphate, filtered and concentrated under reduced pressure.

General Method 1A: Carbohydrazide formation (J. Med. Chem. 1996, 39, 2753-2763)

At room temperature, oxalyl chloride (2.0 eq.) is added to a solution of the appropriate acid (1.0 eq.) in dichloromethane (1 ml/0.24 mmol). The mixture is stirred at RT for 1 h. For work-up, the dichloromethane is removed under reduced pressure, and dichloromethane is added once more to the residue and the mixture is concentrated. The residue is initially charged in dichloromethane, and the appropriate hydrazide is added. After 20 minutes at RT, a saturated aqueous ammonium hydroxide solution is added, and the reaction mixture is extracted with dichloromethane. The combined organic phases are washed with a saturated aqueous sodium chloride solution, dried over magnesium sulphate, filtered and concentrated under reduced pressure.

General Method 12A: Hydrogenation of the Pyridine Using a Flow Hydrogenation Apparatus A solution of the pyridine in concentrated acetic acid (about 35 ml/mmol) is hydrogenated in a flow hydrogenation apparatus ("H-Cube" from ThalesNano, Budapest, Hungary) (conditions: 10% Pd/C catalyst, "controlled" mode, 60 bar, 0.5 ml/min, 85° C.). Removal of the solvent on a rotary evaporator gives the corresponding crude product which, if appropriate, is purified by preparative HPLC.

Example 1A

Methyl 5-(4-ethylphenyl)pyridine-3-carboxylate

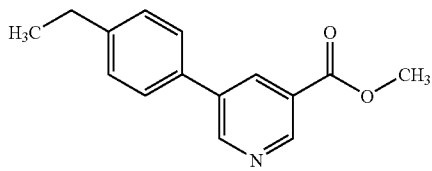

32 g (148 mmol) of methyl 5-bromonicotinate and 27 g (178 mmol, 1.2 eq.) of 4-ethylphenylboronic acid were reacted according to the General Method 1A. Yield: 24 g (64% of theory)

LC-MS (Method 3B): $R_t$=2.03 min; MS (ESIpos): m/z=242 [M+H]$^+$.

Example 2A

Methyl 5-(4-ethylphenyl)piperidine-3-carboxylate [racemic cis/trans isomer mixture]

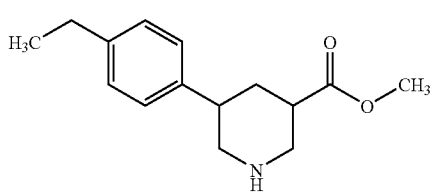

24 g (94 mmol) of methyl 5-(4-ethylphenyl)pyridine-3-carboxylate were hydrogenated according to the General Method 2A. Yield: 20 g (77% of theory)

LC-MS (Method 5B): $R_t$=1.43 min; MS (ESIpos): m/z=248 [M+H]$^+$.

Example 3A

Ethyl 5-(4-ethylphenyl)pyridine-3-carboxylate

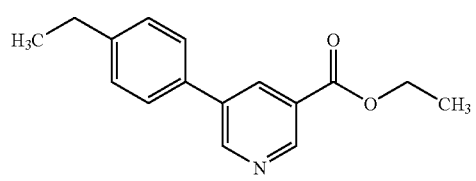

29 g (126 mmol) of ethyl 5-bromonicotinate and 23 g (152 mmol, 1.2 eq.) of 4-ethylphenylboronic acid were reacted according to the General Method 1A. Yield: 32 g (82% of theory)

LC-MS (Method 4B): $R_t$=3.80 min; MS (ESIpos): m/z=256 [M+H]$^+$.

Example 4A

Ethyl 5-(4-ethylphenyl)piperidine-3-carboxylate [racemic cis/trans isomer mixture]

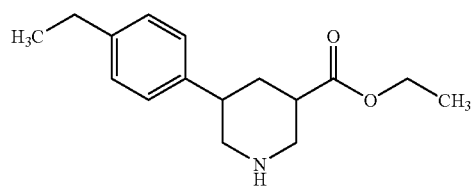

24 g (71 mmol) of ethyl 5-(4-ethylphenyl)pyridine-3-carboxylate were hydrogenated according to the General Method 2A. Yield: 15 g (81% of theory)

LC-MS (Method 5B): $R_t$=1.78 min and 1.91 min (cis/trans isomers); MS (ESIpos): m/z=262 [M+H]$^+$.

Example 5A

Ethyl 1-(cyclopentylcarbonyl)-5-(4-ethylphenyl) piperidine-3-carboxylate [racemic cis/trans isomer mixture]

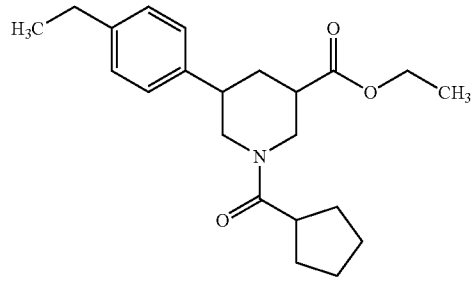

5.2 g (14.0 mmol) of ethyl 5-(4-ethylphenyl)piperidine-3-carboxylate and 2.1 g (2.1 mmol, 1.2 eq.) of cyclopentanecarbonyl chloride were reacted according to the General Method 3A. Yield: 4.8 g (96% of theory)

LC-MS (Method 4B): $R_t$=4.04 min and 4.14 min (cis/trans isomers); MS (ESIpos): m/z=358 [M+H]$^+$.

Example 6A 1-(Cyclopentylcarbonyl)-5-(4-ethylphenyl)piperidine-3-carboxylic acid [racemic cis/trans isomer mixture]

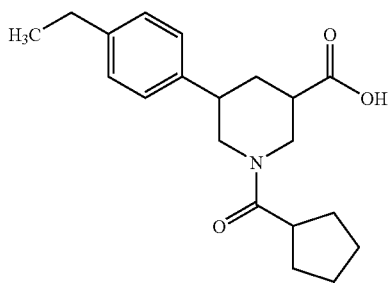

13.8 g (38.6 mmol) of ethyl 1-(cyclopentylcarbonyl)-5-(4-ethylphenyl)piperidine-3-carboxylate were hydrolysed according to the General Method 4A. Yield: 11.5 g (87% of theory)

LC-MS (Method 1B): $R_t$=2.50 min and 2.57 min (cis/trans isomers); MS (ESIpos): m/z=330 [M+H]$^+$.

Diastereomer separation of 11.5 g of the cis/trans isomer mixture according to Method 1C gave 4.1 g of the title compound 7A (cis isomer) and 4.1 g of the trans isomer.

Example 7A 1-(Cyclopentylcarbonyl)-5-(4-ethylphenyl)piperidine-3-carboxylic acid [racemic cis isomer]

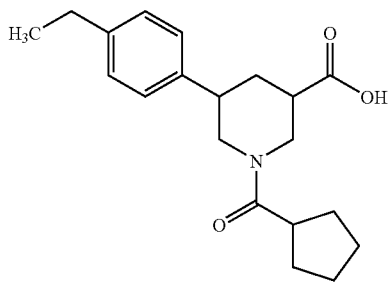

LC-MS (Method 1B): $R_t$=2.57 min; MS (ESIpos): m/z=330 [M+H]$^+$.

Example 8A

Ethyl 5-[4-(1-methylethyl)phenyl]pyridine-3-carboxylate

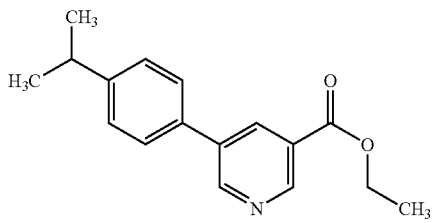

4.68 g (20.32 mmol) of ethyl 5-bromonicotinate, 5.00 g (30.49 mmol) of 4-(1-methylethyl)-phenylboronic acid, 0.12 g (0.10 mmol) of tetrakis(triphenylphosphine)palladium(0) and 4.31 g (40.65 mmol) of sodium carbonate were dissolved in a mixture of 37 ml of 1,2-dimethoxyethane, 10.5 ml of water and 84 ml of dimethylformamide and stirred at 85° C. for 18 h. For work-up, some of the dimethylformamide was removed under reduced pressure, and the reaction mixture was diluted with water and extracted with dichloromethane. The organic phase was dried over sodium sulphate and the crude product was purified by preparative HPLC. Yield: 2.42 g (44% of theory)

LC-MS (Method 6B): $R_t$=2.56 min; MS (ESIpos): m/z=270 [M+H]$^+$.

Example 9A

Ethyl 5-[4-(1-methylethyl)phenyl]piperidine-3-carboxylate [racemic cis/trans isomer mixture]

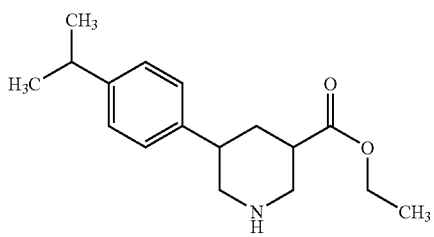

2.4 g (8.9 mmol) of ethyl 5-[4-(1-methylethyl)phenyl]pyridine-3-carboxylate were dissolved in 60 ml of ethanol, 1.33 g Pd/C (10%) were added and the mixture was hydrogenated in an autoclave at 60° C. at a hydrogen pressure of 50 bar overnight. The reaction mixture was filtered through silica gel. The resulting solution was concentrated under reduced pressure. Water was added to the residue and the solution was adjusted to pH 8 using aqueous 1 N sodium hydroxide solution. The mixture was then extracted with dichloromethane. The organic phase was dried over sodium sulphate and concentrated. Yield: 2.1 g (81% of theory)

LC-MS (Method 1B): $R_t$=1.57 min and 2.59 min (cis/trans isomers); MS (ESIpos): m/z=276 [M+H]$^+$.

Example 10A

Ethyl 1-(cyclopentylcarbonyl)-5-[4-(1-methylethyl)phenyl]piperidine-3-carboxylate [racemic cis/trans isomer mixture]

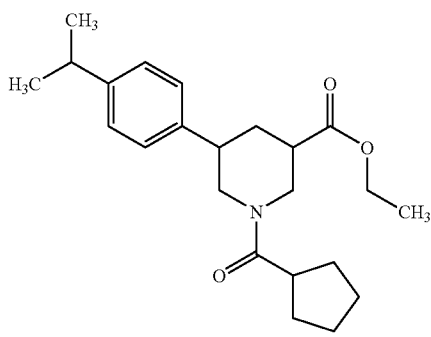

1.5 g (5.3 mmol) of ethyl 5-[4-(1-methylethyl)phenyl]piperidine-3-carboxylate were dissolved in 18 ml of dichloromethane, and 0.81 g (7.9 mmol) of triethylamine was added at 0° C. 1.43 g (10.5 mmol) of cyclopentanecarbonyl chloride were then added dropwise.

The reaction mixture was stirred at RT for 2 h. For work-up, the mixture was twice washed with water. The organic phase was dried over sodium sulphate and concentrated under reduced pressure. Yield: 2.0 g (100% of theory)

LC-MS (Method 3B): $R_t$=2.56 min and 2.63 min (cis/trans isomers); MS (ESIpos): m/z=372 [M+H]$^+$.

Example 11A 1-(Cyclopentylcarbonyl)-5-[4-(1-methylethyl)phenyl]piperidine-3-carboxylic acid [racemic cis/trans isomer mixture]

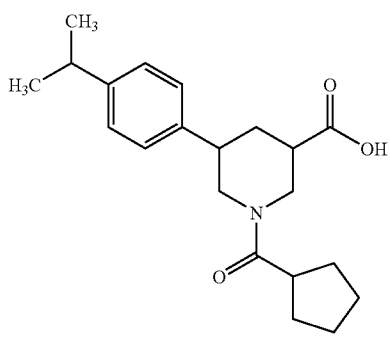

50 ml of dioxane, 25 ml of water and 0.63 g (25.8 mmol) of lithium hydroxide were added to 2.40 g (6.46 mmol) of ethyl 1-(cyclopentylcarbonyl)-5-[4-(1-methylethyl)phenyl]piperidine-3-carboxylate. The mixture was stirred at RT overnight. For work-up, the dioxane was removed under reduced pressure, water was added to the reaction mixture and the mixture was acidified using aqueous 1 N hydrochloric acid solution. The mixture was extracted with dichloromethane. The organic phase was dried with sodium sulphate and concentrated under reduced pressure. Yield: 1.65 g (98% of theory)

Diastereomer separation of 1.65 g of the cis/trans isomer mixture according to Method 2C gave 553 mg of the title compound 12A (cis isomer) and 638 mg of the trans isomer.

Example 12A 1-(Cyclopentylcarbonyl)-5-[4-(1-methylethyl)phenyl]piperidine-3-carboxylic acid [racemic cis isomer]

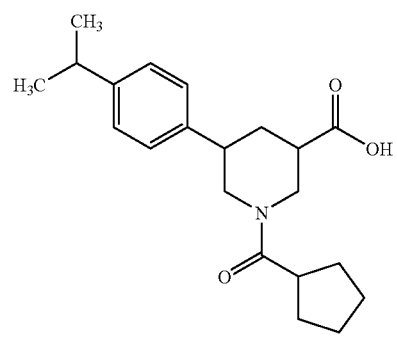

LC-MS (Method 1B): $R_t$=2.72 min; MS (ESIpos): m/z=344 [M+H]$^+$.

Example 13A

Ethyl 5-[4-(trifluoromethyl)phenyl]pyridine-3-carboxylate

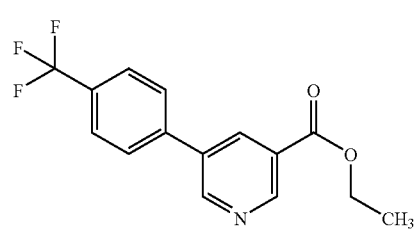

6.74 g (29.3 mmol) of ethyl 5-bromonicotinate, 8.35 g (43.9 mmol) of 4-trifluoromethylphenylboronic acid, 0.17 g (0.15 mmol) of tetrakis(triphenylphosphine)palladium(0) and 6.21 g (58.6 mmol) of sodium carbonate were dissolved in a mixture of 75 ml of 1,2-dimethoxyethane, 15 ml of water and 184 ml of dimethylformamide and stirred at 85° C. for 18 h. For work-up, some of the dimethylformamide was removed under reduced pressure, and the reaction mixture was diluted with water and extracted with dichloromethane. The organic phase was dried over sodium sulphate and the crude product was purified by flash chromatography (dichloromethane/acetonitrile 100:2→100:5). Yield: 6.22 g (72% of theory)

LC-MS (Method 4B): $R_t$=3.71 min; MS (ESIpos): m/z=296 [M+H]$^+$.

Example 14A

Ethyl 5-[4-(trifluoromethyl)phenyl]piperidine-3-carboxylate [racemic cis/trans isomer mixture]

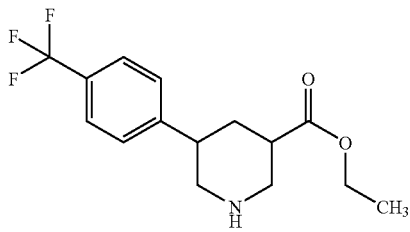

5.9 g (20.0 mmol) of ethyl 5-[4-(trifluoromethyl)phenyl]pyridine-3-carboxylate were dissolved in 140 ml of ethanol, 2.98 g Pd/C (10%) were added and the mixture was hydrogenated in an autoclave at 60° C. at a hydrogen pressure of 50 bar overnight. The reaction mixture was filtered through silica gel. The resulting solution was concentrated under reduced pressure. Water was added to the residue and the solution was adjusted to pH 8 using aqueous 1 N sodium hydroxide solution. The mixture was then extracted with dichloromethane. The organic phase was dried over sodium sulphate and concentrated. Yield: 4.2 g (67% of theory)

LC-MS (Method 4B): $R_t$=1.95 min and 2.03 min (cis/trans isomers); MS (ESIpos): m/z=302 [M+H]$^+$.

Example 15A

Ethyl 1-(cyclopentylcarbonyl)-5-[4-(trifluoromethyl)phenyl]piperidine-3-carboxylate [racemic cis/trans isomer mixture]

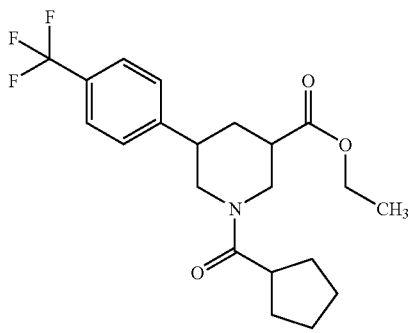

4.2 g (13.5 mmol) of ethyl 5-[4-(trifluoromethyl)phenyl]piperidine-3-carboxylate were dissolved in 33 ml of dichloromethane, and 2.04 g (20.2 mmol) of triethylamine were added at 0° C. 2.37 g (17.5 mmol) of cyclopentanecarbonyl chloride were then added dropwise. The reaction mixture was stirred at RT for 2 h. For work-up, the mixture was twice washed with water. The organic phase was dried over sodium sulphate and concentrated under reduced pressure. Yield: 5.9 g (100% of theory)

LC-MS (Method 7B): $R_t$=4.08 min and 4.15 min (cis/trans isomers); MS (ESIpos): m/z=398 [M+H]$^+$.

Example 16A 1-(Cyclopentylcarbonyl)-5-[4-(trifluoromethyl)phenyl]piperidine-3-carboxylic acid [racemic cis/trans isomer mixture]

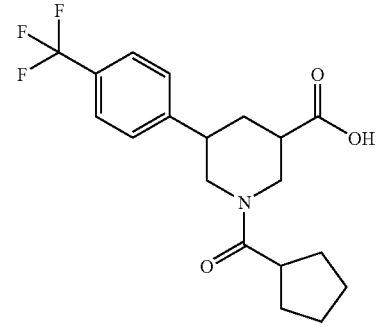

99 ml of dioxane, 50 ml of water and 1.37 g (57.0 mmol) of lithium hydroxide were added to 5.9 g (14.3 mmol) of ethyl 1-(cyclopentylcarbonyl)-5-[4-(trifluoromethyl)phenyl]piperidine-3-carboxylate. The mixture was stirred at RT overnight. For work-up, the dioxane was removed under reduced pressure, water was added to the reaction mixture and the mixture was acidified using aqueous 1 N hydrochloric acid solution. The mixture was extracted with dichloromethane. The organic phase was dried with sodium sulphate and concentrated under reduced pressure. Yield: 5.3 g (95% of theory)

Diastereomer separation of 5.3 g of the cis/trans isomer mixture according to Method 3C gave 1.53 g of the title compound 17A (cis isomer) and 1.949 g of the trans isomer.

Example 17A 1-(Cyclopentylcarbonyl)-5-[4-(trifluoromethyl)phenyl]piperidine-3-carboxylic acid [racemic cis isomer]

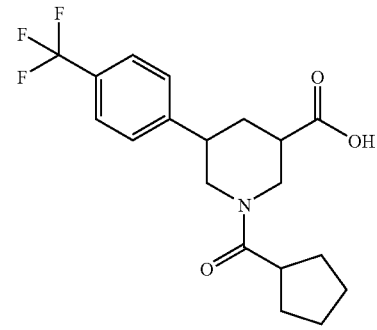

HPLC (Method 3C): $R_t$=3.66 min (cis isomer).

Example 18A

Methyl 5-[4-(trifluoromethoxy)phenyl]pyridine-3-carboxylate

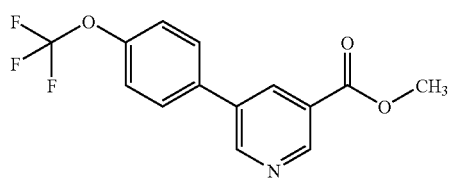

23 g (105 mmol) of methyl 5-bromonicotinate and 26 g (126 mmol, 1.2 eq.) of 4-trifluoromethoxyphenylboronic acid were reacted according to the General Method 1A. Yield: 14 g (41% of theory)

LC-MS (Method 1B): $R_t$=2.44 min; MS (ESIpos): m/z=298 $[M+H]^+$.

Example 19A

Methyl 5-[4-(trifluoromethoxy)phenyl]piperidine-3-carboxylate [racemic cis/trans isomer mixture]

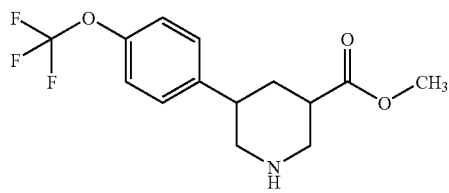

14 g (45 mmol) of methyl 5-[4-(trifluoromethoxy)phenyl]pyridine-3-carboxylate were hydrogenated according to the General Method 2A. Yield: 8 g (59% of theory)

LC-MS (Method 1B): $R_t$=1.29 min and 1.33 min (cis/trans isomers); MS (ESIpos): m/z=304 $[M+H]^+$.

Example 20A

Ethyl 5-[4-(trifluoromethoxy)phenyl]pyridine-3-carboxylate

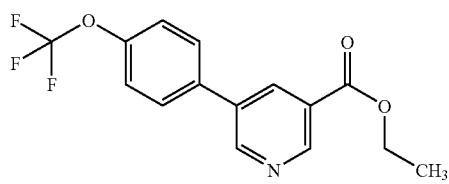

3.35 g (14.6 mmol) of ethyl 5-bromonicotinate, 4.50 g (21.9 mmol) of 4-(trifluoromethoxy)-phenylboronic acid, 0.84 g (0.73 mmol) of tetrakis(triphenylphosphine)palladium (0) and 3.01 g (29.1 mmol) of sodium carbonate were dissolved in a mixture of 38 ml of 1,2-dimethoxyethane, 7.5 ml of water and 91 ml of dimethylformamide and stirred at 85° C. for 18 h. For work-up, some of the dimethylformamide was removed under reduced pressure, and the reaction mixture was diluted with water and extracted with dichloromethane. The organic phase was dried over sodium sulphate and the crude product was purified by flash chromatography (dichloromethane/acetonitrile 100:0→100:5). Yield: 2.64 g (55% of theory)

LC-MS (Method 4B): $R_t$=3.78 min; MS (ESIpos): m/z=312 $[M+H]^+$.

Example 21A

Ethyl 5-[4-(trifluoromethoxy)phenyl]piperidine-3-carboxylate [racemic cis/trans isomer mixture]

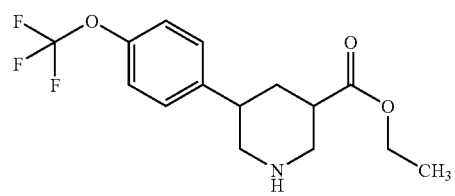

2.5 g (7.6 mmol) of ethyl 5-[4-(trifluoromethoxy)phenyl]pyridine-3-carboxylate were dissolved in 60 ml of ethanol, 1.14 g of Pd/C (10%) were added and the mixture was hydrogenated in an autoclave at 60° C. at a hydrogen pressure of 50 bar overnight. The reaction mixture was filtered through silica gel. The resulting solution was concentrated under reduced pressure. Water was added to the residue, and the solution was adjusted to pH 8 using aqueous 1 N sodium hydroxide solution. The mixture was then extracted with dichloromethane. The organic phase was dried over sodium sulphate and concentrated. Yield: 1.76 g (66% of theory)

LC-MS (Method 7B): $R_t$=2.47 min and 2.56 min (cis/trans isomers); MS (ESIpos): m/z=318 $[M+H]^+$.

Example 22A

Ethyl 1-(cyclopentylcarbonyl)-5-[4-(trifluoromethoxy)phenyl]piperidine-3-carboxylate [racemic cis/trans isomer mixture]

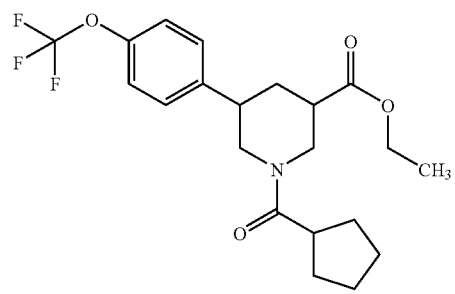

1.76 g (5.08 mmol) of ethyl 5-[4-(trifluoromethoxy)phenyl]piperidine-3-carboxylate were dissolved in 12 ml of dichloromethane, and 0.77 g (7.62 mmol) of triethylamine were added at 0° C. 0.89 g (6.61 mmol) of cyclopentanecarbonyl chloride were then added dropwise. The reaction mixture was stirred at RT for 2 h. For work-up, the mixture was twice washed with water. The organic phase was dried over sodium sulphate and concentrated under reduced pressure. Yield: 2.1 g (100% of theory)

LC-MS (Method 7B): $R_t$=4.14 min and 4.22 min (cis/trans isomers); MS (ESIpos): m/z=414 $[M+H]^+$.

Example 23A 1-(Cyclopentylcarbonyl)-5-[4-(trifluoromethoxy)phenyl]piperidine-3-carboxylic acid [racemic cis/trans isomer mixture]

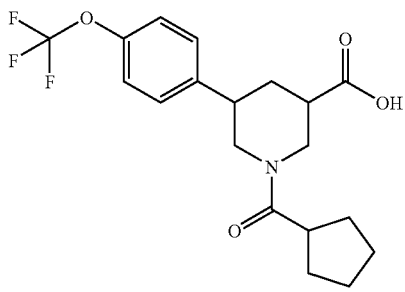

37 ml of dioxane, 18.5 ml of water and 0.51 g (21.4 mmol) of lithium hydroxide were added to 2.30 g (5.34 mmol) of ethyl 1-(cyclopentylcarbonyl)-5-[4-(trifluoromethoxy)phenyl]piperidine-3-carboxylate. The mixture was stirred overnight at RT. For work-up, the dioxane was removed under reduced pressure, water was added to the reaction mixture and the mixture was acidified using aqueous 1 N hydrochloric acid solution. The mixture was extracted with dichloromethane. The organic phase was dried with sodium sulphate and concentrated under reduced pressure. Yield: 2.17 g (99% of theory)

Diastereomer separation of 2.17 g of the cis/trans isomer mixture according to Method 4C gave 514 mg of the title compound 24A (cis isomer) and 796 mg of the trans isomer.

Example 24A 1-(Cyclopentylcarbonyl)-5-[4-(trifluoromethoxy)phenyl]piperidine-3-carboxylic acid [racemic cis isomer]

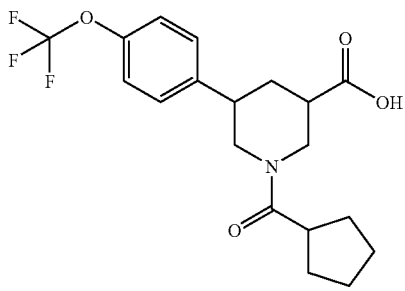

LC-MS (Method 4B): $R_t$=3.51 min; MS (ESIpos): m/z=386 [M+H]$^+$.

Example 25A

Ethyl 5-(4-methoxyphenyl)pyridine-3-carboxylate

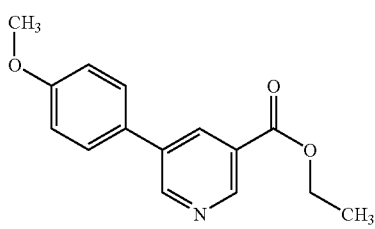

22.26 g (96.78 mmol) of ethyl 5-bromonicotinate, 25.00 g (164.5 mmol) of 4-methoxyphenylboronic acid, 0.56 g (0.48 mmol) of tetrakis(triphenylphosphine)palladium(0) and 20.51 g (193.6 mmol) of sodium carbonate were dissolved in a mixture of 180 ml of 1,2-dimethoxyethane, 50 ml of water and 400 ml of dimethylformamide and stirred at 85° C. for 18 h. For work-up, some of the dimethylformamide was removed under reduced pressure, and the reaction mixture was diluted with water and extracted with dichloromethane. The organic phase was dried over sodium sulphate and the crude product was purified by flash chromatography (dichloromethane/acetonitrile 100:2<100:5). Yield: 20.18 g (72% of theory)

LC-MS (Method 4B): $R_t$=3.21 min; MS (ESIpos): m/z=258 [M+H]$^+$.

Example 26A

Ethyl 5-(4-methoxyphenyl)piperidine-3-carboxylate [racemic cis/trans isomer mixture]

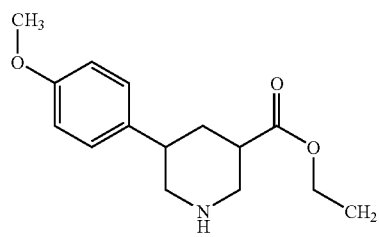

18.2 g (70.6 mmol) of ethyl 5-[4-(methoxy)phenyl]pyridine-3-carboxylate were hydrogenated according to the General Method 2A. Yield: 18.0 g (100% of theory)

LC-MS (Method 3B): $R_t$=0.82 min; MS (ESIpos): m/z=264 [M+H]$^+$.

Example 27A 1-tert-butyl 3-ethyl 5-(4-methoxyphenyl)piperidine-1,3-dicarboxylate [racemic cis/trans isomer mixture]

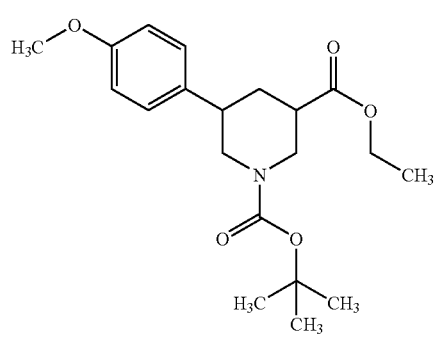

5.2 g (17.8 mmol) of ethyl 5-(4-methoxyphenyl)piperidine-3-carboxylate were dissolved in 12 ml of dichloromethane, and 3.88 g (17.8 mmol) of di-tert-butyl dicarbonate were added at RT. The reaction mixture was stirred at RT for 1 h. For work-up, the mixture was twice washed with water. The organic phase was dried over sodium sulphate and concentrated under reduced pressure. Yield: 6.8 g (81% of theory)

Diastereomer separation of 6.8 g of the cis/trans isomer mixture according to Method 5C gave 1998 mg of the title compound 28A (cis isomer) and 3375 mg of the trans isomer.

Example 28A 1-tert-Butyl 3-ethyl 5-(4-methoxyphenyl)piperidine-1,3-dicarboxylate [racemic cis isomer]

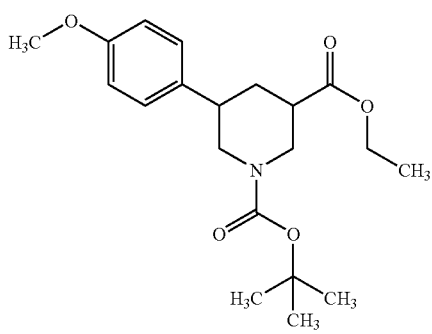

LC-MS (Method 1B): $R_t$=2.93 min; MS (ESIpos): m/z=364 [M+H]$^+$.

Example 29A 5-(4-Methoxyphenyl)piperidine-3-carboxylic acid hydrochloride [racemic cis isomer]

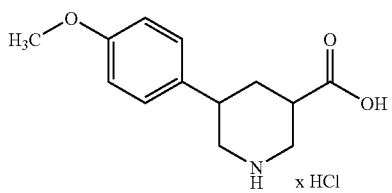

1.13 g (3.11 mmol) of 1-tert-butyl 3-ethyl 5-(4-methoxyphenyl)piperidine-1,3-dicarboxylate were added to 40 ml of aqueous 1 N hydrochloric acid solution, and the mixture was concentrated on a rotary evaporator. Yield: 829 mg (98% of theory)

LC-MS (Method 8B): $R_t$=2.08 min; MS (ESIpos): m/z=236 [M+H]$^+$.

Example 30A 1-(Cyclopentylcarbonyl)-5-(4-methoxyphenyl)piperidine-3-carboxylic acid [racemic cis isomer]

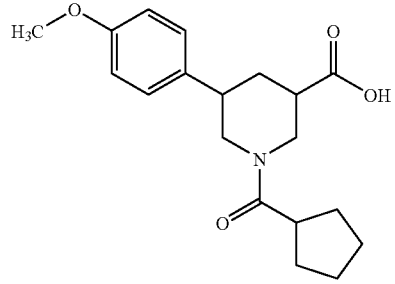

0.83 g (3.05 mmol) of ethyl 5-(4-methoxyphenyl)piperidine-3-carboxylate hydrochloride was dissolved in 10 ml of dichloromethane, and 0.77 g (7.62 mmol) of triethylamine was added at 0° C. 0.83 g (6.09 mmol) of cyclopentanecarbonyl chloride was then added dropwise. The reaction mixture was stirred at RT for 2 h. For work-up, the mixture was twice washed with water. The organic phase was dried over sodium sulphate and concentrated under reduced pressure. 35 ml of dioxane, 17.5 ml of water and 0.29 mg (12.2 mmol) of lithium hydroxide were added to the crude product. The mixture was stirred at RT for 1 h. For work-up, the dioxane was removed under reduced pressure, water was added and the reaction mixture was acidified using aqueous 1 N hydrochloric acid solution. The precipitated solid was filtered off and dried under reduced pressure. Yield: 0.84 g (75% of theory)

LC-MS (Method 3B): $R_t$=1.71 min; MS (ESIpos): m/z=332 [M+H]$^+$.

Example 31A

Ethyl 1-(2,2-dimethylpropanoyl)-5-(4-methoxyphenyl)piperidine-3-carboxylate [racemic cis/trans isomer mixture]

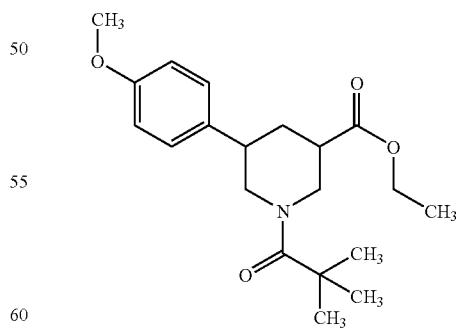

10.0 g (18.99 mmol) of ethyl 1-(cyclopentylcarbonyl)-5-[4-(methoxy)phenyl]piperidine-3-carboxylate were dissolved in 50 ml of dichloromethane, and 2.88 g (28.48 mmol) of triethylamine were added at 0° C. 3.00 g (24.68 mmol) of pivaloyl chloride were then added dropwise. The reaction mixture was stirred at RT for 2 h. For work-up, the mixture was twice washed with water. The organic phase was dried over sodium sulphate and concentrated under reduced pressure.

Diastereomer separation of 10 g of the crude product as cis/trans isomer mixture according to Method 6C gave 2.80 g of the title compound 32A (cis isomer) and 4.61 g of the trans isomer.

Example 32A

Ethyl 1-(2,2-dimethylpropanoyl)-5-(4-methoxyphenyl)piperidine-3-carboxylate [racemic cis isomer]

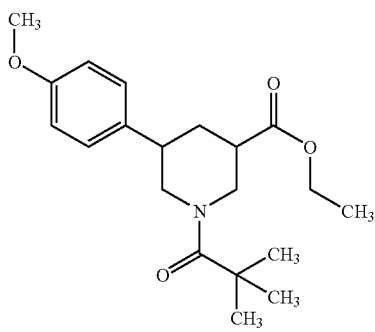

LC-MS (Method 5B): $R_t$=2.41 min; MS (ESIpos): m/z=348 [M+H]$^+$.

Example 33A 1-(2,2-Dimethylpropanoyl)-5-(4-methoxyphenyl)piperidine-3-carboxylic acid [racemic cis isomer]

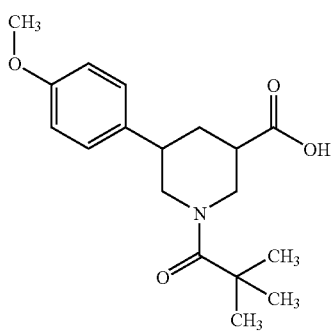

55 ml of dioxane, 28 ml of water and 0.77 g (32.2 mmol) of lithium hydroxide were added to 2.8 g (14.3 mmol) of ethyl 1-(cyclopentylcarbonyl)-5-[4-(methoxy)phenyl]piperidine-3-carboxylate. The mixture was stirred overnight at RT. For work-up, the dioxane was removed under reduced pressure, water was added and the reaction mixture was acidified using aqueous 1 N hydrochloric acid solution. The mixture was extracted with dichloromethane. The organic phase was dried with sodium sulphate and concentrated under reduced pressure. Yield: 2.44 g (95% of theory)

LC-MS (Method 3B): $R_t$=1.55 min; MS (ESIpos): m/z=320 [M+H]$^+$.

Example 34A

Methyl 5-(4-ethylphenyl)-1-(morpholin-4-ylcarbonyl)piperidine-3-carboxylate [racemic cis/trans isomer mixture]

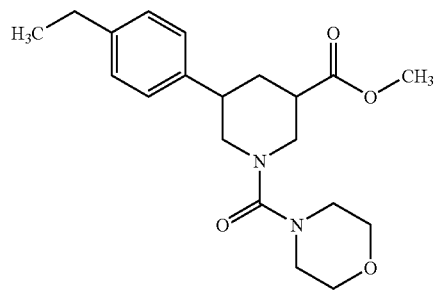

6.2 g (22.6 mmol) of methyl 5-(4-ethylphenyl)piperidine-3-carboxylate and 4.4 g (29.4 mmol, 1.3 eq.) of morpholine-4-carbonyl chloride were reacted according to the General Method 3A. Yield: 7.9 g (97% of theory)

LC-MS (Method 5B): $R_t$=2.14 min and 2.22 min (cis/trans isomers); MS (ESIpos): m/z=361 [M+H]$^+$.

Diastereomer separation of 7.9 g of the cis/trans isomer mixture according to Method 7C gave 2.8 g of the title compound 35A (cis isomer) and 3.9 g of the trans isomer.

Example 35A

Methyl 5-(4-ethylphenyl)-1-(morpholin-4-ylcarbonyl)piperidine-3-carboxylate [racemic cis isomer]

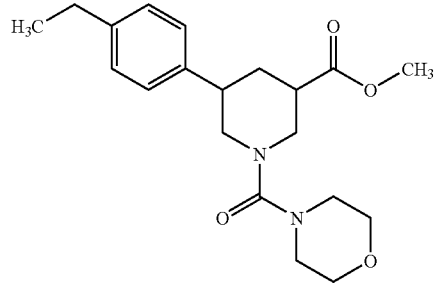

HPLC (Method 4A): $R_t$=9.61 min; MS (ESIpos): m/z=361 [M+H]$^+$.

Example 36A

Ethyl 5-(4-ethylphenyl)-1-(morpholin-4-ylcarbonyl)piperidine-3-carboxylate [racemic cis/trans isomer mixture]

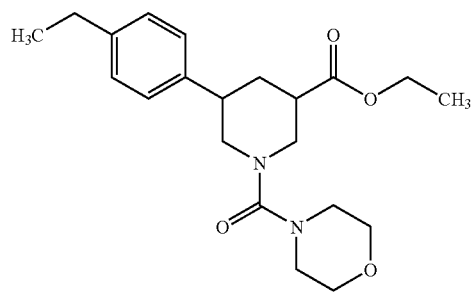

10.0 g (36.0 mmol) of ethyl 5-(4-ethylphenyl)piperidine-3-carboxylate and 7.0 g (46.8 mmol, 1.3 eq.) of morpholine-4-carbonyl chloride were reacted according to the General Method 3A. Yield: 12.0 g (89% of theory)

LC-MS (Method 1B): $R_t$=2.38 min and 2.48 min (cis/trans isomers); MS (ESIpos): m/z=375 [M+H]$^+$.

Diastereomer separation of 12.0 g of the cis/trans isomer mixture according to Method 8C gave 4.4 g of the title compound from Example 37A (cis isomer) and 5.4 g of the trans isomer.

Example 37A

Ethyl 5-(4-ethylphenyl)-1-(morpholin-4-ylcarbonyl)piperidine-3-carboxylate [racemic cis isomer]

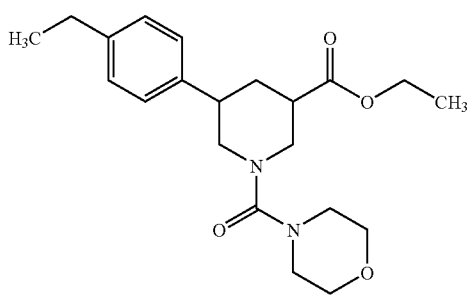

Diastereomer separation of 12.0 g of the cis/trans isomer mixture from Example 36A according to Method 8C gave 4.4 g of the title compound (cis isomer) and 5.4 g of the trans isomer.

LC-MS (Method 1B): $R_t$=2.48 min; MS (ESIpos): m/z=375 [M+H]$^+$.

Example 38A 5-(4-Ethylphenyl)-1-(morpholin-4-ylcarbonyl)piperidine-3-carboxylic acid [racemic cis isomer]

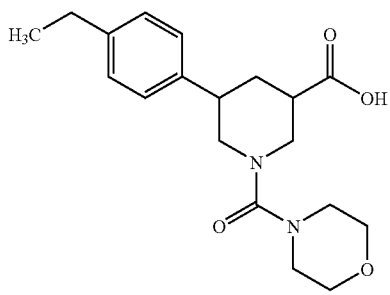

4.4 g (11.7 mmol) of ethyl 5-(4-ethylphenyl)-1-(morpholin-4-ylcarbonyl)piperidine-3-carboxylate (Example 37A) were hydrolysed according to the General Method 4A. Yield: 3.4 g (84% of theory)

LC-MS (Method 1B): $R_t$=2.06 min; MS (ESIpos): m/z=347 [M+H]$^+$.

Example 39A

Methyl 5-(4-ethylphenyl)-1-(pyrrolidin-1-ylcarbonyl)piperidine-3-carboxylate [racemic cis/trans isomer mixture]

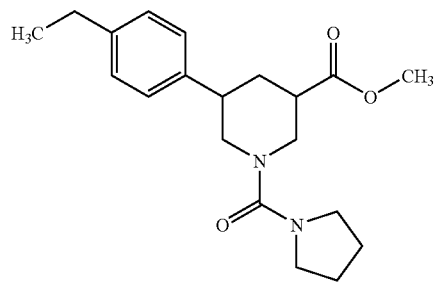

6.7 g (24.1 mmol) of methyl 5-(4-ethylphenyl)piperidine-3-carboxylate and 4.2 g (31.4 mmol, 1.3 eq.) of pyrrolidine-1-carbonyl chloride were reacted according to the General Method 3A. Yield: 7.6 g (91% of theory)

LC-MS (Method 3B): $R_t$=2.08 min and 2.16 min (cis/trans isomers); MS (ESIpos): m/z=345 [M+H]$^+$.

Diastereomer separation of 7.6 g of the cis/trans isomer mixture according to Method 9C gave 1.6 g of the title compound 40A (cis isomer) and 4.1 g of the trans isomer.

Example 40A

Methyl 5-(4-ethylphenyl)-1-(pyrrolidin-1-ylcarbonyl)piperidine-3-carboxylate [racemic cis isomer]

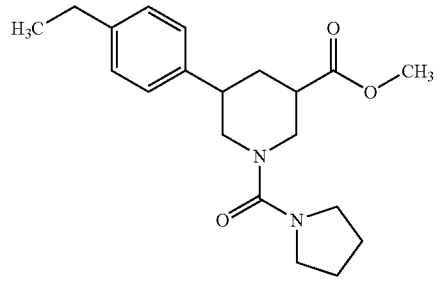

LC-MS (Method 1B): $R_t$=2.55 min; MS (ESIpos): m/z=345 [M+H]$^+$.

Example 41A 5-(4-Ethylphenyl)-1-(pyrrolidin-1-ylcarbonyl)piperidine-3-carboxylic acid [racemic cis isomer]

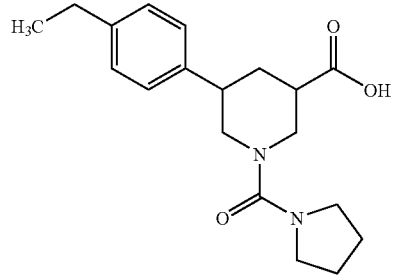

1.4 g (3.9 mmol) of methyl 5-(4-ethylphenyl)-1-(pyrrolidin-1-ylcarbonyl)piperidine-3-carboxylate were hydrolysed according to the General Method 4A. Yield: 1.2 g (92% of theory)

LC-MS (Method 2B): $R_t$=1.18 min; MS (ESIpos): m/z=331 [M+H]$^+$.

Example 42A

Methyl 1-(morpholin-4-ylcarbonyl)-5-[4-(trifluoromethoxy)phenyl]piperidine-3-carboxylate [racemic cis/trans isomer mixture]

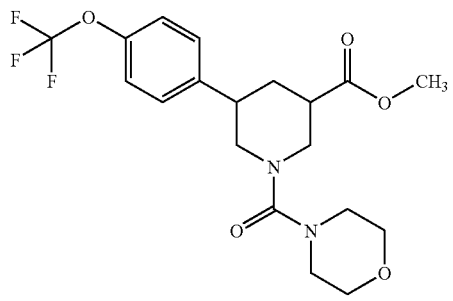

8.3 g (26.5 mmol) of methyl 5-[4-(trifluoromethoxy)phenyl]piperidine-3-carboxylate and 5.2 g (34.5 mmol, 1.3 eq.) of morpholine-4-carbonyl chloride were reacted according to the General Method 3A. Yield: 11.0 g (100% of theory)

LC-MS (Method 2B): $R_t$=1.21 min and 1.24 min (cis/trans isomers); MS (ESIpos): m/z=417 [M+H]$^+$.

Diastereomer separation of 11.0 g of the cis/trans isomer mixture according to Method 10C gave 4.3 g of the title compound from Example 43A (cis isomer) and 5.0 g of the trans isomer.

Example 43A

Methyl 1-(morpholin-4-ylcarbonyl)-5-[4-(trifluoromethoxy)phenyl]piperidine-3-carboxylate [racemic cis isomer]

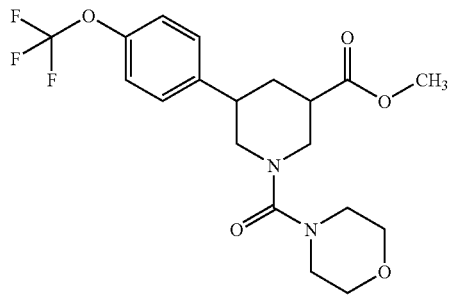

Diastereomer separation of 11.0 g of the cis/trans isomer mixture from Example 42A according to Method 10C gave 4.3 g of the title compound (cis isomer) and 5.0 g of the trans isomer.

LC-MS (Method 3B): $R_t$=1.98 min; MS (ESIpos): m/z=417 [M+H]$^+$.

Example 44A 1-(Morpholin-4-ylcarbonyl)-5-[4-(trifluoromethoxy)phenyl]piperidine-3-carboxylic acid [racemic cis isomer]

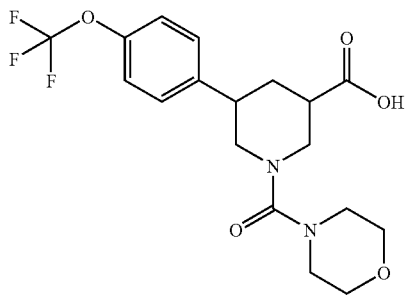

4.3 g (10.4 mmol) of methyl 1-(morpholin-4-ylcarbonyl)-5-[4-(trifluoromethoxy)phenyl]-piperidine-3-carboxylate (Example 43A) were hydrolysed according to the General Method 4A. Yield: 4.1 g (98% of theory)

LC-MS (Method 1B): $R_t$=2.12 min; MS (ESIpos): m/z=403 [M+H]$^+$.

Example 45A

1-[Ethyl(methyl)carbamoyl]-5-(4-ethylphenyl)piperidine-3-carboxylic acid [racemic cis isomer]

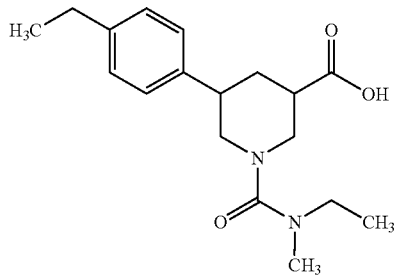

Step a): Methyl 1-[ethyl(methyl)carbamoyl]-5-(4-ethylphenyl)piperidine-3-carboxylate [racemic cis/trans isomer mixture]

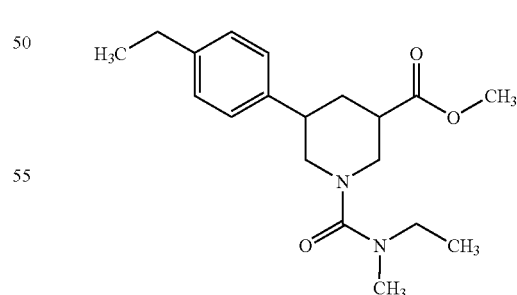

7.0 g (89% pure, 25.1 mmol) of methyl 5-(4-ethylphenyl)piperidine-3-carboxylate and 4.0 g (32.6 mmol, 1.3 eq.) of ethyl(methyl)carbamoyl chloride were reacted according to the General Method 3A. Yield: 8.0 g (96% of theory)

LC-MS (Method 3B): $R_t$=2.10 min and 2.18 min (cis/trans isomers); MS (ESIpos): m/z=333 [M+H]$^+$.

Step b): 1-[Ethyl(methyl)carbamoyl]-5-(4-ethylphenyl)piperidine-3-carboxylic acid [racemic cis/trans isomer mixture]

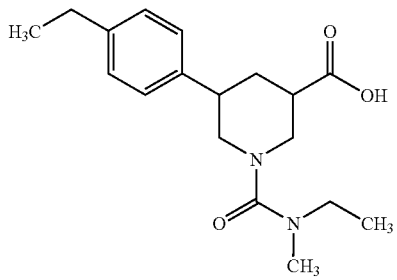

8.0 g (23.2 mmol) of methyl 1-[ethyl(methyl)carbamoyl]-5-(4-ethylphenyl)piperidine-3-carboxylate were hydrolysed according to the General Method 4A. Yield: 1.2 g (16% of theory)
LC-MS (Method 3B): $R_t$=1.79 min and 1.84 min (cis/trans isomers); MS (ESIpos): m/z=319 [M+H]$^+$.
Diastereomer separation of 1.2 g of the cis/trans isomer mixture according to Method 9C gave 538 mg of the title compound 45A (cis isomer).
LC-MS (Method 3B): $R_t$=1.79 min; MS (ESIpos): m/z=319 [M+H]$^+$.

Example 46A

Methyl 5-[4-(trifluoromethyl)phenyl]pyridine-3-carboxylate

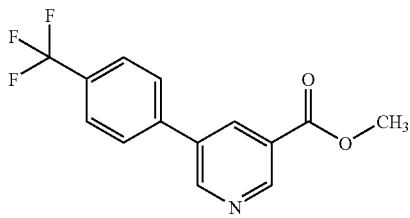

28 g (132 mmol) of methyl 5-bromonicotinate and 30 g (158 mmol, 1.2 eq.) of 4-ethylphenylboronic acid were reacted according to the General Method 1A. Yield: 32 g (85% of theory)
LC-MS (Method 5B): $R_t$=2.27 min; MS (ESIpos): m/z=282 [M+H]$^+$.

Example 47A

Methyl 5-[4-(trifluoromethyl)phenyl]piperidine-3-carboxylate [racemic cis/trans isomer mixture]

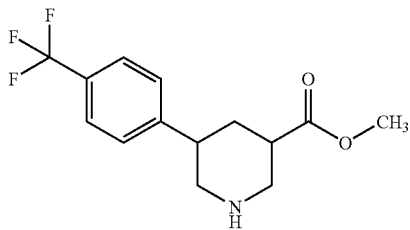

32 g (112 mmol) of methyl 5-[4-(trifluoromethyl)phenyl]pyridine-3-carboxylate (Example 46A) were hydrogenated according to the General Method 2A. Yield: 26 g (82% of theory)
LC-MS (Method 1B): $R_t$=1.35 and 1.41 min (cis/trans isomers); MS (ESIpos): m/z=288 [M+H]$^+$.

Example 48A

Methyl 1-(morpholin-4-ylcarbonyl)-5-[4-(trifluoromethyl)phenyl]piperidine-3-carboxylate [racemic cis/trans isomer mixture]

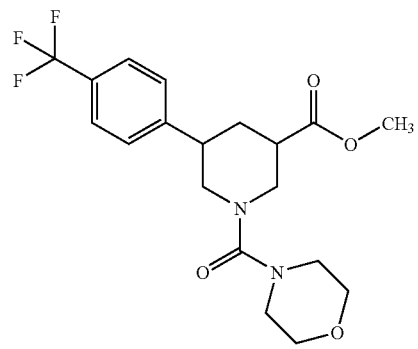

9.25 g (32.2 mmol) of methyl 5-[4-(trifluoromethyl)phenyl]piperidine-3-carboxylate and
9.63 g (64.7 mmol) of morpholine-4-carbonyl chloride were reacted according to the General Method 3A. This gave 16.3 g of crude product in a purity of 76% (LC-MS), which was reacted without any further purification steps.
LC-MS (Method 2B): $R_t$=1.19 and 1.22 min (cis/trans isomers); MS (ESIpos): m/z=401 [M+H]$^+$.

Example 49A 1-(Morpholin-4-ylcarbonyl)-5-[4-(trifluoromethyl)phenyl]piperidine-3-carboxylic acid [racemic cis isomer]

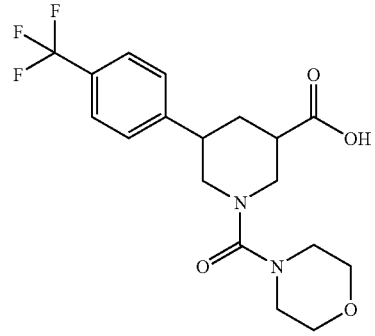

12.9 g (25.7 mmol) of methyl 1-(morpholin-4-ylcarbonyl)-5-[4-(trifluoromethyl)phenyl]piperidine-3-carboxylate were hydrolysed according to the General Method 4A. This gave 12.1 g of crude product in a purity of 80% (LC-MS), which was reacted without any further purification steps.
LC-MS (Method 2B): $R_t$=1.08 min; MS (ESIpos): m/z=387 [M+H]$^+$.

Example 50A

5-[4-(Trifluoromethyl)phenyl]pyridine-3-carboxamide

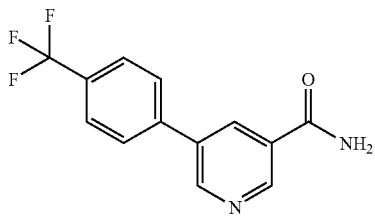

Under argon, 2.0 g (9.75 mmol) of 5-[4-(trifluoromethyl)phenyl]pyridine-3-carboxamide and 2.78 g (14.6 mmol) of 4-(trifluoromethyl)phenylboronic acid were initially charged in 25 ml of 1,2-dimethoxyethane and 9.8 ml of water. 2.07 g (19.5 mmol) of sodium carbonate were then added, and the mixture was stirred at room temperature for 15 minutes. 0.28 g (0.24 mmol) of tetrakis(triphenylphosphine)palladium was added. The reaction mixture was stirred at 120° C. overnight. For work-up, the reaction mixture was filtered through Celite and some of the 1,2-dimethoxyethane was removed under reduced pressure. The reaction mixture was diluted with water and extracted with ethyl acetate and dichloromethane. The organic phase was dried with magnesium sulphate and the solvent was removed under reduced pressure. This gave 2.1 g (81% of theory) of crude product, which was reacted without any further purification steps.

LC-MS (Method 1B): $R_t$=1.88 min; MS (ESIpos): m/z=267 [M+H]$^+$;

$^1$H-NMR (400 MHz, DMSO-d$_6$): δ=9.08 (dd, 2H), 8.55 (t, 1H), 8.28 (bs, 1H), 8.05 (d, 2H), 7.90 (d, 2H), 7.71 (bs, 1H).

Example 51A

5-[4-(Trifluoromethyl)phenyl]piperidine-3-carboxamide acetate [racemic cis/trans isomer mixture]

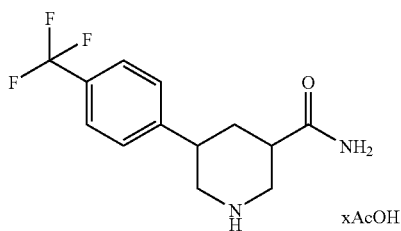

Palladium on activated carbon (moistened with about 50% water, 0.3 g/mmol) was added to a solution of 500 mg (1.88 mmol) of 5-[4-(trifluoromethyl)phenyl]pyridine-3-carboxamide (Example 50A) in 60 ml of acetic acid, and the mixture was hydrogenated in a 60 bar hydrogen atmosphere at 85° C. overnight. The catalyst was then filtered off through a filter layer and washed repeatedly with ethanol. The combined filtrates were concentrated under reduced pressure. This gave 0.61 g (98% of theory) of the target compound, which was reacted without any further purification steps.

LC-MS (Method 5B): $R_t$=1.25 min; MS (ESIpos): m/z=273 [M+H-AcOH]$^+$.

Example 52A 1-(Morpholin-4-ylcarbonyl)-5-[4-(trifluoromethyl)phenyl]piperidine-3-carboxamide [racemic cis/trans isomer mixture]

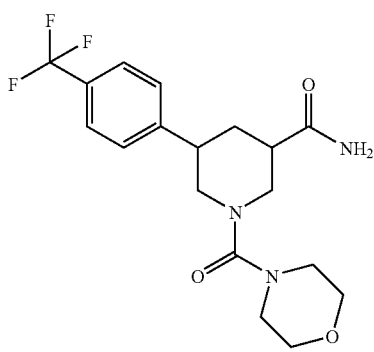

At 0° C., 0.56 g (5.52 mmol) of triethylamine and 0.55 g (3.70 mmol) of morpholine-4-carbonyl chloride were added to a solution of 0.61 mg (1.85 mmol) of 5-[4-(trifluoromethyl)phenyl]piperidine-3-carboxamide acetate (Example 51A) in 10 ml of dichloromethane. The reaction mixture was stirred at RT for 1 h. After addition of water and phase separation, the organic phase was dried over sodium sulphate, filtered and concentrated under reduced pressure. This gave 0.61 g (100% of theory) of crude product in a purity of 77% (LC-MS), which was reacted without any further purification steps.

LC-MS (Method 1B): $R_t$=1.89 min; MS (ESIpos): m/z=386 [M+H]$^+$.

Example 53A 1-(Morpholin-4-ylcarbonyl)-5-[4-(trifluoromethyl)phenyl]piperidine-3-carbothioamide [racemic cis/trans isomer mixture]

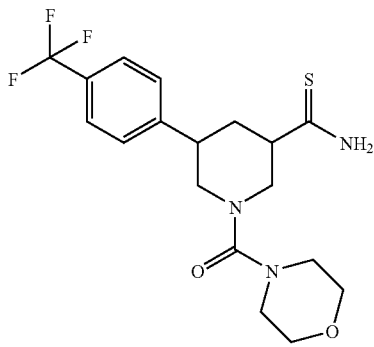

45 mg (0.11 mmol) of Lawesson reagent (2,4-bis[4-methoxyphenyl] 1,3-dithia-2,4-diphosphetane 2,4-disulphide) were added to a solution of 10 mg (0.20 mmol) of 1-(morpholin-4-ylcarbonyl)-5-[4-(trifluoromethyl)phenyl]piperidine-3-carboxamide (Example 52A) in 1 ml of dioxane, and the reaction mixture was stirred at 60° C. for 30 minutes and then at room temperature for 3 h. After addition of saturated aqueous sodium bicarbonate solution and removal of the dioxane, the residue was extracted with ethyl acetate. The organic phase was washed with a saturated aqueous sodium bicarbonate solution, dried over magnesium sulphate, filtered and concentrated under reduced pressure. This gave 43 mg (100% of theory) of crude product, which was reacted without any further purification steps.

LC-MS (Method 5B): $R_t$=2.08 min; MS (ESIpos): m/z=402 [M+H]$^+$.

Example 54A

Ethyl 5-(4-ethylphenyl)piperidine-3-carboxylate [racemic cis isomer]

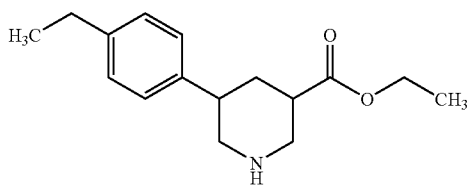

Following chromatographic separation of the diastereomers from Example 4A according to Method 11C, the two isomers were obtained from 15 g (124 mmol) of ethyl 5-(4-ethylphenyl)piperidine-3-carboxylate. Yield: 2.5 g of the cis isomer (17% of theory)

LC-MS (Method 3B): $R_t$=1.02 min; MS (ESIpos): m/z=262 [M+H]$^+$.

Example 55A

Ethyl 5-(4-ethylphenyl)piperidine-3-carboxylate [racemic trans isomer]

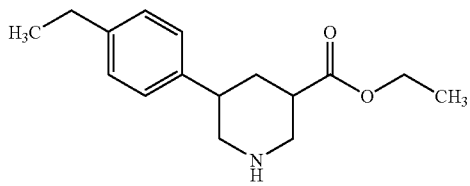

Following chromatographic separation of the diastereomers from Example 4A according to Method 11C, the two isomers were obtained from 15 g (124 mmol) of ethyl 5-(4-ethylphenyl)piperidine-3-carboxylate. Yield: 3.0 g of the trans isomer (20% of theory)

LC-MS (Method 3B): $R_t$=1.09 min; MS (ESIpos): m/z=262 [M+H]$^+$.

Example 56A

3-Ethyl 1-(4-nitrophenyl)5-(4-ethylphenyl)piperidine-1,3-dicarboxylate [racemic cis isomer]

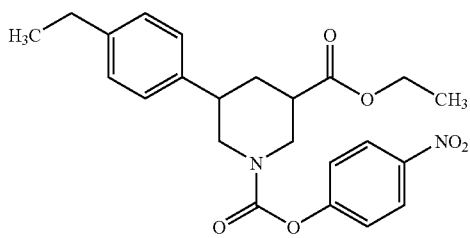

At 0° C., 1.93 g (9.57 mmol) of 4-nitrophenyl chloroformate were added slowly to 2.5 g (9.57 mmol) of ethyl 5-(4-ethylphenyl)piperidine-3-carboxylate (Example 54A) and 1.94 g (19.1 mmol) of triethylamine in 292 ml of dichloromethane. The mixture was stirred at RT for 2 h. For work-up, the reaction mixture was washed first with saturated sodium bicarbonate solution and then with water. The organic phase was dried with sodium sulphate and concentrated under reduced pressure. The residue was purified by preparative HPLC. Yield: 2.66 g (64% of theory)

LC-MS (Method 2B): $R_t$=1.57 min; MS (ESIpos): m/z=427 [M+H]$^+$.

Example 57A

Ethyl 5-(4-ethylphenyl)1-[(4-hydroxypiperidin-1-yl)carbonyl]piperidine-3-carboxylate [racemic cis isomer]

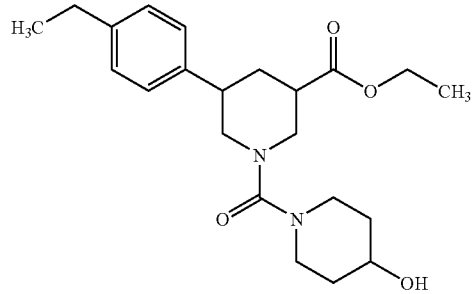

370 mg (0.81 mmol) of 3-ethyl 1-(4-nitrophenyl) 5-(4-ethylphenyl)piperidine-1,3-dicarboxylate, 245 mg (2.42 mmol) of 4-hydroxypiperidine and 112 mg (0.81 mmol) of potassium carbonate were added to 9 ml of DMF and heated in a single-mode microwave (Emrys Optimizer) at 150° C. for 15 min. For work-up, water was added and the reaction solution was extracted with ethyl acetate. The organic phase was dried with sodium sulphate and concentrated under reduced pressure. The residue was purified by preparative HPLC. Yield: 208 mg (66% of theory)

LC-MS (Method 2B): $R_t$=1.23 min; MS (ESIpos): m/z=389 [M+H]$^+$.

Example 58A

Ethyl 5-(4-ethylphenyl)-1-[(4-cyanopiperidin-1-yl)carbonyl]piperidine-3-carboxylate [racemic cis isomer]

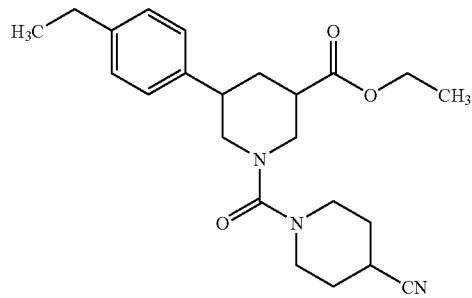

370 mg (0.81 mmol) of 3-ethyl 1-(4-nitrophenyl)5-(4-ethylphenyl)piperidine-1,3-dicarboxylate, 267 mg (2.42 mmol) of 4-cyanopiperidine and 112 mg (0.81 mmol) of potassium carbonate were added to 9 ml of DMF and heated in a single-mode microwave (Emrys Optimizer) at 150° C. for 15 min. For work-up, water was added and the reaction solution was extracted with ethyl acetate. The organic phase was dried with sodium sulphate and concentrated under reduced pressure. The residue was purified by preparative HPLC. Yield: 73 mg (23% of theory)

LC-MS (Method 2B): $R_t$=1.36 min; MS (ESIpos): m/z=398 [M+H]$^+$.

Example 59A 5-(4-Ethylphenyl)-1-[(4-hydroxypiperidin-1-yl)carbonyl]piperidine-3-carboxylic acid [racemic cis isomer]

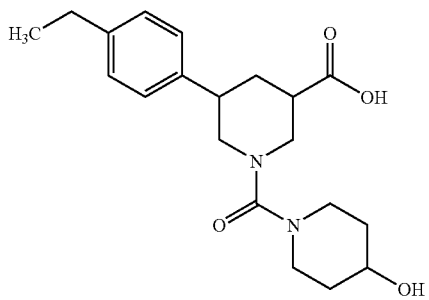

880 mg (2.24 mmol) of ethyl 5-(4-ethylphenyl)-1-[(4-hydroxypiperidin-1-yl)carbonyl]piperidine-3-carboxylate were dissolved in a mixture of 15.5 ml of dioxane and 7.7 ml of water, 215 mg (8.97 mmol) of lithium hydroxide were added and the mixture was stirred at RT overnight. For work-up, the reaction solution was concentrated under reduced pressure, water was then added and the mixture was acidified with 1N hydrochloric acid. The precipitate formed was filtered off and dried under reduced pressure. The filtrate was extracted with ethyl acetate. The combined organic phases were dried with sodium sulphate and concentrated under reduced pressure. The two solids gave a total yield of 764 mg (95% of theory).

LC-MS (Method 3B): $R_t$=1.49 min; MS (ESIpos): m/z=361 [M+H]$^+$.

Example 60A 5-(4-Ethylphenyl)-1-[(4-cyanopiperidin-1-yl)carbonyl]piperidine-3-carboxylic acid [racemic cis isomer]

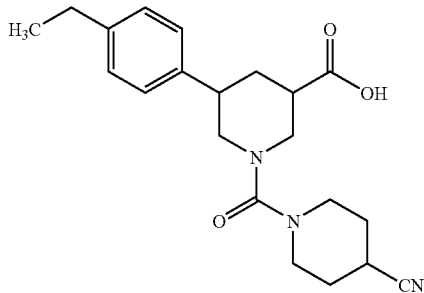

650 mg (1.60 mmol) of ethyl 5-(4-ethylphenyl)-1-[(4-cyanopiperidin-1-yl)carbonyl]piperidine-3-carboxylate were dissolved in a mixture of 20 ml of dioxane and 10 ml of water, 153 mg (6.40 mmol) of lithium hydroxide were added and the mixture was stirred at RT for 15 min. For work-up, the reaction solution was concentrated under reduced pressure, water was then added and the mixture was acidified with 1N hydrochloric acid. The precipitate formed was filtered off and dried under reduced pressure. The residue was purified by preparative HPLC. Yield: 347 mg (59% of theory)

LC-MS (Method 3B): $R_t$=1.13 min; MS (ESIpos): m/z=370 [M+H]$^+$.

Example 61A

3-Methyl 1-(4-nitrophenyl)-5-[4-(trifluoromethoxy)phenyl]piperidine-1,3-dicarboxylate [racemic cis/trans isomer mixture]

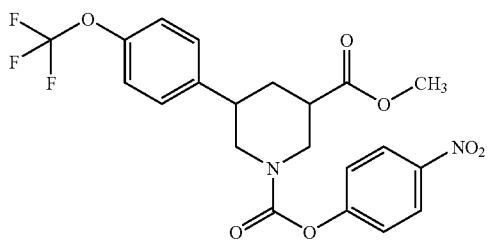

At 0° C., 5.32 g (26.4 mmol) of 4-nitrophenyl chloroformate were added slowly to 8.0 g (26.4 mmol) of methyl 5-(4-(trifluoromethoxy)phenyl)piperidine-3-carboxylate (Example 19A) and 5.34 g (26.3 mmol) of triethylamine in 666 ml of dichloromethane. The mixture was stirred at RT for 2 h. For work-up, the reaction mixture was washed first with saturated sodium bicarbonate solution and then with water. The organic phase was dried with sodium sulphate and concentrated under reduced pressure. The residue was purified by flash chromatography (cyclohexane/ethyl acetate 1:2 to 1:1). Yield: 7.32 g (54% of theory)

LC-MS (Method 3B): $R_t$=2.47 min; MS (ESIpos): m/z=469 [M+H]$^+$.

Example 62A

Methyl 1-[(4-hydroxypiperidin-1-yl)carbonyl]-5-[4-(trifluoromethoxy)phenyl]piperidine-3-carboxylate [racemic cis/trans isomer mixture]

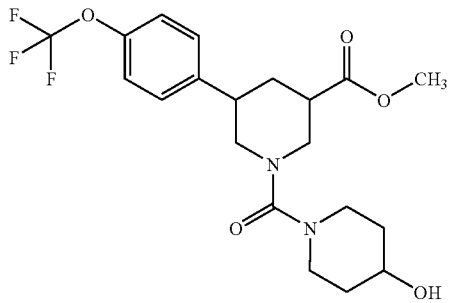

1780 mg (3.80 mmol) of 3-methyl 1-(4-nitrophenyl)5-[4-(trifluoromethoxy)phenyl]piperidine-1,3-dicarboxylate, 1153 mg (11.40 mmol) of 4-hydroxypiperidine and 525 mg (3.80 mmol) of potassium carbonate were added to 37 ml of DMF and, in 2 portions, heated in a single-mode microwave (Emrys Optimizer) at 150° C. for 15 min. For work-up, the two reaction solutions were combined, water was added and the mixture was extracted with ethyl acetate. The organic phase was dried with sodium sulphate and concentrated under reduced pressure. The residue was purified by preparative HPLC. Yield: 849 mg (50% of theory)

LC-MS (Method 2B): $R_t$=1.23 min; MS (ESIpos): m/z=431 [M+H]$^+$.

Example 63A

1-[(4-Hydroxypiperidin-1-yl)carbonyl]-5-[4-(trifluoromethoxy)phenyl]piperidine-3-carboxylic acid [racemic cis isomer]

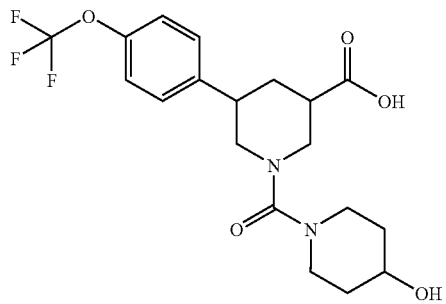

828 mg (1.92 mmol) of methyl 5-(4-(trifluoromethoxy)phenyl)-1-[(4-hydroxypiperidin-1-yl)carbonyl]piperidine-3-carboxylate were dissolved in 70 ml of methanol, 2159 mg (19.24 mmol) of potassium tert-butoxide were added and the mixture was stirred at 60° C. overnight. For work-up, the reaction solution was diluted with water and acidified with 1N hydrochloric acid (pH 1). The mixture was extracted with ethyl acetate. The combined organic phases were dried with sodium sulphate and concentrated under reduced pressure. Yield: 749 mg (94% of theory)

LC-MS (Method 2B): $R_t$=1.04 min; MS (ESIpos): m/z=417 [M+H]$^+$.

Example 64A

N'-Hydroxy-3-methoxypropanimidamide

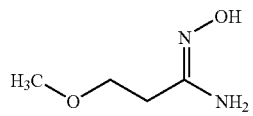

20.0 g (235.0 mmol) of 3-methoxypropionitrile were reacted according to the General Method 6A. Yield: 18.1 g (49% of theory, 74% pure)

HPLC (Method 1A): $R_t$=0.35 min; MS (ESIpos): m/z=119 [M+H]$^+$.

Example 65A

N'-Hydroxy-3-(propan-2-yloxy)propanimidamide

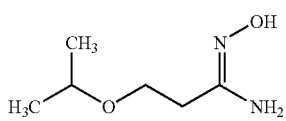

5.0 g (44.2 mmol) of 3-(propan-2-yloxy)propanonitrile were reacted according to the General Method 5A. Yield: 3.0 g (40% of theory, 86% pure)

HPLC (Method 1A): $R_t$=1.24 min; MS (ESIpos): m/z=147 [M+H]$^+$.

Example 66A

N'-3-Dihydroxy-3-methylbutanimidamide

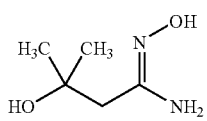

5.0 g (50.4 mmol) of 3-hydroxy-3-methylbutyronitrile were reacted according to the General Method 6A. Yield: 4.8 g (52% of theory, 72% pure)

HPLC (Method 1A): $R_t$=0.28 min; MS (ESIpos): m/z=133 [M+H]$^+$.

Example 67A

N'-Hydroxy-2-[1-(hydroxymethyl)cyclopropyl]ethanimidamide

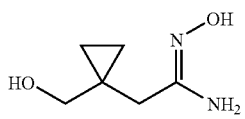

1.1 g (9.4 mmol) of [1-(hydroxymethyl)cyclopropyl]acetonitrile were reacted according to the General Method 5A. Yield: 0.6 g (38% of theory, 87% pure)

HPLC (Method 1A): $R_t$=0.43 min; MS (ESIpos): m/z=145 [M+H]$^+$.

Example 68A 3,4-Difluoro-N'-hydroxybenzenecarboximidamide

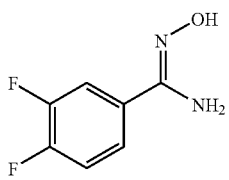

1.0 g (7.2 mmol) of 3,4-difluorobenzonitrile was initially charged in 30 ml of ethanol, and a solution of 0.5 g (7.2 mmol) of hydroxylammonium chloride and 0.6 g (7.2 mmol) of sodium bicarbonate in 11 ml of water was added at RT. The reaction mixture was stirred at RT for 16 h, concentrated under reduced pressure and reacted without further purification.

HPLC (Method 1A): $R_t$=1.36 min; MS (ESIpos): m/z=173 [M+H]$^+$.

Example 69A

N'-Hydroxypyridine-2-carboximidamide

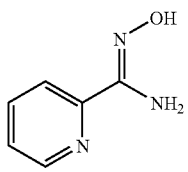

1.0 g (9.6 mmol) of pyridine-2-carbonitrile, 1.0 g (14.4 mmol) of hydroxylammonium chloride and 1.6 ml (11.5 mmol) of triethylamine were reacted according to the General Method 5A. Yield: 1.06 g (80% of theory)

$^1$H-NMR (400 MHz, DMSO-d$_6$): δ=9.90 (s, 1H), 8.55 (d, 1H), 7.86-7.78 (m, 2H), 7.40 (ddd, 1H), 5.83 (s, 2H).

Example 70A

N'-Hydroxy-4-methylpyridine-3-carboximidamide

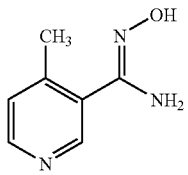

850 mg (7.20 mmol) of 4-methylpyridine-3-carbonitrile, 750 mg (10.79 mmol) of hydroxylammonium chloride and 1.2 ml (8.6 mmol) of triethylamine were reacted according to the General Method 5A. Yield: 666 mg (61% of theory)

$^1$H-NMR (400 MHz, DMSO-d$_6$): δ=9.52 (s, 1H), 8.40 (d, 2H), 7.25 (d, 1H), 5.89 (s, 2H), 3.32 (s, 3H).

Example 71A

N'-Hydroxy-6-methylpyridine-3-carboximidamide

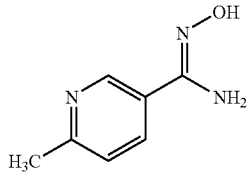

1.0 g (8.5 mmol) of 6-methylpyridine-3-carbonitrile, 882 mg (12.7 mmol) of hydroxylammonium chloride and 1.4 ml (10.2 mmol) of triethylamine were reacted according to the General Method 5A. Yield: 1.11 g (87% of theory)

$^1$H-NMR (400 MHz, DMSO-d$_6$): δ=9.74 (s, 1H), 8.71 (d, 1H), 7.89 (dd, 1H), 7.25 (d, 1H), 5.93 (s, 2H), 2.47 (s, 3H).

Example 72A 2,3-Difluoro-N'-hydroxybenzenecarboximidamide

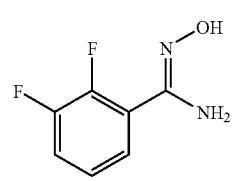

5.0 g (35.2 mmol) of 2,3-difluorobenzonitrile were initially charged in 43 ml of ethanol, and a solution of 3.7 g (52.8 mmol) of hydroxylammonium chloride and 5.9 ml (4.3 g, 42.3 mmol) of triethylamine was added at RT. The reaction mixture was stirred at RT for 16 h, concentrated under reduced pressure, taken up in ethyl acetate and washed with saturated aqueous sodium bicarbonate solution. The organic extracts were dried over sodium sulphate, filtered and concentrated under reduced pressure. Yield: 5.7 g (94% of theory)

LC-MS (Method 5B): $R_t$=0.46 min; MS (ESIpos): m/z=173 [M+H]$^+$.

Example 73A

3-Fluoro-N'-hydroxybenzenecarboximidamide

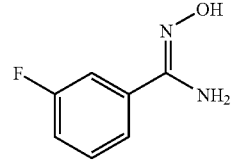

10.0 g (82.6 mmol) of 3-fluorobenzonitrile were reacted according to the General Method 5A. Yield: 12.6 g (99% of theory)

HPLC (Method 1A): $R_t$=1.14 min; MS (ESIpos): m/z=155 [M+H]$^+$.

Example 74A 2,5-Difluoro-N'-hydroxybenzenecarboximidamide

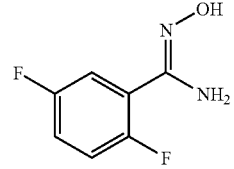

5.0 g (35.9 mmol) of 2,5-difluorobenzonitrile were reacted according to the General Method 5A. Yield: 5.8 g (94% of theory)

LC-MS (Method 5B): $R_t$=0.43 min; MS (ESIpos): m/z=173 [M+H]$^+$.

Example 75A

1-Cyclopropyl-N'-hydroxypiperidine-4-carboximidamide

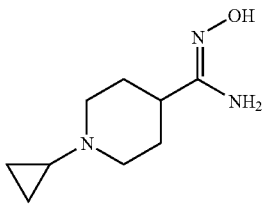

Step a): 1-Cyclopropylpiperidine-4-carbonitrile

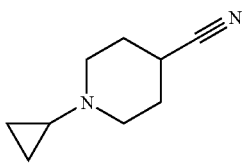

5.0 g (45.4 mmol) of 4-cyanopiperidine were dissolved in 83 ml of methanol, and 11.9 g (68.1 mmol) of [(1-ethoxy-1-cyclopropyl)oxy]trimethylsilane, 2.9 ml (3.0 g, 49.9 mmol) of acetic acid and 6.0 g (91.0 mmol) of sodium cyanoborohydride were added. The reaction mixture was stirred at 60° C. for 16 h, cooled to RT and then filtered through kieselguhr, the filter cake was washed with methanol and the filtrate was concentrated under reduced pressure. The residue was taken up in ethyl acetate and washed twice with 1 N aqueous sodium hydroxide solution and once with saturated aqueous sodium chloride solution. The organic phase was dried over sodium sulphate, filtered and concentrated under reduced pressure. Yield: 6.0 g (88% of theory)

GC-MS (Method 1F): $R_t$=3.83 min; MS (ESIpos): m/z=151 [M+H]$^+$.

Step b): 1-Cyclopropyl-N'-hydroxypiperidine-4-carboximidamide

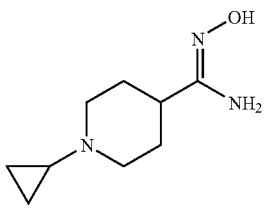

6.0 g (39.9 mmol) of 1-cyclopropylpiperidine-4-carbonitrile were reacted according to the General Method 5A. Yield: 5.3 g (72% of theory)

MS (ESIpos): m/z=184 [M+H]$^+$.

Example 76A

3-Ethoxy-N'-hydroxypropanimidamide

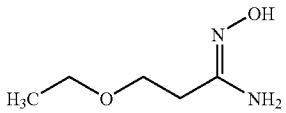

5.0 g (50.4 mmol) of 3-ethoxypropionitrile were reacted according to the General Method
5A. Yield: 0.6 g (8% of theory, 90% pure)

HPLC (Method 1A): $R_t$=0.60 min; MS (ESIpos): m/z=133 [M+H]$^+$.

Example 77A

N',2-Dihydroxy-2-methylpropanimidamide

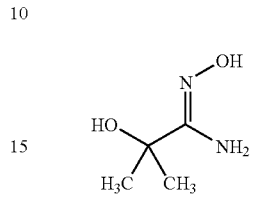

5.0 g (57.6 mmol) of 2-hydroxy-2-methylpropanonitrile were reacted according to the General Method 5A. Yield: 4.0 g (57% of theory, 96% pure)

HPLC (Method 1A): $R_t$=0.45 min; MS (ESIpos): m/z=119 [M+H]$^+$.

Example 78A

N'-Hydroxycyclopropanecarboximidamide

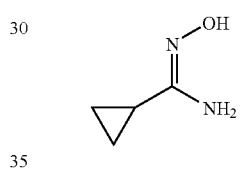

7.2 g (107.3 mmol) of cyclopropanecarbonitrile were reacted according to the General Method 5A. Yield: 4.8 g (44% of theory)

LC-MS (Method 2B): $R_t$=0.16 min; MS (ESIpos): m/z=101 [M+H]$^+$.

Example 79A tert-Butyl {[1-({3-[3-(3-fluorophenyl)-1,2,4-oxadiazol-5-yl]-5-[4-(trifluoromethoxy)phenyl]-piperidin-1-yl}carbonyl)cyclopropyl]methyl} carbamate [racemic cis isomer]

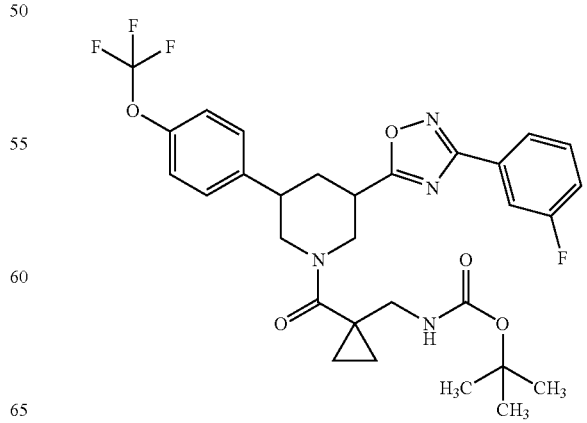

150 mg (0.30 mmol) of the compound from Example 178A and 70 mg (0.32 mmol) of 1-{[(tert-butoxycarbonyl)amino]methyl}cyclopropanecarboxylic acid were reacted according to the General Method 7. Yield: 126 mg (70% of theory)

LC-MS (Method 3B): $R_t$=2.76 min; MS (ESIpos): m/z=606 [M+H]$^+$.

Example 80A

N'-Hydroxy-3-methoxy-2,2-dimethylpropanimidamide

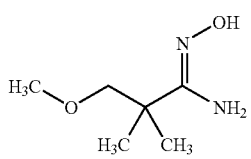

5.0 g (44.2 mmol) of 3-methoxy-2,2-dimethylpropionitrile were reacted according to the General Method 6A. Yield: 4.4 g (68% of theory)

GC-MS (Method 1F): $R_t$=1.20 min; MS (ESIpos): m/z=147 [M+H]$^+$.

Example 81A 1-(Morpholin-4-ylcarbonyl)-5-[4-(trifluoromethyl)phenyl]piperidine-3-carboxylic acid [racemic cis isomer]

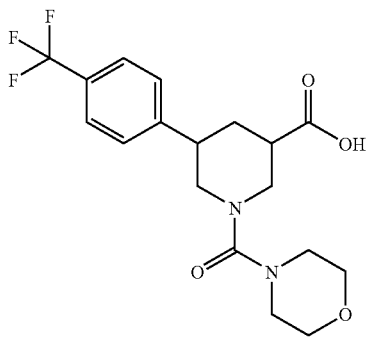

22.19 g (39.90 mmol) of the compound from Example 48A and 44.78 g (399.0 mmol) of potassium tert-butoxide were reacted according to the General Method 9A. Yield: 18.29 g (100% of theory).

LC-MS (Method 5B): $R_t$=1.95 min; MS (ESIpos): m/z=387 [M+H]$^+$.

$^1$H-NMR (400 MHz, DMSO-d$_6$): δ=12.36 (bs, 1H), 7.68 (d, 2H), 7.54 (d, 2H), 3.84 (br d, 1H), 3.58-3.52 (m, 5H), 3.19-3.14 (m, 4H), 2.91-2.80 (m, 3H), 2.60 (tt, 1H), 2.15 (br d, 1H), 1.78 (dd, 1H).

Example 82A 1-(Morpholin-4-ylcarbonyl)-5-[4-(trifluoromethyl)phenyl]piperidine-3-carboxamide [racemic cis isomer]

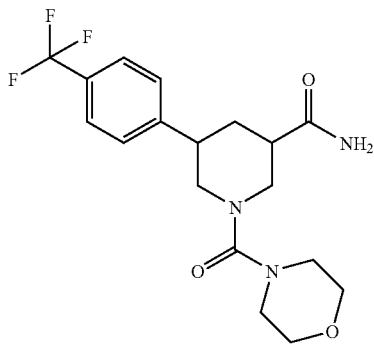

4.77 g (40.1 mmol) of thionyl chloride were added to a solution of 5.16 g (13.4 mmol) of the compound from Example 81A in 180 ml of tetrahydrofuran. The mixture was stirred at reflux temperature for 1 h. For work-up, the dichloromethane was removed under reduced pressure, and once more dichloromethane was added to the residue and the mixture was concentrated. The residue was initially charged in 75 ml of tetrahydrofuran and cooled to 0° C. 19.0 ml (133.4 mmol) of a 7M solution of ammonia in methanol were then added. The reaction mixture was stirred at 0° C. for 1 h. For work-up, the solvent was removed under reduced pressure and the residue was taken up in ethyl acetate. The organic phase was washed successively with water and saturated aqueous sodium chloride solution, dried over magnesium sulphate and concentrated. Yield: 4.42 g (86% of theory).

LC-MS (Method 2B): $R_t$=1.00 min; MS (ESIpos): m/z=386 [M+H]$^+$;

$^1$H-NMR (400 MHz, DMSO-d$_6$): δ=12.36 (br s, 1H), 7.68 (d, 2H), 7.54 (d, 2H), 3.85 (br d, 1H), 3.57-3.52 (m, 5H), 3.18-3.14 (m, 4H), 2.90-2.80 (m, 3H), 2.60 (tt, 1H), 2.15 (br d, 1H), 1.76 (dd, 1H).

Example 83A 1-(Morpholin-4-ylcarbonyl)-5-[4-(trifluoromethyl)phenyl]piperidine-3-carbonitrile [racemic cis isomer]

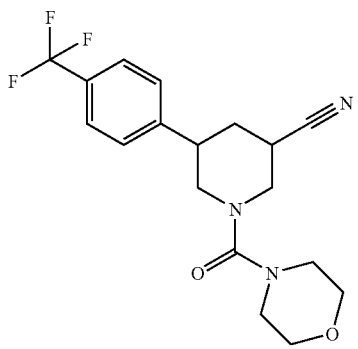

Under argon, 3.83 g (16.1 mmol) of Burgess reagent were added to a solution of 4.42 g (11.5 mmol) of the compound from Example 82A in 208 ml of tetrahydrofuran. The mixture was stirred at 70° C. for 1 h. For work-up, the solvent was removed under reduced pressure and the residue was taken up in ethyl acetate. The organic phase was washed successively with water and saturated aqueous sodium chloride solution, dried over magnesium sulphate and concentrated. Yield: 4.19 g (99% of theory)

LC-MS (Method 1B): $R_t$=2.20 min; MS (ESIpos): m/z=368 [M+H]$^+$.

Example 84A

1-N'-Hydroxy(morpholin-4-ylcarbonyl)-5-[4-(trifluoromethyl)phenyl]piperidine-3-carboximidamide [racemic cis isomer]

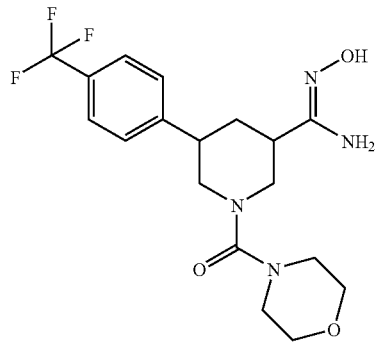

1.7 ml (12.8 mmol) of triethylamine and 1.02 g (14.71 mmol) of hydroxylammonium chloride were added to a solution of 4.19 g (9.81 mmol) of the compound from Example 83A in 144 ml of ethanol. The mixture was stirred at 50° C. for 9 h. The solvent was removed under reduced pressure and the residue was taken up in ethyl acetate. The organic phase was washed with water, dried over magnesium sulphate and concentrated. This gives 3.41 g of crude product in a purity of 85% (LC-MS), which was reacted without any further purification steps.

LC-MS (Method 1B): $R_t$=1.39 min; MS (ESIpos): m/z=401 [M+H]$^+$.

Example 85A tert-Butyl[1-(3-{1-(morpholin-4-ylcarbonyl)-5-[4-(trifluoromethyl)phenyl]piperidin-3-yl}-1,2,4-oxadiazol-5-yl)cyclopropyl]carbamate [racemic cis isomer]

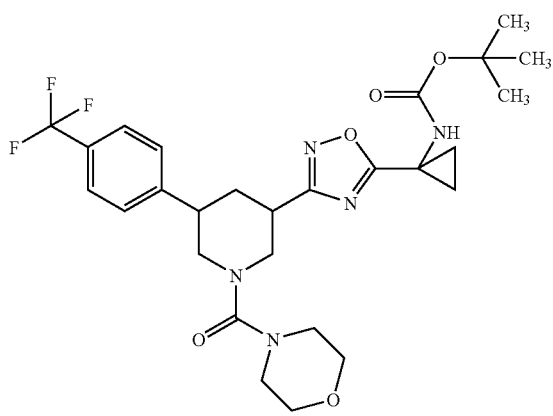

170 mg (0.85 mmol) of 1-[(tert-butoxycarbonyl)amino]cyclopropanecarboxylic acid and 200 mg (0.43 mmol) of the compound from Example 84A were reacted according to the General Method 2. Yield: 134 mg (53% of theory).

LC-MS (Method 3B): $R_t$=2.25 min; MS (ESIpos): m/z=568 [M+H]$^+$;

$^1$H-NMR (400 MHz, DMSO-d$_6$): δ=8.02 (s, 1H), 7.69 (d, 2H), 7.55 (d, 2H), 3.92 (br d, 1H), 3.64 (d, 1H), 3.57-3.53 (m, 4H), 3.20-3.11 (m, 5H), 3.03-2.91 (m, 2H), 2.22 (br d, 1H), 1.90 (q, 1H), 1.52-1.49 (m, 2H), 1.39 (s, 9H), 1.37-1.33 (m, 1H), 1.29-1.24 (m, 2H).

Example 86A tert-Butyl[2-(3-{1-(morpholin-4-ylcarbonyl)-5-[4-(trifluoromethyl)phenyl]piperidin-3-yl}-1,2,4-oxadiazol-5-yl)propan-2-yl]carbamate [racemic cis isomer]

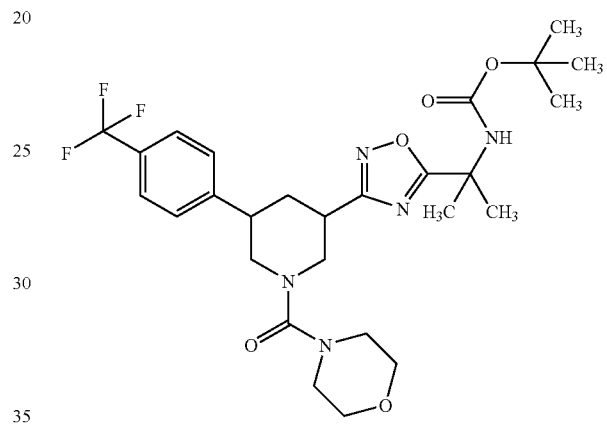

860 mg (0.43 mmol) of N-[(tert-butoxycarbonyl)-2-methylalanine and 100 mg (0.21 mmol) of the compound from Example 84A were reacted according to the General Method 2. Yield: 40 mg (34% of theory).

LC-MS (Method 1B): $R_t$=2.61 min; MS (ESIpos): m/z=568 [M+H]$^+$;

$^1$H-NMR (400 MHz, DMSO-d$_6$): δ=7.69 (d, 2H), 7.56 (d, 2H), 3.93 (br d, 1H), 3.64 (d, 1H), 3.58-3.54 (m, 4H), 3.22-3.12 (m, 5H), 3.08-3.02 (m, 2H), 2.98 (t, 1H), 2.24 (br d, 1H), 1.91 (q, 1H), 1.54 (s, 6H), 1.32 (s, 9H).

Example 87A tert-Butyl[(3-{1-(morpholin-4-ylcarbonyl)-5-[4-(trifluoromethyl)phenyl]piperidin-3-yl}-1,2,4-oxadiazol-5-yl)methyl]carbamate [racemic cis isomer]

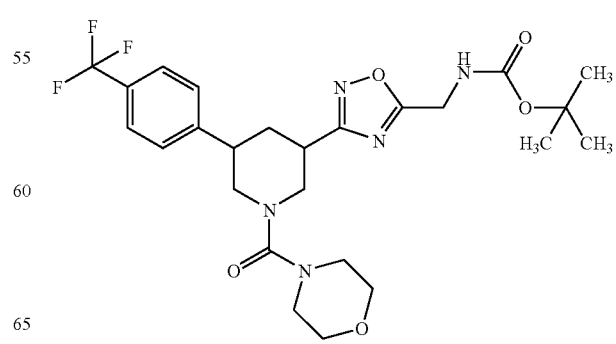

149 mg (0.85 mmol) of N-(tert-butoxycarbonyl)glycine and 200 mg (0.43 mmol) of the compound from Example 84A were reacted according to the General Method 1. Yield: 74 mg (32% of theory).

LC-MS (Method 5B): $R_t$=2.40 min; MS (ESIpos): m/z=540 [M+H]$^+$;

$^1$H-NMR (400 MHz, DMSO-d$_6$): δ=7.69 (d, 2H), 7.65 (t, 1H), 7.56 (d, 2H), 4.40 (d, 2H), 3.93 (br d, 1H), 3.65 (d, 1H), 3.59-3.55 (m, 4H), 3.22-3.15 (m, 5H), 3.05-2.94 (m, 3H), 2.26 (br d, 1H), 1.93 (q, 1H), 1.39 (s, 9H).

Example 88A tert-Butyl[(1S)-1-(3-{1-(morpholin-4-ylcarbonyl)-5-[4-(trifluoromethyl)phenyl]piperidin-3-yl}-1,2,4-oxadiazol-5-yl)ethyl]carbamate [racemic cis isomer]

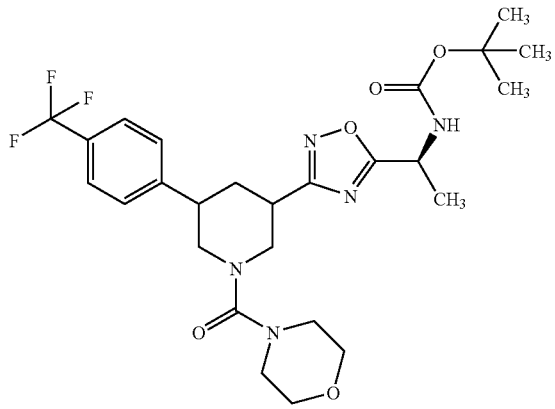

80 mg (0.43 mmol) of N-(tert-butoxycarbonyl)-L-alanine and 100 mg (0.21 mmol) of the compound from Example 84A were reacted according to the General Method 2. Yield: 41 mg (35% of theory).

LC-MS (Method 2B): $R_t$=1.36 min; MS (ESIpos): m/z=554 [M+H]$^+$;

$^1$H-NMR (400 MHz, DMSO-d$_6$): δ=7.69 (d, 1H), 7.56 (d, 2H), 4.92-4.84 (m, 1H), 3.95 (br d, 1H), 3.65 (d, 1H), 3.58-3.53 (m, 4H), 3.22-3.13 (m, 5H), 3.06-2.95 (m, 3H), 2.25 (br d, 1H), 1.92 (q, 1H), 1.43 (d, 3H), 1.38 (s. 9H).

Example 89A

Methyl 1-[(3-oxopiperazin-1-yl)carbonyl]-5-[4-(trifluoromethyl)phenyl]piperidine-3-carboxylate [racemic cis/trans isomer mixture]

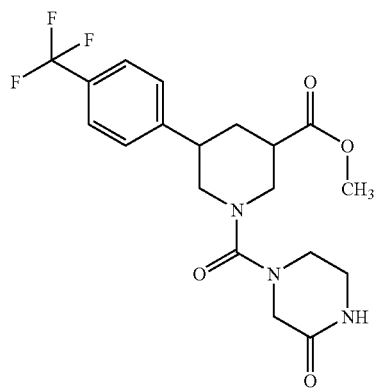

4.00 g (8.84 mmol) of 3-methyl 1-(4-nitrophenyl)5-[4-(trifluoromethyl)phenyl]piperidine-1,3-dicarboxylate and 1.77 g (17.7 mmol) of piperazin-2-one were reacted according to the General Method 8A. Yield: 1.92 g (51% of theory).

LC-MS (Method 2B): $R_t$=1.05 min and 1.08 min (cis/trans isomers); MS (ESIpos): m/z=414 [M+H]$^+$.

Example 90A tert-Butyl methyl-[(3-{1-(morpholin-4-ylcarbonyl)-5-[4-(trifluoromethyl)phenyl]piperidin-3-yl}-1,2,4-oxadiazol-5-yl)methyl]carbamate [racemic cis isomer]

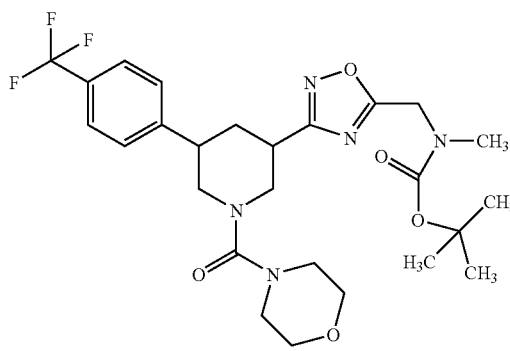

96 mg (0.50 mmol) of N-(tert-butoxycarbonyl)-N-methylglycine and 140 mg (0.25 mmol) of the compound from Example 84A were reacted according to the General Method 2. Yield: 102 mg (73% of theory).

LC-MS (Method 2B): $R_t$=1.39 min; MS (ESIpos): m/z=554 [M+H]$^+$;

Example 91A tert-Butyl (2S)-2-(3-{1-(morpholin-4-ylcarbonyl)-5-[4-(trifluoromethyl)phenyl]piperidin-3-yl}-1,2,4-oxadiazol-5-yl)pyrrolidine-1-carboxylate

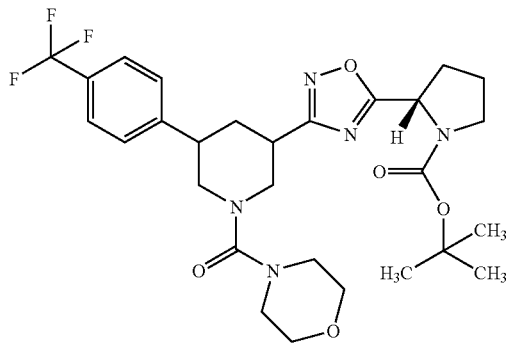

108 mg (0.50 mmol) of 1-(tert-butoxycarbonyl)-L-proline and 140 mg (0.25 mmol) of the compound from Example 84A were reacted according to the General Method 2. Yield: 91 mg (62% of theory).

LC-MS (Method 1B): $R_t$=2.67 min; MS (ESIpos): m/z=580 [M+H]$^+$.

Example 92A tert-Butyl 3-(3-{1-(morpholin-4-ylcarbonyl)-5-[4-(trifluoromethyl)phenyl]piperidin-3-yl}-1,2,4-oxadiazol-5-yl)azetidine-1-carboxylate

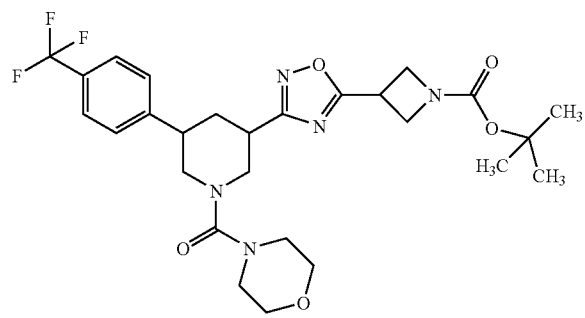

Step a):
1-(tert-Butoxycarbonyl)azetidine-3-carboxylic acid

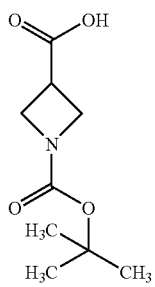

A mixture of 100 mg (0.99 mmol) of azetidine-3-carboxylic acid and 237 mg (1.09 mmol) of di-tert-butyl dicarbonate in 1 ml of dichloromethane was stirred at room temperature for 16 h. For work-up, the solvent was removed under reduced pressure, and the residue was used without any further purification. Yield: 175 mg (88% of theory).

$^1$H-NMR (400 MHz, DMSO-$d_6$): δ=4.00-3.96 (m, 2H), 3.90-3.80 (m, 2H), 3.35-3.28 (m, 1H), 1.37 (s, 9H).

Step b): tert-Butyl-3-(3-{-1-(morpholin-4-ylcarbonyl)-5-[4-(trifluoromethyl)phenyl]piperidin-3-yl}-1,2,4-oxadiazol-5-yl)azetidine-1-carboxylate

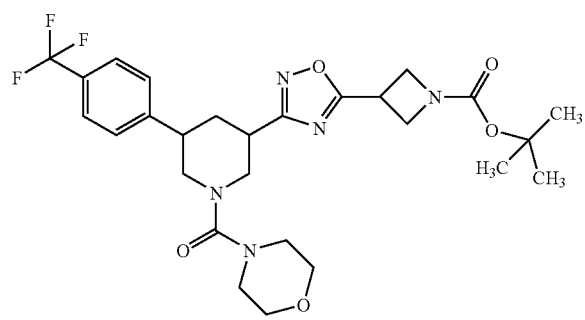

202 mg (1.01 mmol) of 1-(tert-butoxycarbonyl)azetidine-3-carboxylic acid and 140 mg (0.25 mmol) of the compound from Example 84A were reacted according to the General Method 2. Yield: 74 mg (52% of theory).

LC-MS (Method 2B): $R_t$=1.39 min; MS (ESIpos): m/z=567 [M+H]$^+$;

$^1$H-NMR (400 MHz, DMSO-$d_6$): δ=7.70 (d, 2H), 7.57 (d, 2H), 4.28-4.24 (m, 2H), 4.18-4.11 (m, 1H), 4.08-4.00 (m, 2H), 3.96 (br d, 1H), 3.66 (d, 1H), 3.58-3.54 (m, 4H), 3.25-3.15 (m, 5H), 3.10-2.98 (m, 3H), 2.27 (br d, 1H), 1.95 (q, 1H), 1.38 (s. 9H).

Example 93A

3-Methyl 1-(4-nitrophenyl)5-[4-(trifluoromethyl)phenyl]piperidine-1,3-dicarboxylate [racemic cis/trans isomer mixture]

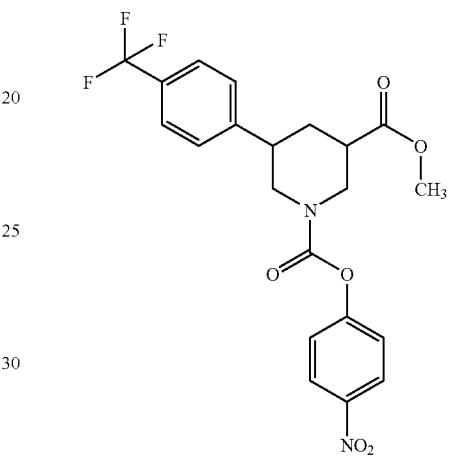

20.0 g (69.6 mmol) of methyl 5-[4-(trifluoromethyl)phenyl]piperidine-3-carboxylate (Example 47A) were dissolved in 1.0 l of dichloromethane, and 14.1 g (139 mmol) of triethylamine were added at 0° C. 14.0 g (69.6 mmol) of 4-nitrophenyl chlorocarbonate were then added dropwise. The reaction mixture was stirred at 0° C. for 2 h and then at RT for 16 h. For work-up, the mixture was washed with saturated aqueous sodium bicarbonate solution. The organic phase was dried over magnesium sulphate, filtered and concentrated under reduced pressure. This gave 31.3 g of crude product, which was reacted without any further purification steps.

LC-MS (Method 3B): $R_t$=2.44 min and 2.48 min (cis/trans isomers); MS (ESIpos): m/z=453 [M+H]$^+$.

Example 94A

Methyl 1-[(4-hydroxypiperidin-1-yl)carbonyl]-5-[4-(trifluoromethyl)phenyl]piperidine-3-carboxylate [racemic cis/trans isomer mixture]

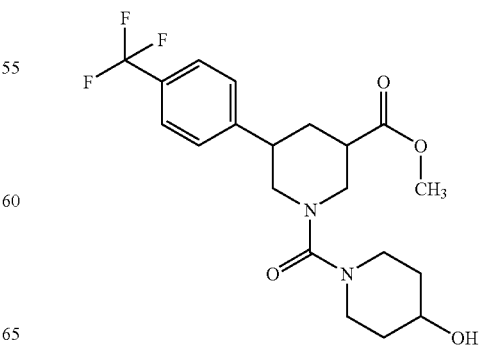

4.00 g (8.84 mmol) of 3-methyl 1-(4-nitrophenyl)5-[4-(trifluoromethyl)phenyl]piperidine-1,3-dicarboxylate (Example 93A) and 2.68 g (26.5 mmol) of 4-hydroxypiperidine were reacted according to the General Method 8A. Yield: 3.10 g (83% of theory).

LC-MS (Method 3B): $R_t$=2.72 min and 2.78 min (cis/trans isomers); MS (ESIpos): m/z=415 [M+H]$^+$.

$^1$H-NMR (400 MHz, DMSO-d$_6$): δ=7.69 (d, 2H), 7.53 (t, 2H), 4.67 (br d, 1H), 3.91-3.78 (m, 1H), 3.66-3.34 (m, 7H), 3.15-3.05 (m, 1H), 2.96-2.65 (m, 5H), 2.25-2.11 (m, 1H), 1.96-1.63 (m, 3H), 1.38-1.18 (m, 2H).

Example 95A

Methyl 1-[(4-cyanopiperidin-1-yl)carbonyl]-5-[4-(trifluoromethyl)phenyl]piperidine-3-carboxylate [racemic cis/trans isomer mixture]

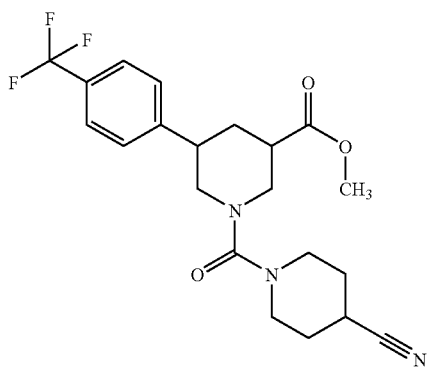

4.00 g (8.84 mmol) of 3-methyl 1-(4-nitrophenyl)5-[4-(trifluoromethyl)phenyl]piperidine-1,3-dicarboxylate (Example 93A) and 2.92 g (26.5 mmol) of piperidine-4-carbonitrile were reacted according to the General Method 8A. Yield: 3.15 g (77% of theory).

LC-MS (Method 1B): $R_t$=2.35 min and 2.41 min (cis/trans isomers); MS (ESIpos): m/z=424 [M+H]$^+$.

Example 96A

Methyl 1-[(3-hydroxyazetidin-1-yl)carbonyl]-5-[4-(trifluoromethyl)phenyl]piperidine-3-carboxylate [racemic cis/trans isomer mixture]

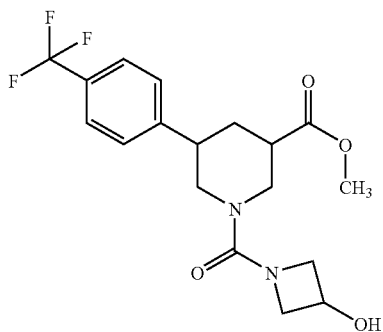

4.00 g (8.84 mmol) of 3-methyl 1-(4-nitrophenyl)5-[4-(trifluoromethyl)phenyl]piperidine-1,3-dicarboxylate (Example 93A), 2.91 g (26.5 mmol) of 4-azetidin-3-ol hydrochloride and potassium carbonate (2.5 eq.) were reacted according to the General Method 8A. Yield: 2.48 g (70% of theory).

LC-MS (Method 2B): $R_t$=1.08 min and 1.10 min (cis/trans isomers); MS (ESIpos): m/z=387 [M+H]$^+$.

Example 97A

Methyl 1-(1,3-thiazolidin-3-ylcarbonyl)-5-[4-(trifluoromethyl)phenyl]piperidine-3-carboxylate [racemic cis/trans isomer mixture]

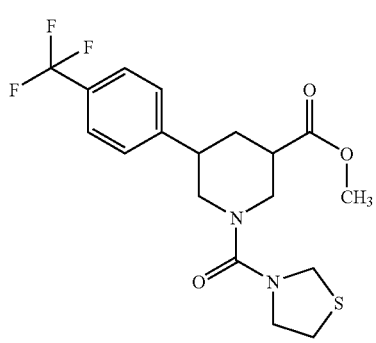

4.00 g (8.84 mmol) of 3-methyl 1-(4-nitrophenyl)5-[4-(trifluoromethyl)phenyl]piperidine-1,3-dicarboxylate (Example 93A) and 1.58 g (17.7 mmol) of 1,3-thiazolidine were reacted according to the General Method 8A. Yield: 0.54 g (15% of theory).

LC-MS (Method 3B): $R_t$=2.11 min and 2.18 min (cis/trans isomers); MS (ESIpos): m/z=403 [M+H]$^+$.

Example 98A

Methyl 1-[(3-methoxyazetidin-1-yl)carbonyl]-5-[4-(trifluoromethyl)phenyl]piperidine-3-carboxylate [racemic cis/trans isomer mixture]

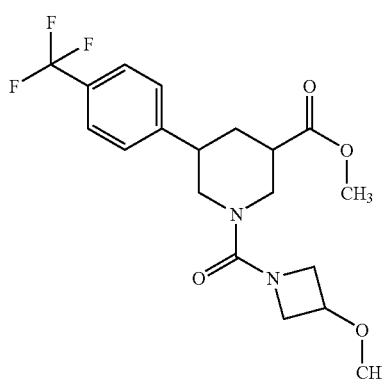

4.00 g (8.84 mmol) of 3-methyl 1-(4-nitrophenyl)5-[4-(trifluoromethyl)phenyl]piperidine-1,3-dicarboxylate (Example 93A), 2.73 g (22.1 mmol) of 3-methoxyazetidine hydrochloride and potassium carbonate (2.5 eq.) were reacted according to the General Method 8A. Yield: 2.98 g (82% of theory).

LC-MS (Method 2B): $R_t$=1.19 min and 1.22 min (cis/trans isomers); MS (ESIpos): m/z=401 [M+H]$^+$.

Example 99A

1-[(4-Hydroxypiperidin-1-yl)carbonyl]-5-[4-(trifluoromethyl)phenyl]piperidine-3-carboxylic acid [racemic cis isomer]

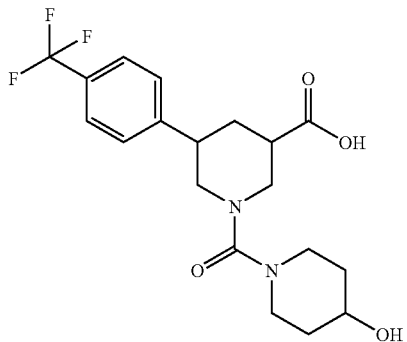

2.10 g (5.07 mmol) of methyl 1-[(4-hydroxypiperidin-1-yl)carbonyl]-5-[4-(trifluoromethyl)phenyl]piperidine-3-carboxylate (Example 94A) were reacted according to the General Method 9A. Yield: 2.02 g (99% of theory).

LC-MS (Method 2B): $R_t$=1.01 min; MS (ESIpos): m/z=401 [M+H]$^+$.

Example 100A

1-[(4-Cyanopiperidin-1-yl)carbonyl]-5-[4-(trifluoromethyl)phenyl]piperidine-3-carboxylic acid [racemic cis isomer]

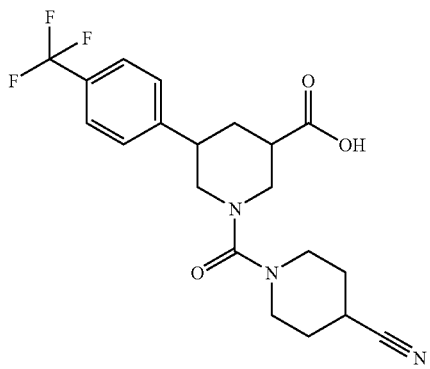

2.90 g (6.85 mmol) of methyl 1-[(4-cyanopiperidin-1-yl)carbonyl]-5-[4-(trifluoromethyl)phenyl]piperidine-3-carboxylate (Example 95A) were reacted according to the General Method 9A (reaction time: 2 h). Yield: 2.86 g (98% of theory).

LC-MS (Method 1B): $R_t$=2.15 min; MS (ESIpos): m/z=410 [M+H]$^+$.

$^1$H-NMR (400 MHz, DMSO-d$_6$): δ=12.4 (br s, 1H), 7.69 (d, 2H), 7.53 (d, 2H), 3.82 (br d, 1H), 3.56 (br d, 1H), 3.35 (obscured, 1H), 3.10-2.99 (m, 3H), 2.95-2.79 (m, 3H), 2.65-2.54 (m, 1H), 2.15 (br d, 1H), 1.91-1.59 (m, 5H).

Example 101A

1-[(3-Hydroxyazetidin-1-yl)carbonyl]-5-[4-(trifluoromethyl)phenyl]piperidine-3-carboxylic acid [racemic cis isomer]

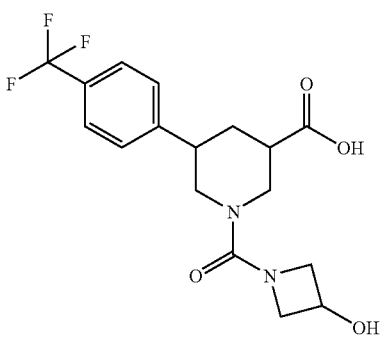

2.48 g (6.42 mmol) of methyl 1-[(3-hydroxyazetidin-1-yl)carbonyl]-5-[4-(trifluoromethyl)phenyl]piperidine-3-carboxylate (Example 96A) were reacted according to the General Method 9A (reaction time: 2 h). Yield: 2.33 g (94% of theory).

LC-MS (Method 1B): $R_t$=1.84 min; MS (ESIpos): m/z=373 [M+H]$^+$.

$^1$H-NMR (400 MHz, DMSO-d$_6$): δ=12.4 (br s, 1H), 7.69 (d, 2H), 7.53 (d, 2H), 5.57 (d, 1H), 4.42-4.32 (m, 1H), 4.11-3.95 (m, 3H), 3.77-3.63 (m, 3H), 3.32 (obscured, 1H), 2.88-2.76 (m, 3H), 2.14 (br d, 1H), 1.85-1.72 (m, 1H).

Example 102A 1-(1,3-Thiazolidin-3-ylcarbonyl)-5-[4-(trifluoromethyl)phenyl]piperidine-3-carboxylic acid [racemic cis isomer]

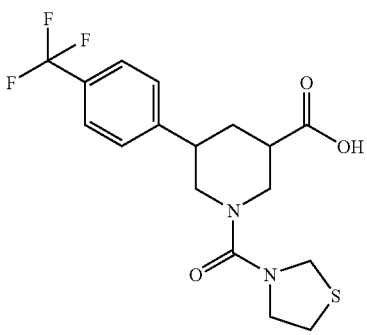

0.54 g (1.33 mmol) of methyl 1-(1,3-thiazolidin-3-ylcarbonyl)-5-[4-(trifluoromethyl)phenyl]piperidine-3-carboxylate (Example 97A) was reacted according to the General Method 9A. Yield: 0.51 g (74% of theory, 75% pure).

LC-MS (Method 2B): R$_t$=1.17 min; MS (ESIpos): m/z=389 [M+H]$^+$.

Example 103A

1-[(3-Methoxyazetidin-1-yl)carbonyl]-5-[4-(trifluoromethyl)phenyl]piperidine-3-carboxylic acid [racemic cis isomer]

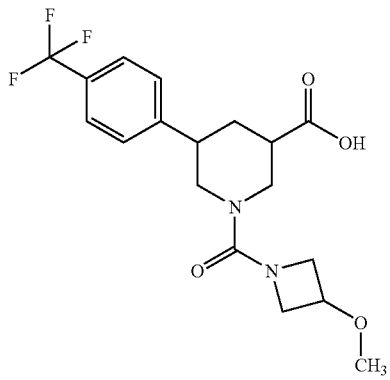

2.90 g (7.24 mmol) of methyl 1-[(3-methoxyazetidin-1-yl)carbonyl]-5-[4-(trifluoromethyl)phenyl]piperidine-3-carboxylate (Example 98A) were reacted according to the General Method 9A. Yield: 2.77 g (99% of theory).

LC-MS (Method 3B): R$_t$=1.71 min; MS (ESIpos): m/z=387 [M+H]$^+$.

$^1$H-NMR (400 MHz, DMSO-d$_6$): δ=12.5 (br s, 1H), 7.69 (d, 2H), 7.53 (d, 2H), 4.16-3.95 (m, 4H), 3.80-3.69 (m, 3H), 3.32 (obscured, 1H), 3.18 (s, 3H), 2.89-2.77 (m, 3H), 2.14 (br d, 1H), 1.85-1.72 (m, 1H).

Example 104A

Methyl 1-[(2-methoxyethyl)carbamoyl]-5-[4-(trifluoromethyl)phenyl]piperidine-3-carboxylate [racemic cis/trans isomer mixture]

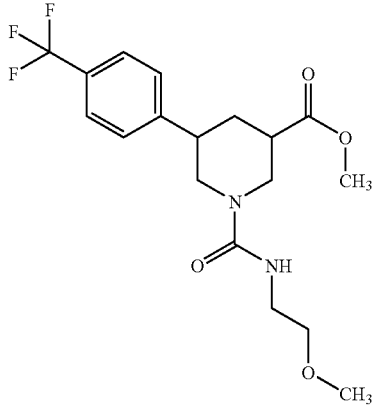

8.83 g (about 14.3 mmol) of the compound from Example 93A and 3.21 g (14.3 mmol) of 2-methoxyethanamine were reacted according to the General Method 8A. Yield: 2.94 g (51% of theory).

LC-MS (Method 1B): R$_t$=2.14 min and 2.19 min (cis/trans isomers); MS (ESIpos): m/z=389 [M+H]$^+$.

Example 105A

1-[(2-Methoxyethyl)carbamoyl]-5-[4-(trifluoromethyl)phenyl]piperidine-3-carboxylic acid [racemic cis/trans isomer mixture]

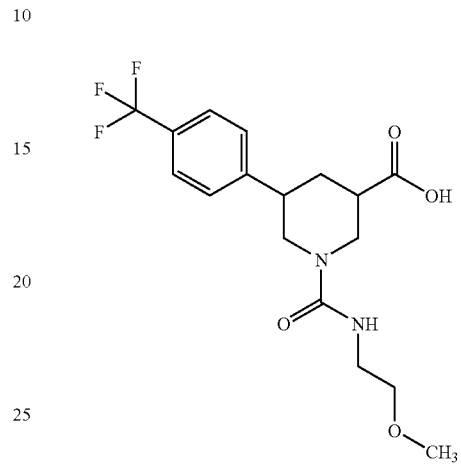

2.94 g (7.57 mmol) of the compound from Example 104A and 8.49 g (75.70 mmol) of potassium tert-butoxide were reacted according to the General Method 9A. Yield: 2.46 g (80% of theory, 92% pure)

LC-MS (Method 1B): R$_t$=1.97 min and 2.02 min (cis/trans isomers); MS (ESIpos): m/z=375 [M+H]$^+$.

Example 106A 1-(Morpholin-4-ylcarbonyl)-N-(2-oxo-2-phenylethyl)-5-[4-(trifluoromethyl)phenyl]piperidine-3-carboxamide [racemic cis/trans isomer mixture]

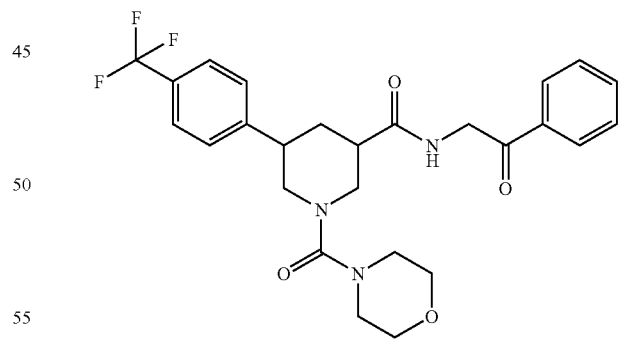

97 mg (0.57 mmol) of thionyl chloride were added to a solution of 200 mg (0.52 mmol) of the compound from Example 49A in 1 ml of dichloromethane. The mixture was stirred under reflux for 1 h. For work-up, the dichloromethane was removed under reduced pressure, and once more dichloromethane was added to the residue and the mixture was concentrated. The residue was initially charged in 5 ml of dichloromethane, and 78 mg (0.78 mmol) of triethylamine and 97 mg (0.57 mmol) of 2-amino-1-phenylethanone were then added. The reaction mixture was stirred at room temperature for 3 h. For work-up, water was added to the mixture, and the organic phase was separated off and washed repeatedly with saturated aqueous sodium chloride solution. The organic phase was dried over magnesium sulphate and evaporated to dryness under reduced pressure. Yield: 300 mg (62% of theory, 70% pure)

LC-MS (Method 2B): $R_t$=1.21 min; MS (ESIpos): m/z=504 [M+H]$^+$.

Example 107A

Methyl 1-[(4-cyanopiperidin-1-yl)carbonyl]-5-[4-(trifluoromethoxy)phenyl]piperidine-3-carboxylate [racemic cis/trans isomer mixture]

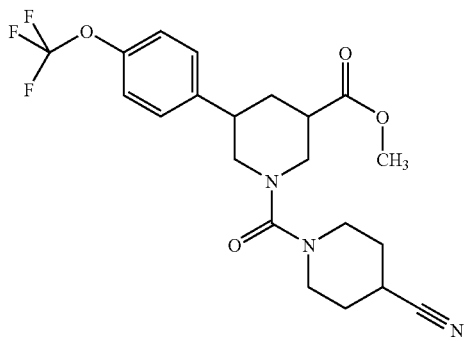

5.15 g (6.60 mmol) of the compound from Example 61A and 2.18 g (19.79 mmol) of 4-cyanopiperidine were reacted according to the General Method 8A. Yield: 1.69 g (40% of theory, 69% pure)

LC-MS (Method 1B): $R_t$=2.40 min and 2.46 min (cis/trans isomers); MS (ESIpos): m/z=440 [M+H]$^+$.

Example 108A

1-[(4-Cyanopiperidin-1-yl)carbonyl]-5-[4-(trifluoromethoxy)phenyl]piperidine-3-carboxylic acid [racemic cis isomer]

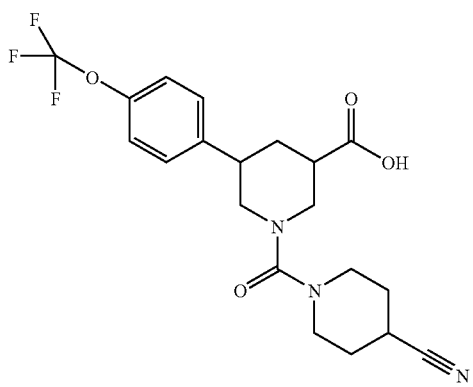

1.69 g (about 2.62 mmol) of the compound from Example 107A and 2.9 g (26.2 mmol) of potassium tert-butoxide were reacted according to the General Method 9A. Yield: 1.53 g (90% of theory, 65% pure)

LC-MS (Method 3B): $R_t$=1.78 min and 1.83 min (cis/trans isomers); MS (ESIpos): m/z=426 [M+H]$^+$.

Example 109A

Methyl 1-[(3-hydroxyazetidin-1-yl)carbonyl]-5-[4-(trifluoromethoxy)phenyl]piperidine-3-carboxylate [racemic cis/trans isomer mixture]

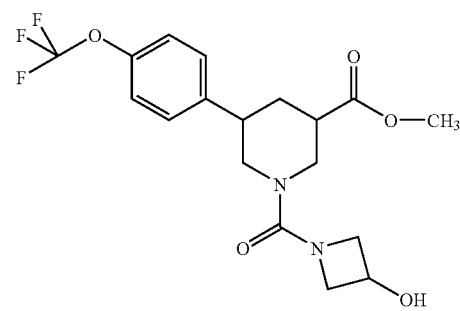

300 mg (0.38 mmol) of the compound from Example 61A and 89 mg (1.15 mmol) of 3-hydroxyazetidine were reacted according to the General Method 8A. Yield: 100 mg (63% of theory).

LC-MS (Method 9B): $R_t$=0.97 min and 0.99 min (cis/trans isomers); MS (ESIpos): m/z=403 [M+H]$^+$.

Example 110A

1-[(3-Hydroxyazetidin-1-yl)carbonyl]-5-[4-(trifluoromethoxy)phenyl]piperidine-3-carboxylic acid [racemic cis isomer]

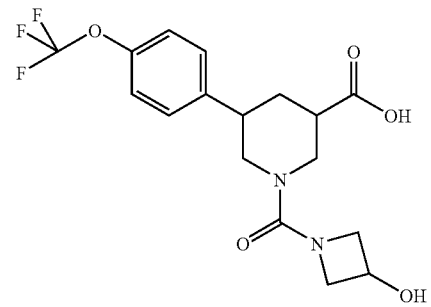

700 mg (1.43 mmol) of the compound from Example 109A and 1.61 g (14.3 mmol) of potassium tert-butoxide were reacted according to the General Method 9A. Yield: 700 g (99% of theory, 84% pure)

LC-MS (Method 9B): $R_t$=0.87 min; MS (ESIpos): m/z=389 [M+H]$^+$.

Example 111A

Methyl 1-[(3-hydroxypyrrolidin-1-yl)carbonyl]-5-[4-(trifluoromethoxy)phenyl]piperidine-3-carboxylate [racemic cis/trans isomer mixture]

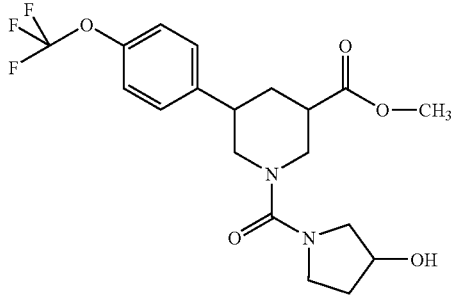

20.0 g (25.6 mmol) of the compound from Example 61A and 6.69 g (76.9 mmol) of 3-pyrrolidinol were reacted according to the General Method 8A. Yield: 6.69 g (63% of theory).

LC-MS (Method 9B): $R_t$=0.99 min and 1.01 min (cis/trans isomers); MS (ESIpos): m/z=417 [M+H]$^+$.

Example 112A

1-[(3-Hydroxypyrrolidin-1-yl)carbonyl]-5-[4-(trifluoromethoxy)phenyl]piperidine-3-carboxylic acid [racemic cis isomer]

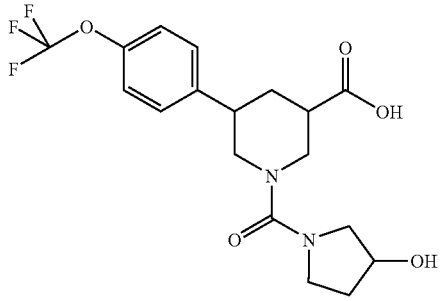

26.05 g (16.06 mmol) of the compound from Example 111A were reacted with 26.05 g (160.6 mmol) of potassium tert-butoxide according to the General Method 9A. Yield: 5.9 g (91% of theory).

LC-MS (Method 9B): $R_t$=0.89 min and 1.01 min; MS (ESIpos): m/z=403 [M+H]$^+$.

Example 113A

Methyl 1-({4-[(tert-butoxycarbonyl)amino]piperidin-1-yl}carbonyl)-5-[4-(trifluoromethoxy)-phenyl]piperidine-3-carboxylate [racemic cis/trans isomer]

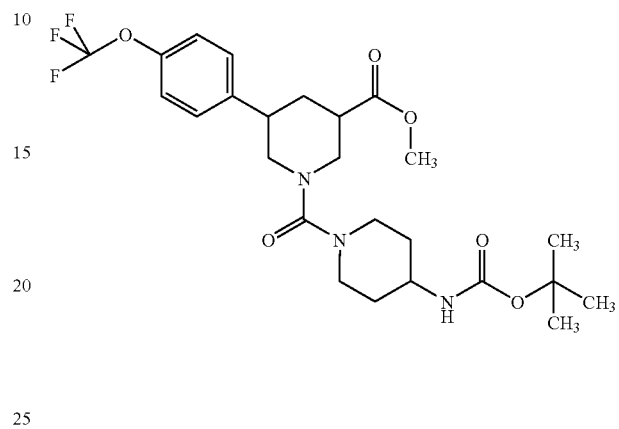

2 g (2.6 mmol) of the compound from Example 61A were reacted with 1.54 g (7.69 mmol) of 4-tert-butyl piperidin-4-ylcarbamate according to the General Method 8A. Yield: 785 mg (58% of theory).

LC-MS (Method 2B): $R_t$=1.37; MS (ESIpos): m/z=530 [M+H]$^+$.

Example 114A 1-({4-[(tert-Butoxycarbonyl)amino]piperidin-1-yl}carbonyl)-5-[4-(trifluoromethoxy)phenyl]-piperidine-3-carboxylic acid [racemic cis isomer]

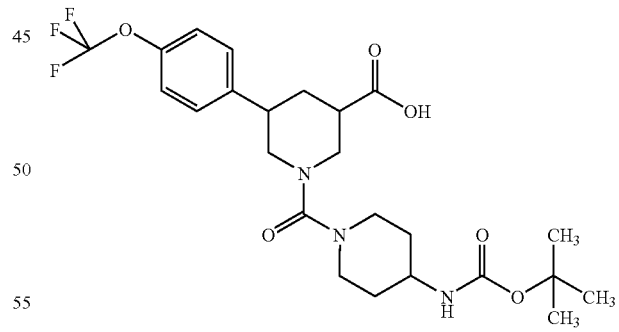

785 mg (1.48 mmol) of the compound from Example 113A and 1.66 g (14.8 mmol) of potassium tert-butoxide were reacted according to the General Method 9A. Yield: 740 mg (97% of theory).

LC-MS (Method 9B): $R_t$=1.13 min; MS (ESIpos): m/z=516 [M+H]$^+$.

Example 115A 1-(Morpholin-4-ylcarbonyl)-5-[4-(trifluoromethoxy)phenyl]piperidine-3-carbothioamide [racemic cis/trans isomer mixture]

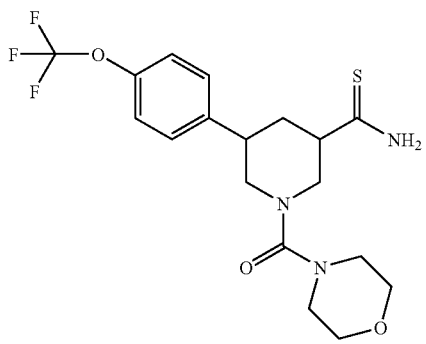

820 mg (1.94 mmol) of 1-(morpholin-4-ylcarbonyl)-5-[4-(trifluoromethoxy)phenyl]piperidine-3-carboxylic acid Example 44A and 432 mg (1.07 mmol) of Lawesson reagent were reacted according to the General Method 10A. Yield: 530 mg (47% of theory, 72% pure)

LC-MS (Method 1B): $R_t$=2.17 min and 2.26 min; MS (ESIpos): m/z=418 [M+H]$^+$.

Example 116A

1-[(4-Cyanopiperidin-1-yl)carbonyl]-5-[4-(trifluoromethoxy)phenyl]piperidine-3-carboxamide [racemic cis isomer mixture]

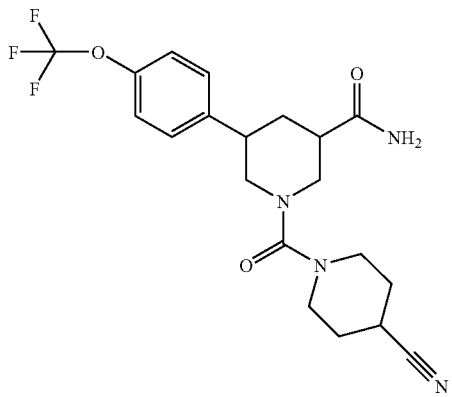

1.56 g (13.12 mmol) of thionyl chloride were added to a solution of 3.0 g (4.4 mmol) of 1-[(4-cyanopiperidin-1-yl)carbonyl]-5-[4-(trifluoromethoxy)phenyl]piperidine-3-carboxylic acid (Example 108A) in 79 ml of dichloromethane. The mixture was stirred under reflux for 3 h. For work-up, the dichloromethane was removed under reduced pressure, and once more dichloromethane was added to the residue and the mixture was concentrated. The residue was initially charged in 28 ml of tetrahydrofuran and cooled to 0° C. 6.24 ml (43.72 mmol) of a 7M solution of ammonia in methanol were then added. The reaction mixture was stirred at 0° C. for 15 minutes. For work-up, the solvent was removed under reduced pressure and the residue was taken up in ethyl acetate. The organic phase was washed successively with water and saturated aqueous sodium chloride solution, dried over magnesium sulphate and concentrated. Yield: 2.92 g (99% of theory, 70% pure)

LC-MS (Method 1B): $R_t$=2.02 min; MS (ESIpos): m/z=425 [M+H]$^+$.

Example 117A

1-[(4-Cyanopiperidin-1-yl)carbonyl]-5-[4-(trifluoromethoxy)phenyl]piperidine-3-carbothioamide [racemic cis/trans isomer mixture]

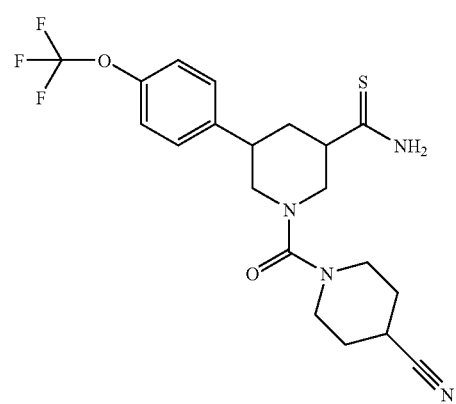

1.50 g (3.53 mmol) of the compound from Example 116A and 786 mg (1.94 mmol) of Lawesson reagent were reacted according to the General Method 10A. Yield: 1.34 mg (39% of theory, 45% pure)

LC-MS (Method 9B): $R_t$=1.04 min and 1.05 (cis/trans isomers); MS (ESIpos): m/z=441 [M+H]$^+$.

Example 118A 1-(Morpholin-4-ylcarbonyl)-5-[4-(trifluoromethoxy)phenyl]piperidine-3-carboxamide

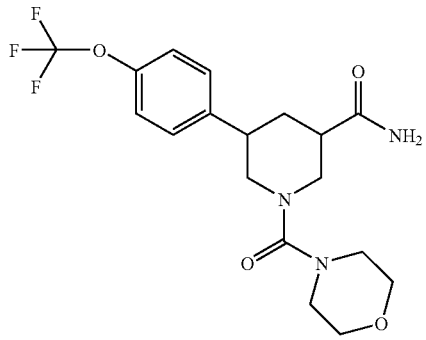

6.34 g (119.0 mmol) of thionyl chloride were added to a solution of 3.0 g (4.4 mmol) of the compound from Example 44A in 58 ml of dichloromethane. The mixture was stirred at reflux temperature for 2 h. For work-up, the dichloromethane was removed under reduced pressure, and once more dichloromethane was added to the residue and the mixture was concentrated. The residue was initially charged in 58 ml of dichloromethane and cooled to 0° C. 3.02 ml (21.1 mmol) of a 7M ammonia solution in methanol were then added. The reaction mixture was stirred at 0° C. for 4 h and at RT for 3 days. For work-up, the solvent was removed under reduced pressure and the residue was taken up in ethyl acetate. The organic phase was washed successively with water and saturated aqueous sodium chloride solution, dried over magnesium sulphate and concentrated. Yield: 820 mg (92% of theory).

LC-MS (Method 2B): $R_t$=1.03 min; MS (ESIpos): m/z=402 [M+H]$^+$.

Example 119A

Methyl 1-[(3-methoxypiperidin-1-yl)carbonyl]-5-[4-(trifluoromethyl)phenyl]piperidine-3-carboxylate [racemic cis/trans isomer mixture]

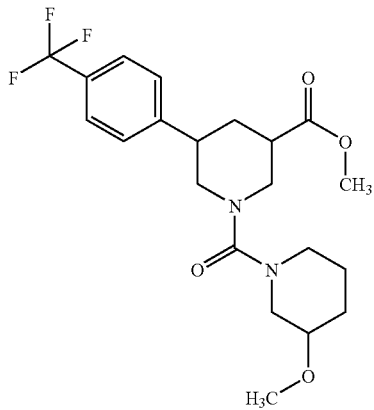

4.00 g (8.84 mmol) of 3-methyl 1-(4-nitrophenyl)5-[4-(trifluoromethyl)phenyl]piperidine-1,3-dicarboxylate and 3.35 g (22.1 mmol) of 3-methoxypiperidine hydrochloride were reacted according to the General Method 8A. Yield: 2.90 g (57% of theory, 74% pure).

LC-MS (Method 2B): $R_t$=1.31 min and 1.34 min (cis/trans isomers); MS (ESIpos): m/z=429 [M+H]$^+$.

Example 120A

N'-(3-Methoxypropanoyl)-1-(morpholin-4-ylcarbonyl)-5-[4-(trifluoromethoxy)phenyl]piperidine-3-carbohydrazide [racemic cis/trans isomer mixture]

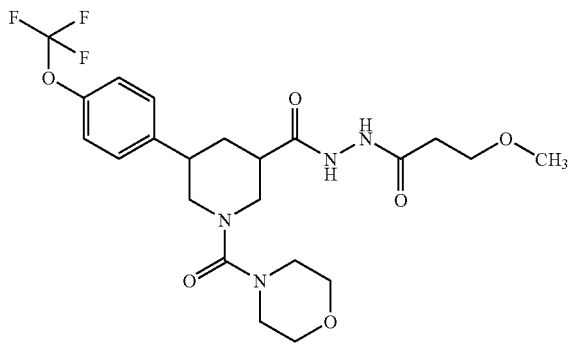

100 mg (0.25 mmol) of the compound from Example 44A and 58 mg (0.50 mmol) of 3-methoxypropanehydrazide were reacted according to the General Method 11A. Yield: 93 mg (75% of theory)

LC-MS (Method 2B): $R_t$=1.02 min; MS (ESIpos): m/z=503 [M+H]$^+$.

Example 121A

N'-Acetyl-1-(morpholin-4-ylcarbonyl)-5-[4-(trifluoromethoxy)phenyl]piperidine-3-carbohydrazide [racemic cis/trans isomer mixture]

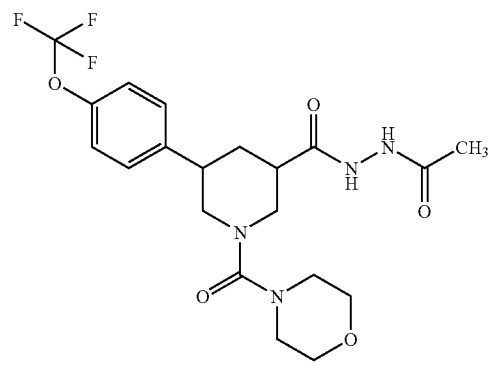

100 mg (0.25 mmol) of the compound from Example 44A and 37 mg (0.50 mmol) of acetohydrazide were reacted according to the General Method 11A. Yield: 106 mg (93% of theory)

LC-MS (Method 2B): $R_t$=0.99 min; MS (ESIpos): m/z=459 [M+H]$^+$.

Example 122A

N'-(2-Methylpropanoyl)-1-(morpholin-4-ylcarbonyl)-5-[4-(trifluoromethoxy)phenyl]piperidine-3-carbohydrazide [racemic cis/trans isomer mixture]

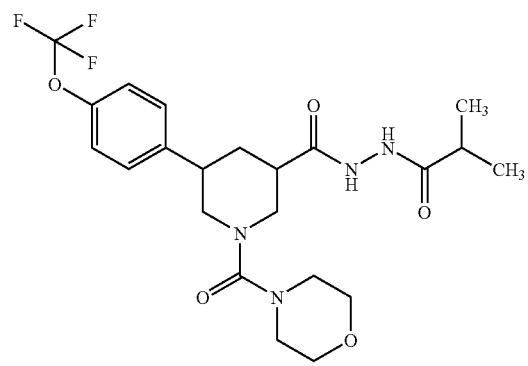

100 mg (0.25 mmol) of the compound from Example 44A and 51 mg (0.50 mmol) of 2-methylpropanehydrazide were reacted according to the General Method 11A. Yield: 80 mg (66% of theory)

LC-MS (Method 2B): $R_t$=1.07 min; MS (ESIpos): m/z=487 [M+H]$^+$.

Example 123A 1-(Morpholin-4-ylcarbonyl)-N'-(phenylcarbonyl)-5-[4-(trifluoromethoxy)phenyl]piperidine-3-carbohydrazide [racemic cis/trans isomer mixture]

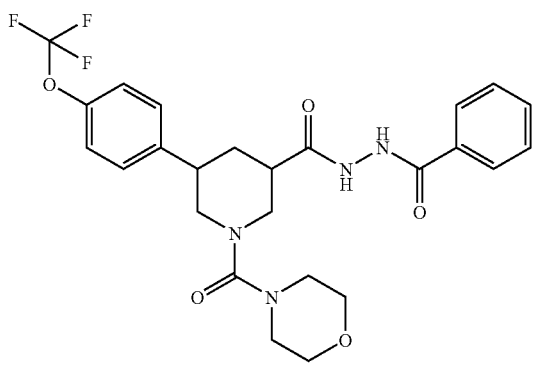

100 mg (0.25 mmol) of the compound from Example 44A and 65 mg (0.50 mmol) of benzenecarbohydrazide were reacted according to the General Method 11A.

LC-MS (Method 2B): $R_t$=1.12 min; MS (ESIpos): m/z=521 [M+H]$^+$.

Example 124A

Methyl 5-(3,4-dimethylphenyl)pyridine-3-carboxylate

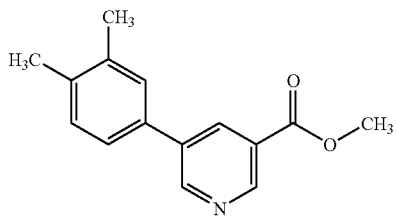

11.0 g (50.1 mmol) of methyl 5-bromonicotinate and 7.7 g (50.1 mmol) of 3,4-dimethylphenylboronic acid were reacted according to the General Method 1A. Yield: 4.0 g (31% of theory)

LC-MS (Method 3B): $R_t$=2.05 min; MS (ESIpos): m/z=242 [M+H]$^+$.

$^1$H-NMR (400 MHz, DMSO-d$_6$): δ=9.10 (d, 1H), 9.04 (d, 1H), 8.43 (dd, 1H), 7.59 (s, 1H), 7.52-7.50 (m, 1H), 7.28 (d, 1H), 3.92 (s, 3H), 2.32 (s, 3H), 2.28 (s, 3H).

Example 125A

Methyl 5-(3,4-dimethylphenyl)piperidine-3-carboxylate [racemic cis/trans isomer mixture]

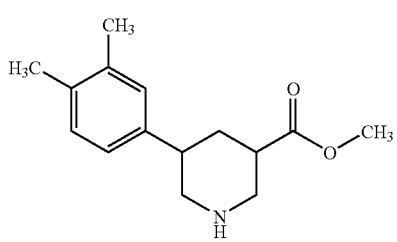

9.1 g (37.8 mmol) of the compound from Example 124A were reacted according to the General Method 2A. Yield: 5.5 g (58% of theory)

LC-MS (Method 5B): $R_t$=1.39 min and 1.43 min (cis/trans isomers); MS (ESIpos): m/z=247 [M+H]$^+$.

Example 126A

3-Methyl 1-(4-nitrophenyl)5-(3,4-dimethylphenyl)piperidine-1,3-dicarboxylate [racemic cis/trans isomer mixture]

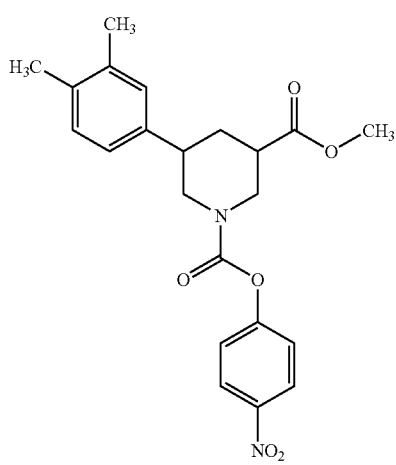

4.0 g (16.2 mmol) of the compound from Example 125A were initially charged in 80 ml of dichloromethane and cooled to 0° C., and 4.5 ml (3.3 g, 32.3 mmol) of triethylamine and 3.3 g (16.2 mmol) of 4-nitrophenyl chloroformate were added. The reaction mixture was allowed to warm slowly to RT. The mixture was twice washed with water, dried over sodium sulphate, filtered and concentrated under reduced pressure. Methanol was added to the residue, and the mixture was filtered, reconcentrated under reduced pressure and purified by preparative HPLC. Yield: 4.0 g (53% of theory, 89% pure)

LC-MS (Method 2B): $R_t$=1.49 min; MS (ESIpos): m/z=413 [M+H]$^+$.

Example 127A

Methyl 5-(3,4-dimethylphenyl)-1-[(4-hydroxypiperidin-1-yl)carbonyl]piperidine-3-carboxylate [racemic cis/trans isomer mixture]

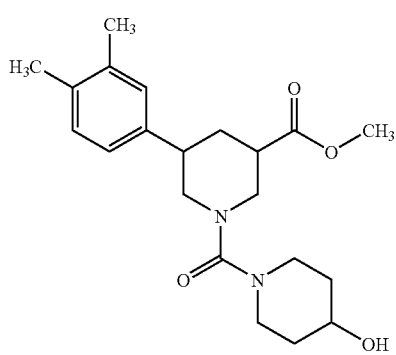

1.5 g (3.6 mmol) of the compound from Example 126A, 1.1 g (10.9 mmol) of 4-hydroxypiperidine and 0.5 g (3.6 mmol) of potassium carbonate were initially charged in 35 ml of N,N-dimethylformamide and reacted in a single-mode microwave (Emrys Optimizer) at 150° C. for 15 min. The crude product was purified by preparative HPLC. Yield: 0.9 g (56% of theory, 82% pure)

LC-MS (Method 3B): $R_t$=1.68 min and 1.74 [cis/trans isomers]; MS (ESIpos): m/z=375 [M+H]$^+$.

Example 128A 5-(3,4-Dimethylphenyl)-1-[(4-hydroxypiperidin-1-yl)carbonyl]piperidine-3-carboxylic acid [racemic cis isomer]

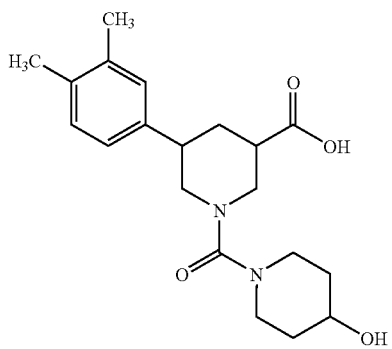

0.9 g (2.5 mmol) of the compound from Example 127A was reacted according to the General Method 9A. Yield: 0.9 g (92% of theory)

LC-MS (Method 5B): $R_t$=1.82 min; MS (ESIpos): m/z=361 [M+H]$^+$.

$^1$H-NMR (400 MHz, DMSO-d$_6$): δ=12.42 (br s, COOH), 7.07-7.03 (m, 2H), 6.97 (d, 1H), 4.66 (d, OH), 3.79 (br d, 1H), 3.58 (br d, 1H), 3.50-3.37 (m, 3H), 2.85 (t, 2H), 2.76-2.62 (m, 3H), 2.58-2.52 (m, 1H), 2.20 (s, 3H), 2.18 (s, 3H), 2.08 (br d, 1H), 1.73-1.64 (m, 3H), 1.36-1.26 (m, 2H).

Example 129A

Methyl 5-(3,4-dimethylphenyl)-1-(morpholin-4-ylcarbonyl)piperidine-3-carboxylate [racemic cis/trans isomer mixture]

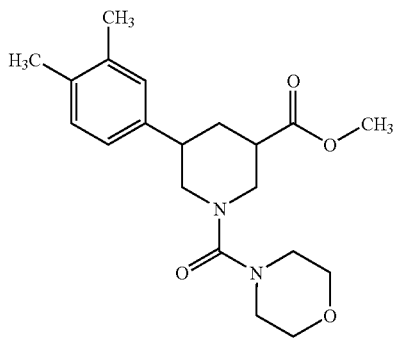

1.5 g (6.1 mmol) of the compound from Example 125A were reacted according to the General Method 3A. Yield: 0.6 g (28% of theory)

LC-MS (Method 2B): $R_t$=1.17 min; MS (ESIpos): m/z=361 [M+H]$^+$.

Example 130A 5-(3,4-Dimethylphenyl)-1-(morpholin-4-ylcarbonyl)piperidine-3-carboxylic acid [racemic cis isomer]

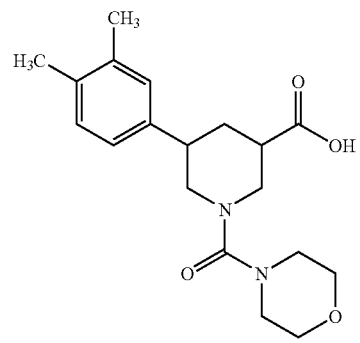

1.6 g (4.4 mmol) of the compound from Example 129A were reacted according to the General Method 9A. Yield: 1.6 g (99% of theory)

LC-MS (Method 2B): $R_t$=1.05 min; MS (ESIpos): m/z=347 [M+H]$^+$.

$^1$H-NMR (400 MHz, DMSO-d$_6$): δ=12.44 (br s, COOH), 7.08-7.02 (m, 2H), 6.96 (d, 1H), 3.84 (br d, 1H), 3.56-3.54 (m, 5H), 3.15-3.13 (m, 4H), 2.82-2.73 (m, 2H), 2.68-2.61 (m, 1H), 2.58-2.54 (m, 1H), 2.20 (s, 3H), 2.18 (s, 3H), 2.09 (br d, 1H), 1.69 (q, 1H).

Example 131A

Methyl 1-[(4-cyanopiperidin-1-yl)carbonyl]-5-(3,4-dimethylphenyl)piperidine-3-carboxylate [racemic cis/trans isomer mixture]

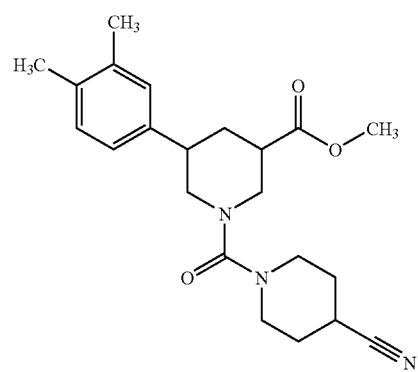

2.0 g (4.3 mmol) of the compound from Example 126A, 1.4 g (12.8 mmol) of piperidine-4-carbonitrile and 0.6 g (4.3 mmol) of potassium carbonate were initially charged in 41 ml of N,N-dimethylformamide and reacted in a single-mode microwave (Emrys Optimizer) at 150° C. for 15 min. The crude product was purified by preparative HPLC. Yield: 0.5 g (32% of theory)

LC-MS (Method 2B): $R_t$=1.23 min and 1.26 [cis/trans isomers]; MS (ESIpos): m/z=384 [M+H]$^+$.

Example 132A

1-[(4-Cyanopiperidin-1-yl)carbonyl]-5-(3,4-dimethylphenyl)piperidine-3-carboxylic acid [racemic cis isomer]

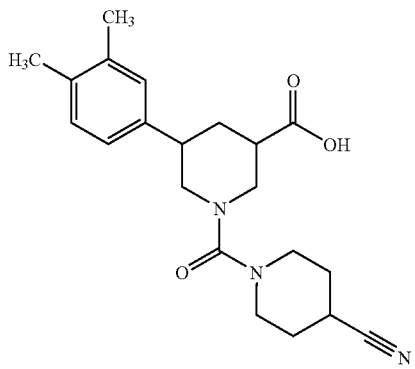

1.2 g (3.1 mmol) of the compound from Example 131A were reacted according to the General Method 9A. Yield: 1.1 g (92% of theory)

LC-MS (Method 1B): $R_t$=2.12 min; MS (ESIpos): m/z=370 [M+H]$^+$.

Example 133A

Methyl 5-(3,4-dimethylphenyl)-1-[(3-hydroxyazetidin-1-yl)carbonyl]piperidine-3-carboxylate [racemic cis/trans isomer mixture]

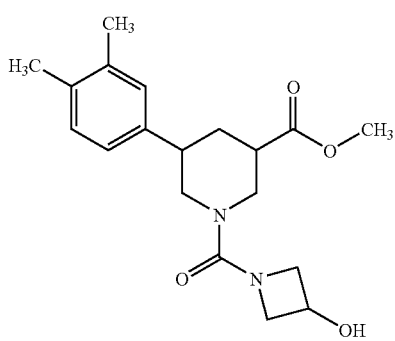

2.0 g (4.3 mmol) of the compound from Example 126A, 1.4 g (12.8 mmol) of 3-hydroxyazetidine hydrochloride and 3.5 g (25.6 mmol) of potassium carbonate were initially charged in 41 ml of N,N-dimethylformamide and reacted in a single-mode microwave (Emrys Optimizer) at 150° C. for 15 min. The crude product was purified by preparative HPLC. Yield: 0.9 g (54% of theory)

LC-MS (Method 2B): $R_t$=1.94 min and 1.99 [cis/trans isomers]; MS (ESIpos): m/z=347 [M+H]$^+$.

Example 134A 5-(3,4-Dimethylphenyl)-1-[(3-hydroxyazetidin-1-yl)carbonyl]piperidine-3-carboxylic acid [racemic cis isomer]

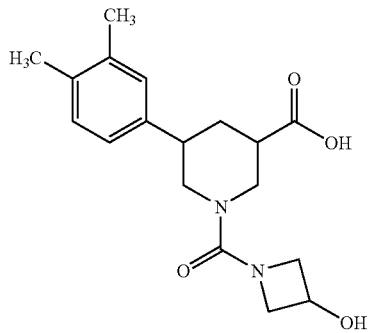

1.0 g (2.8 mmol) of the compound from Example 133A was reacted according to the General Method 9A. Yield: 0.8 g (84% of theory)

LC-MS (Method 3B): $R_t$=1.40 min; MS (ESIpos): m/z=333 [M+H]$^+$.

$^1$H-NMR (400 MHz, DMSO-d$_6$): δ=12.44 (br s, COOH), 7.08-7.04 (m, 2H), 6.96 (d, 1H), 5.55 (d, OH), 4.39-4.33 (m, 1H), 4.06-3.97 (m, 3H), 3.67-3.56 (m, 3H), 2.73 (q, 2H), 2.61-2.43 (m, 2H, tw. under the DMSO signal), 2.20 (s, 3H), 2.18 (s, 3H), 2.07 (br d, 1H), 1.71 (q, 1H).

Example 135A

3-Methyl 1-(4-nitrophenyl)5-(4-ethylphenyl)piperidine-1,3-dicarboxylate [racemic cis/trans isomer mixture]

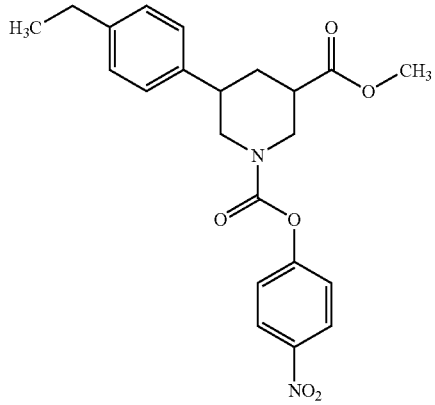

3.0 g (12.1 mmol) of the compound from Example 2A were initially charged in 30 ml of dichloromethane and cooled to 0° C., and 3.4 ml (2.4 g, 12.1 mmol) of triethylamine and 2.4 g (12.1 mmol) of 4-nitrophenyl chloroformate were added. The reaction mixture was allowed to warm slowly to RT and stirred at RT for 16 h. The mixture was washed repeatedly

Example 136A

Methyl 1-[(4-cyanopiperidin-1-yl)carbonyl]-5-(4-ethylphenyl)piperidine-3-carboxylate [racemic cis/trans isomer mixture]

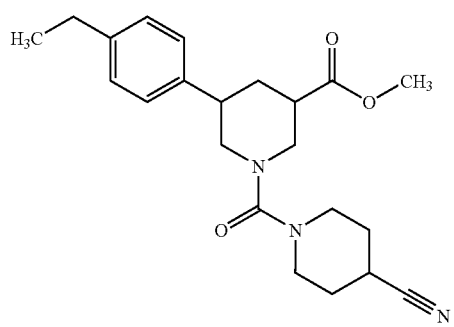

3.1 g (7.5 mmol) of the compound from Example 135A, 2.5 g (22.4 mmol) of piperidine-4-carbonitrile and 2.1 g (15.0 mmol) of potassium carbonate were initially charged in 56 ml of N,N-dimethylformamide and reacted in a single-mode microwave (Emrys Optimizer) at 150° C. for 30 min. The reaction mixture was taken up in ethyl acetate and washed repeatedly with water and saturated aqueous sodium chloride solution. The organic phase was dried over magnesium sulphate, filtered and concentrated under reduced pressure. The residue was purified by column chromatography on silica gel (mobile phase: cyclohexane/ethyl acetate 1:1). Yield: 2.4 g (73% of theory)

HPLC (Method 1A): $R_t$=4.42 min and 4.49 min [cis/trans isomers]; MS (ESIpos): m/z=384 [M+H]$^+$.

Example 137A

Methyl 5-(4-ethylphenyl)-1-[(3-hydroxyazetidin-1-yl)carbonyl]piperidine-3-carboxylate [racemic cis/trans isomer mixture]

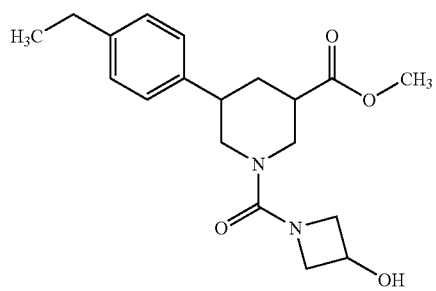

0.3 g (0.7 mmol) of the compound from Example 135A, 0.2 g (2.18 mmol) of 3-hydroxyazetidine hydrochloride and 0.2 g (1.4 mmol) of potassium carbonate were initially charged in 6 ml of N,N-dimethylformamide and reacted in a single-mode microwave (Emrys Optimizer) at 150° C. for 30 min. The crude product was purified by preparative HPLC. Yield: 21 mg (8% of theory)

LC-MS (Method 3B): $R_t$=1.76 min and 1.85 [cis/trans isomers]; MS (ESIpos): m/z=361 [M+H]$^+$.

Example 138A 5-(4-Ethylphenyl)-1-[(3-hydroxyazetidin-1-yl)carbonyl]piperidine-3-carboxylic acid [racemic cis isomer]

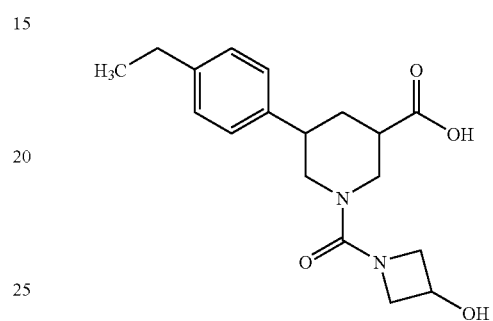

300 mg (0.83 mmol) of the compound from Example 137A were reacted according to the General Method 9A. Yield: 250 mg (90% of theory)

LC-MS (Method 3B): $R_t$=1.44 min; MS (ESIpos): m/z=333 [M+H]$^+$.

$^1$H-NMR (400 MHz, DMSO-$d_6$): δ=12.42 (br s, COOH), 7.18-7.13 (m, 4H), 5.54 (br s, OH), 4.39-4.33 (m, 1H), 4.08-3.97 (m, 3H), 3.68-3.62 (m, 3H), 2.78-2.70 (m, 2H), 2.68-2.54 (m, 3H), 2.48-2.42 (m, 1H), 2.08 (br d, 1H), 1.71 (q, 1H), 1.15 (t, 3H).

Example 139A 5-(4-Ethylphenyl)-1-(morpholin-4-ylcarbonyl)piperidine-3-carboxamide [racemic cis isomer mixture]

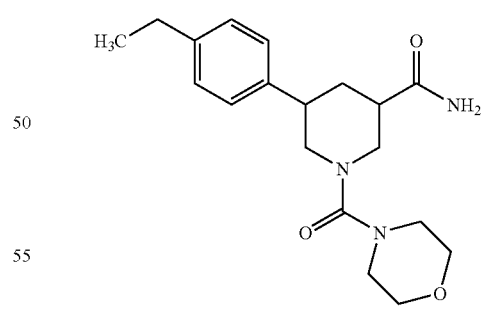

4.77 g (40.15 mmol) of thionyl chloride were added to a solution of 4.80 g (13.39 mmol) of the compound from Example 38A in 180 ml of dichloromethane. The mixture was stirred under reflux for 2 h. For work-up, the dichloromethane was removed under reduced pressure, and once more, dichloromethane was added to the residue and evaporated. The residue was initially charged in 55 ml of tetrahydrofuran and cooled to 0° C. 17 ml (133.4 mmol) of a 7M solution of ammonia in methanol were then added. The reaction mixture

--- with water, dried over sodium sulphate, filtered and concentrated under reduced pressure. The residue was purified by column chromatography on silica gel (mobile phase dichloromethane dichloromethane/methanol 100:2). Yield: 4.7 g (83% of theory, 89% pure)

HPLC (Method 1A): $R_t$=4.94 min and 5.00 min (cis/trans isomer); MS (ESIpos): m/z=413 [M+H]$^+$.

was stirred at 0° C. for 1 h and then overnight at RT. For work-up, the solvent was removed under reduced pressure and the residue was taken up in ethyl acetate. The organic phase was washed successively with water and saturated aqueous sodium chloride solution, dried over magnesium sulphate and concentrated. Yield: 3.74 g (82% of theory).

LC-MS (Method 1B): $R_t$=1.89 min; MS (ESIpos): m/z=346 [M+H]$^+$;

$^1$H-NMR (400 MHz, DMSO-d$_6$): δ=7.39 (br s, 1H), 7.18 (d, 2H), 7.15 (d, 2H), 6.89 (br s, 1H), 3.70 (br d, 1H), 3.60-3.52 (5H), 3.20-3.09 (m, 4H), 2.83-2.64 (m, 3H), 2.57 (q, 2H), 2.44 (tt, 1H), 1.98 (br d, 1H), 1.73 (q, 1H), 1.16 (t, 3H).

Example 140A 5-(4-Ethylphenyl)-1-(morpholin-4-ylcarbonyl)piperidine-3-carbothioamide [racemic cis isomer mixture]

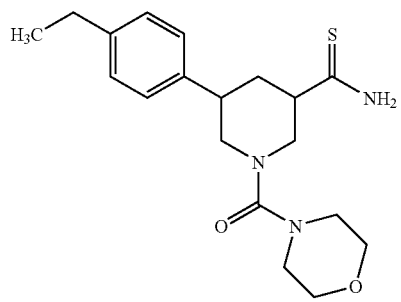

910 mg (2.63 mmol) of 5-(4-ethylphenyl)-1-(morpholin-4-ylcarbonyl)piperidine-3-carboxamide (Example 139A) and 586 mg (1.45 mmol) of Lawesson reagent were reacted according to the General Method 10A. Yield: 849 mg (89% of theory).

LC-MS (Method 2B): $R_t$=1.73 min; MS (ESIpos): m/z=362 [M+H]$^+$.

Example 141A 4-({3-[4-(Chloromethyl)-1,3-thiazol-2-yl]-5-(4-ethylphenyl)piperidin-1-yl}carbonyl)morpholine [racemic cis/trans isomer mixture]

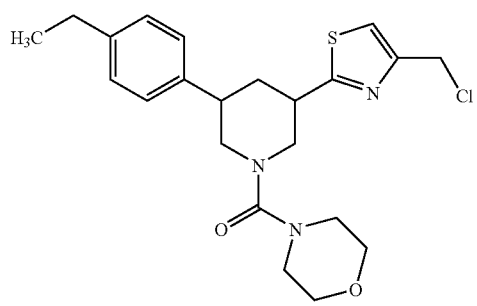

860 mg (2.38 mmol) of 5-(4-ethylphenyl)-1-(morpholin-4-ylcarbonyl)piperidine-3-carbothioamide (Example 140A) and 362 mg (2.85 mmol) of dichloroacetone were reacted according to the General Method 3. Yield: 498 mg (43% of theory).

LC-MS (Method 5B): $R_t$=2.36 min and 2.44 min (cis/trans isomere); MS (ESIpos): m/z=434 [M+H]$^+$.

Example 142A

Ethyl 2-[5-(4-ethylphenyl)-1-(morpholin-4-ylcarbonyl)piperidin-3-yl]-1,3-thiazole-4-carboxylate [racemic cis/trans isomer mixture]

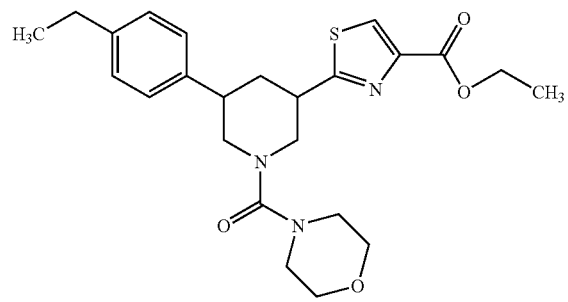

850 mg of the compound from Example 140A and 550 mg (2.82 mmol) of ethyl 3-bromo-oxopropanoate were reacted according to the General Method 3. Yield: 150 mg (12% of theory).

LC-MS (Method 2B): $R_t$=1.33 min; MS (ESIpos): m/z=458 [M+H]$^+$.

Example 143A

2-[5-(4-Ethylphenyl)-1-(morpholin-4-ylcarbonyl)piperidin-3-yl]-1,3-thiazole-4-carboxylic acid [racemic cis/trans isomer mixture]

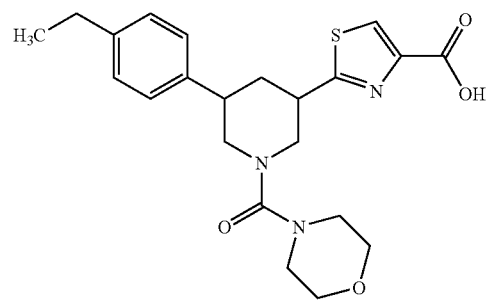

650 mg (1.42 mmol) of the compound from Example 142A were reacted according to the General Method 4A. Yield: 590 mg (97% of theory)

LC-MS (Method 3B): $R_t$=1.67 min and 1.76 min (cis/trans isomers); MS (ESIpos): m/z=430 [M+H]$^+$.

Example 144A

Methyl 5-[3-(trifluoromethyl)phenyl]pyridine-3-carboxylate

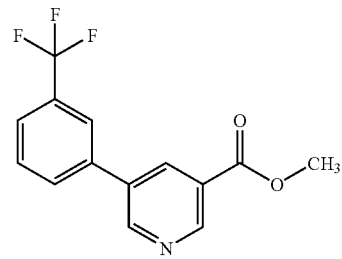

10.0 g (46.3 mmol) of methyl 5-bromonicotinate and 10.6 g (55.5 mmol) of 3-trifluoromethylphenylboronic acid were reacted according to the General Method 1A. Yield: 11.9 g (91% of theory)

LC-MS (Method 2B): $R_t$=1.25 min; MS (ESIpos): m/z=282 [M+H]$^+$;

$^1$H-NMR (400 MHz, DMSO-d$_6$): δ=9.22 (d, 1H), 9.12 (d, 1H), 8.57 (dd, 1H), 8.16-8.12 (m, 2H), 7.84 (d, 1H), 7.79-7.75 (m, 1H), 3.94 (s, 3H).

Example 145A

Methyl 5-[3-(trifluoromethyl)phenyl]piperidine-3-carboxylate [racemic cis/trans isomer mixture]

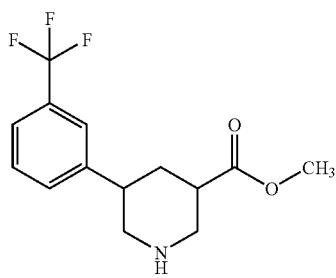

11.0 g (39.1 mmol) of the compound from Example 144A were reacted according to the General Method 2A. Yield: 9.3 g (79% of theory)

LC-MS (Method 2B): $R_t$=0.83 min and 0.85 min (cis/trans isomers); MS (ESIpos): m/z=247 [M+H]$^+$.

Example 146A

Methyl 1-(morpholin-4-ylcarbonyl)-5-[3-(trifluoromethyl)phenyl]piperidine-3-carboxylate [racemic cis/trans isomer mixture]

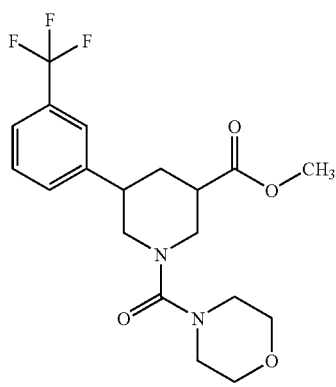

7.0 g (24.4 mmol) of the compound from Example 145A were reacted according to the General Method 3A. Yield: 9.8 g (94% of theory)

LC-MS (Method 1B): $R_t$=2.24 min; MS (ESIpos): m/z=401 [M+H]$^+$.

Example 147A 1-(Morpholin-4-ylcarbonyl)-5-[3-(trifluoromethyl)phenyl]piperidine-3-carboxylic acid [racemic cis isomer]

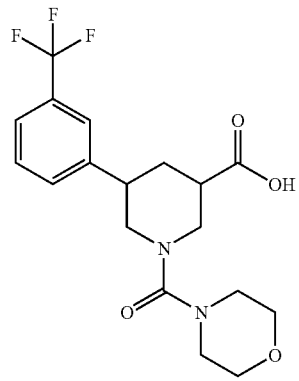

9.8 g (24.5 mmol) of the compound from Example 146A were reacted according to the General Method 9A. Yield: 8.7 g (92% of theory)

LC-MS (Method 2B): $R_t$=1.06 min; MS (ESIpos): m/z=387 [M+H]$^+$;

$^1$H-NMR (400 MHz, DMSO-d$_6$): δ=12.48 (br s, COOH), 7.67-7.55 (m, 4H), 3.83 (br d, 1H), 3.61-3.54 (m, 5H), 3.17-3.11 (m, 4H), 2.91-2.82 (m, 3H), 2.62-2.55 (m, 1H), 2.14 (br d, 1H), 1.79 (q, 1H).

Example 148A

3-Methyl 1-(4-nitrophenyl)5-[3-(trifluoromethyl)phenyl]piperidin-1,3-dicarboxylate [racemic cis/trans isomer mixture]

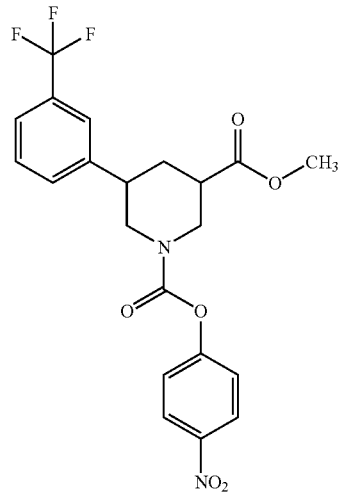

5.0 g (16.2 mmol) of the compound from Example 145A were initially charged in 80 ml of dichloromethane and cooled to 0° C., and 4.5 ml (3.3 g, 32.5 mmol) of triethylamine and 3.3 g (16.2 mmol) of 4-nitrophenyl chloroformate were added. The reaction mixture was allowed to warm slowly to RT. The mixture was twice washed with water, dried over sodium sulphate, filtered and concentrated under reduced pressure. Yield: 6.4 g (78% of theory, 89% pure)

LC-MS (Method 2B): $R_t$=1.44 min and 1.46 min (cis/trans isomer); MS (ESIpos): m/z=453 [M+H]$^+$.

Example 149A

Methyl 1-[(4-hydroxypiperidin-1-yl)carbonyl]-5-[3-(trifluoromethyl)phenyl]piperidine-3-carboxylate [racemic cis/trans isomer mixture]

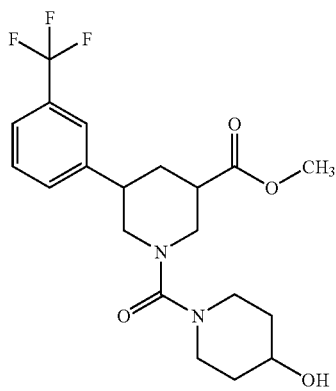

2.2 g (4.3 mmol) of the compound from Example 148A, 1.3 g (13.0 mmol) of 4-hydroxypiperidine and 0.6 g (4.3 mmol) of potassium carbonate were initially charged in 42 ml of N,N-dimethylformamide and reated in a single-mode microwave (Emrys Optimizer) at 150° C. for 15 min. The reaction mixture was purified by preparative HPLC. Yield: 1.0 g (57% of theory)

LC-MS (Method 3B): $R_t$=1.70 min and 1.76 min [cis/trans isomers]; MS (ESIpos): m/z=415 [M+H]$^+$.

Example 150A

1-[(4-Hydroxypiperidin-1-yl)carbonyl]-5-[3-(trifluoromethyl)phenyl]piperidine-3-carboxylic acid [racemic cis isomer]

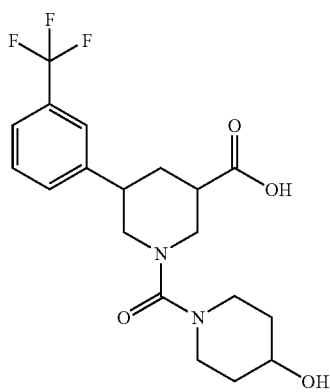

1.0 g (2.5 mmol) of the compound from Example 149A was reacted according to the General Method 9A. Yield: 0.7 g (58% of theory)

LC-MS (Method 2B): $R_t$=0.99 min; MS (ESIpos): m/z=401 [M+H]$^+$;

$^1$H-NMR (400 MHz, CDCl$_3$): δ=12.40 (br s, COOH), 7.64-7.55 (m, 4H), 3.79 (br d, 1H), 3.62-3.56 (m, 1H), 3.52 (br d, 1H), 3.46-3.43 (m, 2H), 2.96-2.82 (m, 5H), 2.61-2.56 (m, 1H), 2.13 (br d, 1H), 1.78 (q, 1H), 1.72-1.70 (m, 2H), 1.33-1.26 (m, 2H).

Example 151A

Methyl 1-[(4-cyanopiperidin-1-yl)carbonyl]-5-[3-(trifluoromethyl)phenyl]piperidine-3-carboxylate [racemic cis/trans isomer mixture]

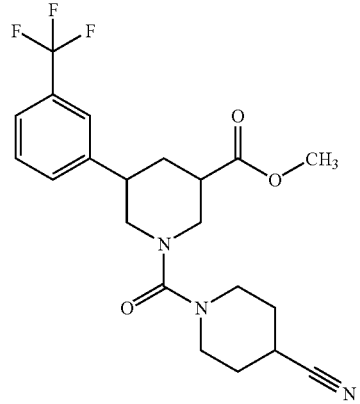

2.5 g (4.9 mmol) of the compound from Example 148A, 1.6 g (14.8 mmol) of piperidine-4-carbonitrile and 0.7 g (4.9 mmol) of potassium carbonate were initially charged in 47 ml of N,N-dimethylformamide and reacted in a single-mode microwave (Emrys Optimizer) at 150° C. for 15 min. The reaction mixture was taken up in ethyl acetate and washed repeatedly with water. The organic phase was dried over sodium sulphate, filtered and concentrated under reduced pressure. The residue was purified by column chromatography on silica gel (mobile phase: dichloromethane/methanol 100:5). The crude product was reacted further without further purification.

LC-MS (Method 5B): $R_t$=2.22 min and 2.28 min [cis/trans isomers]; MS (ESIpos): m/z=424 [M+H]$^+$.

Example 152A

1-[(4-Cyanopiperidin-1-yl)carbonyl]-5-[3-(trifluoromethyl)phenyl]piperidine-3-carboxylic acid [racemic cis isomer]

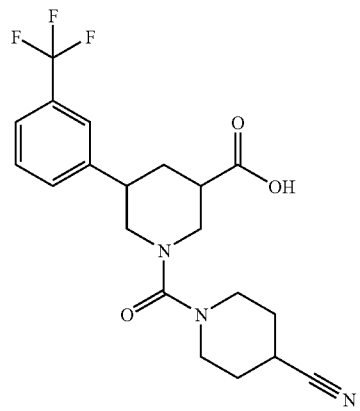

2.9 g (5.6 mmol) of the compound from Example 151A were reacted according to the General Method 9A. Yield: 1.5 g (64% of theory)

LC-MS (Method 2B): $R_t$=1.12 min; MS (ESIpos): m/z=410 [M+H]$^+$.

$^1$H-NMR (400 MHz, CDCl$_3$): δ=12.48 (br s, COOH), 7.66 (s, 1H), 7.62-7.54 (m, 3H), 3.79 (br d, 1H), 3.54 (br d, 1H), 3.36-3.32 (m, 3H), 3.07-3.02 (m, 3H), 2.91-2.81 (m, 2H), 2.62-2.56 (m, 1H), 2.14 (br d, 1H), 1.88-1.76 (m, 3H), 1.70-1.63 (m, 2H).

Example 153A

Methyl 1-[(3-hydroxyazetidin-1-yl)carbonyl]-5-[3-(trifluoromethyl)phenyl]piperidine-3-carboxylate [racemic cis/trans isomer mixture]

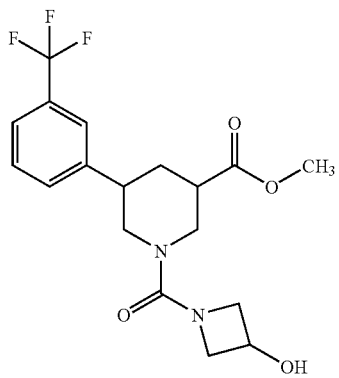

2.5 g (4.9 mmol) of the compound from Example 148A, 1.6 g (14.8 mmol) of 3-hydroxyazetidine hydrochloride and 1.4 g (9.8 mmol) of potassium carbonate were initially charged in 47 ml of N,N-dimethylformamide and reacted in a single-mode microwave (Emrys Optimizer) at 150° C. for 15 min. The crude product was purified by preparative HPLC. Yield: 0.4 g (21% of theory)

LC-MS (Method 5B): $R_t$=1.93 min and 1.98 min [cis/trans isomers]; MS (ESIpos): m/z=387 [M+H]$^+$.

Example 154A

Methyl 1-[(3-hydroxyazetidin-1-yl)carbonyl]-5-[3-(trifluoromethyl)phenyl]piperidine-3-carboxylate [racemic cis isomer]

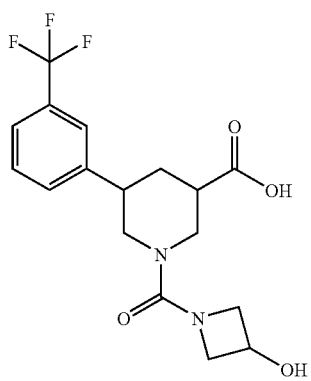

400 mg (1.01 mmol) of the compound from Example 153A were reacted according to the General Method 9A. Yield: 340 mg (89% of theory)

LC-MS (Method 2B): $R_t$=0.97 min; MS (ESIpos): m/z=373 [M+H]$^+$.

$^1$H-NMR (400 MHz, DMSO-d$_6$): δ=12.49 (br s, COOH), 7.66-7.55 (m, 4H), 5.56 (br s, OH), 4.41-4.34 (m, 1H), 4.05 (q, 2H), 3.97 (br d, 1H), 3.69-3.58 (m, 3H), 2.91-2.79 (m, 3H), 2.12 (br d, 1H), 1.85 (q, 1H).

Example 155A

Methyl 1-[(3-hydroxypyrrolidin-1-yl)carbonyl]-5-[3-(trifluoromethyl)phenyl]piperidine-3-carboxylate [mixture of diastereomers]

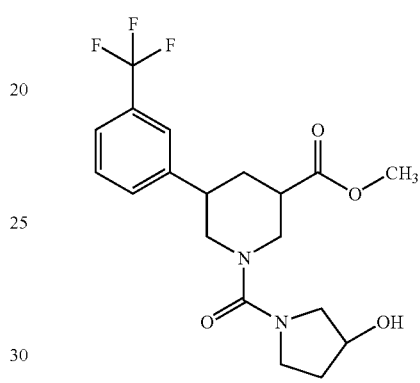

5.0 g (9.8 mmol) of the compound from Example 148A, 2.7 g (29.5 mmol) of 3-pyrrolidinol and 1.4 g (9.8 mmol) of potassium carbonate were initially charged in 95 ml of N,N-dimethylformamide and reacted in a single-mode microwave (Emrys Optimizer) at 150° C. for 15 min. Water was added, and the reaction mixture was extracted with ethyl acetate. The combined organic extracts were dried over sodium sulphate, filtered and concentrated under reduced pressure. The crude product was purified by column chromatography on silica gel (mobile phase dichloromethane/methanol 100:1→100:5). Yield: 3.6 g (83% of theory)

LC-MS (Method 9B): $R_t$=0.96 min and 0.98 min; MS (ESIpos): m/z=401 [M+H]$^+$.

Example 156A

1-[(3-Hydroxypyrrolidin-1-yl)carbonyl]-5-[3-(trifluoromethyl)phenyl]piperidine-3-carboxylic acid [mixture of diastereomers, cis isomer]

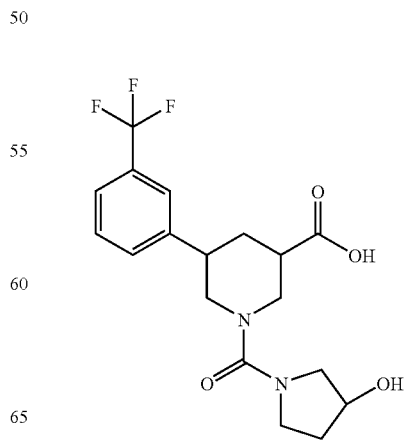

1.3 g (1.6 mmol) of the compound from Example 155A were reacted according to the General Method 9A. Yield: 0.6 g (91% of theory)

LC-MS (Method 2B): $R_t$=1.00 min; MS (ESIpos): m/z=387 [M+H]$^+$.

Example 157A

Methyl 5-[4-methyl-3-(trifluoromethyl)phenyl]pyridine-3-carboxylate

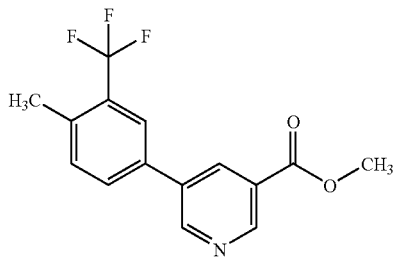

Step a):
[4-Methyl-3-(trifluoromethyl)phenyl]boronic acid

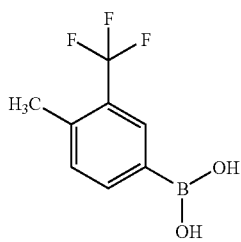

At −78° C., 9.2 ml (1.5 g, 23.0 mmol) of a 2.5M solution of n-butyllithium in hexane were initially charged in 30 ml of THF. 5.0 g (20.9 mmol) of 4-methyl-3-(trifluoromethyl)bromobenzene were dissolved in 15 ml of THF and slowly added dropwise. 3.3 g (31.4 mmol) of trimethylboronic acid were then added dropwise. The mixture was stirred at −78° C. for 2 h, and 11 ml of 2 N hydrochloric acid were then added. The mixture was allowed to warm to RT, and the organic phase was separated off. The solvent was removed under reduced pressure and the residue was recrystallized from n-heptane. Yield: 2.6 g (60% of theory)

LC-MS (Method 9B): $R_t$=0.91 min; MS (ESIpos): m/z=204 [M+H]$^+$.

Step b): Methyl 5-[4-methyl-3-(trifluoromethyl)phenyl]pyridine-3-carboxylate

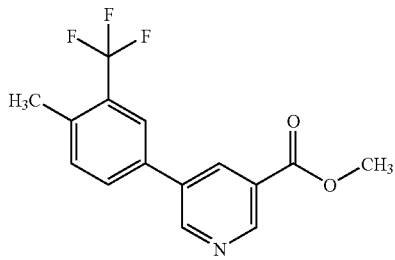

2.2 g (10.3 mmol) of methyl 5-bromonicotinate and 2.5 g (12.4 mmol) of [4-methyl-3-(trifluoromethyl)phenyl]boronic acid were reacted according to the General Method 1A. Yield: 2.6 g (86% of theory)

LC-MS (Method 3B): $R_t$=2.18 min; MS (ESIpos): m/z=296 [M+H]$^+$.

$^1$H-NMR (400 MHz, DMSO-$d_6$): δ=9.20 (d, 1H), 9.10 (d, 1H), 8.54 (dd, 1H), 8.04-8.00 (m, 2H), 7.61 (d, 1H), 3.94 (s, 3H).

Example 158A

Methyl 5-[4-methyl-3-(trifluoromethyl)phenyl]piperidine-3-carboxylate [racemic cis/trans isomer mixture]

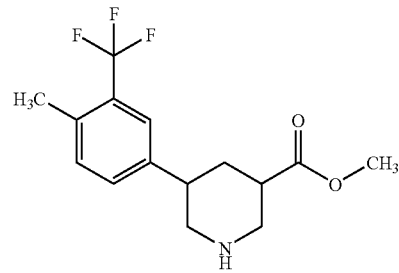

1.0 g (3.4 mmol) of the compound from Example 157A were reacted according to the General Method 12A. Yield: 0.7 g (70% of theory)

LC-MS (Method 9B): $R_t$=0.76 min (cis/trans isomers); MS (ESIpos): m/z=302 [M+H]$^+$.

Example 159A

Methyl 5-[4-methyl-3-(trifluoromethyl)phenyl]-1-(morpholin-4-ylcarbonyl)piperidine-3-carboxylate [racemic cis/trans isomer mixture]

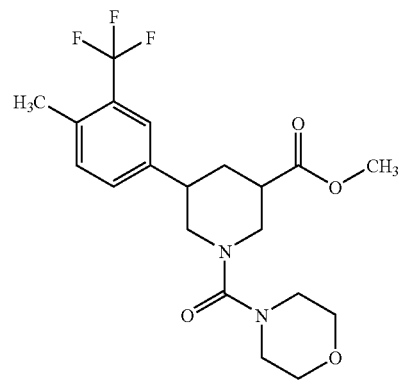

920 mg (3.1 mmol) of the compound from Example 158A were reacted according to the General Method 3A. Yield: 674 mg (53% of theory)

LC-MS (Method 2B): $R_t$=1.26 min and 1.29 min [cis/trans isomers]; MS (ESIpos): m/z=415 [M+H]$^+$.

Example 160A

5-[4-Methyl-3-(trifluoromethyl)phenyl]-1-(morpholin-4-ylcarbonyl)piperidine-3-carboxylic acid [racemic cis isomer]

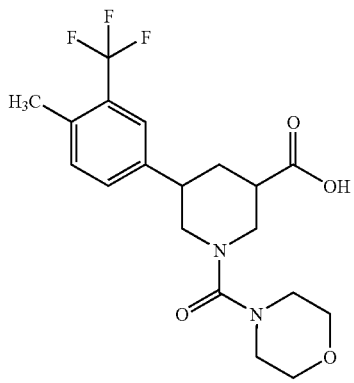

354 mg (0.85 mmol) of the compound from Example 159A were reacted according to the General Method 9A. Yield: 279 mg (78% of theory)

LC-MS (Method 2B): $R_t$=1.14 min; MS (ESIpos): m/z=401 [M+H]$^+$.

$^1$H-NMR (400 MHz, DMSO-d$_6$): δ=12.47 (br s, COOH), 7.57 (s, 1H), 7.52-7.49 (m, 1H), 7.39 (d, 1H), 3.83 (br d, 1H), 3.56-3.53 (m, 5H), 3.16-3.14 (m, 4H), 2.87-2.80 (m, 3H), 2.62-2.55 (m, 1H), 2.12 (br d, 1H), 1.76 (q, 1H).

Example 161A

3-Methyl 1-(4-nitrophenyl)5-[4-methyl-3-(trifluoromethyl)phenyl]piperidine-1,3-dicarboxylate [racemic cis/trans isomer mixture]

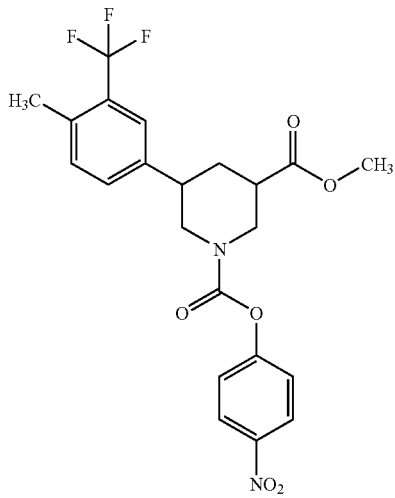

915 mg (3.04 mmol) of the compound from Example 158A were initially charged in 10 ml of dichloromethane and cooled to 0° C., and 0.85 ml (615 mg, 6.07 mmol) of triethylamine and 612 mg (3.04 mmol) of 4-nitrophenyl chloroformate were added. The reaction mixture was allowed to warm slowly to RT. The mixture was twice washed with water, dried over magnesium sulphate, filtered and concentrated under reduced pressure. Methanol was added to the residue, and the mixture was filtered, reconcentrated under reduced pressure and purified by column chromatography on silica gel (mobile phase cyclohexane/ethyl acetate 1:1). Yield: 921 mg (63% of theory)

LC-MS (Method 2B): $R_t$=1.52 min; MS (ESIpos): m/z=467 [M+H]$^+$.

Example 162A

Methyl 1-[(4-hydroxypiperidin-1-yl)carbonyl]-5-[4-methyl-3-(trifluoromethyl)phenyl]piperidine-3-carboxylate [racemic cis/trans isomer mixture]

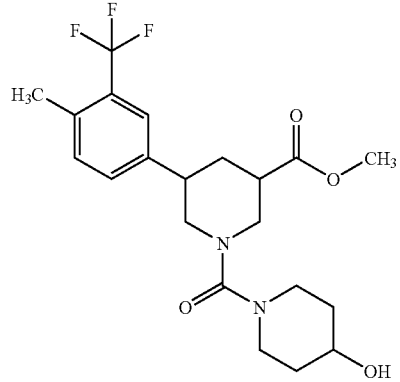

332 mg (0.67 mmol) of the compound from Example 161A, 203 mg (2.01 mmol) of 4-hydroxypiperidine and 92 mg (0.67 mmol) of potassium carbonate were initially charged in 6 ml of N,N-dimethylformamide and reacted in a single-mode microwave (Emrys Optimizer) at 150° C. for 30 min. The crude product was purified by preparative HPLC. Yield: 201 mg (70% of theory)

LC-MS (Method 9B): $R_t$=1.03 min and 1.06 min [cis/trans isomers]; MS (ESIpos): m/z=429 [M+H]$^+$.

Example 163A

1-[(4-Hydroxypiperidin-1-yl)carbonyl]-5-[4-methyl-3-(trifluoromethyl)phenyl]piperidine-3-carboxylic acid [racemic cis isomer]

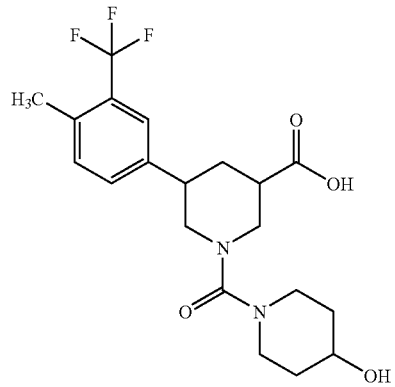

775 mg (1.81 mmol) of the compound from Example 162A were reacted according to the General Method 9A. Yield: 727 mg (97% of theory)

LC-MS (Method 9B): $R_t$=0.93 min; MS (ESIpos): m/z=415 [M+H]$^+$.

Example 164A

Methyl 5-[3-methyl-4-(trifluoromethoxy)phenyl]pyridine-3-carboxylate

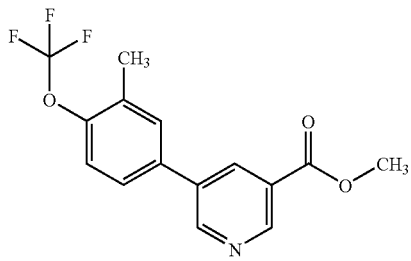

Step a):
[3-Methyl-4-(trifluoromethoxy)phenyl]boronic acid

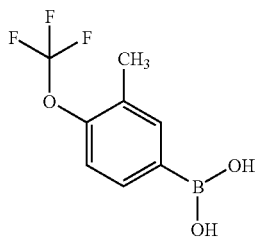

At −78° C., 8.5 ml (1.4 g, 21.1 mmol) of a 2.5M solution of n-butyllithium in hexane were initially charged in 30 ml of THF. 4.9 g (19.2 mmol) of 4-bromo-2-methyl(trifluoromethoxy)benzene were dissolved in 15 ml of THF and slowly added dropwise. 3.0 g (28.8 mmol) of trimethylboronic acid were then added dropwise. The mixture was stirred at −78° C. for 2 h, and 11 ml of 2 N hydrochloric acid were then added. The mixture was allowed to warm to RT, and the organic phase was separated off. The solvent was removed under reduced pressure and the residue was recrystallized from n-heptane. Yield: 3.3 g (78% of theory)

LC-MS (Method 2B): $R_t$=1.08 min; MS (ESIpos): m/z=221 [M+H]$^+$.

Step b): Methyl 5-[3-methyl-4-(trifluoromethoxy)phenyl]pyridine-3-carboxylate

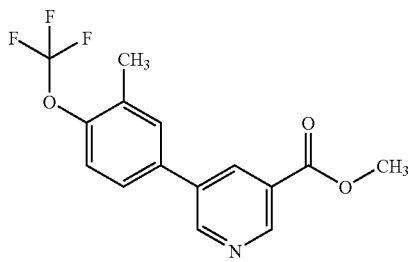

2.7 g (12.5 mmol) of methyl 5-bromonicotinate and 3.3 g (15.0 mmol) of [3-methyl-4-(trifluoromethoxy)phenyl]boronic acid were reacted according to the General Method 1A. Yield: 3.1 g (80% of theory)

LC-MS (Method 2B): $R_t$=1.36 min; MS (ESIpos): m/z=312 [M+H]$^+$.

$^1$H-NMR (400 MHz, DMSO-d$_6$): δ=9.16 (d, 1H), 9.09 (d, 1H), 8.51 (dd, 1H), 7.88 (d, 1H), 7.77-7.75 (m, 1H), 7.46 (dd, 1H), 3.93 (s, 3H), 2.38 (s, 3H).

Example 165A

Methyl 5-[3-methyl-4-(trifluoromethoxy)phenyl]piperidine-3-carboxylate [racemic cis/trans isomer mixture]

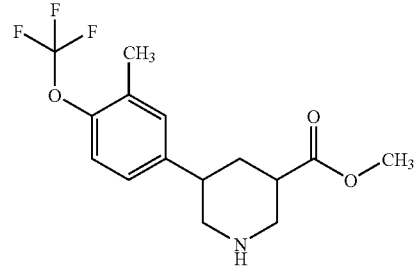

1.0 g (3.4 mmol) of the compound from Example 164A was reacted according to the General Method 12A. Yield: 841 mg (78% of theory)

LC-MS (Method 2B): $R_t$=0.90 min and 0.94 min (cis/trans isomers); MS (ESIpos): m/z=318 [M+H]$^+$.

Example 166A

Methyl 5-[3-methyl-4-(trifluoromethoxy)phenyl]-1-(morpholin-4-ylcarbonyl)piperidine-3-carboxylate [racemic cis/trans isomer mixture]

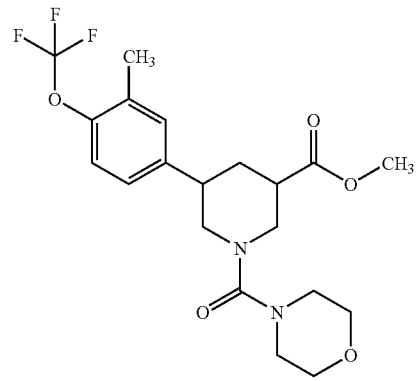

1.2 g (3.6 mmol) of the compound from Example 165A were reacted according to the General Method 3A. Yield: 1.3 g (82% of theory)

LC-MS (Method 2B): $R_t$=2.06 min and 2.13 min [cis/trans isomers]; MS (ESIpos): m/z=431 [M+H]$^+$.

Example 167A

5-[3-Methyl-4-(trifluoromethoxy)phenyl]-1-(morpholin-4-ylcarbonyl)piperidine-3-carboxylic acid [racemic cis isomer]

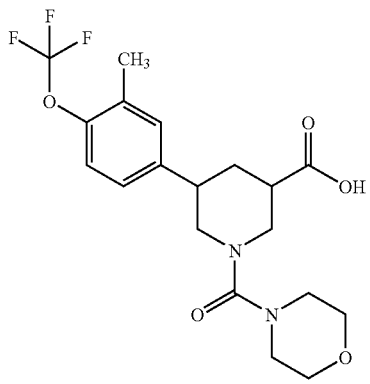

1.28 g (2.97 mmol) of the compound from Example 166A were reacted according to the General Method 9A. Yield: 1.15 g (93% of theory)

LC-MS (Method 2B): $R_t$=1.16 min; MS (ESIpos): m/z=417 [M+H]$^+$.

$^1$H-NMR (400 MHz, DMSO-d$_6$): δ=12.46 (br s, COOH), 7.32 (s, 1H), 7.27-7.21 (m, 2H), 3.84 (br d, 1H), 3.60-3.51 (m, 5H), 3.17-3.15 (m, 4H), 2.85-2.74 (m, 3H), 2.61-2.54 (m, 1H), 2.67 (s, 3H), 2.12 (br d, 1H), 1.72 (q, 1H).

Example 168A

3-Methyl 1-(4-nitrophenyl)5-[3-methyl-4-(trifluoromethoxy)phenyl]piperidine-1,3-dicarboxylate [racemic cis/trans isomer mixture]

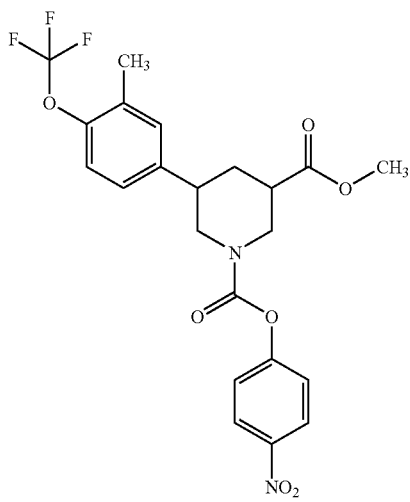

1.15 g (3.62 mmol) of the compound from Example 165A were initially charged in 10 ml of dichloromethane and cooled to 0° C., and 1.01 ml (734 mg, 7.25 mmol) of triethylamine and 731 mg (3.62 mmol) of 4-nitrophenyl chloroformate were added. The reaction mixture was allowed to warm slowly to RT and stirred at RT for 16 h. The mixture was washed repeatedly with water, dried over magnesium sulphate, filtered and concentrated under reduced pressure. Yield: 1.62 g (93% of theory)

LC-MS (Method 2B): $R_t$=1.53 min and 1.55 min [cis/trans isomers]; MS (ESIpos): m/z=483 [M+H]$^+$.

Example 169A

Methyl 1-[(4-hydroxypiperidin-1-yl)carbonyl]-5-[3-methyl-4-(trifluoromethoxy)phenyl]piperidine-3-carboxylate [racemic cis/trans isomer mixture]

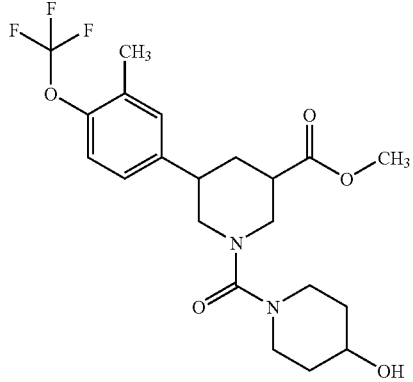

800 mg (1.66 mmol) of the compound from Example 168A, 503 mg (5.00 mmol) of 4-hydroxypiperidine and 229 mg (1.66 mmol) of potassium carbonate were initially charged in 18 ml of N,N-dimethylformamide and reacted in a single-mode microwave (Emrys Optimizer) at 150° C. for 15 min. The crude product was purified by preparative HPLC. Yield: 490 mg (67% of theory)

LC-MS (Method 3B): $R_t$=1.88 min and 1.95 min [cis/trans isomers]; MS (ESIpos): m/z=445 [M+H]$^+$.

Example 170A

1-[(4-Hydroxypiperidin-1-yl)carbonyl]-5-[3-methyl-4-(trifluoromethoxy)phenyl]piperidine-3-carboxylic acid [racemic cis isomer]

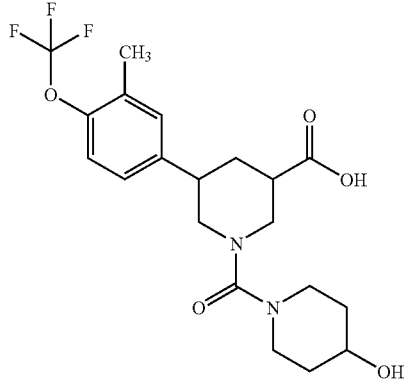

950 mg (2.14 mmol) of the compound from Example 169A were reacted according to the General Method 9A. Yield: 933 mg (99% of theory)

LC-MS (Method 9B): $R_t$=0.96 min; MS (ESIpos): m/z=431 [M+H]$^+$.

$^1$H-NMR (400 MHz, DMSO-d$_6$): δ=12.40 (br s, COOH), 7.32 (s, 1H), 7.27-7.21 (m, 2H), 4.66 (br s, OH), 3.79 (br d, 1H), 3.62-3.57 (m, 1H), 3.51 (br d, 1H), 3.46-3.42 (m, 2H), 2.87 (t, 2H), 2.80-2.75 (m, 3H), 2.60-2.54 (m, 1H), 2.27 (s, 3H), 2.12 (br d, 1H), 1.73-1.70 (m, 3H), 1.33-1.23 (m, 2H).

Example 171A 2,4-Difluoro-N'-hydroxybenzenecarboximidamide

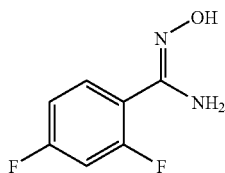

1.00 g (7.19 mmol) of 2,4-difluorobenzenecarbonitrile were reacted according to the General Method 5A. Yield: 1.23 g (99% of theory)

LC-MS (Method 9B): $R_t$=0.24 min; MS (ESIpos): m/z=173 [M+H]$^+$.

$^1$H-NMR (400 MHz, DMSO-d$_6$): δ=9.64 (s, 1H), 7.54 (ddd, 1H), 7.28 (ddd, 1H), 7.10 (ddd, 1H), 5.83 (br s, 2H).

Example 172A 1-tert-Butyl 3-methyl 5-[4-(trifluoromethoxy)phenyl]piperidine-1,3-dicarboxylate [racemic cis/trans isomer mixture]

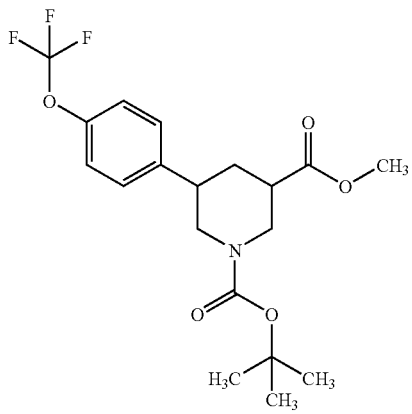

1.0 g (3.40 mmol) of the compound from Example 19A and 0.47 ml (0.34 g, 3.40 mmol) of triethylamine were initially charged in 50 ml of dichloromethane, and 0.78 ml (0.74 g, 3.40 mmol) of di-tert-butyl dicarboxylate was added at RT. The reaction mixture was stirred at RT for 16 h, washed with water, dried over sodium sulphate, filtered and concentrated under reduced pressure. The residue was purified by column chromatography on silica gel (mobile phase dichloromethane/methanol 50:1->20:1). Yield: 1.32 g (78% of theory, 81% pure)

LC-MS (Method 5B): $R_t$=2.66 min and 2.72 min [cis/trans isomers]; MS (ESIpos): m/z=404 [M+H]$^+$.

Example 173A 1-(tert-Butoxycarbonyl)-5-[4-(trifluoromethoxy)phenyl]piperidine-3-carboxylic acid [racemic cis isomer]

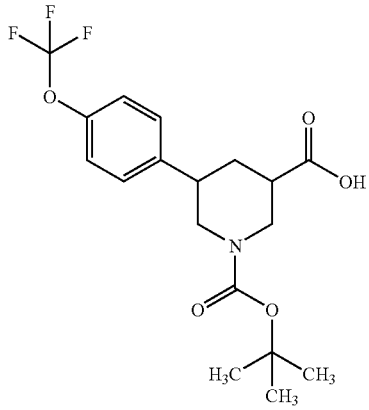

1.3 g (3.27 mmol) of the compound from Example 172A were reacted according to the General Method 9A. Yield: 1.31 g (87% of theory, 85% pure)

LC-MS (Method 5B): $R_t$=2.46 min; MS (ESIpos): m/z=390 [M+H]$^+$.

Example 174A tert-Butyl 3-(3-cyclopropyl-1,2,4-oxadiazol-5-yl)-5-[4-(trifluoromethoxy)phenyl]piperidine-1-carboxylate [racemic cis isomer]

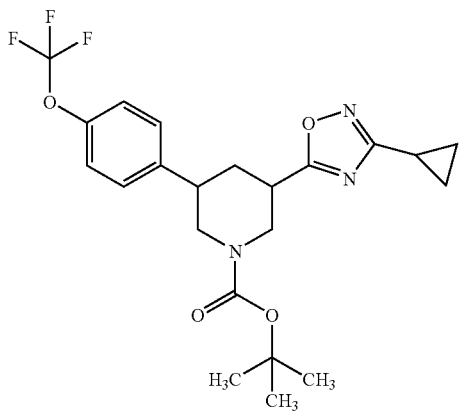

1.00 g (2.57 mmol) of the compound from Example 173A and 386 mg (3.86 mmol) of the compound from Example 78A were reacted according to the General Method 2. Yield: 185 mg (16% of theory)

LC-MS (Method 5B): $R_t$=2.94 min; MS (ESIpos): m/z=454 [M+H]$^+$.

Example 175A 3-(3-Cyclopropyl-1,2,4-oxadiazol-5-yl)-5-[4-(trifluoromethoxy)phenyl]piperidine [racemic cis isomer]

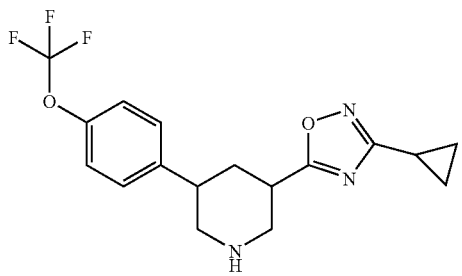

185 mg (0.41 mmol) of the compound from Example 174A were initially charged in 25 ml of dichloromethane and, at RT, reacted with 0.32 ml (466 mg, 4.08 mmol) of trifluoroacetic acid. The reaction mixture was stirred at RT for 16 h and then concentrated under reduced pressure. The residue was taken up in ethyl acetate, washed with saturated aqueous sodium bicarbonate solution, dried over sodium sulphate, filtered and concentrated under reduced pressure. Yield: 126 mg (87% of theory)

LC-MS (Method 2B): $R_t$=0.99 min; MS (ESIpos): m/z=354 $[M+H]^+$.

Example 176A

4-Nitrophenyl 3-(3-cyclopropyl-1,2,4-oxadiazol-5-yl)-5-[4-(trifluoromethoxy)phenyl]piperidine-1-carboxylate [racemic cis isomer]

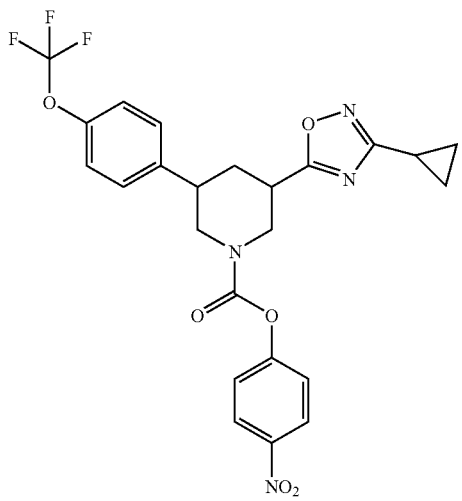

704 mg (1.99 mmol) of the compound from Example 175A were reacted analogously to the procedure from Example 126A. Yield: 879 mg (85% of theory)

LC-MS (Method 2B): $R_t$=1.57 min; MS (ESIpos): m/z=519 $[M+H]^+$.

Example 177A tert-Butyl 3-[3-(3-fluorophenyl)-1,2,4-oxadiazol-5-yl]-5-[4-(trifluoromethoxy)phenyl]piperidine-1-carboxylate [racemic cis isomer]

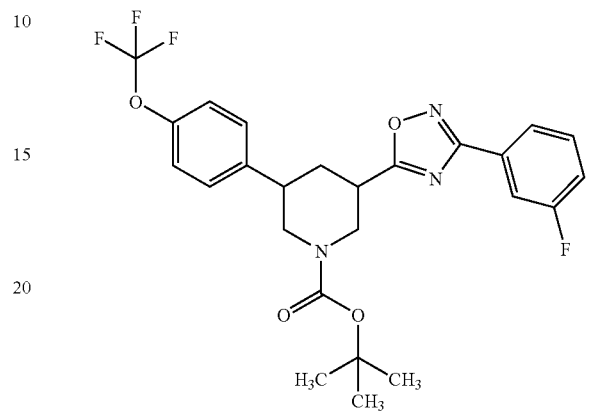

1.03 g (2.65 mmol) of the compound from Example 173A were reacted according to the General Method 2. Yield: 463 mg (31% of theory)

LC-MS (Method 2B): $R_t$=1.76 min; MS (ESIpos): m/z=508 $[M+H]^+$.

Example 178A

3-[3-(3-Fluorophenyl)-1,2,4-oxadiazol-5-yl]-5-[4-(trifluoromethoxy)phenyl]piperidine [racemic cis isomer]

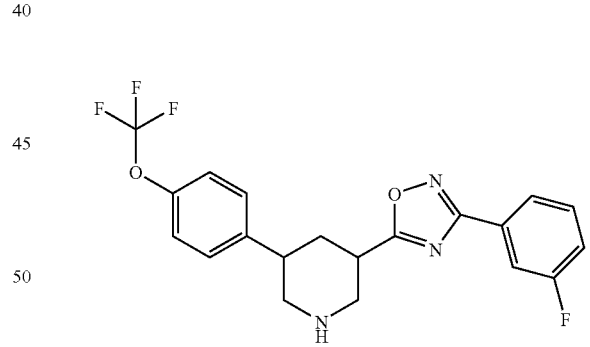

425 mg (0.84 mmol) of the compound from Example 177A were initially charged in 55 ml of dichloromethane and, at RT, reacted with 0.65 ml (955 mg, 8.37 mmol) of trifluoroacetic acid. The reaction mixture was stirred at RT for 20 h and then concentrated under reduced pressure. The residue was taken up in ethyl acetate, washed with saturated aqueous sodium bicarbonate solution, dried over sodium sulphate, filtered and concentrated under reduced pressure. Yield: 340 mg (80% of theory, 80% pure)

LC-MS (Method 1B): $R_t$=1.75 min; MS (ESIpos): m/z=408 $[M+H]^+$.

Example 179A

3-[3-(3-Fluorophenyl)-1,2,4-oxadiazol-5-yl]-5-[4-(trifluoromethoxy)phenyl]piperidine-1-carbonyl chloride [racemic cis isomer]

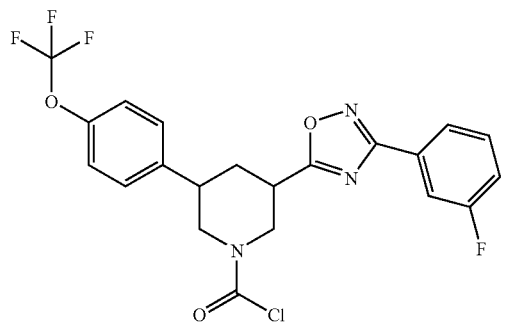

At 0° C., 1.00 g (2.46 mmol) of the compound from Example 178A and 0.34 ml (248 mg, 2.46 mmol) of triethylamine were initially charged in 167 ml of dichloromethane. 0.12 ml (242 mg, 1.23 mmol) of trichloromethyl chloroformate (diphosgene) was added dropwise. The reaction mixture was stirred at RT for 16 h, washed quickly with a little ice-water, dried over sodium sulphate, filtered and concentrated under reduced pressure. The crude product was purified by column chromatography on silica gel. Yield: 944 mg (68% of theory, 83% of theory)

HPLC (Method 2A): $R_t$=5.51 min; MS (ESIpos): m/z=470 [M+H]$^+$.

Example 180A 1-tert-Butyl 3-methyl 5-[4-(trifluoromethyl)phenyl] piperidine-1,3-dicarboxylate [racemic cis/trans isomer mixture]

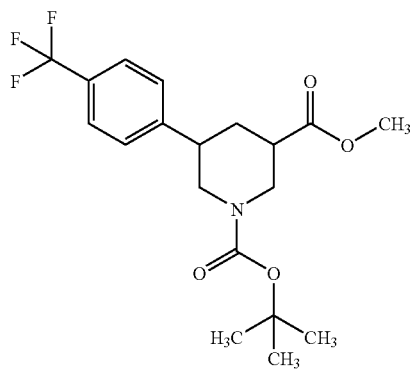

1.00 g (3.48 mmol) of the compound from Example 47A and 0.49 ml (0.35 g, 3.48 mmol) of triethylamine were initially charged in 50 ml of dichloromethane, and 0.76 g (3.48 mmol) of di-tert-butyl dicarboxylate was added at RT. The reaction mixture was stirred at RT for 16 h, washed with water and saturated aqueous sodium chloride solution, dried over sodium sulphate, filtered and concentrated under reduced pressure. The residue was purified by column chromatography on silica gel (mobile phase dichloromethane/methanol 100:1). Yield: 1.01 g (67% of theory, 90% pure)

HPLC (Method 2A): $R_t$=5.21 min and 5.30 min [cis/trans isomers]; MS (DCIpos): m/z=388 [M+H]$^+$.

Example 181A 1-(tert-Butoxycarbonyl)-5-[4-(trifluoromethyl)phenyl]piperidine-3-carboxylic acid [racemic cis isomer]

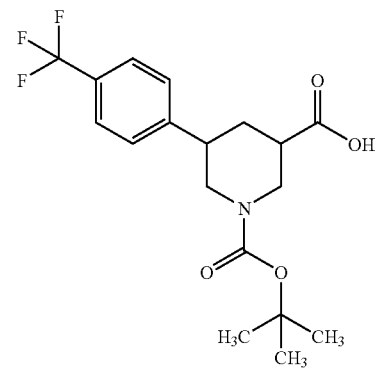

1.18 g (3.07 mmol) of the compound from Example 180A were reacted according to the General Method 9A. Yield: 1.17 g (86% of theory, 84% pure)

HPLC (Method 2A): $R_t$=4.81 min; MS (ESIpos): m/z=374 [M+H]$^+$.

Example 182A tert-Butyl 3-(3-cyclopropyl-1,2,4-oxadiazol-5-yl)-5-[4-(trifluoromethyl)phenyl]piperidine-1-carboxylate [racemic cis isomer]

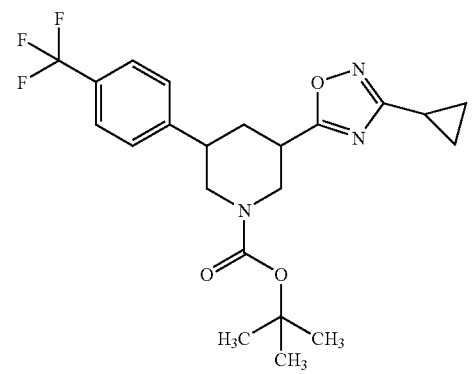

3.75 g (10.0 mmol) of the compound from Example 181A were reacted according to the General Method 2. Yield: 3.45 g (72% of theory)

HPLC (Method 2A): $R_t$=5.47 min; MS (ESIpos): m/z=438 [M+H]$^+$.

Example 183A 3-(3-Cyclopropyl-1,2,4-oxadiazol-5-yl)-5-[4-(trifluoromethyl)phenyl]piperidine [racemic cis isomer]

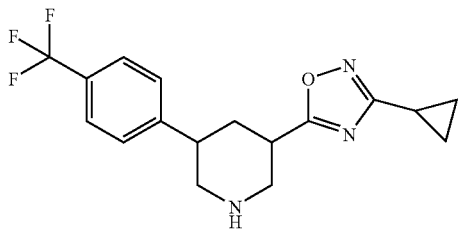

3.23 g (7.38 mmol) of the compound from Example 182A were initially charged in 60 ml of dichloromethane and, at RT, reacted with 5.7 ml (8.42 g, 73.8 mmol) of trifluoroacetic acid. The reaction mixture was stirred at RT for 16 h and then concentrated under reduced pressure. The residue was taken up in ethyl acetate, washed with saturated aqueous sodium bicarbonate solution, dried over magnesium sulphate, filtered and concentrated under reduced pressure. Yield: 2.48 g (92% of theory)

HPLC (Method 2A): $R_t$=4.15 min; MS (ESIpos): m/z=338 [M+H]$^+$.

Example 184A

4-Nitrophenyl 3-(3-cyclopropyl-1,2,4-oxadiazol-5-yl)-5-[4-(trifluoromethyl)phenyl]piperidine-1-carboxylate [racemic cis isomer]

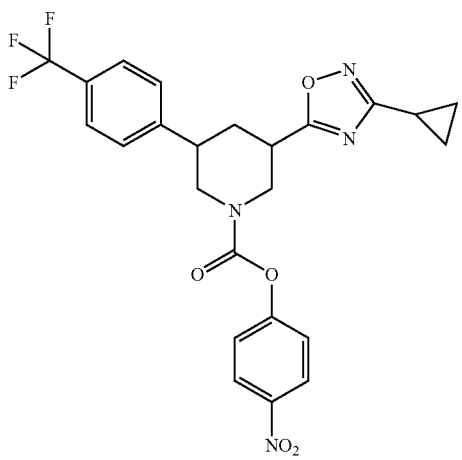

1.00 g (2.96 mmol) of the compound from Example 183A was reacted analogously to the procedure from Example 126A. Yield: 1.34 g (90% of theory)

HPLC (Method 2A): $R_t$=5.14 min; MS (ESIpos): m/z=503 [M+H]$^+$.

Example 185A tert-Butyl 3-[3-(3-fluorophenyl)-1,2,4-oxadiazol-5-yl]-5-[4-(trifluoromethyl)phenyl]piperidine-1-carboxylate [racemic cis isomer]

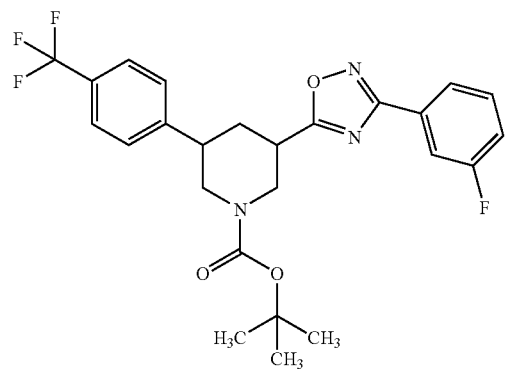

0.75 g (2.01 mmol) of the compound from Example 181A were reacted according to the General Method 2. Yield: 0.84 g (79% of theory)

HPLC (Method 2A): $R_t$=5.83 min; MS (ESIpos): m/z=492 [M+H]$^+$.

Example 186A

3-[3-(3-Fluorophenyl)-1,2,4-oxadiazol-5-yl]-5-[4-(trifluoromethyl)phenyl]piperidine [racemic cis isomer]

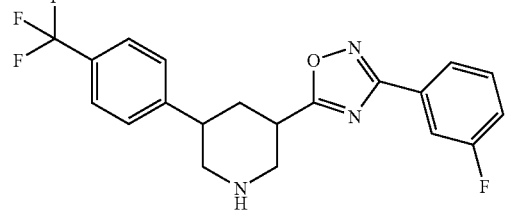

0.82 g (1.67 mmol) of the compound from Example 185A was initially charged in 13 ml of dichloromethane, and 1.3 ml (1.90 g, 16.78 mmol) of trifluoroacetic acid were added at RT. The reaction mixture was stirred at RT for 16 h and then concentrated under reduced pressure. The residue was taken up in ethyl acetate, washed with saturated aqueous sodium bicarbonate solution, dried over magnesium sulphate, filtered and concentrated under reduced pressure. Yield: 0.65 g (99% of theory)

HPLC (Method 2A): $R_t$=4.46 min; MS (ESIpos): m/z=392 [M+H]$^+$.

Example 187A

4-Nitrophenyl 3-[3-(3-fluorophenyl)-1,2,4-oxadiazol-5-yl]-5-[4-(trifluoromethyl)phenyl]-piperidine-1-carboxylate [racemic cis isomer]

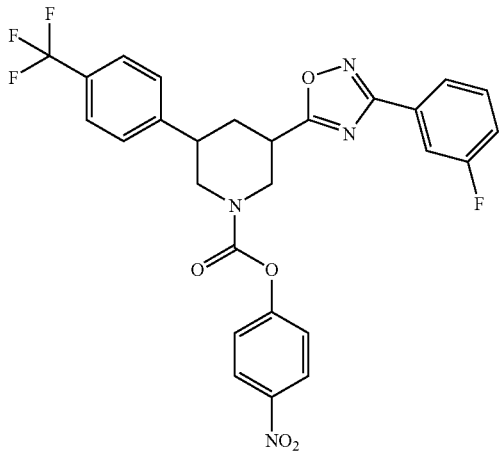

1.00 g (2.56 mmol) of the compound from Example 186A was reacted analogously to the procedure from Example 126A. Yield: 1.29 g (91% of theory)

HPLC (Method 2A): $R_t$=5.43 min; MS (ESIpos): m/z=557 [M+H]$^+$.

Example 188A tert-Butyl (1-{3-[3-(3-fluorophenyl)-1,2,4-oxadiazol-5-yl]-5-[4-(trifluoromethoxy)phenyl]-piperidin-1-yl}-2-methyl-1-oxopropan-2-yl)carbamate [racemic cis isomer]

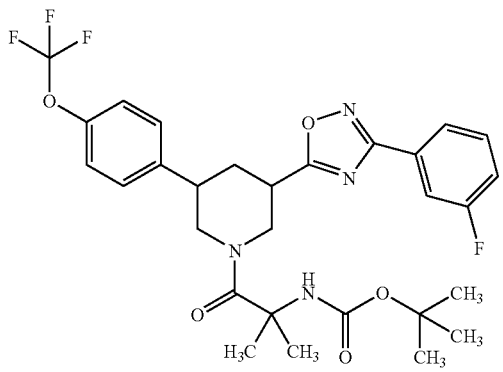

150 mg (0.30 mmol) of the compound from Example 178A and 66 mg (0.32 mmol) of N-(tert-butoxycarbonyl)-2-methylalanine were reacted according to the General Method 7. Yield: 117 mg (64% of theory)

LC-MS (Method 3B): $R_t$=2.77 min; MS (ESIpos): m/z=593 [M+H]$^+$.

Example 189A tert-Butyl[1-({3-(3-cyclopropyl-1,2,4-oxadiazol-5-yl)-5-[4-(trifluoromethyl)phenyl]piperidin-1-yl}carbonyl)cyclopentyl]carbamate [racemic cis isomer]

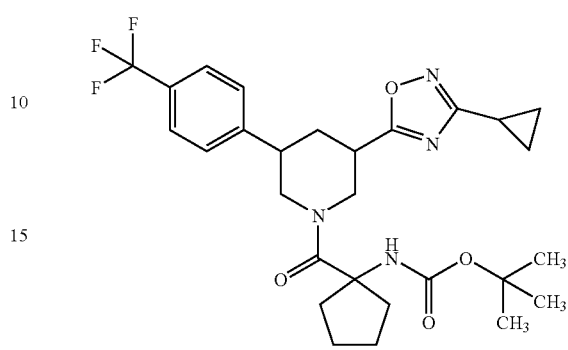

100 mg (0.30 mmol) of the compound from Example 183A and 75 mg (0.33 mmol) of 1-[(tert-butoxycarbonyl)amino]cyclopentanecarboxylic acid were reacted according to the General Method 7. Yield: 127 mg (78% of theory)

HPLC (Method 2A): $R_t$=5.13 min; MS (ESIpos): m/z=549 [M+H]$^+$.

Example 190A

Methyl 5-[3-(trifluoromethoxy)phenyl]pyridine-3-carboxylate

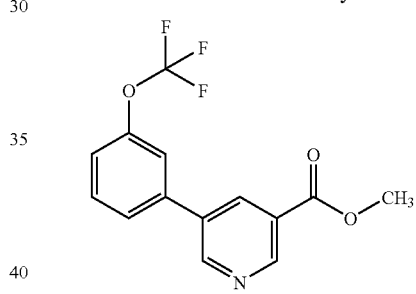

2.61 g (12.09 mmol) of methyl 5-bromonicotinate and 2.49 g (12.09 mmol) of 3-(trifluoromethoxy)phenylboronic acid were reacted according to the General Method 1A. Yield: 2.44 g (68% of theory)

LC-MS (Method 2B): $R_t$=1.29 min; MS (ESIpos): m/z=298 [M+H]$^+$.

Example 191A

Methyl 5-[3-(trifluoromethoxy)phenyl]piperidine-3-carboxylate [racemic cis/trans isomer mixture]

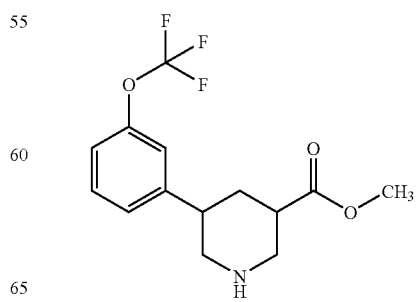

2.42 g (8.14 mmol) of the compound from Example 190A were reacted according to the General Method 2A. Yield: 1.34 g (50% of theory)

LC-MS (Method 3B): $R_t$=0.89 min and 0.97 min [cis/trans isomers]; MS (ESIpos): m/z=304 [M+H]$^+$.

Example 192A

3-Methyl 1-(4-nitrophenyl)5-[3-(trifluoromethoxy)phenyl]piperidine-1,3-dicarboxylate

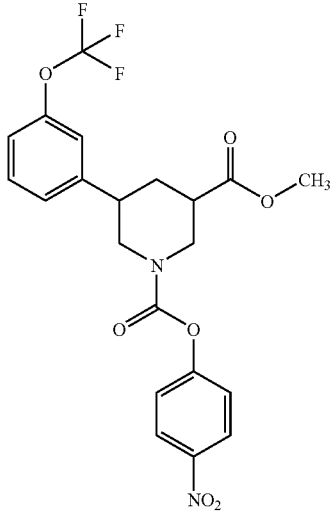

5.0 g (15.4 mmol) of the compound from Example 191A were reacted analogously to the procedure of Example 126A. Yield: 3.8 g (52% of theory)

LC-MS (Method 2B): $R_t$=1.46 min and 1.48 min [cis/trans isomers]; MS (ESIpos): m/z=469 [M+H]$^+$.

Example 193A

Methyl 1-[(4-hydroxypiperidin-1-yl)carbonyl]-5-[3-(trifluoromethoxy)phenyl]piperidine-3-carboxylate [racemic cis/trans isomer mixture]

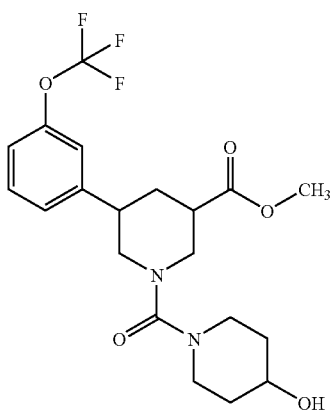

1.5 g (3.1 mmol) of the compound from Example 192A and 0.9 g (9.2 mmol) of 4-hydroxypiperidine were reacted according to the General Method 6. Yield: 1.1 g (84% of theory)

LC-MS (Method 2B): $R_t$=1.13 min and 1.16 min [cis/trans isomers]; MS (ESIpos): m/z=431 [M+H]$^+$.

Example 194A

1-[(4-Hydroxypiperidin-1-yl)carbonyl]-5-[3-(trifluoromethoxy)phenyl]piperidine-3-carboxylic acid [racemic cis isomer]

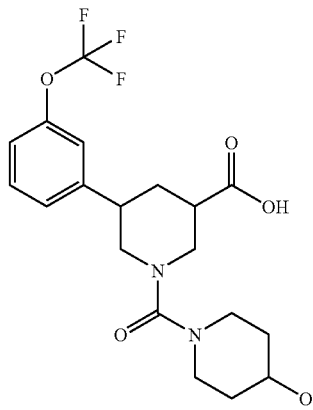

1.1 g (2.6 mmol) of the compound from Example 193A were reacted according to the General Method 9A. Yield: 0.4 g (36% of theory)

LC-MS (Method 3B): $R_t$=1.56 min; MS (ESIpos): m/z=417 [M+H]$^+$.

Example 195A

Methyl 5-[4-(methylsulphonyl)phenyl]pyridine-3-carboxylate

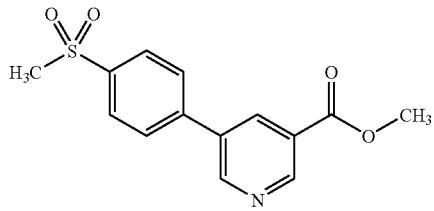

4.5 g (20.8 mmol) of methyl 5-bromonicotinate and 5.0 g (25.0 mmol) of 4-(methylsulphonyl)phenylboronic acid were reacted according to the General Method 1A. Yield: 1.4 g (24% of theory)

LC-MS (Method 2B): $R_t$=0.84 min; MS (ESIpos): m/z=292 [M+H]$^+$.

Example 196A

Methyl 5-[4-(methylsulphonyl)phenyl]piperidine-3-carboxylate [racemic cis/trans isomer mixture]

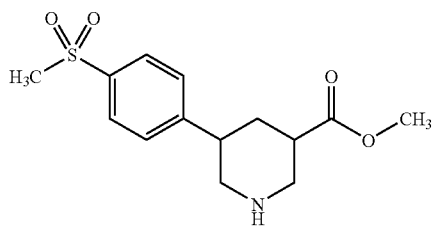

1.5 g (5.1 mmol) of the compound from Example 195A were reacted according to the General Method 12A. Yield: 1.0 g (65% of theory)

LC-MS (Method 2B): $R_t$=0.28 min; MS (ESIpos): m/z=298 [M+H]$^+$.

Example 197A

Methyl 5-[4-(methylsulphonyl)phenyl]-1-(morpholin-4-ylcarbonyl)piperidine-3-carboxylate [racemic cis/trans isomer mixture]

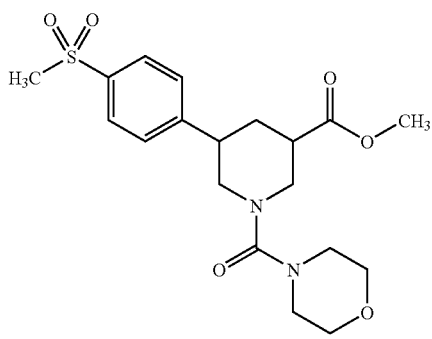

0.22 g (0.74 mmol) of the compound from Example 196A were reacted according to the General Method 3A. Yield: 0.20 g (66% of theory)

LC-MS (Method 1B): $R_t$=1.56 min and 1.63 min [cis/trans isomers]; MS (ESIpos): m/z=411 [M+H]$^+$.

Example 198A

5-[4-(Methylsulphonyl)phenyl]-1-(morpholin-4-ylcarbonyl)piperidine-3-carboxylic acid [racemic cis isomer]

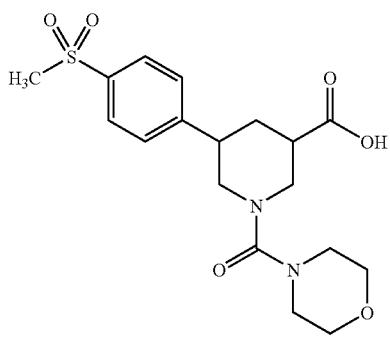

1.1 g (2.7 mmol) of the compound from Example 197A were reacted according to the General Method 9A. Yield: 373 mg (35% of theory.)

LC-MS (Method 2B): $R_t$=0.71 min; MS (ESIpos): m/z=397 [M+H]$^+$.

Example 199A 5-(4-Ethylphenyl)-1-(morpholin-4-ylcarbonyl)-N-(prop-2-yn-1-yl)piperidine-3-carboxamide [racemic cis isomer]

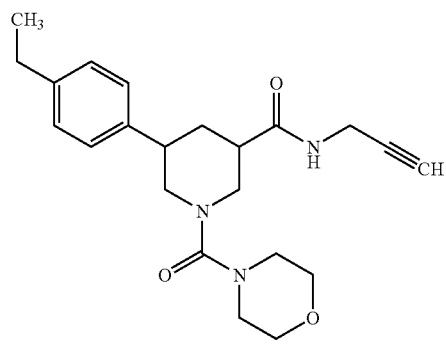

Step a): 5-(4-Ethylphenyl)-1-(morpholin-4-ylcarbonyl)piperidine-3-carbonyl chloride [racemic cis isomer]

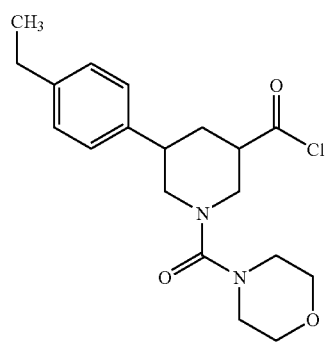

150 mg (0.43 mmol) of the compound from Example 38A were initially charged in 3 ml of dichloromethane, and 63 μl (103 mg, 0.87 mmol) of thionyl chloride were added. The reaction mixture was stirred under RF for 2 h, concentrated under reduced pressure, and then three times toluene was added and the mixture was in each case concentrated again under reduced pressure.

Step b): 5-(4-Ethylphenyl)-1-(morpholin-4-ylcarbonyl)-N-(prop-2-yn-1-yl)piperidine-3-carboxamide

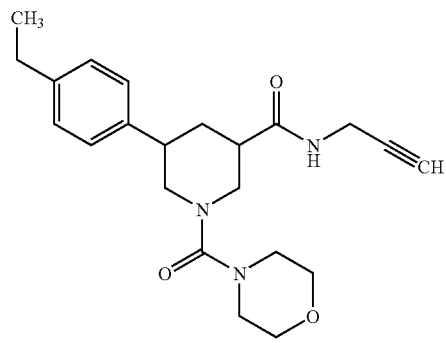

18 μl (16 mg, 0.29 mmol) of propargylamine, 40 μl (29 mg, 0.29 mmol) of triethylamine and 1 mg (0.01 mmol) of N,N-dimethylaminopyridine were initially charged in 0.5 ml of dichloromethane, and 105 mg (0.29 mmol) of 5-(4-ethylphenyl)-1-(morpholin-4-ylcarbonyl)piperidine-3-carbonyl chloride, dissolved in 1 ml of dichloromethane, were added. The reaction mixture was stirred at 0° C. for 30 minutes and at RT for 16 h. For work-up, water was added and the reaction mixture was extracted with ethyl acetate. The combined organic extracts were dried over magnesium sulphate, filtered and concentrated under reduced pressure. The residue was purified by column chromatography on silica gel (mobile phase dichloromethane/methanol 100:5). Yield: 108 mg (98% of theory.)

HPLC (Method 2A): $R_t$=4.10 min; MS (ESIpos): m/z=384 [M+H]$^+$.

Example 200A

Methyl 1-(morpholin-4-ylcarbonyl)-5-[3-(trifluoromethoxy)phenyl]piperidine-3-carboxylate [racemic cis/trans isomer mixture]

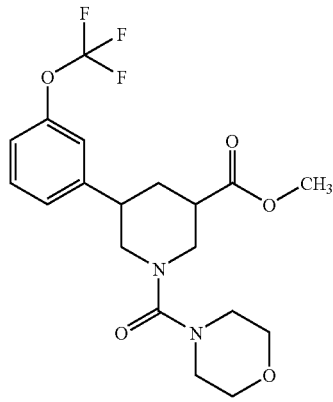

1.67 g (5.14 mmol) of the compound from Example 191A were reacted according to the General Method 3A. Yield: 1.91 g (89% of theory)

LC-MS (Method 2B): $R_t$=1.21 min and 1.24 min [cis/trans isomers]; MS (ESIpos): m/z=417 [M+H]$^+$.

Example 201A 1-(Morpholin-4-ylcarbonyl)-5-[3-(trifluoromethoxy)phenyl]piperidine-3-carboxylic acid [racemic cis isomer]

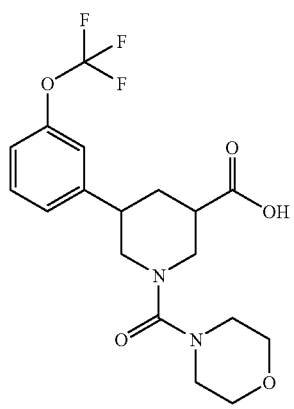

1.9 g (4.6 mmol) of the compound from Example 200A were reacted according to the General Method 9A. Yield: 1.8 g (99% of theory.)

LC-MS (Method 5B): $R_t$=2.01 min; MS (ESIpos): m/z=403 [M+H]$^+$.

Example 202A

Methyl 1-[(4-cyanopiperidin-1-yl)carbonyl]-5-[3-(trifluoromethoxy)phenyl]piperidine-3-carboxylate [racemic cis/trans isomer mixture]

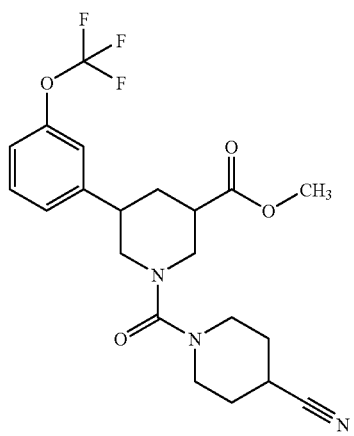

850 mg (1.82 mmol) of the compound from Example 192A and 599 mg (5.44 mmol) of 4-cyanopiperidine were reacted according to the General Method 6. Yield: 464 mg (58% of theory.)

LC-MS (Method 2B): $R_t$=1.27 min and 1.29 min [cis/trans isomers]; MS (ESIpos): m/z=440 [M+H]$^+$.

Example 203A

1-[(4-Cyanopiperidin-1-yl)carbonyl]-5-[3-(trifluoromethoxy)phenyl]piperidine-3-carboxylic acid [racemic cis isomer]

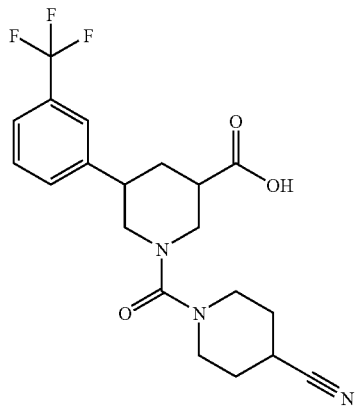

420 mg (0.95 mmol) of the compound from Example 202A were reacted according to the General Method 9A. Yield: 247 mg (59% of theory)

LC-MS (Method 5B): $R_t$=2.08 min; MS (ESIpos): m/z=426 [M+H]$^+$.

Example 204A

Methyl 1-[(2,2-dimethylmorpholin-4-yl)carbonyl]-5-[4-(trifluoromethyl)phenyl]piperidine-3-carboxylate [racemic cis/trans isomer mixture]

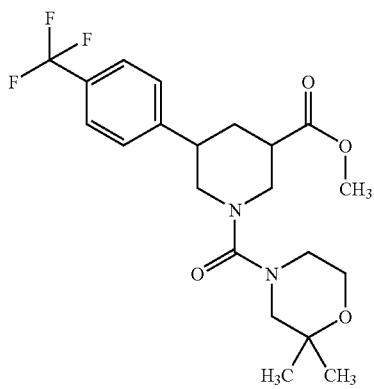

3.00 g (6.63 mmol) of 3-methyl 1-(4-nitrophenyl)5-[4-(trifluoromethyl)phenyl]piperidine-1,3-dicarboxylate (Example 93A) and 2.21 g (14.6 mmol) of 2,2-dimethylmorpholine hydrochloride were reacted according to the General Method 8A. Yield: 1.79 g (39% of theory, 62% pure).

LC-MS (Method 2B): $R_t$=1.28 min and 1.32 min (cis/trans isomers); MS (ESIpos): m/z=429 [M+H]$^+$.

Example 205A

Methyl 1-[(4-methyl-3-oxopiperazin-1-yl)carbonyl]-5-[4-(trifluoromethyl)phenyl]piperidine-3-carboxylate [racemic cis/trans isomer mixture]

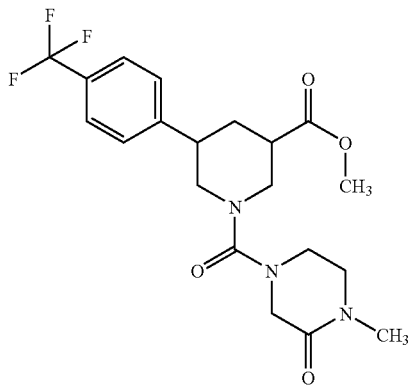

4.00 g (8.84 mmol) of 3-methyl 1-(4-nitrophenyl)5-[4-(trifluoromethyl)phenyl]piperidine-1,3-dicarboxylate (Example 93A) and 5.05 g (22.1 mmol) of 1-methylpiperazin-2-one were reacted according to the General Method 8A. Yield: 2.41 g (62% of theory).

LC-MS (Method 3B): $R_t$=1.69 min and 1.74 min (cis/trans isomers); MS (ESIpos): m/z=428 [M+H]$^+$.

Example 206A

1-[(3-Oxopiperazin-1-yl)carbonyl]-5-[4-(trifluoromethyl)phenyl]piperidine-3-carboxylic acid [racemic cis isomer]

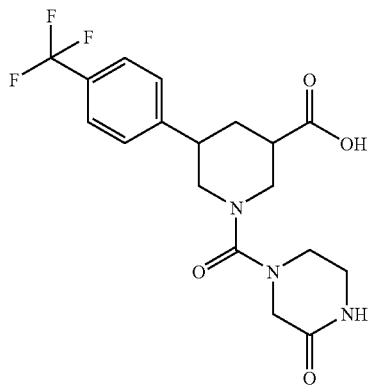

1.90 g (4.60 mmol) of methyl 1-[(3-oxopiperazin-1-yl)carbonyl]-5-[4-(trifluoromethyl)-phenyl]piperidine-3-carboxylate (Example 89A) were reacted according to the General Method 9A. Yield: 1.89 g (97% of theory).

LC-MS (Method 2B): $R_t$=0.95 min; MS (ESIpos): m/z=400 [M+H]$^+$.

Example 207A

1-[(3-Methoxypiperidin-1-yl)carbonyl]-5-[4-(trifluoromethyl)phenyl]piperidine-3-carboxylic acid [racemic cis-diastereomer pair]

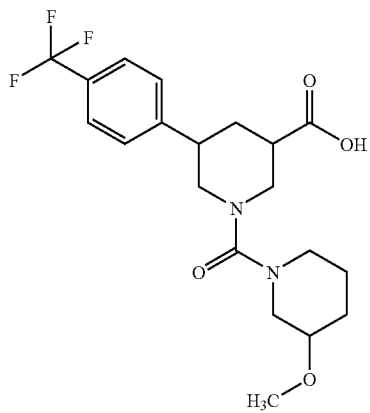

2.90 g (5.01 mmol, 74% pure) of methyl 1-[(3-methoxypiperidin-1-yl)carbonyl]-5-[4-(trifluoromethyl)phenyl]piperidine-3-carboxylate (Example 119A) were reacted according to the General Method 9A. Yield: 2.84 g (98% of theory, 72% pure).

LC-MS (Method 3B): R$_t$=1.85 min; MS (ESIpos): m/z=415 [M+H]$^+$.

Example 208A

1-[(2,2-Dimethylmorpholin-4-yl)carbonyl]-5-[4-(trifluoromethyl)phenyl]piperidine-3-carboxylic acid [racemic cis isomer]

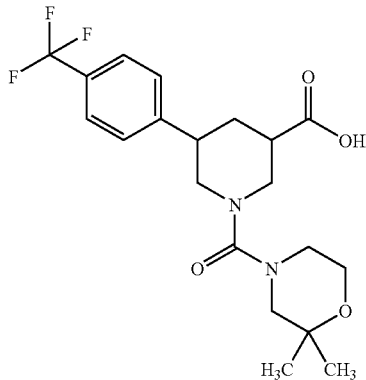

1.79 g (3.09 mmol, 74% pure) of methyl 1-[(2,2-dimethylmorpholin-4-yl)carbonyl]-5-[4-(trifluoromethyl)phenyl]piperidine-3-carboxylate (Example 204A) were reacted according to the General Method 9A. Yield: 1.65 g (87% of theory, 68% pure).

LC-MS (Method 9B): R$_t$=1.02 min; MS (ESIpos): m/z=415 [M+H]$^+$.

Example 209A

1-[(4-Methyl-3-oxopiperazin-1-yl)carbonyl]-5-[4-(trifluoromethyl)phenyl]piperidine-3-carboxylic acid [racemic cis isomer]

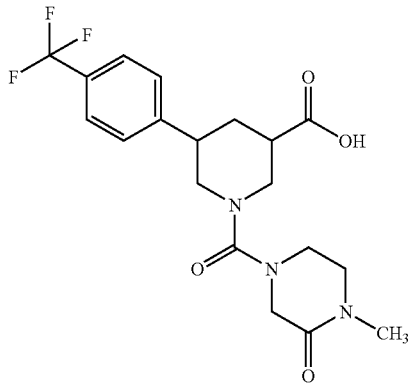

2.41 g (5.64 mmol) of methyl 1-[(4-methyl-3-oxopiperazin-1-yl)carbonyl]-5-[4-(trifluoromethyl)phenyl]piperidine-3-carboxylate (Example 205A) were reacted according to the General Method 9A. Yield: 1.62 g (69% of theory).

LC-MS (Method 2B): R$_t$=1.01 min; MS (ESIpos): m/z=414 [M+H]$^+$.

Example 210A tert-Butyl[1-({3-[3-(propan-2-yl)-1,2,4-oxadiazol-5-yl]-5-[4-(trifluoromethoxy)phenyl]piperidin-1-yl}carbonyl)piperidin-4-yl] carbamate [racemic cis isomer]

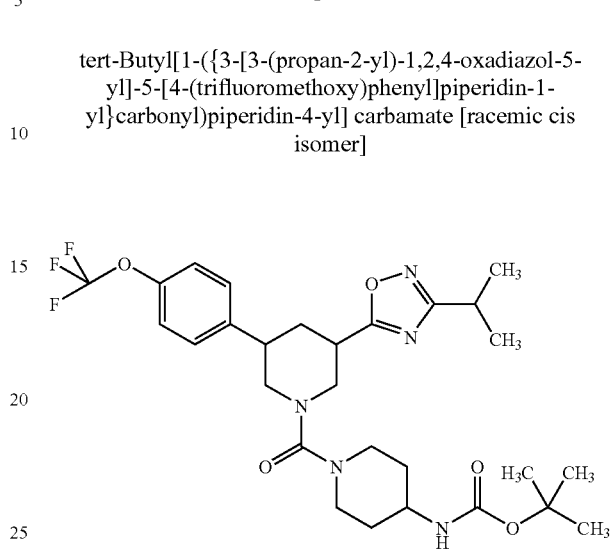

144 mg (0.28 mmol) of the compound from Example 114A and 43 mg (0.42 mmol) of N'-hydroxy-2-methylpropanimidamide were reacted according to the General Method 2. Yield: 54 mg (33% of theory)

LC-MS (Method 9B): R$_t$=1.37 min; MS (ESIpos): m/z=582 [M+H]$^+$;

Example 211A tert-Butyl[1-({3-[3-(2-methoxyethyl)-1,2,4-oxadiazol-5-yl]-5-[4-(trifluoromethoxy)phenyl]piperidin-1-yl}carbonyl)piperidin-4-yl] carbamate [racemic cis isomer]

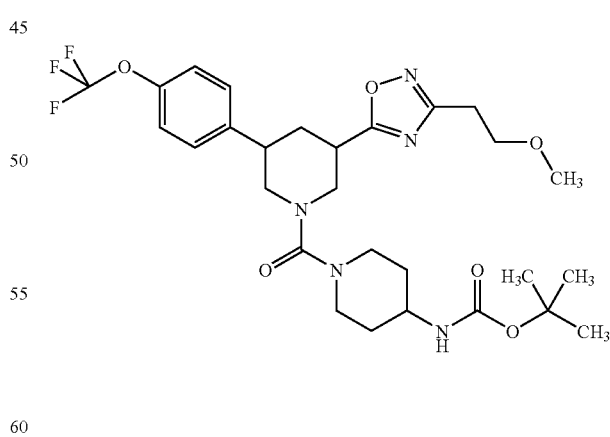

200 mg (0.39 mmol) of the compound from Example 114A and 92 mg (0.58 mmol) of N'-hydroxy-3-methoxypropanimidamide were reacted according to the General Method 2. Yield: 52 mg (23% of theory)

LC-MS (Method 9B): R$_t$=1.26 min; MS (ESIpos): m/z=598 [M+H]$^+$;

Example 212A tert-Butyl[1-({3-(3-methyl-1,2,4-oxadiazol-5-yl)-5-[4-(trifluoromethoxy)phenyl]piperidin-1-yl}carbonyl)piperidin-4-yl] carbamate [racemic cis isomer]

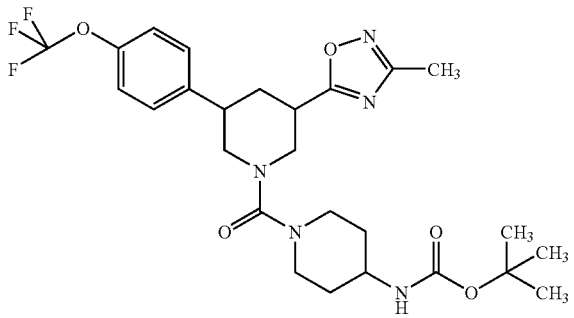

200 mg (0.39 mmol) of the compound from Example 114A and 43 mg (0.58 mmol) of N'-hydroxyethanimidamide were reacted according to the General Method 2. Yield: 73 mg (34% of theory)

LC-MS (Method 9B): $R_t$=1.26 min; MS (ESIpos): m/z=554 [M+H]$^+$.

Example 213A 2,4-Difluoro-N'-hydroxybenzenecarboximidamide

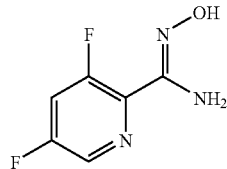

1.00 g (7.14 mmol) of 3,5-difluoropyridine-2-carbonitrile was reacted according to the General Method 5A. Yield: 893 mg (72% of theory)

HPLC (Method 5B): $R_t$=0.58 min; MS (ESIpos): m/z=174 [M+H]$^+$.

$^1$H-NMR (400 MHz, DMSO-d$_6$): δ=10.1 (s, 1H), 8.55 (d, 1H), 8.00 (ddd, 1H), 5.89 (br s, 2H).

Example 214 A

{3-[4-(Chloromethyl)-1,3-thiazol-2-yl]-5-[4-(trifluoromethyl)phenyl]piperidin-1-yl}(morpholin-4-yl)methanone

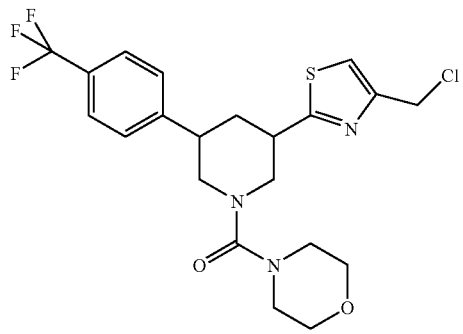

250 mg (about 0.44 mmol) of the compound from Example 53A and 60 mg (0.52 mmol) of 1,3-dichloropropan-2-one were reacted according to the General Method 3. Yield: 150 mg (12% of theory).

LC-MS (Method 2B): $R_t$=1.30 min and 1.34 min (cis/trans isomers); MS (ESIpos): m/z=474 [M+H]$^+$.

Working Examples

General Method 1: Oxadiazole Formation

Under argon and at RT, HATU (1.2 eq.), N,N-diisopropylethylamine (2.2 eq.) and the appropriate N'-hydroxyimidamide (1.1 eq.) are added to a solution of the appropriate piperidine-3-carboxylic acid in dimethylformamide (10 ml/mmol). The reaction mixture is stirred at RT until the formation of the intermediate has gone to completion and then stirred further at 120° C. until the desired product is formed from this intermediate. The reaction mixture is then purified by preparative HPLC.

General Method 2: Oxadiazole Formation

The carboxylic acid is dissolved in dioxane/dimethylformamide (3:1, 1 ml/mmol) and heated to 60° C. After addition of N,N'-carbonyldiimidazole (1.5 eq.), dissolved in dioxane/dimethylformamide (4:1, 1.6 ml/mmol), the mixture is stirred at 60° C. for 3 h. After cooling to RT, the carboximidamide, dissolved in dioxane/dimethylformamide 1:1, is added dropwise, and the mixture is stirred at 40° C. overnight. The dioxane is then removed under reduced pressure. The residue, dissolved in dimethylformamide, is then stirred at 115° C. for 1 h. After cooling, the reaction mixture is diluted with water. After extraction with dichloromethane, the organic phase is dried over sodium sulphate and the crude product is purified by preparative HPLC.

General Method 3: Thiazole Formation

A mixture of the appropriate piperidine-3-carbothiamide in dimethylformamide (4.6 ml/mmol) and bromoketone or chloroketone (1.2 eq.) is stirred at 125° C. overnight. Without further work-up, the reaction mixture is purified by preparative HPLC.

General Method 4: 1,3,4-Oxadiazole formation (J. Med. Chem. 1996, 39, 2753-2763)

Under argon and at reflux temperature, a solution of the appropriate piperidine-3-carboxylic acid in phosphoryl chloride (1 ml/mmol) is stirred with the appropriate hydrazide (1.1 eq.). The reaction mixture is poured onto ice and adjusted to pH 7 using ammonia. After extraction with dichloromethane, the organic phase is dried over sodium sulphate and concentrated using a rotary evaporator. The crude product is purified by preparative HPLC.

General Method 5: Urea Formation I 1.0 equivalent of a piperidinecarbonyl chloride and 1.0 equivalent of triethylamine are initially charged in 10 ml of dichloromethane. At 0° C., 1.0 equivalent of an amine is added, and the mixture is stirred at RT for 16 h. The reaction mixture is washed with water, dried over magnesium sulphate, filtered and concentrated under reduced pressure. The residue is purified by preparative HPLC.

General Method 6: Urea Formation II 3 ml of N,N-dimethylformamide are added to 1.0 equivalent of a 4-nitrophenyl piperidinecarboxylate, 3.0 equivalents of amine and 2.0 equivalents potassium carbonate, and the mixture is reacted in a microwave oven at 150° C. for 30 minutes. The reaction mixture is taken up in ethyl acetate, washed repeatedly with water and a saturated aqueous sodium chloride solution, dried over magnesium sulphate, filtered and concentrated under reduced pressure. The residue is purified by preparative HPLC.

General Method 7: Amide Formation

Under argon and at RT, HATU (1.2 eq.) and N,N-diisopropylethylamine (3.0 eq.) are added to a solution of 1.1 equivalents of the appropriate carboxylic acid in N,N-dimethylformamide. After 30 minutes, 1.0 equivalent of the appropriate piperidine derivative, dissolved in N,N-dimethylformamide, is added. The reaction mixture is stirred at RT for 16 h. The reaction mixture is then purified by preparative HPLC.

General Method 8: Oxadiazole Formation

In each case 0.1 mmol of the appropriate carboxylic acid are distributed on a microtitre plate. 1.55 g (9.57 mmol) of N,N-carbonyldiimidazole are dissolved in 10 ml of DMF and 5 ml of dioxane, and in each case ⅟₄₈ is pipetted into each of the 48 carboxylic acids. The plate is shaken at 60° C. for 3 h, ⅟₄₈ of the solution of 1.922 g (4.8 mmol) of the compound from Example 84A in DMF is then added, and the plate is shaken at 40° C. for 2 h and then at 115° C. for 3 h. The solvent is evaporated in a vacuum centrifuge, and the residue is in each case dissolved in 0.6 ml of DMSO, filtered and purified by preparative HPLC/MS.

General Method 9: Thiadiazole formation (J. Med. Chem. 1996, 39, 2753-2763)

Under argon, a solution of the appropriate carbohydrazide in dioxane (20 ml/mmol) is treated with Lawesson reagent (2,4-bis[4-methoxyphenyl] 1,3-dithia-2,4-diphosphetane 2,4-disulphide) (2.0 eq.) at reflux temperature for 2.5 h. After addition of saturated aqueous sodium bicarbonate solution and removal of the dioxane, the residue is extracted with ethyl acetate. The combined organic phases are washed with a saturated aqueous sodium bicarbonate solution, dried over magnesium sulphate, filtered and concentrated under reduced pressure.

Example 1

1-(Cyclopentylcarbonyl)-3-(4-ethylphenyl)-5-(3-phenyl-1,2,4-oxadiazol-5-yl)piperidine [racemic cis isomer]

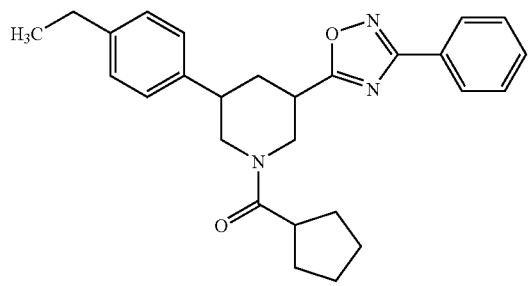

329 mg (1.0 mmol) of 1-(cyclopentylcarbonyl)-5-(4-ethylphenyl)piperidine-3-carboxylic acid (Example 7A) and 149 mg (1.1 mmol, 1.1 eq.) of N'-hydroxybenzenecarboximidamide were reacted according to the General Method 1. Yield: 235 mg (55% of theory)

HPLC (Method 2A): $R_t$=5.64 min; MS (ESIpos): m/z=430 [M+H]$^+$;

$^1$H-NMR (500 MHz, DMSO-d$_6$): δ=8.01 (d, 2H), 7.63-7.54 (m, 3H), 7.28 (d, 1H), 7.23 (d, 1H), 7.19 (d, 2H), 4.95 (br d, 0.5H), 4.53 (br d, 0.5H), 4.48 (br d, 0.5H), 4.03 (br d, 0.5H), 3.50-3.40 (m, 1H), 3.37-3.28 (m, 0.5H), 3.27-3.20 (m, 0.5H), 3.19-3.01 (m, 1H), 2.95-2.82 (m, 1H), 2.70-2.68 (m, 1H), 2.58 (q, 2H), 2.42-2.33 (m, 1H), 2.20-2.02 (m, 1H), 1.90-1.47 (m, 8H), 1.17 (t, 3H).

Example 2

1-(Cyclopentylcarbonyl)-3-(4-ethylphenyl)-5-(3-phenyl-1,2,4-oxadiazol-5-yl)piperidine [enantiomerically pure cis isomer]

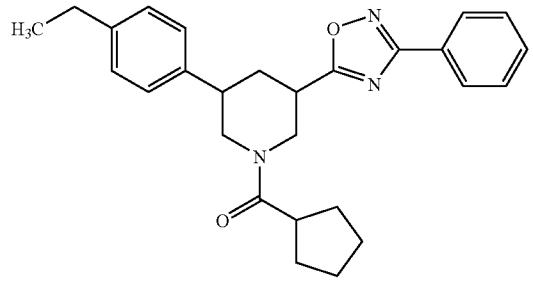

Enantiomer separation of 235 mg of the racemate from Example 1 according to Method 1D gave 117 mg of the title compound from Example 2 (Enantiomer 1) and 119 mg of the title compound from Example 3 (Enantiomer 2).

HPLC (Method 1E): $R_t$=5.25 min, >99.5% ee; MS (ESIpos): m/z=430 [M+H]$^+$.

Example 3

1-(Cyclopentylcarbonyl)-3-(4-ethylphenyl)-5-(3-phenyl-1,2,4-oxadiazol-5-yl)piperidine [enantiomerically pure cis isomer]

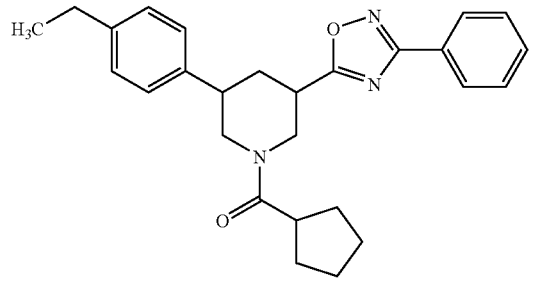

Enantiomer separation of 235 mg of the racemate from Example 1 according to Method 1D gave 117 mg of the title compound from Example 2 (Enantiomer 1) and 119 mg of the title compound from Example 3 (Enantiomer 2).

HPLC (Method 1E): $R_t$=6.98 min, >99.5% ee; MS (ESIpos): m/z=430 [M+H]$^+$.

Example 4 cis-(3,5)-1-(Cyclopentylcarbonyl)-3-[4-(1-methylethyl)phenyl]-5-(3-phenyl-1,2,4-oxadiazol-5-yl)piperidine [racemic cis isomer]

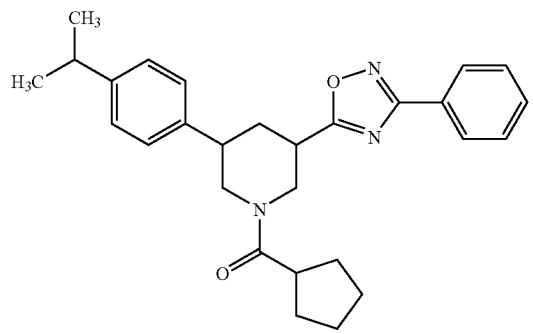

60 mg (0.18 mmol) of cis-(3,5)-1-(cyclopentylcarbonyl)-5-[4-(1-methylethyl)phenyl]piperidine-3-carboxylic acid (Example 12A) and 36 mg (0.26 mmol, 1.5 eq.) of N'-hydroxybenzenecarboximidamide were reacted according to the General Method 2. Yield: 64 mg (83% of theory)

LC-MS (Method 1B): $R_t$=3.28 min; MS (ESIpos): m/z=444 [M+H]$^+$.

Example 5 cis-(3,5)-1-(Cyclopentylcarbonyl)-3-[4-(1-methylethyl)phenyl]-5-(3-phenyl-1,2,4-oxadiazol-5-yl)piperidine [enantiomerically pure cis isomer]

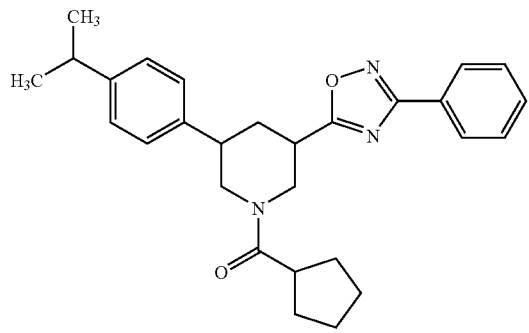

Enantiomer separation of 58 mg of the racemate from Example 4 according to Method 2D gave 15 mg of the title compound from Example 5 (Enantiomer 1) and 17 mg of the title compound from Example 6 (Enantiomer 2).

HPLC (Method 2E): $R_t$=7.09 min.

Example 6 cis-(3,5)-1-(Cyclopentylcarbonyl)-3-[4-(1-methylethyl)phenyl]-5-(3-phenyl-1,2,4-oxadiazol-5-yl)piperidine [enantiomerically pure cis isomer]

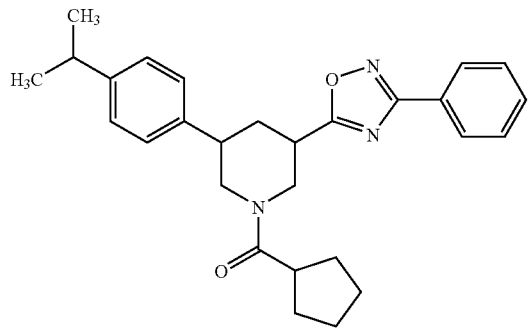

Enantiomer separation of 58 mg of the racemate from Example 4 according to Method 2D gave 15 mg of the title compound from Example 5 (Enantiomer 1) and 17 mg of the title compound from Example 6 (Enantiomer 2).

HPLC (Method 2E): $R_t$=7.79 min.

Example 7 cis-(3,5)-1-(Cyclopentylcarbonyl)-3-(3-phenyl-1,2,4-oxadiazol-5-yl)-5-[4-(trifluoromethyl)phenyl]piperidine [racemic cis isomer]

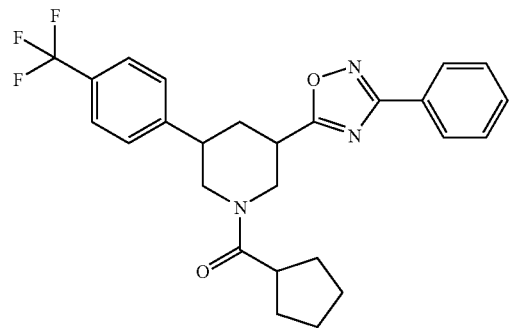

150 mg (0.41 mmol) of cis-(3,5)-1-(cyclopentylcarbonyl)-5-[4-(trifluoromethyl)phenyl]piperidine-3-carboxylic acid (Example 17A) and 83 mg (0.61 mmol, 1.5 eq.) of N'-hydroxybenzenecarboximidamide were reacted according to the General Method 2. Yield: 152 mg (80% of theory)

LC-MS (Method 1B): $R_t$=3.28 min; MS (ESIpos): m/z=470 [M+H]$^+$;

$^1$H-NMR (400 MHz, DMSO-d$_6$): δ=8.05-7.99 (dd, 2H), 7.67-7.54 (t, 2H), 7.86 (m, 5H), 4.96 (br d, 0.5H), 4.57 (br dd, 1H), 4.09 (br d, 0.5H), 3.98 (br d, 2H), 3.19-2.78 (m, 3H), 2.42 (br t, 1H), 2.28-2.10 (m, 1H), 1.91-1.46 (m, 8H).

Example 8 cis-(3,5)-1-(Cyclopentylcarbonyl)-3-(3-phenyl-1,2,4-oxadiazol-5-yl)-5-[4-(trifluoromethyl)phenyl]piperidine [enantiomerically pure cis isomer]

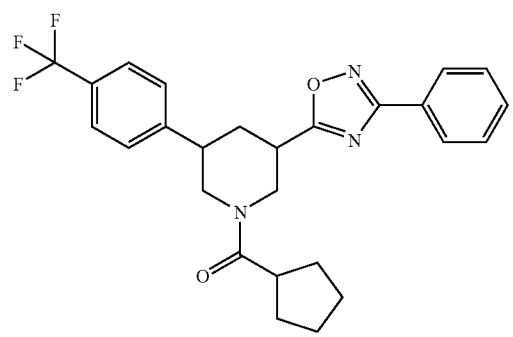

Enantiomer separation of 142 mg of the racemate from Example 7 according to Method 3D gave 58 mg of the title compound from Example 8 (Enantiomer 1) and 58 mg of the title compound from Example 9 (Enantiomer 2).

HPLC (Method 3E): $R_t$=5.62 min.

Example 9 cis-(3,5)-1-(Cyclopentylcarbonyl)-3-(3-phenyl-1,2,4-oxadiazol-5-yl)-5-[4-(trifluoromethyl)phenyl]-piperidine [enantiomerically pure cis isomer]

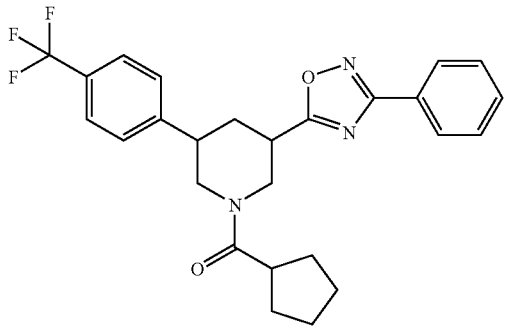

Enantiomer separation of 142 mg of the racemate from Example 7 according to Method 3D gave 58 mg of the title compound from Example 8 (Enantiomer 1) and 58 mg of the title compound from Example 9 (Enantiomer 2).

HPLC (Method 3E): $R_t$=6.16 min.

Example 10 cis-(3,5)-1-(Cyclopentylcarbonyl)-3-(3-phenyl-1,2,4-oxadiazol-5-yl)-5-[4-(trifluoromethoxy)-phenyl]piperidine [racemic cis isomer]

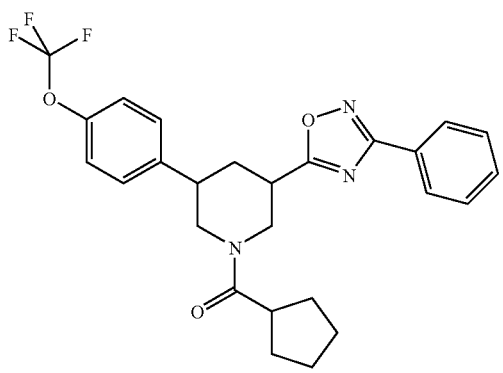

60 mg (0.16 mmol) of cis-(3,5)-1-(cyclopentylcarbonyl)-5-[4-(trifluoromethoxy)phenyl]piperidine-3-carboxylic acid (Example 24A) and 32 mg (0.23 mmol, 1.5 eq.) of N'-hydroxybenzenecarboximidamide were reacted according to the General Method 2. Yield: 62 mg (83% of theory)

LC-MS (Method 3B): $R_t$=3.33 min; MS (ESIpos): m/z=486 [M+H]$^+$.

Example 11 cis-(3,5)-1-(2,2-Dimethylpropanoyl)-3-(4-methoxyphenyl)-5-(3-phenyl-1,2,4-oxadiazol-5-yl)piperidine [racemic cis isomer]

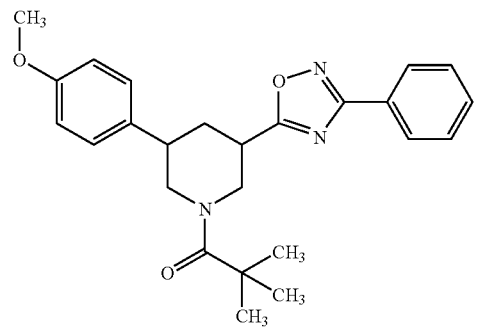

150 mg (0.41 mmol) of cis-(3,5)-1-(2,2-dimethylpropanoyl)-5-(4-methoxyphenyl)piperidine-3-carboxylic acid (Example 33A) and 96 mg (0.70 mmol, 1.5 eq.) of N'-hydroxybenzenecarboximidamide were reacted according to the General Method 2. Yield: 126 mg (64% of theory)

LC-MS (Method 3B): $R_t$=2.49 min; MS (ESIpos): m/z=420 [M+H]$^+$.

Example 12 cis-(3,5)-1-(2,2-Dimethylpropanoyl)-3-(4-methoxyphenyl)-5-(3-phenyl-1,2,4-oxadiazol-5-yl)piperidine [enantiomerically pure cis isomer]

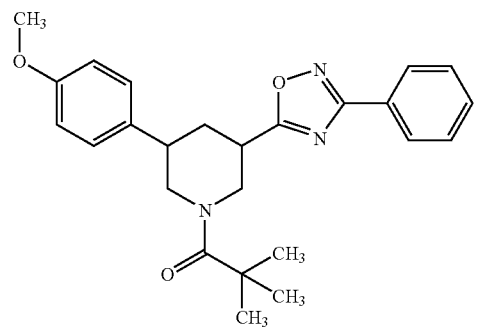

Enantiomer separation of 119 mg of the racemate from Example 11 according to Method 4D gave 20 mg of the title compound from Example 12 (Enantiomer 1) and 17 mg of the title compound from Example 13 (Enantiomer 2).

HPLC (Method 4E): $R_t$=5.72 min.

Example 13 cis-(3,5)-1-(2,2-Dimethylpropanoyl)-3-(4-methoxyphenyl)-5-(3-phenyl-1,2,4-oxadiazol-5-yl)piperidine [enantiomerically pure cis isomer]

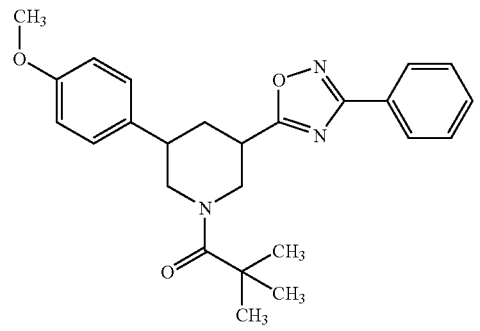

Enantiomer separation of 119 mg of the racemate from Example 11 according to Method 4D gave 20 mg of the title compound from Example 12 (Enantiomer 1) and 17 mg of the title compound from Example 13 (Enantiomer 2).

HPLC (Method 4E): $R_t$=6.42 min.

Example 14

4-{[3-(4-Ethylphenyl)-5-(3-phenyl-1,2,4-oxadiazol-5-yl)piperidin-1-yl]carbonyl}morpholine [racemic cis isomer]

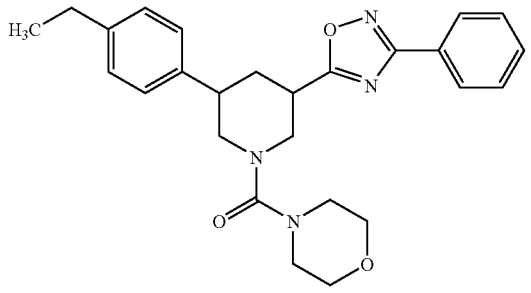

400 mg (1.16 mmol) of 5-(4-ethylphenyl)-1-(morpholin-4-ylcarbonyl)piperidine-3-carboxylic acid (Example 38A) and 173 mg (1.27 mmol, 1.1 eq.) of N'-hydroxybenzenecarboximidamide were reacted according to the General Method 1. Yield: 373 mg (72% of theory)

HPLC (Method 3A): $R_t$=4.98 min; MS (ESIpos): m/z=447 [M+H]$^+$;

$^1$H-NMR (400 MHz, DMSO-$d_6$): δ=8.01 (d, 2H), 7.63-7.52 (m, 3H), 7.25 (d, 2H), 7.18 (d, 2H), 4.09 (br d, 1H), 3.62 (br d, 1H), 3.60-3.54 (m, 4H), 3.53-3.44 (m, 1H), 3.26-3.17 (m, 4H), 3.11 (t, 1H), 2.97 (q, 1H), 2.94-2.85 (m, 1H), 2.58 (q, 2H), 2.38 (br d, 1H), 2.04 (q, 1H), 1.17 (t, 3H).

Example 15

4-{[3-(4-Ethylphenyl)-5-(3-phenyl-1,2,4-oxadiazol-5-yl)piperidin-1-yl]carbonyl}morpholine [enantiomerically pure cis isomer]

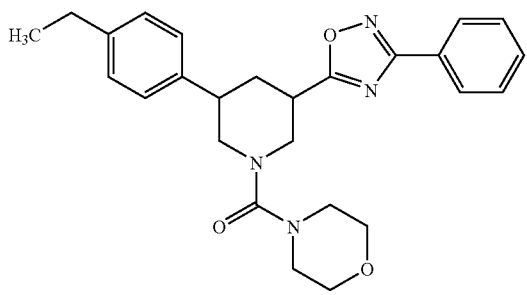

Enantiomer separation of 440 mg of the racemate from Example 14 according to Method 5D gave 187 mg of the title compound from Example 15 (Enantiomer 1) and 190 mg of the title compound from Example 16 (Enantiomer 2).

HPLC (Method 5E): $R_t$=7.95 min, >99.5% ee; MS (ESIpos): m/z=447 [M+H]$^+$.

Example 16

4-{[3-(4-Ethylphenyl)-5-(3-phenyl-1,2,4-oxadiazol-5-yl)piperidin-1-yl]carbonyl} morpholine [enantiomerically pure cis isomer]

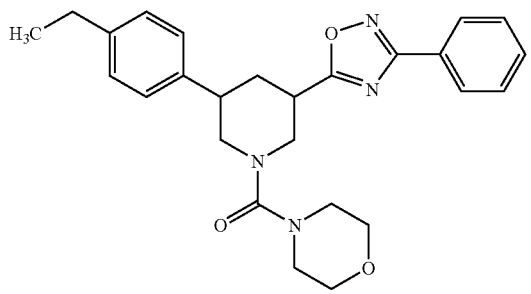

Enantiomer separation of 440 mg of the racemate from Example 14 according to Method 5D gave 187 mg of the title compound from Example 15 (Enantiomer 1) and 190 mg of the title compound from Example 16 (Enantiomer 2).

HPLC (Method 5E): $R_t$=1.13 min, >99.5% ee; MS (ESIpos): m/z=447 [M+H]$^+$.

Example 17

4-({3-(3-Phenyl-1,2,4-oxadiazol-5-yl)-5-[4-(trifluoromethoxy)phenyl]piperidin-1-yl}carbonyl)-morpholine [racemic cis isomer]

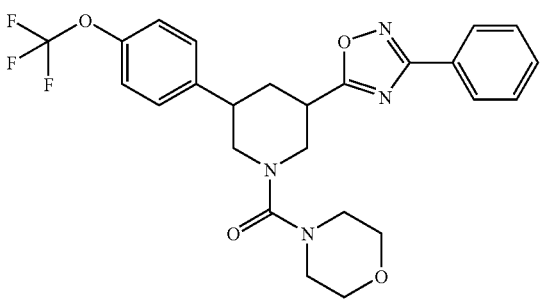

80 mg (0.20 mmol) of 1-(morpholin-4-ylcarbonyl)-5-[4-(trifluoromethoxy)phenyl]piperidine-3-carboxylic acid (Example 44A) and 30 mg (0.22 mmol, 1.1 eq.) of N'-hydroxybenzenecarboximidamide were reacted according to the General Method 1. Yield: 10 mg (10% of theory)

HPLC (Method 2A): $R_t$=5.15 min; MS (ESIpos): m/z=503 [M+H]$^+$;

$^1$H-NMR (500 MHz, DMSO-$d_6$): δ=8.01 (d, 2H), 7.62-7.55 (m, 2H), 7.50 (d, 2H), 7.42 (t, 1H), 7.35 (d, 2H), 4.09 (br d, 1H), 3.64 (br d, 1H), 3.61-3.55 (m, 4H), 3.55-3.46 (m, 1H), 3.25-3.19 (m, 4H), 3.14 (t, 1H), 3.07-2.97 (m, 2H), 2.40 (br d, 1H), 2.07 (q, 1H).

Example 18

4-({3-[3-(2-Chlorophenyl)-1,2,4-oxadiazol-5-yl]-5-(4-ethylphenyl)piperidin-1-yl}carbonyl)-morpholine [racemic cis isomer]

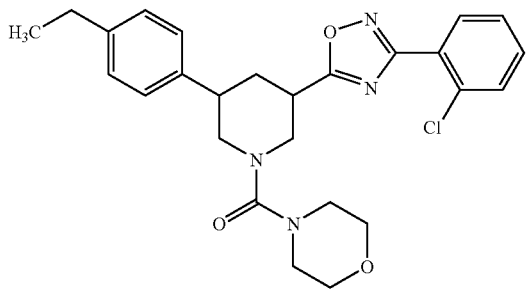

69 mg (0.20 mmol) of 5-(4-ethylphenyl)-1-(morpholin-4-ylcarbonyl)piperidine-3-carboxylic acid (Example 38A) and 38 mg (0.22 mmol, 1.1 eq.) of 2-chloro-N'-hydroxybenzenecarboximidamide were reacted according to the General Method 1. Yield: 49 mg (51% of theory)

HPLC (Method 3A): $R_t$=5.01 min; MS (ESIpos): m/z=481 [M+H]$^+$;

$^1$H-NMR (400 MHz, DMSO-d$_6$): δ=7.92 (dd, 1H), 7.68 (dd, 1H), 7.61 (dt, 1H), 7.54 (dt, 1H), 7.25 (d, 2H), 7.18 (d, 2H), 4.10 (br d, 1H), 3.62 (br d, 1H), 3.61-3.54 (m, 4H), 3.58-3.47 (m, 1H), 3.25-3.18 (m, 4H), 3.11 (t, 1H), 2.97 (q, 1H), 2.95-2.86 (m, 1H), 2.58 (q, 2H), 2.38 (br d, 1H), 2.04 (q, 1H), 1.17 (t, 3H).

Example 19

4-({3-[3-(2-Chlorophenyl)-1,2,4-oxadiazol-5-yl]-5-[4-(trifluoromethoxy)phenyl]piperidin-1-yl}carbonyl)morpholine [racemic cis isomer]

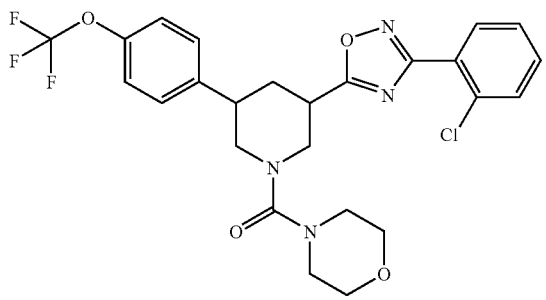

80 mg (0.20 mmol) of 1-(morpholin-4-ylcarbonyl)-5-[4-(trifluoromethoxy)phenyl]piperidine-3-carboxylic acid (Example 44A) and 38 mg (0.22 mmol, 1.1 eq.) of 2-chloro-N'-hydroxybenzenecarboximidamide were reacted according to the General Method 1. Yield: 56 mg (52% of theory)

HPLC (Method 2A): $R_t$=5.17 min; MS (ESIpos): m/z=537 [M+H]$^+$;

$^1$H-NMR (400 MHz, DMSO-d$_6$): δ=7.92 (dd, 1H), 7.69 (dd, 1H), 7.61 (dt, 1H), 7.54 (dt, 1H), 7.49 (d, 2H), 7.34 (d, 2H), 4.09 (br d, 1H), 3.64 (br d, 1H), 3.62-3.48 (m, 5H), 3.26-3.18 (m, 4H), 3.13 (t, 1H), 3.07-2.97 (m, 2H), 2.42 (br d, 1H), 2.07 (q, 1H).

Example 20

4-({3-(4-Ethylphenyl)-5-[3-(2-methylphenyl)-1,2,4-oxadiazol-5-yl]piperidin-1-yl}carbonyl)-morpholine [racemic cis isomer]

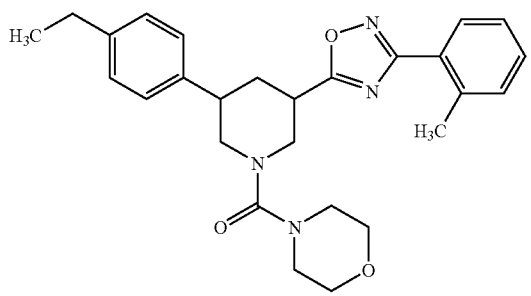

69 mg (0.20 mmol) of 5-(4-ethylphenyl)-1-(morpholin-4-ylcarbonyl)piperidine-3-carboxylic acid (Example 38A) and 33 mg (0.22 mmol, 1.1 eq.) of 1-hydroxy-2-methylbenzenecarboximidamide were reacted according to the General Method 1. Yield: 62 mg (68% of theory)

HPLC (Method 1A): $R_t$=5.12 min; MS (ESIpos): m/z=461 [M+H]$^+$;

$^1$H-NMR (400 MHz, DMSO-d$_6$): δ=7.93 (d, 1H), 7.51-7.44 (m, 1H), 7.43-7.35 (m, 2H), 7.25 (d, 2H), 7.18 (d, 2H), 4.10 (br d, 1H), 3.62 (br d, 1H), 3.60-3.53 (m, 4H), 3.52-3.44 (m, 1H), 3.25-3.18 (m, 4H), 3.11 (t, 1H), 2.97 (q, 1H), 2.95-2.86 (m, 1H), 2.58 (q, 2H), 2.56 (s, 3H), 2.38 (br d, 1H), 2.04 (q, 1H), 1.17 (t, 3H).

Example 21

4-({3-[3-(2-Methylphenyl)-1,2,4-oxadiazol-5-yl]-5-[4-(trifluoromethoxy)phenyl]piperidin-1-yl}carbonyl)morpholine [racemic cis isomer]

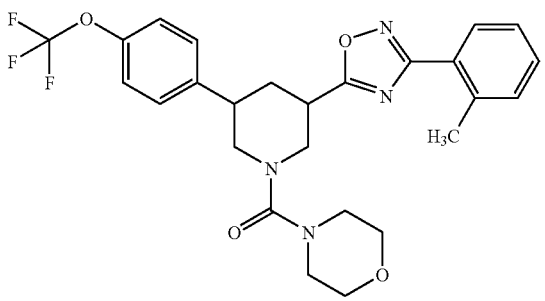

80 mg (0.20 mmol) of 1-(morpholin-4-ylcarbonyl)-5-[4-(trifluoromethoxy)phenyl]piperidine-3-carboxylic acid (Example 44A) and 33 mg (0.22 mmol, 1.1 eq.) of N'-hydroxy-2-methylbenzenecarboximidamide were reacted according to the General Method 1. Yield: 14 mg (13% of theory)

HPLC (Method 2A): $R_t$=5.30 min; MS (ESIpos): m/z=517 [M+H]$^+$;

¹H-NMR (400 MHz, DMSO-d₆): δ=7.92 (dd, 1H), 7.53-7.45 (m, 3H), 7.43-7.33 (m, 4H), 4.09 (br d, 1H), 3.64 (br d, 1H), 3.60-3.55 (m, 4H), 3.54-3.46 (m, 1H), 3.24-3.20 (m, 4H), 3.14 (t, 1H), 3.06-2.99 (m, 2H), 2.42 (br d, 1H), 2.07 (q, 1H).

Example 22

1-(Cyclopentylcarbonyl)-3-(4-ethylphenyl)-5-[3-(3-fluorophenyl)-1,2,4-oxadiazol-5-yl]piperidine [racemic cis isomer]

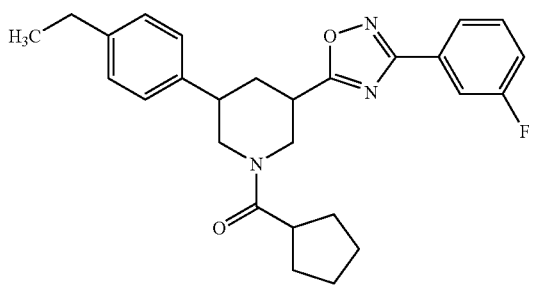

66 mg (0.20 mmol) of 1-(cyclopentylcarbonyl)-5-(4-ethylphenyl)piperidine-3-carboxylic acid (Example 7A) and 34 mg (0.22 mmol, 1.1 eq.) of 3-fluoro-N'-hydroxybenzenecarboximidamide were reacted according to the General Method 1. Yield: 47 mg (53% of theory)

HPLC (Method 2A): R$_t$=5.78 min; MS (ESIpos): m/z=448 [M+H]⁺;

¹H-NMR (500 MHz, DMSO-d₆): δ=7.87 (d, 1H), 7.76 (d, 1H), 7.64 (q, 1H), 7.47 (t, 1H), 7.28 (d, 1H), 7.23 (d, 1H), 7.19 (t, 2H), 4.94 (br d, 0.5H), 4.53 (br d, 0.5H), 4.48 (br d, 0.5H), 4.03 (br d, 0.5H), 3.50-3.40 (m, 1H), 3.38-3.28 (m, 0.5H), 3.27-3.17 (m, 0.5H), 3.17-3.03 (m, 1H), 2.94-2.83 (m, 1H), 2.81-2.68 (m, 1H), 2.58 (q, 2H), 2.44-2.34 (m, 1H), 2.19-2.03 (m, 1H), 1.89-1.46 (m, 8H), 1.17 (t, 3H).

Example 23 cis-(3,5)-1-(Cyclopentylcarbonyl)-3-[3-(3-fluorophenyl)-1,2,4-oxadiazol-5-yl]-5-[4-(trifluoro-methyl)phenyl]piperidine [racemic cis isomer]

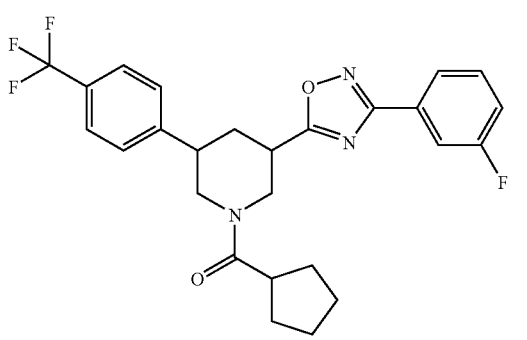

150 mg (0.41 mmol) of cis-(3,5)-1-(cyclopentylcarbonyl)-5-[4-(trifluoromethyl)phenyl]piperidine-3-carboxylic acid (Example 17A) and 93 mg (0.61 mmol, 1.5 eq.) of 3-fluoro-N'-hydroxybenzenecarboximidamide were reacted according to the General Method 2. Yield: 150 mg (76% of theory)

LC-MS (Method 1B): R$_t$=3.31 min; MS (ESIpos): m/z=488 [M+H]⁺.

Example 24 cis-(3,5)-1-(Cyclopentylcarbonyl)-3-[3-(3-fluorophenyl)-1,2,4-oxadiazol-5-yl]-5-[4-(trifluoro-methoxy)phenyl]piperidine [racemic cis isomer]

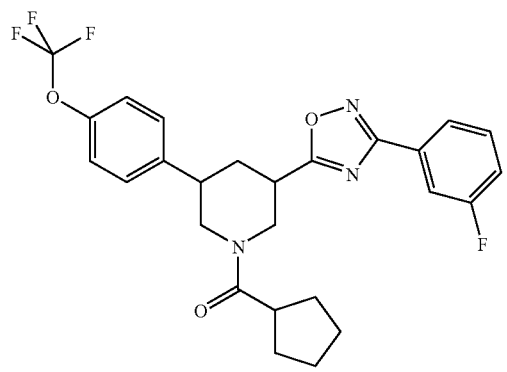

70 mg (0.18 mmol) of cis-(3,5)-1-(cyclopentylcarbonyl)-5-[4-(trifluoromethoxy)phenyl]piperidine-3-carboxylic acid (Example 24A) and 42 mg (0.27 mmol, 1.5 eq.) of 3-fluoro-N'-hydroxybenzenecarboximidamide were reacted according to the General Method 2. Yield: 70 mg (76% of theory)

LC-MS (Method 1B): R$_t$=3.36 min; MS (ESIpos): m/z=504 [M+H]⁺.

Example 25

4-({3-(4-Ethylphenyl)-5-[3-(3-fluorophenyl)-1,2,4-oxadiazol-5-yl]piperidin-1-yl}carbonyl)-morpholine [racemic cis isomer]

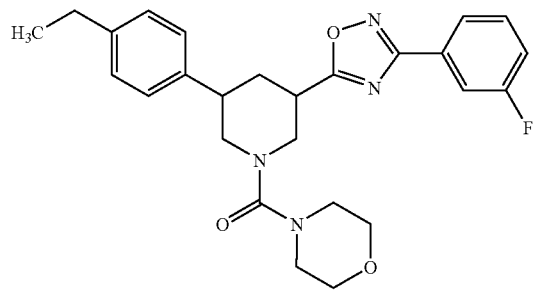

69 mg (0.20 mmol) of 5-(4-ethylphenyl)-1-(morpholin-4-ylcarbonyl)piperidine-3-carboxylic acid (Example 38A) and 34 mg (0.22 mmol, 1.1 eq.) of 3-fluoro-N'-hydroxybenzenecarboximidamide were reacted according to the General Method 1. Yield: 55 mg (58% of theory)

HPLC (Method 3A): R$_t$=5.06 min; MS (ESIpos): m/z=465 [M+H]⁺;

¹H-NMR (400 MHz, DMSO-d₆): δ=7.81 (d, 1H), 7.76 (d, 1H), 7.64 (dt, 1H), 7.46 (dt, 1H), 7.24 (d, 2H), 7.18 (d, 2H), 4.09 (br d, 1H), 3.63 (br d, 1H), 3.62-3.54 (m, 4H), 3.54-3.45

(m, 1H), 3.26-3.18 (m, 4H), 3.11 (t, 1H), 2.97 (q, 1H), 2.94-2.84 (m, 1H), 2.58 (q, 2H), 2.38 (br d, 1H), 2.05 (q, 1H), 1.17 (t, 3H).

Example 26

4-({3-[3-(3-Fluorophenyl)-1,2,4-oxadiazol-5-yl]-5-[4-(trifluoromethoxy)phenyl]piperidin-1-yl}carbonyl)morpholine [racemic cis isomer]

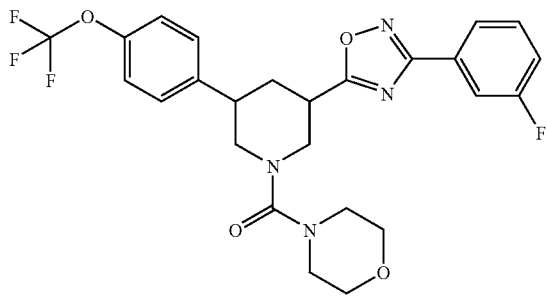

80 mg (0.20 mmol) of 1-(morpholin-4-ylcarbonyl)-5-[4-(trifluoromethoxy)phenyl]piperidine-3-carboxylic acid (Example 44A) and 34 mg (0.22 mmol, 1.1 eq.) of 3-fluoro-N'-hydroxybenzenecarboximidamide were reacted according to the General Method 1. Yield: 71 mg (68% of theory)

HPLC (Method 2A): $R_t$=5.21 min; MS (ESIpos): m/z=521 [M+H]$^+$;

$^1$H-NMR (400 MHz, DMSO-d$_6$): δ=7.88 (d, 1H), 7.76 (d, 1H), 7.64 (dd, 1H), 7.54-7.44 (m, 3H), 7.34 (d, 2H), 4.09 (br d, 1H), 3.64 (br d, 1H), 3.62-3.53 (m, 4H), 3.56-3.47 (m, 1H), 3.26-3.18 (m, 4H), 3.13 (t, 1H), 3.08-2.97 (m, 2H), 2.41 (br d, 1H), 2.07 (q, 1H).

Example 27

4-({3-(4-Ethylphenyl)-5-[3-(3-methylphenyl)-1,2,4-oxadiazol-5-yl]piperidin-1-yl}carbonyl)-morpholine [racemic cis isomer]

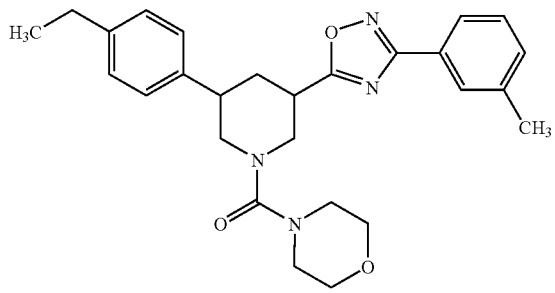

69 mg (0.20 mmol) of 5-(4-ethylphenyl)-1-(morpholin-4-ylcarbonyl)piperidine-3-carboxylic acid (Example 38A) and 33 mg (0.22 mmol, 1.1 eq.) of 1-hydroxy-3-methylbenzenecarboximidamide were reacted according to the General Method 1. Yield: 16 mg (18% of theory)

HPLC (Method 1A): $R_t$=5.45 min; MS (ESIpos): m/z=461 [M+H]$^+$;

$^1$H-NMR (400 MHz, DMSO-d$_6$): δ=7.84 (s, 1H), 7.81 (d, 1H), 7.45 (t, 1H), 7.42 (t, 1H), 7.25 (d, 2H), 7.18 (d, 2H), 4.09 (br d, 1H), 3.63 (br d, 1H), 3.63-3.53 (m, 4H), 3.53-3.43 (m, 1H), 3.26-3.18 (m, 4H), 3.11 (t, 1H), 2.97 (q, 1H), 2.94-2.85 (m, 1H), 2.58 (q, 2H), 2.40 (s, 3H), 2.38 (br d, 1H), 2.04 (q, 1H), 1.17 (t, 3H).

Example 28

4-({3-(4-Ethylphenyl)-5-[3-(3-methoxyphenyl)-1,2,4-oxadiazol-5-yl]piperidin-1-yl}carbonyl)-morpholine [racemic cis isomer]

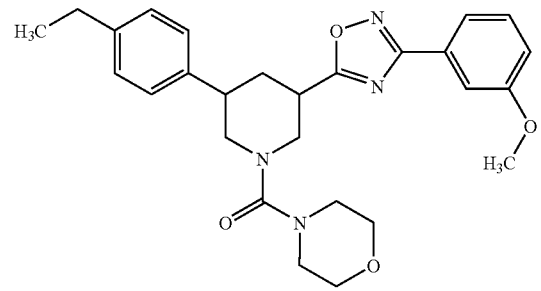

69 mg (0.20 mmol) of 5-(4-ethylphenyl)-1-(morpholin-4-ylcarbonyl)piperidine-3-carboxylic acid (Example 38A) and 37 mg (0.22 mmol, 1.2 eq.) of N'-hydroxy-3-methoxybenzenecarboximidamide were reacted according to the General Method 1. Yield:

60 mg (63% of theory)

HPLC (Method 1A): $R_t$=5.25 min; MS (ESIpos): m/z=477 [M+H]$^+$;

$^1$H-NMR (400 MHz, DMSO-d$_6$): δ=7.60 (d, 1H), 7.53-7.46 (m, 2H), 7.25 (d, 2H), 7.21-7.13 (m, 3H), 4.09 (br d, 1H), 3.84 (s, 3H), 3.62 (br d, 1H), 3.62-3.54 (m, 4H), 3.54-3.43 (m, 1H), 3.24-3.18 (m, 4H), 3.11 (t, 1H), 2.97 (q, 1H), 2.95-2.85 (m, 1H), 2.58 (q, 2H), 2.37 (br d, 1H), 2.04 (q, 1H), 1.17 (t, 3H).

Example 29

4-({3-[3-(3-Chlorophenyl)-1,2,4-oxadiazol-5-yl]-5-(4-ethylphenyl)piperidin-1-yl}carbonyl)-morpholine [racemic cis isomer]

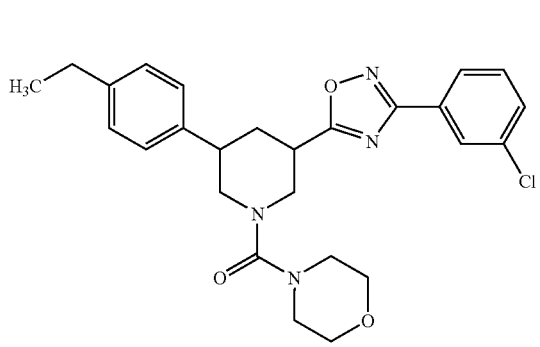

69 mg (0.20 mmol) of 5-(4-ethylphenyl)-1-(morpholin-4-ylcarbonyl)piperidine-3-carboxylic acid (Example 38A) and 38 mg (0.22 mmol, 1.1 eq.) of 3-chloro-N'-hydroxybenzenecarboximidamide were reacted according to the General Method 1. Yield: 40 mg (42% of theory)

HPLC (Method 1A): $R_t$=5.55 min; MS (ESIpos): m/z=481 [M+H]$^+$;

$^1$H-NMR (400 MHz, DMSO-$d_6$): δ=8.03-7.96 (m, 2H), 7.72-7.67 (m, 1H), 7.62 (t, 1H), 7.25 (d, 2H), 7.18 (d, 2H), 4.09 (br d, 1H), 3.63 (br d, 1H), 3.61-3.54 (m, 4H), 3.55-3.45 (m, 1H), 3.26-3.17 (m, 4H), 3.11 (t, 1H), 2.97 (q, 1H), 2.95-2.85 (m, 1H), 2.58 (q, 2H), 2.38 (br d, 1H), 2.04 (q, 1H), 1.17 (t, 3H).

Example 30

4-{[3-(4-Ethylphenyl)-5-{3-[3-(trifluoromethyl)phenyl]-1,2,4-oxadiazol-5-yl}piperidin-1-yl]carbonyl}morpholine [racemic cis isomer]

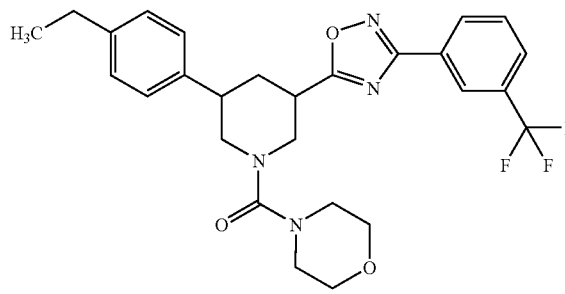

69 mg (0.20 mmol) of 5-(4-ethylphenyl)-1-(morpholin-4-ylcarbonyl)piperidine-3-carboxylic acid (Example 38A) and 45 mg (0.22 mmol, 1.1 eq.) of 1-hydroxy-3-(trifluoromethyl)benzenecarboximidamide were reacted according to the General Method 1. Yield: 60 mg (59% of theory)

HPLC (Method 1A): $R_t$=5.59 min; MS (ESIpos): m/z=515 [M+H]$^+$;

$^1$H-NMR (400 MHz, DMSO-$d_6$): δ=8.33 (d, 1H), 8.25 (s, 1H), 8.00 (d, 1H), 7.85 (t, 1H), 7.25 (d, 2H), 7.18 (d, 2H), 4.09 (br d, 1H), 3.62 (br d, 1H), 3.61-3.55 (m, 4H), 3.58-3.47 (m, 1H), 3.26-3.18 (m, 4H), 3.13 (t, 1H), 2.98 (q, 1H), 2.96-2.86 (m, 1H), 2.58 (q, 2H), 2.38 (br d, 1H), 2.06 (q, 1H), 1.17 (t, 3H).

Example 31

4-{[3-(4-Ethylphenyl)-5-{3-[3-(trifluoromethoxy)phenyl]-1,2,4-oxadiazol-5-yl}piperidin-1-yl]carbonyl}morpholine [racemic cis isomer]

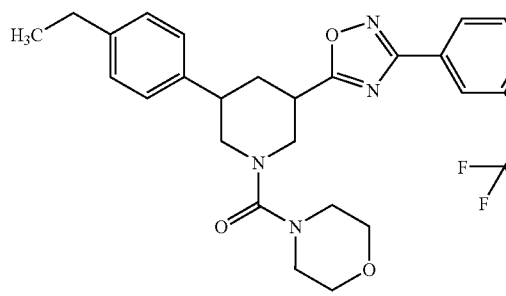

69 mg (0.20 mmol) of 5-(4-ethylphenyl)-1-(morpholin-4-ylcarbonyl)piperidine-3-carboxylic acid (Example 38A) and 48 mg (0.22 mmol, 1.1 eq.) of 1-hydroxy-3-(trifluoromethoxy)benzenecarboximidamide were reacted according to the General Method 1. Yield: 68 mg (64% of theory)

HPLC (Method 1A): $R_t$=5.65 min; MS (ESIpos): m/z=531 [M+H]$^+$;

$^1$H-NMR (400 MHz, DMSO-$d_6$): δ=8.06 (d, 1H), 7.90 (s, 1H), 7.74 (t, 1H), 7.64 (d, 1H), 7.25 (d, 2H), 7.18 (d, 2H), 4.09 (br d, 1H), 3.62 (br d, 1H), 3.60-3.53 (m, 4H), 3.57-3.46 (m, 1H), 3.25-3.18 (m, 4H), 3.12 (t, 1H), 2.97 (q, 1H), 2.95-2.84 (m, 1H), 2.58 (q, 2H), 2.37 (br d, 1H), 2.05 (q, 1H), 1.17 (t, 3H).

Example 32

1-(Cyclopentylcarbonyl)-3-(4-ethylphenyl)-5-[3-(4-fluorophenyl)-1,2,4-oxadiazol-5-yl]piperidine [racemic cis isomer]

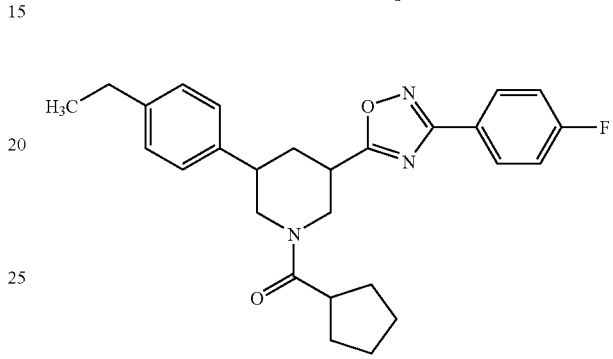

66 mg (0.20 mmol) of 1-(cyclopentylcarbonyl)-5-(4-ethylphenyl)piperidine-3-carboxylic acid (Example 7A) and 34 mg (0.22 mmol, 1.1 eq.) of 4-fluoro-N'-hydroxybenzenecarboximidamide were reacted according to the General Method 1. Yield: 45 mg (50% of theory)

HPLC (Method 2A): $R_t$=5.71 min; MS (ESIpos): m/z=448 [M+H]$^+$;

$^1$H-NMR (500 MHz, DMSO-$d_6$): δ=8.07 (dd, 2H), 7.41 (t, 2H), 7.28 (d, 1H), 7.23 (d, 1H), 7.19 (t, 2H), 4.95 (br d, 0.5H), 4.53 (br d, 0.5H), 4.48 (br d, 0.5H), 4.03 (br d, 0.5H), 3.49-3.40 (m, 1H), 3.37-3.29 (m, 0.5H), 3.26-3.18 (m, 0.5H), 3.17-3.03 (m, 1H), 2.93-2.83 (m, 1H), 2.80-2.68 (m, 1H), 2.58 (q, 2H), 2.43-2.33 (m, 1H), 2.18-2.03 (m, 1H), 1.88-1.47 (m, 8H), 1.17 (t, 3H).

Example 33

4-({3-(4-Ethylphenyl)-5-[3-(4-fluorophenyl)-1,2,4-oxadiazol-5-yl]piperidin-1-yl}carbonyl)-morpholine [racemic cis isomer]

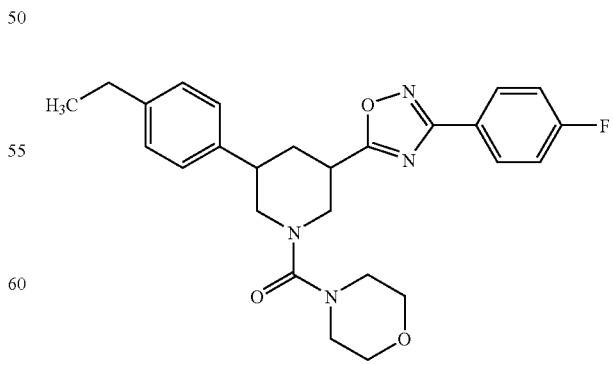

69 mg (0.20 mmol) of 5-(4-ethylphenyl)-1-(morpholin-4-ylcarbonyl)piperidine-3-carboxylic acid (Example 38A) and 34 mg (0.22 mmol, 1.1 eq.) of 4-fluoro-N'-hydroxybenzenecarboximidamide were reacted according to the General Method 1. Yield: 56 mg (60% of theory)

HPLC (Method 1A): $R_t$=5.31 min; MS (ESIpos): m/z=465 [M+H]$^+$;

$^1$H-NMR (400 MHz, DMSO-d$_6$): δ=8.08 (dd, 2H), 7.41 (dd, 2H), 7.24 (d, 2H), 7.18 (d, 2H), 4.09 (br d, 1H), 3.62 (br d, 1H), 3.61-3.54 (m, 4H), 3.54-3.44 (m, 1H), 3.25-3.18 (m, 4H), 3.11 (t, 1H), 2.97 (q, 1H), 2.94-2.85 (m, 1H), 2.58 (q, 2H), 2.37 (br d, 1H), 2.03 (q, 1H), 1.17 (t, 3H).

Example 34

4-({3-[3-(4-Fluorophenyl)-1,2,4-oxadiazol-5-yl]-5-[4-(trifluoromethoxy)phenyl]piperidin-1-yl}carbonyl)morpholine [racemic cis isomer]

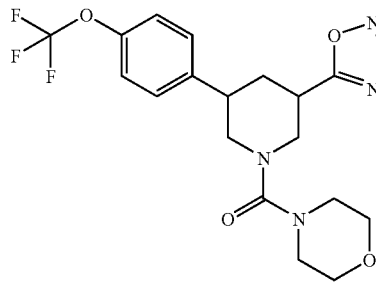

80 mg (0.20 mmol) of 1-(morpholin-4-ylcarbonyl)-5-[4-(trifluoromethoxy)phenyl]piperidine-3-carboxylic acid (Example 44A) and 34 mg (0.22 mmol, 1.1 eq.) of 4-fluoro-N'-hydroxybenzenecarboximidamide were reacted according to the General Method 1. Yield: 55 mg (53% of theory)

HPLC (Method 2A): $R_t$=5.18 min; MS (ESIpos): m/z=521 [M+H]$^+$;

$^1$H-NMR (400 MHz, DMSO-d$_6$): δ=8.07 (d, 2H), 7.49 (d, 2H), 7.42 (t, 2H), 7.34 (d, 2H), 4.09 (br d, 1H), 3.64 (br d, 1H), 3.63-3.54 (m, 4H), 3.54-3.45 (m, 1H), 3.26-3.18 (m, 4H), 3.13 (t, 1H), 3.07-2.97 (m, 2H), 2.40 (br d, 1H), 2.06 (q, 1H).

Example 35

4-({3-(4-Ethylphenyl)-5-[3-(4-chlorophenyl)-1,2,4-oxadiazol-5-yl]piperidin-1-yl}carbonyl)-morpholine [racemic cis isomer]

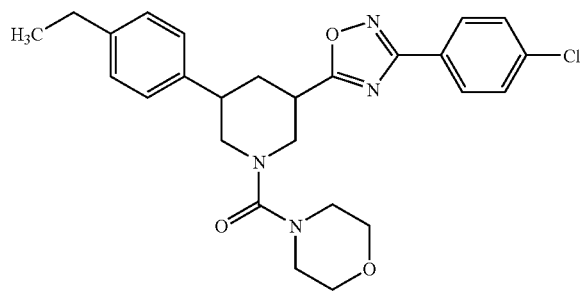

69 mg (0.20 mmol) of 5-(4-ethylphenyl)-1-(morpholin-4-ylcarbonyl)piperidine-3-carboxylic acid (Example 38A) and 38 mg (0.22 mmol, 1.1 eq.) of 4-chloro-N'-hydroxybenzenecarboximidamide were reacted according to the General Method 1. Yield: 61 mg (64% of theory)

HPLC (Method 2A): $R_t$=5.49 min; MS (ESIpos): m/z=481 [M+H]$^+$;

$^1$H-NMR (400 MHz, DMSO-d$_6$): δ=8.03 (d, 2H), 7.65 (d, 2H), 7.25 (d, 2H), 7.18 (d, 2H), 4.09 (br d, 1H), 3.62 (br d, 1H), 3.60-3.54 (m, 4H), 3.53-3.45 (m, 1H), 3.25-3.17 (m, 4H), 3.11 (t, 1H), 2.98 (q, 1H), 2.95-2.84 (m, 1H), 2.58 (q, 2H), 2.42 (br d, 1H), 2.04 (q, 1H), 1.17 (t, 3H).

Example 36

4-({3-[3-(1,3-Benzodioxol-5-yl)-1,2,4-oxadiazol-5-yl]-5-(4-ethylphenyl)piperidin-1-yl}carbonyl)-morpholine [racemic cis isomer]

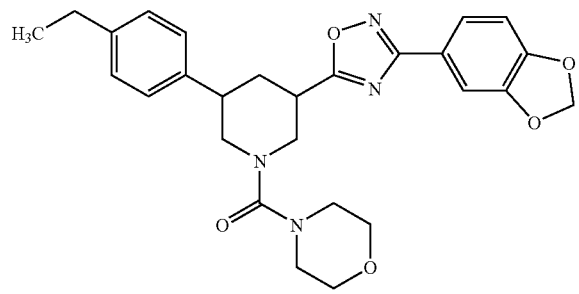

69 mg (0.20 mmol) of 5-(4-ethylphenyl)-1-(morpholin-4-ylcarbonyl)piperidine-3-carboxylic acid (Example 38A) and 40 mg (0.22 mmol, 1.1 eq.) of 1-hydroxy-1,3-benzodioxole-5-carboximidamide were reacted according to the General Method 1. Yield: 55 mg (54% of theory)

HPLC (Method 1A): $R_t$=4.63 min; MS (ESIpos): m/z=491 [M+H]$^+$;

$^1$H-NMR (400 MHz, DMSO-d$_6$): δ=7.58 (dd, 2H), 7.45 (d, 2H), 7.24 (d, 2H), 7.17 (d, 2H), 7.09 (d, 1H), 6.14 (s, 2H), 4.08 (br d, 1H), 3.62 (br d, 1H), 3.60-3.53 (m, 4H), 3.51-3.42 (m, 1H), 3.25-3.17 (m, 4H), 3.09 (t, 1H), 2.95 (q, 1H), 2.93-2.84 (m, 1H), 2.58 (q, 2H), 2.36 (br d, 1H), 2.02 (q, 1H), 1.17 (t, 3H).

Example 37

4-({3-[3-(2,4-Difluorophenyl)-1,2,4-oxadiazol-5-yl]-5-(4-ethylphenyl)piperidin-1-yl}carbonyl)-morpholine [racemic cis isomer]

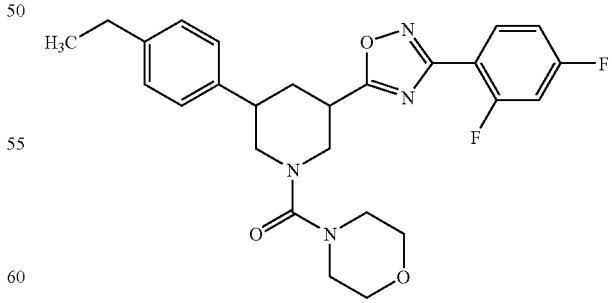

69 mg (0.20 mmol) of 5-(4-ethylphenyl)-1-(morpholin-4-ylcarbonyl)piperidine-3-carboxylic acid (Example 38A) and 38 mg (0.22 mmol, 1.1 eq.) of 2,4-difluoro-N'-hydroxybenzenecarboximidamide were reacted according to the General Method 1. Yield: 47 mg (47% of theory)

HPLC (Method 1A): $R_t$=5.27 min; MS (ESIpos): m/z=483 [M+H]$^+$;

$^1$H-NMR (400 MHz, DMSO-d$_6$): δ=8.10 (dd, 1H), 7.54 (dt, 1H), 7.32 (dt, 1H), 7.24 (d, 2H), 7.18 (d, 2H), 4.09 (br d, 1H), 3.62 (br d, 1H), 3.61-3.54 (m, 4H), 3.56-3.46 (m, 1H), 3.25-3.17 (m, 4H), 3.11 (t, 1H), 2.97 (q, 1H), 2.95-2.85 (m, 1H), 2.58 (q, 2H), 2.38 (br d, 1H), 2.03 (q, 1H), 1.17 (t, 3H).

Example 38

4-({3-[3-(2,4-Difluorophenyl)-1,2,4-oxadiazol-5-yl]-5-[4-(trifluoromethoxy)phenyl]piperidin-1-yl}carbonyl)morpholine [racemic cis isomer]

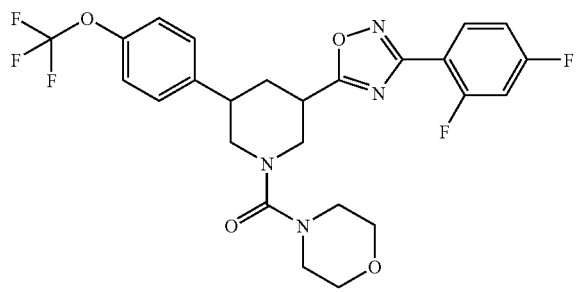

80 mg (0.20 mmol) of 1-(morpholin-4-ylcarbonyl)-5-[4-(trifluoromethoxy)phenyl]piperidine-3-carboxylic acid (Example 44A) and 38 mg (0.22 mmol, 1.1 eq.) of 2,4-difluoro-N'-hydroxybenzenecarboximidamide were reacted according to the General Method 1. Yield: 52 mg (48% of theory)

HPLC (Method 2A): $R_t$=5.12 min; MS (ESIpos): m/z=539 [M+H]$^+$;

$^1$H-NMR (400 MHz, DMSO-d$_6$): δ=8.14-8.05 (m, 1H), 7.59-7.46 (m, 3H), 7.38-7.28 (m, 3H), 4.09 (br d, 1H), 3.64 (br d, 1H), 3.62-3.47 (m, 5H), 3.27-3.17 (m, 4H), 3.13 (t, 1H), 3.08-2.97 (m, 2H), 2.41 (br d, 1H), 2.06 (q, 1H).

Example 39

4-({3-[3-(2,6-Difluorophenyl)-1,2,4-oxadiazol-5-yl]-5-(4-ethylphenyl)piperidin-1-yl}carbonyl)-morpholine [racemic cis isomer]

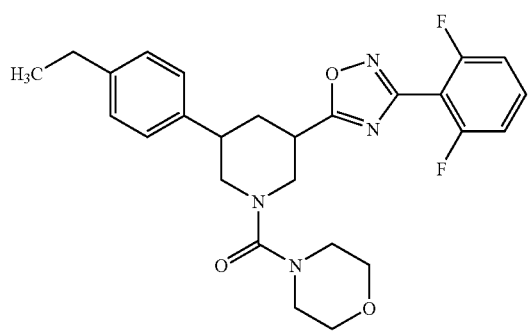

69 mg (0.20 mmol) of 5-(4-ethylphenyl)-1-(morpholin-4-ylcarbonyl)piperidine-3-carboxylic acid (Example 38A) and 38 mg (0.22 mmol, 1.1 eq.) of 2,6-difluoro-N'-hydroxyben- zenecarboximidamide were reacted according to the General Method 1. Yield: 17 mg (18% of theory)

HPLC (Method 2A): $R_t$=5.03 min; MS (ESIpos): m/z=483 [M+H]$^+$;

$^1$H-NMR (400 MHz, DMSO-d$_6$): δ=7.80-7.72 (m, 1H), 7.39 (t, 2H), 7.27 (d, 2H), 7.20 (d, 2H), 4.11 (br d, 1H), 3.64 (br d, 1H), 3.63-3.53 (m, 5H), 3.29-3.19 (m, 4H), 3.14 (t, 1H), 3.00 (t, 1H), 2.97-2.88 (m, 1H), 2.59 (q, 2H), 2.40 (br d, 1H), 2.07 (q, 1H), 1.19 (t, 3H).

Example 40

4-({3-[3-(2,6-Difluorophenyl)-1,2,4-oxadiazol-5-yl]-5-[4-(trifluoromethoxy)phenyl]piperidin-1-yl}carbonyl)morpholine [racemic cis isomer]

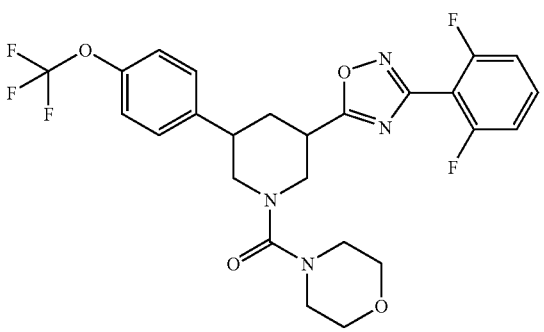

80 mg (0.20 mmol) of 1-(morpholin-4-ylcarbonyl)-5-[4-(trifluoromethoxy)phenyl]piperidine-3-carboxylic acid (Example 44A) and 38 mg (0.22 mmol, 1.1 eq.) of 2,6-difluoro-N'-hydroxybenzenecarboximidamide were reacted according to the General Method 1. Yield: 42 mg (39% of theory)

HPLC (Method 2A): $R_t$=4.98 min; MS (ESIpos): m/z=539 [M+H]$^+$;

$^1$H-NMR (400 MHz, DMSO-d$_6$): δ=7.78-7.69 (m, 1H), 7.49 (d, 2H), 7.40-7.32 (m, 4H), 4.09 (br d, 1H), 3.63 (br d, 1H), 3.61-3.52 (m, 5H), 3.27-3.18 (m, 4H), 3.13 (t, 1H), 3.07-2.97 (m, 2H), 2.41 (br d, 1H), 2.07 (q, 1H).

Example 41

4-({3-[3-(2,5-Dichlorophenyl)-1,2,4-oxadiazol-5-yl]-5-(4-ethylphenyl)piperidin-1-yl}carbonyl)-morpholine [racemic cis isomer]

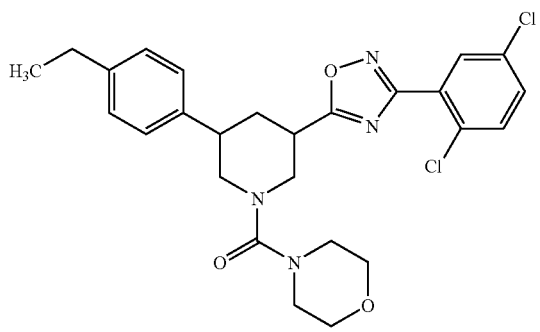

69 mg (0.20 mmol) of 5-(4-ethylphenyl)-1-(morpholin-4-ylcarbonyl)piperidine-3-carboxylic acid (Example 38A) and 45 mg (0.22 mmol, 1.1 eq.) of 2,5-dichloro-N'-hydroxybenzenecarboximidamide were reacted according to the General Method 1. Yield: 28 mg (27% of theory)

HPLC (Method 1A): R$_t$=5.64 min; MS (ESIpos): m/z=515 [M+H]$^+$;

$^1$H-NMR (400 MHz, DMSO-d$_6$): δ=7.97 (d, 1H), 7.77-7.68 (m, 2H), 7.24 (d, 2H), 7.18 (d, 2H), 4.08 (br d, 1H), 3.62 (br d, 1H), 3.61-3.54 (m, 4H), 3.58-3.48 (m, 1H), 3.25-3.17 (m, 4H), 3.11 (t, 1H), 2.97 (q, 1H), 2.95-2.85 (m, 1H), 2.57 (q, 2H), 2.38 (br d, 1H), 2.04 (q, 1H), 1.17 (t, 3H).

Example 42

4-({3-[3-(3-Chloro-4-fluorophenyl)-1,2,4-oxadiazol-5-yl]-5-(4-ethylphenyl)piperidin-1-yl}carbonyl)morpholine [racemic cis isomer]

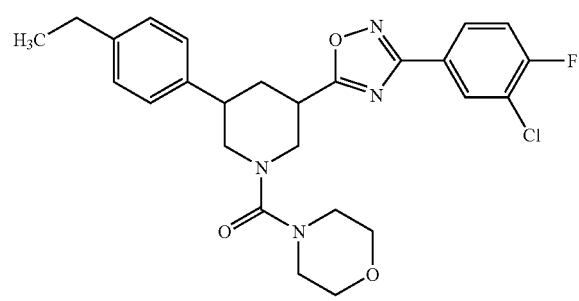

69 mg (0.20 mmol) of 5-(4-ethylphenyl)-1-(morpholin-4-ylcarbonyl)piperidine-3-carboxylic acid (Example 38A) and 41 mg (0.22 mmol, 1.1 eq.) of 3-chloro-4-fluoro-N'-hydroxybenzenecarboximidamide were reacted according to the General Method 1. Yield: 51 mg (51% of theory)

HPLC (Method 1A): R$_t$=5.53 min; MS (ESIpos): m/z=499 [M+H]$^+$;

$^1$H-NMR (400 MHz, DMSO-d$_6$): δ=8.15 (dd, 1H), 8.07 (m, 1H), 7.64 (t, 1H), 7.24 (d, 2H), 7.18 (d, 2H), 4.09 (br d, 1H), 3.63 (br d, 1H), 3.61-3.55 (m, 4H), 3.54-3.45 (m, 1H), 3.25-3.17 (m, 4H), 3.11 (t, 1H), 2.97 (q, 1H), 2.94-2.85 (m, 1H), 2.58 (q, 2H), 2.41 (br d, 1H), 2.03 (q, 1H), 1.17 (t, 3H).

Example 43

4-({3-[3-(3-Chloro-4-fluorophenyl)-1,2,4-oxadiazol-5-yl]-5-[4-(trifluoromethoxy)phenyl]piperidin-1-yl}carbonyl)morpholine [racemic cis isomer]

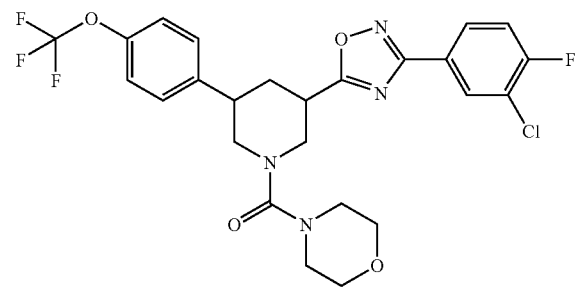

80 mg (0.20 mmol) of 1-(morpholin-4-ylcarbonyl)-5-[4-(trifluoromethoxy)phenyl]piperidine-3-carboxylic acid (Example 44A) and 41 mg (0.22 mmol, 1.1 eq.) of 3-chloro-4-fluoro-N'-hydroxybenzenecarboximidamide were reacted according to the General Method 1. Yield: 51 mg (46% of theory)

HPLC (Method 2A): R$_t$=5.45 min; MS (ESIpos): m/z=555 [M+H]$^+$;

$^1$H-NMR (400 MHz, DMSO-d$_6$): δ=8.18-8.12 (m, 1H), 8.07-8.00 (m, 1H), 7.64 (t, 1H), 7.49 (d, 2H), 7.34 (d, 2H), 4.09 (br d, 1H), 3.64 (br d, 1H), 3.61-3.47 (m, 5H), 3.26-3.18 (m, 4H), 3.13 (t, 1H), 3.08-2.97 (m, 2H), 2.40 (br d, 1H), 2.07 (q, 1H).

Example 44

2-{5-[1-(Cyclopentylcarbonyl)-5-(4-ethylphenyl)piperidin-3-yl]-1,2,4-oxadiazol-3-yl}pyridine [racemic cis isomer]

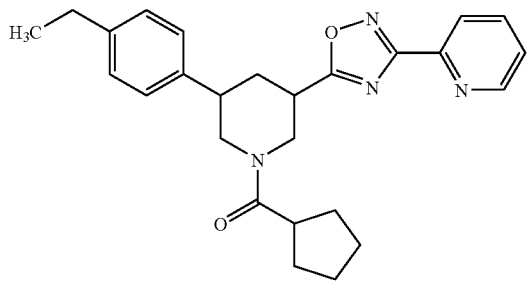

66 mg (0.20 mmol) of 1-(cyclopentylcarbonyl)-5-(4-ethylphenyl)piperidine-3-carboxylic acid (Example 7A) and 30 mg (0.22 mmol, 1.1 eq.) of N'-hydroxypyridine-2-carboximidamide were reacted according to the General Method 1. Yield: 27 mg (30% of theory)

HPLC (Method 2A): R$_t$=4.98 min; MS (ESIpos): m/z=431 [M+H]$^+$;

$^1$H-NMR (500 MHz, DMSO-d$_6$): δ=8.76 (d, 1H), 8.08 (d, 1H), 8.02 (t, 1H), 7.61 (dd, 1H), 7.28 (d, 1H), 7.24 (d, 1H), 7.19 (t, 2H), 4.96 (br d, 0.5H), 4.54 (br d, 0.5H), 4.49 (br d, 0.5H), 4.03 (br d, 0.5H), 3.50-3.40 (m, 1H), 3.38-3.30 (m, 0.5H), 3.26-3.18 (m, 0.5H), 3.18-3.03 (m, 1H), 2.94-2.83 (m, 1H), 2.82-2.67 (m, 1H), 2.58 (q, 2H), 2.44-2.32 (m, 1H), 2.21-2.04 (m, 1H), 1.90-1.45 (m, 8H), 1.17 (t, 3H).

Example 45

3-{5-[1-(Cyclopentylcarbonyl)-5-(4-ethylphenyl)piperidin-3-yl]-1,2,4-oxadiazol-3-yl}pyridine [racemic cis isomer]

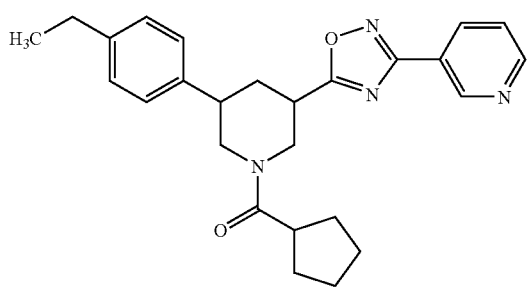

66 mg (0.20 mmol) of 1-(cyclopentylcarbonyl)-5-(4-ethylphenyl)piperidine-3-carboxylic acid (Example 7A) and 30 mg (0.22 mmol, 1.1 eq.) of N'-hydroxypyridine-3-carboximidamide were reacted according to the General Method 1. Yield: 37 mg (43% of theory)

HPLC (Method 2A): $R_t$=4.66 min; MS (ESIpos): m/z=431 [M+H]$^+$;

$^1$H-NMR (500 MHz, DMSO-d$_6$): δ=9.18 (s, 1H), 8.79 (d, 1H), 8.37 (d, 1H), 7.62 (dd, 1H), 7.28 (d, 1H), 7.24 (d, 1H), 7.19 (t, 2H), 4.96 (br d, 0.5H), 4.53 (br d, 0.5H), 4.49 (br d, 0.5H), 4.03 (br d, 0.5H), 3.51-3.41 (m, 1H), 3.39-3.32 (m, 0.5H), 3.27-3.19 (m, 0.5H), 3.18-3.02 (m, 1H), 2.97-2.83 (m, 1H), 2.82-2.68 (m, 1H), 2.58 (q, 2H), 2.43-2.34 (m, 1H), 2.21-2.03 (m, 1H), 1.89-1.47 (m, 8H), 1.17 (t, 3H).

Example 46

3-(5-{cis-(3,5)-1-{(Cyclopentylcarbonyl)-5-[4-(trifluoromethyl)phenyl]piperidin-3-yl}-1,2,4-oxadiazol-3-yl)pyridine [racemic cis isomer]

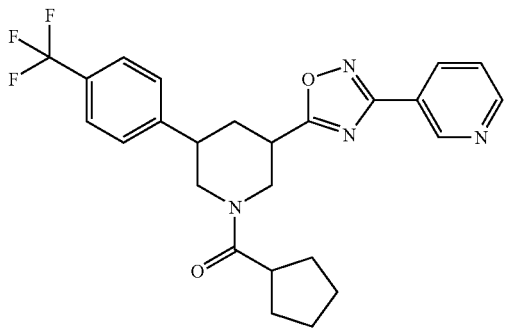

150 mg (0.41 mmol) of cis-(3,5)-1-(cyclopentylcarbonyl)-5-[4-(trifluoromethyl)phenyl]piperidine-3-carboxylic acid (Example 17A) and 83 mg (0.61 mmol, 1.5 eq.) of N'-hydroxypyridine-3-carboximidamide were reacted according to the General Method 2. Yield: 149 mg (78% of theory)

LC-MS (Method 6B): $R_t$=2.51 min; MS (ESIpos): m/z=471 [M+H]$^+$.

Example 47

3-(5-{cis-(3,5)-{1-(Cyclopentylcarbonyl)-5-[4-(trifluoromethoxy)phenyl]piperidin-3-yl}-1,2,4-oxadiazol-3-yl)pyridine [racemic cis isomer]

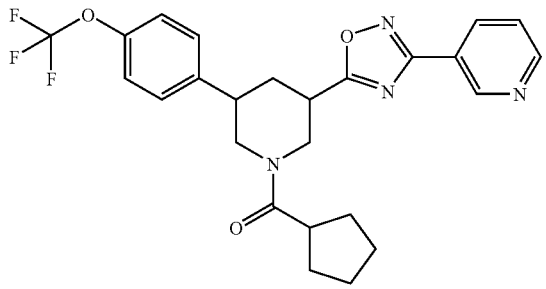

70 mg (0.18 mmol) of cis-(3,5)-1-(cyclopentylcarbonyl)-5-[4-(trifluoromethoxy)phenyl]piperidine-3-carboxylic acid (Example 24A) and 41 mg (0.27 mmol, 1.5 eq.) of N'-hydroxypyridine-3-carboximidamide were reacted according to the General Method 2. Yield: 56 mg (63% of theory)

LC-MS (Method 1B): $R_t$=2.98 min; MS (ESIpos): m/z=487 [M+H]$^+$.

Example 48

4-{5-[1-(Cyclopentylcarbonyl)-5-(4-ethylphenyl)piperidin-3-yl]-1,2,4-oxadiazol-3-yl}pyridine [racemic cis isomer]

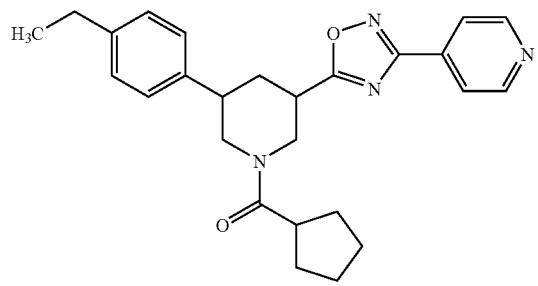

66 mg (0.20 mmol) of 1-(cyclopentylcarbonyl)-5-(4-ethylphenyl)piperidine-3-carboxylic acid (Example 7A) and 30 mg (0.22 mmol, 1.1 eq.) of N'-hydroxypyridine-4-carboximidamide were reacted according to the General Method 1. Yield: 39 mg (45% of theory)

HPLC (Method 2A): $R_t$=4.59 min; MS (ESIpos): m/z=431 [M+H]$^+$;

$^1$H-NMR (500 MHz, DMSO-d$_6$): δ=8.80 (d, 2H), 7.94 (d, 2H), 7.28 (d, 1H), 7.23 (d, 1H), 7.19 (t, 2H), 4.96 (br d, 0.5H), 4.53 (br d, 0.5H), 4.49 (br d, 0.5H), 4.03 (br d, 0.5H), 3.54-3.40 (m, 1H), 3.40-3.32 (m, 0.5H), 3.26-3.18 (m, 0.5H), 3.17-3.03 (m, 1H), 2.96-2.82 (m, 1H), 2.81-2.67 (m, 1H), 2.58 (q, 2H), 2.44-2.34 (m, 1H), 2.20-2.03 (m, 1H), 1.89-1.47 (m, 8H), 1.17 (t, 3H).

Example 49

4-({3-(3-Pyridin-4-yl-1,2,4-oxadiazol-5-yl)-5-[4-(trifluoromethoxy)phenyl]piperidin-1-yl}-carbonyl)morpholine [racemic cis isomer]

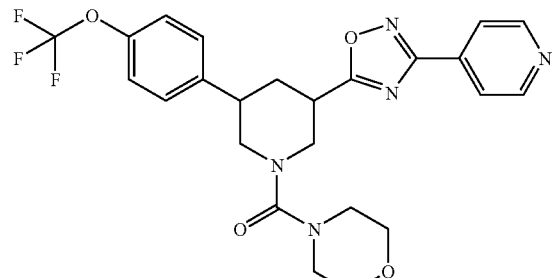

80 mg (0.20 mmol) of 1-(morpholin-4-ylcarbonyl)-5-[4-(trifluoromethoxy)phenyl]piperidine-3-carboxylic acid (Example 44A) and 30 mg (0.22 mmol, 1.1 eq.) of N'-hydroxypyridine-4-carboximidamide were reacted according to the General Method 1. Yield: 52 mg (52% of theory)

HPLC (Method 1A): $R_t$=4.23 min; MS (ESIpos): m/z=503 [M+H]$^+$;

$^1$H-NMR (400 MHz, DMSO-d$_6$): δ=8.81 (d, 2H), 7.95 (d, 2H), 7.49 (d, 2H), 7.34 (d, 2H), 4.10 (br d, 1H), 3.64 (br d, 1H), 3.61-3.50 (m, 5H), 3.27-3.19 (m, 4H), 3.14 (t, 1H), 3.09-2.98 (m, 2H), 2.41 (br d, 1H), 2.08 (q, 1H).

Example 50

4-{[3-(4-Ethylphenyl)-5-(3-pyrazin-2-yl-1,2,4-oxadiazol-5-yl)piperidin-1-yl]carbonyl}morpholine [racemic cis isomer]

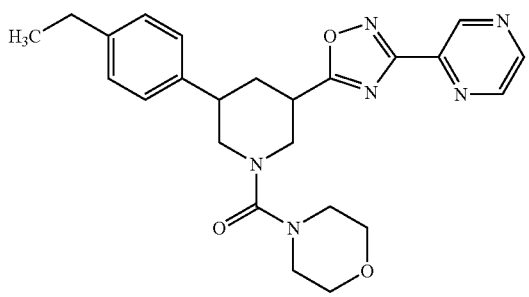

69 mg (0.20 mmol) of 5-(4-ethylphenyl)-1-(morpholin-4-ylcarbonyl)piperidine-3-carboxylic acid (Example 38A) and 30 mg (0.22 mmol, 1.1 eq.) of N'-hydroxypyrazine-2-carboximidamide were reacted according to the General Method 1. Yield: 45 mg (50% of theory)

HPLC (Method 2A): $R_t$=4.52 min; MS (ESIpos): m/z=449 [M+H]$^+$;

$^1$H-NMR (400 MHz, DMSO-d$_6$): δ=9.27 (s, 1H), 8.90-8.85 (m, 2H), 7.25 (d, 2H), 7.18 (d, 2H), 4.12 (br d, 1H), 3.63 (br d, 1H), 3.61-3.50 (m, 5H), 3.26-3.18 (m, 4H), 3.14 (t, 1H), 2.97 (q, 1H), 2.95-2.86 (m, 1H), 2.58 (q, 2H), 2.39 (br d, 1H), 2.07 (q, 1H), 1.17 (t, 3H).

Example 51

4-({3-(4-Ethylphenyl)-5-[3-(4-methylpyridin-2-yl)-1,2,4-oxadiazol-5-yl]piperidin-1-yl}carbonyl)-morpholine [racemic cis isomer]

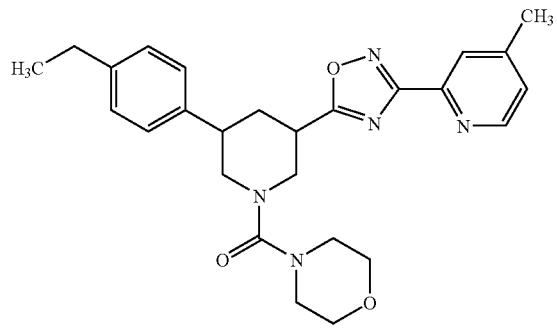

69 mg (0.20 mmol) of 5-(4-ethylphenyl)-1-(morpholin-4-ylcarbonyl)piperidine-3-carboxylic acid (Example 38A) and 33 mg (0.22 mmol, 1.1 eq.) of 1-hydroxy-4-methylpyridine-2-carboximidamide were reacted according to the General Method 1. Yield: 35 mg (38% of theory)

HPLC (Method 1A): $R_t$=4.49 min; MS (ESIpos): m/z=462 [M+H]$^+$;

$^1$H-NMR (400 MHz, DMSO-d$_6$): δ=8.06 (d, 1H), 7.93 (s, 1H), 7.43 (d, 1H), 7.25 (d, 2H), 7.18 (d, 2H), 4.09 (br d, 1H), 3.62 (br d, 1H), 3.61-3.54 (m, 4H), 3.55-3.46 (m, 1H), 3.27-3.18 (m, 4H), 3.11 (t, 1H), 2.96 (q, 1H), 2.95-2.85 (m, 1H), 2.58 (q, 2H), 2.43 (s, 3H), 2.38 (br d, 1H), 2.04 (q, 1H), 1.17 (t, 3H).

Example 52

4-({3-(4-Ethylphenyl)-5-[3-(6-methylpyridin-2-yl)-1,2,4-oxadiazol-5-yl]piperidin-1-yl}carbonyl)-morpholine [racemic cis isomer]

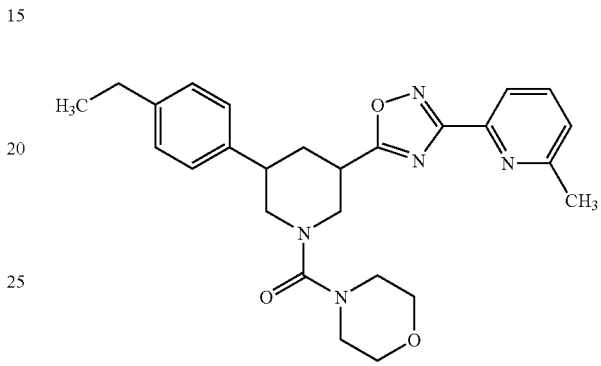

69 mg (0.20 mmol) of 5-(4-ethylphenyl)-1-(morpholin-4-ylcarbonyl)piperidine-3-carboxylic acid (Example 38A) and 33 mg (0.22 mmol, 1.1 eq.) of 1-hydroxy-6-methylpyridine-2-carboximidamide were reacted according to the General Method 1. Yield: 44 mg (47% of theory)

HPLC (Method 1A): $R_t$=4.54 min; MS (ESIpos): m/z=462 [M+H]$^+$;

$^1$H-NMR (400 MHz, DMSO-d$_6$): δ=7.93-7.85 (m, 2H), 7.51-7.42 (m, 1H), 7.25 (d, 2H), 7.18 (d, 2H), 4.09 (br d, 1H), 3.63 (br d, 1H), 3.62-3.53 (m, 4H), 3.55-3.45 (m, 1H), 3.25-3.18 (m, 4H), 3.12 (t, 1H), 2.95 (q, 1H), 2.94-2.83 (m, 1H), 2.57 (q, 2H), 2.37 (br d, 1H), 2.05 (q, 1H), 1.17 (t, 3H).

Example 53

1-(Cyclopentylcarbonyl)-3-(4-ethylphenyl)-5-[3-(2-methyl-1,3-thiazol-4-yl)-1,2,4-oxadiazol-5-yl]piperidine [racemic cis isomer]

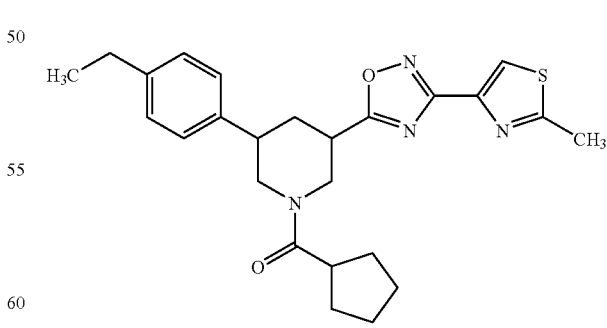

66 mg (0.20 mmol) of 1-(cyclopentylcarbonyl)-5-(4-ethylphenyl)piperidine-3-carboxylic acid (Example 7A) and 35 mg (0.22 mmol, 1.1 eq.) of N'-hydroxy-2-methyl-1,3-thiazole-4-carboximidamide were reacted according to the General Method 1. Yield: 36 mg (40% of theory)

HPLC (Method 2A): R$_t$=5.17 min; MS (ESIpos): m/z=451 [M+H]$^+$;

$^1$H-NMR (500 MHz, DMSO-d$_6$): δ=8.28 (s, 1H), 7.28 (d, 1H), 7.23 (d, 1H), 7.19 (t, 2H), 4.94 (br d, 0.5H), 4.53 (br d, 0.5H), 4.47 (br d, 0.5H), 4.02 (br d, 0.5H), 3.48-3.37 (m, 1H), 3.35-3.27 (m, 0.5H), 3.25-3.18 (m, 0.5H), 3.16-3.03 (m, 1H), 2.92-2.82 (m, 1H), 2.79-2.67 (m, 1H), 2.74 (s, 3H), 2.58 (q, 2H), 2.43-2.34 (m, 1H), 2.18-2.02 (m, 1H), 1.88-1.46 (m, 8H), 1.17 (t, 3H).

Example 54

1-(Cyclopentylcarbonyl)-3-(4-ethylphenyl)-5-[3-(5-methylisoxazol-3-yl)-1,2,4-oxadiazol-5-yl]piperidine [racemic cis isomer]

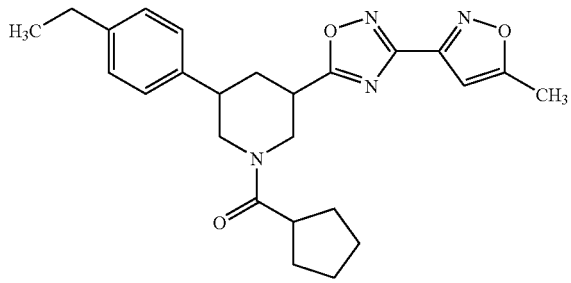

66 mg (0.20 mmol) of 1-(cyclopentylcarbonyl)-5-(4-ethylphenyl)piperidine-3-carboxylic acid (Example 7A) and 31 mg (0.22 mmol, 1.1 eq.) of N'-hydroxy-5-methylisoxazole-3-carboximidamide were reacted according to the General Method 1. Yield: 50 mg (58% of theory)

HPLC (Method 1A): R$_t$=5.23 min; MS (ESIpos): m/z=435 [M+H]$^+$;

$^1$H-NMR (500 MHz, DMSO-d$_6$): δ=7.27 (d, 1H), 7.23 (d, 1H), 7.19 (t, 2H), 6.81 (s, 1H), 4.94 (br d, 0.5H), 4.52 (br d, 0.5H), 4.48 (br d, 0.5H), 4.02 (br d, 0.5H), 3.50-3.40 (m, 1H), 3.40-3.32 (m, 0.5H), 3.25-3.18 (m, 0.5H), 3.17-3.02 (m, 1H), 2.94-2.81 (m, 1H), 2.80-2.65 (m, 1H), 2.58 (q, 2H), 2.42-2.32 (m, 1H), 2.19-2.02 (m, 1H), 1.88-1.47 (m, 8H), 1.17 (t, 3H).

Example 55

3-(3-Benzyl-1,2,4-oxadiazol-5-yl)-1-(cyclopentylcarbonyl)-5-(4-ethylphenyl)piperidine [racemic cis isomer]

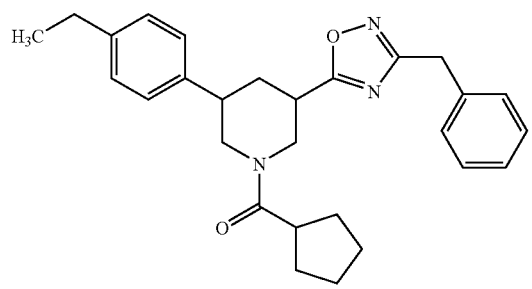

66 mg (0.20 mmol) of 1-(cyclopentylcarbonyl)-5-(4-ethylphenyl)piperidine-3-carboxylic acid (Example 7A) and 33 mg (0.22 mmol, 1.1 eq.) of N'-hydroxy-2-phenylethanimidamide were reacted according to the General Method 1. Yield: 50 mg (56% of theory)

HPLC (Method 1A): R$_t$=5.48 min; MS (ESIpos): m/z=444 [M+H]$^+$;

$^1$H-NMR (500 MHz, DMSO-d$_6$): δ=7.35-7.28 (m, 4H), 7.28-7.22 (m, 2H), 7.21-7.14 (m, 3H), 4.84 (br d, 0.5H), 4.48 (br d, 0.5H), 4.36 (br d, 0.5H), 4.09 (s, 2H), 3.98 (br d, 0.5H), 3.38-3.29 (m, 1H), 3.22-3.13 (m, 1H), 3.11-3.00 (m, 1H), 2.85-2.73 (m, 1H), 2.72-2.61 (m, 1H), 2.57 (q, 2H), 2.32-2.22 (m, 1H), 2.08-1.92 (m, 1H), 1.84-1.45 (m, 8H), 1.16 (t, 3H).

Example 56

3-(3-Benzyl-1,2,4-oxadiazol-5-yl)-1-(cyclopentylcarbonyl)-5-[4-(trifluoromethoxy)phenyl]piperidine [racemic cis isomer]

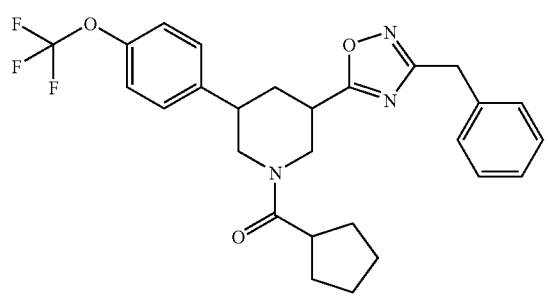

70 mg (0.18 mmol) of cis-(3,5)-1-(cyclopentylcarbonyl)-5-[4-(trifluoromethoxy)phenyl]piperidine-3-carboxylic acid (Example 24A) and 41 mg (0.27 mmol, 1.5 eq.) of N'-hydroxy-2-phenylethanimidamide were reacted according to the General Method 1. Yield: 55 mg (61% of theory)

LC-MS (Method 1B): R$_t$=3.25 min; MS (ESIpos): m/z=500 [M+H]$^+$;

Example 57

4-{[3-(3-Benzyl-1,2,4-oxadiazol-5-yl)-5-(4-ethylphenyl)piperidin-1-yl]carbonyl}morpholine [racemic cis isomer]

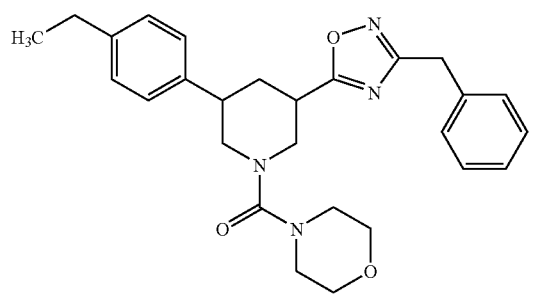

69 mg (0.20 mmol) of 5-(4-ethylphenyl)-1-(morpholin-4-ylcarbonyl)piperidine-3-carboxylic acid (Example 38A) and 33 mg (0.22 mmol, 1.1 eq.) of 1-hydroxy-2-phenylethanimidamide were reacted according to the General Method 1. Yield: 43 mg (47% of theory)

HPLC (Method 1A): R$_t$=4.85 min; MS (ESIpos): m/z=461 [M+H]$^+$;

¹H-NMR (400 MHz, DMSO-d₆): δ=7.38-7.23 (m, 5H), 7.20 (d, 2H), 7.15 (d, 2H), 4.08 (s, 2H), 3.98 (br d, 1H), 3.58 (br d, 1H), 3.58-3.50 (m, 4H), 3.43-3.32 (m, 1H), 3.22-3.13 (m, 4H), 3.00 (t, 1H), 2.91 (q, 1H), 2.89-2.79 (m, 1H), 2.56 (q, 2H), 2.27 (br d, 1H), 1.93 (q, 1H), 1.16 (t, 3H).

Example 58

4-({3-(3-Benzyl-1,2,4-oxadiazol-5-yl)-5-[4-(trifluoromethoxy)phenyl]piperidin-1-yl}carbonyl)-morpholine [racemic cis isomer]

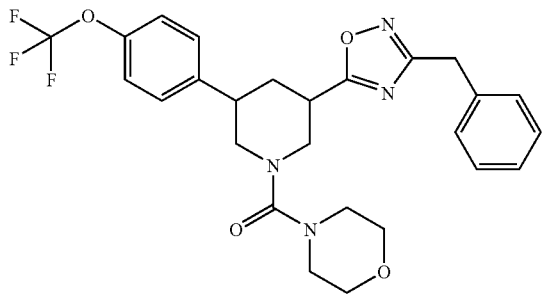

80 mg (0.20 mmol) of 1-(morpholin-4-ylcarbonyl)-5-[4-(trifluoromethoxy)phenyl]piperidine-3-carboxylic acid (Example 44A) and 33 mg (0.22 mmol, 1.1 eq.) of N'-hydroxy-2-phenylethanimidamide were reacted according to the General Method 1. Yield: 46 mg (44% of theory)

HPLC (Method 1A): $R_t$=5.01 min; MS (ESIpos): m/z=517 [M+H]⁺;

¹H-NMR (400 MHz, DMSO-d₆): δ=7.45 (d, 2H), 7.36-7.22 (m, 7H), 4.08 (s, 2H), 3.97 (br d, 1H), 3.59 (br d, 1H), 3.59-3.51 (m, 4H), 3.43-3.33 (m, 1H), 3.22-3.14 (m, 4H), 3.02 (t, 1H), 3.01-2.91 (m, 2H), 2.29 (br d, 1H), 1.96 (q, 1H).

Example 59

3-[3-(2-Chlorobenzyl)-1,2,4-oxadiazol-5-yl]-1-(cyclopentylcarbonyl)-5-(4-ethylphenyl)piperidine [racemic cis isomer]

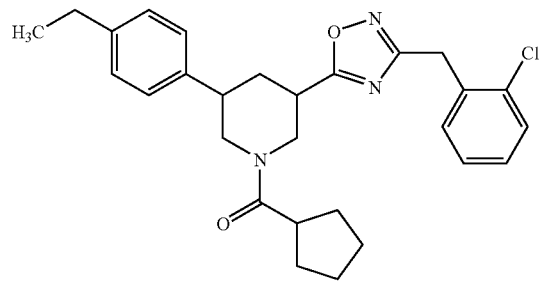

66 mg (0.20 mmol) of 1-(cyclopentylcarbonyl)-5-(4-ethylphenyl)piperidine-3-carboxylic acid (Example 7A) and 41 mg (0.22 mmol, 1.1 eq.) of 2-(2-chlorophenyl)-N'-hydroxyethanimidamide were reacted according to the General Method 1. Yield: 21 mg (22% of theory)

HPLC (Method 2A): $R_t$=5.64 min; MS (ESIpos): m/z=478 [M+H]⁺;

¹H-NMR (500 MHz, DMSO-d₆): δ=7.47 (dd, 1H), 7.42 (dd, 1H), 7.33 (dd, 2H), 7.24 (d, 1H), 7.22-7.13 (m, 3H), 4.83 (br d, 0.5H), 4.48 (br d, 0.5H), 4.37 (br d, 0.5H), 4.21 (s, 2H), 3.98 (br d, 0.5H), 3.38-3.30 (m, 1H), 3.25-3.14 (m, 1H), 3.13-2.99 (m, 1H), 2.86-2.74 (m, 1H), 2.73-2.62 (m, 1H), 2.57 (q, 2H), 2.32-2.22 (m, 1H), 2.08-1.92 (m, 1H), 1.84-1.45 (m, 8H), 1.16 (t, 3H).

Example 60

4-({3-[3-(2-Chlorobenzyl)-1,2,4-oxadiazol-5-yl]-5-(4-ethylphenyl)piperidin-1-yl}carbonyl)-morpholine [racemic cis isomer]

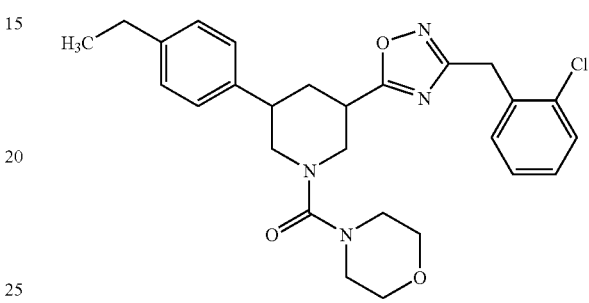

69 mg (0.20 mmol) of 5-(4-ethylphenyl)-1-(morpholin-4-ylcarbonyl)piperidine-3-carboxylic acid (Example 38A) and 41 mg (0.22 mmol, 1.1 eq.) of 2-(2-chlorophenyl)-N'-hydroxyethanimidamide were reacted according to the General Method 1. Yield: 10 mg (10% of theory)

LC-MS (Method 2B): $R_t$=1.49 min; MS (ESIpos): m/z=495 [M+H]⁺;

¹H-NMR (400 MHz, DMSO-d₆): δ=7.50-7.44 (m, 1H), 7.45-7.40 (m, 1H), 7.36-7.30 (m, 2H), 7.21 (d, 2H), 7.16 (d, 2H), 4.21 (s, 2H), 3.98 (br d, 1H), 3.58 (br d, 1H), 3.57-3.50 (m, 4H), 3.43-3.33 (m, 1H), 3.22-3.12 (m, 4H), 3.00 (t, 1H), 2.92 (q, 1H), 2.89-2.79 (m, 1H), 2.56 (q, 2H), 2.27 (br d, 1H), 1.93 (q, 1H), 1.16 (t, 3H).

Example 61

4-({3-(4-Ethylphenyl)-5-[3-(3-methylbenzyl)-1,2,4-oxadiazol-5-yl]piperidin-1-yl}carbonyl)-morpholine [racemic cis isomer]

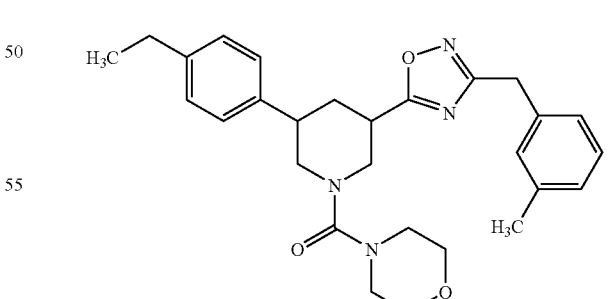

69 mg (0.20 mmol) of 5-(4-ethylphenyl)-1-(morpholin-4-ylcarbonyl)piperidine-3-carboxylic acid (Example 38A) and 36 mg (0.22 mmol, 1.1 eq.) of 1-hydroxy-2-(3-methylphenyl)ethanimidamide were reacted according to the General Method 1. Yield:
57 mg (60% of theory)

HPLC (Method 1A): R$_t$=5.26 min; MS (ESIpos): m/z=475 [M+H]$^+$;

$^1$H-NMR (400 MHz, DMSO-d$_6$): δ=7.25-7.13 (m, 5H), 7.13-7.04 (m, 3H), 4.03 (s, 2H), 3.98 (br d, 1H), 3.57 (br d, 1H), 3.57-3.51 (m, 4H), 3.42-3.33 (m, 1H), 3.21-3.14 (m, 4H), 3.00 (t, 1H), 2.91 (q, 1H), 2.88-2.79 (m, 1H), 2.57 (q, 2H), 2.28 (s, 3H), 2.25 (br d, 1H), 1.93 (q, 1H), 1.16 (t, 3H).

Example 62

1-(Cyclopentylcarbonyl)-3-(4-ethylphenyl)-5-[3-(4-fluorobenzyl)-1,2,4-oxadiazol-5-yl]piperidine [racemic cis isomer]

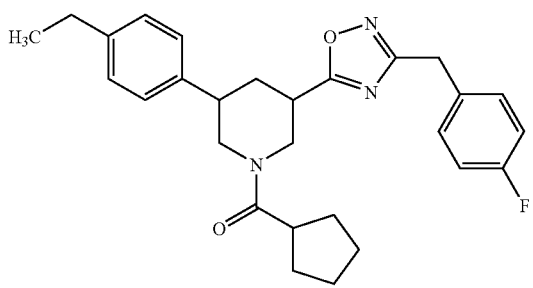

66 mg (0.20 mmol) of 1-(cyclopentylcarbonyl)-5-(4-ethylphenyl)piperidine-3-carboxylic acid (Example 7A) and 37 mg (0.22 mmol, 1.1 eq.) of 2-(4-fluorophenyl)-N'-hydroxyethanimidamide were reacted according to the General Method 1. Yield: 22 mg (24% of theory)

HPLC (Method 2A): R$_t$=5.51 min; MS (ESIpos): m/z=462 [M+H]$^+$;

$^1$H-NMR (500 MHz, DMSO-d$_6$): δ=7.35 (dd, 2H), 7.24 (d, 1H), 7.22-7.13 (5H), 4.84 (br d, 0.5H), 4.49 (br d, 0.5H), 4.37 (br d, 0.5H), 4.09 (s, 2H), 3.98 (br d, 0.5H), 3.38-3.28 (m, 1H), 3.23-3.13 (m, 1H), 3.12-3.00 (m, 1H), 2.86-2.74 (m, 1H), 2.73-2.62 (m, 1H), 2.57 (q, 2H), 2.32-2.22 (m, 1H), 2.08-1.91 (m, 1H), 1.85-1.44 (m, 8H), 1.16 (t, 3H).

Example 63

4-({3-(4-Ethylphenyl)-5-[3-(4-fluorobenzyl)-1,2,4-oxadiazol-5-yl]piperidin-1-yl}carbonyl)-morpholine [racemic cis isomer]

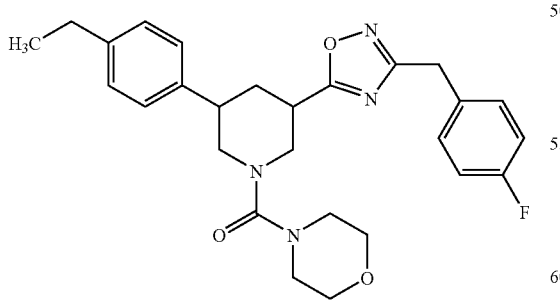

69 mg (0.20 mmol) of 5-(4-ethylphenyl)-1-(morpholin-4-ylcarbonyl)piperidine-3-carboxylic acid (Example 38A) and 37 mg (0.22 mmol, 1.1 eq.) of 2-(4-fluorophenyl)-N'-hydroxyethanimidamide were reacted according to the General Method 1. Yield: 44 mg (45% of theory)

HPLC (Method 1A): R$_t$=5.14 min; MS (ESIpos): m/z=479 [M+H]$^+$;

$^1$H-NMR (400 MHz, DMSO-d$_6$): δ=7.39-7.30 (m, 2H), 7.21 (d, 2H), 7.18-7.10 (m, 4H), 4.09 (s, 2H), 3.98 (br d, 1H), 3.57 (br d, 1H), 3.57-3.51 (m, 4H), 3.43-3.33 (m, 1H), 3.21-3.13 (m, 4H), 3.00 (t, 1H), 2.92 (q, 1H), 2.89-2.79 (m, 1H), 2.56 (q, 2H), 2.27 (br d, 1H), 1.92 (q, 1H), 1.16 (t, 3H).

Example 64

4-({3-[3-(4-Fluorobenzyl)-1,2,4-oxadiazol-5-yl]-5-[4-(trifluoromethoxy)phenyl]piperidin-1-yl}carbonyl)morpholine [racemic cis isomer]

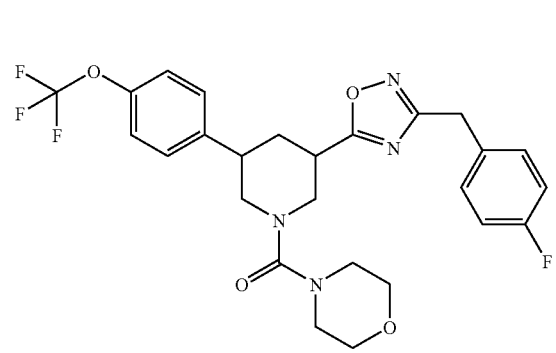

80 mg (0.20 mmol) of 1-(morpholin-4-ylcarbonyl)-5-[4-(trifluoromethoxy)phenyl]piperidine-3-carboxylic acid (Example 44A) and 37 mg (0.22 mmol, 1.1 eq.) of 2-(4-fluorophenyl)-N'hydroxyethanimidamide were reacted according to the General Method 1. Yield: 61 mg (57% of theory)

HPLC (Method 2A): R$_t$=5.02 min; MS (ESIpos): m/z=535 [M+H]$^+$;

$^1$H-NMR (400 MHz, DMSO-d$_6$): δ=7.45 (d, 2H), 7.38-7.30 (m, 4H), 7.15 (t, 2H), 4.09 (s, 2H), 3.97 (br d, 1H), 3.59 (br d, 1H), 3.59-3.51 (m, 4H), 3.43-3.32 (m, 1H), 3.22-3.15 (m, 4H), 3.02 (t, 1H), 3.00-2.91 (m, 2H), 2.29 (br d, 1H), 1.96 (q, 1H).

Example 65

4-({3-[3-(4-Chlorobenzyl)-1,2,4-oxadiazol-5-yl]-5-(4-ethylphenyl)piperidin-1-yl}carbonyl)-morpholine [racemic cis isomer]

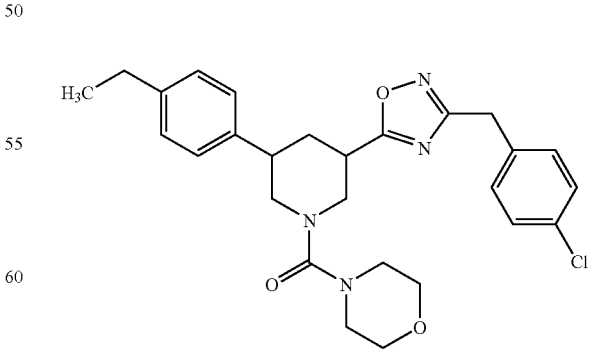

69 mg (0.20 mmol) of 5-(4-ethylphenyl)-1-(morpholin-4-ylcarbonyl)piperidine-3-carboxylic acid (Example 38A) and 41 mg (0.22 mmol, 1.1 eq.) of 2-(4-chlorophenyl)-N'-hydroxyethanimidamide were reacted according to the General Method 1. Yield: 62 mg (63% of theory)

HPLC (Method 1A): $R_t$=5.33 min; MS (ESIpos): m/z=495 [M+H]$^+$;

$^1$H-NMR (400 MHz, DMSO-d$_6$): δ=7.39 (d, 2H), 7.33 (d, 2H), 7.21 (d, 2H), 7.16 (d, 2H), 4.10 (s, 2H), 3.98 (br d, 1H), 3.57 (br d, 1H), 3.57-3.51 (m, 4H), 3.43-3.34 (m, 1H), 3.21-3.14 (m, 4H), 2.99 (t, 1H), 2.92 (q, 1H), 2.89-2.79 (m, 1H), 2.56 (q, 2H), 2.27 (br d, 1H), 1.93 (q, 1H), 1.16 (t, 3H).

Example 66

4-({3-(4-Ethylphenyl)-5-[3-(4-methylbenzyl)-1,2,4-oxadiazol-5-yl]piperidin-1-yl}carbonyl)-morpholine [racemic cis isomer]

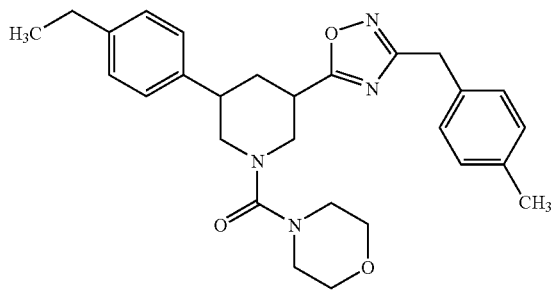

69 mg (0.20 mmol) of 5-(4-ethylphenyl)-1-(morpholin-4-ylcarbonyl)piperidine-3-carboxylic acid (Example 38A) and 36 mg (0.22 mmol, 1.1 eq.) of 1-hydroxy-2-(4-methylphenyl)ethanimidamide were reacted according to the General Method 1. Yield:

57 mg (60% of theory)

HPLC (Method 1A): $R_t$=5.31 min; MS (ESIpos): m/z=475 [M+H]$^+$;

$^1$H-NMR (400 MHz, DMSO-d$_6$): δ=7.23-7.10 (m, 8H), 4.02 (s, 2H), 3.97 (br d, 1H), 3.57 (br d, 1H), 3.57-3.50 (m, 4H), 3.42-3.31 (m, 1H), 3.21-3.12 (m, 4H), 2.99 (t, 1H), 2.91 (q, 1H), 2.88-2.79 (m, 1H), 2.56 (q, 2H), 2.26 (s, 3H), 2.25 (br d, 1H), 1.92 (q, 1H), 1.16 (t, 3H).

Example 67

4-({3-[3-(2-Chloro-4-fluorobenzyl)-1,2,4-oxadiazol-5-yl]-5-(4-ethylphenyl)piperidin-1-yl}-carbonyl)morpholine [racemic cis isomer]

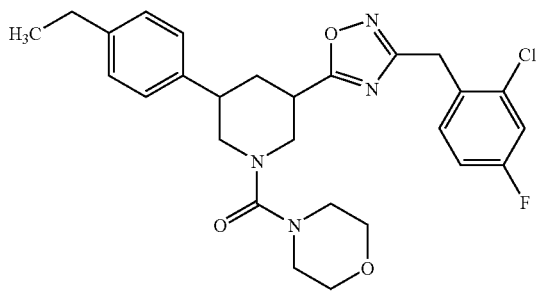

69 mg (0.20 mmol) of 5-(4-ethylphenyl)-1-(morpholin-4-ylcarbonyl)piperidine-3-carboxylic acid (Example 38A) and 45 mg (0.22 mmol, 1.1 eq.) of 2-(2-chloro-4-fluorophenyl)-

N'-hydroxyethanimidamide were reacted according to the General Method 1. Yield: 59 mg (57% of theory)

HPLC (Method 1A): $R_t$=5.29 min; MS (ESIpos): m/z=513 [M+H]$^+$;

$^1$H-NMR (400 MHz, DMSO-d$_6$): δ=7.53-7.45 (m, 2H), 7.26-7.19 (m, 3H), 7.16 (d, 2H), 4.20 (s, 2H), 3.97 (br d, 1H), 3.58 (br d, 1H), 3.58-3.51 (m, 4H), 3.43-3.34 (m, 1H), 3.22-3.14 (m, 4H), 3.05-2.89 (m, 2H), 2.89-2.79 (m, 1H), 2.56 (q, 2H), 2.27 (br d, 1H), 1.92 (q, 1H), 1.16 (t, 3H).

Example 68

4-({3-(4-Ethylphenyl)-5-[3-(phenoxymethyl)-1,2,4-oxadiazol-5-yl]piperidin-1-yl}carbonyl)morpholine [racemic cis isomer]

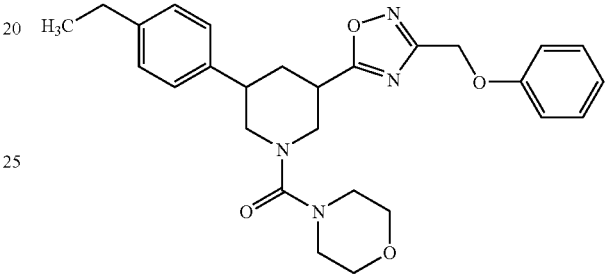

69 mg (0.20 mmol) of 5-(4-ethylphenyl)-1-(morpholin-4-ylcarbonyl)piperidine-3-carboxylic acid (Example 38A) and 37 mg (0.22 mmol, 1.1 eq.) of 1-hydroxy-2-phenoxyethanimidamide were reacted according to the General Method 1. Yield: 40 mg (42% of theory)

HPLC (Method 1A): $R_t$=5.06 min; MS (ESIpos): m/z=477 [M+H]$^+$;

$^1$H-NMR (400 MHz, DMSO-d$_6$): δ=7.32 (t, 2H), 7.23 (d, 2H), 7.17 (d, 2H), 7.05 (d, 2H), 6.99 (t, 1H), 5.26 (s, 2H), 4.02 (br d, 1H), 3.60 (br d, 1H), 3.60-3.52 (m, 4H), 3.50-3.40 (m, 1H), 3.23-3.16 (m, 4H), 3.06 (t, 1H), 2.93 (q, 1H), 2.91-2.82 (m, 1H), 2.57 (q, 2H), 2.32 (br d, 1H), 1.98 (q, 1H), 1.16 (t, 3H).

Example 69

1-(Cyclopentylcarbonyl)-3-(4-ethylphenyl)-5-(3-methyl-1,2,4-oxadiazol-5-yl)piperidine [racemic cis isomer]

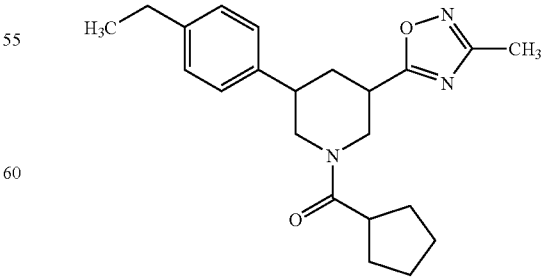

66 mg (0.20 mmol) of 1-(cyclopentylcarbonyl)-5-(4-ethylphenyl)piperidine-3-carboxylic acid (Example 7A) and 24 mg (0.22 mmol, 1.1 eq.) of N'-hydroxyethanimidamide were reacted according to the General Method 1. Yield: 58 mg (79% of theory)

HPLC (Method 2A): $R_t$=5.04 min; MS (ESIpos): m/z=368 [M+H]$^+$;

$^1$H-NMR (500 MHz, DMSO-d$_6$): δ=7.25 (d, 1H), 7.23-7.14 (m, 3H), 4.85 (br d, 0.5H), 4.50 (br d, 0.5H), 4.38 (br d, 0.5H), 3.99 (br d, 0.5H), 3.37-3.28 (m, 1H), 3.23-3.13 (m, 1H), 3.12-3.01 (m, 1H), 2.88-2.74 (m, 1H), 2.73-2.62 (m, 1H), 2.58 (q, 2H), 2.33 (s, 3H), 2.33-2.25 (m, 1H), 2.09-1.94 (m, 1H), 1.86-1.47 (m, 8H), 1.17 (t, 3H).

Example 70

1-(Cyclopentylcarbonyl)-3-(4-ethylphenyl)-5-(3-propyl-1,2,4-oxadiazol-5-yl)piperidine [racemic cis isomer]

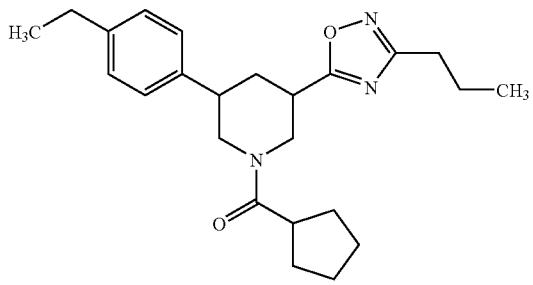

66 mg (0.20 mmol) of 1-(cyclopentylcarbonyl)-5-(4-ethylphenyl)piperidine-3-carboxylic acid (Example 7A) and 22 mg (0.22 mmol, 1.1 eq.) of N'-hydroxybutanimidamide were reacted according to the General Method 1. Yield: 12 mg (15% of theory)

HPLC (Method 2A): $R_t$=5.41 min; MS (ESIpos): m/z=396 [M+H]$^+$;

$^1$H-NMR (500 MHz, DMSO-d$_6$): δ=7.30-7.13 (m, 4H), 4.85 (br d, 0.5H), 4.50 (br d, 0.5H), 4.38 (br d, 0.5H), 3.99 (br d, 0.5H), 3.39-3.29 (m, 1H), 3.24-3.14 (m, 1H), 3.14-3.00 (m, 1H), 2.88-2.75 (m, 1H), 2.75-2.62 (m, 1H), 2.67 (t, 2H), 2.57 (q, 2H), 2.34-2.25 (m, 1H), 2.10-1.93 (m, 1H), 1.86-1.45 (m, 8H), 1.73-1.66 (m, 2H), 1.17 (t, 3H), 0.92 (t, 3H).

Example 71

3-(3-tert-Butyl-1,2,4-oxadiazol-5-yl)-1-(cyclopentylcarbonyl)-5-(4-ethylphenyl)piperidine [racemic cis isomer]

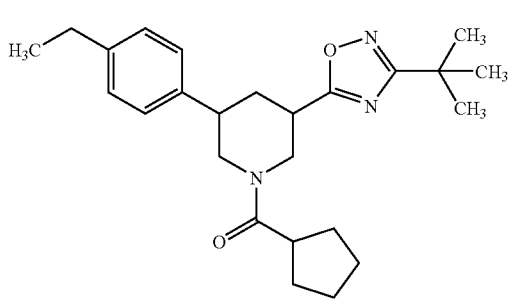

66 mg (0.20 mmol) of 1-(cyclopentylcarbonyl)-5-(4-ethylphenyl)piperidine-3-carboxylic acid (Example 7A) and 26 mg (0.22 mmol, 1.1 eq.) of 1-hydroxy-2,2-dimethylpropanimidamide were reacted according to the General Method 1. Yield: 49 mg (60% of theory)

HPLC (Method 2A): $R_t$=5.63 min; MS (ESIpos): m/z=410 [M+H]$^+$;

$^1$H-NMR (500 MHz, DMSO-d$_6$): δ=7.26 (d, 1H), 7.24-7.14 (m, 3H), 4.85 (br d, 0.5H), 4.49 (br d, 0.5H), 4.37 (br d, 0.5H), 3.99 (br d, 0.5H), 3.40-3.31 (m, 1H), 3.25-3.16 (m, 1H), 3.14-3.01 (m, 1H), 2.87-2.76 (m, 1H), 2.75-2.67 (m, 1H), 2.58 (q, 2H), 2.33-2.23 (m, 1H), 2.09-1.92 (m, 1H), 1.85-1.44 (m, 8H), 1.31 (s, 9H), 1.17 (t, 3H).

Example 72 cis-(3,5)-3-(3-tert-Butyl-1,2,4-oxadiazol-5-yl)-1-(cyclopentylcarbonyl)-5-[4-(1-methylethyl)-phenyl]piperidine [racemic cis isomer]

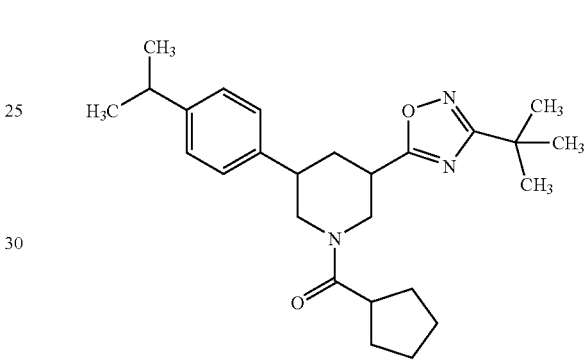

73 mg (0.21 mmol) of cis-(3,5)-1-(cyclopentylcarbonyl)-5-[4-(1-methylethyl)phenyl]piperidine-3-carboxylic acid (Example 12A) and 37 mg (0.32 mmol, 1.5 eq.) of N'-hydroxy-2,2-dimethylpropanimidamide were reacted according to the General Method 2. Yield: 29 mg (33% of theory)

LC-MS (Method 3B): $R_t$=2.88 min; MS (ESIpos): m/z=424 [M+H]$^+$.

Example 73

4-{[3-(3-tert-Butyl-1,2,4-oxadiazol-5-yl)-5-(4-ethylphenyl)piperidin-1-yl]carbonyl}morpholine [racemic cis isomer]

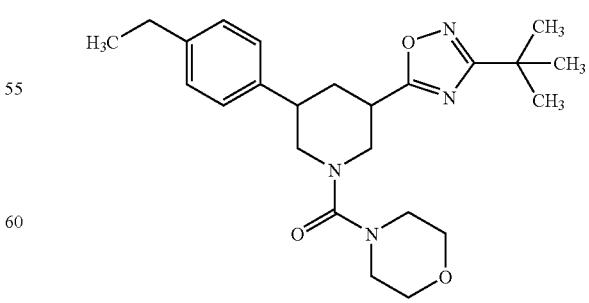

69 mg (0.20 mmol) of 5-(4-ethylphenyl)-1-(morpholin-4-ylcarbonyl)piperidine-3-carboxylic acid (Example 38A) and 26 mg (0.22 mmol, 1.1 eq.) of 1-hydroxy-2,2-dimethylpropanimidamide were reacted according to the General Method 1. Yield: 60 mg (70% of theory)

HPLC (Method 1A): $R_t$=4.90 min; MS (ESIpos): m/z=427 [M+H]$^+$;

$^1$H-NMR (400 MHz, DMSO-d$_6$): δ=7.22 (d, 2H), 7.16 (d, 2H), 3.99 (br d, 1H), 3.59 (br d, 1H), 3.59-3.50 (m, 4H), 3.43-3.32 (m, 1H), 3.23-3.13 (m, 4H), 2.99 (q, 2H), 2.92-2.80 (m, 1H), 2.57 (q, 2H), 2.29 (br d, 1H), 1.94 (q, 1H), 1.30 (s, 9H), 1.16 (t, 3H).

Example 74

4-({3-(3-tert-Butyl-1,2,4-oxadiazol-5-yl)-5-[4-(trifluoromethoxy)phenyl]piperidin-1-yl}carbonyl)-morpholine [racemic cis isomer]

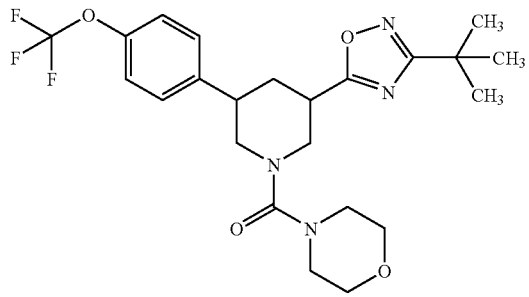

80 mg (0.20 mmol) of 1-(morpholin-4-ylcarbonyl)-5-[4-(trifluoromethoxy)phenyl]piperidine-3-carboxylic acid (Example 44A) and 26 mg (0.22 mmol, 1.1 eq.) of N'-hydroxy-2,2-dimethylpropanimidamide were reacted according to the General Method 1. Yield: 68 mg (70% of theory)

HPLC (Method 2A): $R_t$=5.08 min; MS (ESIpos): m/z=483 [M+H]$^+$;

$^1$H-NMR (400 MHz, DMSO-d$_6$): δ=7.48 (d, 2H), 7.33 (d, 2H), 3.99 (br d, 1H), 3.60 (br d, 1H), 3.59-3.51 (m, 4H), 3.43-3.33 (m, 1H), 3.23-3.15 (m, 4H), 3.09-2.91 (m, 3H), 2.31 (br d, 1H), 1.96 (q, 1H), 1.30 (s, 9H).

Example 75

Ethyl 5-[1-(cyclopentylcarbonyl)-5-(4-ethylphenyl) piperidin-3-yl]-1,2,4-oxadiazole-3-carboxylate [racemic cis isomer]

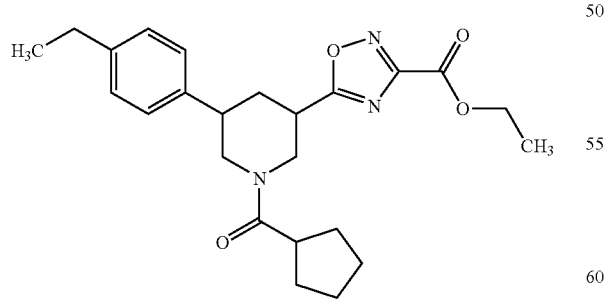

198 mg (0.60 mmol) of 1-(cyclopentylcarbonyl)-5-(4-ethylphenyl)piperidine-3-carboxylic acid (Example 7A) and 87 mg (0.66 mmol, 1.1 eq.) of ethyl 2-amino(hydroxyimino) ethanoate were reacted according to the General Method 1. Yield: 73 mg (27% of theory)

HPLC (Method 1A): $R_t$=5.28 min; MS (ESIpos): m/z=426 [M+H]$^+$;

$^1$H-NMR (500 MHz, DMSO-d$_6$): δ=7.30-7.12 (m, 4H), 4.89 (br d, 0.5H), 4.50 (br d, 0.5H), 4.47-4.37 (m, 2.5H), 4.01 (br d, 0.5H), 3.52-3.32 (m, 1H), 3.20 (t, 1H), 3.14-3.00 (m, 1H), 2.82-2.79 (m, 1H), 2.79-2.63 (m, 1H), 2.58 (q, 2H), 2.39-2.27 (m, 1H), 2.18-1.99 (m, 1H), 1.89-1.43 (m, 8H), 1.33 (t, 3H), 1.17 (t, 3H).

Example 76 cis-(3,5)-1-(Cyclopentylcarbonyl)-3-(4-methoxyphenyl)-5-{3-[(methylsulphonyl)methyl]-1,2,4-oxadiazol-5-yl}piperidine [racemic cis isomer]

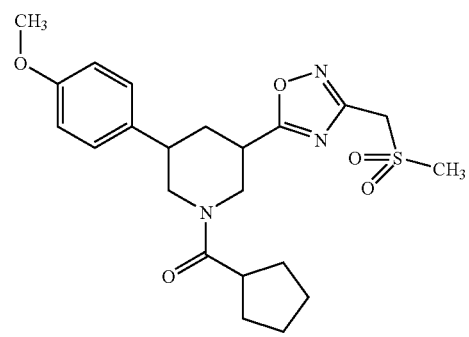

100 mg (0.27 mmol) of cis-(3,5)-1-(cyclopentylcarbonyl)-5-(4-methoxyphenyl)piperidine-3-carboxylic acid (Example 30A) and 63 mg (0.41 mmol, 1.5 eq.) of 1-hydroxy-2-(methylsulphonyl)ethanimidamide were reacted according to the General Method 2. Yield: 17 mg (14% of theory)

LC-MS (Method 3B): $R_t$=1.88 min; MS (ESIpos): m/z=448 [M+H]$^+$.

Example 77

4-[(3-{3-[(Methylsulphonyl)methyl]-1,2,4-oxadiazol-5-yl}-5-[4-(trifluoromethoxy)phenyl]piperidin-1-yl)carbonyl]morpholine [racemic cis isomer]

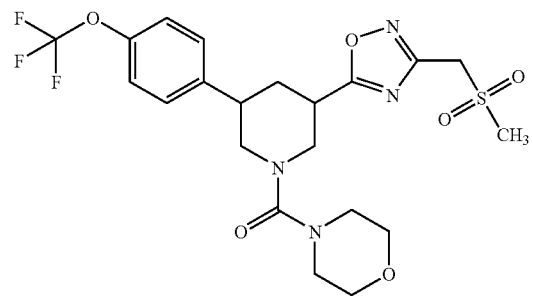

80 mg (0.20 mmol) of 1-(morpholin-4-ylcarbonyl)-5-[4-(trifluoromethoxy)phenyl]piperidine-3-carboxylic acid (Example 44A) and 33 mg (0.22 mmol, 1.1 eq.) of N'-hydroxy-2-(methylsulphonyl)ethanimidamide were reacted according to the General Method 1. Yield: 50 mg (48% of theory)

HPLC (Method 2A): $R_t$=4.37 min; MS (ESIpos): m/z=519 [M+H]$^+$;

$^1$H-NMR (400 MHz, DMSO-d$_6$): δ=7.48 (d, 2H), 7.33 (d, 2H), 4.85 (s, 2H), 4.03 (br d, 1H), 3.61 (br d, 1H), 3.60-3.53 (m, 4H), 3.52-3.43 (m, 1H), 3.25-3.18 (m, 4H), 3.17 (s, 3H), 3.07 (t, 1H), 3.03-2.94 (m, 2H), 2.35 (br d, 1H), 2.00 (q, 1H).

Example 78

4-({5-[1-(Cyclopentylcarbonyl)-5-(4-ethylphenyl)piperidin-3-yl]-1,2,4-oxadiazol-3-yl}methyl)-morpholine [racemic cis isomer]

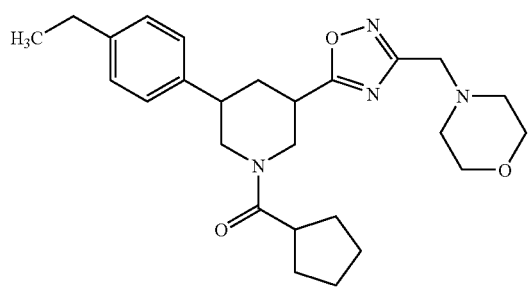

66 mg (0.20 mmol) of 1-(cyclopentylcarbonyl)-5-(4-ethylphenyl)piperidine-3-carboxylic acid (Example 7A) and 35 mg (0.22 mmol, 1.1 eq.) of N'-hydroxy-2-morpholin-4-ylethanimidamide were reacted according to the General Method 1. Yield: 7 mg (8% of theory)

HPLC (Method 2A): R$_t$=4.46 min; MS (ESIpos): m/z=453 [M+H]$^+$;

$^1$H-NMR (500 MHz, DMSO-d$_6$): δ=7.30-7.13 (m, 4H), 4.89 (br d, 0.5H), 4.51 (br d, 0.5H), 4.40 (br d, 0.5H), 4.01 (br d, 0.5H), 3.43-3.30 (m, 1H), 3.24-3.16 (m, 1H), 3.14-3.00 (m, 1H), 2.90-2.77 (m, 1H), 2.77-2.61 (m, 1H), 2.58 (q, 2H), 2.38-2.27 (m, 1H), 2.11-1.94 (m, 1H), 1.87-1.44 (m, 8H), 1.17 (t, 3H).

Example 79

4-[(5-{1-(Morpholin-4-ylcarbonyl)-5-[4-(trifluoromethoxy)phenyl]piperidin-3-yl}-1,2,4-oxadiazol-3-yl)methyl]morpholine [racemic cis isomer]

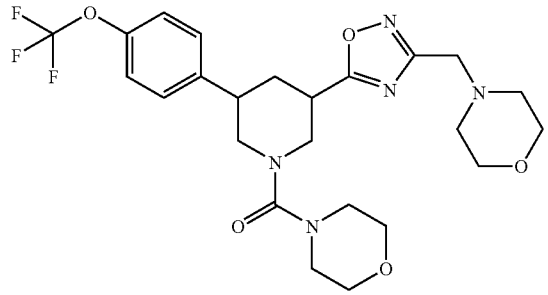

80 mg (0.20 mmol) of 1-(morpholin-4-ylcarbonyl)-5-[4-(trifluoromethoxy)phenyl]piperidine-3-carboxylic acid (Example 44A) and 35 mg (0.22 mmol, 1.1 eq.) of N'-hydroxy-2-morpholin-4-ylethanimidamide were reacted according to the General Method 1. Yield: 28 mg (26% of theory)

HPLC (Method 2A): R$_t$=4.13 min; MS (ESIpos): m/z=526 [M+H]$^+$;

$^1$H-NMR (400 MHz, DMSO-d$_6$): δ=7.47 (d, 2H), 7.33 (d, 2H), 4.00 (br d, 1H), 3.64 (s, 2H), 3.61 (br d, 1H), 3.59-3.52 (m, 4H), 3.47-3.36 (m, 1H), 3.32-3.26 (m, 4H), 3.05 (t, 1H), 3.03-2.93 (m, 2H), 2.32 (br d, 1H), 1.98 (q, 1H).

Example 80

4-({3-(4-Ethylphenyl)-5-[3-(1-methyl-1,2,5,6-tetrahydropyridin-3-yl)-1,2,4-oxadiazol-5-yl]piperidin-1-yl}carbonyl)morpholine [racemic cis isomer]

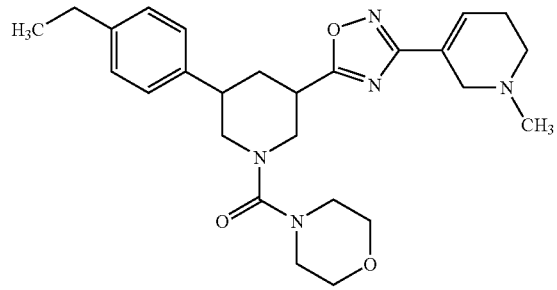

69 mg (0.20 mmol) of 5-(4-ethylphenyl)-1-(morpholin-4-ylcarbonyl)piperidine-3-carboxylic acid (Example 38A) and 34 mg (0.22 mmol, 1.1 eq.) of 1-hydroxy-1-methyl-1,2,5,6-tetrahydropyridine-3-carboximidamide [P. Sauerberg et al. *J. Med. Chem.* 1991, 34, 687-692] were reacted according to the General Method 1. Yield: 35 mg (38% of theory)

HPLC (Method 2A): R$_t$=4.17 min; MS (ESIpos): m/z=466 [M+H]$^+$;

$^1$H-NMR (500 MHz, DMSO-d$_6$): δ=7.22 (d, 2H), 7.17 (d, 2H), 6.90-6.84 (m, 1H), 4.01 (br d, 1H), 3.61 (br d, 1H), 3.60-3.53 (m, 4H), 3.44-3.33 (m, 1H), 3.23-3.14 (m, 6H), 3.03 (t, 1H), 2.95 (q, 1H), 2.91-2.82 (m, 1H), 2.57 (q, 2H), 2.38-2.26 (m, 6H), 1.97 (q, 1H), 1.16 (t, 3H).

Example 81

4-({3-[3-(1-Methyl-1,2,5,6-tetrahydropyridin-3-yl)-1,2,4-oxadiazol-5-yl]-5-[4-(trifluoromethoxy)-phenyl]piperidin-1-yl}carbonyl)morpholine [racemic cis isomer]

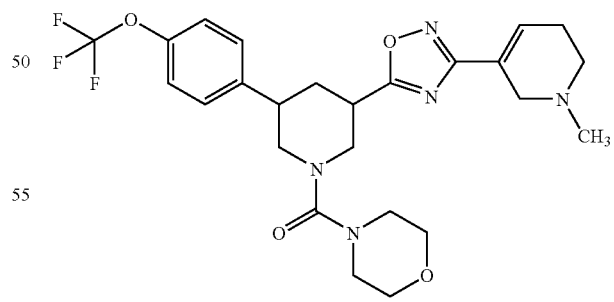

80 mg (0.20 mmol) of 1-(morpholin-4-ylcarbonyl)-5-[4-(trifluoromethoxy)phenyl]piperidine-3-carboxylic acid (Example 44A) and 34 mg (0.22 mmol, 1.1 eq.) of N'-hydroxy-1-methyl-1,2,5,6-tetrahydropyridine-3-carboximidamide [P. Sauerberg et al. *J. Med. Chem.* 1991, 34, 687-692] were reacted according to the General Method 1. Yield: 23 mg (22% of theory)

HPLC (Method 2A): R$_t$=4.21 min; MS (ESIpos): m/z=522 [M+H]$^+$;

$^1$H-NMR (400 MHz, DMSO-d$_6$): δ=7.48 (d, 2H), 7.33 (d, 2H), 6.90-6.84 (m, 1H), 4.01 (br d, 1H), 3.61 (br d, 1H), 3.59-3.53 (m, 4H), 3.46-3.35 (m, 1H), 3.24-3.14 (m, 6H), 3.05 (t, 1H), 3.03-2.93 (m, 2H), 2.38-2.28 (m, 6H), 1.99 (q, 1H).

Example 82 tert-Butyl[(5-{1-(morpholin-4-ylcarbonyl)-5-[4-(trifluoromethoxy)phenyl]piperidin-3-yl}-1,2,4-oxadiazol-3-yl)methyl]carbamate [racemic cis isomer]

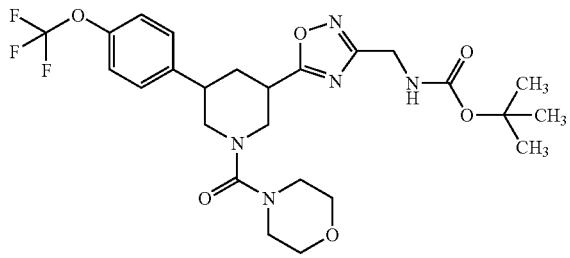

161 mg (0.40 mmol) of 1-(morpholin-4-ylcarbonyl)-5-[4-(trifluoromethoxy)phenyl]piperidine-3-carboxylic acid (Example 44A) and 83 mg (0.44 mmol, 1.1 eq.) of tert-butyl[(2-amino-2-(hydroxyimino)ethyl]carbamate were reacted according to the General Method 1. Yield: 127 mg (57% of theory)

HPLC (Method 2A): R$_t$=4.73 min; MS (ESIpos): m/z=556 [M+H]$^+$;

$^1$H-NMR (400 MHz, DMSO-d$_6$): δ=7.52-7.44 (m, 3H), 7.33 (d, 2H), 4.23 (d, 1H), 3.99 (br d, 1H), 3.67-3.57 (m, 1H), 3.59-3.53 (m, 4H), 3.46-3.36 (m, 1H), 3.23-3.15 (m, 4H), 3.04 (t, 1H), 3.03-2.93 (m, 2H), 2.31 (br d, 1H), 1.98 (q, 1H), 1.38 (s, 9H).

Example 83

1-(5-{1-(Morpholin-4-ylcarbonyl)-5-[4-(trifluoromethoxy)phenyl]piperidin-3-yl}-1,2,4-oxadiazol-3-yl)methanamine [racemic cis isomer]

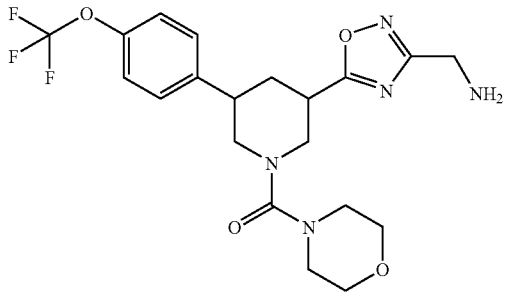

At RT, a solution of 11 mg (0.2 mmol) of tert-butyl[(5-{1-(morpholin-4-ylcarbonyl)-5-[4-(trifluoromethoxy)phenyl]piperidin-3-yl}-1,2,4-oxadiazol-3-yl)methyl] carbamate (Example 82) in 3 ml of dichloromethane was reacted with a total of 185 μl (2.4 mmol, 12 eq.) of trifluoroacetic acid and then concentrated under reduced pressure. The crude product was purified by preparative HPLC (column: Reprosil C18, 10 μm, 250 mm×30 mm; mobile phase: acetonitrile/water with 0.1% triethylamine gradient). Yield: 76 mg (83% of theory)

LC-MS (Method 3B): R$_t$=1.23 min; MS (ESIpos): m/z=456 [M+H]$^+$;

$^1$H-NMR (400 MHz, DMSO-d$_6$): δ=7.47 (d, 2H), 7.33 (d, 2H), 3.99 (br d, 1H), 3.77 (s, 2H), 3.61 (br d, 1H), 3.60-3.52 (m, 4H), 3.45-3.35 (m, 1H), 3.23-3.16 (m, 4H), 3.04 (t, 1H), 3.02-2.93 (m, 2H), 2.32 (br d, 1H), 1.98 (q, 1H), 1.98-1.83 (br s, 2H).

Example 84

N-Ethyl-3-(4-ethylphenyl)-N-methyl-5-(3-phenyl-1,2,4-oxadiazol-5-yl)piperidine-1-carboxamide [racemic cis isomer]

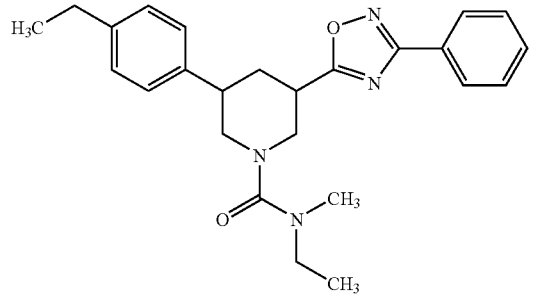

64 mg (0.20 mmol) of 1-[ethyl(methyl)carbamoyl]-5-(4-ethylphenyl)piperidine-3-carboxylic acid (Example 45A) and 30 mg (0.22 mmol, 1.1 eq.) of N'-hydroxybenzenecarboximidamide were reacted according to the General Method 1. Yield: 12 mg (14% of theory)

HPLC (Method 2A): R$_t$=5.36 min; MS (ESIpos): m/z=419 [M+H]$^+$;

$^1$H-NMR (400 MHz, DMSO-d$_6$): δ=8.05-8.00 (m, 2H), 7.62-7.53 (m, 3H), 7.24 (d, 2H), 7.18 (d, 2H), 4.01 (br d, 1H), 3.58-3.46 (m, 2H), 3.17 (q, 2H), 3.06 (t, 1H), 2.95-2.87 (m, 2H), 2.79 (s, 3H), 2.58 (q, 2H), 2.38 (br d, 1H), 2.03 (q, 1H), 1.17 (t, 3H), 1.08 (t, 3H).

Example 85

N-Ethyl-3-(4-ethylphenyl)-5-[3-(4-fluorophenyl)-1,2,4-oxadiazol-5-yl]-N-methylpiperidine-1-carboxamide [racemic cis isomer]

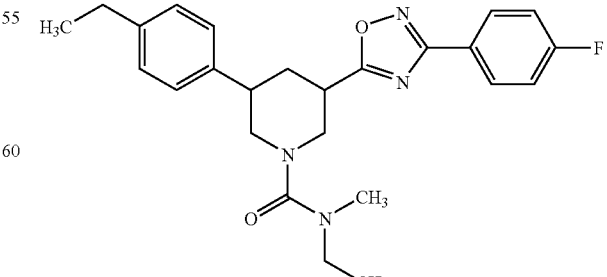

64 mg (0.20 mmol) of 1-[ethyl(methyl)carbamoyl]-5-(4-ethylphenyl)piperidine-3-carboxylic acid (Example 45A) and 34 mg (0.22 mmol, 1.1 eq.) of 4-fluoro-N'-hydroxybenzenecarboximidamide were reacted according to the General Method 1. Yield: 46 mg (52% of theory)

HPLC (Method 2A): $R_t$=5.40 min; MS (ESIpos): m/z=437 [M+H]$^+$;

$^1$H-NMR (500 MHz, DMSO-d$_6$): δ=8.12-8.04 (m, 2H), 7.46-7.38 (m, 2H), 7.24 (d, 2H), 7.17 (d, 2H), 4.01 (br d, 1H), 3.58-3.46 (m, 2H), 3.17 (q, 2H), 3.05 (t, 1H), 2.97-2.85 (m, 2H), 2.79 (s, 3H), 2.57 (q, 2H), 2.37 (br d, 1H), 2.03 (q, 1H), 1.17 (t, 3H), 1.08 (t, 3H).

Example 86

4-({3-[3-(4-Methylphenyl)-1,2,4-oxadiazol-5-yl]-5-[4-(trifluoromethoxy)phenyl]piperidin-1-yl}-carbonyl)morpholine [racemic cis isomer]

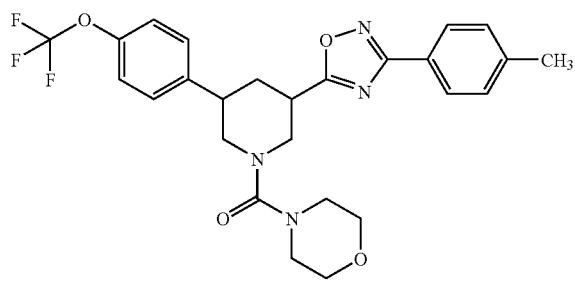

80 mg (0.20 mmol) of 1-(morpholin-4-ylcarbonyl)-5-[4-(trifluoromethoxy)phenyl]piperidine-3-carboxylic acid (Example 44A) and 33 mg (0.22 mmol, 1.1 eq.) of N'-hydroxy-4-methylbenzenecarboximidamide were reacted according to the General Method 1. Yield: 68 mg (66% of theory)

HPLC (Method 2A): $R_t$=5.25 min; MS (ESIpos): m/z=517 [M+H]$^+$;

$^1$H-NMR (400 MHz, DMSO-d$_6$): δ=7.90 (d, 2H), 7.49 (d, 2H), 7.37 (d, 2H), 7.34 (d, 2H), 4.08 (br d, 1H), 3.64 (br d, 1H), 3.62-3.54 (m, 4H), 3.54-3.44 (m, 1H), 3.27-3.18 (m, 4H), 3.13 (t, 1H), 3.07-2.97 (m, 2H), 2.40 (br d, 1H), 2.39 (s, 3H), 2.06 (q, 1H).

Example 87

3-[3-(2,6-Difluorophenyl)-1,2,4-oxadiazol-5-yl]-N-ethyl-5-(4-ethylphenyl)-N-methylpiperidine -1-carboxamide [racemic cis isomer]

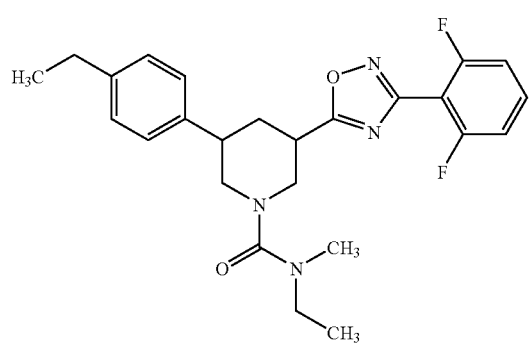

64 mg (0.20 mmol) of 1-[ethyl(methyl)carbamoyl]-5-(4-ethylphenyl)piperidine-3-carboxylic acid (Example 45A) and 38 mg (0.22 mmol, 1.1 eq.) of 2,6-difluoro-N'-hydroxybenzenecarboximidamide were reacted according to the General Method 1. Yield: 23 mg (26% of theory)

HPLC (Method 2A): $R_t$=5.18 min; MS (ESIpos): m/z=455 [M+H]$^+$;

$^1$H-NMR (400 MHz, DMSO-d$_6$): δ=7.77-7.68 (m, 1H), 7.36 (t, 2H), 7.24 (d, 2H), 7.16 (d, 2H), 4.01 (br d, 1H), 3.62-3.50 (m, 2H), 3.17 (q, 2H), 3.05 (t, 1H), 2.97-2.85 (m, 2H), 2.78 (s, 3H), 2.57 (q, 2H), 2.38 (br d, 1H), 2.03 (q, 1H), 1.17 (t, 3H), 1.07 (t, 3H).

Example 88

4-({3-[3-(2-Chloropyridin-4-yl)-1,2,4-oxadiazol-5-yl]-5-[4-(trifluoromethoxy)phenyl]piperidin-1-yl}carbonyl)morpholine [racemic cis isomer]

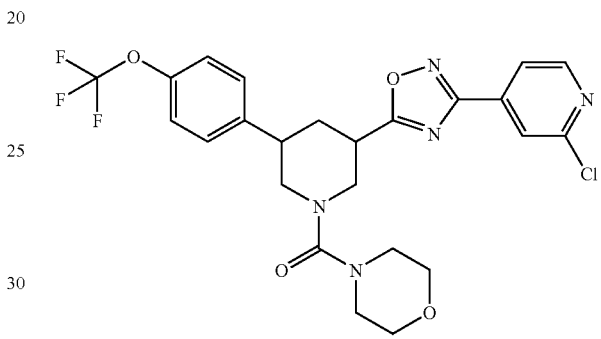

600 mg (1.49 mmol) of 1-(morpholin-4-ylcarbonyl)-5-[4-(trifluoromethoxy)phenyl]piperidine-3-carboxylic acid (Example 44A) and 281 mg (1.64 mmol, 1.1 eq.) of 2-chloro-N'-hydroxypyridine-4-carboximidamide were reacted according to the General Method 1. Yield: 315 mg (39% of theory)

HPLC (Method 2A): $R_t$=4.96 min; MS (ESIpos): m/z=538 [M+H]$^+$;

$^1$H-NMR (400 MHz, DMSO-d$_6$): δ=8.65 (dd, 1H), 8.00 (s, 1H), 7.98 (dd, 1H), 7.49 (d, 2H), 7.36 (d, 2H), 4.10 (br d, 1H), 3.64 (br d, 1H), 3.62-3.50 (m, 5H), 3.27-3.18 (m, 4H), 3.14 (t, 1H), 3.08-2.97 (m, 2H), 2.41 (br d, 1H), 2.08 (q, 1H).

Example 89

3-[3-(2-Chloropyridin-4-yl)-1,2,4-oxadiazol-5-yl]-N-ethyl-5-(4-ethylphenyl)-N-methylpiperidine -1-carboxamide [racemic cis isomer]

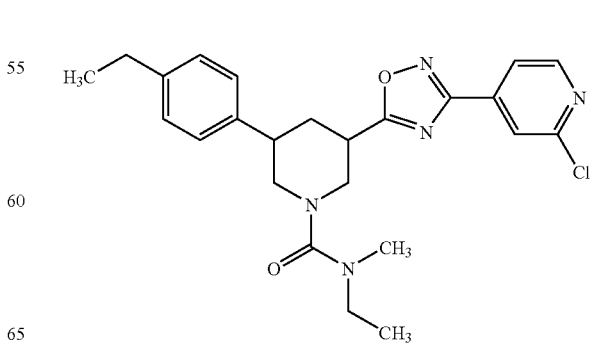

64 mg (0.20 mmol) of 1-[ethyl(methyl)carbamoyl]-5-(4-ethylphenyl)piperidine-3-carboxylic acid (Example 45A) and 38 mg (0.22 mmol, 1.1 eq.) of 2-chloro-N'-hydroxypyridine-4-carboximidamide were reacted according to the General Method 1. Yield: 13 mg (14% of theory)

HPLC (Method 2A): $R_t$=5.22 min; MS (ESIpos): m/z=454 [M+H]$^+$;

$^1$H-NMR (400 MHz, DMSO-$d_6$): δ=8.65 (dd, 1H), 8.00 (s, 1H), 7.98 (dd, 1H), 7.24 (d, 2H), 7.18 (d, 2H), 4.02 (br d, 1H), 3.61-3.50 (m, 2H), 3.17 (q, 2H), 3.06 (t, 1H), 2.98-2.86 (m, 2H), 2.79 (s, 3H), 2.58 (q, 2H), 2.38 (br d, 1H), 2.05 (q, 1H), 1.17 (t, 3H), 1.08 (t, 3H).

Example 90

4-({3-(1,2,4-Oxadiazol-5-yl)-5-[4-(trifluoromethoxy)phenyl]piperidin-1-yl}carbonyl)morpholine [racemic cis isomer]

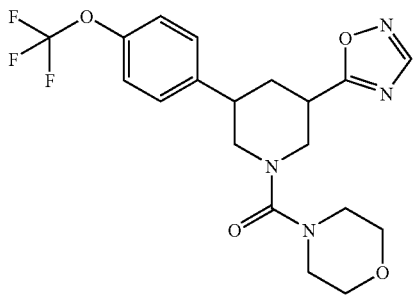

The title compound was isolated from the reaction of Example 92 with lithium hydroxide in tetrahydrofuran/water at room temperature. Yield: 9 mg (57% of theory)

HPLC (Method 2B): $R_t$=1.11 min; MS (ESIpos): m/z=427 [M+H]$^+$;

$^1$H-NMR (500 MHz, DMSO-$d_6$): δ=12.02-11.82 (br s, 1H), 7.45 (d, 2H), 7.33 (d, 2H), 3.80 (br d, 1H), 3.61-3.52 (m, 5H), 3.22-3.13 (m, 4H), 2.92-2.77 (m, 3H), 2.71-2.64 (m, 1H), 2.10 (br d, 1H), 1.80 (q, 1H).

Example 91

3-(3-tert-Butyl-1,2,4-oxadiazol-5-yl)-N-ethyl-5-(4-ethylphenyl)-N-methylpiperidine-1-carboxamide [racemic cis isomer]

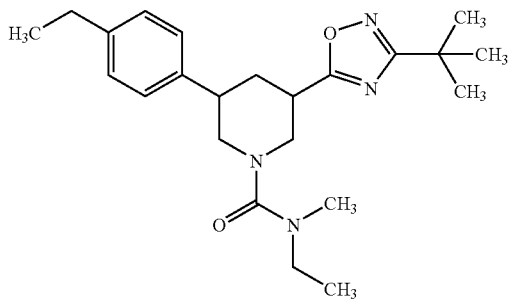

64 mg (0.20 mmol) of 1-[ethyl(methyl)carbamoyl]-5-(4-ethylphenyl)piperidine-3-carboxylic acid (Example 45A) and 26 mg (0.22 mmol, 1.1 eq.) of N'-hydroxy-2,2-dimethylpropanimidamide were reacted according to the General Method 1. Yield: 52 mg (65% of theory)

HPLC (Method 2A): $R_t$=5.30 min; MS (ESIpos): m/z=399 [M+H]$^+$;

$^1$H-NMR (400 MHz, DMSO-$d_6$): δ=7.22 (d, 2H), 7.16 (d, 2H), 3.91 (br d, 1H), 3.53 (br d, 1H), 3.43-3.33 (m, 1H), 3.15 (q, 2H), 3.00-2.80 (m, 3H), 2.76 (s, 3H), 2.57 (q, 2H), 2.29 (br d, 1H), 1.93 (q, 1H), 1.30 (s, 9H), 1.16 (t, 3H), 1.06 (t, 3H).

Example 92

Ethyl 5-{1-(morpholin-4-ylcarbonyl)-5-[4-(trifluoromethoxy)phenyl]piperidin-3-yl}-1,2,4-oxadiazole-3-carboxylate [racemic cis isomer]

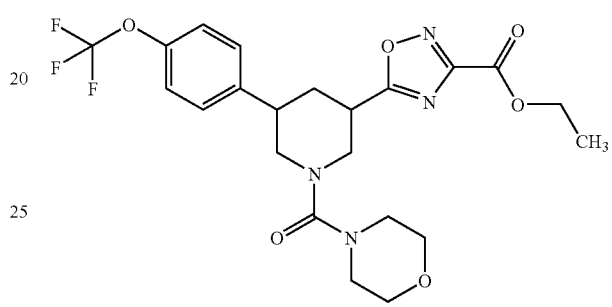

80 mg (0.20 mmol) of 1-(morpholin-4-ylcarbonyl)-5-[4-(trifluoromethoxy)phenyl]piperidine-3-carboxylic acid (Example 44A) and 29 mg (0.22 mmol, 1.1 eq.) of ethyl 2-amino(hydroxyimino)ethanoate were reacted according to the General Method 1. Yield: 24 mg (22% of theory)

HPLC (Method 2A): $R_t$=4.69 min; MS (ESIpos): m/z=499 [M+H]$^+$;

$^1$H-NMR (400 MHz, DMSO-$d_6$): δ=7.48 (d, 2H), 7.34 (d, 2H), 4.41 (q, 2H), 4.03 (br d, 1H), 3.62 (br d, 1H), 3.60-3.47 (m, 5H), 3.25-3.17 (m, 4H), 3.10 (t, 1H), 3.05-2.94 (m, 2H), 2.35 (br d, 1H), 2.03 (q, 1H), 1.33 (t, 3H).

Example 93

N-Ethyl-3-(4-ethylphenyl)-N-methyl-5-[3-(morpholin-4-ylmethyl)-1,2,4-oxadiazol-5-yl]piperidine-1-carboxamide [racemic cis isomer]

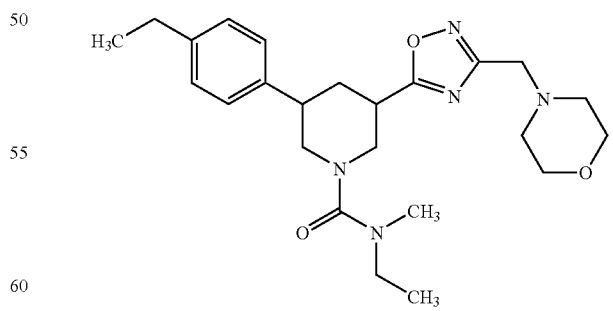

63 mg (0.20 mmol) of 1-[ethyl(methyl)carbamoyl]-5-(4-ethylphenyl)piperidine-3-carboxylic acid (Example 45A) and 35 mg (0.22 mmol, 1.1 eq.) of N'-hydroxy-2-morpholin-4-ylethanimidamide were reacted according to the General Method 1. Yield: 5 mg (5% of theory)

HPLC (Method 2A): R$_t$=4.24 min; MS (ESIpos): m/z=442 [M+H]$^+$;
$^1$H-NMR (400 MHz, DMSO-d$_6$): δ=7.22 (d, 2H), 7.16 (d, 2H), 3.93 (br d, 1H), 3.64 (s, 2H), 3.60-3.50 (m, 5H), 3.47-3.37 (m, 1H), 3.06 (q, 2H), 2.97 (t, 1H), 2.91-2.84 (m, 2H), 2.77 (s, 3H), 2.57 (q, 2H), 2.30 (br d, 1H), 2.00-1.89 (m, 1H), 1.16 (t, 3H), 1.06 (t, 3H).

Example 94

4-({3-(4-Ethylphenyl)-5-[3-(5-fluorothiophen-2-yl)-1,2,4-oxadiazol-5-yl]piperidin-1-yl}carbonyl)-morpholine [racemic cis isomer]

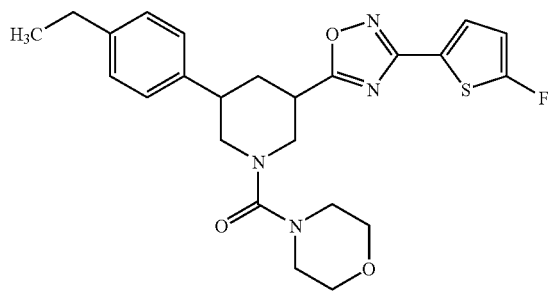

69 mg (0.20 mmol) of 5-(4-ethylphenyl)-1-(morpholin-4-ylcarbonyl)piperidine-3-carboxylic acid (Example 38A) and 35 mg (0.22 mmol, 1.1 eq.) of 5-fluoro-N'-hydroxythiophene-2-carboximidamide were reacted according to the General Method 1. Yield: 51 mg (54% of theory)
HPLC (Method 2A): R$_t$=5.11 min; MS (ESIpos): m/z=471 [M+H]$^+$;
$^1$H-NMR (400 MHz, DMSO-d$_6$): δ=7.56 (t, 1H), 7.23 (d, 2H), 7.17 (d, 2H), 6.95 (dd, 1H), 4.05 (br d, 1H), 3.61 (br d, 1H), 3.60-3.52 (m, 4H), 3.51-3.41 (m, 1H), 3.24-3.15 (m, 4H), 3.08 (t, 1H), 2.96 (q, 1H), 2.93-2.82 (m, 1H), 2.57 (q, 1H), 2.34 (br d, 1H), 2.01 (q, 1H), 1.17 (t, 3H).

Example 95

N-(2-Methoxyethyl)-4-(5-{1-(morpholin-4-ylcarbonyl)-5-[4-(trifluoromethoxy)phenyl]piperidin-3-yl}-1,2,4-oxadiazol-3-yl)pyridine-2-amine [racemic cis isomer]

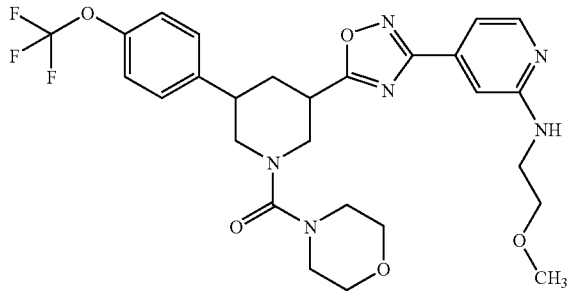

69 mg (0.13 mmol) of 4-({3-[3-(2-chloropyridin-4-yl)-1,2,4-oxadiazol-5-yl]-5-[4-(trifluoromethoxy)phenyl]piperidin-1-yl}carbonyl)morpholine (Example 88) were reacted in 1.2 ml of 2-methoxyethylamine according to the General Method 3. Yield: 31 mg (43% of theory)
HPLC (Method 2A): R$_t$=4.28 min; MS (ESIpos): m/z=577 [M+H]$^+$;
$^1$H-NMR (400 MHz, DMSO-d$_6$): δ=8.12 (d, 1H), 7.49 (d, 2H), 7.34 (d, 2H), 7.15 (s, 1H), 7.02 (t, 1H), 6.97 (dd, 1H), 4.08 (br d, 1H), 3.64 (br d, 1H), 3.61-3.54 (m, 4H), 3.54-3.46 (m, 1H), 3.46-3.43 (m, 4H), 3.27 (s, 3H), 3.25-3.18 (m, 4H), 3.11 (t, 1H), 3.07-2.97 (m, 2H), 2.39 (br d, 1H), 2.05 (q, 1H).

Example 96

4-[4-(5-{1-(Morpholin-4-ylcarbonyl)-5-[4-(trifluoromethoxy)phenyl]piperidin-3-yl}-1,2,4-oxadiazol-3-yl)pyridin-2-yl]morpholine [racemic cis isomer]

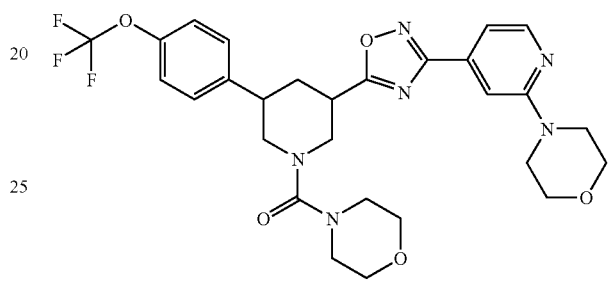

69 mg (0.13 mmol) of 4-({3-[3-(2-chloropyridin-4-yl)-1,2,4-oxadiazol-5-yl]-5-[4-(trifluoromethoxy)phenyl]piperidin-1-yl}carbonyl)morpholine (Example 88) were reacted in 0.6 ml of morpholine according to the General Method 3. Yield: 38 mg (50% of theory)
HPLC (Method 2A): R$_t$=4.29 min; MS (ESIpos): m/z=589 [M+H]$^+$;
$^1$H-NMR (400 MHz, DMSO-d$_6$): δ=8.31 (d, 1H), 7.49 (d, 2H), 7.34 (d, 2H), 7.28 (s, 1H), 7.20 (dd, 1H), 4.09 (br d, 1H), 3.76-3.68 (m, 4H), 3.63 (br d, 1H), 3.60-3.54 (m, 4H), 3.54-3.47 (m, 5H), 3.27-3.18 (m, 4H), 3.13 (t, 1H), 3.08-2.97 (m, 2H), 2.39 (br d, 1H), 2.13-2.02 (m, 1H).

Example 97

N,N-Dimethyl-N'-[4-(5-{1-(morpholin-4-ylcarbonyl)-5-[4-(trifluoromethoxy)phenyl]piperidin-3-yl}-1,2,4-oxadiazol-3-yl)pyridin-2-yl]ethane-1,2-diamine [racemic cis isomer]

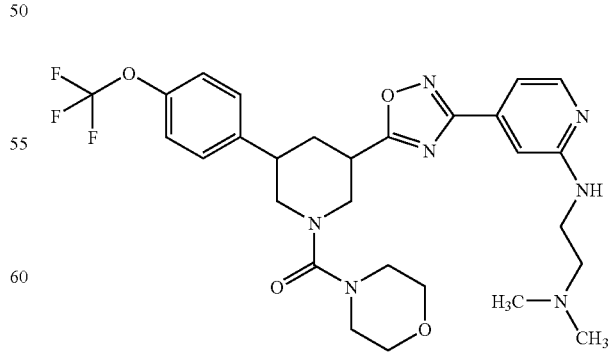

69 mg (0.13 mmol) of 4-({3-[3-(2-chloropyridin-4-yl)-1,2,4-oxadiazol-5-yl]-5-[4-(trifluoromethoxy)phenyl]piperidin-1-yl}carbonyl)morpholine (Example 88) were reacted in 0.6 ml of N,N-dimethylenediamine according to the General Method 3. Yield: 8 mg (10% of theory)

HPLC (Method 2A): $R_t$=4.09 min; MS (ESIpos): m/z=590 [M+H]$^+$;

$^1$H-NMR (500 MHz, DMSO-d$_6$): δ=8.15 (d, 1H), 7.51 (d, 2H), 7.37 (d, 2H), 7.16 (s, 1H), 6.99 (d, 1H), 6.88 (t, 1H), 4.10 (br d, 1H), 3.65 (br d, 1H), 3.64-3.57 (m, 4H), 3.56-3.48 (m, 1H), 3.39 (q, 2H), 3.28-3.20 (m, 4H), 3.14 (t, 1H), 3.08-2.98 (m, 2H), 2.48-2.38 (m, 3H), 2.20 (s, 6H), 2.07 (q, 1H).

Example 98

4-({3-[3-(2-Fluorophenyl)-1,2,4-oxadiazol-5-yl]-5-[4-(trifluoromethoxy)phenyl]piperidin-1-yl}carbonyl)morpholine [racemic cis isomer]

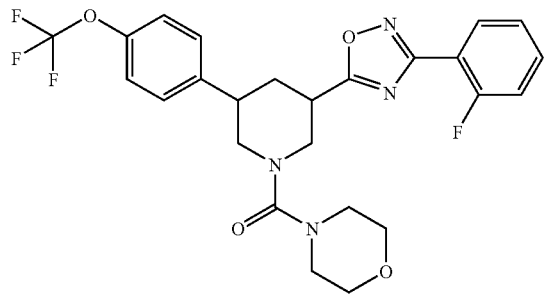

80 mg (0.20 mmol) of 1-(morpholin-4-ylcarbonyl)-5-[4-(trifluoromethoxy)phenyl]piperidine-3-carboxylic acid (Example 44A) and 42 mg (0.22 mmol, 1.1 eq.) of 2-fluoro-N'-hydroxybenzenecarboximidamide were reacted according to the General Method 1. Yield: 59 mg (57% of theory)

HPLC (Method 1A): $R_t$=5.11 min; MS (ESIpos): m/z=521 [M+H]$^+$;

$^1$H-NMR (400 MHz, DMSO-d$_6$): δ=8.03 (dt, 1H), 7.70-7.64 (m, 1H), 7.53-7.39 (m, 4H), 7.35 (d, 2H), 4.09 (br d, 1H), 3.64 (br d, 1H), 3.62-3.53 (m, 4H), 3.58-3.48 (m, 1H), 3.27-3.18 (m, 4H), 3.14 (t, 1H), 3.08-2.97 (m, 2H), 2.41 (br d, 1H), 2.07 (q, 1H).

Example 99

4-({3-[3-(5-Chlorothiophen-2-yl)-1,2,4-oxadiazol-5-yl]-5-[4-(trifluoromethoxy)phenyl]piperidin-1-yl}carbonyl)morpholine [racemic cis isomer]

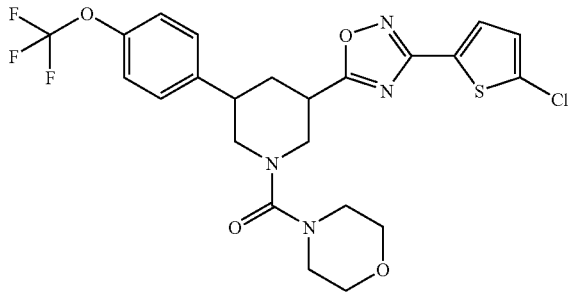

80 mg (0.20 mmol) of 1-(morpholin-4-ylcarbonyl)-5-[4-(trifluoromethoxy)phenyl]piperidine-3-carboxylic acid (Example 44A) and 39 mg (0.22 mmol, 1.1 eq.) of 5-chloro-N'-hydroxythiophene-2-carboximidamide were reacted according to the General Method 1. Yield: 57 mg (53% of theory)

HPLC (Method 1A): $R_t$=5.47 min; MS (ESIpos): m/z=543 [M+H]$^+$;

$^1$H-NMR (400 MHz, DMSO-d$_6$): δ=7.69 (d, 1H), 7.49 (d, 2H), 7.37-7.31 (m, 3H), 4.05 (br d, 1H), 3.62 (br d, 1H), 3.60-3.53 (m, 4H), 3.52-3.43 (m, 1H), 3.26-3.18 (m, 4H), 3.11 (t, 1H), 3.06-2.95 (m, 2H), 2.37 (br d, 1H), 2.04 (q, 1H).

Example 100

4-({3-[3-(5-Chlorothiophen-2-yl)-1,2,4-oxadiazol-5-yl]-5-(4-ethylphenyl)piperidin-1-yl}carbonyl)morpholine [racemic cis isomer]

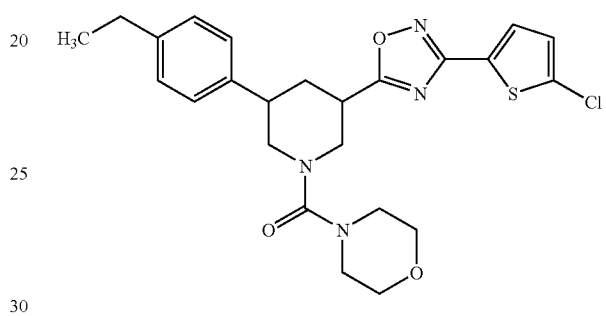

69 mg (0.20 mmol) of 5-(4-ethylphenyl)-1-(morpholin-4-ylcarbonyl)piperidine-3-carboxylic acid (Example 38A) and 39 mg (0.22 mmol, 1.1 eq.) of 5-chloro-N'-hydroxythiophene-2-carboximidamide were reacted according to the General Method 1. Yield: 60 mg (62% of theory)

HPLC (Method 2A): $R_t$=5.51 min; MS (ESIpos): m/z=487 [M+H]$^+$;

$^1$H-NMR (400 MHz, DMSO-d$_6$): δ=7.70 (d, 1H), 7.32 (d, 1H), 7.24 (d, 2H), 7.18 (d, 2H), 4.06 (br d, 1H), 3.61 (br d, 1H), 3.60-3.53 (m, 4H), 3.52-3.42 (m, 1H), 3.23-3.16 (m, 4H), 3.09 (t, 1H), 2.98 (t, 1H), 2.93-2.83 (m, 1H), 2.58 (q, 2H), 2.34 (br d, 1H), 2.01 (q, 1H), 1.17 (t, 3H).

Example 101

4-({3-[3-(5-Fluorothiophen-2-yl)-1,2,4-oxadiazol-5-yl]-5-[4-(trifluoromethoxy)phenyl]piperidin-1-yl}carbonyl)morpholine [racemic cis isomer]

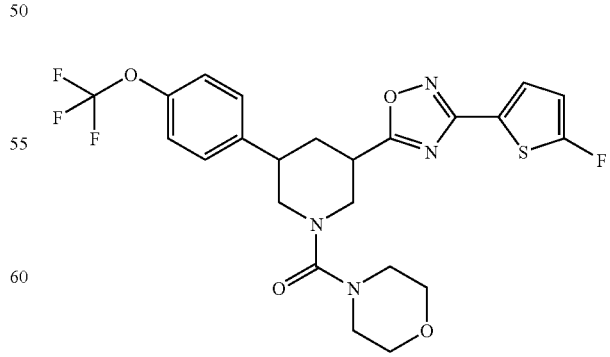

80 mg (0.20 mmol) of 1-(morpholin-4-ylcarbonyl)-5-[4-(trifluoromethoxy)phenyl]piperidine-3-carboxylic acid (Example 44A) and 35 mg (0.22 mmol, 1.1 eq.) of 5-fluoro-N'- hydroxythiopheno-2-carboximidamide were reacted according to the General Method 1. Yield: 61 mg (58% of theory)

HPLC (Method 1A): $R_t$=5.27 min; MS (ESIpos): m/z=527 [M+H]$^+$;

$^1$H-NMR (400 MHz, DMSO-d$_6$): δ=7.56 (dd, 1H), 7.49 (d, 2H), 7.34 (d, 2H), 6.95 (dd, 1H), 4.05 (br d, 1H), 3.62 (br d, 1H), 3.61-3.53 (m, 4H), 3.52-3.43 (m, 1H), 3.24-3.16 (m, 4H), 3.10 (t, 1H), 3.06-2.94 (m, 2H), 2.37 (br d, 1H), 2.03 (q, 1H).

Example 102

4-({3-(4-Ethylphenyl)-5-[3-(2-fluorophenyl)-1,2,4-oxadiazol-5-yl]piperidin-1-yl}carbonyl)-morpholine [racemic cis isomer]

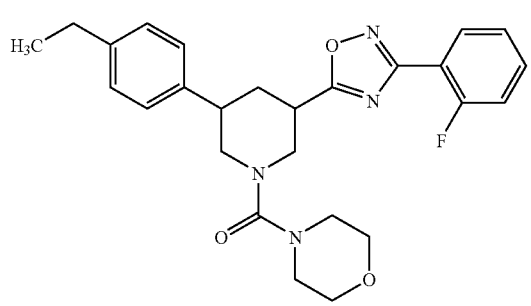

69 mg (0.20 mmol) of 5-(4-ethylphenyl)-1-(morpholin-4-ylcarbonyl)piperidine-3-carboxylic acid (Example 38A) and 34 mg (0.22 mmol, 1.1 eq.) of 2-fluoro-N'-hydroxybenzenecarboximidamide were reacted according to the General Method 1. Yield: 39 mg (42% of theory)

HPLC (Method 1A): $R_t$=5.14 min; MS (ESIpos): m/z=465 [M+H]$^+$;

$^1$H-NMR (400 MHz, DMSO-d$_6$): δ=8.03 (dt, 1H), 7.70-7.63 (m, 1H), 7.49-7.39 (m, 2H), 7.25 (d, 2H), 7.18 (d, 2H), 4.09 (br d, 1H), 3.62 (br d, 1H), 3.59-3.54 (m, 4H), 3.56-3.46 (m, 1H), 3.24-3.18 (m, 4H), 3.11 (t, 1H), 2.99 (t, 1H), 2.96-2.85 (m, 1H), 2.58 (q, 2H), 2.38 (br d, 1H), 2.04 (q, 1H), 1.17 (t, 3H).

Example 103

4-({3-[3-(4-Fluorophenyl)-1,2,4-oxadiazol-5-yl]-5-[4-(trifluoromethoxy)phenyl]piperidin-1-yl}carbonyl)morpholine [enantiomerically pure cis isomer]

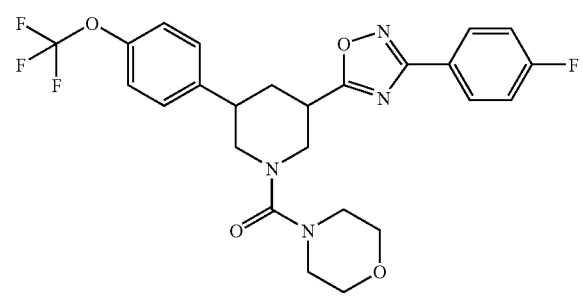

Enantiomer separation of 44 mg of the racemate from Example 34 according to Method 6D gave 18 mg of the title compound from Example 103 (Enantiomer 1) and 19 mg of the title compound from Example 104 (Enantiomer 2).

HPLC (Method 4E): $R_t$=10.16 min; MS (ESIpos): m/z=521 [M+H]$^+$.

Example 104

4-({3-[3-(4-Fluorophenyl)-1,2,4-oxadiazol-5-yl]-5-[4-(trifluoromethoxy)phenyl]piperidin-1-yl}carbonyl)morpholine [enantiomerically pure cis isomer]

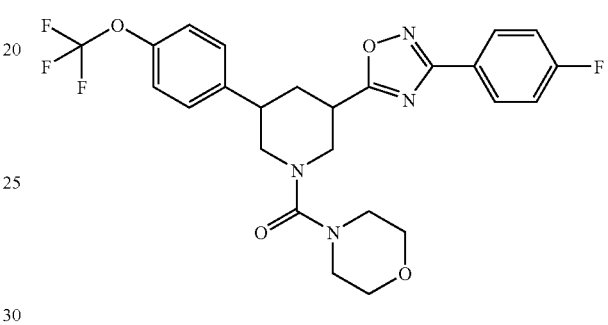

Enantiomer separation of 44 mg of the racemate from Example 34 according to Method 6D gave 18 mg of the title compound from Example 103 (Enantiomer 1) and 19 mg of the title compound from Example 104 (Enantiomer 2).

HPLC (Method 4E): $R_t$=12.64 min; MS (ESIpos): m/z=521 [M+H]$^+$.

Example 105

4-({3-(3-tert-Butyl-1,2,4-oxadiazol-5-yl)-5-[4-(trifluoromethoxy)phenyl]piperidin-1-yl}carbonyl)-morpholine [enantiomerically pure cis isomer]

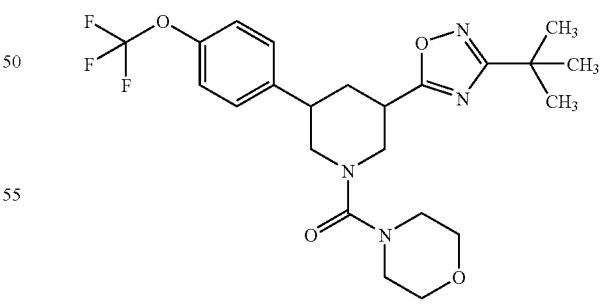

Enantiomer separation of 57 mg of the racemate from Example 74 according to Method 7D gave 23 mg of the title compound from Example 105 (Enantiomer 1) and 26 mg of the title compound from Example 106 (Enantiomer 2).

HPLC (Method 3E): $R_t$=4.68 min; MS (ESIpos): m/z=483 [M+H]$^+$.

Example 106

4-({3-(3-tert-Butyl-1,2,4-oxadiazol-5-yl)-5-[4-(trifluoromethoxy)phenyl]piperidin-1-yl}carbonyl)-morpholine [enantiomerically pure cis isomer]

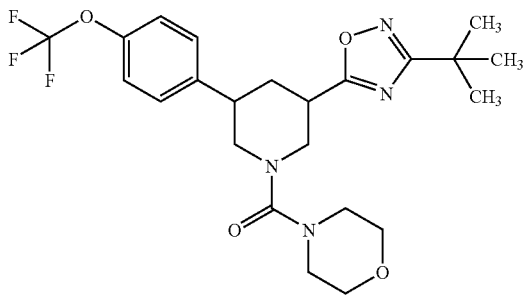

Enantiomer separation of 57 mg of the racemate from Example 74 according to Method 7D gave 23 mg of the title compound from Example 105 (Enantiomer 1) and 26 mg of the title compound from Example 106 (Enantiomer 2).

HPLC (Method 3E): $R_t$=5.34 min; MS (ESIpos): m/z=483 [M+H]$^+$.

Example 107

4-({3-[3-(2,4-Difluorophenyl)-1,2,4-oxadiazol-5-yl]-5-[4-(trifluoromethoxy)phenyl]piperidin-1-yl}carbonyl)morpholine [enantiomerically pure cis isomer]

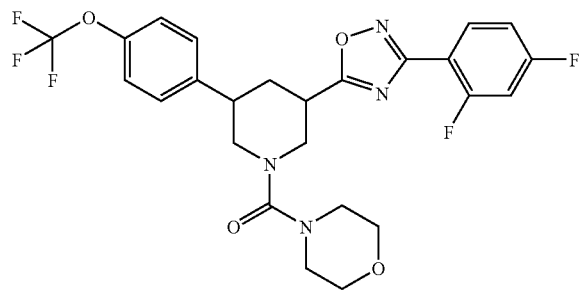

Enantiomer separation of 40 mg of the racemate from Example 38 according to Method 4D gave 14 mg of the title compound from Example 107 (Enantiomer 1) and 14 mg of the title compound from Example 108 (Enantiomer 2).

HPLC (Method 1E): $R_t$=6.89 min; MS (ESIpos): m/z=539 [M+H]$^+$.

Example 108

4-({3-[3-(2,4-Difluorophenyl)-1,2,4-oxadiazol-5-yl]-5-[4-(trifluoromethoxy)phenyl]piperidin-1-yl}carbonyl)morpholine [enantiomerically pure cis isomer]

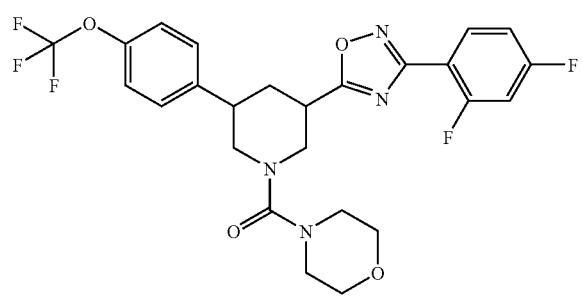

Enantiomer separation of 40 mg of the racemate from Example 38 according to Method 4D gave 14 mg of the title compound from Example 107 (Enantiomer 1) and 14 mg of the title compound from Example 108 (Enantiomer 2).

HPLC (Method 1E): $R_t$=8.40 min; MS (ESIpos): m/z=539 [M+H]$^+$.

Example 109

3-(4-Ethylphenyl)-5-(3-phenyl-1,2,4-oxadiazol-5-yl)-1-(pyrrolidin-1-ylcarbonyl)piperidine [racemic cis isomer]

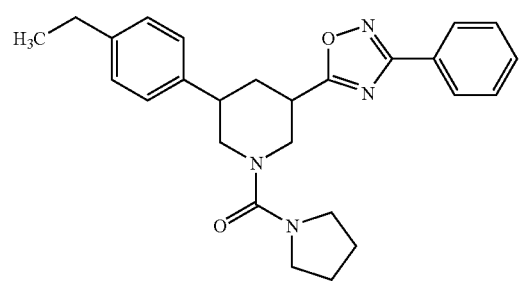

73 mg (0.22 mmol) of 5-(4-ethylphenyl)-1-(pyrrolidin-1-ylcarbonyl)piperidine-3-carboxylic acid (Example 41A) and 33 mg (0.24 mmol, 1.1 eq.) of N'-hydroxybenzenecarboximidamide were reacted according to the General Method 1. Yield: 32 mg (33% of theory)

HPLC (Method 2A): $R_t$=5.39 min; MS (ESIpos): m/z=431 [M+H]$^+$;

$^1$H-NMR (400 MHz, DMSO-d$_6$): δ=8.05-8.00 (m, 2H), 7.63-7.54 (m, 3H), 7.25 (d, 2H), 7.18 (d, 2H), 4.16 (br d, 1H), 3.72 (br d, 1H), 3.54-3.44 (m, 1H), 3.06 (t, 1H), 2.97-2.85 (m, 2H), 2.58 (q, 2H), 2.39 (br d, 1H), 2.05 (q, 1H), 1.82-1.71 (m, 4H), 1.17 (t, 3H).

Example 110

3-(4-Ethylphenyl)-5-[3-(2-fluorophenyl)-1,2,4-oxadiazol-5-yl]-1-(pyrrolidin-1-ylcarbonyl)-piperidine [racemic cis isomer]

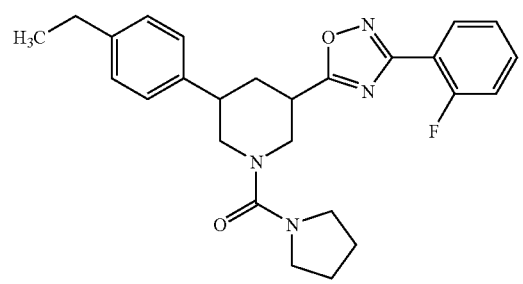

73 mg (0.22 mmol) of 5-(4-ethylphenyl)-1-(pyrrolidin-1-ylcarbonyl)piperidine-3-carboxylic acid (Example 41A) and 47 mg (0.24 mmol, 1.1 eq.) of 2-fluoro-N'-hydroxybenzenecarboximidamide were reacted according to the General Method 1. Yield: 46 mg (47% of theory)

HPLC (Method 2A): R$_t$=5.29 min; MS (ESIpos): m/z=449 [M+H]$^+$;
$^1$H-NMR (400 MHz, DMSO-d$_6$): δ=8.04 (dt, 1H), 7.70-7.63 (m, 1H), 7.49-7.38 (m, 2H), 7.25 (d, 2H), 7.18 (d, 2H), 4.17 (br d, 1H), 3.72 (br d, 1H), 3.55-3.45 (m, 1H), 3.06 (t, 1H), 2.97-2.85 (m, 2H), 2.58 (q, 2H), 2.39 (br d, 1H), 2.11-1.99 (m, 1H), 1.81-1.72 (m, 4H), 1.17 (t, 3H).

Example 111

3-(3-tert-Butyl-1,2,4-oxadiazol-5-yl)-5-(4-ethylphenyl)-1-(pyrrolidin-1-ylcarbonyl)piperidine [racemic cis isomer]

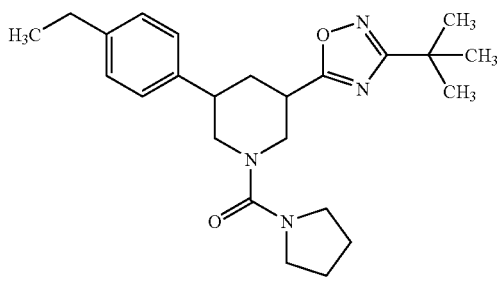

73 mg (0.22 mmol) of 5-(4-ethylphenyl)-1-(pyrrolidin-1-ylcarbonyl)piperidine-3-carboxylic acid (Example 41A) and 35 mg (0.24 mmol, 1.1 eq.) of 1-hydroxy-2,2-dimethylpropanimidamide were reacted according to the General Method 1. Yield: 71 mg (79% of theory)
HPLC (Method 2A): R$_t$=5.32 min; MS (ESIpos): m/z=411 [M+H]$^+$;
$^1$H-NMR (400 MHz, DMSO-d$_6$): δ=7.23 (d, 2H), 7.16 (d, 2H), 4.05 (br d, 1H), 3.69 (br d, 1H), 3.41-3.30 (m, 1H), 3.30-3.25 (m, 4H), 2.96 (t, 1H), 2.91 (t, 1H), 2.89-2.80 (m, 1H), 2.57 (d, 2H), 2.29 (br d, 1H), 1.94 (q, 1H), 1.80-1.70 (m, 4H), 1.30 (s, 9H), 1.16 (t, 3H).

Example 112

4-({3-(3-tert-Butyl-1,2,4-oxadiazol-5-yl)-5-[4-(trifluoromethyl)phenyl]piperidin-1-yl}carbonyl)-morpholine [racemic cis isomer]

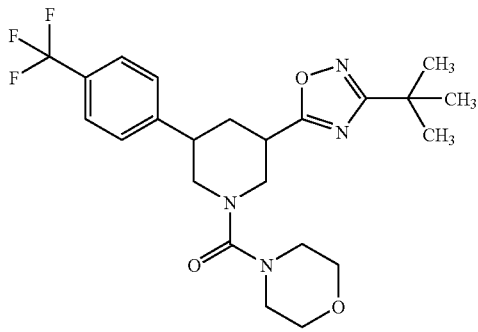

250 mg (0.65 mmol) of 1-(morpholin-4-ylcarbonyl)-5-[4-(trifluoromethyl)phenyl]piperidine-3-carboxylic acid (Example 49A) and 83 mg (0.71 mmol) of N'-hydroxy-2,2-dimethylpropanimidamide were reacted according to the General Method 1. Yield: 70 mg (70% of theory)

LC-MS (Method 5B): R$_t$=2.51 min; MS (ESIpos): m/z=467 [M+H]$^+$;
$^1$H-NMR (400 MHz, DMSO-d$_6$): δ=7.70 (d, 2H), 7.58 (d, 2H), 3.99 (br d, 1H), 3.62 (d, 1H), 3.61-3.55 (m, 4H), 3.40 (tt, 1H), 3.22-3.19 (m, 4H), 3.09-3.02 (3H), 2.33 (br d, 1H), 2.01 (q, 1H), 1.30 (s, 9H).

Example 113

4-({3-[4-(4-Methylpyridin-3-yl)-1,3-thiazol-2-yl]-5-[4-(trifluoromethyl)phenyl]piperidin-1-yl}carbonyl) morpholine [racemic cis isomer]

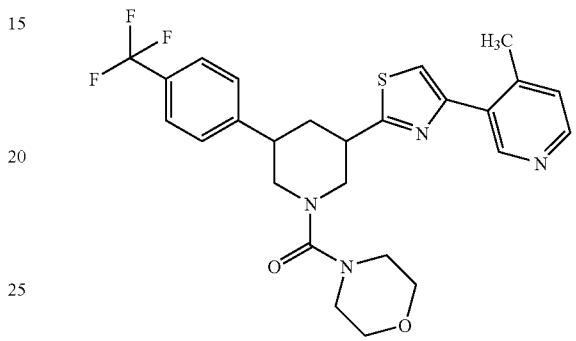

100 mg (0.224 mmol) of 1-(morpholin-4-ylcarbonyl)-5-[4-(trifluoromethyl)phenyl]piperidine-3-carbothioamide (Example 53A) and 67 mg (0.269 mmol) of 2-bromo-1-(4-methylpyridin-3-yl)ethanone hydrochloride were reacted according to the General Method 3. Yield: 13 mg (12% of theory).
LC-MS (Method 2B): R$_t$=1.15 min; MS (ESIpos): m/z=517 [M+H]$^+$;
$^1$H-NMR (400 MHz, DMSO-d$_6$): δ=8.75 (s, 1H), 8.42 (d, 1H), 7.89 (s, 1H), 7.72 (br d, 2H), 7.60 (br d, 2H), 7.33 (d, 1H), 4.07 (br d, 1H), 3.68 (br d, 1H), 3.58-3.56 (m, 4H), 3.46 (tt, 1H), 3.22-3.19 (m, 4H), 3.13-3.01 (m, 3H), 2.46 (s, 3H), 2.38 (br d, 1H), 2.06 (q, 1H).

Example 114

4-({3-(4-tert-Butyl-1,3-thiazol-2-yl)-5-[4-(trifluoromethyl)phenyl]piperidin-1-yl}carbonyl)-morpholine [racemic cis isomer]

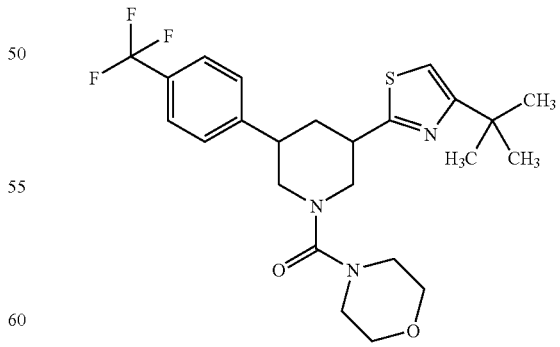

100 mg (0.224 mmol) of 1-(morpholin-4-ylcarbonyl)-5-[4-(trifluoromethyl)phenyl]piperidine-3-carbothioamide (Example 53A) and 48 mg (0.269 mmol) of 1-bromo-3,3-dimethylbutan-2-one were reacted according to the General Method 3. Yield: 19 mg (17% of theory)

LC-MS (Method 2B): $R_t$=1.52 min; MS (ESIpos): m/z=482 [M+H]$^+$;
$^1$H-NMR (400 MHz, DMSO-d$_6$): δ=7.70 (d, 2H), 7.59 (d, 2H), 7.16 (s, 1H), 4.00 (br d, 1H), 3.65 (br d, 1H), 3.58-3.55 (m, 4H), 3.20-3.18 (m, 4H), 3.05 (d, 2H), 2.97 (t, 1H), 2.31 (br d, 1H), 1.95 (q, 1H), 1.28 (s, 9H). 1H was not assigned

Example 115

4-({3-[4-(6-Methylpyridin-3-yl)-1,3-thiazol-2-yl]-5-[4-(trifluoromethyl)phenyl]piperidin-1-yl}-carbonyl)morpholine [racemic cis isomer]

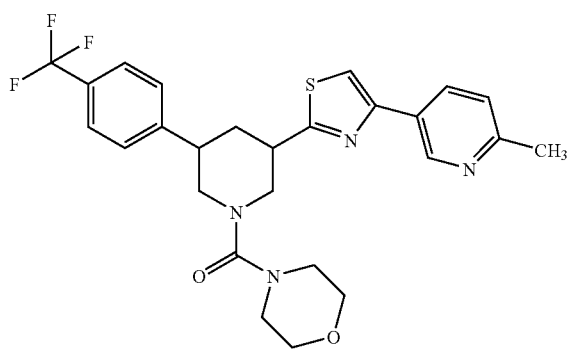

100 mg (0.224 mmol) of 1-(morpholin-4-ylcarbonyl)-5-[4-(trifluoromethyl)phenyl]piperidine-3-carbothioamide (Example 53A) and 58 mg (0.269 mmol) of 2-bromo-1-(6-methylpyridin-3-yl)ethanone were reacted according to the General Method 3. Yield: 18 mg (15% of theory)
LC-MS (Method 2B): $R_t$=1.31 min; MS (ESIpos): m/z=517 [M+H]$^+$;
$^1$H-NMR (400 MHz, DMSO-d$_6$): δ=8.75 (s, 1H), 8.43 (d, 1H), 7.89 (s, 1H), 7.71 (br d, 2H), 7.60 (br d, 2H), 7.33 (d, 1H), 4.07 (br d, 1H), 3.68 (br d, 1H), 3.58-3.56 (m, 4H), 3.48 (tt, 1H), 3.22-3.19 (m, 4H), 3.11-3.01 (m, 3H), 2.46 (s, 3H), 2.39 (br d, 1H), 2.07 (q, 1H).

Example 116

4-({3-(4-Pyridin-2-yl-1,3-thiazol-2-yl)-5-[4-(trifluoromethyl)phenyl]piperidin-1-yl}carbonyl)-morpholine [racemic cis isomer]

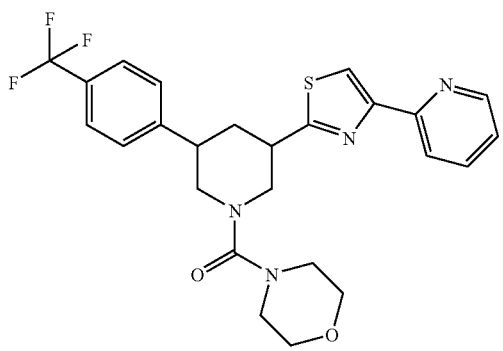

100 mg (0.224 mmol) of 1-(morpholin-4-ylcarbonyl)-5-[4-(trifluoromethyl)phenyl]piperidine-3-carbothioamide (Example 53A) and 76 mg (0.269 mmol) of 2-bromo-1-pyridin-2-ylethanone were reacted according to the General Method 3. Yield: 8 mg (7% of theory)
LC-MS (Method 2B): $R_t$=1.30 min; MS (ESIpos): m/z=503 [M+H]$^+$;
$^1$H-NMR (400 MHz, DMSO-d$_6$): δ=8.61 (br d, 2H), 8.21 (s, 1H), 8.07 (d, 1H), 7.90 (td, 1H), 7.71 (br d, 2H), 7.61 (br d, 2H), 7.35 (dd, 1H), 4.08 (br d, 1H), 3.69 (d, 1H), 3.59-3.57 (m, 4H), 3.47 (t, 1H), 3.23-3.21 (m, 4H), 3.12-3.04 (m, 3H), 2.42 (br d, 1H), 2.07 (q, 1H).

Example 117

4-({3-[4-(2,6-Dimethylpyridin-3-yl)-1,3-thiazol-2-yl]-5-[4-(trifluoromethyl)phenyl]piperidin-1-yl}-carbonyl)morpholine [racemic cis isomer]

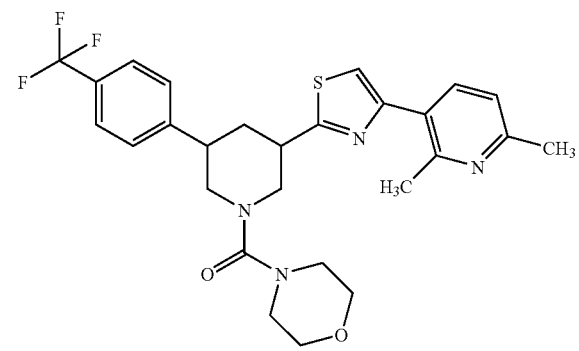

100 mg (0.224 mmol) of 1-(morpholin-4-ylcarbonyl)-5-[4-(trifluoromethyl)phenyl]piperidine-3-carbothioamide (Example 53A) and 83 mg (0.269 mmol) of 2-bromo-1-(2,6-dimethylpyridin-3-yl)ethanone were reacted according to the General Method 3. Yield: 13 mg (10% of theory)
LC-MS (Method 2B): $R_t$=1.09 min; MS (ESIpos): m/z=531[M+H]$^+$;
$^1$H-NMR (400 MHz, DMSO-d$_6$): δ=7.95 (bs, 1H), 7.81 (s, 1H), 7.71 (d, 2H), 7.60 (d, 2H), 7.22 (bs, 1H), 4.06 (br d, 1H), 3.68 (r d, 1H), 3.58-3.56 (m, 4H), 3.45 (tt, 1H), 3.22-3.19 (m, 4H), 3.10-3.01 (m, 3H), 2.62 (s, 3H), 2.38 (br d, 1H), 2.06 (q, 1H). 3Hs were not assigned.

Example 118

4-({3-[4-(6-Chloropyridin-3-yl)-1,3-thiazol-2-yl]-5-[4-(trifluoromethyl)phenyl]piperidin-1-yl}-carbonyl)morpholine [racemic cis isomer]

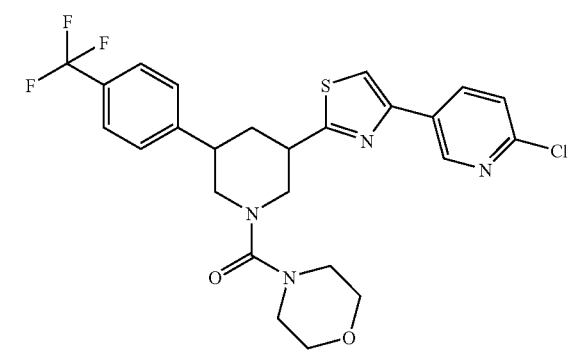

100 mg (0.224 mmol) of 1-(morpholin-4-ylcarbonyl)-5-[4-(trifluoromethyl)phenyl]piperidine-3-carbothioamide (Example 53A) and 85 mg (0.269 mmol) of 2-bromo-1-(6-chloropyridin-3-yl)ethanone were reacted according to the General Method 3. Yield: 17 mg (14% of theory)

LC-MS (Method 2B): $R_t$=1.40 min; MS (ESIpos): m/z=537 [M+H]$^+$;

$^1$H-NMR (400 MHz, DMSO-d$_6$): δ 9.09 (d, 1H), 8.36 (dd, 1H), 8.29 (s, 1H), 7.71 (br d, 2H), 7.61 (br d, 3H), 4.06 (br d, 1H), 3.68 (br d, 1H), 3.61-3.57 (m, 4H), 3.47 (t, 1H), 3.24-3.21 (m, 4H), 3.11-3.03 (m, 3H), 2.38 (br d, 1H), 2.06 (q, 1H).

Example 119

4-({3-(4-Pyridin-3-yl-1,3-thiazol-2-yl)-5-[4-(trifluoromethyl)phenyl]piperidin-1-yl}carbonyl)-morpholine [racemic cis isomer]

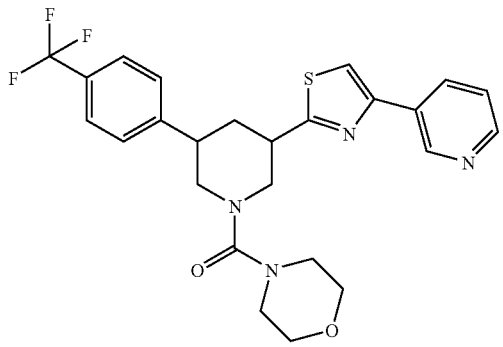

100 mg (0.224 mmol) of 1-(morpholin-4-ylcarbonyl)-5-[4-(trifluoromethyl)phenyl]piperidine-3-carbothioamide (Example 53A) and 54 mg (0.269 mmol) of 2-bromo-1-pyridin-3-ylethanone were reacted according to the General Method 3. Yield: 24 mg (21% of theory)

LC-MS (Method 5B): $R_t$=2.10 min; MS (ESIpos): m/z=503 [M+H]$^+$;

$^1$H-NMR (400 MHz, DMSO-d$_6$): δ=9.17 (d, 1H), 8.54 (dd, 1H), 8.30 (dt, 1H), 8.23 (s, 1H), 7.71 (br d, 2H), 7.61 (br d, 2H), 7.46 (dd, 1H), 4.07 (br d, 1H), 3.68 (br d, 1H), 3.59-3.57 (m, 4H), 3.48 (tt, 1H), 3.23-3.20 (m, 4H), 3.12-3.03 (m, 3H), 2.40 (br d, 1H), 2.07 (q, 1H).

Example 120

4-({3-[4-(2,4-Dichlorophenyl)-1,3-thiazol-2-yl]-5-[4-(trifluoromethyl)phenyl]piperidin-1-yl}-carbonyl)morpholine [racemic cis isomer]

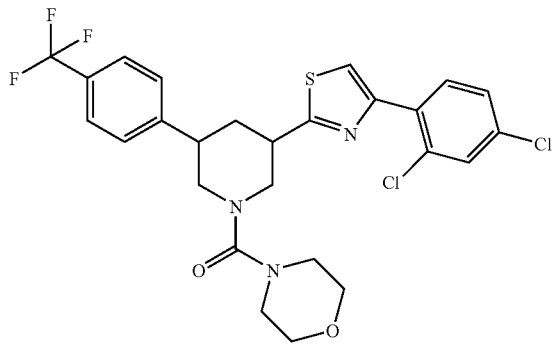

100 mg (0.224 mmol) of 1-(morpholin-4-ylcarbonyl)-5-[4-(trifluoromethyl)phenyl]piperidine-3-carbothioamide (Example 53A) and 72 mg (0.269 mmol) of 2-bromo-1-(2,4-dichlorophenyl)ethanone were reacted according to the General Method 3. Yield: 43 mg (34% of theory)

LC-MS (Method 5B): $R_t$=3.04 min; MS (ESIpos): m/z=570 [M+H]$^+$;

$^1$H-NMR (400 MHz, DMSO-d$_6$): δ=8.09 (s, 1H), 7.94 (d, 1H), 7.74 (d, 1H), 7.72 (br d, 2H), 7.60 (br d, 2H), 6.53 (dd, 1H), 4.05 (br d, 1H), 3.68 (d, 1H), 3.58-3.56 (m, 4H), 3.46 (tt, 1H), 3.21-3.19 (m, 4H), 3.11-3.02 (m, 3H), 2.38 (br d, 1H), 2.06 (q, 1H).

Example 121

4-({3-[4-(4-Fluorophenyl)-1,3-thiazol-2-yl]-5-[4-(trifluoromethyl)phenyl]piperidin-1-yl}-carbonyl)morpholine [racemic cis isomer]

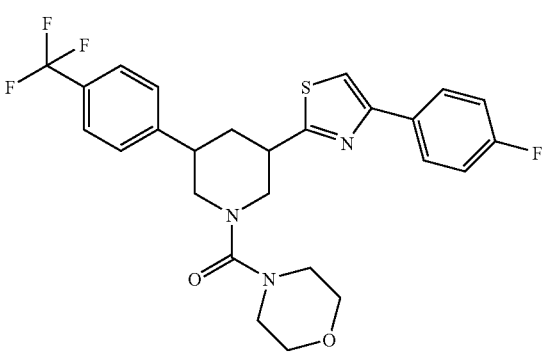

100 mg (0.152 mmol) of 1-(morpholin-4-ylcarbonyl)-5-[4-(trifluoromethyl)phenyl]piperidine-3-carbothioamide (Example 53A) and 32 mg (0.182 mmol) of 2-chloro-1-(4-fluorophenyl)ethanone were reacted according to the General Method 3. Yield: 30 mg (39% of theory)

LC-MS (Method 5B): $R_t$=2.76 min; MS (ESIpos): m/z=520 [M+H]$^+$;

$^1$H-NMR (400 MHz, DMSO-d$_6$): δ=8.03-7.99 (3H), 7.71 (d, 2H), 7.61 (d, 2H), 7.28 (t, 2H), 4.06 (br d, 1H), 3.68 (d, 1H), 3.60-3.57 (m, 4H), 3.44 (tt, 1H), 3.23-3.20 (m, 4H), 3.10-3.02 (m, 3H), 2.38 (br d, 1H), 2.06 (q, 1H).

Example 122

4-({3-[4-(4-Chlorophenyl)-1,3-thiazol-2-yl]-5-[4-(trifluoromethyl)phenyl]piperidin-1-yl}-carbonyl)morpholine [racemic cis isomer]

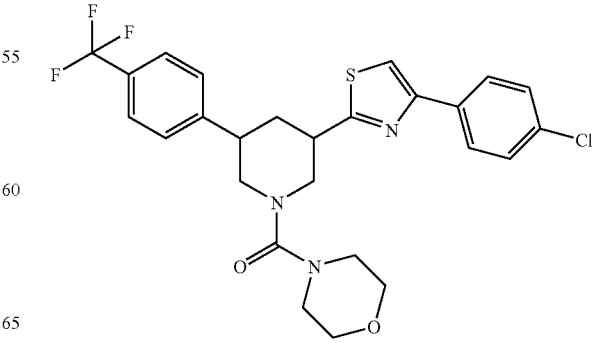

100 mg (0.224 mmol) of 1-(morpholin-4-ylcarbonyl)-5-[4-(trifluoromethyl)phenyl]piperidine-3-carbothioamide (Example 53A) and 63 mg (0.269 mmol) of 2-bromo-1-(4-chlorophenyl)ethanone were reacted according to the General Method 3. Yield: 15 mg (12% of theory)

LC-MS (Method 5B): $R_t$=2.89 min; MS (ESIpos): m/z=536 [M+H]$^+$;

$^1$H-NMR (400 MHz, DMSO-d$_6$): δ=8.11 (s, 1H), 8.08 (d, 2H), 7.72 (br d, 2H), 7.61 (br d, 2H), 7.50 (d, 2H), 4.06 (br d, 1H), 3.68 (d, 1H), 3.60-3.57 (m, 4H), 3.45 (tt, 1H), 3.23-3.20 (m, 4H), 3.11-3.03 (m, 3H), 2.35 (br d, 1H), 2.06 (q, 1H).

Example 123

4-({3-(4-Phenyl-1,3-thiazol-2-yl)-5-[4-(trifluoromethyl)phenyl]piperidin-1-yl}carbonyl)morpholine [racemic cis isomer]

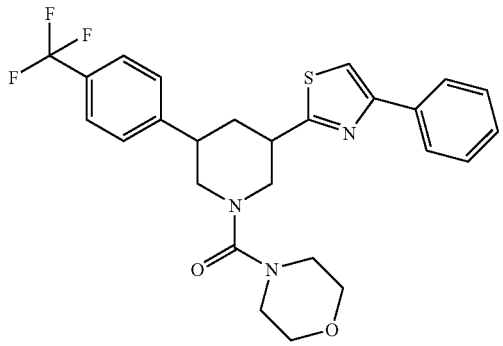

42 mg (0.064 mmol) of 1-(morpholin-4-ylcarbonyl)-5-[4-(trifluoromethyl)phenyl]piperidine-3-carbothioamide (Example 53A) and 15 mg (0.077 mmol) of 2-bromo-1-phenylethanone were reacted according to the General Method 3. Yield: 11 mg (34% of theory)

LC-MS (Method 5B): $R_t$=2.74 min; MS (ESIpos): m/z=502 [M+H]$^+$;

$^1$H-NMR (400 MHz, DMSO-d$_6$): δ=8.04 (s, 1H), 7.96 (d, 2H), 7.71 (d, 2H), 7.61 (d, 2H), 7.44 (t, 2H), 7.34 (t, 1H), 4.07 (br d, 1H), 3.68 (d, 1H), 3.60-3.27 (m, 4H), 3.45 (tt, 1H), 3.23-3.20 (m, 4H), 3.11-3.03 (m, 3H), 2.39 (br d, 1H), 2.06 (q, 1H).

Example 124

4-({3-[4-(2,5-Dimethoxyphenyl)-1,3-thiazol-2-yl]-5-[4-(trifluoromethyl)phenyl]piperidin-1-yl}-carbonyl)morpholine [racemic cis isomer]

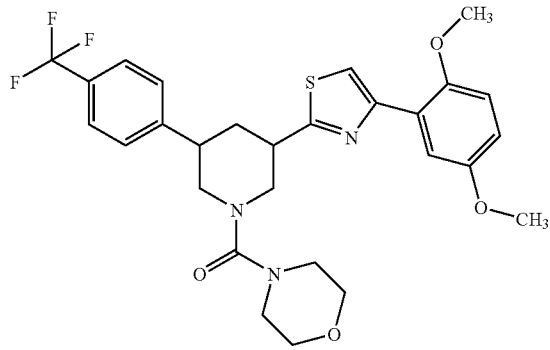

100 mg (0.152 mmol) of 1-(morpholin-4-ylcarbonyl)-5-[4-(trifluoromethyl)phenyl]piperidine-3-carbothioamide (Example 53A) and 49 mg (0.182 mmol) of 2-bromo-1-(2,5-dimethoxyphenyl)ethanone were reacted according to the General Method 3. Yield: 20 mg (24% of theory)

LC-MS (Method 5B): $R_t$=2.76 min; MS (ESIpos): m/z=562 [M+H]$^+$;

$^1$H-NMR (400 MHz, DMSO-d$_6$): δ=8.03 (s, 1H), 7.72 (d, 1H), 7.71 (br d, 2H), 7.61 (br d, 2H), 7.07 (d, 1H), 6.91 (dd, 1H), 4.07 (br d, 1H), 3.86 (s, 3H), 3.76 (s, 3H), 3.68 (br d, 1H), 3.60-3.57 (m, 4H), 3.45 (tt, 1H), 3.22-3.20 (m, 4H), 3.13-3.02 (m, 3H), 2.38 (br d, 1H), 2.06 (q, 1H).

Example 125

4-({3-[4-(3-Methoxyphenyl)-1,3-thiazol-2-yl]-5-[4-(trifluoromethyl)phenyl]piperidin-1-yl}-carbonyl)morpholine [racemic cis isomer]

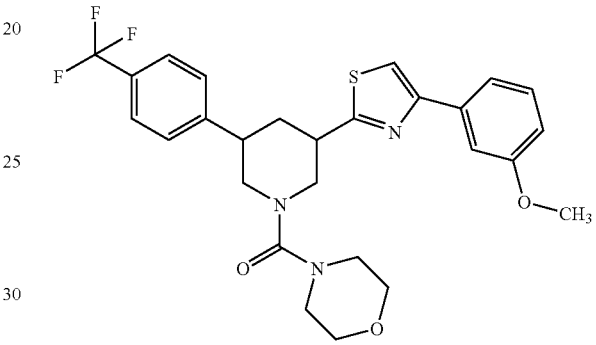

100 mg (0.152 mmol) of 1-(morpholin-4-ylcarbonyl)-5-[4-(trifluoromethyl)phenyl]piperidine-3-carbothioamide (Example 53A) and 42 mg (0.182 mmol) of 2-bromo-1-(3-methoxyphenyl)ethanone were reacted according to the General Method 3. Yield: 29 mg (35% of theory)

LC-MS (Method 5B): $R_t$=2.72 min; MS (ESIpos): m/z=532 [M+H]$^+$;

$^1$H-NMR (400 MHz, DMSO-d$_6$): δ=8.07 (s, 1H), 7.71 (br d, 2H), 7.61 (br d, 2H), 7.54 (d, 1H), 7.50 (bs, 1H), 7.35 (t, 1H), 6.92 (dd, 1H), 4.07 (br d, 1H), 3.81 (s, 3H), 3.68 (d, 1H), 3.59-3.57 (m, 4H), 3.44 (tt, 1H), 3.24-3.20 (m, 4H), 3.13-3.03 (m, 3H), 2.38 (br d, 1H), 2.06 (q, 1H).

Example 126

(4-Hydroxypiperidin-1-yl) {3-(3-phenyl-1,2,4-oxadiazol-5-yl)-5-[4-(trifluoromethoxy)phenyl]-piperidin-1-yl}methanone [racemic cis isomer]

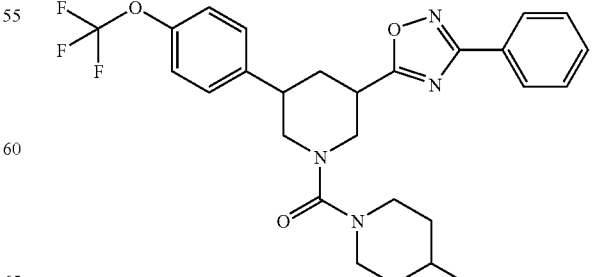

100 mg (0.24 mmol) of 1-[(4-hydroxypiperidin-1-yl)carbonyl]-5-[4-(trifluoromethoxy)phenyl]piperidine-3-carboxylic acid (Example 63A) and 49 mg (0.36 mmol, 1.5 eq.) of N'-hydroxybenzenecarboximidamide were reacted according to the General Method 2. Yield: 58 mg (47% of theory)

LC-MS (Method 3B): $R_t$=2.28 min; MS (ESIpos): m/z=517 [M+H]$^+$;

$^1$H-NMR (400 MHz, DMSO-d$_6$): δ=8.05-7.99 (m, 2H), 7.63-7.54 (m, 3H), 7.49 (d, 2H), 7.35 (d, 2H), 4.69 (d, 1H), 4.05 (br d, 1H), 3.67-3.55 (m, 1H and br d, 1H), 3.55-3.45 (m, 3H), 3.10 (t, 1H), 3.05-2.98 (m, 2H), 2.93 (br t, 2H), 2.41 (br d, 1H), 2.07 (q, 1H), 1.79-1.68 (m, 2H), 1.39-1.27 (m, 2H).

Example 127

{3-[3-(3-Fluorophenyl)-1,2,4-oxadiazol-5-yl]-5-[4-(trifluoromethoxy)phenyl]piperidin-1-yl}(4-hydroxypiperidin-1-yl)methanone [racemic cis isomer]

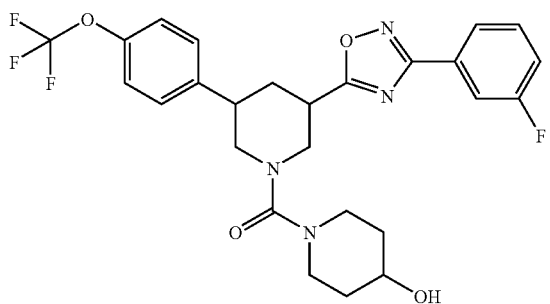

60 mg (0.14 mmol) of 1-[(4-hydroxypiperidin-1-yl)carbonyl]-5-[4-(trifluoromethoxy)phenyl]piperidine-3-carboxylic acid (Example 63A) and 35 mg (0.22 mmol, 1.5 eq.) of 3-fluoro-N'-hydroxybenzenecarboximidamide were reatced according to the General Method 2. Yield: 35 mg (45% of theory)

LC-MS (Method 3B): $R_t$=2.33 min; MS (ESIpos): m/z=535 [M+H]$^+$;

$^1$H-NMR (400 MHz, DMSO-d$_6$): δ=7.87 (d, 1H), 7.76 (dt, 1H), 7.64 (dt, 1H), 7.52-7.44 (d, 2H and dt, 1H), 7.35 (d, 2H), 4.69 (d, 1H), 4.05 (br d, 1H), 3.67-3.55 (m, 1H and br d, 1H), 3.55-3.45 (m, 3H), 3.10 (t, 1H), 3.05-2.98 (m, 2H), 2.98-2.88 (m, 2H), 2.41 (br d, 1H), 2.07 (q, 1H), 1.78-1.69 (m, 2H), 1.38-1.27 (m, 2H).

Example 128

{3-[3-(3-Chlorophenyl)-1,2,4-oxadiazol-5-yl]-5-[4-(trifluoromethoxy)phenyl]piperidin-1-yl}(4-hydroxypiperidin-1-yl)methanone [racemic cis isomer]

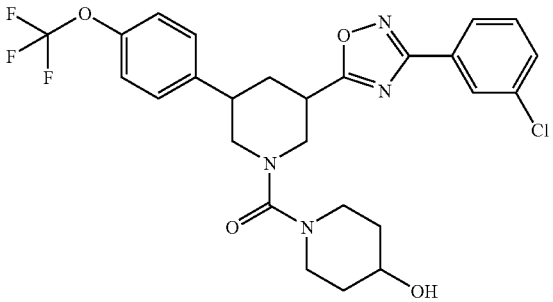

100 mg (0.24 mmol) of 1-[(4-hydroxypiperidin-1-yl)carbonyl]-5-[4-(trifluoromethoxy)phenyl]piperidine-3-carboxylic acid (Example 63A) and 61 mg (0.36 mmol, 1.5 eq.) of 3-chloro-N'-hydroxybenzenecarboximidamide were reacted according to the General Method 2. Yield: 69 mg (52% of theory)

LC-MS (Method 3B): $R_t$=2.47 min; MS (ESIpos): m/z=551 [M+H]$^+$;

$^1$H-NMR (400 MHz, DMSO-d$_6$): δ=8.02-7.97 (m, 2H), 7.72-7.68 (m, 1H), 7.62 (t, 1H), 7.49 (d, 2H), 7.34 (d, 2H), 4.69 (d, 1H), 4.04 (br d, 1H), 3.68-3.56 (m, 1H and br d, 1H), 3.56-3.46 (m, 3H), 3.10 (t, 1H), 3.05-2.98 (m, 2H), 2.93 (br t, 2H), 2.41 (br d, 1H), 2.05 (q, 1H), 1.78-1.68 (m, 2H), 1.38-1.27 (m, 2H).

Example 129

{3-[3-(2-Fluorophenyl)-1,2,4-oxadiazol-5-yl]-5-[4-(trifluoromethoxy)phenyl]piperidin-1-yl}(4-hydroxypiperidin-1-yl)methanone [racemic cis isomer]

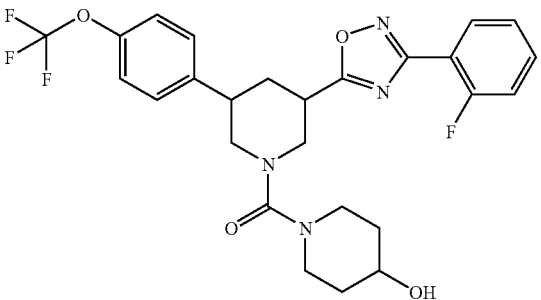

100 mg (0.24 mmol) of 1-[(4-hydroxypiperidin-1-yl)carbonyl]-5-[4-(trifluoromethoxy)phenyl]piperidine-3-carboxylic acid (Example 63A) and 56 mg (0.36 mmol, 1.5 eq.) of 2-fluoro-N'-hydroxybenzenecarboximidamide were reacted according to the General Method 2. Yield: 73 mg (57% of theory)

LC-MS (Method 2B): $R_t$=1.38 min; MS (ESIpos): m/z=535 [M+H]$^+$;

$^1$H-NMR (400 MHz, DMSO-d$_6$): δ=8.03 (dt, 1H), 7.70-7.64 (m, 1H), 7.49 (d, 2H), 7.48-7.39 (m, 2H), 7.35 (d, 2H), 4.69 (d, 1H), 4.05 (br d, 1H), 3.67-3.56 (m, 1H and br d, 1H), 3.56-3.46 (m, 3H), 3.10 (t, 1H), 3.05-2.98 (m, 2H), 2.93 (br t, 2H), 2.41 (br d, 1H), 2.07 (q, 1H), 1.79-1.69 (m, 2H), 1.38-1.27 (m, 2H).

Example 130

(4-Hydroxypiperidin-1-yl) {3-[3-(pyrazin-2-yl)-1,2,4-oxadiazol-5-yl]-5-[4-(trifluoromethoxy)-phenyl]piperidin-1-yl}methanone [racemic cis isomer]

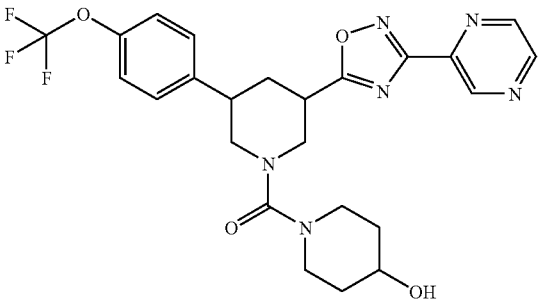

100 mg (0.24 mmol) of 1-[(4-hydroxypiperidin-1-yl)carbonyl]-5-[4-(trifluoromethoxy)phenyl]piperidine-3-carboxylic acid (Example 63A) and 50 mg (0.36 mmol, 1.5 eq.) of N'-hydroxypyrazine-2-carboximidamide were reacted according to the General Method 2. Yield: 34 mg (27% of theory)

LC-MS (Method 1B): $R_t$=2.18 min; MS (ESIpos): m/z=519 [M+H]$^+$;

$^1$H-NMR (400 MHz, DMSO-d$_6$): δ=9.27 (d, 1H), 8.90-8.85 (m, 2H), 7.49 (d, 2H), 7.35 (d, 2H), 4.69 (d, 1H), 4.07 (br d, 1H), 3.68-3.46 (m, 5H), 3.12 (t, 1H), 3.08-2.98 (m, 2H), 2.93 (br t, 2H), 2.43 (br d, 1H), 2.09 (q, 1H), 1.79-1.68 (m, 2H), 1.38-1.27 (m, 2H).

Example 131

{3-(3-tert-Butyl-1,2,4-oxadiazol-5-yl)-5-[4-(trifluoromethoxy)phenyl]piperidin-1-yl}(4-hydroxy-piperidin-1-yl)methanone [racemic cis isomer]

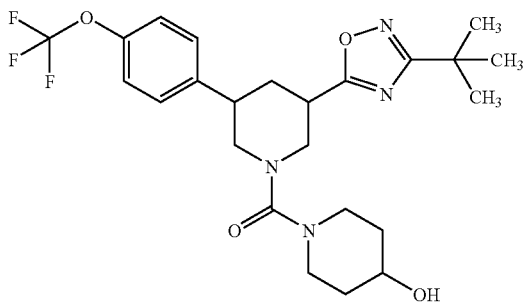

100 mg (0.24 mmol) of 1-[(4-hydroxypiperidin-1-yl)carbonyl]-5-[4-(trifluoromethoxy)phenyl]piperidine-3-carboxylic acid (Example 63A) and 42 mg (0.36 mmol, 1.5 eq.) of N'-hydroxy-2,2-dimethylpropanimidamide were reacted according to the General Method 2. Yield: 60 mg (51% of theory)

LC-MS (Method 2B): $R_t$=1.40 min; MS (ESIpos): m/z=497 [M+H]$^+$;

$^1$H-NMR (400 MHz, DMSO-d$_6$): δ=7.47 (d, 2H), 7.33 (d, 2H), 4.68 (d, 1H), 3.95 (br d, 1H), 3.66-3.57 (m, 1H), 3.55 (br d, 1H), 3.52-3.43 (m, 2H), 3.43-3.33 (m, 1H), 3.05-2.94 (m, 3H), 2.90 (br t, 2H), 2.33 (br d, 1H), 1.97 (q, 1H), 1.77-1.68 (m, 2H), 1.35-1.26 (m, 2H), 1.30 (s, 9H).

Example 132

[3-(4-Ethylphenyl)-5-(3-phenyl-1,2,4-oxadiazol-5-yl)piperidin-1-yl](4-hydroxypiperidin-1-yl)methanone [racemic cis isomer]

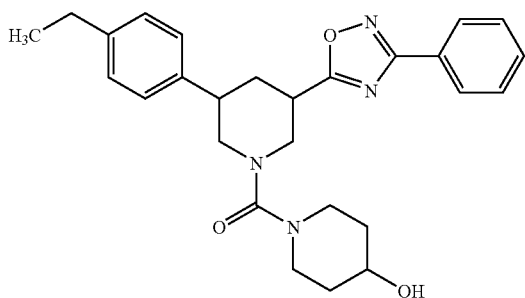

80 mg (0.22 mmol) of 5-(4-ethylphenyl)-1-[(4-hydroxypiperidin-1-yl)carbonyl]piperidine-3-carboxylic acid (Example 59A) and 45 mg (0.33 mmol, 1.5 eq.) of 1-hydroxybenzene-carboximidamide were reacted according to the General Method 2. Yield: 76 mg (74% of theory)

LC-MS (Method 2B): $R_t$=1.41 min; MS (ESIpos): m/z=461 [M+H]$^+$;

$^1$H-NMR (400 MHz, DMSO-d$_6$): δ=8.05-8.00 (m, 2H), 7.63-7.54 (m, 3H), 7.24 (d, 2H), 7.18 (d, 2H), 4.69 (d, 1H), 4.05 (br d, 1H), 3.67-3.58 (m, 1H), 3.57 (br d, 1H), 3.54-3.43 (m, 3H), 3.08 (t, 1H), 3.00-2.85 (m, 4H), 2.58 (q, 2H), 2.38 (br d, 1H), 2.05 (q, 1H), 1.78-1.69 (m, 2H), 1.38-1.26 (m, 2H), 1.17 (t, 3H).

Example 133

{3-(4-Ethylphenyl)-5-[3-(3-fluorophenyl)-1,2,4-oxadiazol-5-yl]piperidin-1-yl}(4-hydroxypiperidin-1-yl)methanone [racemic cis isomer]

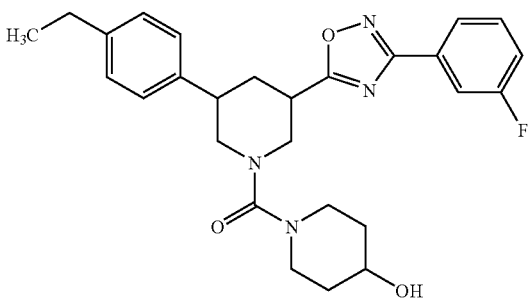

71 mg (0.20 mmol) of 5-(4-ethylphenyl)-1-[(4-hydroxypiperidin-1-yl)carbonyl]piperidine-3-carboxylic acid (Example 59A) and 46 mg (0.30 mmol, 1.5 eq.) of 3-fluoro-N'-hydroxybenzenecarboximidamide were reacted according to the General Method 2. Yield: 68 mg (72% of theory)

LC-MS (Method 2B): $R_t$=1.45 min; MS (ESIpos): m/z=479 [M+H]$^+$;

$^1$H-NMR (400 MHz, DMSO-d$_6$): δ=7.87 (d, 1H), 7.75 (dt, 1H), 7.64 (dt, 1H), 7.47 (dt, 1H), 7.24 (d, 2H), 7.18 (d, 2H), 4.69 (d, 1H), 4.05 (br d, 1H), 3.67-3.58 (m, 1H), 3.57 (br d, 1H), 3.54-3.45 (m, 3H), 3.07 (t, 1H), 3.01-2.84 (m, 4H), 2.58 (q, 2H), 2.38 (br d, 1H), 2.05 (q, 1H), 1.78-1.68 (m, 2H), 1.38-1.27 (m, 2H), 1.17 (t, 3H).

Example 134

{3-[3-(3-Chlorophenyl)-1,2,4-oxadiazol-5-yl]-5-(4-ethylphenyl)piperidin-1-yl}(4-hydroxy-piperidin-1-yl)methanone [racemic cis isomer]

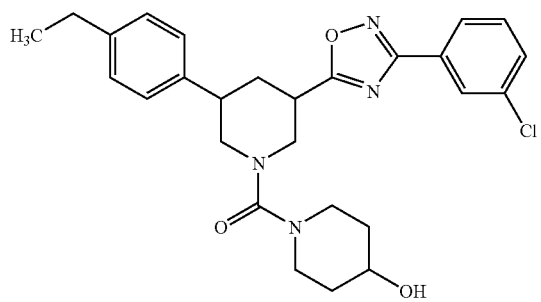

80 mg (0.22 mmol) of 5-(4-ethylphenyl)-1-[(4-hydroxypiperidin-1-yl)carbonyl]piperidine-3-carboxylic acid (Example 59A) and 57 mg (0.33 mmol, 1.5 eq.) of 3-chloro-N'-hydroxybenzenecarboximidamide were reacted according to the General Method 2. Yield: 86 mg (78% of theory)

LC-MS (Method 2B): $R_t$=1.53 min; MS (ESIpos): m/z=495 [M+H]$^+$;

$^1$H-NMR (400 MHz, DMSO-d$_6$): δ=8.02-7.97 (m, 2H), 7.69 (d, 1H), 7.62 (t, 1H), 7.24 (d, 2H), 7.18 (d, 2H), 4.69 (d, 1H), 4.05 (br d, 1H), 3.67-3.58 (m, 1H), 3.56 (br d, 1H), 3.54-3.45 (m, 3H), 3.08 (t, 1H), 3.01-2.84 (m, 4H), 2.58 (q, 2H), 2.38 (br d, 1H), 2.05 (q, 1H), 1.78-1.69 (m, 2H), 1.38-1.27 (m, 2H), 1.17 (t, 3H).

Example 135

{3-(4-Ethylphenyl)-5-[3-(pyrazin-2-yl)-1,2,4-oxadiazol-5-yl]piperidin-1-yl}(4-hydroxypiperidin-1-yl)methanone [racemic cis isomer]

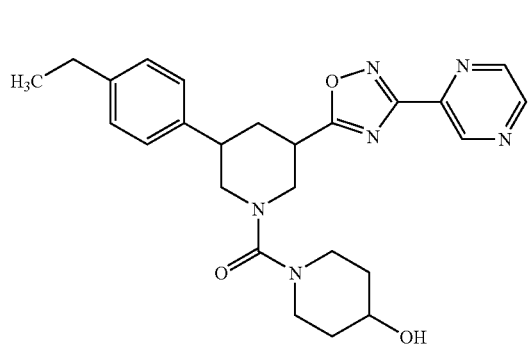

80 mg (0.22 mmol) of 5-(4-ethylphenyl)-1-[(4-hydroxypiperidin-1-yl)carbonyl]piperidine-3-carboxylic acid (Example 59A) and 46 mg (0.33 mmol, 1.5 eq.) of N'-hydroxypyrazine-2-carboximidamide were reacted according to the General Method 2. Yield: 24 mg (23% of theory)

LC-MS (Method 3B): $R_t$=1.75 min; MS (ESIpos): m/z=463 [M+H]$^+$;

$^1$H-NMR (400 MHz, DMSO-d$_6$): δ=9.27 (d, 1H), 8.91-8.84 (m, 2H), 7.25 (d, 2H), 7.18 (d, 2H), 4.69 (d, 1H), 4.06 (br d, 1H), 3.68-3.45 (m, 5H), 3.10 (t, 1H), 3.01-2.86 (m, 4H), 2.58 (q, 2H), 2.40 (br d, 1H), 2.07 (q, 1H), 1.78-1.69 (m, 2H), 1.38-1.27 (m, 2H), 1.17 (t, 3H).

Example 136

1-({3-(4-Ethylphenyl)-5-[3-(3-fluorophenyl)-1,2,4-oxadiazol-5-yl]piperidin-1-yl}carbonyl)-piperidine-4-carbonitrile [racemic cis isomer]

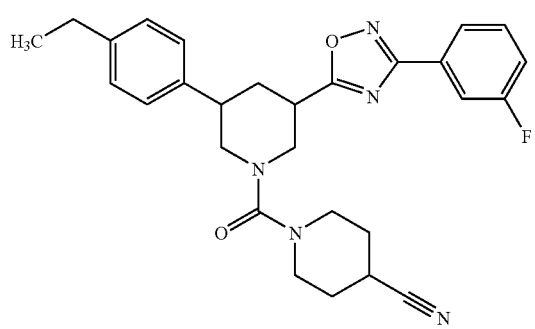

80 mg (0.22 mmol) of 5-(4-ethylphenyl)-1-[(4-cyanopiperidin-1-yl)carbonyl]piperidine-3-carboxylic acid (Example 60A) and 50 mg (0.33 mmol, 1.5 eq.) of 3-fluoro-N'-hydroxybenzenecarboximidamide were reacted according to the General Method 2. Yield: 81 mg (77% of theory)

LC-MS (Method 1B): $R_t$=2.99 min; MS (ESIpos): m/z=488 [M+H]$^+$;

$^1$H-NMR (400 MHz, DMSO-d$_6$): δ=7.88 (d, 1H), 7.76 (dt, 1H), 7.64 (dt, 1H), 7.47 (dt, 1H), 7.24 (d, 2H), 7.18 (d, 2H), 4.06 (br d, 1H), 3.58 (br d, 1H), 3.55-3.45 (m, 1H), 3.43-3.34 (m, 2H), 3.15-3.02 (m, 4H), 3.01-2.86 (m, 2H), 2.58 (q, 2H), 2.38 (br d, 1H), 2.04 (q, 1H), 1.93-1.84 (m, 2H), 1.75-1.64 (m, 2H), 1.17 (t, 3H).

Example 137

{3-[3-(3,5-Difluorophenyl)-1,2,4-oxadiazol-5-yl]-5-[4-(trifluoromethoxy)phenyl]piperidin-1-yl}-(morpholin-4-yl)methanone [racemic cis isomer]

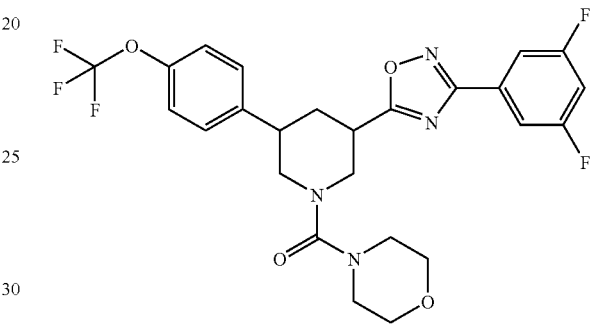

80 mg (0.20 mmol) of 1-(morpholin-4-ylcarbonyl)-5-[4-(trifluoromethoxy)phenyl]piperidine-3-carboxylic acid (Example 44A) and 38 mg (0.22 mmol, 1.1 eq.) of 3,5-difluoro-N'-hydroxybenzenecarboximidamide were reacted according to the General Method 1. Yield: 75 mg (68% of theory)

HPLC (Method 1A): $R_t$=5.28 min; MS (ESIpos): m/z=539 [M+H]$^+$;

$^1$H-NMR (400 MHz, DMSO-d$_6$): δ=7.71-7.65 (m, 2H), 7.61-7.53 (m, 1H), 7.49 (d, 2H), 7.35 (d, 2H), 4.09 (br d, 1H), 3.64 (br d, 1H), 3.61-3.53 (m, 4H), 3.58-3.48 (m, 1H), 3.26-3.18 (m, 4H), 3.13 (t, 1H), 3.08-2.98 (m, 2H), 2.41 (br d, 1H), 2.07 (q, 1H).

Example 138

4-({3-(3-Phenyl-1,2,4-oxadiazol-5-yl)-5-[4-(trifluoromethyl)phenyl]piperidin-1-yl}carbonyl)-morpholine [racemic cis isomer]

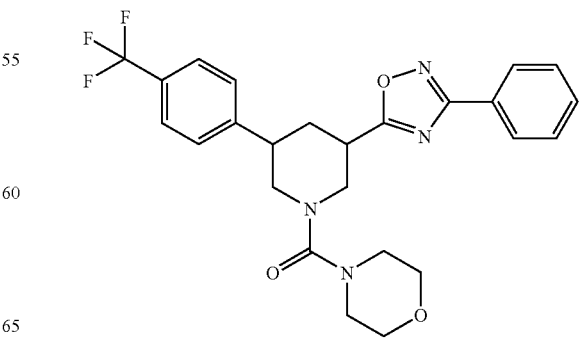

250 mg (0.65 mmol) of 1-(morpholin-4-ylcarbonyl)-5-[4-(trifluoromethyl)phenyl]piperidine-3-carboxylic acid (Example 49A) and 97 mg (0.71 mmol) of N'-hydroxybenzenecarboximidamide were reacted according to the General Method 1. Yield: 35 mg (12% of theory)

LC-MS (Method 1B): $R_t$=2.75 min; MS (ESIpos): m/z=487 [M+H]$^+$;

$^1$H-NMR (400 MHz, DMSO-d$_6$): δ=8.02 (dd, 2H), 2.71 (d, 2H), 7.61-7.55 (m, 5H), 4.10 (br d, 1H), 3.66 (br d, 1H), 3.60-3.56 (m, 4H), 3.52 (tt, 1H), 3.24-3.20 (m, 4H), 3.16 (t, 1H), 3.08-3.05 (m, 2H), 2.42 (br d, 1H), 2.11 (q, 1H).

Example 139

4-({3-(3-Benzyl-1,2,4-oxadiazol-5-yl)-5-[4-(trifluoromethyl)phenyl]piperidin-1-yl}carbonyl)-morpholine [racemic cis isomer]

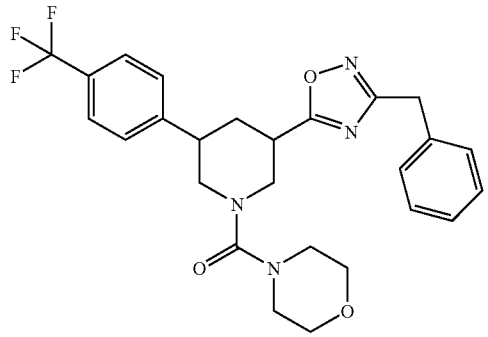

250 mg (0.65 mmol) of 1-(morpholin-4-ylcarbonyl)-5-[4-(trifluoromethyl)phenyl]piperidine-3-carboxylic acid and 107 mg (0.71 mmol) of N'-hydroxy-2-phenylethanimidamide were reacted according to the General Method 1. Yield: 44 mg (14% of theory)

LC-MS (Method 1B): $R_t$=2.67 min; MS (ESIpos): m/z=501[M+H]$^+$;

$^1$H-NMR (400 MHz, DMSO-d$_6$): δ=7.69 (d, 2H), 7.56 (d, 2H), 7.35-7.23 (m, 5H), 4.08 (s, 2H), 3.98 (br d, 1H), 3.61 (br d, 1H), 3.56-3.54 (m, 4H), 3.41 (tt, 1H), 3.21-3.17 (m, 4H), 3.07-2.97 (m, 3H), 2.30 (br d, 1H), 1.99 (m, 1H).

Example 140

4-({3-(3-(Pyridin-4-yl)-1,2,4-oxadiazol-5-yl)-5-[4-(trifluoromethyl)phenyl]piperidin-1-yl}-carbonyl)morpholine [racemic cis isomer]

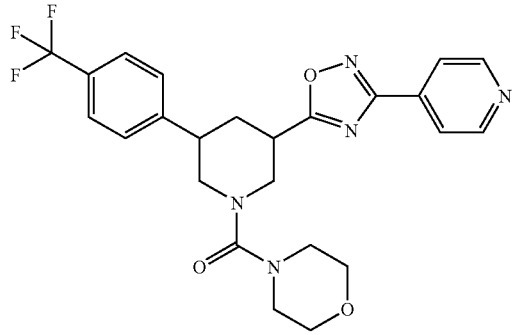

250 mg (about 0.65 mmol) of 1-(morpholin-4-ylcarbonyl)-5-[4-(trifluoromethyl)phenyl]piperidine-3-carboxylic acid and 97 mg (0.71 mmol) of N'-hydroxypyridine-4-carboximidamide were reacted according to the General Method 1. Yield: 45 mg (14% of theory)

LC-MS (Method 3B): $R_t$=1.98 min; MS (ESIpos): m/z=488 [M+H]$^+$;

$^1$H-NMR (400 MHz, DMSO-d$_6$): δ=8.81 (d, 2H), 7.94 (d, 2H), 7.72 (d, 2H), 7.60 (d, 2H), 4.10 (br d, 1H), 3.65 (br d, 1H), 3.58-3.53 (m, 5H), 3.24-3.20 (m, 4H), 3.13-3.00 (m, 3H), 2.42 (br d, 1H), 2.11 (q, 1H).

Example 141

4-({3-(3-(Pyridin-3-yl)-1,2,4-oxadiazol-5-yl)-5-[4-(trifluoromethyl)phenyl]piperidin-1-yl}-carbonyl)morpholine [racemic cis isomer]

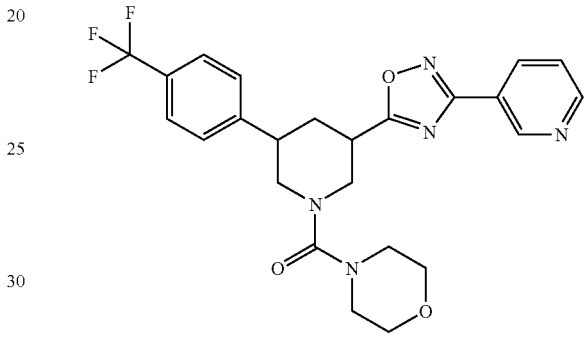

250 mg (about 0.65 mmol) of 1-(morpholin-4-ylcarbonyl)-5-[4-(trifluoromethyl)phenyl]piperidine-3-carboxylic acid and 98 mg (0.71 mmol) of N'-hydroxypyridine-3-carboximidamide were reacted according to the General Method 1. Yield: 35 mg (11% of theory)

LC-MS (Method 1B): $R_t$=2.35 min; MS (ESIpos): m/z=488 [M+H]$^+$;

$^1$H-NMR (400 MHz, DMSO-d$_6$): δ=9.17 (d, 1H), 8.78 (dd, 1H), 8.38 (d, 1H), 7.71 (d, 2H), 7.64-7.57 (m, 3H), 4.10 (br d, 1H), 3.66 (br d, 1H), 3.60-3.55 (m, 5H), 3.27-3.20 (m, 4H), 3.17-3.04 (m, 3H), 2.42 (br d, 1H), 2.12 (q, 1H).

Example 142

4-({3-(3-Methylsulphonylmethyl-1,2,4-oxadiazol-5-yl)-5-[4-(trifluoromethyl)phenyl]piperidin-1-yl}carbonyl)morpholine [racemic cis isomer]

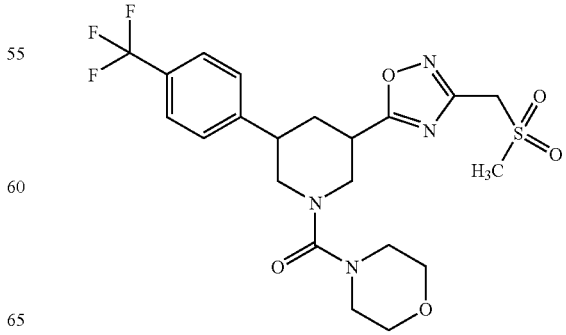

250 mg (about 0.65 mmol) of 1-(morpholin-4-ylcarbonyl)-5-[4-(trifluoromethyl)phenyl]piperidine-3-carboxylic acid and 108 mg (0.71 mmol) of N'-hydroxy-2-(methylsulphonyl)ethanimidamide were reacted according to the General Method 1. Yield: 5 mg (2% of theory)

LC-MS (Method 1B): $R_t$=2.17 min; MS (ESIpos): m/z=503 [M+H]$^+$;

$^1$H-NMR (400 MHz, DMSO-d$_6$): δ=7.70 (d, 2H), 7.58 (d, 2H), 4.85 (d, 2H), 4.04 (br d, 1H), 3.63 (br d, 1H), 3.60-3.58 (m, 4H), 3.45 (tt, 1H), 3.25-3.19 (m, 4H), 3.17 (s, 3H), 3.12-2.99 (m, 3H), 2.37 (br d, 1H), 2.05 (q, 1H).

Example 143

4-({3-(5-Phenyl-1,3,4-oxadiazol-2-yl)-5-[4-(trifluoromethyl)phenyl]piperidin-1-yl}carbonyl)-morpholine [racemic cis isomer]

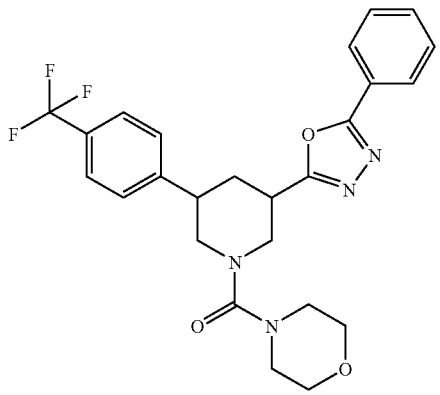

200 mg (0.52 mmol) of 1-(morpholin-4-ylcarbonyl)-5-[4-(trifluoromethyl)phenyl]piperidine-3-carboxylic acid and 77 mg (0.57 mmol) of N-benzoylhydrazide were reacted according to the General Method 4. Yield: 36 mg (14% of theory)

LC-MS (Method 1B): $R_t$=2.48 min; MS (ESIpos): m/z=487 [M+H]$^+$;

$^1$H-NMR (400 MHz, DMSO-d$_6$): δ=8.02 (dd, 2H), 7.71 (d, 2H), 7.63-7.57 (m, 5H), 4.09 (br d, 1H), 3.67 (br d, 1H), 3.61-3.55 (m, 4H), 3.44 (tt, 1H), 3.25-3.20 (m, 4H), 3.13 (t, 1H), 3.09-3.02 (m, 2H), 2.42 (br d, 1H), 2.08 (q, 1H).

Example 144

{3-(3-Cyclopropyl-1,2,4-oxadiazol-5-yl)-5-[4-(trifluoromethoxy)phenyl]piperidin-1-yl}(3,3-difluoropyrrolidin-1-yl)methanone [racemic cis isomer]

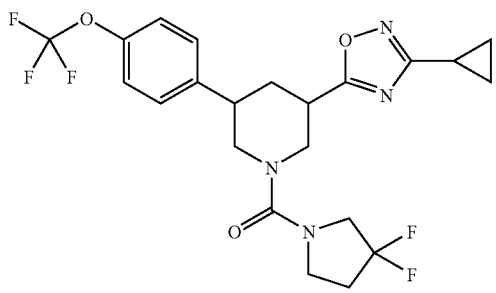

100 mg (0.19 mmol) of the compound from Example 176A and 83 mg (0.58 mmol) of 3,3-difluoropyrrolidine hydrochloride were reacted according to the General Method 6. Yield: 44 mg (45% of theory)

LC-MS (Method 1B): $R_t$=2.80 min; MS (ESIpos): m/z=487 [M+H]$^+$;

$^1$H-NMR (400 MHz, DMSO-d$_6$): δ=7.46 (d, 2H), 7.32 (d, 2H), 4.01 (br d, 1H), 3.77-3.64 (m, 3H), 3.58-3.53 (m, 2H), 3.38-3.34 (m, 1H), 3.04-2.94 (m, 3H), 2.46-2.20 (m, 3H), 2.14-2.07 (m, 1H), 1.98-1.89 (m, 1H), 1.08-1.03 (m, 2H), 0.90-0.86 (m, 2H).

Example 145

(4,4-Difluoropiperidin-1-yl){3-[3-(3-fluorophenyl)-1,2,4-oxadiazol-5-yl]-5-[4-(trifluoromethoxy)-phenyl]piperidin-1-yl}methanone [racemic cis isomer]

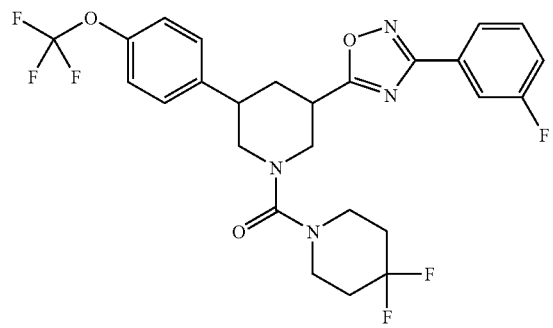

100 mg (0.21 mmol) of the compound from Example 179A and 33 mg (0.2 mmol) of 4,4-difluoropiperidine hydrochloride were reacted according to the General Method 5. Yield: 37 mg (30% of theory)

LC-MS (Method 1B): $R_t$=3.04 min; MS (ESIpos): m/z=555 [M+H]$^+$;

$^1$H-NMR (400 MHz, DMSO-d$_6$): δ=7.86 (d, 1H), 7.78-7.74 (m, 1H), 7.67-7.61 (m, 1H), 7.51-7.44 (m, 3H), 7.34 (d, 2H), 4.10 (br d, 1H), 3.68 (br d, 1H), 3.56-3.49 (m, 1H), 3.35-3.31 (m, 4H), 3.15 (t, 1H), 3.06-2.99 (m, 2H), 2.41 (br d, 1H), 2.09-1.95 (m, 5H).

Example 146

{3-(3-Cyclopropyl-1,2,4-oxadiazol-5-yl)-5-[4-(trifluoromethyl)phenyl]piperidin-1-yl}(3-hydroxy-pyrrolidin-1-yl)methanone [mixture of diastereomers]

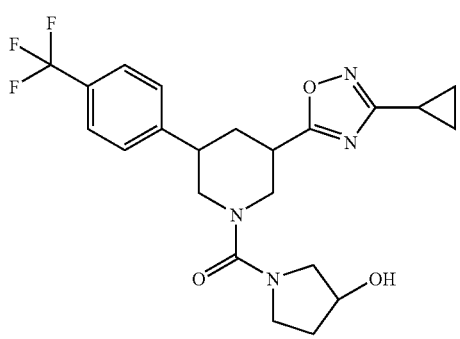

100 mg (0.20 mmol) of the compound from Example 184A and 52 mg (0.6 mmol) of 3-pyrrolidinol were reacted according to the General Method 6. Yield: 50 mg (55% of theory)

LC-MS (Method 3B): $R_t$=4.39 min; MS (ESIpos): m/z=451 [M+H]$^+$;

$^1$H-NMR (400 MHz, DMSO-d$_6$): δ=7.69 (d, 2H), 7.56 (d, 2H), 4.88 (d, OH), 4.21 (br s, 1H), 4.04-4.00 (m, 1H), 3.69 (t, 1H), 3.48-3.42 (m, 2H), 3.30-3.25 (m, 2H), 3.10-2.90 (m, 4H), 2.32 (br d, 1H), 2.14-2.07 (m, 1H), 2.02-1.92 (m, 1H), 1.83-1.80 (m, 1H), 1.74-1.70 (m, 1H), 1.07-1.03 (m, 2H), 0.90-0.86 (m, 2H).

Example 147

[3-(3-Cyclopropyl-1,2,4-oxadiazol-5-yl)-5-(4-ethylphenyl)piperidin-1-yl] (3-hydroxyazetidin-1-yl) methanone] [racemic cis isomer]

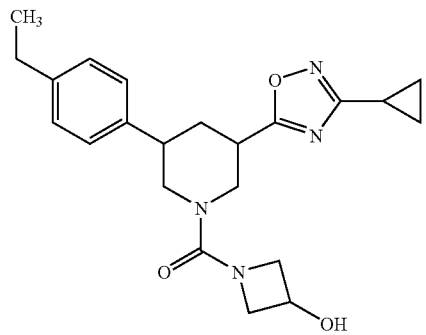

60 mg (0.18 mmol) of the compound from Example 138A and 27 mg (0.27 mmol) of N'-hydroxycyclopropanecarboximidamide were reacted according to the General Method 2. Yield: 24 mg (33% of theory)

LC-MS (Method 1B): $R_t$=2.29 min; MS (ESIpos): m/z=397 [M+H]$^+$;

$^1$H-NMR (400 MHz, DMSO-d$_6$): δ=7.20 (d, 2H), 7.16 (d, 2H), 5.57 (d, OH), 4.41-4.34 (m, 1H), 4.13-4.04 (m, 3H), 3.71-3.65 (m, 3H), 3.27-3.20 (m, 1H), 2.94 (t, 1H), 2.90 (t, 1H), 2.80-2.72 (m, 1H), 2.57 (q, 2H), 2.23 (br d, 1H), 2.14-2.07 (m, 1H), 1.92 (q, 1H), 1.16 (t, 3H), 1.07-1.02 (m, 2H), 0.91-0.87 (m, 2H).

Example 148

{3-(3,4-Dimethylphenyl)-5-[3-(propan-2-yl)-1,2,4-oxadiazol-5-yl]piperidin-1-yl}(morpholin-4-yl) methanone [racemic cis isomer]

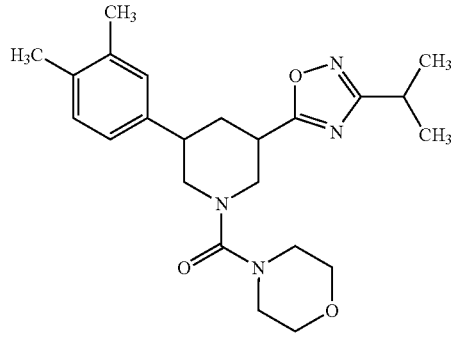

100 mg (0.29 mmol) of the compound from Example 130A and 46 mg (0.43 mmol) of N'-hydroxy-2-methylpropanimidamide were reacted according to the General Method 2. Yield: 107 mg (90% of theory)

LC-MS (Method 3B): $R_t$=2.25 min; MS (ESIpos): m/z=413 [M+H]$^+$;

$^1$H-NMR (400 MHz, DMSO-d$_6$): δ=7.09-7.07 (m, 2H), 7.01 (d, 1H), 3.97 (br d, 1H), 3.58-3.51 (m, 5H), 3.40-3.33 (m, 1H), 3.20-3.17 (m, 4H), 3.10-2.93 (m, 3H), 2.82-2.76 (m, 1H), 2.25 (br d, 1H), 2.20 (s, 3H), 2.18 (s, 3H), 1.93 (q, 1H), 1.25 (d, 6H).

Example 149

1-{[3-[3-(2,6-Difluorophenyl)-1,2,4-oxadiazol-5-yl]-5-(4-ethylphenyl)piperidin-1-yl]carbonyl}-piperidine-4-carbonitrile [racemic cis isomer]

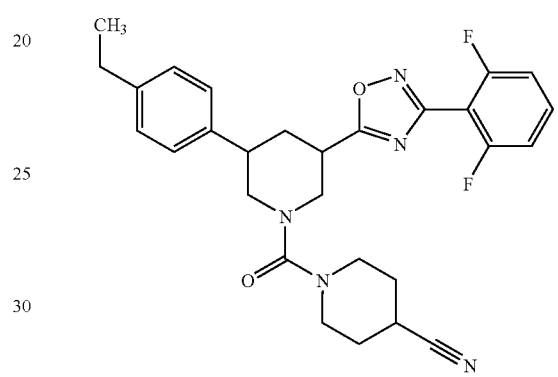

60 mg (0.16 mmol) of the compound from Example 60A and 42 mg (0.24 mmol) of 2,6-difluoro-N'-hydroxybenzenecarboximidamide were reacted according to the General Method 2. Yield: 53 mg (65% of theory)

LC-MS (Method 2B): $R_t$=1.47 min; MS (ESIpos): m/z=506 [M+H]$^+$;

$^1$H-NMR (400 MHz, DMSO-d$_6$): δ=7.75-7.71 (m, 1H), 7.38-7.33 (m, 2H), 7.24 (d, 2H), 7.17 (d, 2H), 4.05 (br d, 1H), 3.58-3.50 (m, 2H), 3.41-3.35 (m, 2H), 3.11-3.02 (m, 4H), 2.91 (q, 2H), 2.57 (q, 2H), 2.36 (br d, 1H), 2.03 (q, 1H), 1.89-1.85 (m, 2H), 1.72-1.64 (m, 2H), 1.17 (t, 3H).

Example 150

{3-(4-Ethylphenyl)-5-[3-(2-methoxyethyl)-1,2,4-oxadiazol-5-yl]piperidin-1-yl}(morpholin-4-yl) methanone [racemic cis isomer]

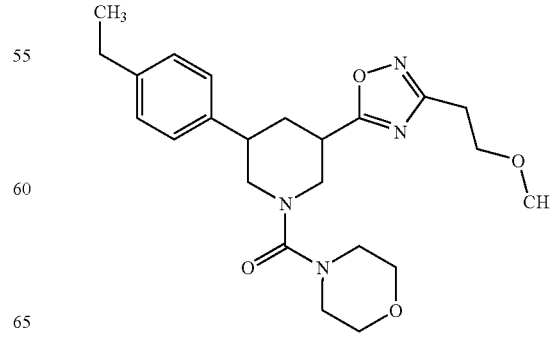

60 mg (0.17 mmol) of the compound from Example 38A and 32 mg (0.26 mmol) of N'-hydroxy-3-methoxypropanimidamide were reacted according to the General Method 2. Yield: 31 mg (42% of theory)

LC-MS (Method 3B): R$_t$=1.97 min; MS (ESIpos): m/z=429 [M+H]$^+$;

$^1$H-NMR (400 MHz, DMSO-d$_6$): δ=7.22 (d, 2H), 7.16 (d, 2H), 3.98 (br d, 1H), 3.67 (t, 2H), 3.60-3.54 (m, 5H), 3.42-3.34 (m, 1H), 3.23 (s, 3H), 3.20-3.17 (m, 4H), 3.04-2.89 (m, 5H), 2.57 (q, 2H), 2.28 (br d, 1H), 1.94 (q, 1H), 1.16 (t, 3H).

Example 151

[3-(3-Cyclopropyl-1,2,4-oxadiazol-5-yl)-5-(4-ethylphenyl)piperidin-1-yl] (morpholin-4-yl)-methanone [racemic cis isomer]

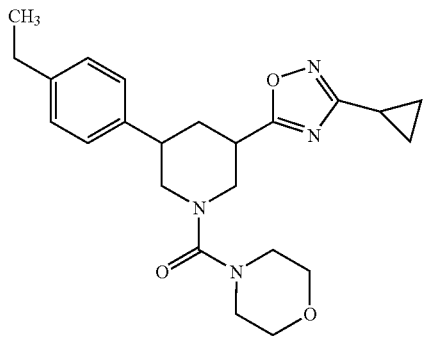

60 mg (0.17 mmol) of the compound from Example 38A and 27 mg (0.26 mmol) of N'-hydroxycyclopropanecarboximidamide were reacted according to the General Method 2. Yield: 51 mg (70% of theory)

LC-MS (Method 1B): R$_t$=2.54 min; MS (ESIpos): m/z=411 [M+H]$^+$;

$^1$H-NMR (400 MHz, DMSO-d$_6$): δ=7.21 (d, 2H), 7.16 (d, 2H), 3.95 (br d, 1H), 3.58-3.54 (m, 5H), 3.35-3.32 (m, 1H), 3.19-3.16 (m, 4H), 3.00-2.90 (m, 2H), 2.86-2.81 (m, 1H), 2.57 (q, 2H), 2.24 (br d, 1H), 2.14-2.07 (m, 1H), 1.90 (q, 1H), 1.16 (t, 3H), 1.07-1.03 (m, 2H), 0.90-0.86 (m, 2H).

Example 152

3-(3-tert-Butyl-1,2,4-oxadiazol-5-yl)-5-(4-ethylphenyl)piperidin-1-yl](4-hydroxypiperidin-1-yl)methanone [racemic cis isomer]

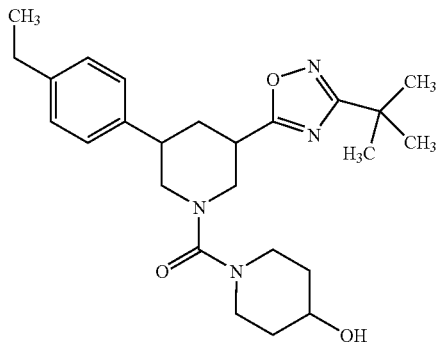

80 mg (0.22 mmol) of 5-(4-ethylphenyl)-1-[(4-hydroxypiperidin-1-yl)carbonyl]piperidine-3-carboxylic acid (Example 59A) and 39 mg (0.33 mmol) of 1-hydroxy-2,2-dimethyl-propanimidamide were reacted according to the General Method 2. Yield: 66 mg (68% of theory)

LC-MS (Method 1B): R$_t$=2.56 min; MS (ESIpos): m/z=441.2 [M+H]$^+$;

$^1$H-NMR (400 MHz, DMSO-d$_6$): δ=7.22 (d, 2H), 7.16 (d, 1H), 4.68 (d, 1H), 3.95 (bd, 1H), 3.66-3.42 (m, 4H), 3.41-3.29 (m, 1H), 2.79-3.03 (m, 5H), 2.91-3.09 (m, 2H), 2.52-2.62 (m, 2H), 2.28 (bd, 1 h), 1.93 (q, 1H), 1.71 (bd, 2H), 1.30 (bs, 11H), 1.64 (t, 3H).

Example 153

{3-(4-Ethylphenyl)-5-[3-(2-fluorophenyl)-1,2,4-oxadiazol-5-yl]piperidin-1-yl}(4-hydroxypiperidin-1-yl) methanone [racemic cis isomer]

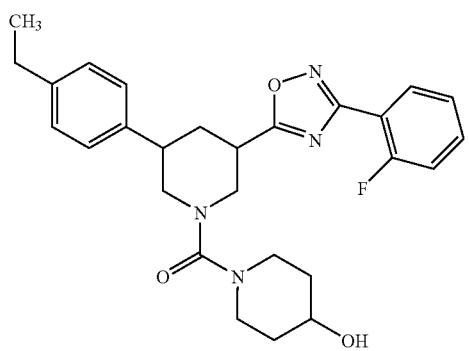

80 mg (0.22 mmol) of 5-(4-ethylphenyl)-1-[(4-hydroxypiperidin-1-yl)carbonyl]piperidine -3-carboxylic acid (Example 59A) and 51 mg (0.33 mmol) of 2-fluoro-N'-hydroxy-benzene-carboximidamide were reacted according to the General Method 2. Yield: 71 mg (67% of theory)

LC-MS (Method 1B): R$_t$=2.61 min; MS (ESIpos): m/z=479 [M+H]$^+$;

$^1$H-NMR (400 MHz, DMSO-d$_6$): δ=8.03 (dt, 1H), 7.62-7.70 (m, 1H), 7.39-7.49 (m, 2H), 7.24 (d, 2H), 7.18 (d, 2H), 4.69 (d, 1H), 4.05 (bd, 1H), 3.44-3.69 (m, 5H), 3.07 (t, 1H), 2.84-3.01 (m, 4H), 2.58 (q, 2H), 2.38 (br d, 1H), 2.04 (q, 1H), 1.73 (br d, 2H), 1.26-1.39 (m, 2H), 1.17 (t, 3H).

Example 154

[3-(4-Ethylphenyl)-5-{3-[3-(trifluoromethyl)phenyl]-1,2,4-oxadiazol-5-yl}piperidin-1-yl](4-hydroxypiperidin-1-yl)methanone [racemic cis isomer]

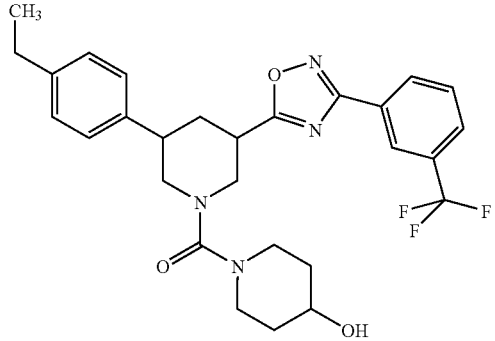

80 mg (0.22 mmol) of 5-(4-ethylphenyl)-1-[(4-hydroxypiperidin-1-yl)carbonyl]piperidine-3-carboxylic acid (Example 59A) and 68 mg (0.33 mmol) of 1-hydroxy-3-(trifluoromethyl)benzenecarboximidamide were reacted according to the General Method 2. Yield: 75 mg (64% of theory)

LC-MS (Method 1B): R*t*=2.91 min; MS (ESIpos): m/z=429 [M+H]⁺.

Example 155

{3-[3-(2,6-Difluorophenyl)-1,2,4-oxadiazol-5-yl]-5-(4-ethylphenyl)piperidin-1-yl}(4-hydroxy-piperidin-1-yl)methanone [racemic cis isomer]

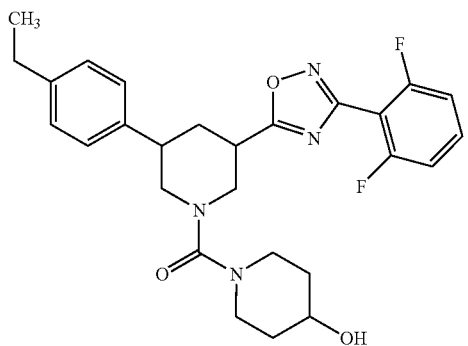

80 mg (0.22 mmol) of 5-(4-ethylphenyl)-1-[(4-hydroxypiperidin-1-yl)carbonyl]piperidine-3-carboxylic acid (Example 59A) and 57 mg (0.33 mmol) of 2,6-difluoro-N'-hydroxybenzenecarboximidamide were reacted according to the General Method 2. Yield: 57 mg (52% of theory)

HPLC (Method 3B): R*t*=2.18 min; MS (ESIpos): m/z=497 [M+H]⁺;

¹H-NMR (400 MHz, DMSO-d₆): δ=7.69-7.78 (m, 1H), 7.36 (t, 2H), 7.24 (d, 2H), 7.17 (d, 2H), 4.69 (d, 1H), 4.04 (bd, 1H), 3.44-3.66 (m, 5H), 3.07 (t, 1H), 2.83-3.01 (m, 4H), 2.57 (dd, 2H), 2.38 (br d, 1H), 2.04 (q, 1H), 1.73 (br d, 2H), 1.25-1.41 (m, 2H), 1.17 (t, 3H).

Example 156

{3-[3-(2,4-Difluorophenyl)-1,2,4-oxadiazol-5-yl]-5-(4-ethylphenyl)piperidin-1-yl}(4-hydroxy-piperidin-1-yl)methanone [racemic cis isomer]

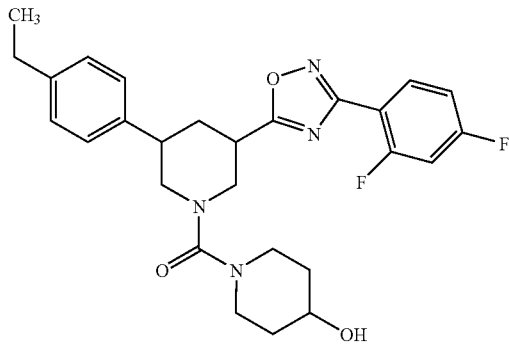

80 mg (0.22 mmol) of 5-(4-ethylphenyl)-1-[(4-hydroxypiperidin-1-yl)carbonyl]piperidine-3-carboxylic acid (Example 59A) and 60 mg (0.33 mmol) of 2,4-difluoro-N'-hydroxybenzenecarboximidamide were reacted according to the General Method 2. Yield: 69 mg (60% of theory)

HPLC (Method 3B): R*t*=2.28 min; MS (ESIpos): m/z=497 [M+H]⁺;

¹H-NMR (400 MHz, DMSO-d₆): δ=8.06-8.14 (m, 1H), 7.51-7.58 (m, 1H), 7.32 (dt, 1H), 7.26 (d, 2H), 7.18 (d, 2H), 4.69 (d, 1H), 4.04 (bd, 1H), 3.44-3.67 (m, 5H), 3.07 (t, 1H), 2.84-2.99 (m, 4H), 2.58 (dd, 2H), 2.38 (br d, 1H), 2.03 (q, 1H), 1.73 (br d, 2H), 1.26-1.39 (m, 2H), 1.17 (t, 3H).

Example 157

[3-(4-Ethylphenyl)-5-{3-[4-methyl-5-(trifluoromethyl)-4H-1,2,4-triazol-3-yl]-1,2,4-oxadiazol-5-yl}piperidin-1-yl](4-hydroxypiperidin-1-yl)methanone [racemic cis isomer]

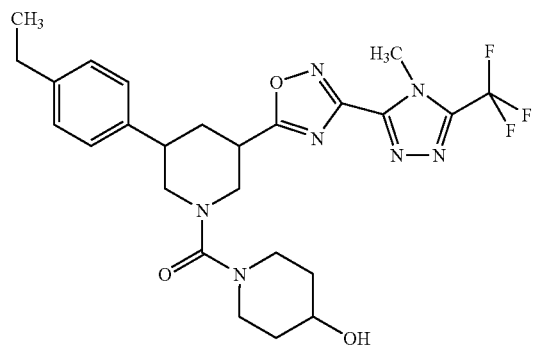

80 mg (0.22 mmol) of 5-(4-ethylphenyl)-1-[(4-hydroxypiperidin-1-yl)carbonyl]piperidine-3-carboxylic acid (Example 59A) and 70 mg (0.33 mmol) of 1-hydroxy-4-methyl-5-(trifluoromethyl)-4H-1,2,4-triazole-3-carboximidamide were reacted according to the General Method 2. Yield: 37 mg (30% of theory)

HPLC (Method 5B): R*t*=2.21 min; MS (ESIpos): m/z=534 [M+H]⁺;

Example 158

{3-(4-Ethylphenyl)-5-[3-(pyrimidin-2-yl)-1,2,4-oxadiazol-5-yl]piperidin-1-yl}(4-hydroxypiperidin-1-yl)methanone [racemic cis isomer]

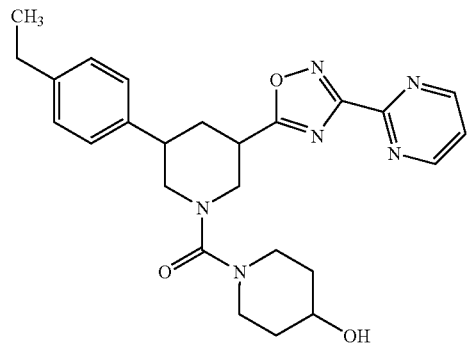

80 mg (0.22 mmol) of 5-(4-ethylphenyl)-1-[(4-hydroxypiperidin-1-yl)carbonyl]piperidine-3-carboxylic acid (Example 59A) and 46 mg (0.33 mmol) of N'-hydroxypyrimidine-2-carboximidamide were reacted according to the General Method 2. Yield: 66 mg (64% of theory)

LC-MS (Method 1B): R$_t$=2.02 min; MS (ESIpos): m/z=463 [M+H]$^+$;

$^1$H-NMR (400 MHz, DMSO-d$_6$): δ=9.03 (d, 2h), 7.72 (t, 1H), 7.24 (d, 2H), 7.18 (d, 2H), 4.69 (d, 1H), 4.04 (bd, 1H), 3.45-3.67 (m, 5H), 3.09 (t, 1H), 2.85-2.97 (m, 4H), 2.58 (dd, 2H), 2.39 (br d, 1H), 2.06 (q, 1H), 1.73 (br d, 2H), 1.26-1.39 (m, 2H), 1.17 (t, 3H).

Example 159

{3-[5-(3-Fluorophenyl)-1,2,4-oxadiazol-3-yl]-5-[4-(trifluoromethyl)phenyl]piperidin-1-yl}-(morpholin-4-yl)methanone [racemic cis isomer]

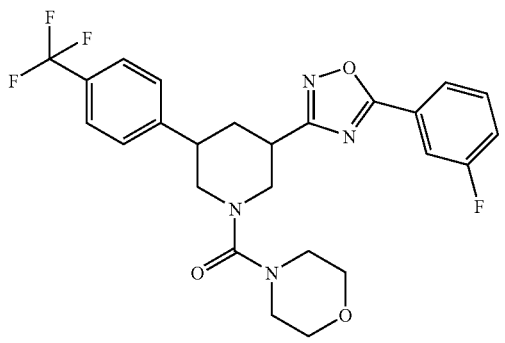

60 mg (0.43 mmol) of m-fluorobenzoic acid and 120 mg (about 0.22 mmol) of the compound from Example 84A were reacted according to the General Method 2. Yield: 61 mg (56% of theory).

LC-MS (Method 2B): R$_t$=1.48 min; MS (ESIpos): m/z=505 [M+H]$^+$;

$^1$H-NMR (400 MHz, DMSO-d$_6$): δ=7.96 (d, 1H), 7.90 (br d, 1H), 7.73-7.67 (m, 3H), 7.60-7.57 (m, 3H), 4.05 (br d, 1H), 3.68 (d, 1H), 3.58-3.55 (m, 4H), 3.27-3.20 (m, 4H), 3.09-3.02 (m, 4H), 2.35 (br d, 1H), 2.03 (q, 1H).

Example 160

Morpholin-4-yl{3-(5-phenyl-1,2,4-oxadiazol-3-yl)-5-[4(trifluoromethyl)phenyl]piperidin-1-yl}-methanone [racemic cis isomer]

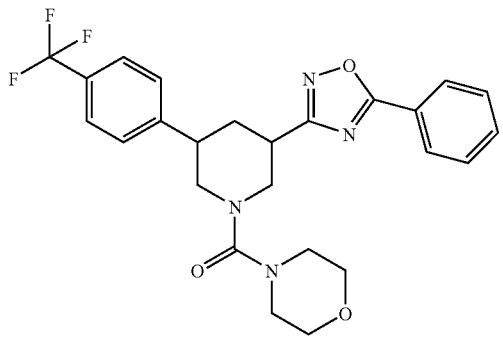

52 mg (0.43 mmol) of benzoic acid and 120 mg (about 0.22 mmol) of the compound from Example 84A were reacted according to the General Method 2. Yield: 9 mg (9% of theory).

LC-MS (Method 2B): R$_t$=1.46 min; MS (ESIpos): m/z=487 [M+H]$^+$;

$^1$H-NMR (400 MHz, DMSO-d$_6$): δ=8.11 (d, 2H), 7.73-7.70 (m, 3H), 7.65-7.59 (m, 4H), 4.05 (br d, 1H), 3.68 (d, 1H), 3.61-3.55 (m, 4H), 3.26-3.19 (m, 5H), 3.10-3.02 (m, 3H), 2.34 (br d, 1H), 2.02 (q, 1H).

Example 161

3-(5-Cyclopropyl-1,2,4-oxadiazol-3-yl)-5-[4-(trifluoromethyl)phenyl]piperidin-1-yl}(morpholin-4-yl)methanone [racemic cis isomer]

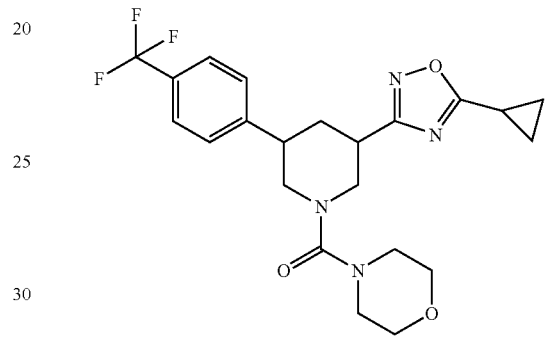

36 mg (0.43 mmol) of cyclopropanecarboxylic acid and 100 mg (about 0.22 mmol) of the compound from Example 84A were reacted according to the General Method 2. Yield: 33 mg (34% of theory).

LC-MS (Method 2B): R$_t$=1.31 min; MS (ESIpos): m/z=451 [M+H]$^+$;

$^1$H-NMR (400 MHz, DMSO-d$_6$): δ=7.69 (d, 2H), 7.56 (d, 2H), 3.91 (br d, 1H), 3.64 (d, 1H), 3.58-3.52 (m, 4H), 3.21-3.13 (m, 4H), 3.10 (tt, 1H), 3.03-2.92 (m, 3H), 2.41-2.28 (m, 1H), 2.22 (br d, 1H), 1.90 (q, 1H), 1.25-1.20 (m, 2H), 1.10-1.06 (m, 2H).

Example 162

3-(5-Ethyl-1,2,4-oxadiazol-3-yl)-5-[4-(trifluoromethyl)phenyl]piperidin-1-yl}(morpholin -4-yl)-methanone [racemic cis isomer]

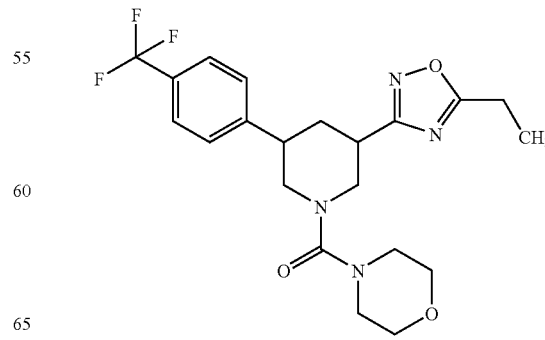

31 mg (0.43 mmol) of propanecarboxylic acid and 100 mg (about 0.22 mmol) of the compound from Example 84A were reacted according to the General Method 2. Yield: 32 mg (34% of theory).

LC-MS (Method 3B): $R_t$=2.08 min; MS (ESIpos): m/z=439 [M+H]$^+$;

$^1$H-NMR (400 MHz, DMSO-d$_6$): δ=7.69 (d, 2H), 7.57 (d, 2H), 3.93 (br d, 1H), 3.65 (d, 1H), 3.59-3.53 (m, 4H), 3.21-3.11 (m, 5H), 3.07-2.98 (m, 3H), 2.92 (q, 2H), 2.26 (br d, 1H), 1.93 (q, 1H), 1.27 (t, 3H).

Example 163

3-(5-tert-Butyl-1,2,4-oxadiazol-3-yl)-5-[4-(trifluoromethyl)phenyl]piperidin-1-yl}(morpholin-4-yl)methanone [racemic cis isomer]

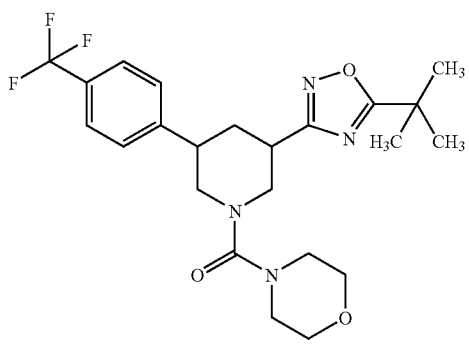

43 mg (0.43 mmol) of tert-butylcarboxylic acid and 100 mg (about 0.22 mmol) of the compound from Example 84A were reacted according to the General Method 2. Yield: 58 mg (59% of theory).

LC-MS (Method 3B): $R_t$=2.38 min; MS (ESIpos): m/z=467 [M+H]$^+$;

$^1$H-NMR (400 MHz, DMSO-d$_6$): δ=7.69 (d, 2H), 7.57 (d, 2H), 3.95 (br d, 1H), 3.64 (d, 1H), 3.59-3.53 (m, 4H), 3.22-3.10 (m, 5H), 3.04-2.95 (m, 3H), 2.26 (br d, 1H), 1.92 (q, 1H), 1.37 (s, 9H).

Example 164

3-(5-Benzyl-1,2,4-oxadiazol-3-yl)-5-[4-(trifluoromethyl)phenyl]piperidin-1-yl}(morpholin-4-yl)-methanone [racemic cis isomer]

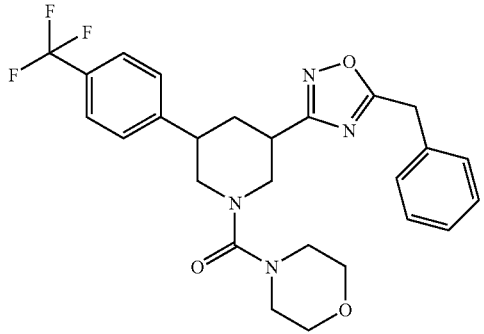

69 mg (0.51 mmol) of phenylacetic acid and 200 mg (about 0.43 mmol) of the compound from Example 84A were reacted according to the General Method 1. Yield: 17 mg (7% of theory).

LC-MS (Method 1B): $R_t$=2.68 min; MS (ESIpos): m/z=501 [M+H]$^+$;

$^1$H-NMR (400 MHz, DMSO-d$_6$): δ=7.69 (d, 2H), 7.56 (d, 2H), 7.38-7.28 (m, 5H), 4.35 (s, 2H), 3.93 (br d, 1H), 3.64 (d, 1H), 3.58-3.52 (m, 4H), 3.21-3.13 (m, 5H), 3.05-2.94 (m, 3H), 2.25 (br d, 1H), 1.92 (q, 1H).

Example 165

3-(5-Cyclobutyl-1,2,4-oxadiazol-3-yl)-5-[4-(trifluoromethyl)phenyl]piperidin-1-yl}(morpholin-4-yl)methanone [racemic cis isomer]

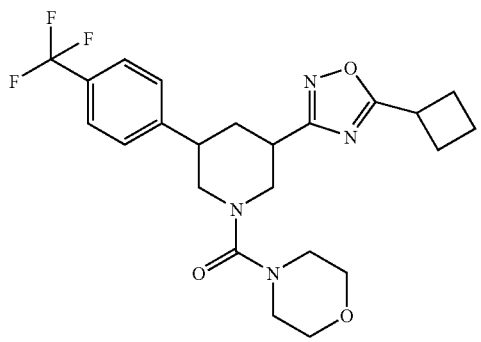

47 mg (0.43 mmol) of cyclobutylcarboxylic acid and 100 mg (about 0.22 mmol) of the compound from Example 84A were reacted according to the General Method 2. Yield: 47 mg (47% of theory).

LC-MS (Method 3B): $R_t$=2.28 min; MS (ESIpos): m/z=465 [M+H]$^+$;

$^1$H-NMR (400 MHz, DMSO-d$_6$): δ=7.69 (d, 2H), 7.57 (d, 2H), 3.95 (br d, 1H), 3.83 (quintuplet, 1H), 3.65 (d, 1H), 3.59-3.53 (m, 4H), 3.22-3.12 (m, 5H), 3.08-2.96 (m, 3H), 2.40-2.24 (m, 5H), 2.12-2.01 (m, 1H), 2.99-1.89 (m, 2H).

Example 166 tert-Butyl[1-(3-{1-(morpholin-4-ylcarbonyl)-5-[4-(trifluoromethyl)phenyl]piperidin-3-yl}-1,2,4-oxadiazol-5-yl)cyclobutyl]carbamate [racemic cis isomer]

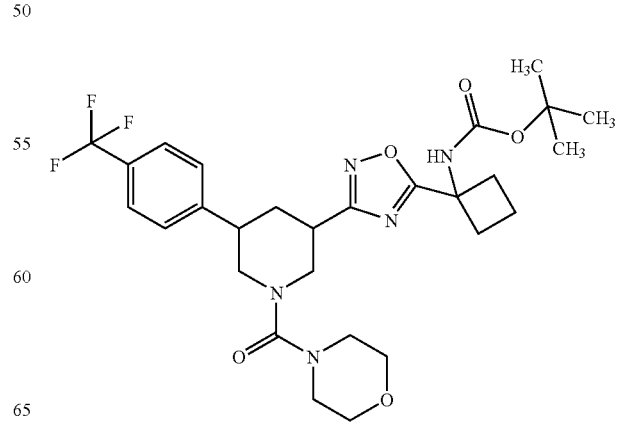

170 mg (0.85 mmol) of 1-[(tert-butoxycarbonyl)amino]cyclobutanecarboxylic acid and 200 mg (about 0.43 mmol) of the compound from Example 84A were reacted according to the General Method 2. Yield: 106 mg (42% of theory).

LC-MS (Method 3B): $R_t$=2.34 min; MS (ESIpos): m/z=580 [M+H]$^+$;

$^1$H-NMR (400 MHz, DMSO-d$_6$): δ=8.08 (s, 1H), 7.70 (d, 2H), 7.57 (d, 2H), 3.96 (br d, 1H), 3.65 (d, 1H), 3.59-3.55 (m, 4H), 3.21-3.14 (m, 5H), 3.08-2.96 (m, 3H), 2.41-2.33 (m, 2H), 2.27 (br d, 1H), 2.03-1.87 (m, 3H), 1.35 (s, 9H), 1.18-1.12 (m, 2H).

Example 167

{3-[5-(2-Aminopropan-2-yl)-1,2,4-oxadiazol-3-yl]-5-[4-(trifluoromethyl)phenyl]piperidin-1-yl}-(morpholin-4-yl)methanone hydrochloride [racemic cis isomer]

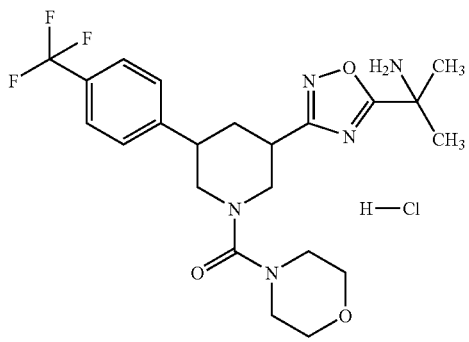

0.12 ml (0.50 mmol) of a 4N solution of hydrogen chloride in dioxane was added to a solution of 29 mg (about 0.05 mmol) of the compound from Example 86A in 0.2 ml of dioxane. The reaction mixture was stirred at room temperature for 20 hours. The mixture was then concentrated to dryness under reduced pressure and dried until the weight remained constant. Yield: 24 mg (96% of theory).

LC-MS (Method 3B): $R_t$=1.22 min; MS (ESIpos): m/z=468 [M+H—HCl]$^+$;

$^1$H-NMR (400 MHz, DMSO-d$_6$): δ=8.99 (br s, 1H), 7.71 (d, 2H), 7.56 (d, 2H), 4.01 (br d, 1H), 3.65 (d, 1H), 3.62-3.54 (m, 4H), 3.28-3.18 (m, 5H), 3.07-3.04 (m, 2H), 2.98 (t, 1H), 2.30 (br d, 1H), 1.95 (q, 1H), 1.70 (s, 6H).

Example 168

{3-{5-[(1S)-1-Aminoethyl]-1,2,4-oxadiazol-3-yl}-5-[4-(trifluoromethyl)phenyl]piperidin-1-yl}-(morpholin-4-yl)methanone hydrochloride [racemic cis isomer]

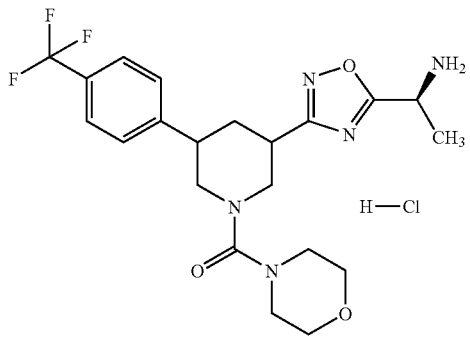

0.11 ml (0.45 mmol) of a 4N solution of hydrogen chloride in dioxane was added to a solution of 25 mg (0.05 mmol) of the compound from Example 88A in 0.2 ml of dioxane. The reaction mixture was stirred at room temperature for 20 hours. The mixture was then concentrated to dryness under reduced pressure and dried until the weight remained constant. Yield: 20 mg (93% of theory).

LC-MS (Method 3B): $R_t$=1.17 min; MS (ESIpos): m/z=454 [M+H—HCl]$^+$;

$^1$H-NMR (400 MHz, DMSO-d$_6$): δ=8.85 (br s, 1H), 7.73 (d, 2H), 7.56 (d, 2H), 4.93 (m, 1H), 3.99 (br d, 1H), 3.66 (d, 1H), 3.60-3.53 (m, 4H), 3.27 (tt, 1H), 3.26-3.12 (m, 4H), 3.10-3.04 (m, 2H), 2.98 (t, 1H), 2.30 (br d, 1H), 1.96 (q, 1H), 1.60 (d, 3H).

Example 169

Morpholin-4-yl{3-[5-(propan-2-yl)-1,2,4-oxadiazol-3-yl]-5-[4-(trifluoromethyl)phenyl]piperidin-1-yl}methanone [racemic cis isomer]

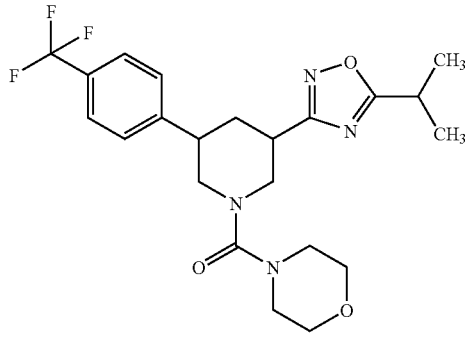

26 mg (0.297 mmol) of 2-methylpropanecarboxylic acid and 70 mg (about 0.15 mmol) of the compound from Example 84A were reacted according to the General Method 2. Yield: 9 mg (42% of theory).

LC-MS (Method 2B): $R_t$=1.36 min; MS (ESIpos): m/z=453 [M+H]$^+$;

$^1$H-NMR (400 MHz, DMSO-d$_6$): δ=7.69 (d, 2H), 7.57 (d, 2H), 3.94 (br d, 1H), 3.65 (d, 1H), 3.59-3.53 (m, 4H), 3.30-3.23 (m, 1H), 3.22-3.13 (m, 5H), 3.06-2.95 (m, 3H), 2.26 (br d, 1H), 1.92 (q, 1H), 1.50 (d, 6H).

Example 170

{3-{5-[(Dimethylamino)methyl]-1,2,4-oxadiazol-3-yl}-5-[4-(trifluoromethyl)phenyl]piperidin-1-yl}(morpholin-4-yl)methanone hydrochloride [enantiomerically pure cis isomer]

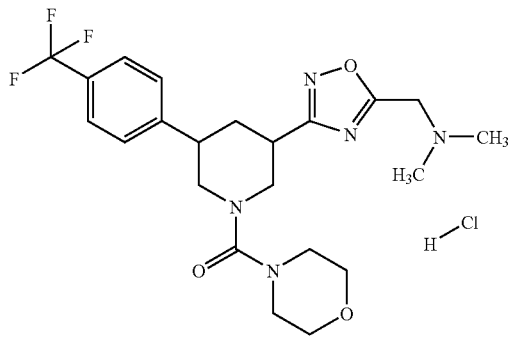

10 mg (0.09 mmol) of N,N-dimethylglycine and 83 mg (about 0.09 mmol) of the compound from Example 84A were reacted according to the General Method 1. Enantiomer separation of 20 mg of the racemate according to Method 8D gave 5 mg of the title compound from Example 170 and 4 mg of the title compound from Example 171.

HPLC (Method 6E): $R_t$=12.56 min, >99% ee;
LC-MS (Method 3B): $R_t$=1.26 min; MS (ESIpos): m/z=468[M+H]$^+$;
$^1$H-NMR (400 MHz, DMSO-$d_6$): δ=7.70 (d, 2H), 7.57 (d, 2H), 3.95 (br d, 1H), 3.81 (d, 2H), 3.66 (d, 1H), 3.59-3-52 (m, 4H), 3.22-3-17 (m, 4H), 3.07-2.97 (m, 3H), 2.31 (d, 1H), 2.24 (s, 6H), 1.94 (q, 1H).

Example 171

{3-{5-[(Dimethylamino)methyl]-1,2,4-oxadiazol-3-yl}-5-[4-(trifluoromethyl)phenyl]piperidin-1-yl}(morpholin-4-yl)methanone hydrochloride [enantiomerically pure cis isomer]

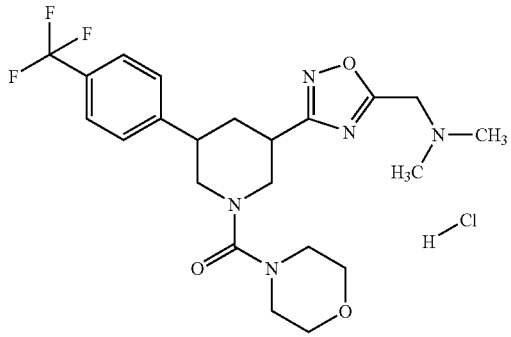

10 mg (0.09 mmol) of N,N-dimethylglycine and 83 mg (about 0.09 mmol) of the compound from Example 84A were reacted according to the General Method 1. Enantiomer separation of 20 mg of the racemate according to Method 8D gave 5 mg of the title compound from Example 170 and 4 mg of the title compound from Example 171.

HPLC (Method 6E): $R_t$=24.18 min, >99% ee;
LC-MS (Method 3B): $R_t$=1.26 min; MS (ESIpos): m/z=468[M+H]$^+$;
$^1$H-NMR (400 MHz, DMSO-$d_6$): δ=7.70 (d, 2H), 7.57 (d, 2H), 3.95 (br d, 1H), 3.81 (d, 2H), 3.66 (d, 1H), 3.59-3-52 (m, 4H), 3.22-3-17 (m, 4H), 3.07-2.97 (m, 3H), 2.31 (d, 1H), 2.24 (s, 6H), 1.94 (q, 1H).

Example 172

{3-[5-(2-Methoxyethyl)-1,2,4-oxadiazol-3-yl]-5-[4-(trifluoromethyl)phenyl]piperidin-1-yl}-(morpholin-4-yl)methanone [enantiomerically pure cis isomer]

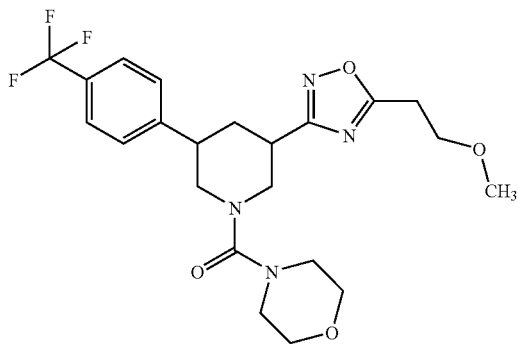

53 mg (0.51 mmol) of 3-methoxypropanecarboxylic acid and 200 mg (about 0.42 mmol) of the compound from Example 84A were reacted according to the General Method 1. Enantiomer separation of 30 mg of the racemate according to Method 8D gave 11 mg of the title compound from Example 172 and 11 mg of the title compound from Example 173.

HPLC (Method 6E): $R_t$=12.23 min, >99% ee;
LC-MS (Method 3B): $R_t$=1.98 min; MS (ESIpos): m/z=469[M+H]$^+$;
$^1$H-NMR (400 MHz, DMSO-$d_6$): δ=7.70 (d, 2H), 7.57 (d, 2H), 3.95 (br d, 1H), 3.72 (t, 2H), 3.65 (d, 1H), 3.59-3-53 (m, 4H), 3.24 (s, 3H), 3.25-3.14 (m, 7H), 3.05-2.95 (m, 3H), 2.26 (br d, 1H), 1.93 (q, 1H).

Example 173

{3-[5-(2-Methoxyethyl)-1,2,4-oxadiazol-3-yl]-5-[4-(trifluoromethyl)phenyl]piperidin-1-yl}-(morpholin-4-yl)methanone [enantiomerically pure cis isomer]

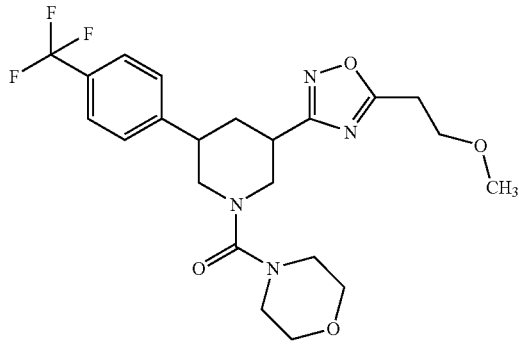

53 mg (0.51 mmol) of 3-methoxypropanecarboxylic acid and 200 mg (about 0.43 mmol) of the compound from Example 84A were reacted according to the General Method 1. Enantiomer separation of 30 mg of the racemate according to Method 8D gave 11 mg of the title compound from Example 172 and 11 mg of the title compound from Example 173

HPLC (Method 6E): $R_t$=19.17 min, >99% ee;
LC-MS (Method 3B): $R_t$=1.98 min; MS (ESIpos): m/z=469[M+H]$^+$;
$^1$H-NMR (400 MHz, DMSO-$d_6$): δ=7.70 (d, 2H), 7.57 (d, 2H), 3.95 (br d, 1H), 3.72 (t, 2H), 3.65 (d, 1H), 3.59-3-53 (m, 4H), 3.24 (s, 3H), 3.25-3.14 (m, 7H), 3.05-2.95 (m, 3H), 2.26 (br d, 1H), 1.93 (q, 1H).

Example 174

{3-[5-(1-Aminocyclobutyl)-1,2,4-oxadiazol-3-yl]-5-[4-(trifluoromethyl)phenyl]piperidin-1-yl}-(morpholin-4-yl)methanone hydrochloride [racemic cis isomer]

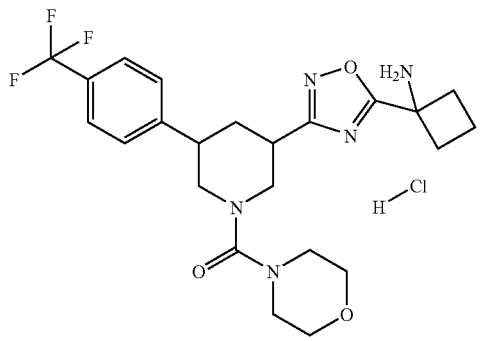

0.4 ml (1.7 mmol) of a 4N solution of hydrogen chloride in dioxane was added to a solution of 100 mg (0.17 mmol) of the compound from Example 166 in 0.25 ml of dioxane. The reaction mixture was stirred at room temperature for 20 h. The mixture was concentrated under reduced pressure, again taken up in 0.25 ml of dioxane, and once more 0.4 ml (1.7 mmol) of a 4N solution of hydrogen chloride in dioxane was added. The reaction mixture was stirred at room temperature for 16 h. The mixture was then concentrated to dryness under reduced pressure and dried until the weight remained constant. Yield: 92 mg (100% of theory).

LC-MS (Method 1B): $R_t$=1.51 min; MS (ESIpos): m/z=480 [M+H—HCl]$^+$.

Example 175

{3-[5-(1-Aminocyclopropyl)-1,2,4-oxadiazol-3-yl]-5-[4-(trifluoromethyl)phenyl]piperidin-1-yl}-(morpholin-4-yl)methanone hydrochloride [racemic cis isomer]

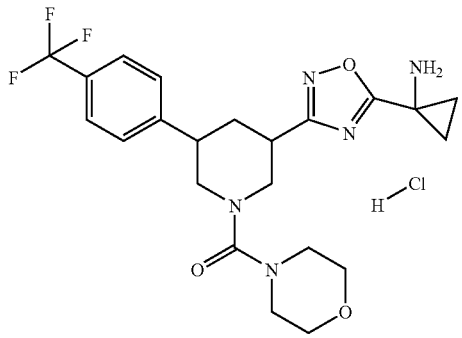

0.6 ml (2.3 mmol) of a 4N solution of hydrogen chloride in dioxane was added to a solution of 130 mg (0.230 mmol) of the compound from Example 85A in 0.25 ml of dioxane. The reaction mixture was stirred at room temperature for 20 h. The mixture was concentrated under reduced pressure, again taken up in 0.25 ml of dioxane, and once more 0.6 ml (2.3 mmol) of a 4N solution of hydrogen chloride in dioxane was added. The reaction mixture was stirred at room temperature for 16 h. The mixture was then concentrated to dryness under reduced pressure and dried until the weight remained constant. Yield: 115 mg (92% of theory).

LC-MS (Method 1B): $R_t$=1.65 min; MS (ESIpos): m/z=466 [M+H—HCl]$^+$.

Example 176

{3-[5-(2-Ethoxypropan-2-yl)-1,2,4-oxadiazol-3-yl]-5-[4-(trifluoromethyl)phenyl]piperidin-1-yl}-(morpholin-4-yl)methanone [racemic cis isomer]

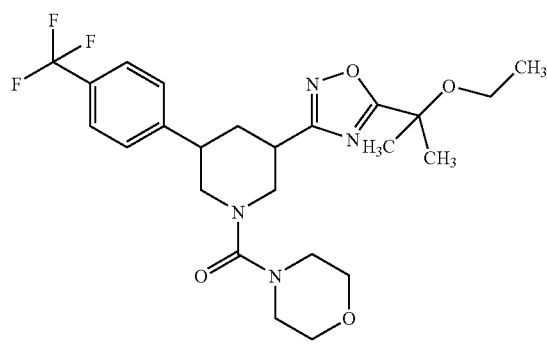

57 mg (0.43 mmol) of 2-ethoxy-2-methylpropanoic acid and 120 mg (about 0.22 mmol) of the compound from Example 84A were reacted according to the General Method 2. Yield: 24 mg (22% of theory).

LC-MS (Method 2B): $R_t$=1.40 min; MS (ESIpos): m/z=497 [M+H]$^+$;

$^1$H-NMR (400 MHz, DMSO-d$_6$): δ=7.70 (d, 2H), 7.57 (d, 2H), 3.97 (br d, 1H), 3.65 (d, 1H), 3.59-3.53 (m, 4H), 3.29 (q, 2H), 3.24-3.17 (m, 5H), 3.06-2.96 (m, 3H), 2.29 (br d, 1H), 1.92 (q, 1H), 1.58 (s, 6H), 1.06 (t, 3H).

Example 177

{3-{5-[(Methylsulphonyl)methyl]-1,2,4-oxadiazol-3-yl}-5-[4-(trifluoromethyl)phenyl]piperidin-1-yl}(morpholin-4-yl)methanone [racemic cis isomer]

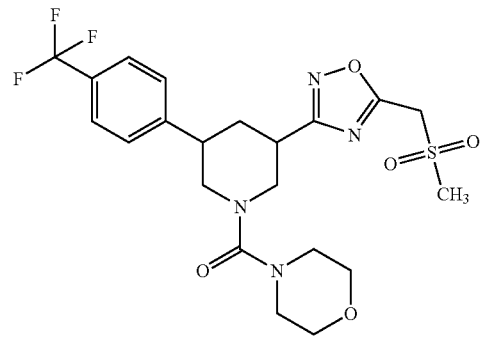

60 mg (0.43 mmol) of (methylsulphonyl)acetic acid and 120 mg (about 0.216 mmol) of the compound from Example 84A were reacted according to the General Method 2. Yield: 41 mg (38% of theory).

LC-MS (Method 3B): $R_t$=1.84 min; MS (ESIpos): m/z=503 [M+H]$^+$;

$^1$H-NMR (400 MHz, DMSO-d$_6$): δ=7.70 (d, 2H), 7.57 (d, 2H), 5.20 (d, 2H), 3.98 (br d, 1H), 3.65 (d, 1H), 3.59-3.53 (m, 4H), 3.28-3.17 (8H), 3.10-2.98 (m, 3H), 2.30 (br d, 1H), 1.96 (q, 1H).

Example 178

{3-[3-(2-Methoxyethyl)-1,2,4-oxadiazol-5-yl]-5-[4-(trifluoromethoxy)phenyl]piperidin-1-yl}-(morpholin-4-yl)methanone [enantiomerically pure cis isomer]

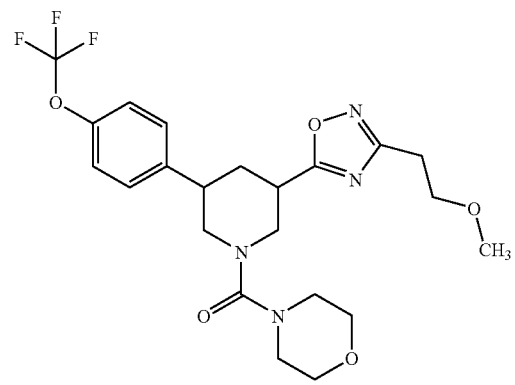

The enantiomer separation of 1.25 g (2.58 mmol) of the compound from Example 250 according to Method 9D gave 551 mg of the title compound from Example 178 and 493 mg of the title compound from Example 179.

HPLC (Method 9E): $R_t$=6.97 min, >99.0% ee;
LC-MS (Method 3B): $R_t$=2.01 min; MS (ESIpos): m/z=485 [M+H]$^+$;
$^1$H-NMR (400 MHz, DMSO-d$_6$): δ=7.47 (d, 2H), 7.33 (d, 2H), 3.99 (br d, 1H), 3.68 (t, 2H), 3.61 (br d, 1H), 57-3.55 (m, 4H), 3.40-3.36 (m, 1H), 3.23 (s, 3H), 3.21-3.19 (m, 4H), 3.06-2.99 (m, 3H), 2.93 (t, 2H), 2.33-2.30 (m, 1H), 1.97 (q, 1H).
$[α]_{365}^{20}$=−3.4, methanol Example 179

{3-[3-(2-Methoxyethyl)-1,2,4-oxadiazol-5-yl]-5-[4-(trifluoromethoxy)phenyl]piperidin-1-yl}-(morpholin-4-yl)methanone [enantiomerically pure cis isomer]

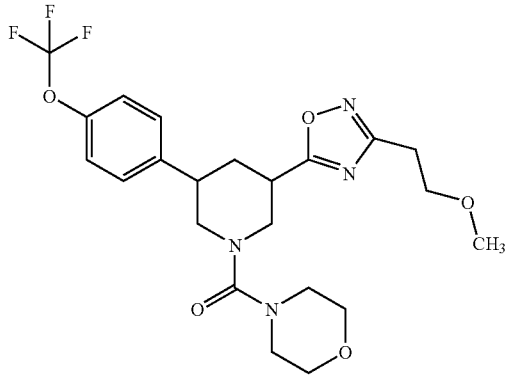

The enantiomer separation of 1.25 g (2.58 mmol) of the compound from Example 250 according to Method 9D gave 551 mg of the title compound from Example 178 and 493 mg of the title compound from Example 179.

HPLC (Method 9E): $R_t$=8.24 min, >99.0% ee;
LC-MS (Method 3B): $R_t$=2.01 min; MS (ESIpos): m/z=485 [M+H]$^+$.
$^1$H-NMR (400 MHz, DMSO-d$_6$): δ=7.48 (d, 2H), 7.33 (d, 2H), 3.99 (br d, 1H), 3.68 (t, 2H), 3.61 (br d, 1H), 0.58-3.55 (m, 4H), 3.47-3.36 (m, 1H), 3.23 (s, 3H), 3.21-3.19 (m, 4H), 3.06-2.97 (m, 3H), 2.93 (t, 2H), 2.31 (br d, 1H), 1.97 (q, 1H).

Example 180

{3-(3-Cyclopropyl-1,2,4-oxadiazol-5-yl)-5-[4-(trifluoromethoxy)phenyl]piperidin-1-yl}(4,4-difluoropiperidin-1-yl)methanone [racemic cis isomer]

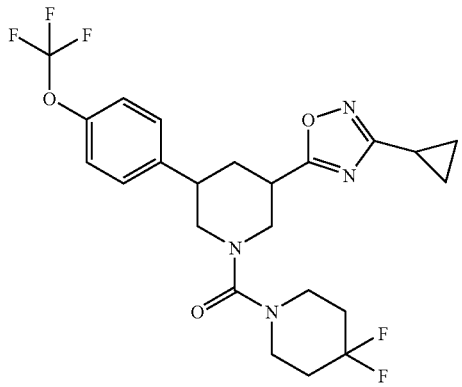

100 mg (0.19 mmol) of the compound from Example 176A and 91 mg (0.58 mmol) of 4,4-difluoropiperidine hydrochloride were reacted according to the General Method 6. Yield: 48 mg (50% of theory)

LC-MS (Method 3B): $R_t$=2.01 min; MS (ESIpos): m/z=413 [M+H]$^+$;
$^1$H-NMR (400 MHz, DMSO-d$_6$): δ=7.46 (d, 2H), 7.32 (d, 2H), 3.97 (br d, 1H), 3.64 (br d, 1H), 3.39-3.34 (m, 5H), 3.31-3.28 (m, 4H), 3.04-2.97 (m, 2H), 2.31 (br d, 1H), 2.14-2.07 (m, 1H), 2.00-1.86 (m, 2H), 1.08-1.03 (m, 2H), 1.90-1.86 (m, 2H).

Example 181

{3-(3-Cyclopropyl-1,2,4-oxadiazol-5-yl)-5-[4-(trifluoromethyl)phenyl]piperidin-1-yl}(3-methylazetidin-1-yl)methanone [racemic cis isomer]

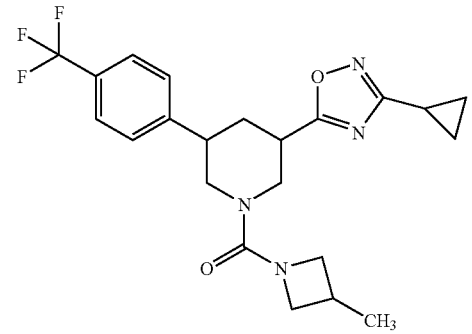

95 mg (0.19 mmol) of the compound from Example 184A and 61 mg (0.57 mmol) of 3-methylazetidine hydrochloride were reacted according to the General Method 6. Work-up of the crude product was carried out initially by column chromatography on silica gel (mobile phase: dichloromethane->dichloromethane/methanol 100:5) and additionally by preparative HPLC. Yield: 14 mg (17% of theory)

HPLC (Method 2A): $R_t$=4.83 min; MS (ESIpos): m/z=435 [M+H]$^+$;
$^1$H-NMR (400 MHz, DMSO-d$_6$): δ=7.69 (d, 2H), 7.55 (d, 2H), 4.11 (br d, 1H), 4.05-4.00 (m, 2H), 3.75 (br d, 1H), 3.50 (q, 2H), 3.27-3.22 (m, 1H), 3.00-2.91 (m, 3H), 2.61-2.57 (m, 1H), 2.27 (br d, 1H), 2.14-2.07 (m, 1H), 2.03-1.94 (m, 1H), 1.14 (d, 3H). 1.07-1.03 (m, 2H), 0.90-0.86 (m, 2H).

Example 182

{3-[3-(3-Fluorophenyl)-1,2,4-oxadiazol-5-yl]-5-[4-(trifluoromethyl)phenyl]piperidin-1-yl}(3-hydroxypyrrolidin-1-yl)methanone [mixture of diastereomers]

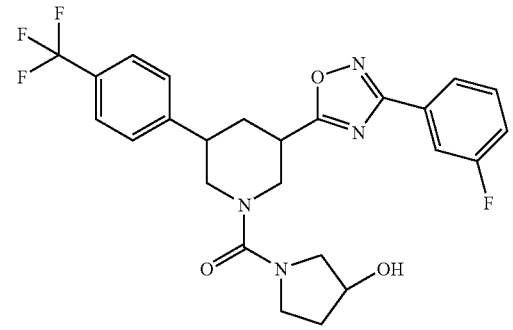

100 mg (0.18 mmol) of the compound from Example 187A and 47 mg (0.54 mmol) of 3-pyrrolidinol were reacted according to the General Method 6. Yield: 25 mg (26% of theory)

HPLC (Method 2A): $R_t$=4.74 min; MS (ESIpos): m/z=505 [M+H]$^+$;

$^1$H-NMR (400 MHz, DMSO-$d_6$): δ=7.87 (d, 1H), 7.77 (d, 1H), 7.71 (d, 2H), 7.66-7.63 (m, 1H), 7.59 (d, 2H), 7.49-7.44 (m, 1H), 4.89 (d, OH), 4.22 (br s, 1H), 4.16 (br d, 1H), 3.74 (t, 1H), 3.57-3.47 (m, 3H), 3.39-3.33 (m, 1H), 3.16-2.92 (m, 4H), 2.45 (br d, 1H), 2.13-2.08 (m, 1H), 2.84-2.81 (m, 1H), 2.76-2.72 (m, 1H).

Example 183

{3-(4-Ethylphenyl)-5-[3-(2-methoxyethyl)-1,2,4-oxadiazol-5-yl]piperidin-1-yl}(4-hydroxy-piperidin-1-yl)methanone [racemic cis isomer]

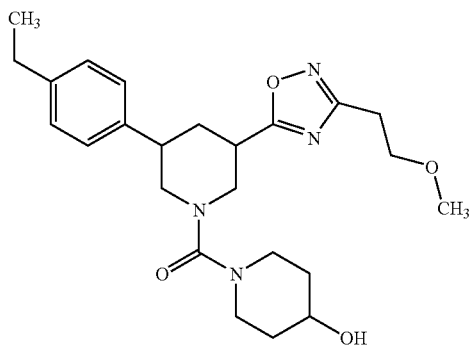

60 mg (0.17 mmol) of the compound from Example 59A and 30 mg (0.25 mmol) of N'-hydroxy-3-methoxypropanimidamide were reacted according to the General Method 2. Yield: 32 mg (44% of theory)

LC-MS (Method 1B): $R_t$=2.15 min; MS (ESIpos): m/z=443 [M+H]$^+$;

$^1$H-NMR (400 MHz, DMSO-$d_6$): δ=7.21 (d, 2H), 7.16 (d, 2H), 4.67 (d, OH), 3.93 (br d, 1H), 3.67 (t, 2H), 3.59-3.45 (m, 4H), 3.42-3.34 (m, 1H), 3.32 (s, 3H), 3.00-2.85 (m, 7H), 2.57 (q, 2H), 2.30 (br d, 1H), 1.94 (q, 1H), 1.73-1.70 (m, 2H), 1.34-1.25 (m, 2H), 1.16 (t, 3H).

Example 184

(3-Hydroxyazetidin-1-yl) {3-[3-(2-ethoxyethyl)-1,2,4-oxadiazol-5-yl]-5-[4-(trifluoromethyl)phenyl]piperidin-1-yl}methanone [racemic cis isomer]

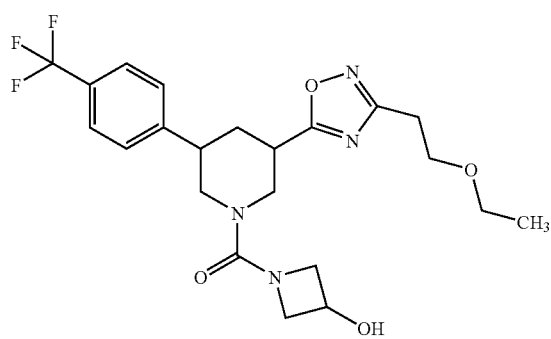

100 mg (0.27 mmol) of the compound from Example 101A and 58 mg (0.40 mmol) of the compound from Example 76A were reacted according to the General Method 2. Yield: 25 mg (19% of theory)

HPLC (Method 2A): $R_t$=4.29 min; MS (ESIpos): m/z=469 [M+H]$^+$;

$^1$H-NMR (400 MHz, DMSO-$d_6$): δ=7.70 (d, 2H), 7.56 (d, 2H), 5.58 (d, OH), 4.38 (sextet, 1H), 4.14 (br d, 1H), 4.08 (q, 2H), 3.78 (br d, 1H), 3.72-3.67 (m, 4H), 3.42 (q, 2H), 3.06-2.92 (m, 3H), 2.90 (t, 2H), 2.32 (br d, 1H), 2.02 (q, 1H), 1.06 (t, 3H).

Example 185

[3-(4-Ethylphenyl)-5-{3-[(methylsulphonyl)methyl]-1,2,4-oxadiazol-5-yl}piperidin-1-yl]-(morpholin-4-yl)methanone [racemic cis isomer]

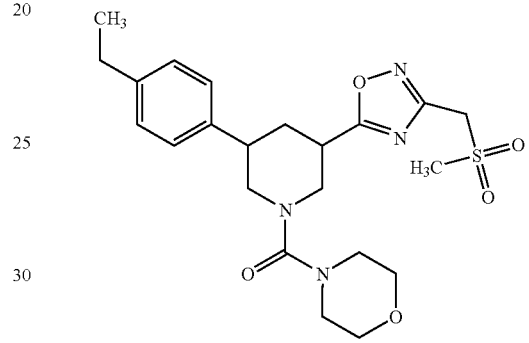

60 mg (0.17 mmol) of the compound from Example 38A and 40 mg (0.26 mmol) of N'-hydroxy-2-(methylsulphonyl)ethanimidamide were reacted according to the General Method 2. Yield: 15 mg (18% of theory)

LC-MS (Method 3B): $R_t$=1.81 min; MS (ESIpos): m/z=463 [M+H]$^+$.

$^1$H-NMR (400 MHz, DMSO-$d_6$): δ=7.25 (d, 2H), 7.17 (d, 2H), 4.85 (s, 2H), 4.04 (br d, 1H), 3.60-3.55 (m, 5H), 3.49-3.42 (m, 1H), 3.23-3.18 (m, 4H), 3.16 (s, 3H), 3.12-2.84 (m, 3H), 2.57 (q, 2H), 2.36 (br d, 1H), 1.97 (q, 1H), 1.16 (t, 3H).

Example 186

{3-(3,4-Dimethylphenyl)-5-[3-(2-methoxyethyl)-1,2,4-oxadiazol-5-yl]piperidin-1-yl}(4-hydroxypiperidin-1-yl)methanone [racemic cis isomer]

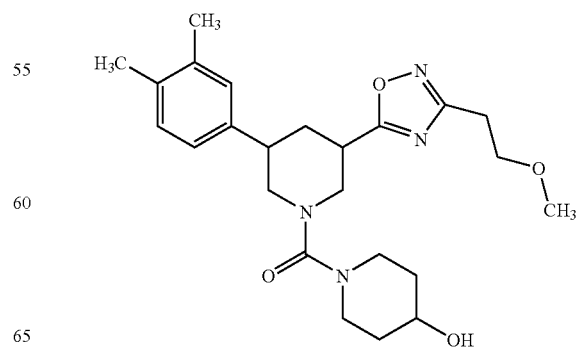

200 mg (0.54 mmol) of the compound from Example 128A and 128 mg (0.81 mmol) of N'-hydroxy-3-methoxypropanimidamide were reacted according to the General Method 2. Yield: 138 mg (56% of theory)

LC-MS (Method 2B): $R_t$=1.14 min; MS (ESIpos): m/z=443 [M+H]$^+$.

$^1$H-NMR (400 MHz, DMSO-d$_6$): δ=7.09-7.07 (m, 2H), 6.68 (d, 1H), 4.68 (d, OH), 3.94 (br d, 1H), 3.67 (t, 2H), 3.63-3.57 (m, 1H), 3.53-3.45 (m, 3H), 3.40-3.34 (m, 1H), 3.23 (s, 3H), 3.00-2.86 (m, 6H), 2.83-2.77 (m, 1H), 2.26 (br d, 1H), 2.20 (s, 3H), 2.18 (s, 3H), 1.93 (q, 1H), 1.73-1.69 (m, 2H), 1.34-1.25 (m, 2H).

Example 187

{3-(4-Ethylphenyl)-5-[3-(2-hydroxypropan-2-yl)-1,2,4-oxadiazol-5-yl]piperidin-1-yl}(4-hydroxy-piperidin-1-yl)methanone [racemic cis isomer]

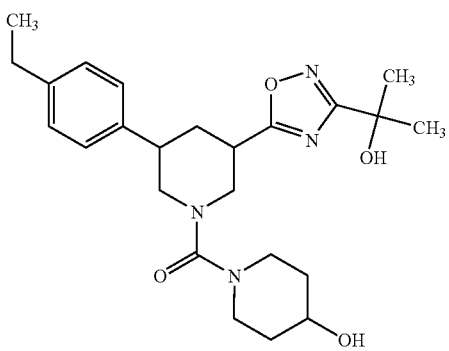

60 mg (0.17 mmol) of the compound from Example 59A and 31 mg (0.25 mmol) of the compound from Example 66A were reacted according to the General Method 2. Yield: 43 mg (55% of theory)

LC-MS (Method 5B): $R_t$=2.01 min; MS (ESIpos): m/z=443 [M+H]$^+$.

$^1$H-NMR (400 MHz, DMSO-d$_6$): δ=7.22 (d, 2H), 7.17 (d, 2H), 5.53 (s, OH), 4.67 (d, OH), 3.95 (br d, 1H), 3.62-3.41 (m, 4H), 3.41-3.34 (m, 1H), 3.01-2.82 (m, 5H), 2.57 (q, 2H), 2.30 (br d, 1H), 1.95 (q, 1H), 1.77-1.70 (m, 2H), 1.47 (s, 6H), 1.34-1.25 (m, 2H), 1.17 (t, 3H).

Example 188

{3-(3,4-Dimethylphenyl)-5-[3-(2-methoxyethyl)-1,2,4-oxadiazol-5-yl]piperidin-1-yl}(morpholin-4-yl)methanone [racemic cis isomer]

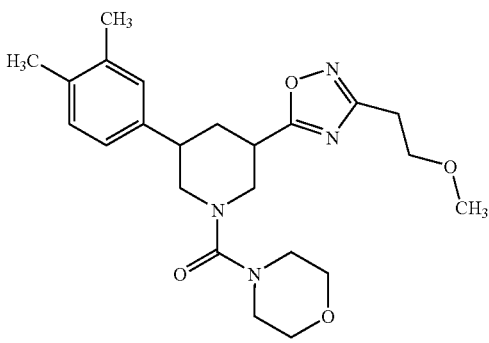

200 mg (0.58 mmol) of the compound from Example 130A and 136 mg (0.87 mmol) of N'-hydroxy-3-methoxypropanimidamide were reacted according to the General Method 2. Yield: 98 mg (40% of theory)

LC-MS (Method 1B): $R_t$=2.27 min; MS (ESIpos): m/z=429 [M+H]$^+$;

$^1$H-NMR (400 MHz, DMSO-d$_6$): δ=7.09-7-07 (m, 2H), 7.00 (d, 1H), 3.97 (br d, 1H), 3.67 (t, 2H), 3.58-3.54 (m, 5H), 3.41-3.34 (m, 1H), 3.23 (s, 3H), 3.19-3.17 (m, 4H), 3.05-2.89 (m, 4H), 2.84-2.77 (m, 1H), 2.25 (br d, 1H), 2.20 (s, 3H), 2.18 (s, 3H), 1.95 (q, 1H).

Example 189

{3-(3,4-Dimethylphenyl)-5-[3-(2-methoxyethyl)-1,2,4-oxadiazol-5-yl]piperidin-1-yl}(morpholin-4-yl)methanone [enantiomerically pure cis isomer]

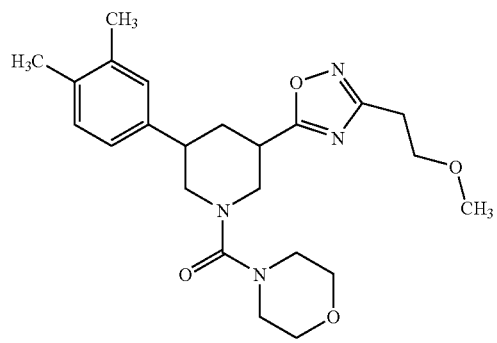

The enantiomer separation of 98 mg (0.2 mmol) of the compound from Example 188 according to Method 17D gave 30 mg of the title compound from Example 189 and 25 mg of the title compound from Example 190.

HPLC (Method 13E): $R_t$=7.40 min, >99.0% ee;

LC-MS (Method 3B): $R_t$=1.92 min; MS (ESIpos): m/z=429 [M+H]$^+$;

$^1$H-NMR (400 MHz, DMSO-d$_6$): δ=7.08-7-07 (m, 2H), 7.01 (d, 1H), 3.98 (br d, 1H), 3.68 (t, 2H), 3.58-3.54 (m, 5H), 3.39-3.34 (m, 1H), 3.23 (s, 3H), 3.20-3.17 (m, 4H), 3.04-2.90 (m, 4H), 2.83-2.77 (m, 1H), 2.26 (br d, 1H), 2.20 (s, 3H), 2.18 (s, 3H), 1.94 (q, 1H).

Example 190

{3-(3,4-Dimethylphenyl)-5-[3-(2-methoxyethyl)-1,2,4-oxadiazol-5-yl]piperidin-1-yl}(morpholin-4-yl)methanone [enantiomerically pure cis isomer]

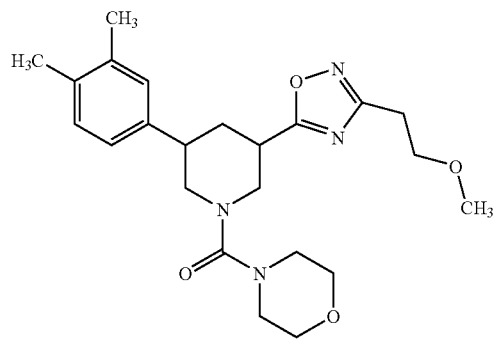

The enantiomer separation of 98 mg (0.2 mmol) of the compound from Example 188 according to Method 17D gave 30 mg of the title compound from Example 189 and 25 mg of the title compound from Example 190.

HPLC (Method 13E): R$_t$=9.82 min, >99.0% ee;
LC-MS (Method 3B): R$_t$=1.92 min; MS (ESIpos): m/z=429 [M+H]$^+$;
$^1$H-NMR (400 MHz, DMSO-d$_6$): δ=7.09-7.07 (m, 2H), 7.01 (d, 1H), 3.99 (br d, 1H), 3.68 (t, 2H), 3.58-3.55 (m, 5H), 3.38-3.34 (m, 1H), 3.23 (s, 3H), 3.20-3.18 (m, 4H), 3.10-2.89 (m, 4H), 2.84-2.78 (m, 1H), 2.26 (br d, 1H), 2.20 (s, 3H), 2.18 (s, 3H), 1.95 (q, 1H).

Example 191

1-({3-[3-(2-Ethoxyethyl)-1,2,4-oxadiazol-5-yl]-5-[4-(trifluoromethyl)phenyl]piperidin-1-yl}-carbonyl) piperidine-4-carbonitrile [racemic cis isomer]

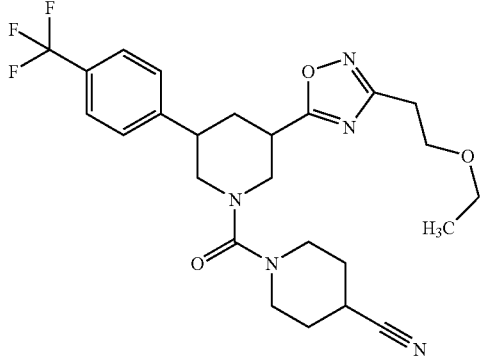

100 mg (0.24 mmol) of the compound from Example 100A and 53 mg (0.37 mmol) of the compound from Example 76A were reacted according to the General Method 2. Yield: 89 mg (72% of theory)

HPLC (Method 2A): R$_t$=4.63 min; MS (ESIpos): m/z=506 [M+H]$^+$;
$^1$H-NMR (400 MHz, DMSO-d$_6$): δ=7.70 (d, 2H), 7.57 (d, 2H), 3.96 (br d, 1H), 3.71 (t, 2H), 3.59 (br d, 1H), 3.46-3.35 (m, 5H), 3.10-2.97 (m, 6H), 2.92 (t, 2H), 2.32 (br d, 1H), 2.01 (q, 1H), 1.88-1.85 (m, 2H), 1.71-1.64 (m, 2H), 1.06 (t, 3H).

Example 192

1-({3-(4-Ethylphenyl)-5-[3-(2-methoxyethyl)-1,2,4-oxadiazol-5-yl]piperidin-1-yl}carbonyl)-piperidine-4-carbonitrile [racemic cis isomer]

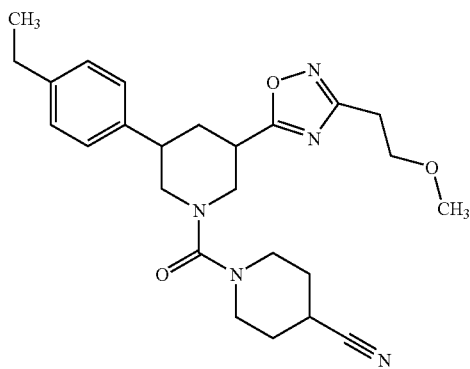

60 mg (0.16 mmol) of the compound from Example 100A and 30 mg (0.37 mmol) of N'-hydroxy-3-methoxypropanimidamide were reacted according to the General Method 2. Yield: 42 mg (55% of theory)

LC-MS (Method 5B): R$_t$=2.34 min; MS (ESIpos): m/z=452 [M+H]$^+$;
$^1$H-NMR (400 MHz, DMSO-d$_6$): δ=7.22 (d, 2H), 7.17 (d, 2H), 3.96 (br d, 1H), 3.67 (t, 2H), 3.55 (br d, 1H), 3.41-3.29 (m, 3H), 3.23 (s, 3H), 3.09-2.97 (m, 4H), 2.95-2.82 (m, 4H), 2.57 (q, 2H), 2.29 (br d, 1H), 1.95 (q, 1H), 1.90-1.84 (m, 2H), 1.70-1.64 (m, 2H), 1.16 (t, 3H).

Example 193

{3-[3-(2-Methoxyethyl)-1,2,4-oxadiazol-5-yl]-5-[3-(trifluoromethoxy)phenyl]piperidin-1-yl}-(morpholin-4-yl)methanone [racemic cis isomer]

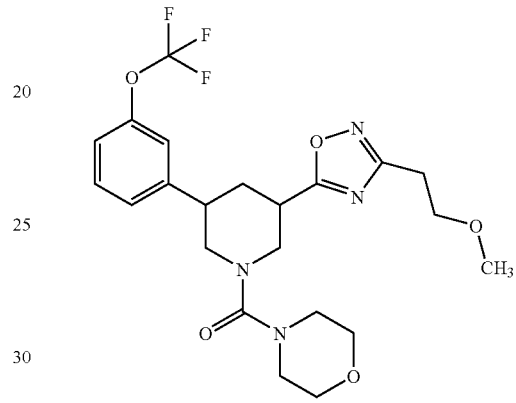

200 mg (0.50 mmol) of the compound from Example 201A and 117 mg (0.75 mmol) of N'-hydroxy-3-methoxypropanimidamide were reacted according to the General Method 2. Yield: 106 mg (44% of theory)

LC-MS (Method 3B): R$_t$=2.00 min; MS (ESIpos): m/z=485 [M+H]$^+$;
$^1$H-NMR (400 MHz, DMSO-d$_6$): δ=7.50-7.46 (m, 1H), 7.40-7.36 (m, 2H), 7.25 (d, 1H), 3.98 (br d, 1H), 3.68 (t, 2H), 3.62-3.55 (m, 5H), 3.42-3.36 (m, 1H), 3.23 (s, 3H), 3.21-3.19 (m, 4H), 3.09-3.00 (m, 3H), 2.93 (t, 2H), 2.34 (br d, 1H), 2.00 (q, 1H).

Example 194

{3-[3-(2-Methoxyethyl)-1,2,4-oxadiazol-5-yl]-5-[3-(trifluoromethoxy)phenyl]piperidin-1-yl}-(morpholin-4-yl)methanone [enantiomerically pure cis isomer]

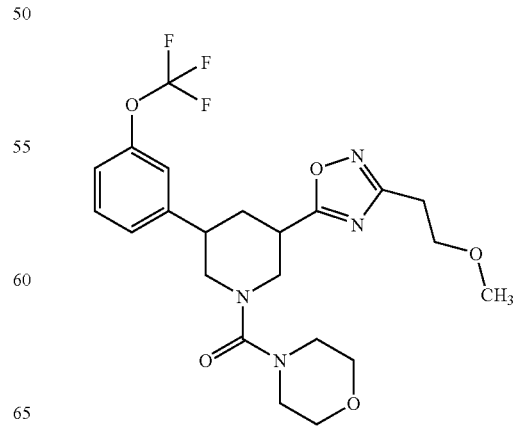

The enantiomer separation of 95 mg (0.2 mmol) of the compound from Example 193 according to Method 18D gave 16 mg of the title compound from Example 194 and 22 mg of the title compound from Example 195.

HPLC (Method 14E): R$_t$=5.34 min, >99.0% ee;
LC-MS (Method 2B): R$_t$=1.24 min; MS (ESIpos): m/z=485 [M+H]$^+$;
$^1$H-NMR (400 MHz, DMSO-d$_6$): δ=7.50-7.45 (m, 1H), 7.40-7.36 (m, 2H), 7.25 (d, 1H), 3.98 (br d, 1H), 3.67 (t, 2H), 3.61-3.55 (m, 5H), 3.42-3.35 (m, 1H), 3.23 (s, 3H), 3.21-3.19 (m, 4H), 3.09-2.99 (m, 3H), 2.93 (t, 2H), 2.33 (br d, 1H), 2.02 (q, 1H).

Example 195

{3-[3-(2-Methoxyethyl)-1,2,4-oxadiazol-5-yl]-5-[3-(trifluoromethoxy)phenyl]piperidin-1-yl}-(morpholin-4-yl)methanone [enantiomerically pure cis isomer]

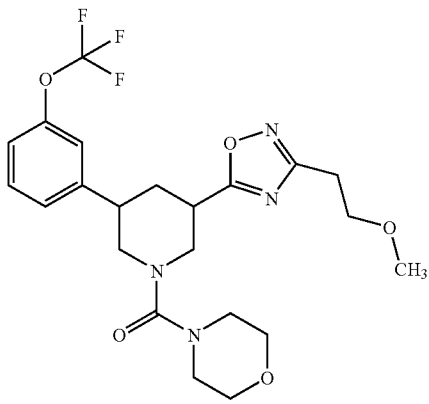

The enantiomer separation of 95 mg (0.2 mmol) of the compound from Example 193 according to Method 18D gave 16 mg of the title compound from Example 194 and 22 mg of the title compound from Example 195.

HPLC (Method 14E): R$_t$=6.21 min, >99.0% ee;
LC-MS (Method 2B): R$_t$=1.24 min; MS (ESIpos): m/z=485 [M+H]$^+$;
$^1$H-NMR (400 MHz, DMSO-d$_6$): δ=7.50-7.46 (m, 1H), 7.40-7.36 (m, 2H), 7.25 (d, 1H), 3.97 (br d, 1H), 3.67 (t, 2H), 3.62-3.55 (m, 5H), 3.43-3.35 (m, 1H), 3.23 (s, 3H), 3.21-3.19 (m, 4H), 3.11-2.99 (m, 3H), 2.93 (t, 2H), 2.31 (br d, 1H), 2.00 (q, 1H).

Example 196

1-({3-(3-{[1-(Hydroxymethyl)cyclopropyl]methyl}-1,2,4-oxadiazol-5-yl)-5-[4-(trifluoromethyl)-phenyl]piperidin-1-yl}carbonyl)piperidine-4-carbonitrile [racemic cis isomer]

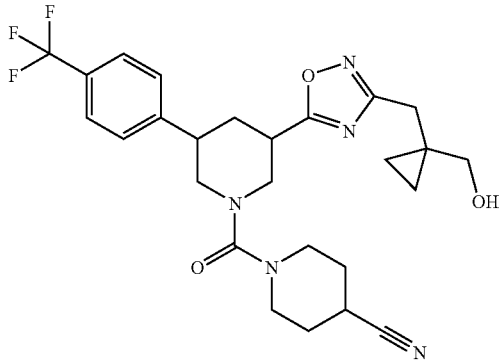

100 mg (0.24 mmol) of the compound from Example 100A and 61 mg (0.37 mmol) of the compound from Example 67A were reacted according to the General Method 2. Yield: 70 mg (56% of theory)

HPLC (Method 2A): R$_t$=4.41 min; MS (ESIpos): m/z=518 [M+H]$^+$;
$^1$H-NMR (400 MHz, DMSO-d$_6$): δ=7.70 (d, 2H), 7.57 (d, 2H), 4.58 (t, OH), 4.00 (br d, 1H), 3.59 (br d, 1H), 3.43-3.34 (m, 3H), 3.25 (s, 2H), 3.11-3.01 (m, 6H), 2.77 (s, 2H), 2.36 (br d, 1H), 2.01 (q, 1H), 1.88-1.85 (m, 2H), 1.71-1.64 (m, 2H), 0.43-0.41 (m, 4H).

Example 197

1-({3-(3,4-Dimethylphenyl)-5-[3-(propan-2-yl)-1,2,4-oxadiazol-5-yl]piperidin-1-yl}carbonyl)-piperidine-4-carbonitrile [racemic cis isomer]

80 mg (0.210 mmol) of the compound from Example 132A and 33 mg (0.315 mmol) of N'-hydroxy-2-methylpropanimidamide were reacted according to the General Method 2. Yield: 47 mg (51% of theory)

LC-MS (Method 3B): R$_t$=2.36 min; MS (ESIpos): m/z=436 [M+H]$^+$;
$^1$H-NMR (400 MHz, DMSO-d$_6$): δ=7.09-7.07 (m, 2H), 7.01 (d, 1H), 3.95 (br d, 1H), 3.53 (br d, 1H), 3.38-3.33 (m, 3H), 3.09-3.01 (m, 4H), 2.99-2.88 (m, 2H), 2.86-2.76 (m, 1H), 2.26 (br d, 1H), 2.20 (s, 3H), 2.18 (s, 3H), 1.93 (q, 1H), 1.88-1.84 (m, 2H), 1.68-1.63 (m, 2H), 1.25 (d, 6H).

Example 198

[(3-(3,4-Dimethylphenyl)-5-(3-methyl-1,2,4-oxadiazol-5-yl)piperidin-1-yl] (4-hydroxypiperidin-1-yl)methanone [racemic cis isomer]

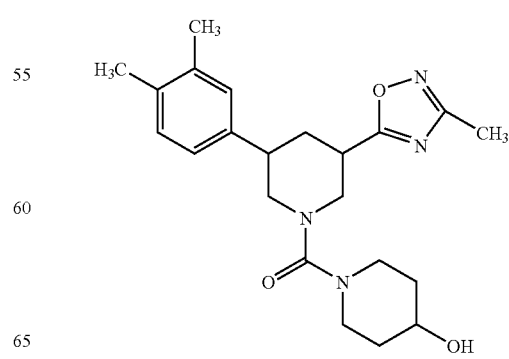

200 mg (0.54 mmol) of the compound from Example 128A and 62 mg (0.81 mmol) of N'-hydroxyacetamidine were reacted according to the General Method 2. Yield: 154 mg (69% of theory)

LC-MS (Method 2B): $R_t$=1.13 min; MS (ESIpos): m/z=399 [M+H]$^+$;

$^1$H-NMR (400 MHz, DMSO-d$_6$): δ=7.09-7.07 (m, 2H), 6.99 (d, 1H), 4.68 (d, OH), 3.93 (br d, 1H), 3.63-3.57 (m, 1H), 3.52 (br d, 1H), 3.48-3.45 (m, 2H), 3.39-3.32 (m, 1H), 2.99-2.76 (m, 5H), 2.32 (s, 3H), 2.25 (br d, 1H), 2.20 (s, 3H), 2.18 (s, 3H), 1.93 (q, 1H), 1.73-1.69 (m, 2H), 1.34-1.25 (m, 2H).

Example 199

N-(2-Methoxyethyl)-3-(3-methyl-1,2,4-oxadiazol-5-yl)-5-[4(trifluoromethyl)phenyl]piperidine-1-carboxamide [racemic cis isomer]

100 mg (0.26 mmol) of the compound from Example 105A and 40 mg (0.534 mmol) of N'-hydroxyethanimidamide were reacted according to the General Method 2. Diastereomer separation of 62 mg of the cis/trans isomer mixture according to Method 12C gave 46 mg of the title compound and 5.7 mg of the trans isomer.

LC-MS (Method 3B): $R_t$=1.85 min; MS (ESIpos): m/z=413 [M+H]$^+$;

$^1$H-NMR (400 MHz, DMSO-d$_6$): δ=7.70 (d, 2H), 7.57 (d, 2H), 6.81 (dd, 1H), 4.43 (br d, 1H), 4.09 (d, 1H), 3.24 (s, 3H), 3.28-3.18 (m, 3H), 2.97-2.80 (m, 3H), 2.33 (s, 3H), 2.31 (br d, 1H), 1.98 (dd, 1H).

Example 200

{3-(3-Cyclopropyl-1,2,4-oxadiazol-5-yl)-5-[3-(trifluoromethoxy)phenyl]piperidin-1-yl}(4-hydroxypiperidin-1-yl)methanone [racemic cis isomer]

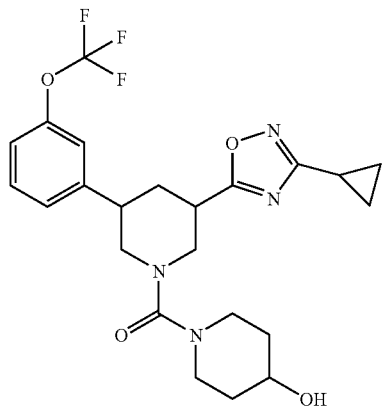

60 mg (0.14 mmol) of the compound from Example 194A and 22 mg (0.22 mmol) of N'-hydroxycyclopropanecarboximidamide were reacted according to the General Method 2. Yield: 45 mg (64% of theory)

LC-MS (Method 3B): $R_t$=2.02 min; MS (ESIpos): m/z=481 [M+H]$^+$;

$^1$H-NMR (400 MHz, CDCl$_3$): δ=7.36 (t, 1H), 7.18 (d, 1H), 7.12 (d, 1H), 7.09 (br s, 1H), 4.05 (br d, 1H), 3.90-3.85 (m, 1H), 3.81 (br d, 1H), 3.61 (br d, 2H), 3.34-3.26 (m, 1H), 3.06-3.01 (m, 3H), 2.99-2.92 (m, 1H), 2.85 (t, 1H), 2.44 (br d, 1H), 2.10-2.04 (m, 1H), 1.99-1.89 (m, 3H), 1.56-1.50 (m, 2H), 1.49 (d, 1H), 1.08-1.02 (m, 4H).

Example 201

(3-Hydroxyazetidin-1-yl){3-{3-[2-(propan-2-yloxy)ethyl]-1,2,4-oxadiazol-5-yl}-5-[4-(trifluoromethyl)phenyl]piperidin-1-yl}methanone [racemic cis isomer]

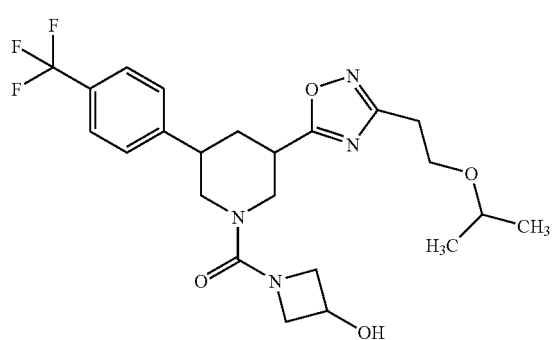

100 mg (0.27 mmol) of the compound from Example 101A and 66 mg (0.40 mmol) of the compound from Example 65A were reacted according to the General Method 2. Yield: 28 mg (20% of theory)

HPLC (Method 2A): $R_t$=4.41 min; MS (DCIpos): m/z=483 [M+H]$^+$;

$^1$H-NMR (400 MHz, DMSO-d$_6$): δ=7.70 (d, 2H), 7.56 (d, 2H), 5.58 (d, OH), 3.43-3.35 (m, 1H), 4.15 (br d, 1H), 4.09 (q, 2H), 3.76 (br d, 1H), 3.72-3.67 (m, 4H), 3.55 (quintett, 1H), 3.05-2.97 (m, 3H), 2.89 (t, 2H), 2.32 (br d, 1H), 2.02 (q, 1H), 1.04 (d, 6H).

Example 202

Morpholin-4-yl{3-[3-(propan-2-yl)-1,2,4-oxadiazol-5-yl]-5-[3-(trifluoromethoxy)phenyl]piperidin-1-yl}methanone [racemic cis isomer]

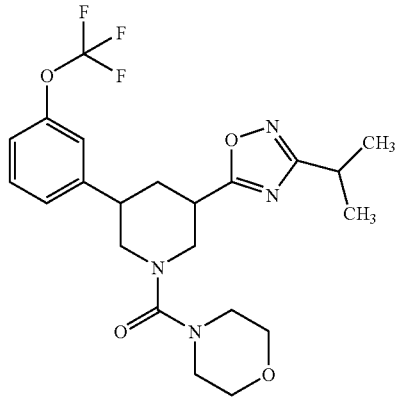

100 mg (0.25 mmol) of the compound from Example 201A and 39 mg (0.37 mmol) of N'-hydroxy-2-propanimidamide were reacted according to the General Method 2. Yield: 79 mg (68% of theory)

LC-MS (Method 2B): R$_t$=1.38 min; MS (ESIpos): m/z=469 [M+H]$^+$;

$^1$H-NMR (400 MHz, DMSO-d$_6$): δ=7.49-7.45 (m, 1H), 7.40-7.36 (m, 2H), 7.25 (d, 1H), 3.98 (br d, 1H), 3.62 (br d, 1H), 3.59-3.55 (m, 4H), 3.41-3.34 (m, 1H), 3.21-3.18 (m, 4H), 3.10-2.85 (m, 4H), 2.31 (br d, 1H), 1.98 (q, 1H), 1.25 (d, 6H).

Example 203

1-{[3-(3-Cyclopropyl-1,2,4-oxadiazol-5-yl)-5-(3,4-dimethylphenyl)piperidin-1-yl]carbonyl}-piperidine-4-carbonitrile [racemic cis isomer]

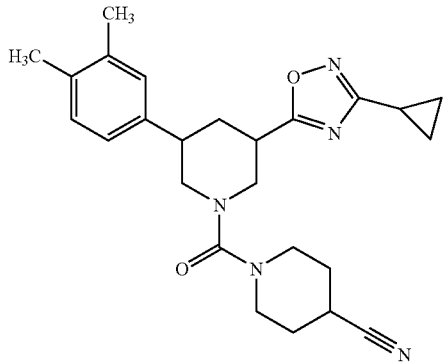

80 mg (0.21 mmol) of the compound from Example 132A and 32 mg (0.32 mmol) of N'-hydroxycyclopropanimidamide were reacted according to the General Method 2. Yield: 41 mg (45% of theory)

LC-MS (Method 3B): R$_t$=2.27 min; MS (ESIpos): m/z=434 [M+H]$^+$;

$^1$H-NMR (400 MHz, DMSO-d$_6$): δ=7.09-7.07 (m, 2H), 6.99 (d, 1H), 3.92 (br d, 1H), 3.52 (br d, 1H), 3.37-3.27 (m, 3H), 3.09-3.03 (m, 3H), 2.96-2.84 (m, 2H), 2.81-2.75 (m, 1H), 2.22 (br d, 1H), 2.20 (s, 3H), 2.18 (s, 3H), 2.14-2.07 (m, 1H), 1.94-1.84 (m, 3H), 1.70-1.62 (m, 2H), 1.09-1.03 (m, 2H), 0.90-0.86 (m, 2H).

Example 204

{3-[3-(3-Fluorophenyl)-1,2,4-oxadiazol-5-yl]-5-[4-(trifluoromethoxy)phenyl]piperidin-1-yl}(3-hydroxypyrrolidin-1-yl)methanone [mixture of diastereomers]

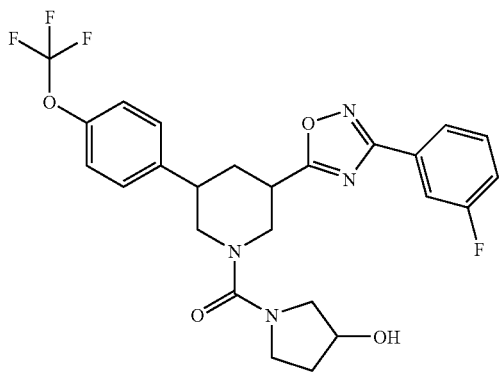

100 mg (0.21 mmol) of the compound from Example 179A and 19 mg (0.21 mmol) of 3-pyrrolidinol were reacted according to the General Method 5. Yield: 43 mg (39% of theory)

LC-MS (Method 1B): R$_t$=2.68 min; MS (ESIpos): m/z=521 [M+H]$^+$;

$^1$H-NMR (400 MHz, DMSO-d$_6$): δ=7.87 (d, 1H), 7.75 (d, 1H), 7.66-7.61 (m, 1H), 7.51-7.44 (m, 3H), 7.34 (d, 2H), 4.89 (d, OH), 4.23 (br s, 1H), 4.17-4.13 (m, 1H), 3.72 (br t, 1H), 3.57-3.41 (m, 3H), 3.15-2.88 (m, 4H), 2.41 (br d, 1H), 2.12-2.01 (m, 1H), 1.87-1.82 (m, 1H), 1.75-1.73 (m, 1H).

Example 205

1-({3-[3-(3-Fluorophenyl)-1,2,4-oxadiazol-5-yl]-5-[4-(trifluoromethoxy)phenyl]piperidin-1-yl}-carbonyl)piperidine-4-carbonitrile [racemic cis isomer]

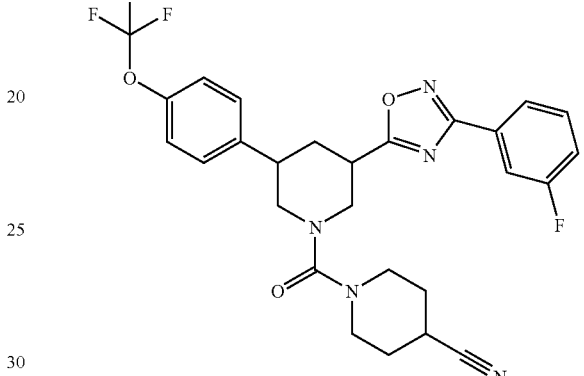

85 mg (0.20 mmol) of 1-[(4-cyanopiperidin-1-yl)carbonyl]-5-[4-(trifluoromethoxy)phenyl]-piperidine-3-carboxylic acid (Example 108A) and 49 mg (0.3 mmol) of 3-fluoro-N'-hydroxybenzenecarboximidamide were reacted according to the General Method 2. Yield: 69 mg (63% of theory).

HPLC (Method 3B): R$_t$=2.59 min; MS (ESIpos): m/z=544.2 [M+H]$^+$;

$^1$H-NMR (400 MHz, DMSO-d$_6$): δ=7.87 (d, 1H), 7.76 (d, 1H), 7.64 (dd, 1H), 7.44-7.52 (m, 3H), 7.34 (bd, 2H), 4.05 (bd, 1H), 3.46-3.65 (m, 2H), 3.35-3.45 (m, 2H), 2.97-3.17 (m, 6H), 2.41 (br d, 1H), 2.07 (q, 1H), 1.83-1.93 (bs, 2H), 1.64-1.75 (bs, 2H).

Example 206

1-({3-(3-tert-Butyl-1,2,4-oxadiazol-5-yl)-5-[4-(trifluoromethoxy)phenyl]piperidin-1-yl}carbonyl)-piperidine-4-carbonitrile [racemic cis isomer]

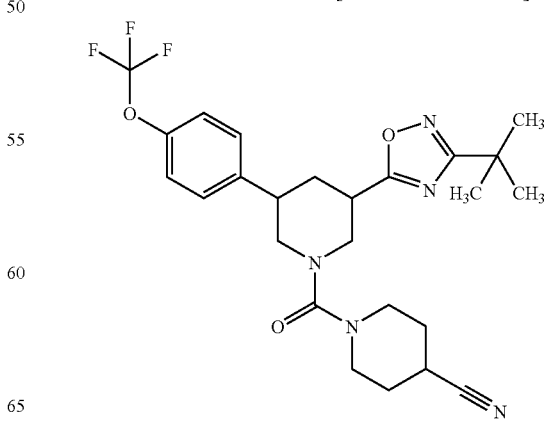

85 mg (0.20 mmol) of 1-[(4-cyanopiperidin-1-yl)carbonyl]-5-[4-(trifluoromethoxy)phenyl]-piperidine-3-carboxylic acid (Example 108A) and 35 mg (0.3 mmol) of N'-hydroxy-2,2-dimethylpropanimidamide were reacted according to the General Method 2. Yield: 61 mg (60% of theory).

HPLC (Method 3B): $R_t$=2.52 min; MS (ESIpos): m/z=506 [M+H]$^+$;

$^1$H-NMR (400 MHz, DMSO-d$_6$): δ=7.47 (d, 2H), 7.33 (d, 2H), 3.96 (bd, 1H), 3.68 (t, 2H), 3.56 (bd, 1H), 3.32-3.43 (m, 3H), 2.93-3.14 (m, 6H), 2.31 (br d, 1H), 1.97 (q, 1H), 1.85 (bd, 2H), 1.61-1.71 (m, 2H), 1.30 (s, 9H).

Example 207

1-({3-[3-(Pyrazin-2-yl)-1,2,4-oxadiazol-5-yl]-5-[4-(trifluoromethoxy)phenyl]piperidin-1-yl}-carbonyl)piperidine-4-carbonitrile [racemic cis isomer]

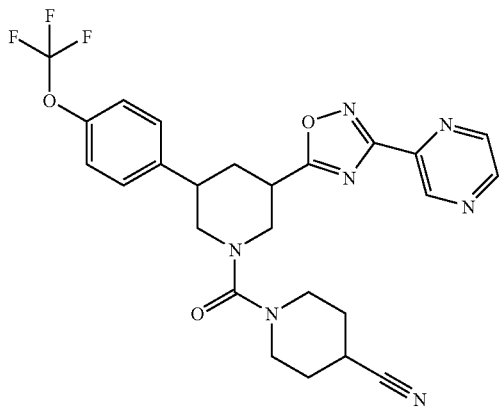

100 mg (0.24 mmol) of 1-[(4-cyanopiperidin-1-yl)carbonyl]-5-[4-(trifluoromethoxy)phenyl]piperidine-3-carboxylic acid (Example 108A) and 49 mg (0.35 mmol) of N'-hydroxypyrazine-2-carboximidamide were reacted according to the General Method 2. Yield: 69 mg (56% of theory).

HPLC (Method 2B): $R_t$=1.28 min; MS (ESIpos): m/z=528 [M+H]$^+$;

$^1$H-NMR (400 MHz, DMSO-d$_6$): δ=9.27 (d, 1H), 8.86-8.90 (m, 2H), 7.49 (d, 2H), 7.34 (d, 1H), 4.07 (bd, 1H), 3.51-3.66 (m, 2H), 3.34-3.45 (m, 2H), 2.97-3.20 (m, 6H), 2.43 (br d, 1H), 2.08 (q, 1H). 1.83-1.94 (m, 2H), 1.64-1.76 (m, 2H).

Example 208

1-({3-[3-(2-Fluorophenyl)-1,2,4-oxadiazol-5-yl]-5-[4-(trifluoromethoxy)phenyl]piperidin-1-yl}-carbonyl)piperidine-4-carbonitrile [racemic cis isomer]

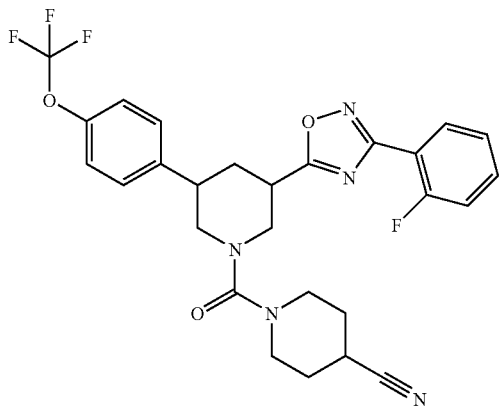

85 mg (0.2 mmol) of 1-[(4-cyanopiperidin-1-yl)carbonyl]-5-[4-(trifluoromethoxy)phenyl]-piperidine-3-carboxylic acid (Example 108A) and 46 mg (0.3 mmol) of 2-fluoro-N'-hydroxybenzenecarboximidamide were reacted according to the General Method 2. Yield: 69 mg (63% of theory).

HPLC (Method 3B): $R_t$=2.48 min; MS (ESIpos): m/z=544 [M+H]$^+$;

$^1$H-NMR (400 MHz, DMSO-d$_6$): δ=8.03 (dt, 1H), 7.62-7.70 (m, 1H), 7.39-7.52 (m, 4H), 7.34 (d, 1H), 4.06 (bd, 1H), 3.47-3.66 (m, 2H), 3.35-3.44 (m, 2H), 2.96-3.17 (m, 6H), 2.41 (br d, 1H), 2.07 (q, 1H), 1.82-1.93 (m, 2H), 1.64-1.76 (m, 2H).

Example 209

{3-[3-(3-Fluorophenyl)-1,2,4-oxadiazol-5-yl]-5-[3-(trifluoromethyl)phenyl]piperidin-1-yl}-(morpholin-4-yl)methanone [racemic cis isomer]

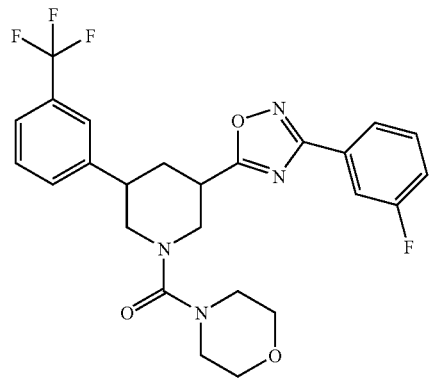

100 mg (0.26 mmol) of the compound from Example 147A and 60 mg (0.39 mmol) of the compound from Example 73A were reacted according to the General Method 2. Yield: 75 mg (57% of theory)

LC-MS (Method 3B): $R_t$=2.46 min; MS (ESIpos): m/z=505 [M+H]$^+$;

$^1$H-NMR (400 MHz, DMSO-d$_6$): δ=7.87 (d, 1H), 7.78-7.76 (m, 2H), 7.68 (d, 1H), 7.62-7.57 (m, 3H), 7.49-7.44 (m, 1H), 4.09 (br d, 1H), 3.64 (br d, 1H), 3.59-3.54 (m, 4H), 3.52-3.47 (m, 1H), 3.24-3.21 (m, 4H), 3.17-3.07 (m, 3H), 2.40 (br d, 1H), 2.14 (q, 1H).

Example 210

(3-Hydroxyazetidin-1-yl) {3-(3-{[1-(hydroxymethyl)cyclopropyl]methyl}-1,2,4-oxadiazol-5-yl)-5-[4-(trifluoromethyl)phenyl]piperidin-1-yl}methanone [racemic cis isomer]

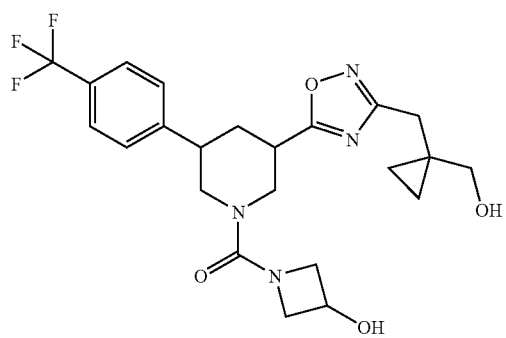

100 mg (0.27 mmol) of the compound from Example 101A and 67 mg (0.40 mmol) of the compound from Example 67A were reacted according to the General Method 2. Yield: 33 mg (26% of theory)

HPLC (Method 2A): $R_t$=4.10 min; MS (DCIpos): m/z=481 [M+H]$^+$;

$^1$H-NMR (400 MHz, CDCl$_3$): δ=7.60 (d, 2H), 7.36 (d, 2H), 4.67-4.63 (m, 1H), 4.32-4.23 (m, 3H), 4.02 (br d, 1H), 3.92-3.89 (m, 2H), 3.51 (s, 2H), 3.32-3.26 (m, 1H), 3.04 (t, 1H), 2.96-2.92 (m, 1H), 2.88-2.78 (m, 2H), 2.85 (s, 2H), 2.50 (br d, 1H), 2.00 (q, 1H), 0.56 (s, 4H).

Example 211

[3-(3,4-Dimethylphenyl)-5-{3-[(propan-2-ylsulphonyl)methyl]-1,2,4-oxadiazol-5-yl}piperidin-1-yl](morpholin-4-yl)methanone [racemic cis isomer]

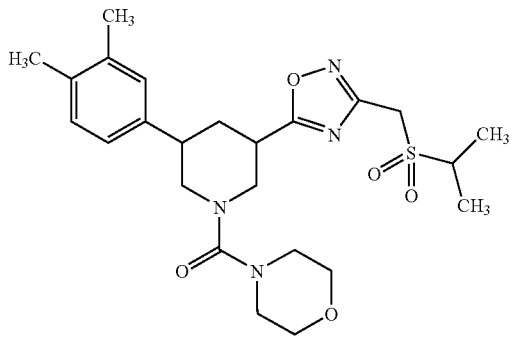

100 mg (0.289 mmol) of the compound from Example 130A and 78 mg (0.433 mmol) of N'-hydroxy-2-(propan-2-ylsulphonyl)ethanimidamide were reacted according to the General Method 2. Yield: 108 mg (75% of theory)

LC-MS (Method 2B): $R_t$=1.21 min; MS (ESIpos): m/z=491 [M+H]$^+$;

$^1$H-NMR (400 MHz, DMSO-d$_6$): δ=7.10-7.08 (m, 2H), 7.01 (d, 1H), 4.82 (s, 2H), 4.06 (br d, 1H), 3.58-3.55 (m, 5H), 3.48-3.42 (m, 2H), 3.20-3.16 (m, 4H), 3.21-3.06 (m, 2H), 2.85-2.80 (m, 1H), 2.31 (br d, 1H), 2.21 (s, 3H), 2.18 (s, 3H), 1.95 (q, 1H), 1.31 (d, 6H).

Example 212

1-({3-[3-(2-Hydroxy-2-methylpropyl)-1,2,4-oxadiazol-5-yl]-5-[4-(trifluoromethyl)phenyl]-piperidin-1-yl}carbonyl)piperidine-4-carbonitrile [racemic cis isomer]

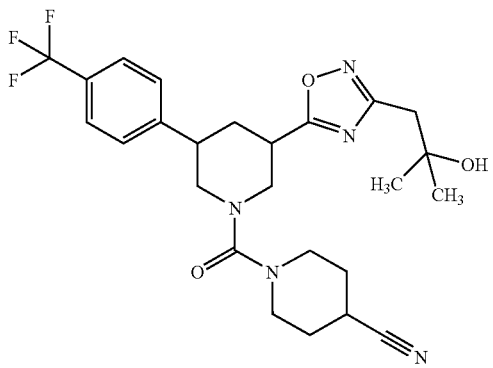

80 mg (0.188 mmol) of the compound from Example 100A and 52 mg (0.281 mmol) of N',3-dihydroxy-3-methylbutanimidamide were reacted according to the General Method 2. Yield: 65 mg (67% of theory)

LC-MS (Method 3B): $R_t$=1.96 min; MS (ESIpos): m/z=506 [M+H]$^+$;

$^1$H-NMR (400 MHz, DMSO-d$_6$): δ=7.70 (d, 2H), 7.57 (d, 2H), 3.98 (br d, 1H), 3.58 (br d, 1H), 3.43-3.36 (m, 3H), 3.11-2.98 (m, 6H), 2.78 (s, 2H), 2.35 (br d, 1H), 2.01 (q, 1H), 1.88-1.85 (m, 2H), 1.71-1.64 (m, 2H), 1.16 (s, 6H).

Example 213

1-({3-{3-[2-(Propan-2-yloxy)ethyl]-1,2,4-oxadiazol-5-yl}-5-[4-(trifluoromethyl)phenyl]piperidin-1-yl}carbonyl)piperidine-4-carbonitrile [racemic cis isomer]

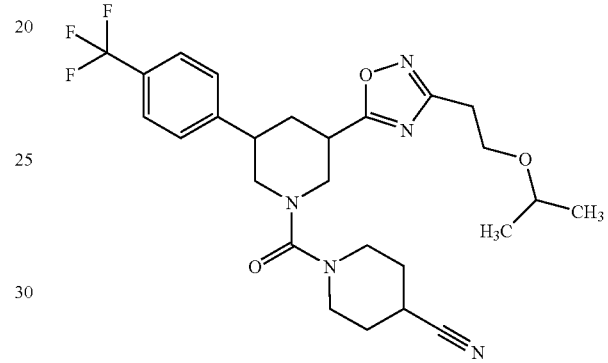

100 mg (0.24 mmol) of the compound from Example 100A and 60 mg (0.37 mmol) of the compound from Example 65A were reacted according to the General Method 2. Yield: 54 mg (42% of theory)

HPLC (Method 1A): $R_t$=4.75 min; MS (ESIpos): m/z=420 [M+H]$^+$;

$^1$H-NMR (400 MHz, DMSO-d$_6$): δ=7.70 (d, 2H), 7.57 (d, 2H), 3.96 (br d, 1H), 3.71 (t, 2H), 3.61-3.51 (m, 2H), 3.44-3.35 (m, 3H), 3.10-2.97 (m, 6H), 2.89 (t, 2H), 2.32 (br d, 1H), 2.01 (q, 1H), 1.88-1.85 (m, 2H), 1.71-1.64 (m, 2H), 1.10 (d, 6H).

Example 214

{3-[3-(3-Fluorophenyl)-1,2,4-oxadiazol-5-yl]-5-[4-(methylsulphonyl)phenyl]piperidin-1-yl}-(morpholin-4-yl)methanone [racemic cis isomer]

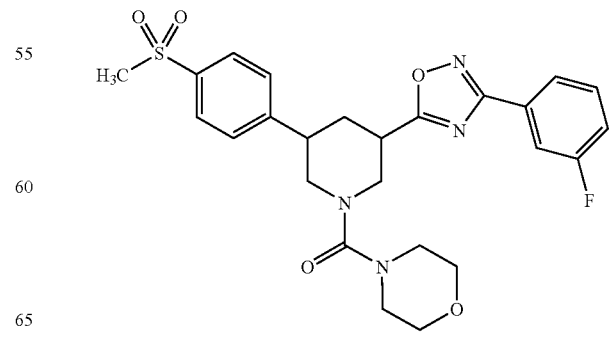

60 mg (0.151 mmol) of the compound from Example 198A and 35 mg (0.227 mmol) of 3-fluoro-N'-hydroxybenzenecarboximidamide were reacted according to the General Method 2. Yield: 54 mg (67% of theory)

LC-MS (Method 1B): $R_t$=2.24 min; MS (ESIpos): m/z=515 [M+H]$^+$;

$^1$H-NMR (400 MHz, DMSO-d$_6$): δ=7.90 (d, 2H), 7.86 (d, 1H), 7.77 (dd, 1H), 7.68-7.61 (m, 3H), 7.49-7.44 (m, 1H), 4.09 (br d, 1H), 3.70 (br d, 1H), 3.59-3.56 (m, 4H), 3.54-3.50 (m, 1H), 3.23-3.19 (m, 6H), 3.17-3.04 (m, 4H), 2.42 (br d, 1H), 2.12 (q, 1H).

Example 215

(1-Aminocyclopentyl) {3-(3-cyclopropyl-1,2,4-oxadiazol-5-yl)-5-[4-(trifluoromethyl)phenyl-piperidin-1-yl}methanone [racemic cis isomer]

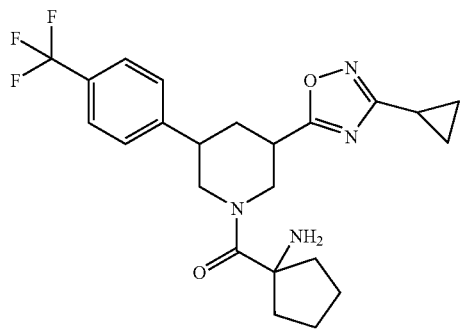

114 mg (0.21 mmol) of the compound from Example 189A were initially charged in 2 ml of dichloromethane, and 160 μl (237 mg, 2.08 mmol) of trifluoroacetic acid were added.

The mixture was stirred at RT for 16 h, 5 ml of ethyl acetate were added and the organic phase was extracted three times with saturated aqueous sodium bicarbonate solution. The organic phase was dried over magnesium sulphate, filtered and concentrated under reduced pressure. Yield: 59 mg (63% of theory)

HPLC (Method 1A): $R_t$=4.32 min; MS (ESIpos): m/z=449 [M+H]$^+$;

$^1$H-NMR (400 MHz, DMSO-d$_6$): δ=7.70 (d, 2H), 7.55 (d, 2H), 5.17-4.54 (2H, NH$_2$), 2.99 (br s, 2H), 2.30 (br d, 1H), 2.15-1.84 (m, 6H), 1.69-1.67 (m, 2H), 1.56-1.51 (m, 4H), 1.08-1.02 (m, 2H), 0.91-0.87 (m, 2H).

Example 216

3-(3,4-Dimethylphenyl)-5-[3-(2-methoxyethyl)-1,2,4-oxadiazol-5-yl]piperidin-1-yl}(3-hydroxy-azetidin-1-yl)methanone [racemic cis isomer]

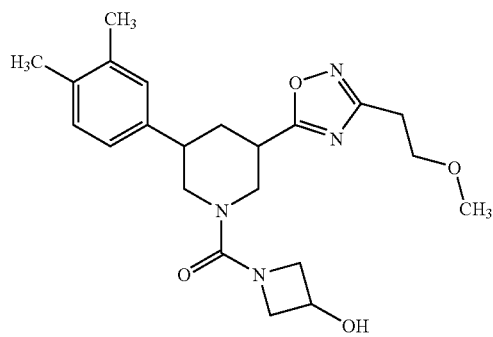

200 mg (0.602 mmol) of the compound from Example 134A and 142 mg (0.903 mmol) of N'-hydroxy-3-methoxypropammidamide were reacted according to the General Method 2. Yield: 99 mg (40% of theory)

LC-MS (Method 1B): $R_t$=2.07 min; MS (ESIpos): m/z=415 [M+H]$^+$.

$^1$H-NMR (400 MHz, DMSO-d$_6$): δ=7.09-7.07 (m, 2H), 6.99 (d, 1H), 5.57 (d, OH), 4.37 (sextet, 1H), 4.14 (br d, 1H), 4.07 (q, 2H), 3.71-3.66 (m, 5H), 3.23 (s, 3H), 3.00-2.85 (m, 4H), 2.77-2.71 (m, 1H), 2.25 (br d, 1H), 2.20 (s, 3H), 2.18 (s, 3H), 1.99 (q, 1H).

Example 217

(4-Hydroxypiperidin-1-yl){3-[3-(2-methoxyethyl)-1,2,4-oxadiazol-5-yl]-5-[3-(trifluoromethoxy)-phenyl]piperidin-1-yl}methanone [racemic cis isomer]

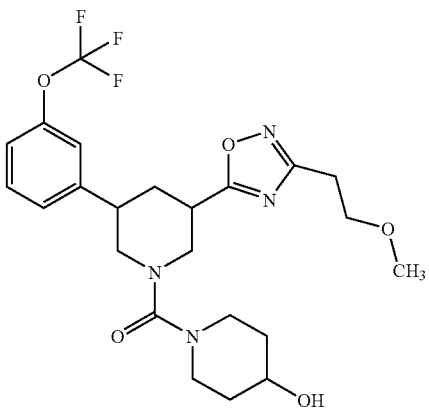

200 mg (0.48 mmol) of the compound from Example 194A and 113 mg (0.72 mmol) of N'-hydroxy-3-methoxypropanimidamide were reacted according to the General Method 2. Yield: 182 mg (73% of theory)

LC-MS (Method 1B): $R_t$=2.20 min; MS (ESIpos): m/z=499 [M+H]$^+$;

$^1$H-NMR (400 MHz, DMSO-d$_6$): δ=7.50-7.44 (m, 1H), 7.39-7.35 (m, 2H), 7.25 (d, 1H), 4.68 (d, OH), 3.94 (br d, 1H), 3.68 (t, 2H), 3.64-3.58 (m, 1H), 3.57 (br d, 1H), 3.50-3.46 (m, 2H), 3.43-3.35 (m, 1H), 3.23 (s, 3H), 3.05-2.88 (m, 7H), 2.34 (br d, 1H), 2.00 (q, 1H), 1.73-1.70 (m, 2H), 1.35-1.26 (m, 2H).

Example 218

[3-[4-(Methylsulphonyl)phenyl]-5-{3-[3-(trifluoromethyl)phenyl]-1,2,4-oxadiazol-5-yl}piperidin-1-yl](morpholin-4-yl)methanone [racemic cis isomer]

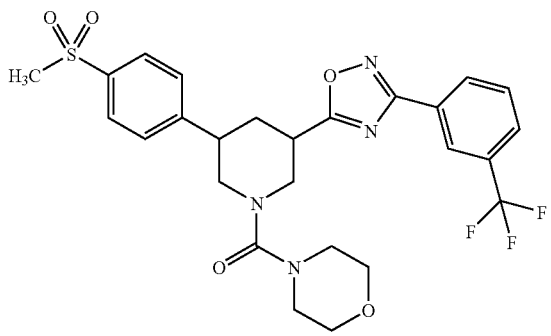

60 mg (0.15 mmol) of the compound from Example 198A and 46 mg (0.23 mmol) of N'-hydroxy-3-(trifluoromethyl)benzenecarboximidamide were reacted according to the General Method 2. Yield: 61 mg (69% of theory)

LC-MS (Method 2B): $R_t$=1.28 min; MS (ESIpos): m/z=565 [M+H]$^+$;

$^1$H-NMR (400 MHz, DMSO-d$_6$): δ=8.35 (d, 1H), 8.25 (s, 1H), 8.02 (d, 1H), 7.91 (d, 2H), 7.82 (dd, 1H), 7.65 (d, 2H), 4.10 (br d, 1H), 3.66 (br d, 1H), 3.59-3.53 (m, 5H), 3.24-3.21 (m, 7H), 3.18-3.08 (m, 3H), 2.42 (br d, 1H), 2.12 (q, 1H).

Example 219

(4-Hydroxypiperidin-1-yl) {3-[3-(pyrazin-2-yl)-1,2,4-oxadiazol-5-yl]-5-[3-(trifluoromethoxy)-phenyl]piperidin-1-yl}methanone [racemic cis isomer]

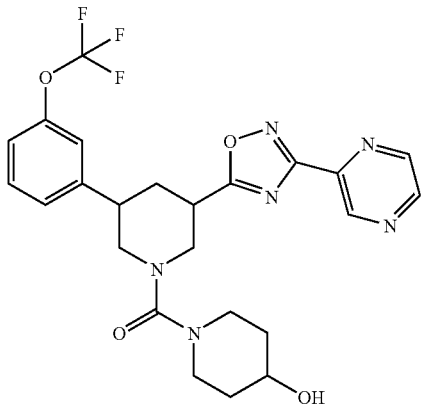

60 mg (0.14 mmol) of the compound from Example 194A and 30 mg (0.22 mmol) of N'-hydroxypyrazin-2-carboximidamide were reacted according to the General Method 2. Yield: 36 mg (48% of theory)

LC-MS (Method 3B): $R_t$=1.79 min; MS (ESIpos): m/z=519 [M+H]$^+$;

$^1$H-NMR (400 MHz, DMSO-d$_6$): δ=9.27 (d, 1H), 8.90-8.86 (m, 2H), 7.50 (dd, 1H), 7.42-7.37 (m, 2H), 7.26 (d, 1H), 4.69 (d, OH), 4.05 (br d, 1H), 3.65-3.39 (m, 5H), 3.14 (t, 1H), 3.09-3.03 (m, 2H), 2.93 (br t, 2H), 2.36 (br d, 1H), 2.08 (q, 1H), 1.74-1.72 (m, 2H), 1.36-1.29 (m, 2H).

Example 220

[3-(3,4-Dimethylphenyl)-5-(3-methyl-1,2,4-oxadiazol-5-yl)piperidin-1-yl] (morpholin-4-yl)-methanone [racemic cis isomer]

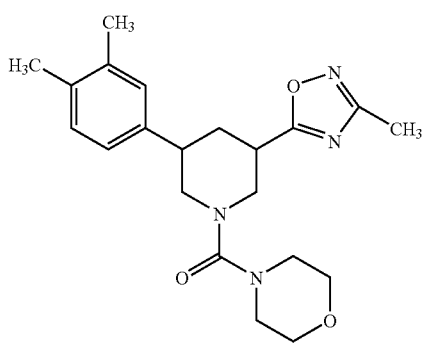

100 mg (0.29 mmol) of the compound from Example 130A and 33 mg (0.43 mmol) of N'-hydroxyacetamidine were reacted according to the General Method 2. Yield: 68 mg (61% of theory)

LC-MS (Method 3B): $R_t$=1.91 min; MS (ESIpos): m/z=385 [M+H]$^+$;

$^1$H-NMR (400 MHz, DMSO-d$_6$): δ=7.09-7.07 (m, 2H), 6.99 (d, 1H), 3.97 (br d, 1H), 3.59-3.55 (m, 5H), 3.40-3.34 (m, 1H), 3.19-3.16 (m, 4H), 3.00 (t, 1H), 2.90 (t, 1H), 2.84-2.75 (m, 1H), 2.33 (s, 3H), 2.26 (br d, 1H), 2.20 (s, 3H), 2.18 (s, 3H), 1.94 (q, 1H).

Example 221

1-({3-[3-(1-Methoxy-2-methylpropan-2-yl)-1,2,4-oxadiazol-5-yl]-5-[4-(trifluoromethyl)phenyl]-piperidin-1-yl}carbonyl)piperidine-4-carbonitrile [racemic cis isomer]

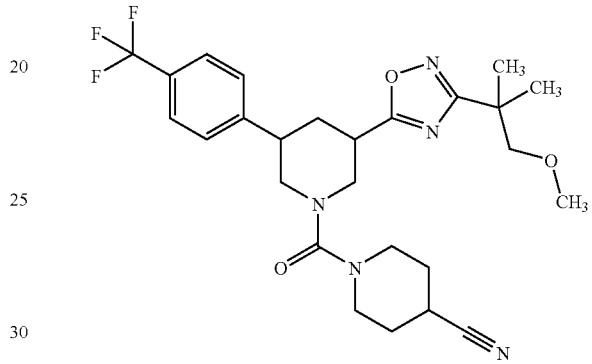

80 mg (0.188 mmol) of the compound from Example 100A and 41 mg (0.281 mmol) of N'-hydroxy-3-methoxy-2,2-dimethylpropanimidamide were reacted according to the General Method 2. Yield: 55 mg (56% of theory)

LC-MS (Method 1B): $R_t$=2.70 min; MS (ESIpos): m/z=520 [M+H]$^+$;

$^1$H-NMR (400 MHz, DMSO-d$_6$): δ=7.70 (d, 2H), 7.58 (d, 2H), 5.57 (d, OH), 3.97 (br d, 1H), 3.58 (br d, 1H), 3.45 (s, 2H), 3.40-3.37 (m, 3H), 3.21 (s, 3H), 3.10-3.00 (m, 5H), 2.32 (br d, 1H), 1.99 (q, 1H), 1.87-1.83 (m, 2H), 1.71-1.67 (m, 2H), 1.26 (s, 6H).

Example 222

1-({3-[3-(1-Cyclopropylpiperidin-4-yl)-1,2,4-oxadiazol-5-yl]-5-[4-(trifluoromethyl)phenyl]-piperidin-1-yl}carbonyl)piperidine-4-carbonitrile [racemic cis isomer]

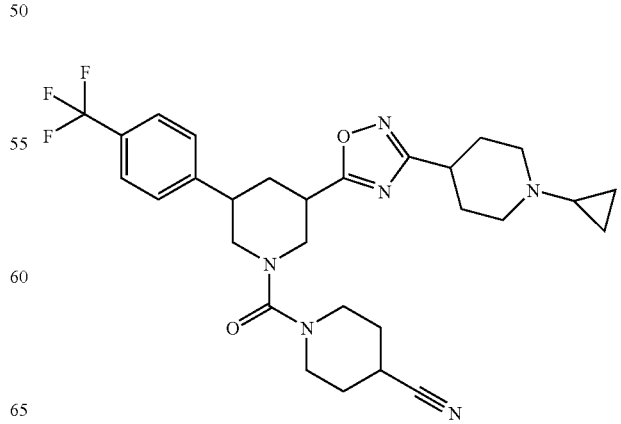

155 mg (0.363 mmol) of the compound from Example 100A and 100 mg (0.545 mmol) of the compound from Example 75A were reacted according to the General Method 2. Yield: 76 mg (38% of theory)

LC-MS (Method 3B): $R_t$=1.36 min; MS (ESIpos): m/z=557 [M+H]$^+$;

$^1$H-NMR (400 MHz, DMSO-d$_6$): δ=7.70 (d, 2H), 7.57 (d, 2H), 3.96 (br d, 1H), 3.58 (br d, 1H), 3.43-3.35 (m, 2H), 3.11-2.93 (m, 8H), 2.80-2.71 (m, 2H), 2.36-2.24 (m, 3H), 2.00 (q, 1H), 1.90-1.85 (m, 4H), 1.71-1.55 (m, 5H), 0.43-0.39 (m, 2H), 0.30-0.27 (m, 2H).

Example 223

{3-(3-Cyclopropyl-1,2,4-oxadiazol-5-yl)-5-[4-(trifluoromethyl)phenyl]piperidin-1-yl}[1-(dimethylamino)cyclopropyl]methanone [racemic cis isomer]

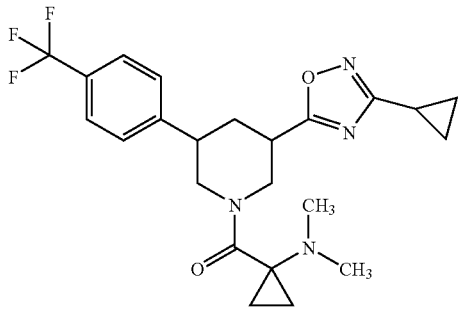

100 mg (0.30 mmol) of the compound from Example 183A and 42 mg (0.33 mmol) of 1-(dimethylamino)cyclopropanecarboxylic acid were reacted according to the General Method 7. Yield: 120 mg (90% of theory)

HPLC (Method 1A): $R_t$=4.31 min; MS (ESIpos): m/z=449 [M+H]$^+$;

$^1$H-NMR (400 MHz, DMSO-d$_6$): δ=7.71 (d, 2H), 7.57 (d, 2H), 4.70 (br d, 1H), 4.38 (br d, 1H), 3.28-3.24 (m, 1H), 3.10-3.01 (m, 3H), 2.32 (br d, 1H), 2.15 (s, 6H), 2.14-2.04 (m, 2H), 1.08-1.03 (m, 2H), 0.91-0.87 (m, 4H), 0.82-0.77 (m, 2H).

Example 224

(3-Aminopyrrolidin-1-yl){3-[3-(3-fluorophenyl)-1,2,4-oxadiazol-5-yl]-5-[4-(trifluoromethoxy)-phenyl]piperidin-1-yl}methanone [mixture of diastereomers]

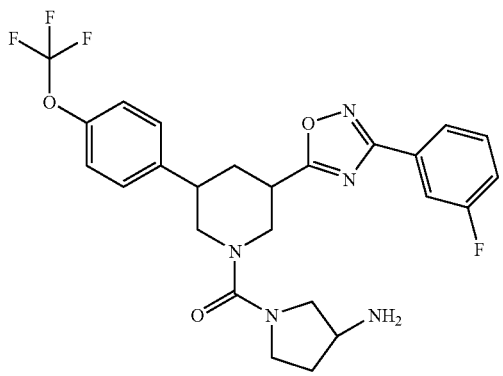

100 mg (0.21 mmol) of the compound from Example 179A and 34 mg (0.21 mmol) of pyrrolidine-3-amine were reacted according to the General Method 5. Yield: 32 mg (28% of theory)

LC-MS (Method 2B): $R_t$=1.17 min; MS (ESIpos): m/z=520 [M+H]$^+$;

$^1$H-NMR (400 MHz, DMSO-d$_6$): δ=7.87 (d, 1H), 7.77 (dd, 1H), 7.66-7.61 (m, 1H), 7.50-7.45 (m, 3H), 7.34 (d, 2H), 4.14 (br d, 1H), 3.72 (br d, 1H), 3.52-3.41 (m, 3H), 3.37-3.35 (m, 2H), 3.06 (t, 1H), 3.01-2.92 (m, 3H), 2.42 (br d, 1H), 2.05 (q, 1H), 1.86 (sextet, 1H), 1.77 (br s, 1H), 1.53 (sextet, 1H).

Example 225

{3-(3-tert-Butyl-1,2,4-oxadiazol-5-yl)-5-[3-(trifluoromethyl)phenyl]piperidin-1-yl}(morpholin-4-yl)methanone [racemic cis isomer]

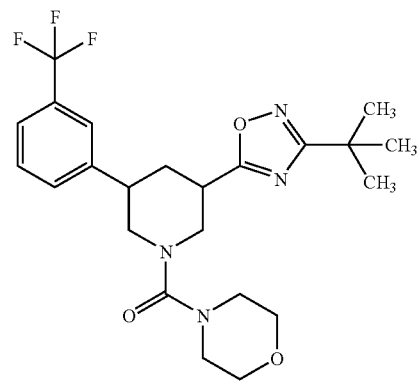

100 mg (0.26 mmol) of the compound from Example 147A and 45 mg (0.39 mmol) of t-hydroxy -2,2-dimethylpropanimidamide (A. Hamze et al. J. Org. Chem. 2003, 68, 7316) were reacted according to the General Method 2. Yield: 89 mg (70% of theory)

LC-MS (Method 2B): $R_t$=1.44 min; MS (ESIpos): m/z=467 [M+H]$^+$;

$^1$H-NMR (400 MHz, DMSO-d$_6$): δ=7.73 (br s, 1H), 7.67 (d, 1H), 7.62 (d, 1H), 7.59-7.55 (m, 1H), 3.98 (br d, 1H), 3.62 (br d, 1H), 3.58-3.54 (m, 4H), 3.42-3.34 (m, 1H), 3.21-3.19 (m, 4H), 3.14-3.04 (m, 3H), 2.32 (br d, 1H), 2.02 (q, 1H), 1.30 (s, 9H).

Example 226

{3-[3-(3-Fluorophenyl)-1,2,4-oxadiazol-5-yl]-5-[3-(trifluoromethyl)phenyl]piperidin-1-yl}(4-hydroxypiperidin-1-yl)methanone [racemic cis isomer]

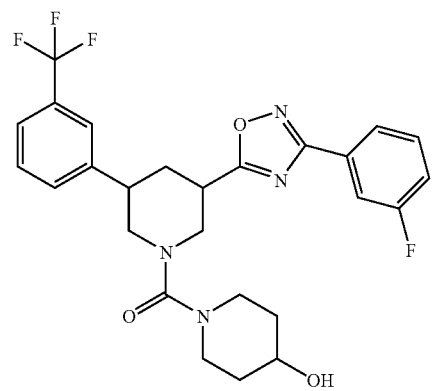

75 mg (0.2 mmol) of the compound from Example 150A and 52 mg (0.3 mmol) of 3-fluoro-N'-hydroxybenzenecarboximidamide were reacted according to the General Method 2. Yield: 16 mg (18% of theory)

LC-MS (Method 2B): $R_t$=1.42 min; MS (ESIpos): m/z=519 [M+H]$^+$;

$^1$H-NMR (400 MHz, DMSO-d$_6$): δ=7.87 (d, 1H), 7.78-7.73 (m, 2H), 7.69-7.59 (m, 4H), 7.49-7.44 (m, 1H), 4.69 (d, OH), 4.04 (br d, 1H), 3.65-3.58 (m, 2H), 3.52-3.49 (m, 3H), 3.18-3.07 (m, 3H), 2.93 (t, 2H), 2.40 (br d, 1H), 2.11 (q, 1H), 1.75-1.71 (m, 2H), 1.37-1.28 (m, 2H).

Example 227

[1-(Aminomethyl)cyclopropyl]{3-[3-(3-fluorophenyl)-1,2,4-oxadiazol-5-yl]-5-[4-(trifluoro-methoxy)phenyl]piperidin-1-yl}methanone [racemic cis isomer]

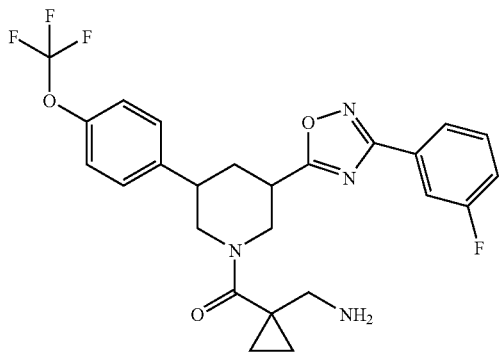

124 mg (0.21 mmol) of the compound from Example 79A were initially charged in 5 ml of dichloromethane, and 158 µl (234 mg, 2.05 mmol) of trifluoroacetic acid were added. The reaction mixture was stirred at RT for 4 h, and then taken up in ethyl acetate and washed with saturated aqueous sodium bicarbonate solution. The organic phase was dried over sodium sulphate, filtered and concentrated under reduced pressure. Yield: 92 mg (88% of theory)

LC-MS (Method 2B): $R_t$=1.21 min; MS (ESIpos): m/z=505 [M+H]$^+$;

$^1$H-NMR (400 MHz, DMSO-d$_6$): δ=7.87 (dd, 1H), 7.75 (dd, 1H), 7.67-7.61 (m, 1H), 7.51-7.45 (m, 3H), 7.36 (d, 2H), 4.81 (br d, 1H), 4.38 (br d, 1H), 3.50-3.45 (m, 1H), 3.25-2.95 (m, 3H), 2.71-2.66 (m, 2H), 2.40 (br d, 1H), 2.15 (q, 1H), 0.79-0.71 (m, 4H).

Example 228

2-Amino-1-{3-[3-(3-fluorophenyl)-1,2,4-oxadiazol-5-yl]-5-[4-(trifluoromethoxy)phenyl]piperidin-1-yl}-2-methylpropan-1-one [racemic cis isomer]

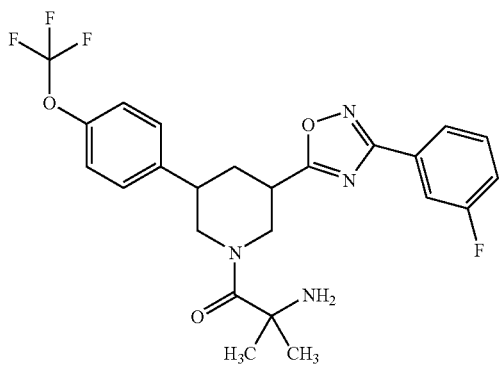

110 mg (0.186 mmol) of the compound from Example 188A were initially charged in 1.4 ml of dichloromethane, and 143 µl (212 mg, 1.87 mmol) of trifluoroacetic acid were added. The reaction mixture was stirred at RT for 12 h, and then taken up in ethyl acetate and washed with saturated aqueous sodium bicarbonate solution and saturated aqueous sodium chloride solution. The organic phase was dried over sodium sulphate, filtered and concentrated under reduced pressure. The crude product was purified by preparative HPLC. Yield: 48 mg (53% of theory)

LC-MS (Method 1B): $R_t$=1.84 min; MS (ESIpos): m/z=493 [M+H]$^+$;

$^1$H-NMR (400 MHz, DMSO-d$_6$): δ=7.87 (dd, 1H), 7.75 (ddd, 1H), 7.67-7.62 (m, 1H), 7.50-7.45 (m, 3H), 7.35 (d, 2H), 5.39 (br s, NH), 5.02 (br s, NH), 3.46-3.42 (m, 1H), 3.08-2.89 (m, 1H), 3.08-2.95 (m, 3H), 2.50 (br d, 1H), 2.16 (q, 1H), 2.04-1.98 (m, 2H), 1.32 (s, 3H), 1.31 (s, 3H).

Example 229

{3-[3-(3-Fluorophenyl)-1,2,4-oxadiazol-5-yl]-5-[3-methyl-4-(trifluoromethoxy)phenyl]piperidin-1-yl}(4-hydroxypiperidin-1-yl)methanone [racemic cis isomer]

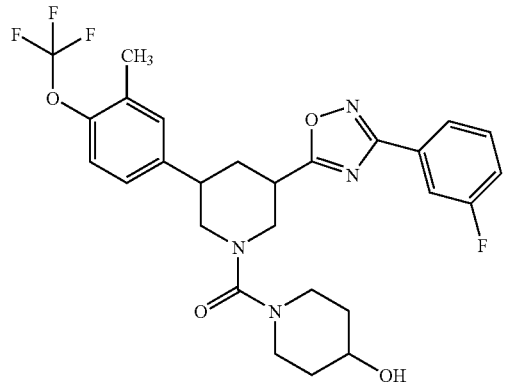

100 mg (0.22 mmol) of the compound from Example 170A and 51 mg (0.33 mmol) of 3-fluoro-N'-hydroxybenzenecarboximidamide were reacted according to the General Method 2. Yield: 60 mg (50% of theory)

LC-MS (Method 2B): $R_t$=1.52 min; MS (ESIpos): m/z=549 [M+H]$^+$;

$^1$H-NMR (400 MHz, DMSO-d$_6$): δ=7.87 (d, 1H), 7.75 (dd, 1H), 7.67-7.61 (m, 1H), 7.49-7.45 (m, 1H), 7.39 (s, 1H), 7.28 (s, 2H), 4.69 (d, OH), 4.05 (br d, 1H), 3.64-3.57 (m, 2H), 3.52-3.49 (m, 3H), 3.09 (t, 1H), 3.02-2.90 (m, 4H), 2.37 (br d, 1H), 2.28 (s, 3H), 2.05 (q, 1H), 1.74-1.71 (m, 2H), 1.37-1.28 (m, 2H).

Example 230

{3-(3-Cyclopropyl-1,2,4-oxadiazol-5-yl)-5-[3-methyl-4-(trifluoromethoxy)phenyl]piperidin-1-yl}(4-hydroxypiperidin-1-yl)methanone [racemic cis isomer]

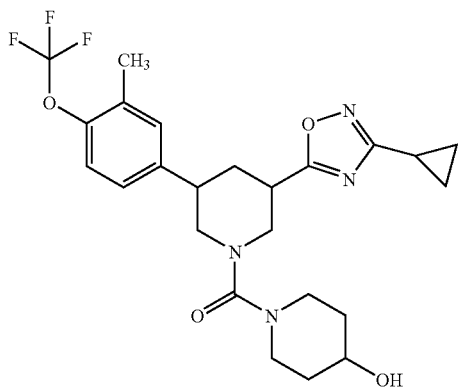

100 mg (0.22 mmol) of the compound from Example 170A and 33 mg (0.331 mmol) of N'-hydroxycyclopropanecarboximidamide were reacted according to the General Method 2. Yield: 41 mg (37% of theory)

LC-MS (Method 9B): $R_t$=1.18 min; MS (ESIpos): m/z=495 [M+H]$^+$;

$^1$H-NMR (400 MHz, DMSO-d$_6$): δ=7.36 (s, 1H), 7.26 (s, 2H), 4.68 (d, OH), 3.90 (br d, 1H), 3.62-3.58 (m, 1H), 3.53 (br d, 1H), 3.49-3.45 (m, 2H), 2.98-2.87 (m, 5H), 2.38-2.35 (m, 4H), 2.14-2.09 (m, 1H), 1.91 (q, 1H), 1.72-1.70 (m, 2H), 1.34-1.25 (m, 2H), 1.08-1.03 (m, 2H), 0.90-0.86 (m, 2H).

Example 231

(4-Hydroxypiperidin-1-yl){3-[3-(2-methoxyethyl)-1,2,4-oxadiazol-5-yl]-5-[3-methyl-4-(trifluoromethoxy)phenyl]piperidin-1-yl}methanone [racemic cis isomer]

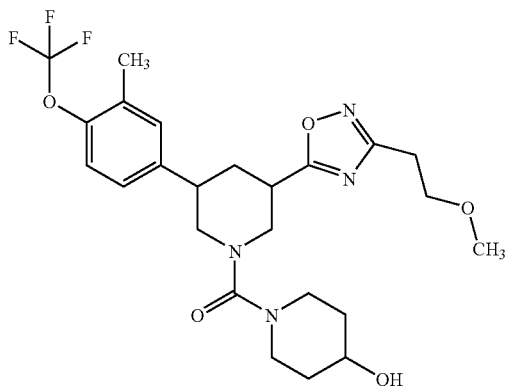

100 mg (0.221 mmol) of the compound from Example 170A and 52 mg (0.331 mmol) of the compound from Example 64A were reacted according to the General Method 2. Yield: 39 mg (35% of theory)

LC-MS (Method 2B): $R_t$=1.26 min; MS (ESIpos): m/z=513 [M+H]$^+$;

$^1$H-NMR (400 MHz, DMSO-d$_6$): δ=7.36 (s, 1H), 7.26 (s, 2H), 4.67 (d, OH), 3.93 (br d, 1H), 3.68 (t, 2H), 3.62-3.58 (m, 1H), 3.56 (br d, 1H), 3.50-3.42 (m, 2H), 3.39-3.33 (m, 1H), 3.23 (s, 3H), 2.96-2.78 (m, 7H), 2.28-2.24 (m, 4H), 1.96 (q, 1H), 1.73-1.70 (m, 2H), 1.32-1.29 (m, 2H).

Example 232

{3-(3,4-Dimethylphenyl)-5-[3-(3-fluorophenyl)-1,2,4-oxadiazol-5-yl]piperidin-1-yl}(4-hydroxy-piperidin-1-yl)methanone [racemic cis isomer]

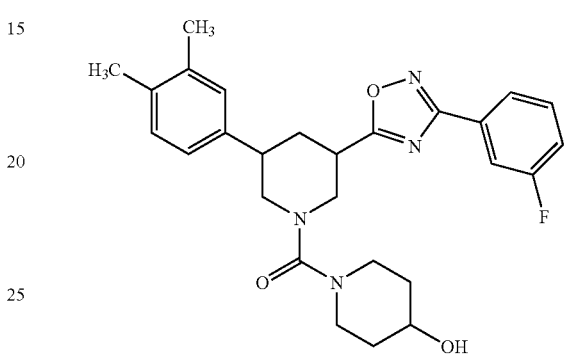

80 mg (0.22 mmol) of the compound from Example 128A and 51 mg (0.33 mmol) of the compound from Example 73A were reacted according to the General Method 2. Yield: 69 mg (65% of theory)

LC-MS (Method 2B): $R_t$=1.45 min; MS (ESIpos): m/z=479 [M+H]$^+$;

$^1$H-NMR (400 MHz, DMSO-d$_6$): δ=7.87 (d, 1H), 7.75 (dd, 1H), 7.67-7.61 (m, 1H), 7.46 (ddd, 1H), 7.10-7.08 (m, 2H), 7.01 (d, 1H), 4.68 (d, OH), 4.04 (br d, 1H), 3.64-3.59 (m, 1H), 3.56-3.46 (m, 4H), 3.07 (t, 1H), 2.97-2.81 (m, 4H), 2.36 (br d, 1H), 2.21 (s, 3H), 2.19 (s, 3H), 2.03 (q, 1H), 1.74-1.71 (m, 2H), 1.36-1.27 (m, 2H).

Example 233

{3-(3,4-Dimethylphenyl)-5-[3-(propan-2-yl)-1,2,4-oxadiazol-5-yl]piperidin-1-yl}(3-hydroxyazetidin-1-yl)methanone [racemic cis isomer]

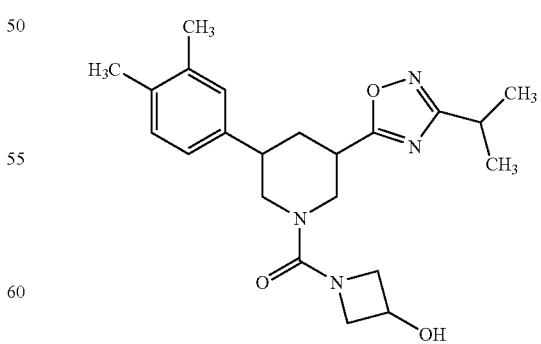

72 mg (0.22 mmol) of the compound from Example 134A and 43 mg (0.33 mmol) of N'-hydroxy-2-methylpropanimidamide were reacted according to the General Method 2. Yield: 17 mg (19% of theory)

LC-MS (Method 2B): R$_t$=1.27 min; MS (ESIpos): m/z=399 [M+H]$^+$;
$^1$H-NMR (400 MHz, DMSO-d$_6$): δ=7.10-7.07 (m, 2H), 7.02 (d, 1H), 5.57 (d, OH), 4.38 (sextet, 1H), 4.15 (br d, 1H), 4.07 (q, 2H), 3.71-3.66 (m, 3H), 3.26-3.22 (m, 1H), 3.09-2.86 (m, 3H), 2.76-2.67 (m, 1H), 2.25 (br d, 1H), 2.21 (s, 3H), 2.18 (s, 3H), 1.96 (q, 1H), 1.25 (d, 6H).

Example 234

{3-(3,4-Dimethylphenyl)-5-[3-(propan-2-yl)-1,2,4-oxadiazol-5-yl]piperidin-1-yl}(4-hydroxy-piperidin-1-yl)methanone [racemic cis isomer]

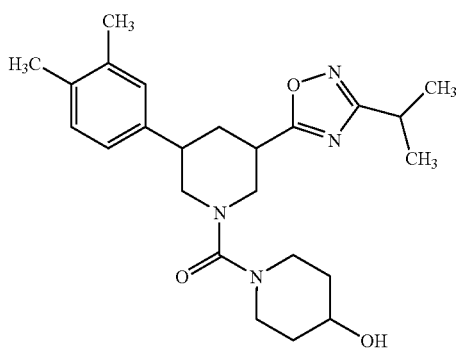

80 mg (0.222 mmol) of the compound from Example 128A and 35 mg (0.333 mmol) of N'-hydroxy-2-methylpropanimidamide were reacted according to the General Method 2.
Yield: 55 mg (59% of theory)
LC-MS (Method 2B): R$_t$=1.32 min; MS (ESIpos): m/z=427 [M+H]$^+$;
$^1$H-NMR (400 MHz, DMSO-d$_6$): δ=7.09-7.07 (m, 2H), 7.00 (d, 1H), 4.68 (d, OH), 3.93 (br d, 1H), 3.63-3.56 (m, 1H), 3.53-3.45 (m, 3H), 3.39-3.34 (m, 1H), 3.09-3.00 (m, 2H), 2.97-2.82 (m, 3H), 2.80-2.76 (m, 1H), 2.26 (br d, 1H), 2.20 (s, 3H), 2.18 (s, 3H), 1.93 (q, 1H), 1.73-1.70 (m, 2H), 1.34-1.26 (m, 2H), 1.25 (d, 6H).

Example 235

(3-Aminopyrrolidin-1-yl) {3-(3-cyclopropyl-1,2,4-oxadiazol-5-yl)-5-[4-(trifluoromethoxy)phenyl]-piperidin-1-yl}methanone [mixture of diastereomers]

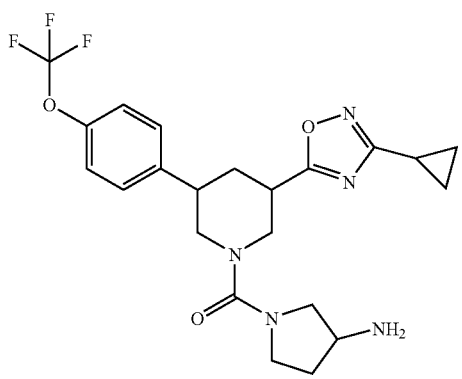

90 mg (0.17 mmol) of the compound from Example 176A and 83 mg (0.52 mmol) of 3-aminopyrrolidine hydrochloride were reacted according to the General Method 6. Yield: 13 mg (15% of theory)
LC-MS (Method 2B): R$_t$=1.05 min; MS (ESIpos): m/z=466 [M+H]$^+$;
$^1$H-NMR (400 MHz, DMSO-d$_6$): δ=7.46 (d, 2H), 7.32 (d, 2H), 4.01 (br d, 1H), 3.68 (br d, 1H), 3.46-3.38 (m, 4H), 2.96-2.87 (m, 4H), 2.28 (br d, 1H), 2.14-2.01 (m, 1H), 1.94-1.84 (m, 2H), 1.51 (sextet, 1H), 1.01-1.07 (m, 2H), 0.90-0.83 (m, 2H).

Example 236

Morpholin-4-yl{3-[3-(propan-2-yl)-1,2,4-oxadiazol-5-yl]-5-[4-(trifluoromethoxy)phenyl]piperidin-1-yl}methanone [racemic cis isomer]

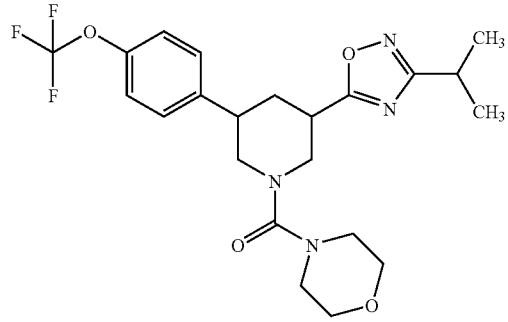

200 mg (0.50 mmol) of the compound from Example 44A and 76 mg (0.75 mmol) of N'-hydroxy-2-methylpropanimidamide were reacted according to the General Method 2.
Yield: 144 mg (58% of theory)
LC-MS (Method 1B): R$_t$=2.58 min; MS (ESIpos): m/z=469 [M+H]$^+$;
$^1$H-NMR (400 MHz, DMSO-d$_6$): δ=7.47 (d, 2H), 7.33 (d, 2H), 3.99 (d, 1H), 3.60 (d, 1H), 3.58-3.54 (m, 4H), 3.38 (tt, 1H), 3.20-3.18 (m, 4H), 3.08-2.92 (m, 4H), 2.31 (br d, 1H), 1.96 (q, 1H), 1.25 (d, 6H).

Example 237

{3-(3-Methyl-1,2,4-oxadiazol-5-yl)-5-[4-(trifluoromethoxy)phenyl]piperidin-1-yl}(morpholin-4-yl)methanone [racemic cis isomer]

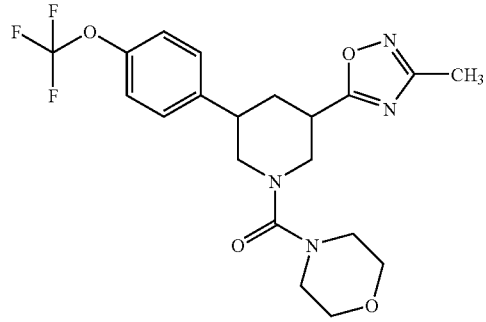

200 mg (0.50 mmol) of the compound from Example 44A and 74 mg (0.75 mmol) of N'-hydroxyethanimidamide were reacted according to the General Method 2. Yield: 119 mg (52% of theory)

LC-MS (Method 1B): $R_t$=2.31 min; MS (ESIpos): m/z=441[M+H]$^+$;

$^1$H-NMR (400 MHz, DMSO-d$_6$): δ=7.46 (d, 2H), 7.33 (d, 2H), 3.98 (d, 1H), 3.61 (d, 1H), 3.58-3.54 (m, 4H), 3.38 (tt, 1H), 3.21-3.19 (m, 4H), 3.03 (t, 1H), 3.00-2.95 (m, 2H), 2.33 (s, 3H), 2.31 (br d, 1H), 1.96 (q, 1H).

Example 238

{3-[3-(Methoxymethyl)-1,2,4-oxadiazol-5-yl]-5-[4-(trifluoromethoxy)phenyl]piperidin-1-yl}-(morpholin-4-yl)methanone [racemic cis isomer]

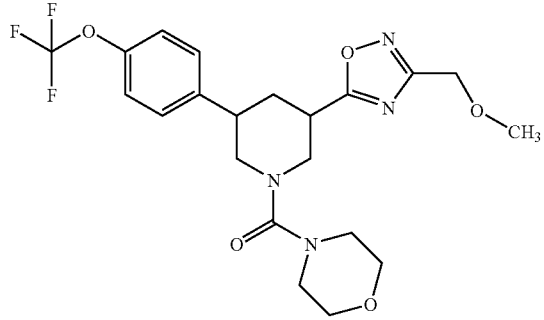

100 mg (0.25 mmol) of the compound from Example 44A and 31 mg (0.30 mmol) of N'-hydroxy-2-methoxyethanimidamide (J. Med. Chem., 1997, 40, 8, 1230-1246) were reacted according to the General Method 1. Yield: 19 mg (16% of theory).

LC-MS (Method 2B): $R_t$=1.25 min; MS (ESIpos): m/z=471[M+H]$^+$;

$^1$H-NMR (400 MHz, DMSO-d$_6$): δ=7.47 (d, 2H), 7.33 (d, 2H), 4.54 (s, 2H), 4.01 (br d, 1H), 3.61 (d, 1H), 3.58-3.54 (m, 4H), 3.44 (tt, 1H), 3.34 (s, 3H), 3.22-3.18 (m, 4H), 3.09-2.94 (m, 3H), 2.33 (br d, 1H), 1.98 (q, 1H).

Example 239

{3-(3-Methyl-1,2,4-oxadiazol-5-yl)-5-[4-(trifluoromethoxy)phenyl]piperidin-1-yl}(morpholin-4-yl)methanone [enantiomerically pure cis isomer]

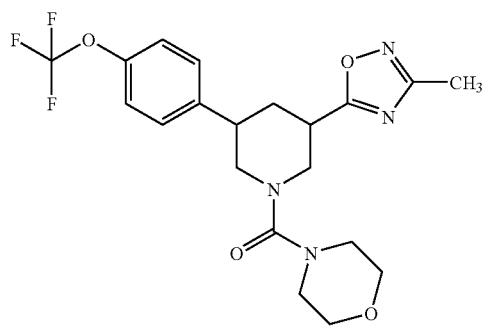

Enantiomer separation of 95 mg of the racemate from Example 237 according to Method 9D gave 42 mg of the title compound from Example 239 and 41 mg of the title compound from Example 240.

HPLC (Method 7E): $R_t$=17.58 min, >99.5% ee;

LC-MS (Method 5B): $R_t$=2.26 min; MS (ESIpos): m/z=441[M+H]$^+$.

Example 240

{3-(3-Methyl-1,2,4-oxadiazol-5-yl)-5-[4-(trifluoromethoxy)phenyl]piperidin-1-yl}(morpholin-4-yl)methanone [enantiomerically pure cis isomer]

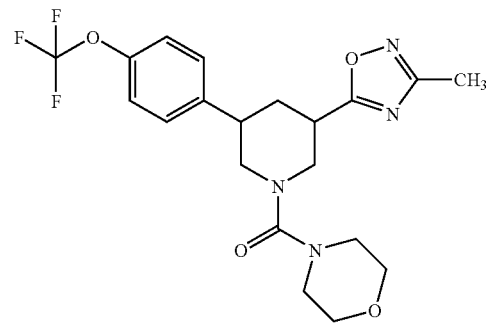

Enantiomer separation of 95 mg of the racemate from Example 237 according to Method 9D gave 42 mg of the title compound from Example 239 and 41 mg of the title compound from Example 240.

HPLC (Method 7E): $R_t$=42.67 min, >99.5% ee;

LC-MS (Method 5B): $R_t$=2.26 min; MS (ESIpos): m/z=441[M+H]$^+$.

Example 241

Morpholin-4-yl {3-[3-(propan-2-yl)-1,2,4-oxadiazol-5-yl]-5-[4-(trifluoromethoxy)phenyl]-piperidin-1-yl}methanone [enantiomerically pure cis isomer]

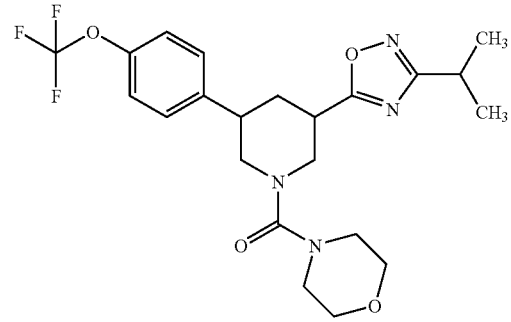

Enantiomer separation of 130 mg of the racemate from Example 236 according to Method 9D gave 52 mg of the title compound from Example 241 and 55 mg of the title compound from Example 242.

HPLC (Method 7E): $R_t$=12.40 min, >99.5% ee;

LC-MS (Method 3B): R$_t$=2.29 min; MS (ESIpos): m/z=469[M+H]$^+$.

Example 242

Morpholin-4-yl {3-[3-(propan-2-yl)-1,2,4-oxadiazol-5-yl]-5-[4-(trifluoromethoxy)phenyl]-piperidin-1-yl}methanone [enantiomerically pure cis isomer]

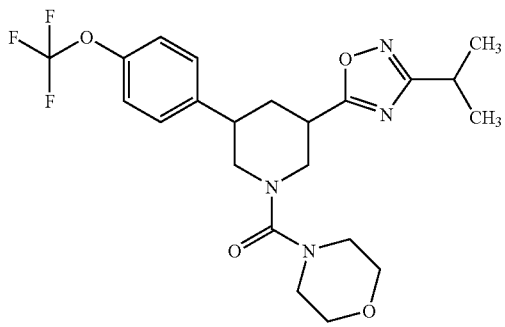

Enantiomer separation of 130 mg of the racemate from Example 236 according to Method 9D gave 52 mg of the title compound from Example 241 and 55 mg of the title compound from Example 242.

HPLC (Method 7E): R$_t$=19.54 min, >99.5% ee;

LC-MS (Method 3B): R$_t$=2.29 min; MS (ESIpos): m/z=469[M+H]$^+$.

Example 243

Morpholin-4-yl{3-(3-propyl-1,2,4-oxadiazol-5-yl)-5-[4-(trifluoromethoxy)phenyl]piperidin-1-yl}-methanone [racemic cis isomer]

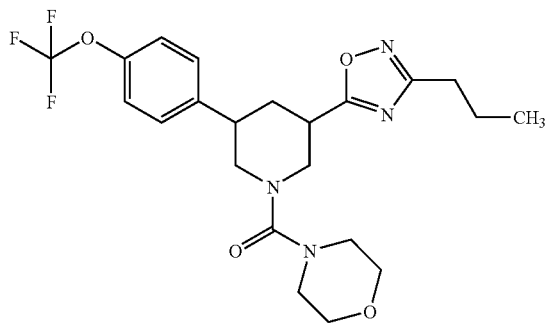

150 mg (0.373 mmol) of the compound from Example 44A and 70 mg (0.746 mmol) of N'-hydroxybutanimidamide were reacted according to the General Method 2. Yield: 174 mg (93% of theory).

LC-MS (Method 2B): R$_t$=1.39 min; MS (ESIpos): m/z=469[M+H]$^+$;

$^1$H-NMR (400 MHz, DMSO-d$_6$): δ=7.47 (d, 2H), 7.33 (d, 2H), 3.98 (br d, 1H), 3.61 (d, 1H), 3.59-3.53 (m, 4H), 3.39 (tt, 1H), 3.22-3.16 (m, 4H), 3.06-2.94 (m, 3H), 2.67 (t, 2H), 2.31 (br d, 1H), 1.96 (q, 1H), 1.72-1.63 (m, 2H), 0.92 (t, 3H).

Example 244

{3-(3-Ethyl-1,2,4-oxadiazol-5-yl)-5-[4-(trifluoromethoxy)phenyl]piperidin-1-yl}(morpholin-4-yl)-methanone [racemic cis isomer]

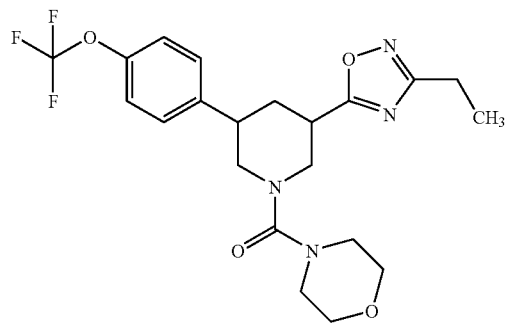

150 mg (0.373 mmol) of the compounds from Example 44A and 66 mg (0.746 mmol) of N'-hydroxypropanimidamide were reacted according to the General Method 2. Yield: 81 mg (93% of theory)

LC-MS (Method 2B): R$_t$=1.32 min; MS (ESIpos): m/z=455 [M+H]$^+$;

$^1$H-NMR (400 MHz, DMSO-d$_6$): δ=7.47 (d, 2H), 7.33 (d, 2H), 3.98 (br d, 1H), 3.61 (d, 1H), 3.59-3.53 (m, 4H), 3.38 (tt, 1H), 3.22-3.16 (m, 4H), 3.07-2.94 (m, 3H), 2.70 (q, 2H), 2.30 (br d, 1H), 1.96 (q, 1H), 1.22 (t, 3H).

Example 245

Morpholin-4-yl{3-[3-(pyrimidin-2-yl)-1,2,4-oxadiazol-5-yl]-5-[4-(trifluoromethoxy)phenyl]-piperidin-1-yl}methanone [racemic cis isomer]

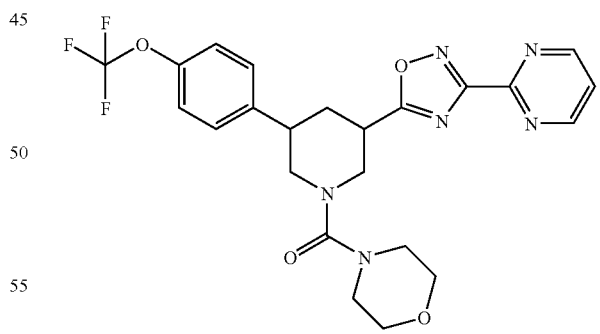

150 mg (0.20 mmol) of 1-(morpholin-4-ylcarbonyl)-5-[4-(trifluoromethoxy)phenyl]piperidine-3-carboxylic acid (Example 44A) and 77 mg (0.56 mmol) of N'-hydroxypyrimidine-2-carboximidamide were reacted according to the General Method 2. Yield: 100 mg (51% of theory).

HPLC (Method 3B): R$_t$=1.84 min; MS (ESIpos): m/z=505 [M+H]$^+$;

$^1$H-NMR (400 MHz, DMSO-d$_6$): δ=9.03 (d, 2H), 7.72 (t, 1H), 7.50 (d, 2H), 7.34 (d, 2H), 4.10 (br d, 1H), 3.65 (br d,

1H), 3.62-3.49 (m, 5H), 3.26-3.18 (m, 4H), 3.15 (t, 1H), 3.08-2.96 (m, 2H), 2.42 (br d, 1H), 2.08 (q, 1H).

Example 246

Morpholin-4-yl(3-[4-(trifluoromethoxy)phenyl]-5-{3-[3-(trifluoromethyl)phenyl]-1,2,4-oxadiazol-5-yl}piperidin-1-yl)methanone [racemic cis isomer]

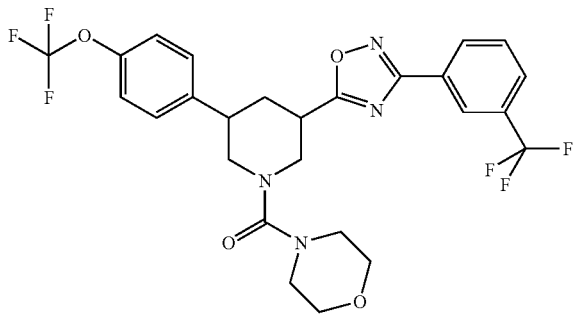

150 mg (0.20 mmol) of 1-(morpholin-4-ylcarbonyl)-5-[4-(trifluoromethoxy)phenyl]piperidine-3-carboxylic acid (Example 44A) and 114 mg (0.56 mmol, 1.5 eq.) of N'-hydroxy-3-(trifluoromethyl)benzenecarboximidamide were reacted according to the General Method 2. Yield: 123 mg (58% of theory).

HPLC (Method 3B): $R_t$=2.69 min; MS (ESIpos): m/z=571 [M+H]$^+$.

Example 247

{3-(3-Cyclopropyl-1,2,4-oxadiazol-5-yl)-5-[4-(trifluoromethoxy)phenyl]piperidin-1-yl}-(morpholin-4-yl)methanone [racemic cis isomer]

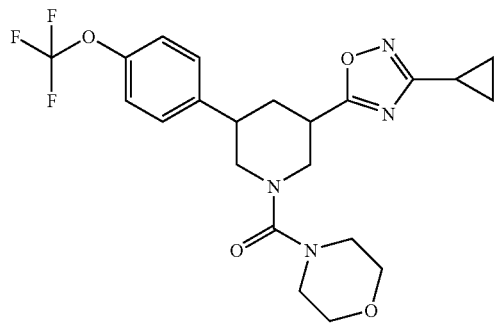

150 mg (0.20 mmol) of 1-(morpholin-4-ylcarbonyl)-5-[4-(trifluoromethoxy)phenyl]piperidine-3-carboxylic acid (Example 44A) and 60 mg (0.56 mmol, 1.5 eq.) of N'-hydroxycyclopropanecarboximidamide were reacted according to the General Method 2. Yield: 104 mg (59% of theory)

HPLC (Method 3B): $R_t$=2.22 min; MS (ESIpos): m/z=467 [M+H]$^+$;

$^1$H-NMR (400 MHz, DMSO-d$_6$): δ=7.46 (d, 2H), 7.32 (d, 2H), 3.96 (br d, 1H), 3.65-3.49 (m, 6H), 3.26-3.39 (m, 1H), 3.19 (t, 4H), 3.09-2.91 (m, 3H), 2.07-2.15 (m, 1H), 1.94 (q, 1H), 1.01-1.10 (m, 2H), 0.85-0.92 (m, 2H).

Example 248

{3-[3-(3,5-Difluoropyridin-2-yl)-1,2,4-oxadiazol-5-yl]-5-[4-(trifluoromethoxy)phenyl]piperidin-1-yl}(morpholin-4-yl)methanone [racemic cis isomer]

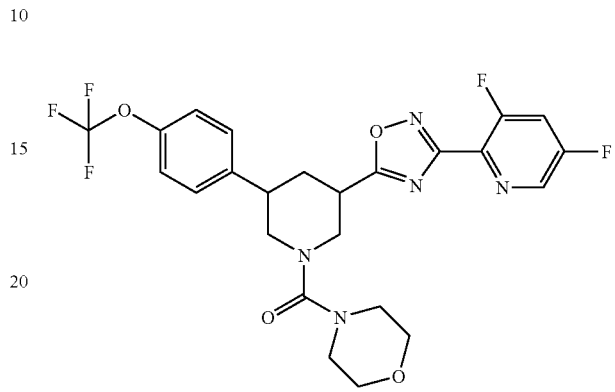

150 mg (0.20 mmol) of 1-(morpholin-4-ylcarbonyl)-5-[4-(trifluoromethoxy)phenyl]piperidine-3-carboxylic acid (Example 44A) and 91 mg (0.56 mmol) of 3,5-difluoro-N'-hydroxypyridine-2-carboximidamide were reacted according to the General Method 2. Yield: 131 mg (63% of theory).

HPLC (Method 2B): $R_t$=1.33 min; MS (ESIpos): m/z=540 [M+H]$^+$.

Example 249

{3-[3-(5-Methylisoxazol-3-yl)-1,2,4-oxadiazol-5-yl]-5-[4-(trifluoromethoxy)phenyl]piperidin-1-yl}(morpholin-4-yl)methanone [racemic cis isomer]

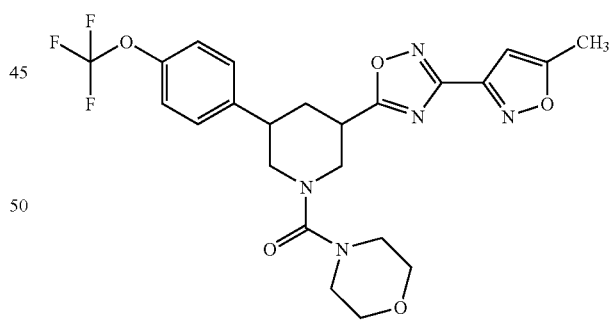

150 mg (0.20 mmol) of 1-(morpholin-4-ylcarbonyl)-5-[4-(trifluoromethoxy)phenyl]piperidine-3-carboxylic acid (Example 44A) and 80 mg (0.56 mmol) of N'-hydroxy-5-methylisoxazole-3-carboximidamide were reacted according to the General Method 2. Yield: 101 mg (54% of theory).

HPLC (Method 2B): $R_t$=1.35 min; MS (ESIpos): m/z=508.1 [M+H]$^+$;

$^1$H-NMR (400 MHz, DMSO-d$_6$): δ=7.49 (d, 2H), 7.34 (d, 2H), 4.08 (br d, 1H), 3.63 (br d, 1H), 3.62-3.49 (m, 5H), 3.22 (t, 4H), 3.13 (t, 1H), 3.01 (bd, 2H), 2.42 (br d, 1H), 2.07 (q, 1H).

Example 250

{3-[3-(2-Methoxyethyl)-1,2,4-oxadiazol-5-yl]-5-[4-(trifluoromethoxy)phenyl]piperidin-1-yl}-(morpholin-4-yl)methanone [racemic cis isomer]

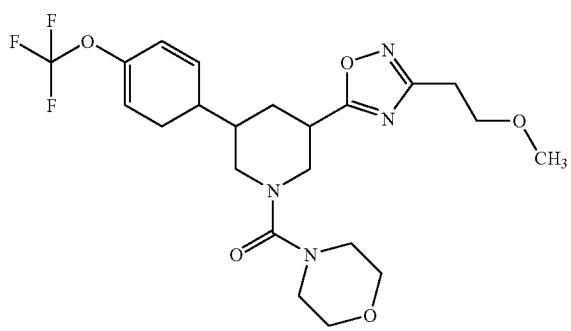

150 mg (0.20 mmol) of 1-(morpholin-4-ylcarbonyl)-5-[4-(trifluoromethoxy)phenyl]piperidine-3-carboxylic acid (Example 44A) and 66 mg (0.56 mmol) of N'-hydroxy-3-methoxypropanimidamide were reacted according to the General Method 2. Yield: 77 mg (42% of theory).

HPLC (Method 2B): $R_t$=1.26 min; MS (ESIpos): m/z=485 [M+H]$^+$;

$^1$H-NMR (400 MHz, DMSO-d$_6$): δ=7.47 (d, 2H), 7.33 (d, 1H), 3.99 (bd, 1H), 3.68 (t, 2H), 3.49-3.64 (m, 5H), 3.34-3.47 (m, 1H), 3.14-3.28 (m, 5H), 2.91-3.09 (m, 5H), 2.32 (br d, 1H), 1.98 (q, 1H).

Example 251

{3-[3-(2-Methylpropyl)isoxazol-5-yl]-5-[4-(trifluoromethoxy)phenyl]piperidin-1-yl}(morpholin-4-yl)methanone [racemic cis isomer]

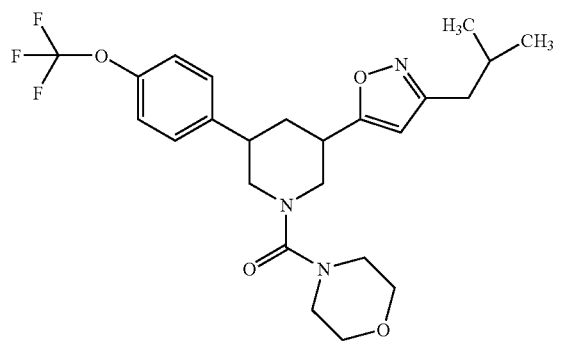

At 0° C., 0.5 ml of a 2.5 M solution of n-butyllithium in hexane was added to a solution of 72 mg (0.62 mmol) of 4-methylpentan-2-one oxime in 0.65 ml of THF. The reaction mixture was stirred at 0° C. for 1 h. A solution of 100 mg (about 0.24 mmol) of the compound from Example 43A in 0.45 ml of THF was then added dropwise. The mixture was allowed to warm to RT and then stirred at RT overnight. Saturated aqueous sodium carbonate solution was added, and the reaction mixture was extracted with dichloromethane. The organic phase was dried over sodium sulphate, filtered and concentrated under reduced pressure. The residue was purified by preparative HPLC. Yield: 51 mg (42% of theory).

LC-MS (Method 9B): $R_t$=1.14 min; MS (ESIpos): m/z=482 [M+H]$^+$.

Example 252

(4-Hydroxypiperidin-1-yl) {3-(3-methyl-1,2,4-oxadiazol-5-yl)-5-[3-(trifluoromethyl)phenyl]-piperidin-1-yl}methanone [racemic cis isomer]

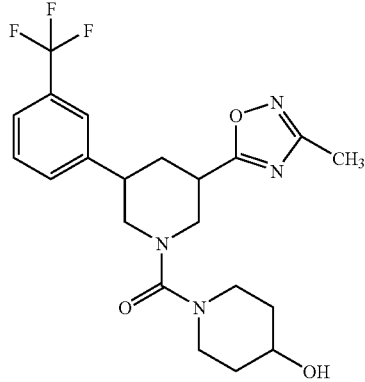

150 mg (0.34 mmol) of the compound from Example 150A and 39 mg (0.51 mmol) of N'-hydroxyacetamidine were reacted according to the General Method 2. Yield: 71 mg (48% of theory)

LC-MS (Method 3B): $R_t$=1.76 min; MS (ESIpos): m/z=439 [M+H]$^+$.

$^1$H-NMR (400 MHz, DMSO-d$_6$): δ=7.70 (s, 1H), 7.66-7.56 (m, 3H), 4.68 (d, OH), 3.93 (br d, 1H), 3.63-3.35 (m, 4H), 3.07-2.97 (m, 3H), 2.93-2.82 (m, 3H), 2.33-2.30 (m, 4H), 2.03 (q, 1H), 1.73-1.70 (m, 2H), 1.32-1.29 (m, 2H).

Example 253

(4-Hydroxypiperidin-1-yl) {3-[3-(propan-2-yl)-1,2,4-oxadiazol-5-yl]-5-[3-(trifluoromethyl)phenyl]-piperidin-1-yl}methanone [racemic cis isomer]

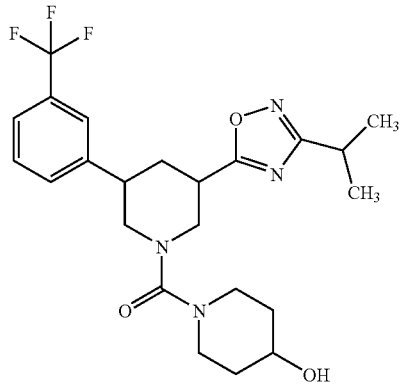

75 mg (0.17 mmol) of the compound from Example 150A and 27 mg (0.25 mmol) of N'-hydroxy-2-methylpropanimidamide were reacted according to the General Method 2. Yield: 26 mg (33% of theory)

LC-MS (Method 3B): R$_t$=2.02 min; MS (ESIpos): m/z=467 [M+H]$^+$;

$^1$H-NMR (400 MHz, DMSO-d$_6$): δ=7.71 (s, 1H), 7.67-7.56 (m, 3H), 4.68 (d, OH), 3.94 (br d, 1H), 3.63-3.57 (m, 1H), 3.57 (br d, 1H), 3.50-3.47 (m, 2H), 3.41-3.34 (m, 1H), 3.08-3.01 (m, 4H), 2.91 (t, 2H), 2.33 (br d, 1H), 2.04 (q, 1H), 1.73-1.70 (m, 2H), 1.34-1.29 (m, 2H), 1.25 (d, 6H).

Example 254

(3-Aminopyrrolidin-1-yl) {3-(3-cyclopropyl-1,2,4-oxadiazol-5-yl)-5-[4-(trifluoromethyl)phenyl]-piperidin-1-yl}methanone [mixture of diastereomers]

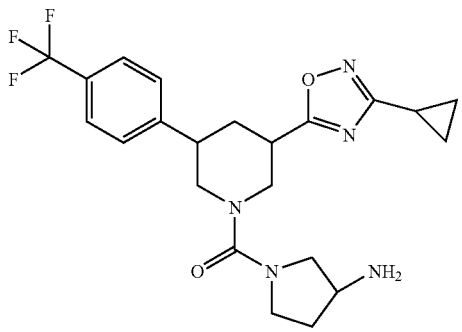

100 mg (0.20 mmol) of the compound from Example 184A and 95 mg (0.60 mmol) of 3-aminopyrrolidine dihydrochloride were reacted according to the General Method 6. Yield: 25 mg (27% of theory)

HPLC (Method 2A): R$_t$=4.17 min; MS (ESIpos): m/z=450 [M+H]$^+$;

$^1$H-NMR (400 MHz, DMSO-d$_6$): δ=7.69 (d, 2H), 7.56 (d, 2H), 4.02 (br d, 1H), 3.70 (br d, 1H), 3.48-3.40 (m, 2H), 3.01-2.91 (m, 4H), 2.29 (br d, 1H), 2.15-2.11 (m, 1H), 1.96 (q, 1H), 1.07-0.99 (m, 2H), 0.90-0.86 (m, 2H).

Example 255

(4-Hydroxypiperidin-1-yl) {3-(3-phenyl-1,2,4-oxadiazol-5-yl)-5-[4-trifluoromethyl)phenyl]-piperidin-1-yl}methanone [racemic cis isomer]

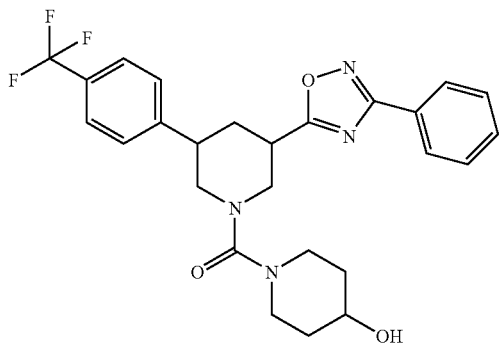

100 mg (0.25 mmol) of 1-[(4-hydroxypiperidin-1-yl)carbonyl]-5-[4-(trifluoromethyl)phenyl]piperidine-3-carboxylic acid (Example 99A) and 39.4 mg (0.28 mmol) of N'-hydroxybenzenecarboximidamide (95% pure) were reacted according to the General Method 1. Yield: 68.3 mg (53% of theory).

LC-MS (Method 1B): R$_t$=2.62 min; MS (ESIpos): m/z=501 [M+H]$^+$;

$^1$H-NMR (400 MHz, DMSO-d$_6$): δ=8.02 (dd, 2H), 7.72 (d, 2H), 7.63-7.54 (m, 5H), 4.69 (d, 1H), 4.05 (br d, 1H), 3.66-3.58 (m, 2H), 3.57-3.45 (m, 3H), 3.17-2.99 (m, 3H), 2.94 (br t, 2H), 2.43 (br d, 1H), 2.11 (dd, 1H), 1.73 (br d, 2H), 1.33 (br q, 2H).

Example 256

{3-[3-(3-Chlorophenyl)-1,2,4-oxadiazol-5-yl]-5-[4-(trifluoromethyl)phenyl]piperidin-1-yl}(4-hydroxypiperidin-1-yl)methanone [racemic cis isomer]

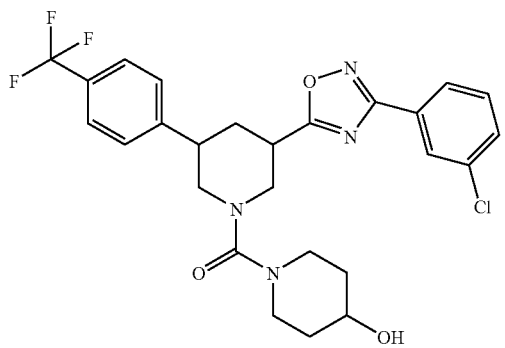

100 mg (0.25 mmol) of 1-[(4-hydroxypiperidin-1-yl)carbonyl]-5-[4-(trifluoromethyl)phenyl]piperidine-3-carboxylic acid (Example 99A) and 46.9 mg (0.28 mmol) of 3-chloro-N'-hydroxybenzenecarboximidamide were reacted according to the General Method 1. Yield: 69.5 mg (52% of theory).

LC-MS (Method 2B): R$_t$=1.49 min; MS (ESIpos): m/z=553 [M+H]$^+$;

$^1$H-NMR (400 MHz, DMSO-d$_6$): δ=8.02-7.96 (m, 2H), 7.75-7.67 (m, 3H), 7.65-7.56 (m, 3H), 4.69 (d, 1H), 4.05 (br d, 1H), 3.67-3.56 (m, 2H), 3.56-3.45 (m, 3H), 3.17-3.02 (m, 3H), 2.93 (br t, 2H), 2.43 (br d, 1H), 2.11 (dd, 1H), 1.74 (br d, 2H), 1.33 (br q, 2H).

Example 257

{3-[3-(3-Fluorophenyl)-1,2,4-oxadiazol-5-yl]-5-[4-(trifluoromethyl)phenyl]piperidin-1-yl}(4-hydroxypiperidin-1-yl)methanone [racemic cis isomer]

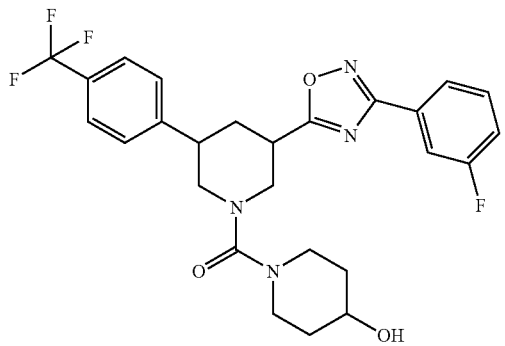

100 mg (0.250 mmol) of 1-[(4-hydroxypiperidin-1-yl)carbonyl]-5-[4-(trifluoromethyl)phenyl]piperidine-3-carboxylic acid (Example 99A) and 42.3 mg (0.275 mmol) of 3-fluoro-N'-hydroxybenzenecarboximidamide (Example 73A) were reacted according to the General Method 1. Yield: 63.9 mg (48% of theory).

LC-MS (Method 2B): $R_t$=1.41 min; MS (ESIpos): m/z=519 [M+H]$^+$;

$^1$H-NMR (400 MHz, DMSO-d$_6$): δ=7.88 (br d, 2H), 7.76 (ddd, 1H), 7.72 (d, 2H), 7.68-7.61 (m, 1H), 7.59 (d, 2H), 7.47 (ddd, 1H), 4.69 (d, 1H), 4.05 (br d, 1H), 3.67-3.58 (m, 2H), 3.56-3.45 (m, 3H), 3.17-2.99 (m, 3H), 2.93 (brt, 2H), 2.43 (br d, 1H), 2.11 (dd, 1H), 1.73 (br d, 2H), 1.33 (br q, 2H).

Example 258

{3-(3-Cyclopropyl-1,2,4-oxadiazol-5-yl)-5-[4-(trifluoromethyl)phenyl]piperidin-1-yl}(4-hydroxy-piperidin-1-yl)methanone [racemic cis isomer]

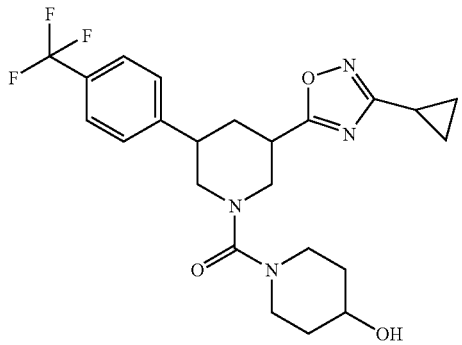

100 mg (0.250 mmol) of 1-[(4-hydroxypiperidin-1-yl)carbonyl]-5-[4-(trifluoromethyl)phenyl]piperidine-3-carboxylic acid (Example 99A) and 27.5 mg (0.275 mmol) of N'-hydroxycyclopropanecarboximidamide (Example 78A) were reacted according to the General Method 1. Yield: 51.8 mg (45% of theory).

LC-MS (Method 3B): $R_t$=1.99 min; MS (ESIpos): m/z=465 [M+H]$^+$;

$^1$H-NMR (400 MHz, DMSO-d$_6$): δ=7.70 (d, 2H), 7.56 (d, 2H), 4.68 (d, 1H), 3.92 (br d, 1H), 3.66-3.53 (m, 2H), 3.52-3.42 (m, 2H), 3.41-3.30 (m, 2H), 3.05-2.94 (m, 3H), 2.90 (br t, 2H), 2.30 (br d, 1H), 2.11 (sept, 1H), 1.97 (dd, 1H), 1.71 (br d, 2H), 1.30 (br q, 2H), 1.09-1.02 (m, 2H), 0.91-0.85 (m, 2H)

Example 259

(4-Hydroxypiperidin-1-yl) {(3-(3-methyl-1,2,4-oxadiazol-5-yl)-5-[4-trifluoromethyl)phenyl]-piperidin-1-yl}methanone [racemic cis isomer]

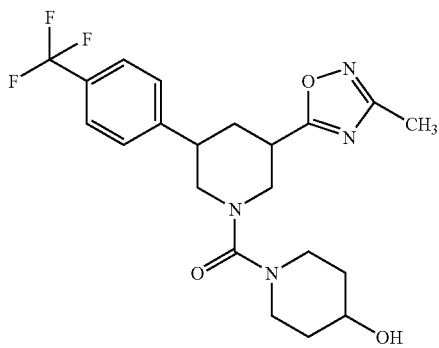

100 mg (0.250 mmol) of 1-[(4-hydroxypiperidin-1-yl)carbonyl]-5-[4-(trifluoromethyl)phenyl]piperidine-3-carboxylic acid (Example 99A) and 20.4 mg (0.275 mmol) of N'-hydroxyacetamidine were reacted according to the General Method 1. Yield: 57.9 mg (51% of theory).

LC-MS (Method 3B): $R_t$=1.78 min; MS (ESIpos): m/z=439 [M+H]$^+$;

$^1$H-NMR (400 MHz, DMSO-d$_6$): δ=7.70 (d, 2H), 7.56 (d, 2H), 4.69 (d, 1H), 3.95 (br d, 1H), 3.66-3.54 (m, 2H), 3.52-3.44 (m, 2H), 3.40 (tt, 1H), 3.10-2.95 (m, 3H), 2.90 (br t, 2H), 2.33 (br s, 4H), 2.01 (dd, 1H), 1.72 (br d, 2H), 1.30 (br q, 2H).

Example 260

(4-Hydroxypiperidin-1-yl){(3-(3-methyl-1,2,4-oxadiazol-5-yl)-5-[4-trifluoromethyl)phenyl]-piperidin-1-yl}methanone [enantiomerically pure cis isomer]

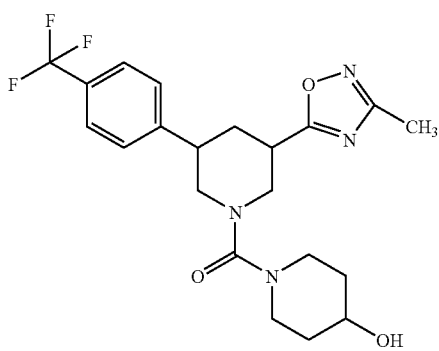

Enantiomer separation of 175 mg of the racemate from Example 259 according to Method 10D gave 73 mg of the title compound from Example 260 and 73 mg of the title compound from Example 261.

HPLC (Method 18E): $R_t$=5.09 min, >99% ee;

LC-MS (Method 3B): $R_t$=1.78 min; MS (ESIpos): m/z=439 [M+H]$^+$.

Example 261

(4-Hydroxypiperidin-1-yl) {(3-(3-methyl-1,2,4-oxadiazol-5-yl)-5-[4-trifluoromethyl)phenyl]-piperidin-1-yl}methanone [enantiomerically pure cis isomer]

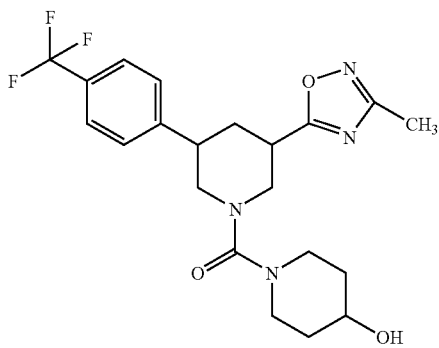

Enantiomer separation of 175 mg of the racemate from Example 259 according to Method 10D gave 73 mg of the title compound from Example 260 and 73 mg of the title compound from Example 261.

HPLC (Method 18E): $R_t$=19.4 min, >99% ee;

LC-MS (Method 3B): $R_t$=1.78 min; MS (ESIpos): m/z=439 [M+H]$^+$.

Example 262

{3-(3-tert-Butyl-1,2,4-oxadiazol-5-yl)-5-[4-(trifluoromethyl)phenyl]piperidin-1-yl}(4-hydroxypiperidin-1-yl)methanone [racemic cis isomer]

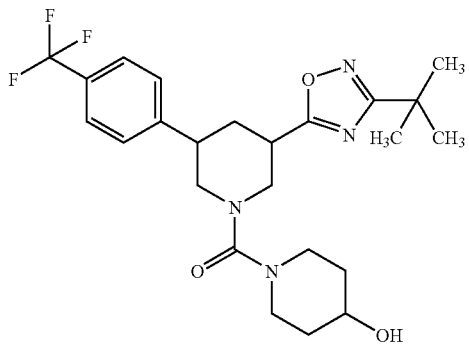

100 mg (0.250 mmol) of 1-[(4-hydroxypiperidin-1-yl)carbonyl]-5-[4-(trifluoromethyl)phenyl]piperidine-3-carboxylic acid (Example 99A) and 31.9 mg (0.275 mmol) of N'-hydroxy-2,2-dimethylpropanimidamide were reacted according to the General Method 1. Yield: 55.6 mg (46% of theory).

LC-MS (Method 3B): $R_t$=2.20 min; MS (ESIpos): m/z=481 [M+H]$^+$.

$^1$H-NMR (400 MHz, DMSO-d$_6$): δ=7.70 (d, 2H), 7.57 (d, 2H), 4.68 (d, 1H), 3.95 (br d, 1H), 3.66-3.53 (m, 2H), 3.52-3.44 (m, 2H), 3.39 (tt, 1H), 3.10-2.98 (m, 3H), 2.90 (br t, 2H), 2.33 (br d, 4H), 2.01 (dd, 1H), 1.72 (br d, 2H), 1.30 (br s, 2H).

Example 263

(4-Hydroxypiperidin-1-yl) {(3-[3-(propan-2-yl)-1,2,4-oxadiazol-5-yl]-5-[4-(trifluoromethyl)phenyl]piperidin-1-yl}methanone [racemic cis isomer]

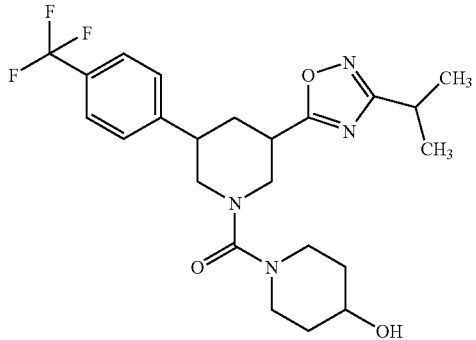

100 mg (0.250 mmol) of 1-[(4-hydroxypiperidin-1-yl)carbonyl]-5-[4-(trifluoromethyl)phenyl]piperidine-3-carboxylic acid (Example 99A) and 28.1 mg (0.275 mmol) of N'-hydroxy-2-methylpropanimidamide were reacted according to the General Method 1. Yield: 71.4 mg (60% of theory).

LC-MS (Method 1B): $R_t$=2.40 min; MS (ESIpos): m/z=467 [M+H]$^+$;

$^1$H-NMR (400 MHz, DMSO-d$_6$): δ=7.70 (d, 2H), 7.57 (d, 2H), 4.67 (d, 1H), 3.95 (br d, 1H), 3.66-3.54 (m, 2H), 3.53-3.44 (m, 2H), 3.40 (tt, 1H), 3.10-2.96 (m, 4H), 2.90 (br t, 2H), 2.33 (br d, 1H), 2.01 (dd, 1H), 1.72 (br d, 2H), 1.31 (br q, 2H), 1.25 (d, 6H).

Example 264

(4-Hydroxypiperidin-1-yl) {(3-[3-(propan-2-yl)-1,2,4-oxadiazol-5-yl]-5-[4-(trifluoromethyl)phenyl]piperidin-1-yl}methanone [enantiomerically pure cis isomer]

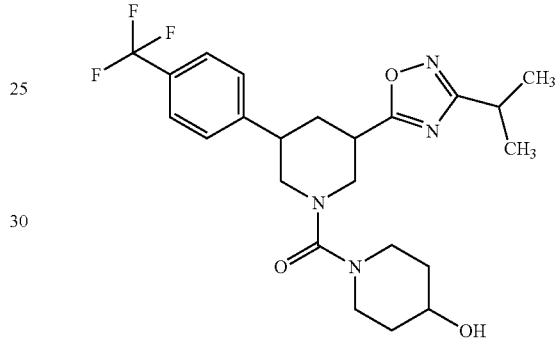

Enantiomer separation of 209 mg of the racemate from Example 263 according to Method 10D gave 90.4 mg of the title compound from Example 264 and 94.5 mg of the title compound from Example 265.

HPLC (Method 18E) $R_t$=4.34 min, >99% ee;

LC-MS (Method 1B): $R_t$=2.40 min; MS (ESIpos): m/z=467 [M+H]$^+$.

Example 265

(4-Hydroxypiperidin-1-yl) {(3-[3-(propan-2-yl)-1,2,4-oxadiazol-5-yl]-5-[4-(trifluoromethyl)phenyl]piperidin-1-yl}methanone [enantiomerically pure cis isomer]

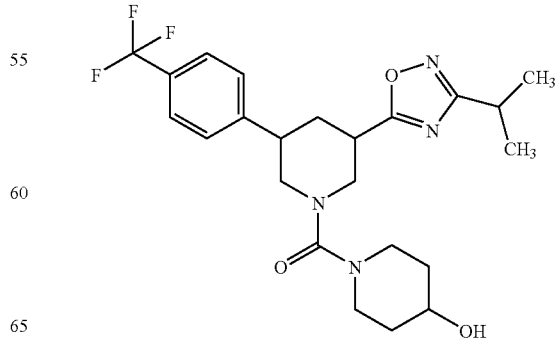

Enantiomer separation of 209 mg of the racemate from Example 263 according to Method 10D gave 90.4 mg of the title compound from Example 264 and 94.5 mg of the title compound from Example 265.

HPLC (Method 18E): R$_t$=7.37 min, >99% ee;
LC-MS (Method 1B): R$_t$=2.40 min; MS (ESIpos): m/z=467 [M+H]$^+$.

Example 266

(4-Hydroxypiperidin-1-yl) {3-[3-(pyridin-3-yl)-1,2,4-oxadiazol-5-yl]-5-[4-(trifluoromethyl)phenyl]piperidin-1-yl}methanone [racemic cis isomer]

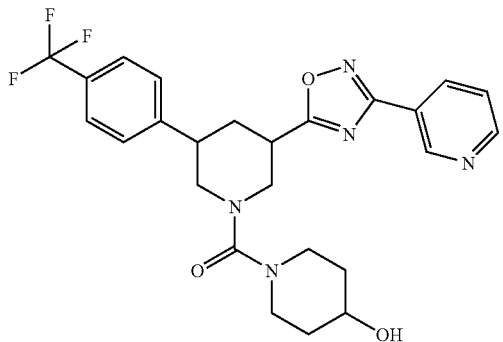

100 mg (0.250 mmol) of 1-[(4-hydroxypiperidin-1-yl)carbonyl]-5-[4-(trifluoromethyl)phenyl]piperidine-3-carboxylic acid (Example 99A) and 37.7 mg (0.275 mmol) of N'-hydroxypyridine-3-carboximidamide were reacted according to the General Method 1. Yield: 26.0 mg (21% of theory).

LC-MS (Method 1B): R$_t$=2.20 min; MS (ESIpos): m/z=502 [M+H]$^+$;
$^1$H-NMR (400 MHz, DMSO-d$_6$): δ=9.17 (dd, 1H), 8.79 (dd, 1H), 8.37 (dt, 1H), 7.72 (d, 2H), 7.62 (ddd, 1H), 7.60 (d, 2H), 7.69 (d, 1H), 4.69 (d, 1H), 4.06 (br d, 1H), 3.67-3.45 (m, 5H), 3.18-3.00 (m, 3H), 2.93 (br t, 2H), 2.43 (br d, 1H), 2.12 (dd, 1H), 1.73 (br d, 2H), 1.33 (br q, 2H).

Example 267

{3-(3-Benzyl-1,2,4-oxadiazol-5-yl)-5-[4-(trifluoromethyl)phenyl]piperidin-1-yl}(4-hydroxypiperidin-1-yl)methanone [racemic cis isomer]

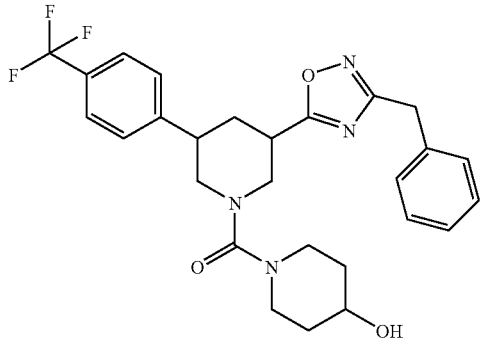

100 mg (0.250 mmol) of 1-[(4-hydroxypiperidin-1-yl)carbonyl]-5-[4-(trifluoromethyl)phenyl]piperidine-3-carboxylic acid (Example 99A) and 41.3 mg (0.275 mmol) of N'-hydroxy-2-phenylethanimidamide were reacted according to the General Method 1. Yield: 61.5 mg (47% of theory).

LC-MS (Method 2B): R$_t$=1.34 min; MS (ESIpos): m/z=515 [M+H]$^+$;
$^1$H-NMR (400 MHz, DMSO-d$_6$): δ=7.69 (d, 2H), 7.55 (d, 2H), 7.36-7.22 (m, 5H), 4.67 (d, 1H), 4.09 (s, 2H), 3.94 (br d, 1H), 3.65-3.53 (m, 2H), 3.52-3.44 (m, 2H), 3.40 (tt, 1H), 3.07-2.94 (m, 3H), 2.90 (br t, 2H), 2.31 (br d, 1H), 1.99 (dd, 1H), 1.71 (br d, 2H), 1.30 (br q, 2H).

Example 268

(4-Hydroxypiperidin-1-yl) {3-[3-(pyridin-4-yl)-1,2,4-oxadiazol-5-yl]-5-[4-(trifluoromethyl)phenyl]-piperidin-1-yl}methanone [racemic cis isomer]

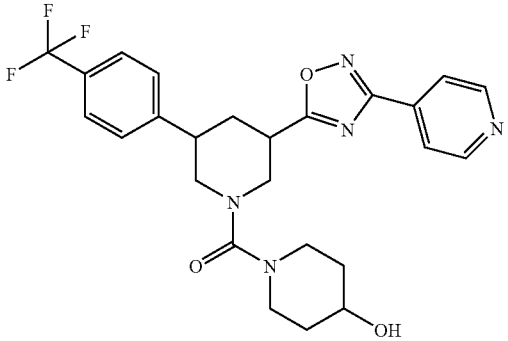

100 mg (0.250 mmol) of 1-[(4-hydroxypiperidin-1-yl)carbonyl]-5-[4-(trifluoromethyl)phenyl]piperidine-3-carboxylic acid (Example 99A) and 37.7 mg (0.275 mmol) of N'-hydroxypyridine-4-carboximidamide were reacted according to the General Method 1. Yield: 88.7 mg (69% of theory).

LC-MS (Method 2B): R$_t$=1.18 min; MS (ESIpos): m/z=502 [M+H]$^+$;
$^1$H-NMR (400 MHz, DMSO-d$_6$): δ=8.83 (dd, 2H), 7.98 (dd, 2H), 7.72 (d, 2H), 7.59 (d, 2H), 4.03 (br d, 1H), 3.68-3.45 (m, 3H), 3.18-3.00 (m, 3H), 2.93 (br t, 2H), 2.44 (br d, 1H), 2.11 (dd, 2H), 1.73 (br d, 2H), 1.32 (br q, 2H).

Example 269

{3-[3-(2-Fluorophenyl)-1,2,4-oxadiazol-5-yl]-5-[4-(trifluoromethyl)phenyl]piperidin-1-yl}(4-hydroxypiperidin-1-yl)methanone [racemic cis isomer]

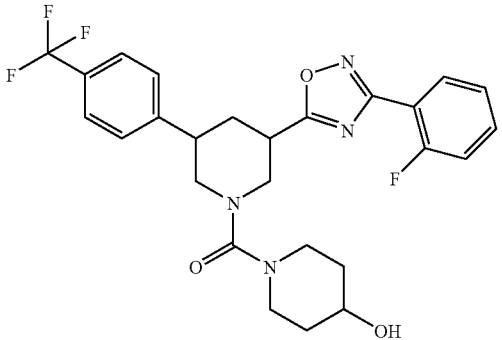

100 mg (0.250 mmol) of 1-[(4-hydroxypiperidin-1-yl)carbonyl]-5-[4-(trifluoromethyl)phenyl]piperidine-3-carboxylic acid (Example 99A) and 42.3 mg (0.275 mmol) of 2-fluoro-N'-hydroxybenzenecarboximidamide were reacted according to the General Method 1. Yield: 55.6 mg (42% of theory).

LC-MS (Method 3B): $R_t$=2.19 min; MS (ESIpos): m/z=519 [M+H]$^+$;

$^1$H-NMR (400 MHz, DMSO-d$_6$): δ=8.03 (dt, 1H), 7.72 (d, 2H), 7.70-7.63 (m, 1H), 7.59 (d, 2H), 4.69 (d, 1H), 4.05 (br d, 1H), 3.66-3.45 (m, 5H), 3.17-2.99 (m, 3H), 2.93 (br t, 2H), 2.43 (br d, 1H), 2.11 (dd, 1H), 1.74 (br d, 2H), 1.33 (br q, 2H).

Example 270

{3-[3-(4-Fluorophenyl)-1,2,4-oxadiazol-5-yl]-5-[4-(trifluoromethyl)phenyl]piperidin-1-yl}(4-hydroxypiperidin-1-yl)methanone [racemic cis isomer]

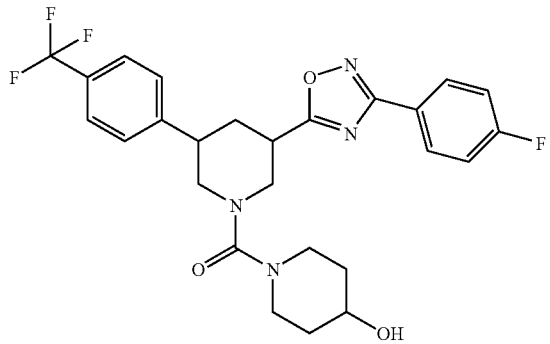

100 mg (0.250 mmol) of 1-[(4-hydroxypiperidin-1-yl)carbonyl]-5-[4-(trifluoromethyl)phenyl]piperidine-3-carboxylic acid (Example 99A) and 42.3 (0.275 mmol) of 4-fluoro-N'-hydroxybenzenecarboximidamide were reacted according to the General Method 1. Yield: 59.1 mg (46% of theory).

LC-MS (Method 3B): $R_t$=2.29 min; MS (ESIpos): m/z=519 [M+H]$^+$;

$^1$H-NMR (400 MHz, DMSO-d$_6$): δ=8.07 (m$_c$, 2H), 7.72 (d, 2H), 7.59 (d, 2H), 7.41 (tt, 2H), 4.69 (d, 1H), 4.05 (br d, 1H), 3.67-3.57 (m, 2H), 3.56-3.45 (m, 3H), 3.16-2.98 (m, 3H), 2.93 (br t, 2H), 2.42 (br d, 1H), 2.10 (dd, 1H), 1.73 (br d, 2H), 1.32 (br q, 2H).

Example 271

(4-Hydroxypiperidin-1-yl) {3-{3-[(methylsulphonyl)methyl]-1,2,4-oxadiazol-5-yl}-5-[4-(trifluoro-methyl)phenyl]piperidin-1-yl}methanone [racemic cis isomer]

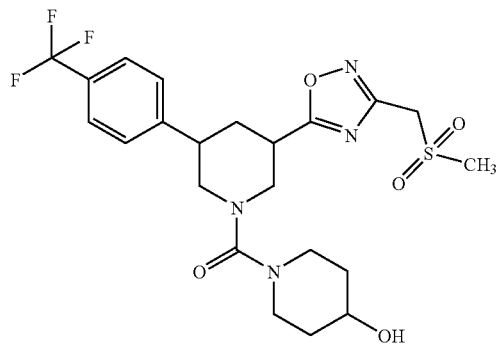

100 mg (0.250 mmol) of 1-[(4-hydroxypiperidin-1-yl)carbonyl]-5-[4-(trifluoromethyl)phenyl]piperidine-3-carboxylic acid (Example 99A) and 41.8 mg (0.275 mmol) of N'-hydroxy-2-(methylsulphonyl)ethanimidamide were reacted according to the General Method 1. Yield: 20.6 mg (16% of theory).

LC-MS (Method 1B): $R_t$=2.03 min; MS (ESIpos): m/z=517 [M+H]$^+$;

$^1$H-NMR (400 MHz, DMSO-d$_6$): δ=7.71 (d, 2H), 7.57 (d, 2H), 4.85 (s, 2H), 4.69 (d, 1H), 3.99 (br d, 1H), 3.67-3.55 (m, 2H), 3.55-3.44 (m, 3H), 3.17 (s, 3H), 3.03 (quin, 3H), 2.92 (br t, 2H), 2.37 (br d, 1H), 2.04 (dd, 1H), 1.72 (br d, 2H), 1.31 (br q, 2H).

Example 272

{3-[3-(2,4-Difluorophenyl)-1,2,4-oxadiazol-5-yl]-5-[4-(trifluoromethyl)phenyl]piperidin-1-yl}(4-hydroxypiperidin-1-yl)methanone [racemic cis isomer]

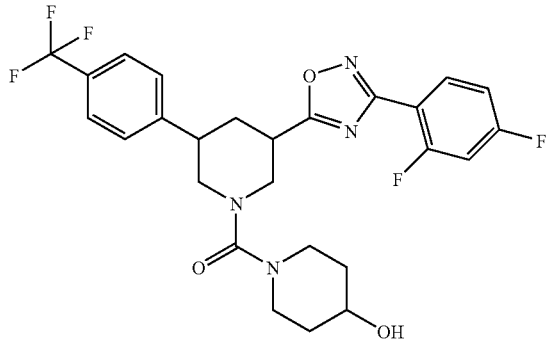

100 mg (0.250 mmol) of 1-[(4-hydroxypiperidin-1-yl)carbonyl]-5-[4-(trifluoromethyl)phenyl]piperidine-3-carboxylic acid (Example 99A) and 47.3 (0.275 mmol) of 2,4-difluoro-N'-hydroxybenzenecarboximidamide were reacted according to the General Method 1. Yield: 52.1 mg (38% of theory).

LC-MS (Method 1B): $R_t$=2.62 min; MS (ESIpos): m/z=537 [M+H]$^+$;

$^1$H-NMR (400 MHz, DMSO-d$_6$): δ=8.09 (m$_c$, 1H), 7.72 (d, 2H), 7.59 (d, 2H), 7.54 (m$_c$, 1H), 7.32 (dt, 1H), 4.69 (d, 1H), 4.05 (br d, 1H), 3.67-3.56 (m, 2H), 3.55-3.45 (m, 3H), 3.17-2.99 (m, 3H), 2.93 (br t, 2H), 2.42 (br d, 1H), 2.10 (dd, 1H), 1.73 (br d, 2H), 1.33 (br q, 2H).

Example 273

{3-[3-(2,5-Difluorophenyl)-1,2,4-oxadiazol-5-yl]-5-[4-(trifluoromethyl)phenyl]piperidin-1-yl}(4-hydroxypiperidin-1-yl)methanone [racemic cis isomer]

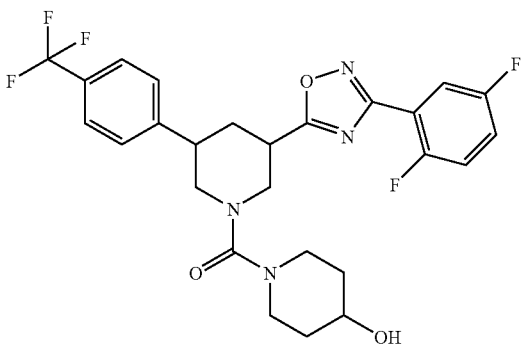

100 mg (0.250 mmol) of 1-[(4-hydroxypiperidin-1-yl)carbonyl]-5-[4-(trifluoromethyl)phenyl]piperidine-3-carboxylic acid (Example 99A) and 47.3 (0.275 mmol) of 2,5-difluoro-N'-hydroxybenzenecarboximidamide (Example 74A) were reacted according to the General Method 1. Yield: 68.1 mg (51% of theory).

LC-MS (Method 1B): $R_t$=2.62 min; MS (ESIpos): m/z=537 [M+H]$^+$;

$^1$H-NMR (400 MHz, DMSO-d$_6$): δ=7.82-7.75 (m, 1H), 7.72 (d, 2H), 7.59 (d, 2H), 7.54 (dt, 2H), 4.69 (d, 1H), 4.05 (br d, 1H), 3.68-3.45 (m, 5H), 3.17-2.99 (m, 3H), 2.93 (br t, 2H), 2.43 (br d, 1H), 2.11 (dd, 1H), 1.73 (br d, 2H), 1.33 (br q, 2H).

Example 274

{3-[3-(2-Chlorophenyl)-1,2,4-oxadiazol-5-yl]-5-[4-(trifluoromethyl)phenyl]piperidin-1-yl}(4-hydroxypiperidin-1-yl)methanone [racemic cis isomer]

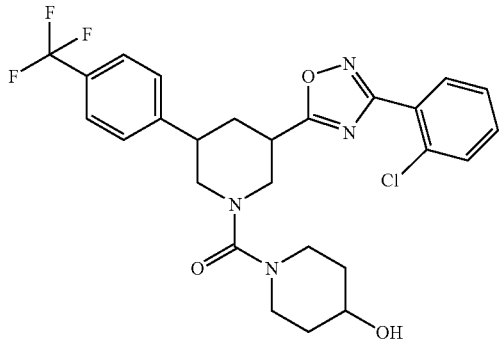

100 mg (0.250 mmol) of 1-[(4-hydroxypiperidin-1-yl)carbonyl]-5-[4-(trifluoromethyl)phenyl]piperidine-3-carboxylic acid (Example 99A) and 46.9 (0.275 mmol) of 2-chloro-N'-hydroxybenzenecarboximidamide were reacted according to the General Method 1. Yield: 53.0 mg (39% of theory).

LC-MS (Method 1B): $R_t$=2.65 min; MS (ESIpos): m/z=535 [M+H]$^+$;

$^1$H-NMR (400 MHz, DMSO-d$_6$): δ=7.92 (dd, 1H), 7.72 (d, 2H), 7.69 (dd, 1H), 7.64-7.57 (m, 3H), 7.54 (dt, 1H), 4.69 (d, 1H), 4.06 (br d, 1H), 3.67-3.45 (m, 5H), 3.17-2.99 (m, 3H), 2.93 (br t, 2H), 2.44 (br d, 1H), 2.10 (dd, 1H), 1.74 (br d, 2H), 1.33 (br q, 2H).

Example 275

(4-Hydroxypiperidin-1-yl) {3-[3-(2-methoxyethyl)-1,2,4-oxadiazol-5-yl]-5-[4-(trifluoromethyl)-phenyl]piperidin-1-yl}methanone [enantiomerically pure cis isomer]

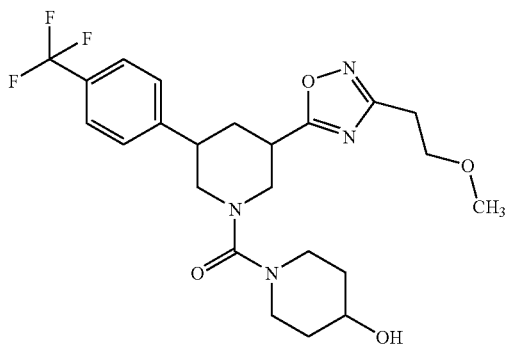

250 mg (0.624 mmol) of 1-[(4-hydroxypiperidin-1-yl)carbonyl]-5-[4-(trifluoromethyl)phenyl]piperidine-3-carboxylic acid (Example 99A) and 108 mg (0.687 mmol, 75% pure) of N'-hydroxy-3-methoxypropanimidamide (Example 64A) were reacted according to the General Method 1. Enantiomer separation of the racemate according to Method 16D gave 56.0 mg of the title compound from Example 275 and 55.0 mg of the title compound from Example 276 (36% of theory).

HPLC (Method 18E): $R_t$=5.70 min, >99.5% ee;

LC-MS (Method 2B): $R_t$=1.15 min; MS (ESIpos): m/z=483 [M+H]$^+$;

$^1$H-NMR (400 MHz, DMSO-d$_6$): δ=7.70 (d, 2H), 7.57 (d, 2H), 4.68 (d, 1H), 3.95 (br d, 1H), 3.68 (t, 2H), 3.65-3.53 (m, 2H), 3.52-3.36 (m, 3H), 3.23 (s, 3H), 3.09-2.98 (m, 3H), 2.98-2.86 (m, 4H), 2.33 (br d, 1H), 2.01 (dd, 1H), 1.73 (br d, 2H), 1.31 (br q, 2H).

Example 276

(4-Hydroxypiperidin-1-yl) {3-[3-(2-methoxyethyl)-1,2,4-oxadiazol-5-yl]-5-[4-(trifluoromethyl)-phenyl]piperidin-1-yl}methanone [enantiomerically pure cis isomer]

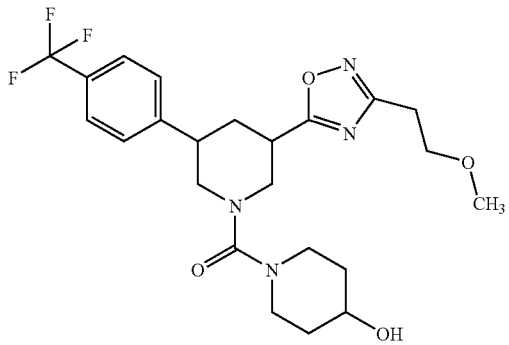

250 mg (0.624 mmol) of 1-[(4-hydroxypiperidin-1-yl)carbonyl]-5-[4-(trifluoromethyl)phenyl]piperidine-3-carboxylic acid (Example 99A) and 108 mg (0.687 mmol, 75% pure) of N'-hydroxy-3-methoxypropanimidamide (Example 64A) were reacted according to the General Method 1. Enantiomer separation of the racemate according to Method 16D gave 56.0 mg of the title compound from Example 275 and 55.0 mg of the title compound from Example 276 (36% of theory).

HPLC (Method 18E): $R_t$=17.4 min, >99.5% ee;

LC-MS (Method 2B): $R_t$=1.15 min; MS (ESIpos): m/z=483 [M+H]$^+$.

Example 277

1-({3-[3-(2-Methoxyethyl)-1,2,4-oxadiazol-5-yl]-5-[4-(trifluoromethyl)phenyl]piperidin-1-yl}carbonyl)piperidine-4-carbonitrile [enantiomerically pure cis isomer]

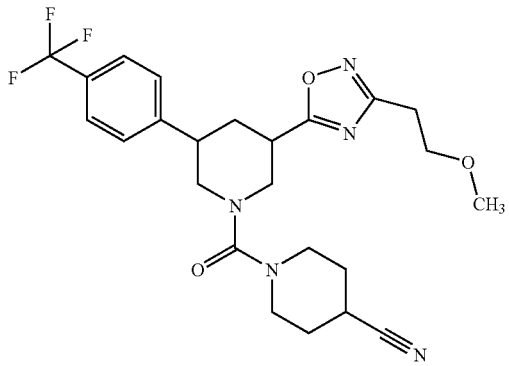

250 mg (0.611 mmol) of 1-[(4-cyanopiperidin-1-yl)carbonyl]-5-[4-(trifluoromethyl)phenyl]piperidine-3-carboxylic acid (Example 100A) and 106 mg (0.672 mmol, 75% pure) of N'-hydroxy-3-methoxypropanimidamide (Example 64A) were reacted according to the General Method 1. Enantiomer separation of the racemate according to Method 16D gave 77.0 mg of the title compound from Example 277 and 70.0 mg of the title compound from Example 278 (47% of theory).

HPLC (Method 16E): $R_t$=6.88 min, >99.0% ee;
LC-MS (Method 2B): $R_t$=1.26 min; MS (ESIpos): m/z=492 [M+H]$^+$;
$^1$H-NMR (400 MHz, DMSO-d$_6$): δ=7.70 (d, 2H), 7.57 (d, 2H), 3.98 (br d, 1H), 3.68 (t, 2H), 3.59 (br d, 1H), 3.43-3.34 (m, 3H), 3.23 (s, 3H), 3.12-2.99 (m, 6H), 2.93 (t, 2H), 2.34 (br d, 1H), 2.02 (dd, 1H), 1.91 (m, 2H), 1.74-1.62 (m, 2H).

Example 278

1-({3-[3-(2-Methoxyethyl)-1,2,4-oxadiazol-5-yl]-5-[4-(trifluoromethyl)phenyl]piperidin-1-yl}-carbonyl)piperidine-4-carbonitrile [enantiomerically pure cis isomer]

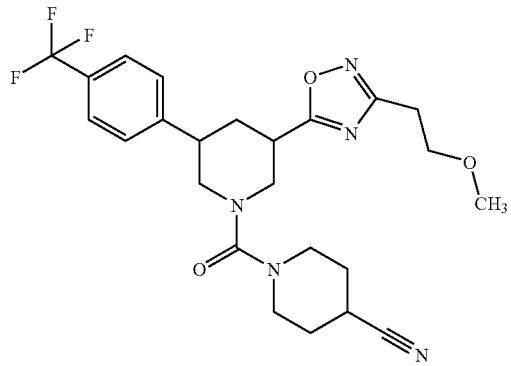

250 mg (0.611 mmol) of 1-[(4-cyanopiperidin-1-yl)carbonyl]-5-[4-(trifluoromethyl)phenyl]piperidine-3-carboxylic acid (Example OOA) and 106 mg (0.672 mmol, 75% pure) of N'-hydroxy-3-methoxypropanimidamide (Example 64A) were reacted according to the General Method 1. Enantiomer separation of the racemate according to Method 16D gave 77.0 mg of the title compound from Example 277 and 70.0 mg of the title compound from Example 278 (47% of theory).

HPLC (Method 16E): $R_t$=9.41 min, >98.0% ee;
LC-MS (Method 2B): $R_t$=1.26 min; MS (ESIpos): m/z=492 [M+H]$^+$.

Example 279

(3-Hydroxyazetidin-1-yl) {3-[3-(2-methoxyethyl)-1,2,4-oxadiazol-5-yl]-5-[4-(trifluoromethyl)-phenyl]piperidin-1-yl}methanone [enantiomerically pure cis isomer]

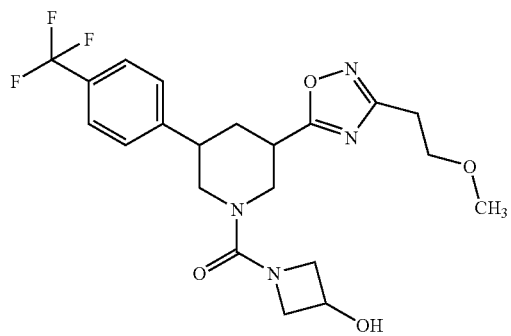

250 mg (0.671 mmol) of 1-[(3-hydroxyazetidin-1-yl)carbonyl]-5-[4-(trifluoromethyl)phenyl]piperidine-3-carboxylic acid (Example 101A) and 116 mg (0.739 mmol, 75% pure) of N'-hydroxy-3-methoxypropanimidamide (Example 64A) were reacted according to the General Method 1. Enantiomer separation of the racemate according to Method 10D gave 40.0 mg of the title compound from Example 279 and 30.0 mg of the title compound from Example 280 (22% of theory).

HPLC (Method 16E): $R_t$=4.89 min, >99.0% ee; $R_t$=1.11 min;
LC-MS (Method 2B): $R_t$=1.11 min; MS (ESIpos): m/z=455 [M+H]$^+$;
$^1$H-NMR (400 MHz, DMSO-d$_6$): δ=7.70 (d, 2H), 7.56 (d, 1H), 5.58 (d, 1H), 4.43-4.34 (m, 1H), 4.16 (br d, 1H), 4.10 (q, 2H), 3.79-3.65 (m, 5H), 3.23 (s, 3H), 3.07-2.90 (m, 5H), 2.32 (br d, 1H), 2.04 (dd, 1H).

Example 280

(3-Hydroxyazetidin-1-yl) {3-[3-(2-methoxyethyl)-1,2,4-oxadiazol-5-yl]-5-[4-(trifluoromethyl)-phenyl]piperidin-1-yl}methanone [enantiomerically pure cis isomer]

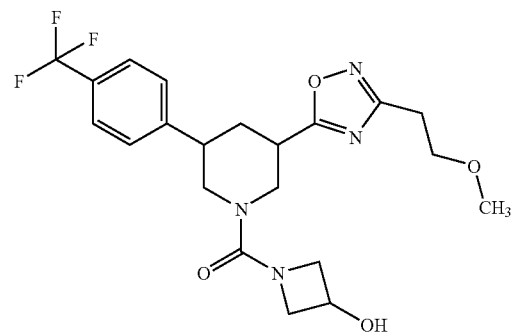

250 mg (0.671 mmol) of 1-[(3-hydroxyazetidin-1-yl)carbonyl]-5-[4-(trifluoromethyl)phenyl]piperidine-3-carboxylic acid (Example 101A) and 116 mg (0.739 mmol, 75% pure) of N'-hydroxy-3-methoxypropanimidamide (Example 64A) were reacted according to the General Method 1. Enantiomer separation of the racemate according to Method 10D gave 40.0 mg of the title compound from Example 279 and 30.0 mg of the title compound from Example 280 (22% of theory).

HPLC (Method 16E): $R_t$=7.62 min, >99.0% ee;
LC-MS (Method 2B): $R_t$=1.11 min; MS (ESIpos): m/z=455 [M+H]$^+$.

Example 281

1-({3-(3-Cyclopropyl-1,2,4-oxadiazol-5-yl)-5-[4-(trifluoromethyl)phenyl]piperidin-1-yl}carbonyl)piperidine-4-carbonitrile [racemic cis isomer]

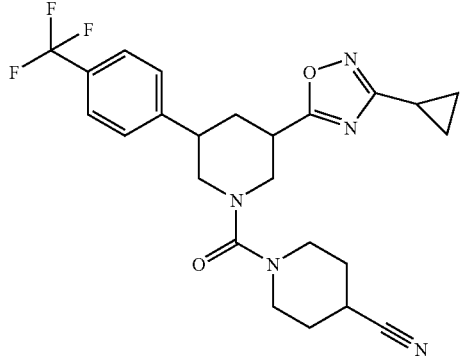

100 mg (0.244 mmol) of 1-[(4-cyanopiperidin-1-yl)carbonyl]-5-[4-(trifluoromethyl)phenyl]piperidine-3-carboxylic acid (Example 100A) and 26.9 mg (0.269 mmol) of N'-hydroxycyclopropanecarboximidamide (Example 78A) were reacted according to the General Method 1. Yield: 78.3 mg (66% of theory).

LC-MS (Method 1B): $R_t$=2.60 min; MS (ESIpos): m/z=474 [M+H]$^+$;

$^1$H-NMR (400 MHz, DMSO-$d_6$): δ=7.70 (dd, 2H), 7.56 (d, 2H), 3.93 (br d, 1H), 3.58 (d, 1H), 3.41-3.31 (m, 3H), 3.12-2.95 (m, 6H), 2.30 (br d, 1H), 2.11 (sept, 1H), 1.97 (dd, 1H), 1.90-1.81 (m, 2H), 1.74-1.62 (m, 2H), 1.09-1.02 (m, 2H), 0.91-0.85 (m, 2H).

Example 282

1-({3-(3-Methyl-1,2,4-oxadiazol-5-yl)-5-[4-(trifluoromethyl)phenyl]piperidin-1-yl}carbonyl)-piperidine-4-carbonitrile [racemic cis isomer]

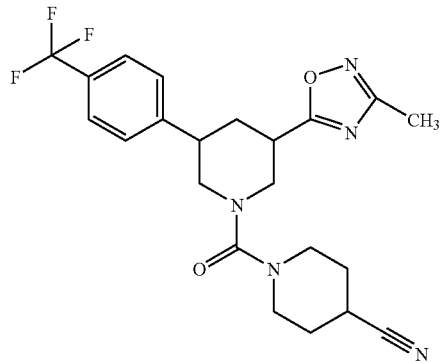

100 mg (0.244 mmol) of 1-[(4-cyanopiperidin-1-yl)carbonyl]-5-[4-(trifluoromethyl)phenyl]piperidine-3-carboxylic acid (Example 100A) and 19.9 mg (0.269 mmol) of N'-hydroxyethanimidamide were reacted according to the General Method 1. Yield: 55.5 mg (47% of theory).

LC-MS (Method 1B): $R_t$=2.39 min; MS (ESIpos): m/z=448 [M+H]$^+$;

$^1$H-NMR (400 MHz, DMSO-$d_6$): δ=7.70 (dd, 2H), 7.56 (d, 2H), 3.96 (br d, 1H), 3.60 (d, 1H), 3.45-3.32 (m, 3H), 3.13-2.94 (m, 6H), 2.33 (br s, 4H), 2.01 (dd, 1H), 1.91-1.82 (m, 2H), 1.74-1.63 (m, 2H).

Example 283

1-({3-(3-tert-Butyl-1,2,4-oxadiazol-5-yl)-5-[4-(trifluoromethyl)phenyl]piperidin-1-yl}carbonyl)-piperidine-4-carbonitrile [racemic cis isomer]

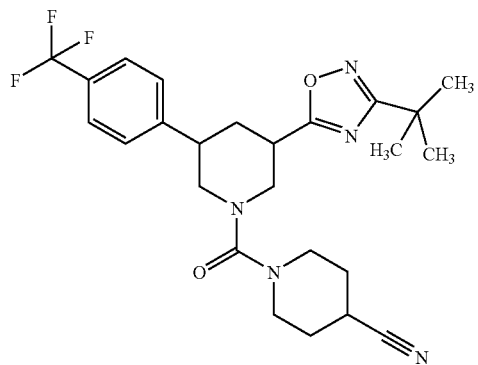

100 mg (0.244 mmol) of 1-[(4-cyanopiperidin-1-yl)carbonyl]-5-[4-(trifluoromethyl)phenyl]piperidine-3-carboxylic acid (Example 100A) and 31.2 mg (0.269 mmol) of N'-hydroxy-2,2-dimethylpropanimidamide were reacted according to the General Method 1. Yield: 79.1 mg (66% of theory).

LC-MS (Method 1B): $R_t$=2.80 min; MS (ESIpos): m/z=490 [M+H]$^+$;

$^1$H-NMR (400 MHz, DMSO-$d_6$): δ=7.70 (dd, 2H), 7.58 (d, 2H), 3.96 (br d, 1H), 3.58 (d, 1H), 3.45-3.32 (m, 3H), 3.13-2.98 (m, 6H), 2.36-2.29 (m, 1H), 2.01 (dd, 1H), 1.91-1.82 (m, 2H), 1.68 (dd, 2H), 1.30 (s, 9H).

Example 284

1-({3-[3-(Propan-2-yl)-1,2,4-oxadiazol-5-yl]-5-[4-(trifluoromethyl)phenyl]piperidin-1-yl}-carbonyl)piperidine-4-carbonitrile [racemic cis isomer]

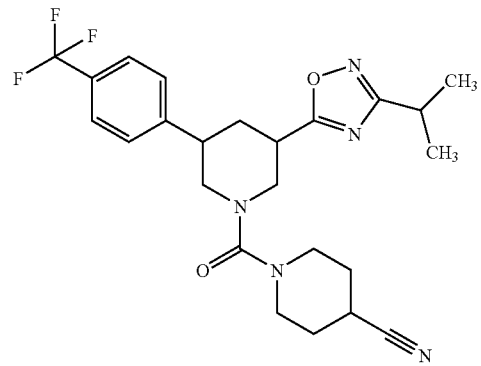

100 mg (0.244 mmol) of 1-[(4-cyanopiperidin-1-yl)carbonyl]-5-[4-(trifluoromethyl)phenyl]piperidine-3-carboxylic acid (Example 100A) and 27.4 mg (0.269 mmol) of N'-hydroxy-2-methylpropanimidamide were reacted according to the General Method 1. Yield: 78.9 mg (68% of theory).

LC-MS (Method 1B): $R_t$=2.66 min; MS (ESIpos): m/z=477 [M+H]$^+$;

$^1$H-NMR (400 MHz, DMSO-$d_6$): δ=7.70 (dd, 2H), 7.57 (d, 2H), 3.96 (br d, 1H), 3.56 (d, 1H), 3.45-3.34 (m, 3H), 3.13-2.97 (m, 7H), 2.36-2.29 (m, 1H), 2.01 (dd, 1H), 1.91-1.82 (m, 2H), 1.74-1.62 (m, 2H), 1.26 (d, 6H).

Example 285

1-({3-(3-Phenyl-1,2,4-oxadiazol-5-yl)-5-[4-(trifluoromethyl)phenyl]piperidin-1-yl}carbonyl)-piperidine-4-carbonitrile [racemic cis isomer]

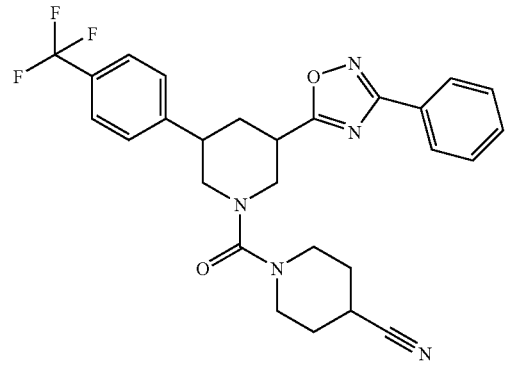

100 mg (0.244 mmol) of 1-[(4-cyanopiperidin-1-yl)carbonyl]-5-[4-(trifluoromethyl)phenyl]piperidine-3-carboxylic acid (Example 100A) and 38.5 mg (0.269 mmol) of N'-hydroxybenzenecarboximidamide were reacted according to the General Method 1. Yield: 84.2 mg (66% of theory).

LC-MS (Method 1B): $R_t$=2.86 min; MS (ESIpos): m/z=510 [M+H]$^+$;

$^1$H-NMR (400 MHz, DMSO-d$_6$): δ=8.02 (d, 2H), 7.72 (d, 2H), 7.63-7.54 (m, 5H), 4.07 (br d, 1H), 3.62 (d, 1H), 3.51 (tt, 1H), 3.45-3.35 (m, 2H), 3.20-3.00 (m, 6H), 2.42 (br d, 1H), 2.11 (dd, 1H), 1.92-1.83 (m, 2H), 1.76-1.64 (m, 2H).

Example 286

1-({3-[3-(3-Fluorophenyl)-1,2,4-oxadiazol-5-yl]-5-[4-(trifluoromethyl)phenyl]piperidin-1-yl}-carbonyl)piperidine-4-carbonitrile [racemic cis isomer]

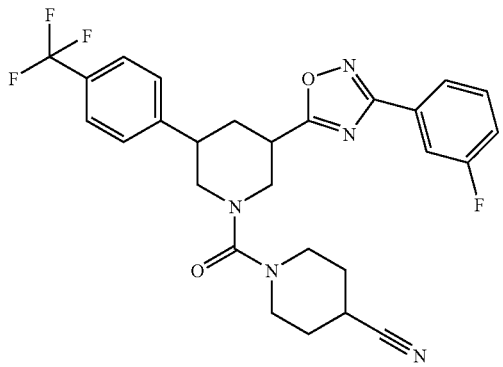

100 mg (0.244 mmol) of 1-[(4-cyanopiperidin-1-yl)carbonyl]-5-[4-(trifluoromethyl)phenyl]piperidine-3-carboxylic acid (Example 100A) and 41.4 mg (0.269 mmol) of 3-fluoro-N'-hydroxybenzenecarboximidamide were reacted according to the General Method 1. Yield: 76.4 mg (58% of theory).

LC-MS (Method 1B): $R_t$=2.92 min; MS (ESIpos): m/z=528 [M+H]$^+$;

$^1$H-NMR (400 MHz, DMSO-d$_6$): δ=7.87 (d, 1H), 7.75 (d, 1H), 7.71 (d, 2H), 7.63 (dd, 1H), 7.59 (d, 2H), 7.47 (dd, 1H), 4.06 (br d, 1H), 3.62 (d, 1H), 3.52 (tt, 1H), 3.44-3.36 (m, 2H), 3.18-3.01 (m, 6H), 2.42 (br d, 1H), 2.11 (dd, 1H), 1.92-1.83 (m, 2H), 1.75-1.65 (m, 2H).

Example 287

1-({3-[3-(Pyridin-3-yl)-1,2,4-oxadiazol-5-yl]-5-[4-(trifluoromethyl)phenyl]piperidin-1-yl}-carbonyl)piperidine-4-carbonitrile [racemic cis isomer]

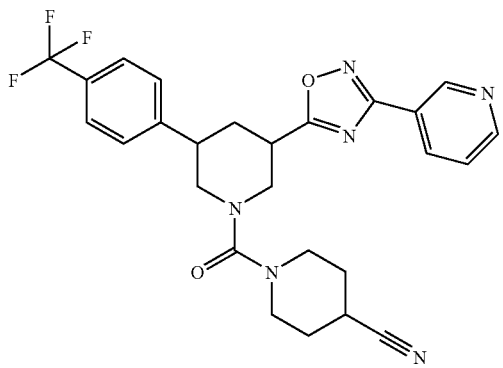

100 mg (0.244 mmol) of 1-[(4-cyanopiperidin-1-yl)carbonyl]-5-[4-(trifluoromethyl)phenyl]piperidine-3-carboxylic acid (Example 100A) and 36.8 mg (0.269 mmol) of N'-hydroxypyridine-3-carboximidamide were reacted according to the General Method 1. Yield: 58.6 mg (46% of theory).

LC-MS (Method 1B): $R_t$=2.47 min; MS (ESIpos): m/z=511 [M+H]$^+$;

$^1$H-NMR (400 MHz, DMSO-d$_6$): δ=9.17 (d, 1H), 8.78 (dd, 1H), 8.37 (dd, 1H), 7.71 (d, 2H), 7.63-7.59 (m, 3H), 4.07 (br d, 1H), 3.62 (d, 1H), 3.55 (tt, 1H), 3.43-3.35 (m, 1H), 3.18-3.02 (m, 6H), 2.42 (br d, 1H), 2.11 (dd, 1H), 1.92-1.84 (m, 2H), 1.75-1.65 (m, 2H).

Example 288

1-({3-(3-Benzyl-1,2,4-oxadiazol-5-yl)-5-[4-(trifluoromethyl)phenyl]piperidin-1-yl}carbonyl)piperidine-4-carbonitrile [racemic cis isomer]

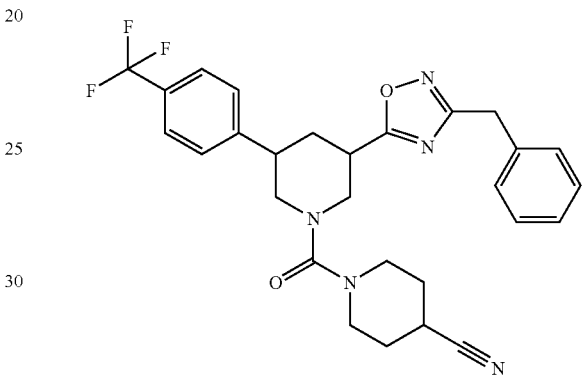

100 mg (0.244 mmol) of 1-[(4-cyanopiperidin-1-yl)carbonyl]-5-[4-(trifluoromethyl)phenyl]piperidine-3-carboxylic acid (Example 100A) and 40.3 mg (0.269 mmol) of N'-hydroxy-2-phenylethanimidamide were reacted according to the General Method 1. Yield: 48.3 mg (38% of theory).

LC-MS (Method 3B): $R_t$=2.41 min; MS (ESIpos): m/z=524 [M+H]$^+$;

$^1$H-NMR (400 MHz, DMSO-d$_6$): δ=7.69 (d, 2H), 7.55 (d, 2H), 7.34-7.23 (m, 5H), 4.08 (d, 1H), 3.94 (br d, 1H), 3.57 (d, 1H), 3-44-3.33 (m, 3H), 3.09-2.95 (m, 5H), 2.30 (br d, 1H), 1.99 (dd, 1H), 1.90-1.80 (m, 2H), 1.72-1.62 (m, 2H).

Example 289

1-({3-[3-(Pyridin-4-yl)-1,2,4-oxadiazol-5-yl]-5-[4-(trifluoromethyl)phenyl]piperidin-1-yl}-carbonyl)piperidine-4-carbonitrile [racemic cis isomer]

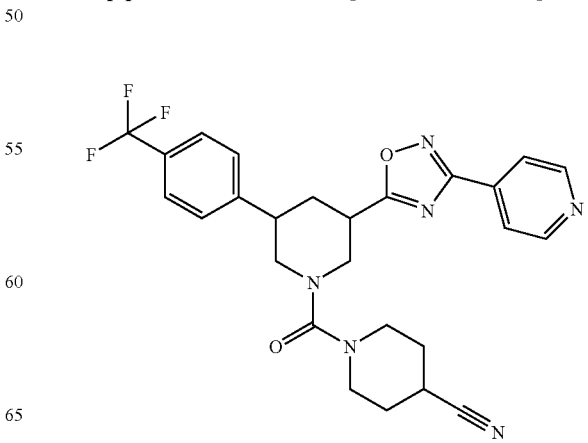

100 mg (0.244 mmol) of 1-[(4-cyanopiperidin-1-yl)carbonyl]-5-[4-(trifluoromethyl)phenyl]piperidine-3-carboxylic acid (Example 100A) and 36.8 mg (0.269 mmol) of N'-hydroxypyridine-4-carboximidamide were reacted according to the General Method 1. Yield: 70.3 mg (56% of theory).

LC-MS (Method 3B): $R_t$=2.10 min; MS (ESIpos): m/z=511 [M+H]$^+$;

$^1$H-NMR (400 MHz, DMSO-d$_6$): δ=8.80 (d, 2H), 7.94 (d, 2H), 7.71 (d, 2H), 7.59 (d, 2H), 4.07 (br d, 1H), 3.62 (d, 1H), 3.55 (tt, 1H), 3.44-3.35 (m, 2H), 3.18-3.01 (m, 6H), 2.42 (br d, 1H), 2.11 (dd, 1H), 1.92-1.83 (m, 2H), 1.75-1.64 (m, 2H).

Example 290

1-({3-[3-(2-Fluorophenyl)-1,2,4-oxadiazol-5-yl]-5-[4-(trifluoromethyl)phenyl]piperidin-1-yl}-carbonyl)piperidine-4-carbonitrile [racemic cis isomer]

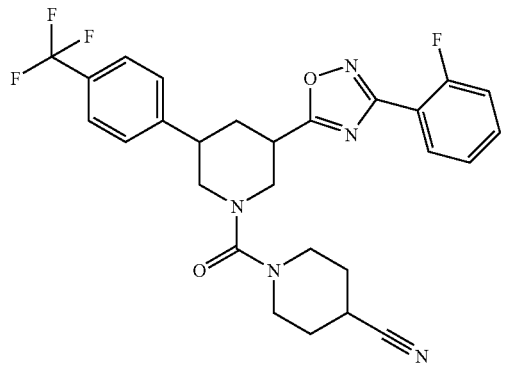

100 mg (0.244 mmol) of 1-[(4-cyanopiperidin-1-yl)carbonyl]-5-[4-(trifluoromethyl)phenyl]piperidine-3-carboxylic acid (Example 100A) and 41.4 mg (0.269 mmol) of 2-fluoro-N'-hydroxybenzenecarboximidamide were reacted according to the General Method 1. Yield: 72.8 mg (55% of theory).

LC-MS (Method 2B): $R_t$=1.46 min; MS (ESIpos): m/z=528 [M+H]$^+$;

$^1$H-NMR (400 MHz, DMSO-d$_6$): δ=8.03 (td, 1H), 7.71 (d, 2H), 7.69-7.63 (m, 1H), 7.60 (d, 2H), 7.47-7.40 (m, 2H), 4.06 (d, 1H), 3.62 (d, 1H), 3.55 (tt, 1H), 3.44-3.36 (m, 2H), 3.22-3.01 (m, 6H), 2.42 (br d, 1H), 2.10 (dd, 1H), 1.93-1.84 (m, 2H), 1.75-1.64 (m, 2H).

Example 291

1-({3-[3-(4-Fluorophenyl)-1,2,4-oxadiazol-5-yl]-5-[4-(trifluoromethyl)phenyl]piperidin-1-yl}-carbonyl)piperidine-4-carbonitrile [racemic cis isomer]

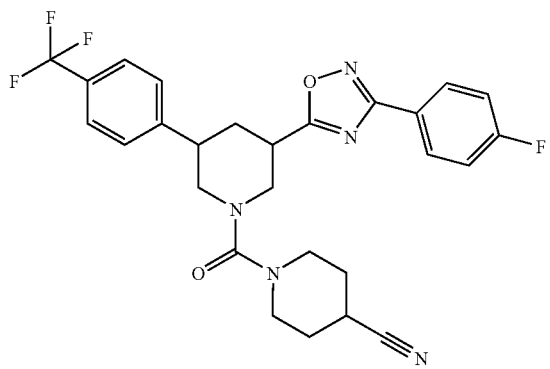

100 mg (0.244 mmol) of 1-[(4-cyanopiperidin-1-yl)carbonyl]-5-[4-(trifluoromethyl)phenyl]piperidine-3-carboxylic acid (Example 100A) and 41.4 mg (0.269 mmol) of 4-fluoro-N'-hydroxybenzenecarboximidamide were reacted according to the General Method 1. Yield: 78.2 mg (59% of theory).

LC-MS (Method 2B): $R_t$=1.50 min; MS (ESIpos): m/z=528 [M+H]$^+$;

$^1$H-NMR (400 MHz, DMSO-d$_6$): δ=8.07 (dd, 2H), 7.71 (d, 2H), 7.59 (d, 2H), 7.42 (dd, 2H), 4.05 (d, 1H), 3.62 (d, 1H), 3.51 (tt, 1H), 3.43-3.35 (m, 2H), 3.17-3.00 (m, 6H), 2.41 (br d, 1H), 2.09 (dd, 1H), 1.92-1.83 (m, 2H), 1.75-1.64 (m, 2H).

Example 292

1-({3-{3-[(Methylsulphonyl)methyl]-1,2,4-oxadiazol-5-yl}-5-[4-(trifluoromethyl)phenyl]piperidin-1-yl}carbonyl)piperidine-4-carbonitrile [racemic cis isomer]

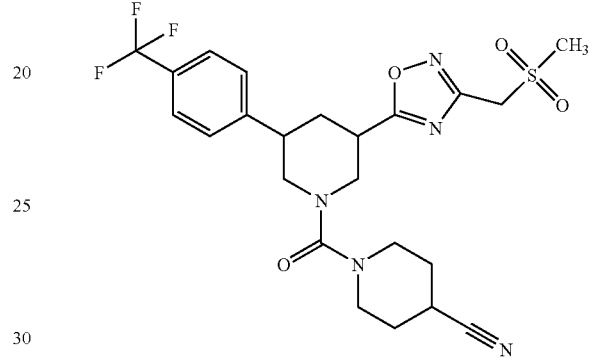

100 mg (0.244 mmol) of 1-[(4-cyanopiperidin-1-yl)carbonyl]-5-[4-(trifluoromethyl)phenyl]piperidine-3-carboxylic acid (Example 100A) and 40.9 mg (0.269 mmol) of N'-hydroxy-2-(methylsulphonyl)ethanimidamide were reacted according to the General Method 1. Yield: 31.2 mg (24% of theory).

LC-MS (Method 2B): $R_t$=1.18 min; MS (ESIpos): m/z=526 [M+H]$^+$;

$^1$H-NMR (400 MHz, DMSO-d$_6$): δ=7.70 (d, 2H), 7.58 (d, 2H), 4.85 (s, 2H), 4.00 (br d, 1H), 3.59 (d, 1H), 3.49 (tt, 1H), 3.42-3.35 (m, 2H), 3.17 (s, 3H), 3.11-2.98 (m, 6H), 2.37 (br d, 1H), 2.03 (dd, 1H), 1.90-1.82 (m, 2H), 1.72-1.63 (m, 2H).

Example 293

1-({3-[3-(2,4-Difluorophenyl)-1,2,4-oxadiazol-5-yl]-5-[4-(trifluoromethyl)phenyl]piperidin-1-yl}-carbonyl)piperidine-4-carbonitrile [racemic cis isomer]

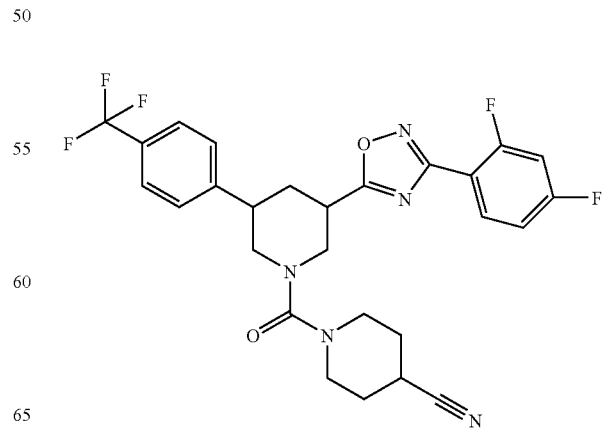

100 mg (0.244 mmol) of 1-[(4-cyanopiperidin-1-yl)carbonyl]-5-[4-(trifluoromethyl)phenyl]piperidine-3-carboxylic acid (Example 100A) and 46.2 mg (0.269 mmol) of 2,4-difluoro-N'-hydroxybenzenecarboximidamide were reacted according to the General Method 1. Yield: 63.9 mg (47% of theory).

LC-MS (Method 3B): $R_t$=2.50 min; MS (ESIpos): m/z=546 [M+H]$^+$;

$^1$H-NMR (400 MHz, DMSO-d$_6$): δ=8.09 (d, 2H), 7.71 (d, 2H), 7.59 (d, 2H), 7.54 (dd, 1H), 7.32 (dd, 1H), 4.06 (br d, 1H), 3.62 (d, 1H), 3.53 (tt, 1H), 3.43-3.35 (m, 2H), 3.17-3.01 (m, 6H), 2.41 (br d, 1H), 2.09 (dd, 1H), 1.92-1.83 (m, 2H), 1.75-1.63 (m, 2H).

Example 294

1-({3-[3-(2,5-Difluorophenyl)-1,2,4-oxadiazol-5-yl] 5-[4-(trifluoromethyl)phenyl]piperidin-1-yl}-carbonyl)piperidine-4-carbonitrile [racemic cis isomer]

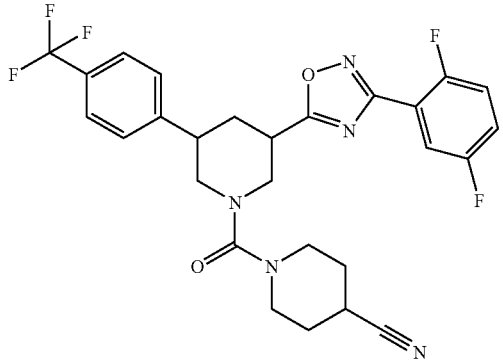

100 mg (0.244 mmol) of 1-[(4-cyanopiperidin-1-yl)carbonyl]-5-[4-(trifluoromethyl)phenyl]piperidine-3-carboxylic acid (Example 100A) and 46.2 mg (0.269 mmol) of 2,5-difluoro-N'-hydroxybenzenecarboximidamide (Example 74A) were reacted according to the General Method 1. Yield: 72.5 mg (54% of theory).

LC-MS (Method 3B): $R_t$=2.49 min; MS (ESIpos): m/z=546 [M+H]$^+$;

$^1$H-NMR (400 MHz, DMSO-d$_6$): δ=7.78 (br s, 1H), 7.71 (d, 2H), 7.59 (d, 2H), 7.55 (dd, 2H), 4.06 (br d, 1H), 3.62 (d, 1H), 3.59-3.50 (m, 1H), 3.39 (br d, 1H), 3.17-3.02 (m, 6H), 2.42 (br d, 1H), 2.11 (dd, 1H), 1.93-1.83 (m, 2H), 1.75-1.65 (m, 2H).

Example 295

1-({3-[3-(2-Chlorophenyl)-1,2,4-oxadiazol-5-yl]-5-[4-(trifluoromethyl)phenyl]piperidin-1-yl}-carbonyl)piperidine-4-carbonitrile [racemic cis isomer]

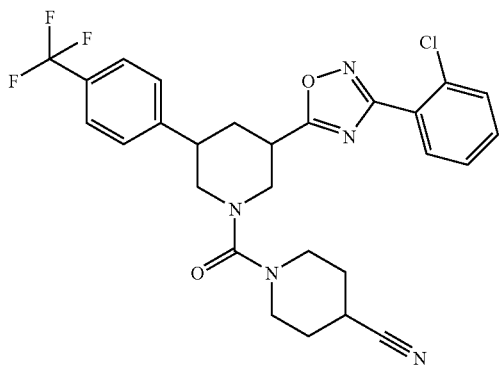

100 mg (0.244 mmol) of 1-[(4-cyanopiperidin-1-yl)carbonyl]-5-[4-(trifluoromethyl)phenyl]piperidine-3-carboxylic acid (Example 100A) and 45.8 mg (0.269 mmol) of 2-chloro-N'-hydroxybenzenecarboximidamide were reacted according to the General Method 1. Yield: 72.4 mg (55% of theory).

LC-MS (Method 3B): $R_t$=2.53 min; MS (ESIpos): m/z=544 [M+H]$^+$;

$^1$H-NMR (400 MHz, DMSO-d$_6$): δ=7.92 (dd, 1H), 7.71 (d, 2H), 7.69-7.52 (m, 5H), 4.06 (br d, 1H), 3.62 (d, 1H), 3.54 (tt, 1H), 3.43-3.37 (m, 2H), 3.18-3.01 (m, 6H), 2.42 (br d, 1H), 2.10 (dd, 1H), 1.92-1.84 (m, 2H), 1.75-1.64 (m, 2H).

Example 296

1-({3-[3-(3-Chlorophenyl)-1,2,4-oxadiazol-5-yl]-5-[4-(trifluoromethyl)phenyl]piperidin-1-yl}-carbonyl)piperidine-4-carbonitrile [racemic cis isomer]

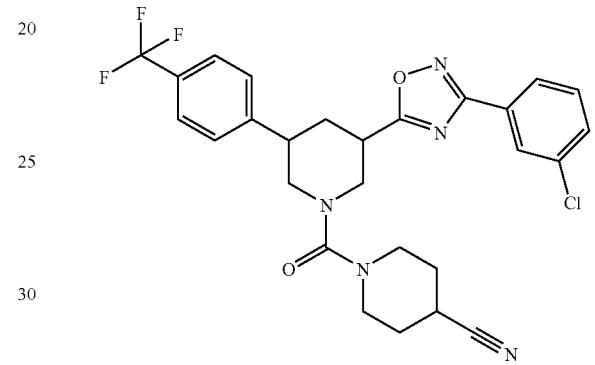

100 mg (0.244 mmol) of 1-[(4-cyanopiperidin-1-yl)carbonyl]-5-[4-(trifluoromethyl)phenyl]piperidine-3-carboxylic acid (Example 100A) and 45.8 mg (0.269 mmol) of 3-chloro-N'-hydroxybenzenecarboximidamide were reacted according to the General Method 1. Yield: 73.3 mg (55% of theory).

LC-MS (Method 3B): $R_t$=2.68 min; MS (ESIpos): m/z=544 [M+H]$^+$;

$^1$H-NMR (400 MHz, DMSO-d$_6$): δ=7.99-7.97 (m, 2H), 7.71-7.68 (m, 3H), 7.64-7.58 (m, 3H), 4.06 (br d, 1H), 3.62 (d, 1H), 3.53 (tt, 1H), 3.43-3.36 (m, 2H), 3.18-2.99 (m, 6H), 2.42 (br d, 1H), 2.10 (dd, 1H), 1.92-1.84 (m, 2H), 1.74-1.64 (m, 2H).

Example 297

{3-(3-Cyclopropyl-1,2,4-oxadiazol-5-yl)-5-[4-(trifluoromethyl)phenyl]piperidin-1-yl}(3-hydroxyazetidin-1-yl)methanone [racemic cis isomer]

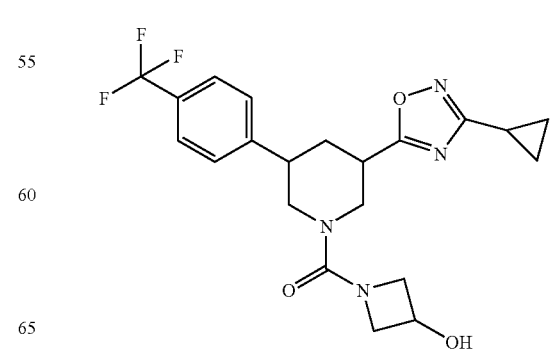

100 mg (0.269 mmol) of 1-[(3-hydroxyazetidin-1-yl)carbonyl]-5-[4-(trifluoromethyl)phenyl]piperidine-3-carboxylic acid (Example 101A) and 29.6 mg (0.295 mmol) of N'-hydroxycyclopropanecarboximidamide (Example 78A) were reacted according to the General Method 1. Yield: 54 mg (44% of theory).

LC-MS (Method 2B): $R_t$=1.19 min; MS (ESIpos): m/z=437 [M+H]$^+$;

$^1$H-NMR (400 MHz, DMSO-d$_6$): δ=7.70 (d, 2H), 7.56 (d, 2H), 5.58 (d, 1H), 4.43-4.34 (m, 1H), 4.12 (br d, 1H), 4.09 (q, 2H), 3.75 (br d, 1H), 3.66-3.73 (m, 2H), 3.26 (tt, 1H), 3.04-2.92 (m, 3H), 2.28 (br d, 1H), 2.11 (sept, 1H), 2.00 (dd, 1H), 1.09-1.02 (m, 2H), 0.88 (m, 2H).

Example 298

(3-Hydroxyazetidin-1-yl) {3-(3-methyl-1,2,4-oxadiazol-5-yl)-5-[4-(trifluoromethyl)phenyl]-piperidin-1-yl}methanone [racemic cis isomer]

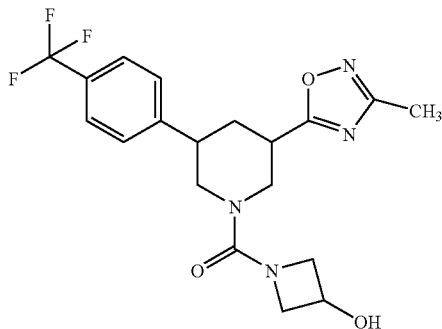

100 mg (0.269 mmol) of 1-[(3-hydroxyazetidin-1-yl)carbonyl]-5-[4-(trifluoromethyl)phenyl]piperidine-3-carboxylic acid (Example 101A) and 21.9 mg (0.269 mmol) of N'-hydroxyethanimidamide were reacted according to the General Method 1. Yield: 41.6 mg (32% of theory).

LC-MS (Method 2B): $R_t$=1.09 min; MS (ESIpos): m/z=411 [M+H]$^+$;

$^1$H-NMR (400 MHz, DMSO-d$_6$): δ=7.70 (d, 2H), 7.56 (d, 2H), 5.58 (d, 1H), 4.43-4.34 (m, 1H), 4.15 (br d, 1H), 4.10 (q, 2H), 3.77 (br d, 1H), 3.73-3.66 (m, 2H), 3.30 (obscured, 1H), 3.07-2.92 (m, 3H), 2.2.35-2.28 (m, 4H), 2.04 (dd, 1H).

Example 299

{3-(3-tert-Butyl-1,2,4-oxadiazol-5-yl)-5-[4-(trifluoromethyl)phenyl]piperidin-1-yl}(3-hydroxyazetidin-1-yl)methanone [racemic cis isomer]

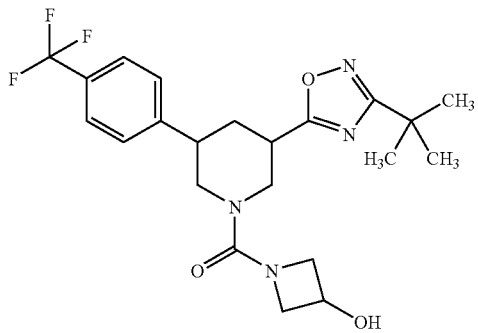

100 mg (0.269 mmol) of 1-[(3-hydroxyazetidin-1-yl)carbonyl]-5-[4-(trifluoromethyl)phenyl]piperidine-3-carboxylic acid (Example 101A) and 34.3 mg (0.295 mmol) of N'-hydroxy-2,2-dimethylpropanimidamide were reacted according to the General Method 1. Yield: 45 mg (37% of theory).

LC-MS (Method 3B): $R_t$=2.13 min; MS (ESIpos): m/z=453 [M+H]$^+$;

$^1$H-NMR (400 MHz, DMSO-d$_6$): δ=7.70 (d, 2H), 7.56 (d, 2H), 5.58 (d, 1H), 4.43-4.33 (m, 1H), 4.16 (br d, 1H), 4.09 (q, 2H), 3.74 (br d, 1H), 3.71-3.64 (m, 2H), 3.06-2.93 (m, 3H), 2.31 (br d, 1H), 2.03 (dd, 1H), 1.30 (s, 9H).

Example 300

(3-Hydroxyazetidin-1-yl) {3-[3-(propan-2-yl)-1,2,4-oxadiazol-5-yl]-5-[4-(trifluoromethyl)phenyl]-piperidin-1-yl}methanone [racemic cis isomer]

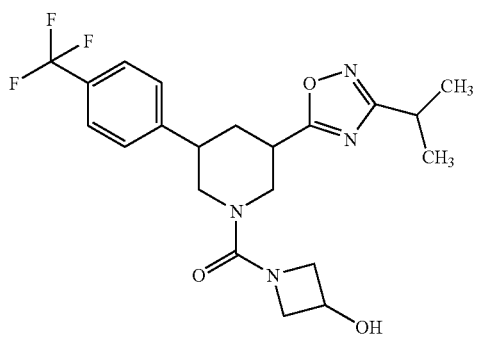

100 mg (0.269 mmol) of 1-[(3-hydroxyazetidin-1-yl)carbonyl]-5-[4-(trifluoromethyl)phenyl]piperidine-3-carboxylic acid (Example 101A) and 30.7 mg (0.295 mmol) of N'-hydroxy-2-methylpropanimidamide were reacted according to the General Method 1. Yield: 47 mg (39% of theory).

LC-MS (Method 3B): $R_t$=1.99 min; MS (ESIpos): m/z=439 [M+H]$^+$;

$^1$H-NMR (400 MHz, DMSO-d$_6$): δ=7.70 (d, 2H), 7.56 (d, 2H), 5.58 (d, 1H), 4.43-4.36 (m, 1H), 4.16 (br d, 1H), 4.09 (q, 2H), 3.75 (br d, 1H), 3.73-3.67 (m, 2H), 3.08-2.96 (m, 4H), 2.31 (br d, 1H), 2.03 (dd, 1H), 1.25 (d, 6H).

Example 301

(3-Hydroxyazetidin-1-yl) {3-(3-phenyl-1,2,4-oxadiazol-5-yl)-5-[4-(trifluoromethyl)phenyl]-piperidin-1-yl}methanone [racemic cis isomer]

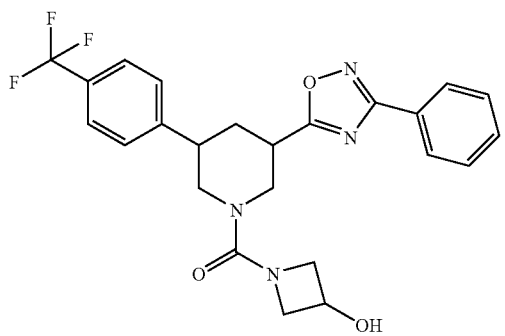

100 mg (0.269 mmol) of 1-[(3-hydroxyazetidin-1-yl)carbonyl]-5-[4-(trifluoromethyl)phenyl]piperidine-3-carboxylic acid (Example 101A) and 42.3 mg (0.295 mmol) of N'-hydroxybenzenecarboximidamide (95% pure) were reacted according to the General Method 1. Yield: 48 mg (36% of theory).

LC-MS (Method 3B): $R_t$=2.17 min; MS (ESIpos): m/z=473 [M+H]$^+$;

$^1$H-NMR (400 MHz, DMSO-d$_6$): δ=8.01 (dd, 2H), 7.71 (d, 2H), 7.62-7.53 (m, 5H), 5.06 (d, 1H), 4.44-4.36 (m, 1H), 4.25 (br d, 1H), 4.11 (q, 2H), 3.80 (br d, 1H), 3.75-3.70 (m, 2H), 3.43 (tt, 1H), 3.13 (t, 1H), 3.07-2.98 (m, 2H), 2.40 (br d, 1H), 2.12 (dd, 1H).

Example 302

{3-[3-(3-Fluorophenyl)-1,2,4-oxadiazol-5-yl]-5-[4-(trifluoromethyl)phenyl]piperidin-1-yl}(3-hydroxyazetidin-1-yl)methanone [racemic cis isomer]

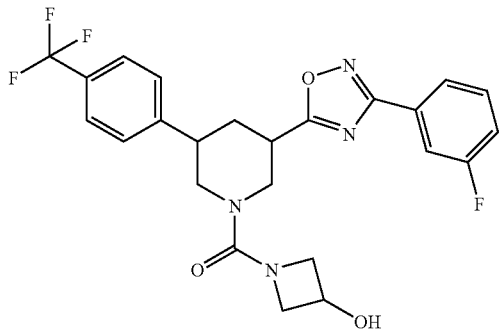

100 mg (0.269 mmol) of 1-[(3-hydroxyazetidin-1-yl)carbonyl]-5-[4-(trifluoromethyl)phenyl]piperidine-3-carboxylic acid (Example 101A) and 45.5 mg (0.295 mmol) of 3-fluoro-N'-hydroxybenzenecarboximidamide were reacted according to the General Method 1. Yield: 46 mg (34% of theory).

LC-MS (Method 3B): $R_t$=2.23 min; MS (ESIpos): m/z=491 [M+H]$^+$;

$^1$H-NMR (400 MHz, DMSO-d$_6$): δ=7.87 (d, 1H), 7.75 (d, 1H), 7.71 (d, 2H), 7.66-7.63 (m, 1H), 7.61 (d, 2H), 7.46 (dd, 1H), 5.59 (d, 1H), 4.44-4.36 (m, 1H), 4.25 (br d, 1H), 4.11 (q, 2H), 3.79 (br d, 1H), 3.75-3.66 (m, 2H), 3.44 (tt, 1H), 3.13 (t, 1H), 3.05-3.01 (m, 2H), 2.40 (br d, 1H), 2.12 (dd, 1H).

Example 303

(3-Hydroxyazetidin-1-yl) {3-[3-(pyridin-3-yl)-1,2,4-oxadiazol-5-yl]-5-[4-(trifluoromethyl)phenyl]-piperidin-1-yl}methanone [racemic cis isomer]

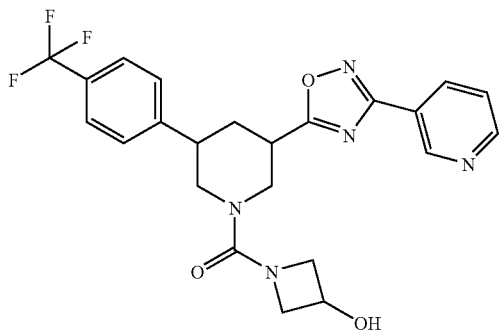

100 mg (0.269 mmol) of 1-[(3-hydroxyazetidin-1-yl)carbonyl]-5-[4-(trifluoromethyl)phenyl]piperidine-3-carboxylic acid (Example 101A) and 40.5 mg (0.295 mmol) of N'-hydroxypyridine-3-carboximidamide were reacted according to the General Method 1. Yield: 28.8 mg (21% of theory).

LC-MS (Method 3B): $R_t$=1.77 min; MS (ESIpos): m/z=474 [M+H]$^+$;

$^1$H-NMR (400 MHz, DMSO-d$_6$): δ=9.18 (d, 1H), 8.77 (dd, 1H), 8.37 (tt, 1H), 7.72 (d, 2H), 7.62 (dd, 1H), 7.59 (d, 2H), 5.60 (d, 1H), 4.44-4.36 (m, 1H), 4.26 (br d, 1H), 4.12 (q, 2H), 3.80 (br d, 1H), 3.76-3.68 (m, 2H), 3.48 (tt, 1H), 3.14 (t, 1H), 3.03 (dd, 2H), 2.42 (br d, 1H), 2.14 (dd, 1H).

Example 304

{3-(3-Benzyl-1,2,4-oxadiazol-5-yl)-5-[4-(trifluoromethyl)phenyl]piperidin-1-yl}(3-hydroxyazetidin-1-yl)methanone [racemic cis isomer]

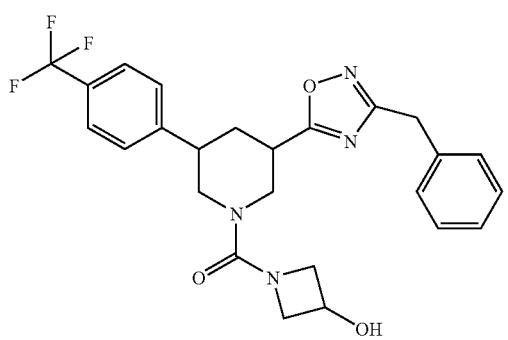

100 mg (0.269 mmol) of 1-[(3-hydroxyazetidin-1-yl)carbonyl]-5-[4-(trifluoromethyl)phenyl]piperidine-3-carboxylic acid (Example 101A) and 44.4 mg (0.295 mmol) of N'-hydroxy-2-phenylethanimidamide were reacted according to the General Method 1. Yield: 40.0 mg (29% of theory).

LC-MS (Method 2B): $R_t$=1.31 min; MS (ESIpos): m/z=487 [M+H]$^+$;

$^1$H-NMR (400 MHz, DMSO-d$_6$): δ=7.69 (d, 2H), 7.54 (d, 1H), 7.34-7.23 (m, 5H), 5.57 (d, 1H), 4.41-4.34 (m, 1H), 4.14 (br d, 1H), 4.11-4.05 (m, 4H), 3.74 (br d, 1H), 3.72-3.66 (m, 2H), 3.04-2.93 (m, 3H), 2.30 (br d, 1H), 2.01 (dd, 1H).

Example 305

{3-[3-(4-Fluorophenyl)-1,2,4-oxadiazol-5-yl]-5-[4-(trifluoromethyl)phenyl]piperidin-1-yl}(3-hydroxyazetidin-1-yl)methanone [racemic cis isomer]

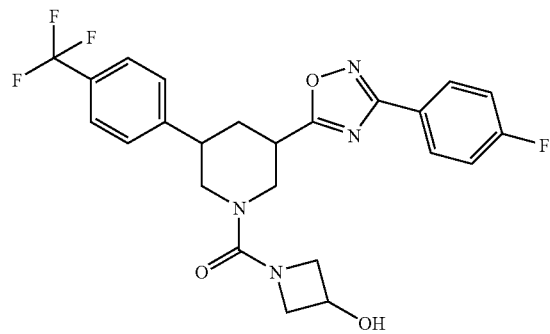

90.0 mg (0.242 mmol) of 1-[(3-hydroxyazetidin-1-yl)carbonyl]-5-[4-(trifluoromethyl)phenyl]piperidine-3-carboxylic acid (Example 101A) and 41.0 mg (0.266 mmol) of 4-fluoro-N'-hydroxybenzenecarboximidamide were reacted according to the General Method 1. Yield: 52.1 mg (42% of theory).

LC-MS (Method 3B): $R_t$=2.22 min; MS (ESIpos): m/z=491 [M+H]$^+$;

$^1$H-NMR (400 MHz, DMSO-d$_6$): δ=8.11-8.04 (m, 2H), 7.72 (d, 2H), 7.59 (d, 2H), 7.42 (tt, 2H), 5.59 (d, 1H), 4.44-4.35 (m, 1H), 4.25 (br d, 1H), 4.12 (q, 2H), 3.82-3.77 (br d, 1H), 3.76-3.68 (m, 2H), 3.43 (tt, 1H), 3.13 (t, 1H), 3.07-2.98 (m, 2H), 2.41 (br d, 1H), 2.13 (dd, 1H).

Example 306

{3-[3-(2,4-Difluorophenyl)-1,2,4-oxadiazol-5-yl]-5-[4-(trifluoromethyl)phenyl]piperidin-1-yl}(3-hydroxyazetidin-1-yl)methanone [racemic cis isomer]

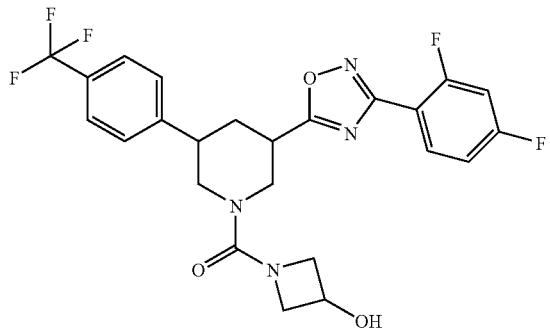

90.0 mg (0.242 mmol) of 1-[(3-hydroxyazetidin-1-yl)carbonyl]-5-[4-(trifluoromethyl)phenyl]piperidine-3-carboxylic acid (Example 101A) and 47.3 (0.266 mmol) of 2,4-difluoro-N'-hydroxybenzenecarboximidamide were reacted according to the General Method 1. Yield: 35.2 mg (27% of theory).

LC-MS (Method 3B): $R_t$=2.19 min; MS (ESIpos): m/z=509 [M+H]$^+$;

$^1$H-NMR (400 MHz, DMSO-d$_6$): δ=8.10 (q, 1H), 7.71 (d, 2H), 7.58 (d, 2H), 7.54 (t, 1H), 7.32 (td, 1H), 4.43-4.37 (m, 1H), 4.24 (br d, 1H), 4.11 (q, 2H), 3.79 (br d, 1H), 3.75-3.65 (m, 2H), 3.44 (tt, 1H), 3.12 (t, 1H), 3.06-2.97 (m, 2H), 2.40 (br d, 1H), 2.12 (dd, 1H).

Example 307

{3-[3-(2,5-Difluorophenyl)-1,2,4-oxadiazol-5-yl]-5-[4-(trifluoromethyl)phenyl]piperidin-1-yl}(3-hydroxyazetidin-1-yl)methanone [racemic cis isomer]

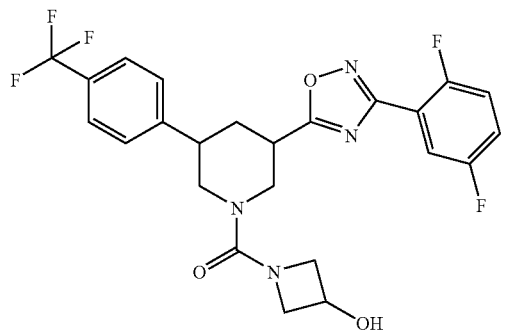

90.0 mg (0.242 mmol) of 1-[(3-hydroxyazetidin-1-yl)carbonyl]-5-[4-(trifluoromethyl)phenyl]piperidine-3-carboxylic acid (Example 101A) and 45.7 (0.266 mmol) of 2,5-difluoro-N'-hydroxybenzenecarboximidamide (Example 74A) were reacted according to the General Method 1. Yield: 42.9 mg (34% of theory).

LC-MS (Method 3B): $R_t$=2.18 min; MS (ESIpos): m/z=509 [M+H]$^+$;

$^1$H-NMR (400 MHz, DMSO-d$_6$): δ=7.81-7.77 (m, 1H), 7.71 (d, 2H), 7.58 (d, 1H), 7.54 (td, 2H), 5.59 (d, 1H), 4.44-4.36 (m, 1H), 4.25 (br d, 1H), 4.11 (q, 2H), 3.82 (br d, 1H), 3.75-3.69 (m, 2H), 3.45 (tt, 1H), 3.13 (t, 1H), 3.07-2.98 (m, 2H), 2.40 (br d, 1H), 2.12 (dd, 1H).

Example 308

{3-[3-(2-Chlorophenyl)-1,2,4-oxadiazol-5-yl]-5-[4-(trifluoromethyl)phenyl]piperidin-1-yl}(3-hydroxyazetidin-1-yl)methanone [racemic cis isomer]

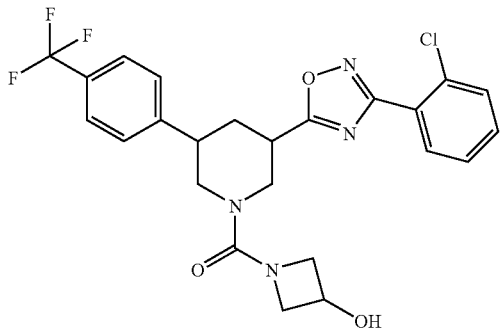

90.0 mg (0.242 mmol) of 1-[(3-hydroxyazetidin-1-yl)carbonyl]-5-[4-(trifluoromethyl)phenyl]piperidine-3-carboxylic acid (Example 101A) and 34.8 mg (0.266 mmol) of 2-chloro-N'-hydroxybenzenecarboximidamide were reacted according to the General Method 1. Yield: 34.8 mg (27% of theory).

LC-MS (Method 3B): $R_t$=2.21 min; MS (ESIpos): m/z=507 [M+H]$^+$;

$^1$H-NMR (400 MHz, DMSO-d$_6$): δ=7.92 (dd, 1H), 7.72-7.67 (m, 3H), 7.63-7.52 (m, 4H), 5.59 (d, 1H), 4.43-4.36 (m, 1H), 4.25 (br d, 1H), 4.11 (q, 2H), 3.79 (br d, 1H), 3.75-3.69 (m, 2H), 3.45 (tt, 1H), 3.12 (t, 1H), 3.06-3.01 (m, 2H), 2.41 (br d, 1H), 2.12 (dd, 1H).

Example 309

{3-[3-(3-Chlorophenyl)-1,2,4-oxadiazol-5-yl]-5-[4-(trifluoromethyl)phenyl]piperidin-1-yl}(3-hydroxyazetidin-1-yl)methanone [racemic cis isomer]

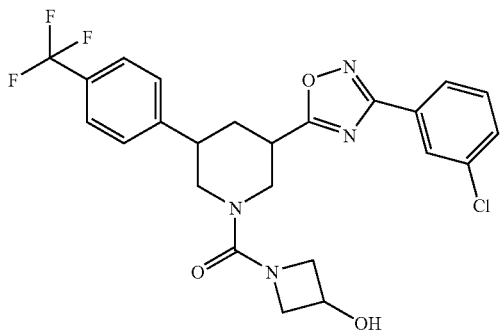

90.0 mg (0.242 mmol) of 1-[(3-hydroxyazetidin-1-yl)carbonyl]-5-[4-(trifluoromethyl)phenyl]piperidine-3-carboxylic acid (Example 101A) and 45.4 mg (0.266 mmol) of 3-chloro-N'-hydroxybenzenecarboximidamide were reacted according to the General Method 1. Yield: 34.7 mg (28% of theory).

LC-MS (Method 3B): $R_t$=2.38 min; MS (ESIpos): m/z=507 [M+H]$^+$;

$^1$H-NMR (400 MHz, DMSO-d$_6$): δ=7.99-7.97 (m, 2H), 7.73-7.68 (m, 3H), 7.64-7.58 (m, 3H), 5.59 (d, 1H), 4.43-4.36 (m, 1H), 4.25 (br d, 1H), 4.11 (q, 2H), 3.79 (br d, 1H), 3.75-3.69 (m, 2H), 3.44 (tt, 1H), 3.13 (t, 1H), 3.03-3.01 (m, 2H), 2.41 (br d, 1H), 2.13 (q, 1H).

Example 310

{3-[3-(3,5-Difluoropyridin-2-yl)-1,2,4-oxadiazol-5-yl]-5-[4-(trifluoromethyl)phenyl]piperidin-1-yl}(3-hydroxyazetidin-1-yl)methanone [racemic cis isomer]

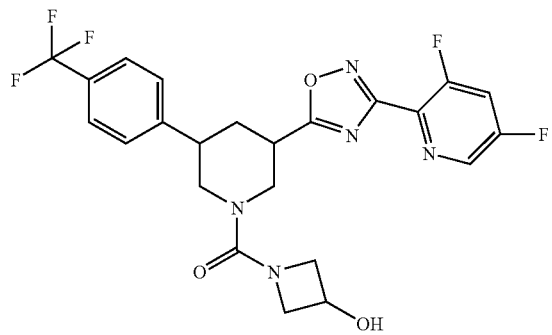

90.0 mg (0.242 mmol) of 1-[(3-hydroxyazetidin-1-yl)carbonyl]-5-[4-(trifluoromethyl)phenyl]piperidine-3-carboxylic acid (Example 101A) and 61.0 mg (0.266 mmol) of 3,5-difluoro-N'-hydroxypyridine-2-carboximidamide were reacted according to the General Method 1. Yield: 24 mg (19% of theory).

LC-MS (Method 3B): $R_t$=1.90 min; MS (ESIpos): m/z=510 [M+H]$^+$;

$^1$H-NMR (400 MHz, DMSO-d$_6$): δ=8.75 (d, 1H), 8.25 (dd, 1H), 7.71 (d, 2H), 7.58 (d, 2H), 5.59 (d, 1H), 4.42-4.36 (m, 1H), 4.26 (br d, 1H), 4.11 (q, 2H), 3.79 (br d, 1H), 3.75-3.69 (m, 2H), 3.47 (tt, 1H), 3.13 (t, 1H), 3.00 (br d, 2H), 2.41 (br d, 1H), 2.14 (q, 1H).

Example 311

(3-Methoxyazetidin-1-yl) {3-(3-methyl-1,2,4-oxadiazol-5-yl)-5-[4-(trifluoromethyl)phenyl]-piperidin-1-yl}methanone [enantiomerically pure cis isomer]

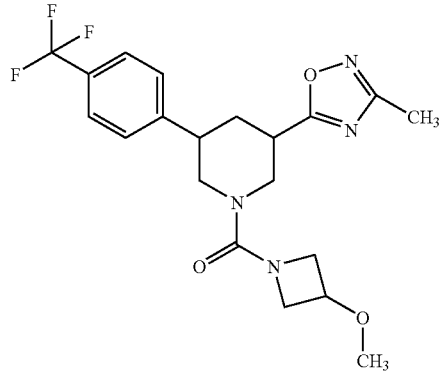

250 mg (0.647 mmol) of 1-[(3-methoxyazetidin-1-yl)carbonyl]-5-[4-(trifluoromethyl)phenyl]piperidine-3-carboxylic acid (Example 103A) and 52.7 mg (0.712 mmol) of N'-hydroxyethanimidamide were reacted according to the General Method 1. Enantiomer separation of the racemate according to Method 16D gave 73.0 mg of the title compound from Example 311 and 64.0 mg of the title compound from Example 312 (50% of theory).

HPLC (Method 16E): $R_t$=7.27 min, >99.0% ee; LC-MS (Method 3B): $R_t$=1.96 min; MS (ESIpos): m/z=425 [M+H]$^+$;

$^1$H-NMR (400 MHz, DMSO-d$_6$): δ=7.70 (d, 2H), 7.56 (d, 2H), 4.20-4.05 (m, 4H), 3.82-3.72 (m, 3H), 3.36-3.27 (obscured, 1H), 3.18 (s, 3H), 3.08-2.93 (m, 3H), 2.33 (s, 3H), 2.31 (br d, 1H), 2.03 (dd, 1H).

Example 312

(3-Methoxyazetidin-1-yl) {3-(3-methyl-1,2,4-oxadiazol-5-yl)-5-[4-(trifluoromethyl)phenyl]-piperidin-1-yl}methanone [enantiomerically pure cis isomer]

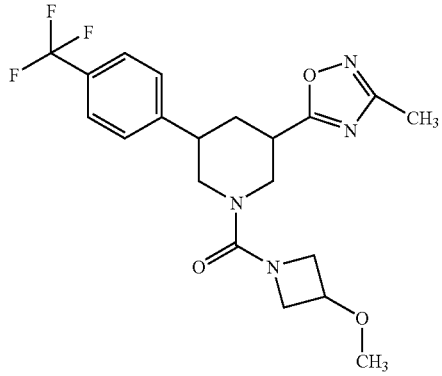

250 mg (0.647 mmol) of 1-[(3-methoxyazetidin-1-yl)carbonyl]-5-[4-(trifluoromethyl)phenyl]piperidine-3-carboxylic acid (Example 103A) and 52.7 mg (0.712 mmol) of N'-hydroxyethanimidamide were reacted according to the General Method 1. Enantiomer separation of the racemate according to Method 16D gave 73.0 mg of the title compound from Example 311 and 64.0 mg of the title compound from Example 312 (50% of theory).

HPLC (Method 16E): $R_t$=15.66 min, >99.0% ee; LC-MS (Method 3B): $R_t$=1.96 min; MS (ESIpos): m/z=425 [M+H]$^+$.

Example 313

(3-Methoxyazetidin-1-yl) {3-[3-(2-methoxyethyl)-1,2,4-oxadiazol-5-yl]-5-[4-(trifluoromethyl)-phenyl]piperidin-1-yl}methanone [enantiomerically pure cis isomer]

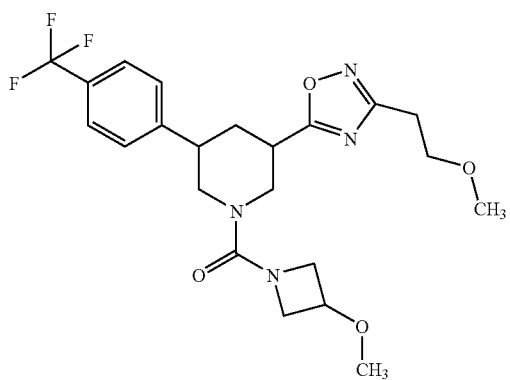

250 mg (0.647 mmol) of 1-[(3-methoxyazetidin-1-yl)carbonyl]-5-[4-(trifluoromethyl)phenyl]piperidine-3-carboxylic acid (Example 103A) and 112 mg (0.712 mmol, 75% pure) of N'-hydroxy-3-methoxypropanimidamide (Example 64A) were reacted according to the General Method 1. Enantiomer separation of the racemate according to Method 16D gave 67.0 mg of the title compound from Example 313 and 67.0 mg of the title compound from Example 314 (44% of theory).

HPLC (Method 16E): $R_t$=7.88 min, >99.0% ee; LC-MS (Method 3B): $R_t$=1.98 min; MS (ESIpos): m/z=469 [M+H]$^+$;
$^1$H-NMR (400 MHz, DMSO-d$_6$): δ=7.71 (d, 2H), 7.57 (d, 2H), 4.21-4.04 (m, 4H), 3.81-3.72 (m, 3H), 3.68 (t, 2H), 3.39-3.30 (obscured, 1H), 3.24 (s, 3H), 3.19 (s, 3H), 3.09-2.96 (m, 3H), 2.94 (t, 2H), 2.32 (br d, 1H), 2.04 (dd, 1H).

Example 314

(3-Methoxyazetidin-1-yl) {3-[3-(2-methoxyethyl)-1,2,4-oxadiazol-5-yl]-5-[4-(trifluoromethyl)phenyl]piperidin-1-yl}methanone [enantiomerically pure cis isomer]

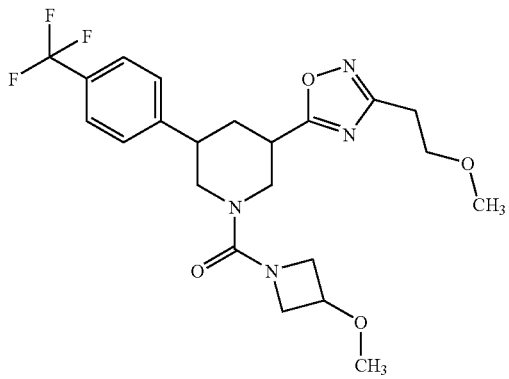

250 mg (0.647 mmol) of 1-[(3-methoxyazetidin-1-yl)carbonyl]-5-[4-(trifluoromethyl)phenyl]piperidine-3-carboxylic acid (Example 103A) and 112 mg (0.712 mmol, 75% pure) of N'-hydroxy-3-methoxypropanimidamide (Example 64A) were reacted according to the General Method 1. Enantiomer separation of the racemate according to Method 16D gave 67.0 mg of the title compound from Example 313 and 67.0 mg of the title compound from Example 314 (44% of theory).

HPLC (Method 16E): $R_t$=9.75 min, >99.0% ee; LC-MS (Method 3B): $R_t$=1.98 min; MS (ESIpos): m/z=469 [M+H]$^+$.

Example 315

{3-(3-Methyl-1,2,4-oxadiazol-5-yl)-5-[4-(trifluoromethyl)phenyl]piperidin-1-yl}(1,3-thiazolidin-3-yl)methanone [enantiomerically pure cis isomer]

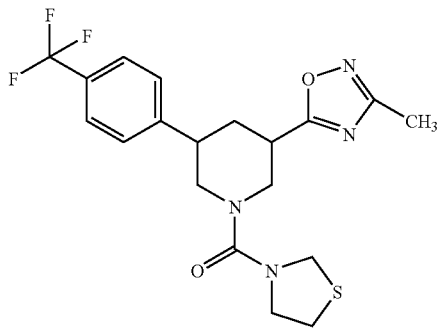

250 mg (0.644 mmol) of 1-(1,3-thiazolidin-3-ylcarbonyl)-5-[4-(trifluoromethyl)phenyl]piperidine-3-carboxylic acid (Example 102A) and 52.5 mg (0.708 mmol) of N'-hydroxyethanimidamide were reacted according to the General Method 1. Enantiomer separation of the racemate according to Method 16D gave 38.0 mg of the title compound from Example 315 and 41.0 mg of the title compound from Example 316 (29% of theory).

HPLC (Method 16E): $R_t$=8.92 min, >99.0% ee; LC-MS (Method 3B): $R_t$=2.17 min; MS (ESIpos): m/z=427 [M+H]$^+$;
$^1$H-NMR (400 MHz, DMSO-d$_6$): δ=7.71 (d, 2H), 7.57 (d, 2H), 4.48 (d, 1H), 4.45 (d, 1H), 4.17 (br d, 1H), 3.84 (br d, 1H), 3.62-3.50 (m, 3H), 3.42 (tt, 1H), 3.13 (t, 1H), 3.07 (br d, 2H), 2.90 (t, 2H), 2.36-2.30 (m, 4H), 2.05 (dd, 1H).

Example 316

{3-(3-Methyl-1,2,4-oxadiazol-5-yl)-5-[4-(trifluoromethyl)phenyl]piperidin-1-yl}(1,3-thiazolidin-3-yl)methanone [enantiomerically pure cis isomer]

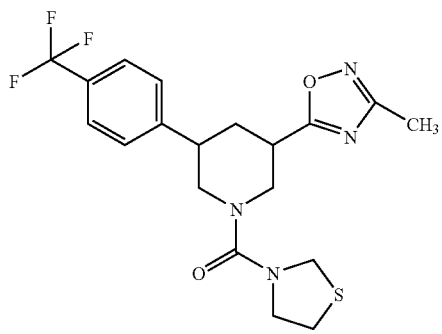

250 mg (0.644 mmol) of 1-(1,3-thiazolidin-3-ylcarbonyl)-5-[4-(trifluoromethyl)phenyl]piperidine-3-carboxylic acid (Example 102A) and 52.5 mg (0.708 mmol) of N'-hydroxyethanimidamide were reacted according to the General Method 1. Enantiomer separation of the racemate according to Method 16D gave 38.0 mg of the title compound from Example 315 and 41.0 mg of the title compound from Example 316 (29% of theory)

HPLC (Method 16E): $R_t$=35.97 min, >99.0% ee; LC-MS (Method 3B): $R_t$=2.17 min; MS (ESIpos): m/z=427 [M+H]$^+$.

Example 317

{3-[3-(2-Methoxyethyl)-1,2,4-oxadiazol-5-yl]-5-[4-(trifluoromethyl)phenyl]piperidin-1-yl}(1,3-thiazolidin-3-yl)methanone [enantiomerically pure cis isomer]

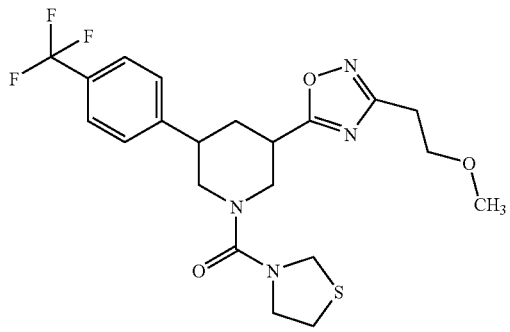

250 mg (0.644 mmol) of 1-(1,3-thiazolidin-3-ylcarbonyl)-5-[4-(trifluoromethyl)phenyl]piperidine-3-carboxylic acid (Example 102A) and 112 mg (0.708 mmol, 75% pure) of N'-hydroxy-3-methoxypropanimidamide (Example 64A) were reacted according to the General Method 1. Enantiomer separation of the racemate according to Method 16D gave 35.0 mg of the title compound from Example 317 and 38.0 mg of the title compound from Example 318 (24% of theory).

HPLC (Method 16E): $R_t$=8.21 min, >99.0% ee; LC-MS (Method 3B): $R_t$=8.21 min; MS (ESIpos): m/z=471 [M+H]+;
$^1$H-NMR (400 MHz, DMSO-d$_6$): δ=7.71 (d, 2H), 7.59 (d, 2H), 4.48 (d, 1H), 4.45 (d, 1H), 4.18 (br d, 1H), 3.84 (br d, 1H), 3.68 (t, 2H), 3.62-3.51 (m, 2H), 3.44 (tt, 1H), 3.23 (s, 3H), 3.18-3.05 (m, 3H), 2.94 (t, 2H), 2.90 (t, 2H), 2.35 (br d, 1H), 2.05 (dd, 1H).

Example 318

{3-[3-(2-Methoxyethyl)-1,2,4-oxadiazol-5-yl]-5-[4-(trifluoromethyl)phenyl]piperidin-1-yl}(1,3-thiazolidin-3-yl)methanone [enantiomerically pure cis isomer]

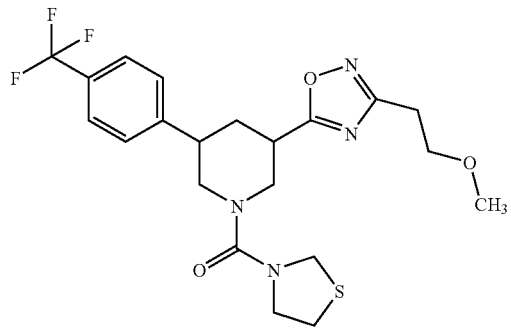

250 mg (0.644 mmol) of 1-(1,3-thiazolidin-3-ylcarbonyl)-5-[4-(trifluoromethyl)phenyl]piperidine-3-carboxylic acid (Example 102A) and 112 mg (0.708 mmol, 75% pure) of N'-hydroxy-3-methoxypropanimidamide (Example 64A) were reacted according to the General Method 1. Enantiomer separation of the racemate according to Method 16D gave 35.0 mg of the title compound from Example 317 and 38.0 mg of the title compound from Example 318 (24% of theory).

HPLC (Method 16E): $R_t$=16.51 min, >99.0% ee; LC-MS (Method 3B): $R_t$=8.21 min; MS (ESIpos): m/z=471 [M+H]+.

Example 319

{3-(4-Ethylphenyl)-5-[3-(2-methoxyethyl)-1,2,4-oxadiazol-5-yl]piperidin-1-yl}(3-hydroxyazetidin-1-yl)methanone [enantiomerically pure cis isomer]

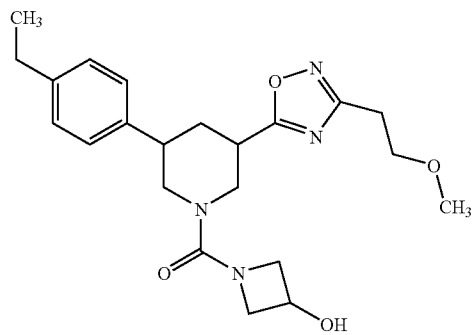

Enantiomer separation of 860 mg of the racemate from Example 394 according to Method 14D gave 415 mg of the title compound from Example 319 (Enantiomer 1) and 420 mg of the title compound from Example 320 (Enantiomer 2).

HPLC (Method 19E): $R_t$=4.72 min, >97.0% ee;

LC-MS (Method 9B): $R_t$=1.00 min; MS (ESIpos): m/z=415 [M+H]+.

$[α]_{365}^{20}$=−17.5, methanol

Example 320

{3-(4-Ethylphenyl)-5-[3-(2-methoxyethyl)-1,2,4-oxadiazol-5-yl]piperidin-1-yl}(3-hydroxyazetidin-1-yl)methanone [enantiomerically pure cis isomer]

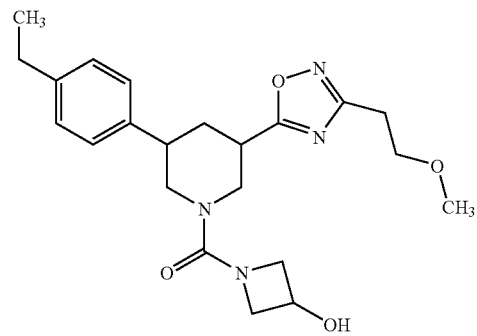

Enantiomer separation of 860 mg of the racemate from Example 394 according to Method 14D gave 415 mg of the title compound from Example 319 (Enantiomer 1) and 420 mg of the title compound from Example 320 (Enantiomer 2).

HPLC (Method 19E): $R_t$=8.12 min, >99.0% ee;

LC-MS (Method 9B): $R_t$=1.00 min; MS (ESIpos): m/z=415 [M+H]+.

$[α]_{365}^{20}$=+15.8, methanol

Example 321

{3-[3-(2-Methoxyethyl)-1,2,4-oxadiazol-5-yl]-5-[3-methyl-4-(trifluoromethoxy)phenyl]piperidin-1-yl}(morpholin-4-yl)methanone [enantiomerically pure cis isomer]

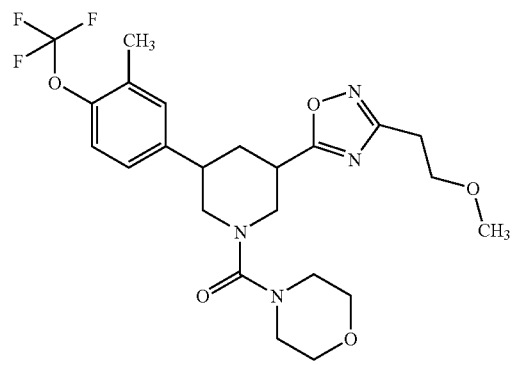

Enantiomer separation of 50 mg of the racemate from Example 399 according to Method 23D gave 13 mg of the title compound from Example 321 (Enantiomer 1) and 12 mg of the title compound from Example 322 (Enantiomer 2).

HPLC (Method 20E): $R_t$=24.15 min, >99.5% ee;
LC-MS (Method 9B): $R_t$=1.16 min; MS (ESIpos): m/z=499 [M+H]$^+$.

Example 322

{3-[3-(2-Methoxyethyl)-1,2,4-oxadiazol-5-yl]-5-[3-methyl-4-(trifluoromethoxy)phenyl]piperidin-1-yl}(morpholin-4-yl)methanone [enantiomerically pure cis isomer]

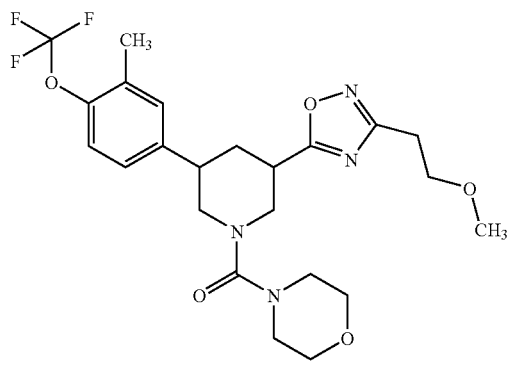

Enantiomer separation of 50 mg of the racemate from Example 399 according to Method 23D gave 13 mg of the title compound from Example 321 (Enantiomer 1) and 12 mg of the title compound from Example 322 (Enantiomer 2).

HPLC (Method 20E): $R_t$=68.57 min, >99.5% ee;
LC-MS (Method 9B): $R_t$=1.16 min; MS (ESIpos): m/z=499 [M+H]$^+$.

Example 323

1-({3-[3-(Propan-2-yl)-1,2,4-oxadiazol-5-yl]-5-[4-(trifluoromethyl)phenyl]piperidin-1-yl}-carbonyl)piperidine-4-carbonitrile [enantiomerically pure cis isomer]

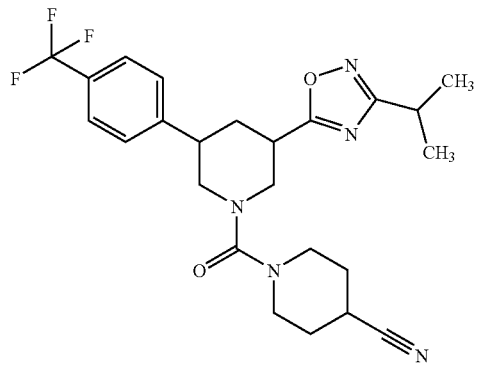

Enantiomer separation of 350 mg of the racemate from Example 284 according to Method 13D gave 160 mg of the title compound from Example 323 (Enantiomer 1) and 170 mg of the title compound from Example 324 (Enantiomer 2).

HPLC (Method 16E): $R_t$=5.33 min, >99.5% ee;
LC-MS (Method 9B): $R_t$=1.24 min; MS (ESIpos): m/z=475 [M+H]$^+$.

$^1$H-NMR (400 MHz, DMSO-d$_6$): δ=7.70 (dd, 2H), 7.57 (d, 2H), 3.96 (br d, 1H), 3.56 (d, 1H), 3.45-3.34 (m, 3H), 3.13-2.97 (m, 7H), 2.36-2.29 (m, 1H), 2.01 (dd, 1H), 1.91-1.82 (m, 2H), 1.74-1.62 (m, 2H), 1.26 (d, 6H).

Example 324

1-({3-[3-(Propan-2-yl)-1,2,4-oxadiazol-5-yl]-5-[4-(trifluoromethyl)phenyl]piperidin-1-yl}-carbonyl)piperidine-4-carbonitrile [enantiomerically pure cis isomer]

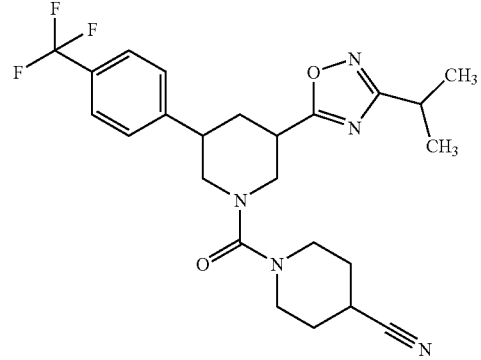

Enantiomer separation of 350 mg of the racemate from Example 284 according to Method 13D gave 160 mg of the title compound from Example 323 (Enantiomer 1) and 170 mg of the title compound from Example 324 (Enantiomer 2).

HPLC (Method 16E): $R_t$=6.18 min, >99.5% ee;
LC-MS (Method 9B): $R_t$=1.24 min; MS (ESIpos): m/z=475 [M+H]$^+$.

Example 325

(3-Hydroxyazetidin-1-yl) {3-(3-methyl-1,2,4-oxadiazol-5-yl)-5-[4-(trifluoromethyl)phenyl]-piperidin-1-yl}methanone [enantiomerically pure cis isomer]

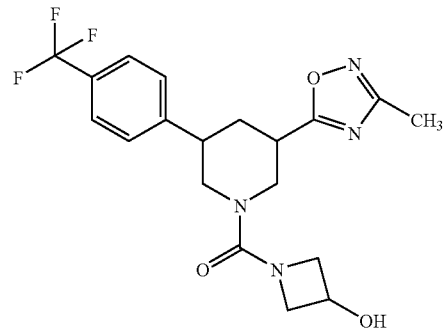

Enantiomer separation of 250 mg of the racemate from Example 298 according to Method 24D gave 86 mg of the title compound from Example 325 (Enantiomer 1) and 77 mg of the title compound from Example 326 (Enantiomer 2).

HPLC (Method 11E): $R_t$=4.69 min, >99.5% ee;
LC-MS (Method 9B): $R_t$=0.97 min; MS (ESIpos): m/z=410 [M+H]$^+$.
$^1$H-NMR (400 MHz, DMSO-$d_6$): δ=7.70 (d, 2H), 7.56 (d, 2H), 5.58 (d, 1H), 4.43-4.34 (m, 1H), 4.15 (br d, 1H), 4.10 (q, 2H), 3.77 (br d, 1H), 3.73-3.66 (m, 2H), 3.30 (obscured, 1H), 3.07-2.92 (m, 3H), 2.2.35-2.28 (m, 4H), 2.04 (dd, 1H).

Example 326

(3-Hydroxyazetidin-1-yl) {3-(3-methyl-1,2,4-oxadiazol-5-yl)-5-[4-(trifluoromethyl)phenyl]-piperidin-1-yl}methanone [enantiomerically pure cis isomer]

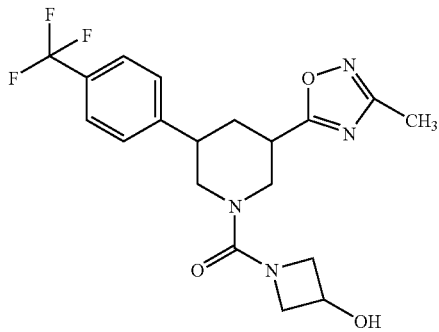

Enantiomer separation of 250 mg of the racemate from Example 298 according to Method 24D gave 86 mg of the title compound from Example 325 (Enantiomer 1) and 77 mg of the title compound from Example 326 (Enantiomer 2).

HPLC (Method 11E): $R_t$=7.46 min, >99.5% ee;
LC-MS (Method 9B): $R_t$=0.97 min; MS (ESIpos): m/z=410 [M+H]$^+$.

Example 327

{3-[3-Methyl-4-(trifluoromethoxy)phenyl]-5-[3-(propan-2-yl)-1,2,4-oxadiazol-5-yl]piperidin-1-yl}(morpholin-4-yl)methanone [enantiomerically pure cis isomer]

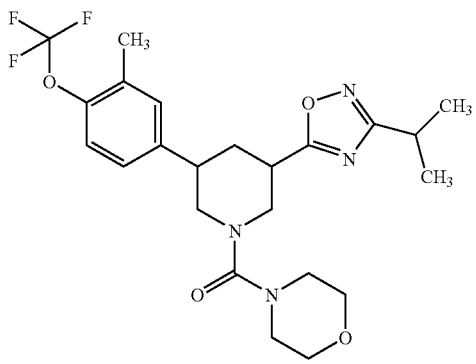

Enantiomer separation of 286 mg of the racemate from Example 403 according to Method 25D gave 117 mg of the title compound from Example 327 (Enantiomer 1) and 121 mg of the title compound from Example 328 (Enantiomer 2).

HPLC (Method 21E): $R_t$=6.67 min, >99.5% ee;
LC-MS (Method 9B): $R_t$=1.29 min; MS (ESIpos): m/z=482 [M+H]$^+$.
$^1$H-NMR (400 MHz, DMSO-$d_6$): δ=7.37 (s, 2H), 7.27 (s, 2H), 3.99 (d, 1H), 3.51-3.64 (m, 5H), 3.35-3.44 (m, 1H), 3.15-3.25 (m, 4H), 2.85-3.10 (m, 4H), 2.22-2.35 (m, 4H), 1.96 (q, 1H), 1.26 (d, 6H).

Example 328

{3-[3-Methyl-4-(trifluoromethoxy)phenyl]-5-[3-(propan-2-yl)-1,2,4-oxadiazol-5-yl]piperidin-1-yl}-(morpholin-4-yl)methanone [enantiomerically pure cis isomer]

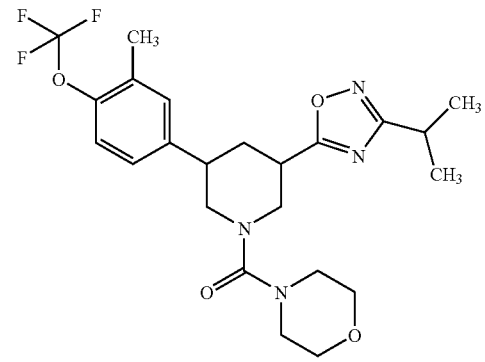

Enantiomer separation of 286 mg of the racemate from Example 403 according to Method 25D gave 117 mg of the title compound from Example 327 (Enantiomer 1) and 121 mg of the title compound from Example 328 (Enantiomer 2).

HPLC (Method 21E): $R_t$=10.82 min, >99.5% ee;
LC-MS (Method 9B): $R_t$=1.29 min; MS (ESIpos): m/z=482 [M+H]$^+$.
$^1$H-NMR (400 MHz, DMSO-$d_6$): δ=7.37 (s, 2H), 7.27 (s, 2H), 3.99 (d, 1H), 3.51-3.64 (m, 5H), 3.35-3.44 (m, 1H), 3.15-3.25 (m, 4H), 2.85-3.10 (m, 4H), 2.22-2.35 (m, 4H), 1.96 (q, 1H), 1.26 (d, 6H).

Example 329

{3-[3-(4-Methylpyridin-3-yl)-1,2,4-oxadiazol-5-yl]-5-[4-(trifluoromethyl)phenyl]piperidin-1-yl}-(morpholin-4-yl)methanone [racemic cis isomer]

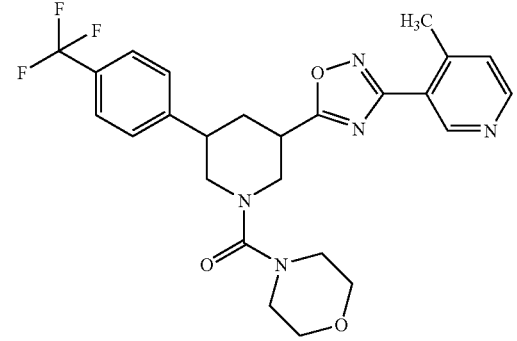

250 mg (about 0.520 mmol) of the compound from Example 49A and 87 mg (0.580 mmol) of N'-hydroxy-4-methylpyridine-3-carboximidamide (Example 70A) were reacted according to the General Method 1. Yield: 22 mg (8% of theory).

LC-MS (Method 1B): $R_t$=2.37 min; MS (ESIpos): m/z=502 [M+H]$^+$;

$^1$H-NMR (400 MHz, DMSO-d$_6$): δ=9.02 (s, 1H), 8.60 (d, 1H), 7.71 (d, 2H), 7.60 (d, 2H), 7.47 (d, 1H), 4.11 (br d, 1H), 3.66 (d, 1H), 3.62-3.50 (m, 5H), 3.26-3.14 (m, 5H), 3.12-3.06 (m, 2H), 2.59 (s, 3H), 2.43 (br d, 1H), 2.11 (q, 1H).

Example 330

{3-[3-(5-Methylpyridin-2-yl)-1,2,4-oxadiazol-5-yl]-5-[4-(trifluoromethyl)phenyl]piperidin-1-yl}-(morpholin-4-yl)methanone [racemic cis isomer]

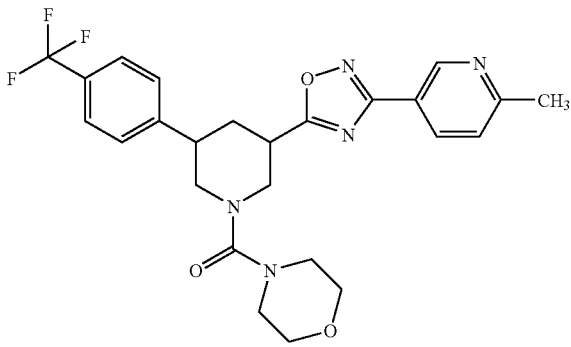

250 mg (about 0.520 mmol) of the compound from Example 49A and 87 mg (0.58 mmol) of N'-hydroxy-5-methylpyridine-3-carboximidamide (Example 71A) were reacted according to the General Method 1. Yield: 47 mg (18% of theory).

LC-MS (Method 1B): $R_t$=2.38 min; MS (ESIpos): m/z=502 [M+H]$^+$;

$^1$H-NMR (400 MHz, DMSO-d$_6$): δ=9.04 (s, 1H), 8.24 (dd, 1H), 7.71 (d, 2H), 7.60 (d, 2H), 7.47 (d, 1H), 4.09 (br d, 1H), 3.65 (d, 1H), 3.61-3.50 (m, 5H), 3.23-3.21 (m, 4H), 3.16 (t, 1H), 3.08-3.03 (m, 2H), 2.56 (s, 3H), 2.42 (br d, 1H), 2.11 (q, 1H).

Example 331

{3-(3-Ethyl-1,2,4-oxadiazol-5-yl)-5-[4-(trifluoromethyl)phenyl]piperidin-1-yl}(morpholin-4-yl)-methanone [racemic cis isomer]

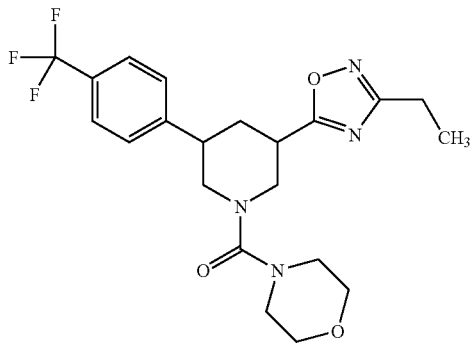

150 mg (0.388 mmol) of the compounds from Example 81A and 68 mg (0.78 mmol) of t-hydroxypropanimidamide were reacted according to the General Method 2. Yield: 123 mg (70% of theory)

LC-MS (Method 2B): $R_t$=1.29 min; MS (ESIpos): m/z=439 [M+H]$^+$;

$^1$H-NMR (400 MHz, DMSO-d$_6$): δ=7.70 (d, 2H), 7.57 (d, 2H), 3.98 (br d, 1H), 3.63 (d, 1H), 3.59-3.53 (m, 4H), 3.40 (tt, 1H), 3.23-3.15 (m, 4H), 3.09-2.98 (m, 3H), 2.71 (q, 2H), 2.33 (br d, 1H), 2.01 (q, 1H), 1.22 (t, 3H).

Example 332

Morpholin-4-yl {3-(3-propyl-1,2,4-oxadiazol-5-yl)-5-[4-(trifluoromethyl)phenyl]piperidin-1-yl}-methanone [racemic cis isomer]

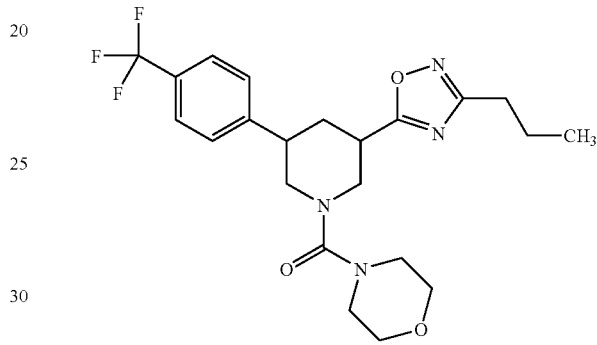

150 mg (0.388 mmol) of the compound from Example 81A and 79 mg (0.78 mmol) of N'-hydroxybutananimidamide were reacted according to the General Method 2. Yield: 185 mg (100% of theory)

LC-MS (Method 2B): $R_t$=1.36 min; MS (ESIpos): m/z=453[M+H]$^+$;

$^1$H-NMR (400 MHz, DMSO-d$_6$): δ=7.70 (d, 2H), 7.57 (d, 2H), 3.99 (br d, 1H), 3.63 (d, 1H), 3.59-3.53 (m, 4H), 3.40 (tt, 1H), 3.23-3.17 (m, 4H), 3.08-2.98 (m, 3H), 2.66 (t, 2H), 2.32 (br d, 1H), 2.01 (q, 1H), 1.73-1.64 (m, 2H), 0.92 (t, 3H).

Example 333

Morpholin-4-yl{3-[3-(propan-2-yl)-1,2,4-oxadiazol-5-yl]-5-[4-(trifluoromethyl)phenyl]piperidin-1-yl}methanone [enantiomerically pure cis isomer]

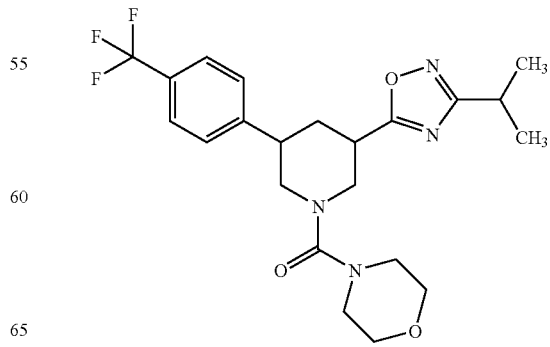

Enantiomer separation of 50 mg of the racemate from Example 402 according to Method 8D gave 22 mg of the title compound from Example 333 and 21 mg of the title compound from Example 334.

HPLC (Method 6E): $R_t$=9.65 min, >99% ee; LC-MS (Method 2B): $R_t$=1.36 min; MS (ESIpos): m/z=453[M+H]$^+$.

Example 334

Morpholin-4-yl{3-[3-(propan-2-yl)-1,2,4-oxadiazol-5-yl]-5-[4-(trifluoromethyl)phenyl]piperidin-1-yl}methanone [enantiomerically pure cis isomer]

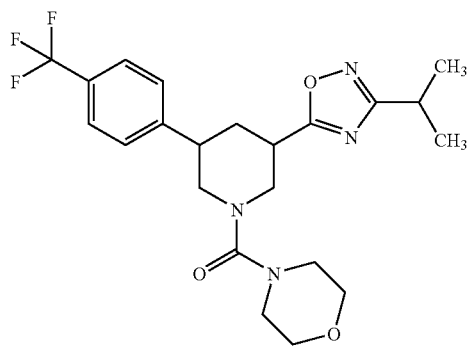

Enantiomer separation of 50 mg of the racemate from Example 402 according to Method 8D gave 22 mg of the title compound from Example 333 and 21 mg of the title compound from Example 334.

HPLC (Method 6E): $R_t$=20.25 min, >99% ee; LC-MS (Method 2B): $R_t$=1.36 min; MS (ESIpos): m/z=453[M+H]$^+$.

Example 335

{3-(3-Methyl-1,2,4-oxadiazol-5-yl)-5-[4-(trifluoromethyl)phenyl]piperidin-1-yl}(morpholin-4-yl)-methanone [enantiomerically pure cis isomer]

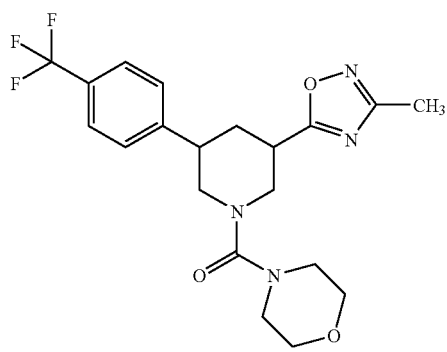

Enantiomer separation of 80 mg of the racemate from Example 416 according to Method 10D gave 34 mg of the title compound from Example 335 and 34 mg of the title compound from Example 336.

HPLC (Method 8E): $R_t$=6.93 min, >99.0% ee; LC-MS (Method 2B): $R_t$=1.21 min; MS (ESIpos): m/z=425[M+H]$^+$.

Example 336

{3-(3-Methyl-1,2,4-oxadiazol-5-yl)-5-[4-(trifluoromethyl)phenyl]piperidin-1-yl}(morpholin-4-yl)-methanone [enantiomerically pure cis isomer]

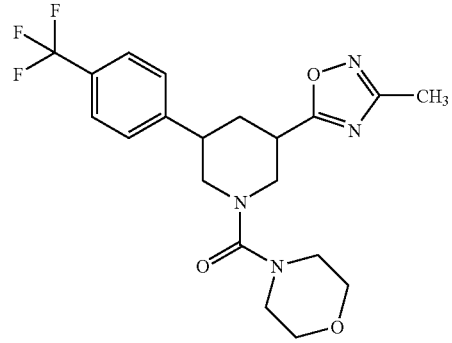

Enantiomer separation of 80 mg of the racemate from Example 416 according to Method 10D gave 34 mg of the title compound from Example 335 and 34 mg of the title compound from Example 336.

HPLC (Method 8E): $R_t$=13.30 min, >99.0% ee; LC-MS (Method 2B): $R_t$=1.21 min; MS (ESIpos): m/z=425[M+H]$^+$.

Example 337

Morpholin-4-yl {3-[5-(trifluoromethyl)-1,2,4-oxadiazol-3-yl]-5-[4-(trifluoromethyl)phenyl]piperidin-1-yl}methanone [racemic cis isomer]

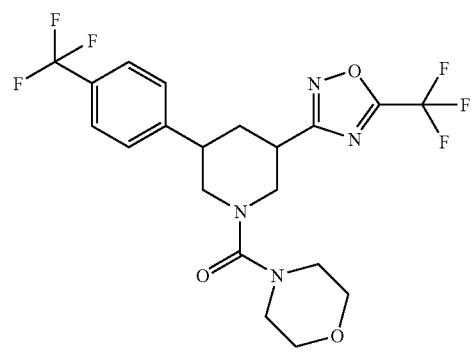

49 mg (0.43 mmol) of trifluoroacetic acid and 120 mg (about 0.216 mmol) of the compound from Example 84A were reacted according to the General Method 2. Yield: 13 mg (12% of theory).

LC-MS (Method 2B): $R_t$=1.42 min; MS (ESIpos): m/z=479 [M+H]$^+$;

¹H-NMR (400 MHz, DMSO-d₆): δ=7.70 (d, 2H), 7.58 (d, 2H), 3.98 (br d, 1H), 3.65 (d, 1H), 3.59-3.53 (m, 4H), 3.37 (tt, 1H), 3.23-3.16 (m, 4H), 3.08-3.02 (m, 3H), 2.32 (br d, 1H), 2.01 (q, 1H).

Example 338

{3-{5-[(Methylamino)methyl]-1,2,4-oxadiazol-3-yl}-5-[4-(trifluoromethyl)phenyl]piperidin-1-yl}-(morpholin-4-yl)methanone hydrochloride [racemic cis isomer]

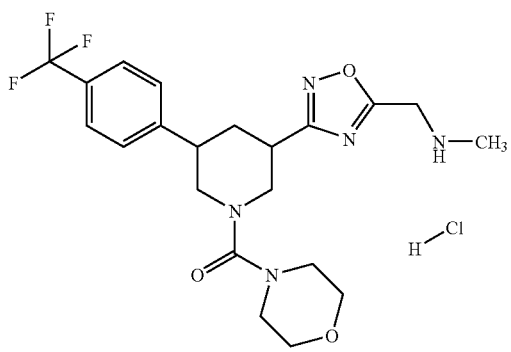

0.43 ml (1.73 mmol) of a 4N solution of hydrogen chloride in dioxane was added to a solution of 96 mg (0.17 mmol) of the compound from Example 90A in 0.8 ml of dioxane, and the mixture was stirred at room temperature for 24 h. The reaction mixture was then concentrated under reduced pressure, dichloromethane was added and the mixture was concentrated again. Yield: 85 mg (99% of theory).

LC-MS (Method 2B): $R_t$=0.91 min; MS (ESIpos): m/z=454 [M+H—HCl]⁺;

¹H-NMR (400 MHz, DMSO-d₆): δ=9.64 (br s, 1H), 7.71 (d, 2H), 7.57 (d, 2H), 4.65 (d, 2H), 4.00 (br d, 1H), 3.66 (d, 2H), 3.24 (tt, 1H), 3.22-3.19 (m, 4H), 3.09-2.93 (m, 3H), 2.70 (s, 3H), 2.30 (br d, 1H), 1.96 (q, 1H).

Example 339

Morpholin-4-yl {3-(5-phenyl-1,3-thiazol-2-yl)-5-[4-(trifluoromethyl)phenyl]piperidin-1-yl}methanone [racemic cis isomer]

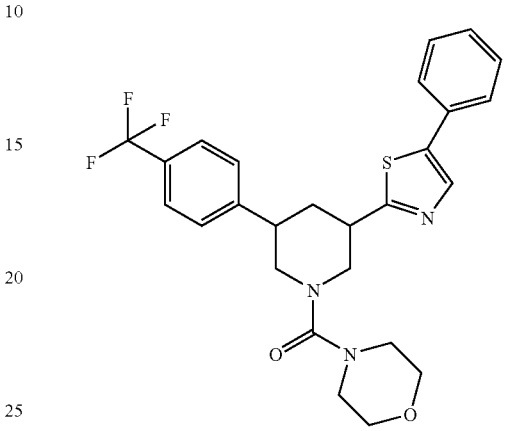

600 mg (1.484 mmol) of Lawesson reagent were added to a solution of 300 mg (about 0.371 mmol) of the compound from Example 106A in 5 ml of dioxane. The reaction mixture was stirred at 50° C. for 5 h and, without any further purification, was purified by preparative HPLC. Yield: 5 mg (3% of theory)

LC-MS (Method 2B): $R_t$=1.49 min; MS (ESIpos): m/z=502 [M+H]⁺;

¹H-NMR (400 MHz, DMSO-d₆): δ=8.14 (s, 1H), 7.71 (d, 2H), 7.62 (dd, 4H), 7.44 (dd, 2H), 7.35 (dd, 1H), 4.03 (br d, 1H), 3.68 (d, 1H), 3.59-3.55 (m, 4H), 3.41 (tt, 1H), 3.23-3.18 (m, 4H), 3.09-2.99 (m, 3H), 2.36 (d, 1H), 2.05 (q, 1H).

The compounds listed in Table 1 were prepared from the appropriate starting materials according to the General Method 2.

TABLE 1

| Ex. No. | Structure | Yield (% of theory) | LC-MS: $R_t$ (Method) | ¹H-NMR (400 MHz, DMSO-d₆) MS (ESI) [M + H]⁺ |
|---|---|---|---|---|
| 340 | 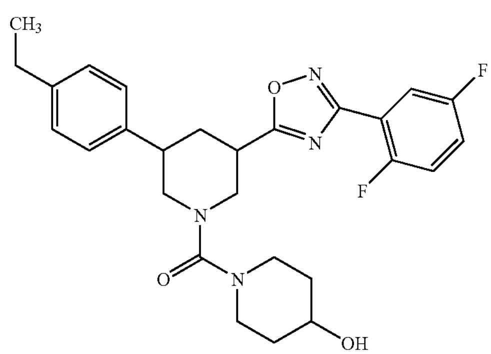 | 51 | m/z = 497; 1.41 min (Method 2B) | δ = 7.81-7.76 (m, 1H), 7.56-7.52 (m, 2H), 7.24 (d, 2H), 7.18 (d, 2H), 4.69 (d, OH), 4.06 (br d, 1H), 3.63-3.47 (m, 5H), 3.07 (t, 1H), 2.99-2.86 (m, 4H), 2.58 (q, 2H), 2.38 (br d, 1H), 2.03 (q, 1H), 1.74-1.71 (m, 2H), 1.36-1.27 (m, 2H), 1.17 (t, 3H). |

TABLE 1-continued

| Ex. No. | Structure | Yield (% of theory) | MS (ESI) [M + H]+; LC-MS: R_t (Method) | ¹H-NMR (400 MHz, DMSO-d₆) |
|---|---|---|---|---|
| 341 | 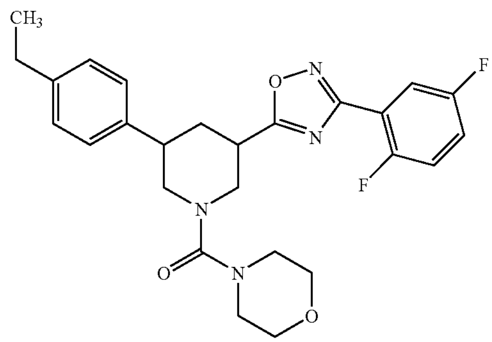 | 54 | m/z = 483; 1.48 min (Method 2B) | δ = 7.81-7.77 (m, 1H), 7.57-7.53 (m, 2H), 7.24 (d, 2H), 7.18 (d, 2H), 4.09 (br d, 1H), 3.62 (br d, 1H), 3.58-3.56 (m, 4H), 3.54-3.48 (m, 1H), 3.22-3.19 (m, 4H), 3.11 (t, 1H), 3.01-2.88 (m, 2H), 2.56 (q, 2H), 2.38 (br d, 1H), 2.04 (q, 1H), 1.17 (t, 3H). |
| 342 | 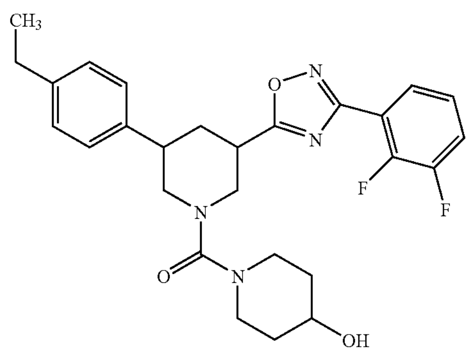 | 57 | m/z = 487; 1.42 min (Method 2B) | δ = 7.85 (dd, 1H), 7.75-7.68 (m, 1H), 7.46-7.40 (m, 1H), 7.24 (d, 2H), 7.18 (d, 2H), 4.68 (d, OH), 4.05 (br d, 1H), 3.63-3.48 (m, 5H), 3.08 (t, 1H), 2.96-2.86 (m, 4H), 2.56 (q, 2H), 2.37 (br d, 1H), 2.04 (q, 1H), 1.75-1.71 (m, 2H), 1.36-1.28 (m, 2H), 1.17 (t, 3H). |
| 343 | 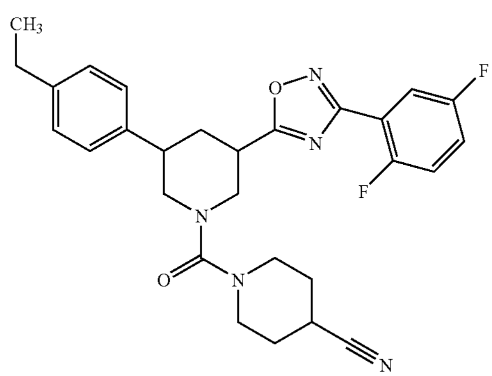 | 68 | m/z = 506; 1.52 min (Method 2B) | δ = 7.78 (dd, 1H), 7.56-7.50 (m, 2H), 7.24 (d, 2H), 7.18 (d, 2H), 4.06 (br d, 1H), 3.57 (br d, 1H), 3.54-3.47 (m, 1H), 3.41-3.37 (m, 2H), 3.13-3.03 (m, 4H), 3.00-2.87 (m, 2H), 2.58 (q, 2H), 2.37 (br d, 1H), 2.03 (q, 1H), 1.90-1.86 (m, 2H), 1.73-1.65 (m, 2H), 1.17 (t, 3H). |
| 344 | 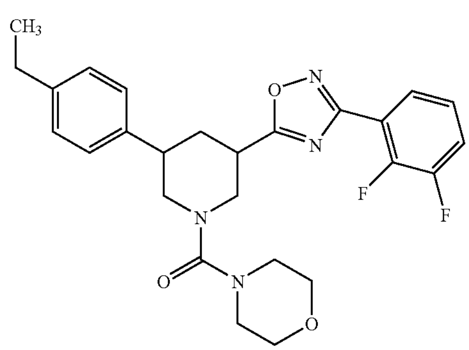 | 60 | m/z = 483; 2.85 min (Method 1B) | δ = 7.87-7.83 (m, 1H), 7.74-7.67 (m, 1H), 7.46-7.41 (m, 1H), 7.24 (d, 2H), 7.18 (d, 2H), 4.10 (br d, 1H), 3.63-3.48 (m, 6H), 3.22-3.20 (m, 4H), 3.11 (t, 1H), 3.02-2.87 (m, 2H), 2.58 (q, 2H), 2.39 (br d, 1H), 2.05 (q, 1H), 1.17 (t, 3H). |

TABLE 1-continued

| Ex. No. | Structure | Yield (% of theory) | MS (ESI) [M + H]+; LC-MS: R<sub>t</sub> (Method) | ¹H-NMR (400 MHz, DMSO-d₆) |
|---|---|---|---|---|
| 345 | 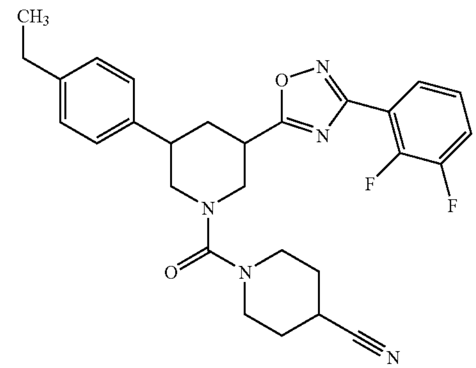 | 71 | m/z = 506; 1.53 min (Method 2B) | δ = 7.86 (dd, 1H), 7.74-7.67 (m, 1H), 7.46-7.41 (m, 1H), 7.24 (d, 2H), 7.18 (d, 2H), 4.07 (br d, 1H), 3.57 (br d, 1H), 3.55-3.48 (m, 1H), 3.40-3.37 (m, 2H), 3.16-3.02 (m, 4H), 2.97-2.87 (m, 2H), 2.58 (q, 2H), 2.36 (br d, 1H), 2.04 (q, 1H), 1.90-1.86 (m, 2H), 1.73-1.65 (m, 2H), 1.17 (t, 3H). |
| 346 | 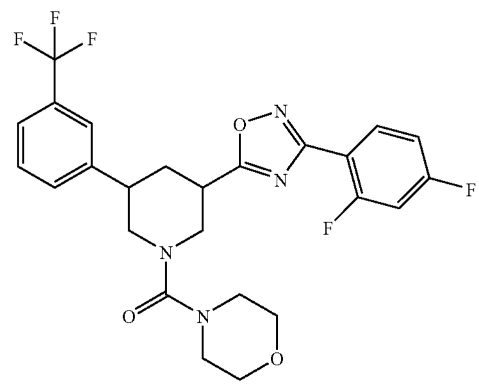 | 68 | m/z = 523; 2.73 min (Method 1B) | δ = 8.13-8.07 (m, 1H), 7.74 (s, 1H), 7.69 (d, 1H), 7.64-7.52 (m, 3H), 7.32 (dd, 1H), 4.08 (br d, 1H), 3.64 (br d, 1H), 3.58-3.54 (m, 4H), 3.53-3.48 (m, 1H), 3.23-3.21 (m, 4H), 3.17-3.07 (m, 3H), 2.41 (br d, 1H), 2.13 (q, 1H). |
| 347 | 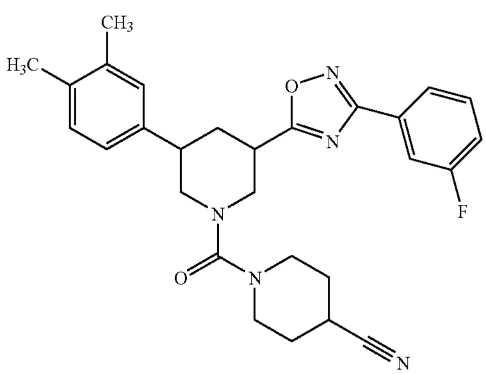 | 73 | m/z = 488; 1.54 min (Method 2B) | δ = 7.87 (d, 1H), 7.76 (dd, 1H), 7.67-7.61 (m, 1H), 7.49-7.44 (m, 1H), 7.11-7.08 (m, 2H), 7.03 (d, 1H), 4.05 (br d, 1H), 3.56 (br d, 1H), 3.55-3.43 (m, 1H), 3.40-3.37 (m, 2H), 3.12-3.02 (m, 4H), 2.95 (t, 1H), 2.88-2.82 (m, 1H), 2.35 (br d, 1H), 2.21 (s, 3H), 2.19 (s, 3H), 2.07-1.99 (m, 1H), 1.90-1.86 (m, 2H), 1.70-1.65 (m, 2H). |
| 348 | 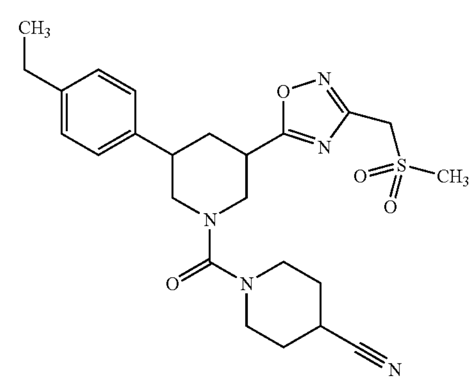 | 41 | m/z = 486; 1.93 min (Method 3B) | δ = 7.22 (d, 2H), 7.17 (d, 2H), 4.85 (s, 2H), 4.00 (br d, 1H), 3.55 (br d, 1H), 3.50-3.42 (m, 1H), 3.39-3.35 (m, 2H), 3.16 (s, 3H), 3.10-2.97 (m, 4H), 2.94-2.84 (m, 2H), 2.57 (q, 2H), 2.33 (br d, 1H), 1.97 (q, 1H), 1.88-1.85 (m, 2H), 1.69-1.64 (m, 2H), 1.16 (t, 3H). |

TABLE 1-continued

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 349 | 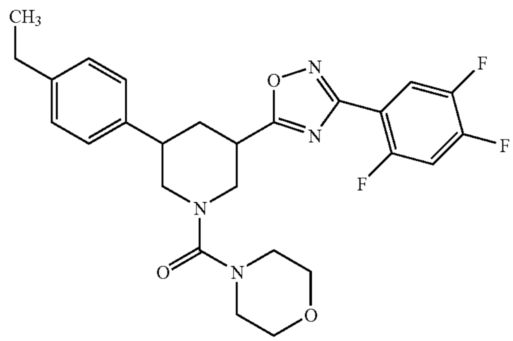 | 64 | m/z = 501; 2.91 min (Method 1B) | δ = 8.08-8.02 (m, 1H), 7.91-7.84 (m, 1H), 7.24 (d, 2H), 7.18 (d, 2H), 4.09 (br d, 1H), 3.63-3.49 (m, 6H), 3.22-3.20 (m, 4H), 3.10 (t, 1H), 3.01-2.90 (m, 2H), 2.57 (q, 2H), 2.36 (br d, 1H), 2.03 (q, 1H), 1.17 (t, 3H). |
| 350 | 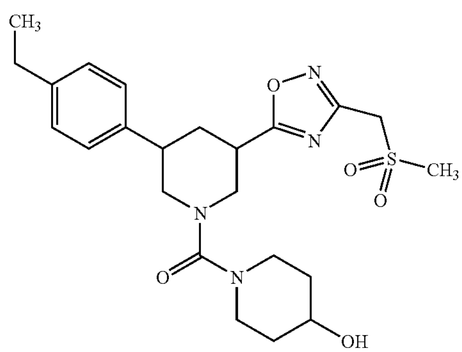 | 34 | m/z = 477; 2.03 min (Method 1B) | δ = 7.22-7.18 (m, 4H), 4.85 (s, 2H), 4.68 (br s, 1H), 3.99 (br d, 1H), 3.60-3.46 (m, 6H), 3.16 (s, 3H), 3.01 (t, 1H), 2.92-2.87 (m, 4H), 2.34 (br d, 1H), 2.01 (q, 1H), 1.73-1.67 (m, 2H), 1.31-1.29 (m, 2H), 1.16 (t, 3H). |
| 351 | 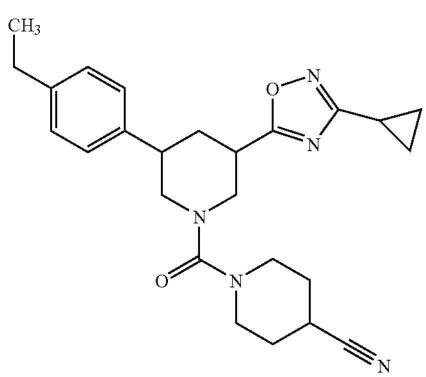 | 36 | m/z = 434; 2.29 min (Method 3B) | δ = 7.19-7.13 (m, 4H), 4.07 (br d, 1H), 3.75 (br d, 1H), 3.52-3.47 (m, 2H), 3.33-3.19 (m, 3H), 3.01 (t, 1H), 2.88-2.80 (m, 3H), 2.63 (q, 2H), 2.42 (br d, 1H), 2.10-2.05 (m, 1H), 1.97-1.80 (m, 5H), 1.23 (t, 3H), 1.07-0.99 (m, 4H). |
| 352 | 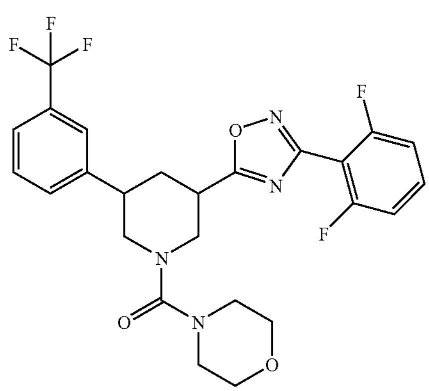 | 51 | m/z = 523; 2.30 min (Method 3B) | δ = 7.77-7.73 (m, 2H), 7.68 (d, 1H), 7.64-7.57 (m, 2H), 7.36 (dd, 2H), 4.07 (br d, 1H), 3.63 (br d, 1H), 3.58-3.53 (m, 5H), 3.23-3.21 (m, 4H), 3.17-3.06 (m, 3H), 2.41 (br d, 1H), 2.14 (q, 1H). |

TABLE 1-continued

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 353 | 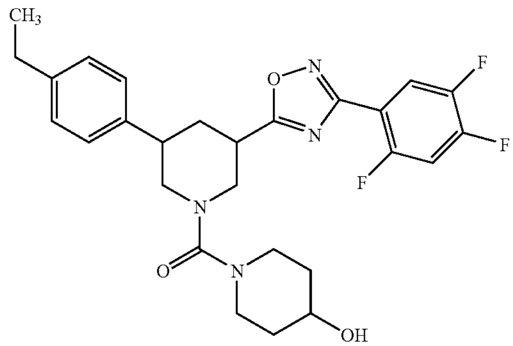 | 49 | m/z = 515; 1.45 min (Method 2B) | δ = 8.08-8.03 (m, 1H), 7.90-7.83 (m, 1H), 7.23 (d, 2H), 7.18 (d, 2H), 4.68 (d, OH), 4.07 (br d, 1H), 3.64-3.48 (m, 5H), 3.07 (t, 1H), 2.99-2.68 (m, 4H), 2.58 (q, 2H), 2.37 (br d, 1H), 2.03 (q, 1H), 1.74-1.71 (m, 2H), 1.36-1.27 (m, 2H), 1.17 (t, 3H). |
| 354 | 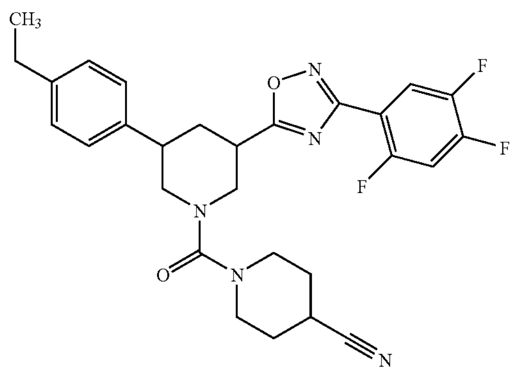 | 73 | m/z = 524; 2.94 min (Method 1B) | δ = 8.08-8.02 (m, 1H), 7.90-7.84 (m, 1H), 7.24 (d, 2H), 7.18 (d, 2H), 4.06 (br d, 1H), 3.57 (br d, 1H), 3.54-3.47 (m, 1H), 3.40-3.37 (m, 2H), 3.12-3.02 (m, 4H), 2.99-2.87 (m, 2H), 2.58 (q, 2H), 2.34 (br d, 1H), 2.03 (q, 1H), 1.89-1.86 (m, 2H), 1.72-1.65 (m, 2H), 1.17 (t, 3H). |
| 355 | 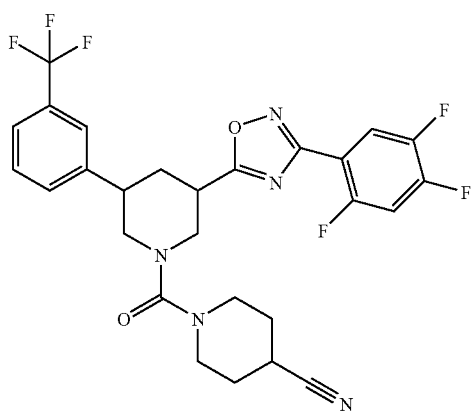 | 62 | m/z = 541; 2.45 min (Method 3B) | δ = 8.08-8.01 (m, 1H), 7.91-7.83 (m, 1H), 7.73 (s, 1H), 7.68 (d, 1H), 7.64-7.57 (m, 2H), 4.08 (br d, 1H), 3.64 (br d, 1H), 3.58-3.50 (m, 5H), 3.23-3.19 (m, 4H), 3.16-3.09 (m, 3H), 2.40 (br d, 1H), 2.12 (q, 1H). |
| 356 | 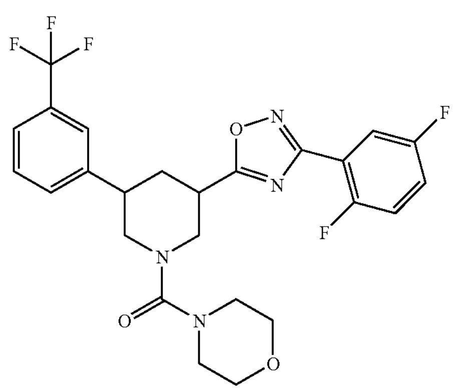 | 70 | m/z = 523; 2.73 min (Method 1B) | δ = 7.80-7.76 (m, 1H), 7.73 (s, 1H), 7.68 (d, 1H), 7.64-7.61 (m, 2H), 7.61-7.57 (m, 2H), 4.08 (br d, 1H), 3.64 (br d, 1H), 3.58-3.49 (m, 4H), 3.23-3.21 (m, 4H), 3.17-3.07 (m, 3H), 2.41 (br d, 1H), 2.14 (q, 1H). |

TABLE 1-continued

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 357 | 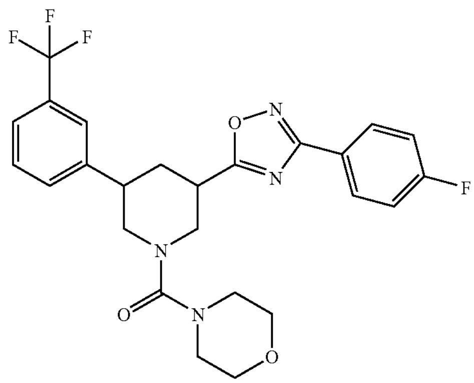 | 73 | m/z = 505; 2.44 min (Method 3B) | δ = 8.10-8.05 (m, 2H), 7.74 (s, 1H), 7.68 (d, 1H), 7.64-7.54 (m, 2H), 7.45-7.39 (m, 2H), 4.08 (br d, 1H), 3.64 (br d, 1H), 3.58-3.54 (m, 4H), 3.53-3.46 (m, 1H), 3.23-3.21 (m, 4H), 3.17-3.05 (m, 3H), 2.41 (br d, 1H), 2.13 (q, 1H). |
| 358 | 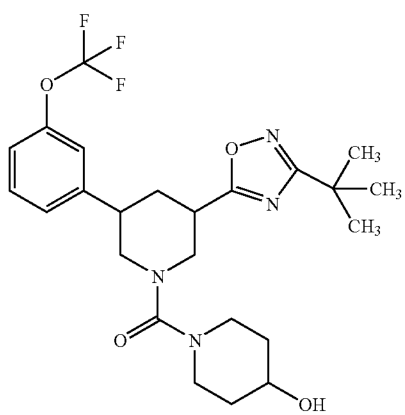 | 36 | m/z = 497; 2.24 min (Method 3B) | δ = 7.48 (dd, 1H), 7.39-7.35 (m, 2H), 7.25 (d, 1H), 4.68 (d, OH), 3.94 (br d, 1H), 3.63-3.58 (m, 1H), 3.55 (br d, 1H), 3.50-3.46 (m, 2H), 3.39-3.36 (m, 1H), 3.05-2.87 (m, 5H), 2.31 (br d, 1H), 1.98 (q, 1H), 1.73-1.70 (m, 2H), 1.34-1.27 (m, 11H). |
| 359 | 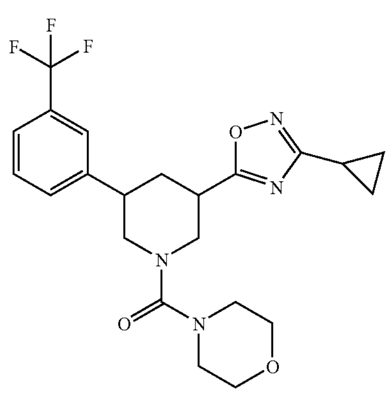 | 56 | m/z = 451; 1.32 min (Method 2B) | δ = 7.71 (s, 1H), 7.64-7.55 (m, 3H), 3.95 (br d, 1H), 3.63-3.54 (m, 5H), 3.38-3.32 (m, 1H), 3.20-3.16 (m, 4H), 3.06-3.01 (m, 3H), 2.30 (br d, 1H), 2.13-2.07 (m, 1H), 2.00 (q, 1H), 1.08-1.03 (m, 2H), 0.90-0.86 (m, 2H). |

TABLE 1-continued

| Ex. No. | Structure | Yield (% of theory) | MS (ESI) [M + H]+; LC-MS: R_t (Method) | ¹H-NMR (400 MHz, DMSO-d₆) |
|---|---|---|---|---|
| 360 | 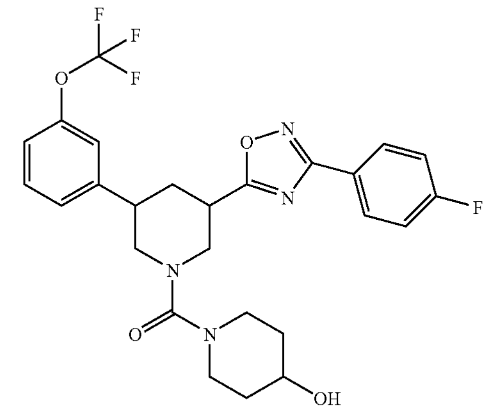 | 45 | m/z = 535; 2.33 min (Method 3B) | δ = 8.09-8.05 (m, 2H), 7.50 (dd, 1H), 7.44-7.36 (m, 4H), 7.26 (d, 1H), 4.69 (d, OH), 4.03 (br d, 1H), 3.63-3.57 (m, 2H), 3.52-3.49 (m, 3H), 3.17-3.02 (m, 3H), 2.93 (t, 2H), 2.39 (br d, 1H), 2.08 (q, 1H), 1.74-1.71 (m, 2H), 1.36-1.28 (m, 2H). |
| 361 | 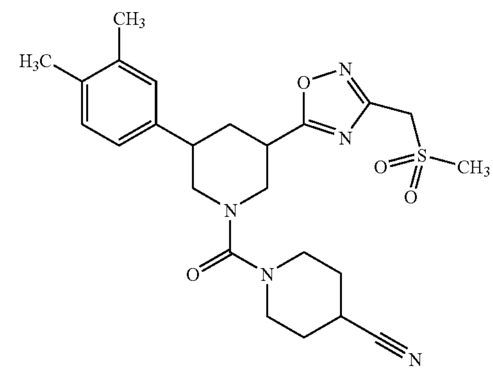 | 59 | m/z = 486; 1.18 min (Method 2B) | δ = 7.10-7.08 (m, 2H), 7.01 (d, 1H), 4.85 (s, 2H), 4.00 (br d, 1H), 3.53 (br d, 1H), 3.49-3.41 (m, 1H), 3.39-3.34 (m, 2H), 3.32 (s, 3H), 3.30 (s, 3H), 3.16 (s, 3H), 3.10-3.00 (m, 4H), 2.92 (t, 1H), 2.85-2.77 (m, 1H), 2.30 (br d, 1H), 1.96 (q, 1H), 1.88-1.84 (m, 2H), 1.71-1.63 (m, 2H). |
| 362 | 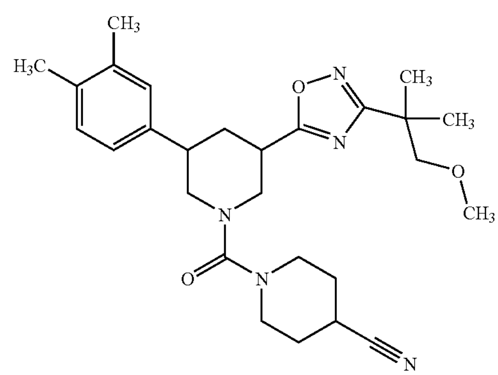 | 73 | m/z = 480; 1.43 min (Method 2B) | δ = 7.09-7.07 (m, 2H), 7.00 (d, 1H), 3.95 (br d, 1H), 3.52 (br d, 1H), 3.44 (s, 2H), 3.39-3.33 (m, 3H), 3.20 (s, 3H), 3.10-2.90 (m, 5H), 2.83-2.76 (m, 1H), 2.25 (br d, 1H), 2.20 (s, 3H), 2.18 (s, 3H), 1.97-1.85 (m, 3H), 1.71-1.62 (m, 2H), 1.26 (s, 6H). |
| 363 | 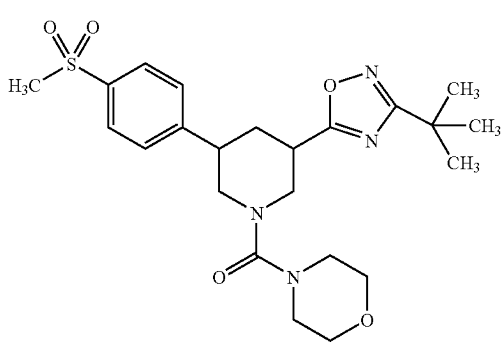 | 57 | m/z = 477; 2.08 min (Method 1B) | δ = 7.89 (d, 2H), 7.63 (d, 2H), 4.00 (br d, 1H), 3.62 (br d, 1H), 3.57-3.55 (m, 4H), 3.44-3.34 (m, 1H), 3.20-3.16 (m, 7H), 3.09-3.03 (m, 3H), 2.34 (br d, 1H), 2.02 (q, 1H), 1.30 (s, 9H). |

TABLE 1-continued
| Ex. No. | Structure | Yield (% of theory) | MS (ESI) [M + H]+; LC-MS: R_t (Method) | 1H-NMR (400 MHz, DMSO-d_6) |
|---|---|---|---|---|
| 364 | 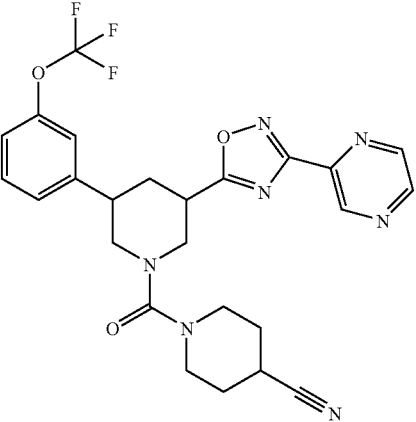 | 42 | m/z = 528; 2.05 min (Method 3B) | δ = 9.28 (d, 1H), 8.90-8.87 (m, 2H), 7.50 (dd, 1H), 7.42-7.38 (m, 2H), 7.27 d, 1H), 4.05 (br d, 1H), 3.61 (br d, 1H), 3.58-3.51 (m, 1H), 3.42-3.38 (m, 2H), 3.19-3.00 (m, 6H), 2.41 (br d, 1H), 2.11 (q, 1H), 1.91-1.87 (m, 2H), 1.74-1.66 (m, 2H). |
| 365 | 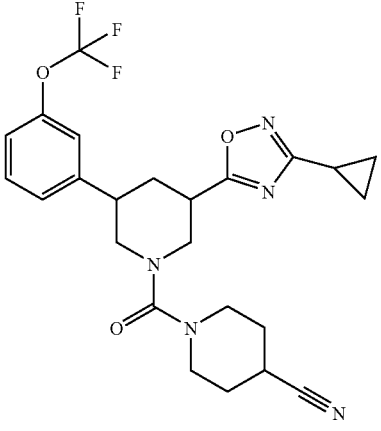 | 88 | m/z = 490; 1.40 min (Method 2B) | δ = 7.48 (dd, 1H), 7.38-7.34 (m, 2H), 7.24 (d, 1H), 3.91 (br d, 1H), 3.55 (br d, 1H), 3.39-3.34 (m, 4H), 3.10-2.94 (m, 6H), 2.30 (br d, 1H), 1.95 (q, 1H), 1.88-1.84 (m, 2H), 1.71-1.63 (m, 2H), 1.08-1.03 (m, 2H), 0.90-0.86 (m, 2H). |
| 366 | 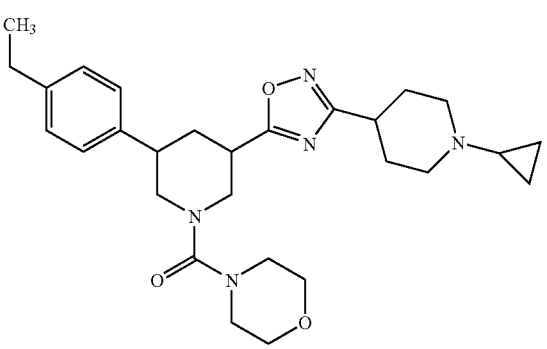 | 22 | m/z = 494; 1.49 min (Method 1B) | δ = 7.22 (d, 2H), 7.16 (d, 2H), 3.99 (br d, 1H), 3.59-3.44 (m, 5H), 3.39-3.34 (m, 1H), 3.20-3.18 (m, 4H), 3.03-2.85 (m, 4H), 2.80-2.71 (m, 2H), 2.57 (q, 2H), 2.30-2.25 (m, 3H), 1.98-1.88 (m, 3H), 1.64-1.54 (m, 3H), 1.16 (t, 3H), 0.43-0.39 (m, 2H), 0.30-0.27 (m, 2H). |

TABLE 1-continued

| Ex. No. | Structure | Yield (% of theory) | MS (ESI) [M + H]+; LC-MS: R_t (Method) | 1H-NMR (400 MHz, DMSO-d6) |
|---|---|---|---|---|
| 367 | 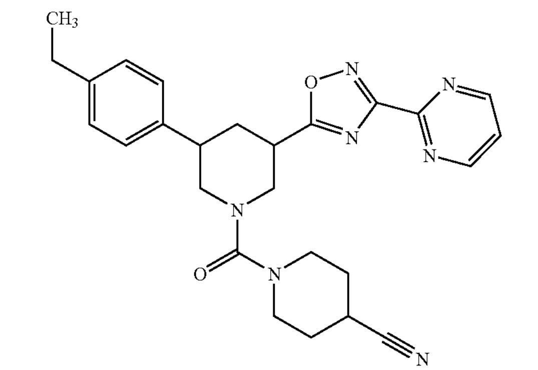 | 70 | m/z = 472; 1.21 min (Method 2B) | δ = 9.03 (d, 2H), 7.72 (dd, 1H), 7.25 (d, 2H), 7.18 (d, 2H), 4.09 (br d, 1H), 3.58 (br d, 1H), 3.54-3.50 (m, 1H), 3.41-3.37 (m, 2H), 3.19-3.02 (m, 4H), 2.95-2.88 (m, 2H), 2.58 (q, 2H), 2.38 (br d, 1H), 2.06 (q, 1H), 1.90-1.86 (m, 2H), 1.73-1.65 (m, 2H), 1.17 (t, 3H). |
| 368 | 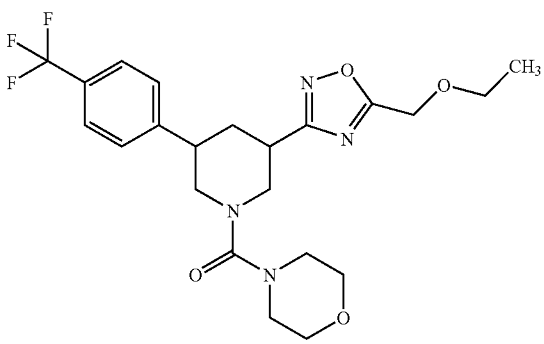 | 46 | m/z = 547; 1.18 min (Method 2B) | δ = 7.37 (s, 1H), 7.27 (br s, 2H), 4.85 (s, 2H), 4.66 (d, OH), 3.98 (br d, 1H), 3.68-3.60 (m, 1H), 3.55 (br d, 1H), 3.50-3.44 (m, 3H), 3.17 (s, 3H), 3.00 (t, 1H), 3.00-2.88 (m, 4H), 2.34 (br d, 1H), 2.27 (s, 3H), 1.98 (q, 1H), 1.73-1.70 (m, 2H), 1.35-1.24 (m, 2H). |
| 369 | 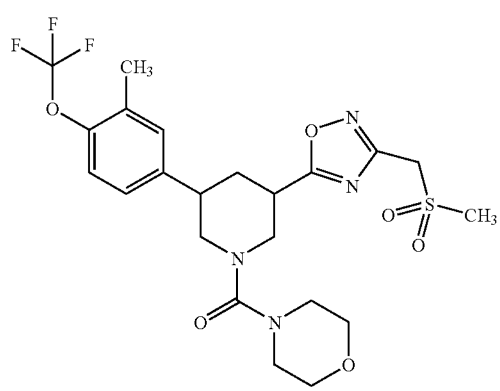 | 72 | m/z = 533; 1.09 min (Method 9B) | δ = 7.37 (s, 1H), 7.27 (br s, 2H), 4.85 (s, 2H), 4.03 (br d, 1H), 3.63 (br d, 1H), 3.60-3.55 (m, 4H), 3.51-3.44 (m, 1H), 3.21-3.19 (m, 4H), 3.17 (s, 3H), 3.06 (t, 1H), 3.01-2.90 (m, 2H), 2.34 (br d, 1H), 2.27 (s, 3H), 1.99 (q, 1H). |
| 370 | 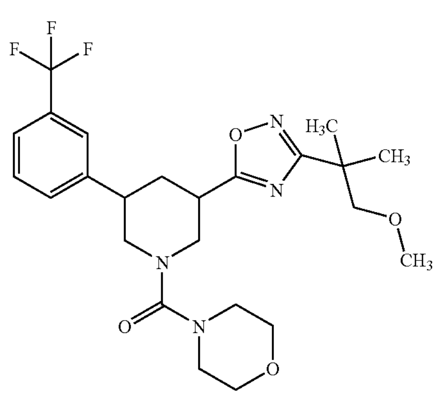 | 87 | m/z = 497; 1.39 min (Method 2B) | δ = 7.73 (s, 1H), 7.67 (d, 1H), 7.63-7.56 (m, 2H), 3.97 (br d, 1H), 3.61 (br d, 1H), 3.57-3.54 (m, 4H), 3.44 (s, 2H), 3.42-3.34 (m, 1H), 3.22-3.16 (m, 7H), 3.14-3.02 (m, 3H), 2.31 (br d, 1H), 2.03 (q, 1H), 1.27 (s, 6H). |

TABLE 1-continued

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 371 | 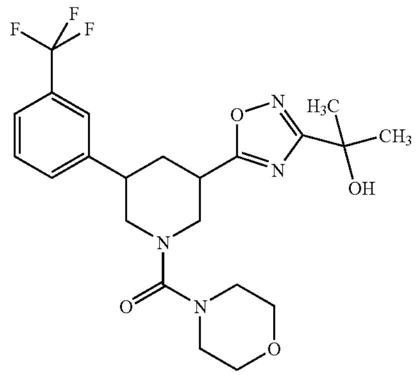 | 40 | m/z = 469; 2.06 min (Method 5B) | δ = 7.72 (s, 1H), 7.67 (d, 1H), 7.64-7.56 (m, 2H), 5.52 (s, OH), 3.99 (br d, 1H), 3.61 (br d, 1H), 3.60-3.55 (m, 4H), 3.44-3.37 (m, 1H), 3.21-3.16 (m, 4H), 3.12-3.02 (m, 3H), 2.32 (br d, 1H), 2.05 (q, 1H), 1.48 (s, 6H). |
| 372 | 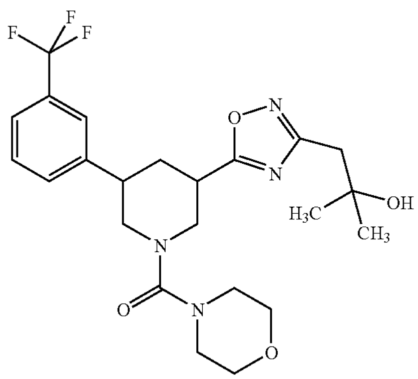 | 59 | m/z = 483; 1.19 min (Method 2B) | δ = 7.72 (s, 1H), 7.67 (d, 1H), 7.63-7.56 (m, 2H), 4.59 (s, OH), 3.99 (br d, 1H), 3.61 (br d, 1H), 3.58-3.55 (m, 4H), 3.42-3.34 (m, 1H), 3.21-3.19 (m, 4H), 3.12-3.04 (m, 3H), 2.78 (s, 2H), 2.32 (br d, 1H), 2.04 (q, 1H), 1.18 (s, 6H). |
| 373 | 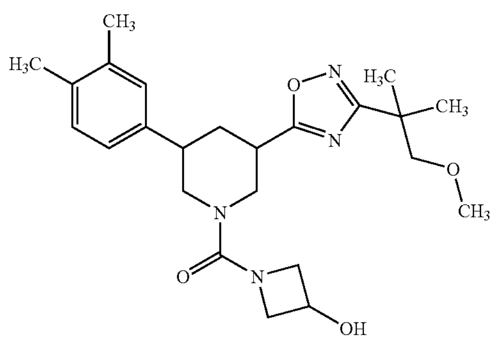 | 45 | m/z = 443; 1.99 min (Method 3B) | δ = 7.09-7.07 (m, 2H), 7.00 (d, 1H), 5.58 (d, OH), 4.42-4.34 (m, 1H), 4.15 (br d, 1H), 4.08 (q, 2H), 3.71-3.65 (m, 3H), 3.45 (s, 2H), 3.29-3.23 (m, 1H), 3.20 (s, 3H), 3.00-2.89 (m, 2H), 2.77-2.67 (m, 1H), 2.24 (br d, 1H), 2.21 (s, 3H), 2.18 (s, 3H), 1.94 (q, 1H), 1.27 (s, 6H). |
| 374 | 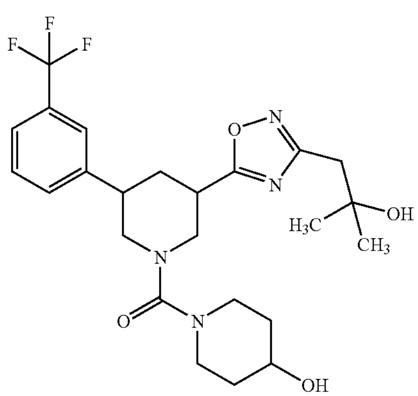 | 26 | m/z = 497; 0.97 min (Method 9B) | δ = 7.71 (s, 1H), 7.67-7.56 (m, 3H), 4.68 (d, OH), 4.59 (s, OH), 3.95 (br d, 1H), 3.63-3.55 (m, 2H), 3.50-3.47 (m, 2H), 3.42-3.34 (m, 1H), 3.07-3.01 (m, 3H), 2.88 (t, 2H), 2.78 (s, 2H), 2.33 (br d, 1H), 2.03 (q, 1H), 1.73-1.70 (m, 2H), 1.34-1.26 (m, 2H), 1.18 (s, 6H). |

TABLE 1-continued

| Ex. No. | Structure | Yield (% of theory) | MS (ESI) [M + H]+; LC-MS: R_t (Method) | ¹H-NMR (400 MHz, DMSO-d₆) |
|---|---|---|---|---|
| 375 | 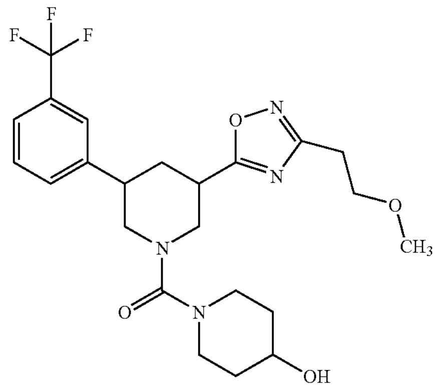 | 37 | m/z = 483; 1.16 min (Method 2B) | δ = 7.71 (s, 1H), 7.67-7.55 (m, 3H), 4.68 (d, OH), 3.94 (br d, 1H), 3.67 (t, 2H), 3.61-3.55 (m, 1H), 3.50-3.35 (m, 4H), 3.23 (s, 3H), 3.07-3.00 (m, 3H), 2.95-2.85 (m, 4H), 2.32 (br d, 1H), 2.05 (q, 1H), 1.73-1.70 (m, 2H), 1.34-1.27 (m, 2H). |
| 376 | 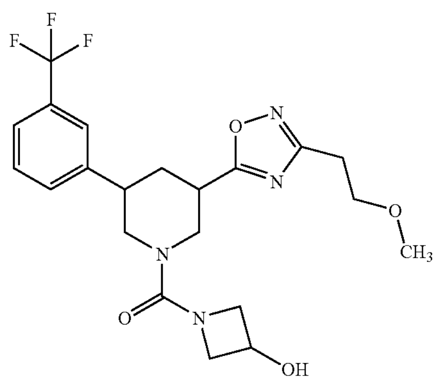 | 15 | m/z = 455; 0.98 min (Method 9B) | δ = 7.70 (s, 1H), 7.67-7.56 (m, 3H), 5.58 (d, OH), 4.42-4.35 (m, 1H), 4.15 (br d, 1H), 4.12-4.06 (m, 2H), 3.75-3.65 (m, 5H), 3.30-3.24 (m, 1H), 3.23 (s, 3H), 3.05 (t, 2H), 2.98-2.91 (m, 2H), 2.30 (br d, 1H), 2.06 (q, 1H). |
| 377 | 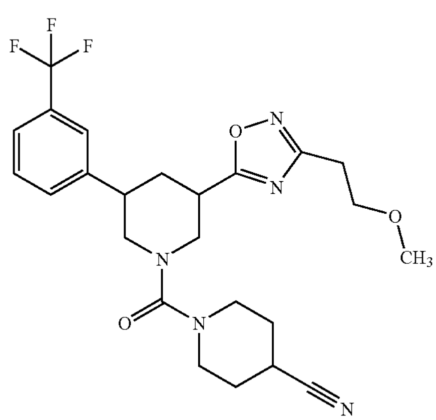 | 50 | m/z = 492; 1.12 min (Method 9B) | δ = 7.71 (s, 1H), 7.67-7.56 (m, 3H), 3.95 (br d, 1H), 3.67 (t, 2H), 3.57 (br d, 1H), 3.43-3.36 (m, 3H), 3.23 (s, 3H), 3.11-3.01 (m, 6H), 2.91 (t, 2H), 2.33 (br d, 1H), 2.04 (q, 1H), 1.89-1.85 (m, 2H), 1.71-1.65 (m, 2H). |

TABLE 1-continued

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 378 | (3-trifluoromethylphenyl)-piperidine with 3-methyl-1,2,4-oxadiazole and 3-hydroxyazetidine carbonyl | 19 | m/z = 411; 0.96 min (Method 9B) | δ = 7.75 (s, 1H), 7.69-7.56 (m, 3H), 5.58 (d, OH), 4.40-4.37 (m, 1H), 4.16-4.06 (m, 3H), 3.76-3.66 (m, 3H), 3.07-2.97 (m, 3H), 2.33-2.28 (m, 4H), 2.06 (q, 1H). |

The compounds listed in Table 2 were prepared from the appropriate starting materials according to the General Method 5.

TABLE 2

| Ex. No. | Structure | Yield (% of theory) | MS (ESI) [M + H]+; LC-MS: R_t (Method) | 1H-NMR (400 MHz, DMSO-d_6) |
|---|---|---|---|---|
| 379 | (4-trifluoromethoxyphenyl)-piperidine with 3-(3-fluorophenyl)-1,2,4-oxadiazole and 3,3-difluoropyrrolidine carbonyl | 48 | m/z = 541; 3.07 min (Method 1B) | δ = 7.86 (dd, 1H), 7.76 (dd, 1H), 7.66-7.61 (m, 1H), 7.51-7.44 (m, 3H), 7.34 (d, 2H), 4.15 (br d, 1H), 3.81-3.71 (m, 3H), 3.61-3.48 (m, 3H), 3.14 (t, 1H), 3.04-3.01 (m, 2H), 2.42-2.32 (m, 3H), 2.07 (q, 1H). |
| 380 | (4-trifluoromethoxyphenyl)-piperidine with 3-(3-fluorophenyl)-1,2,4-oxadiazole and 3-methylazetidine carbonyl | 37 | m/z = 505; 2.69 min (Method 3B) | δ = 7.87 (d, 1H), 7.76 (d, 1H), 7.67-7.61 (m, 1H), 7.50-7.45 (m, 3H), 7.34 (d, 2H), 4.26 (br d, 1H), 4.08-4.03 (m, 2H), 3.78 (br d, 1H), 3.53 (q, 2H), 3.48-3.39 (m, 1H), 3.09 (t, 1H), 3.01-2.91 (m, 2H), 2.67-2.56 (m, 1H), 2.37 (br d, 1H), 2.06 (q, 1H), 1.16 (d, 3H). |

TABLE 2-continued

| Ex. No. | Structure | Yield (% of theory) | MS (ESI) [M + H]+; LC-MS: R_t (Method) | ¹H-NMR (400 MHz, DMSO-d₆) |
|---|---|---|---|---|
| 381 | 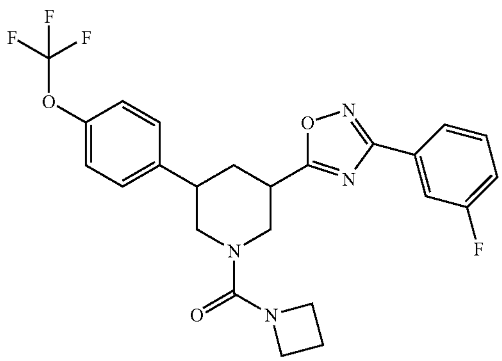 | 39 | m/z = 491; 2.95 min (Method 1B) | δ = 7.87 (d, 1H), 7.76 (dd, 1H), 7.67-7.61 (m, 1H), 7.49-7.44 (m, 3H), 7.34 (d, 2H), 4.25 (br d, 1H), 3.98-3.93 (m, 4H), 3.77 (br d, 1H), 3.46-3.38 (m, 1H), 3.10 (t, 1H), 3.02-2.91 (m, 2H), 2.38 (br d, 1H), 2.20-2.04 (m, 3H). |
| 382 | 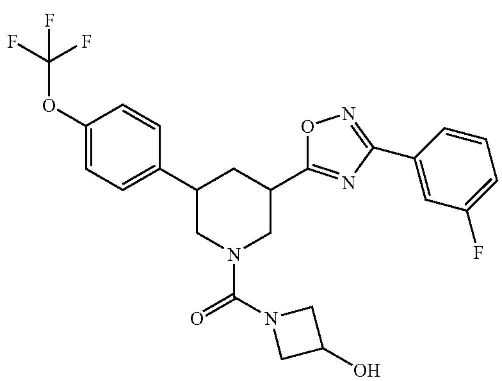 | 47 | m/z = 507; 2.65 min (Method 1B) | δ = 7.87 (d, 1H), 7.76 (dd, 1H), 7.66-7.61 (m, 1H), 7.50-7.45 (m, 3H), 7.34 (d, 2H), 5.59 (d, OH), 4.39 (quintet, 1H), 4.25 (br d, 1H), 4.11 (q, 2H), 3.78 (br d, 1H), 3.73-3.69 (m, 2H), 3.46-3.38 (m, 1H), 3.11 (t, 1H), 3.02-2.91 (m, 2H), 2.37 (br d, 1H), 2.09 (q, 1H). |
| 383 | 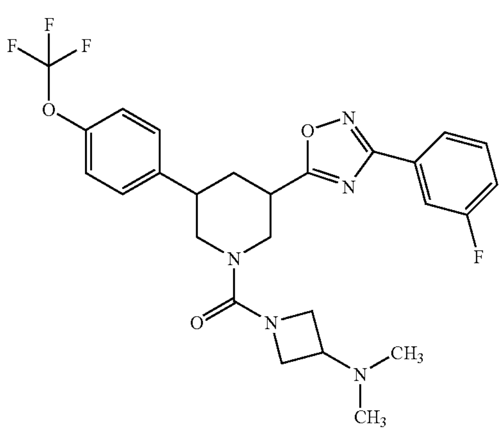 | 55 | m/z = 534; 1.86 min (Method 1B) | δ = 7.87 (d, 1H), 7.77 (dd, 1H), 7.67-7.61 (m, 1H), 7.50-7.43 (m, 3H), 7.34 (d, 2H), 4.25 (br d, 1H), 3.94 (q, 2H), 3.83-3.72 (m, 3H), 3.47-3.40 (m, 1H), 3.11 (t, 1H), 3.02-2.92 (m, 3H), 2.37 (brd, 1H), 2.12-2.05 (m, 7H). |

The compounds listed in Table 3 were prepared from the appropriate starting materials according to the General Method 6.

TABLE 3

| Ex. No. | Structure | Yield (% of theory) | MS (ESI) [M + H]+; LC-MS: $R_t$ (Method) | $^1$H-NMR (400 MHz, DMSO-$d_6$) |
|---|---|---|---|---|
| 384 | 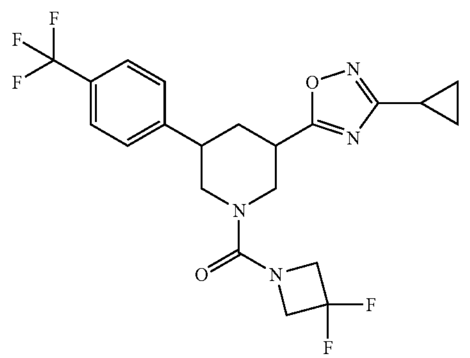 | 45 | m/z = 457; 1.41 min (Method 2B) | δ = 7.70 (d, 2H), 7.56 (d, 2H), 4.42-4.35 (m, 4H), 4.17 (br d, 1H), 3.79 (br d, 1H), 3.11-3.00 (m, 3H), 2.27 (br d, 1H), 2.14-2.05 (m, 1H), 2.00 (q, 1H), 1.33-1.24 (m, 1H), 1.11-1.03 (m, 2H), 0.91-0.85 (m, 2H). |
| 385 | 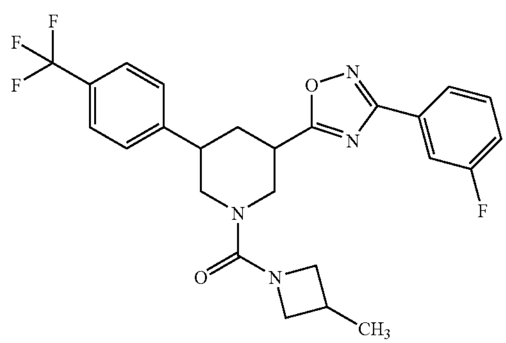 | 33 | m/z = 489; 5.22 min (Method 1A) | δ = 7.87 (d, 1H), 7.76 (d, 1H), 7.71 (d, 2H), 7.67-7.61 (m, 1H), 7.59 (d, 2H), 7.45 (dd, 1H), 4.26 (br d, 1H), 4.09-4.03 (m, 2H), 3.80 (br d, 1H), 3.53 (q, 2H), 3.47-3.38 (m, 1H), 3.11 (t, 1H), 3.05-2.96 (m, 2H), 2.40 (br d, 1H), 2.14-2.05 (m, 1H), 2.11 (q, 1H), 1.16 (d, 3H). |
| 386 | 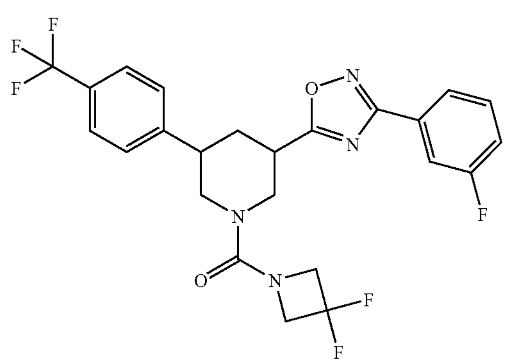 | 30 | m/z = 511; 5.19 min (Method 1A) | δ = 7.87 (d, 1H), 7.78 (d, 1H), 7.73 (d, 2H), 7.67-7.63 (m, 1H), 7.60 (d, 2H), 7.47 (dd, 1H), 4.41 (dt, 4H), 4.29 (br d, 1H), 3.86 (br d, 1H), 3.54-3.47 (m, 1H), 3.21 (t, 1H), 3.13-3.06 (m, 2H), 2.40 (br d, 1H), 2.14 (q, 1H). |

TABLE 3-continued

| Ex. No. | Structure | Yield (% of theory) | MS (ESI) [M + H]+; LC-MS: $R_t$ (Method) | $^1$H-NMR (400 MHz, DMSO-$d_6$) |
|---|---|---|---|---|
| 387 | 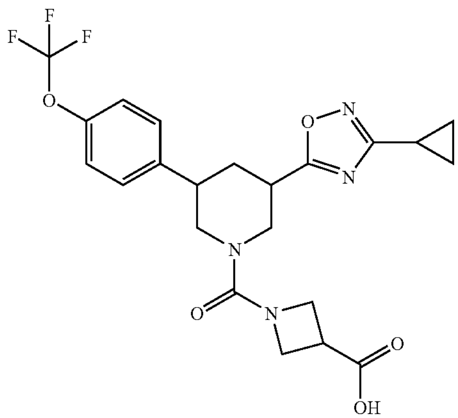 | 57 | m/z = 481; 2.41 min (Method 1B) | δ = 12.63 (br s, COOH), 7.45 (d, 2H), 7.32 (d, 2H), 4.12-4.06 (m, 3H), 4.01-3.95 (m, 2H), 3.73 (br d, 1H), 3.30-3.23 (m, 1H), 3.02-2.85 (m, 3H), 2.26 (br d, 1H), 2.14-2.07 (m, 1H), 1.94 (q, 1H), 1.08-1.03 (m, 2H), 0.90-0.87 (m, 2H). |
| 388 | 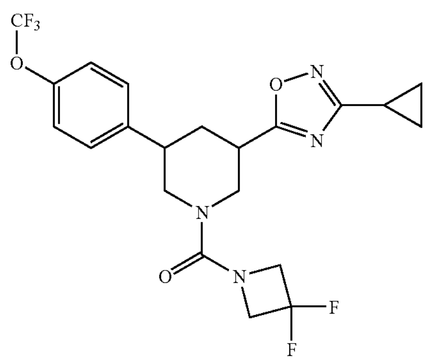 | 26 | m/z = 473; 2.41 min (Method 3B) | δ = 7.46 (d, 2H), 7.33 (d, 2H), 4.44-4.34 (m, 4H), 4.16 (br d, 1H), 3.77 (br d, 1H), 3.32-3.27 (m, 1H), 3.08-2.90 (m, 3H), 2.25 (br d, 1H), 2.15-2.07 (m, 1H), 1.96 (q, 1H), 1.08-1.03 (m, 2H), 0.91-0.87 (m, 2H). |

The compounds listed in Table 4 were prepared from the appropriate starting materials according to the General Method 1.

TABLE 4

| Ex. No. | Structure | Yield (% of theory) | MS (ESI) [M + H]+; LC-MS: $R_t$ (Method) | $^1$H-NMR (400 MHz, DMSO-$d_6$) |
|---|---|---|---|---|
| 389 | 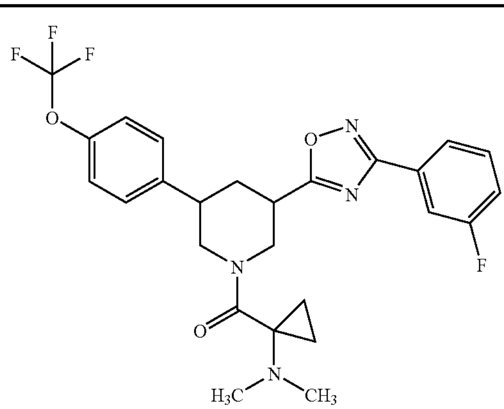 | 68 | m/z = 519; 2.35 min (Method 3B) | δ = 7.87 (d, 1H), 7.78-7.75 (m, 1H), 7.67-7.62 (m, 1H), 7.51-7.45 (m, 3H), 7.36 (d, 2H), 4.82 (br d, 1H), 4.41 (br d, 1H), 3.36-3.34 (m, 1H), 3.18-3.12 (m, 1H), 3.01-2.98 (m, 2H), 2.44 (br d, 1H), 2.20-2.16 (br s, 5H), 0.95-0.91 (m, 2H), 0.83-0.79 (m, 2H). |

TABLE 4-continued

| Ex. No. | Structure | Yield (% of theory) | MS (ESI) [M + H]+; LC-MS: $R_t$ (Method) | 1H-NMR (400 MHz, DMSO-$d_6$) |
|---|---|---|---|---|
| 390 | 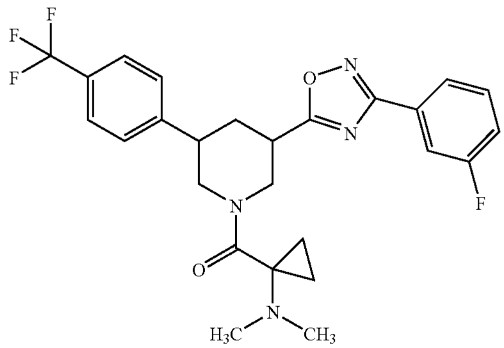 | 89 | m/z = 503; 4.63 min (Method 1A) | δ = 7.87 (d, 1H), 7.78-7.72 (m, 3H), 7.67-7.59 (m, 3H), 7.50-7.45 (m, 1H), 4.83 (br d, 1H), 4.42 (br d, 1H), 3.39-3.35 (m, 1H), 3.20-3.15 (m, 1H), 3.08-3.02 (m, 2H), 2.44 (br d, 1H), 2.23 (q, 1H), 2.18 (br s, 6H), 0.93-0.89 (m, 2H), 0.84-0.80 (m, 2H). |

Example 391

{3-[3-(2-Methoxyethyl)-1,2,4-oxadiazol-5-yl]-5-[4-methyl-3-(trifluoromethyl)phenyl]piperidin-1-yl}(morpholin-4-yl)methanone [racemic cis isomer]

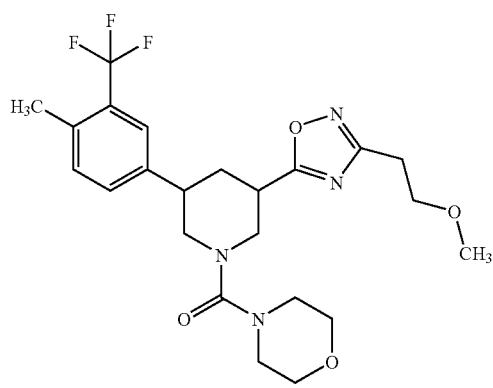

200 mg (0.48 mmol) of the compound from Example 160A and 113 mg (0.71 mmol) of t-hydroxy-3-methoxypropanimidamide were reacted according to the General Method 2. Yield: 104 mg (45% of theory)

LC-MS (Method 5B): $R_t$=2.27 min; MS (ESIpos): m/z=483 [M+H]+;

1H-NMR (400 MHz, DMSO-$d_6$): δ=7.62 (s, 1H), 7.52 (d, 1H), 7.40 (d, 1H), 3.98 (br d, 1H), 3.67 (t, 2H), 3.60-3.55 (m, 5H), 3.42-3.33 (m, 1H), 3.23 (s, 3H), 3.21-3.16 (m, 4H), 3.10-3.00 (m, 3H), 2.93 (t, 2H), 2.42 (s, 3H), 2.30 (br d, 1H), 2.01 (q, 1H).

Example 392

1-({3-[3-(2-Hydroxypropan-2-yl)-1,2,4-oxadiazol-5-yl]-5-[3-(trifluoromethyl)phenyl]piperidin-1-yl}carbonyl)piperidine-4-carbonitrile [racemic cis isomer]

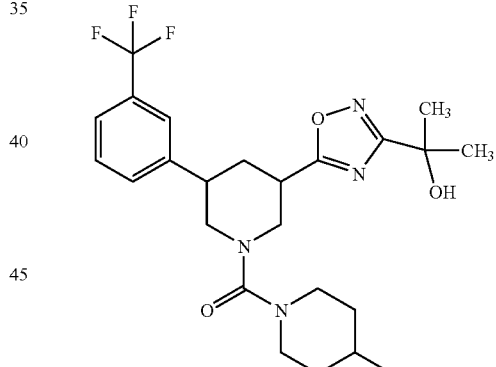

100 mg (0.24 mmol) of the compound from Example 152A and 45 mg (0.37 mmol) of the compound from Example 77A were reacted according to the General Method 2. Yield: 45 mg (35% of theory)

LC-MS (Method 2B): $R_t$=1.21 min; MS (ESIpos): m/z=492 [M+H]+;

1H-NMR (400 MHz, DMSO-$d_6$): δ=7.72 (s, 1H), 7.67-7.56 (m, 3H), 5.54 (s, OH), 3.96 (br d, 1H), 3.57 (br d, 1H), 3.43-3.36 (m, 3H), 3.12-3.01 (m, 6H), 2.33 (br d, 1H), 2.05 (q, 1H), 1.88-1.85 (m, 2H), 1.71-1.63 (m, 2H), 1.48 (s, 6H).

Example 393

{3-(3-Cyclopropyl-1,2,4-oxadiazol-5-yl)-5-[4-(trifluoromethoxy)phenyl]piperidin-1-yl}(3-hydroxypyrrolidin-1-yl)methanone [mixture of diastereomers]

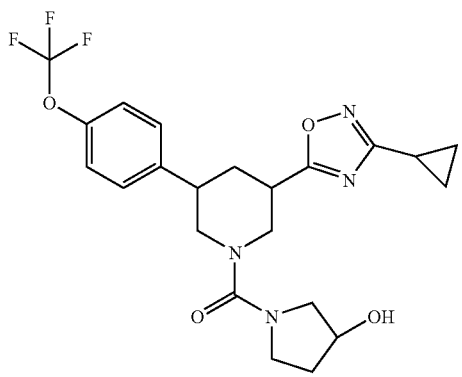

100 mg (0.19 mmol) of the compound from Example 176A and 50 mg (0.58 mmol) of 3-pyrrolidinol were reacted according to the General Method 6. Yield: 50 mg (53% of theory)

LC-MS (Method 1B): $R_t$=2.34 min; MS (ESIpos): m/z=467 [M+H]$^+$;

$^1$H-NMR (400 MHz, DMSO-d$_6$): δ=7.46 (d, 2H), 7.32 (d, 2H), 4.87 (d, OH), 4.22-4.18 (m, 1H), 4.03-3.99 (m, 1H), 3.67 (br t, 1H), 3.52-3.44 (m, 2H), 3.38-3.34 (m, 1H), 3.10 (br t, 1H), 3.03-2.86 (m, 3H), 2.28 (br d, 1H), 2.14-2.07 (m, 1H), 1.98-1.88 (m, 1H), 1.84-1.80 (m, 1H), 1.74-1.70 (m, 1H), 1.08-1.03 (m, 2H), 0.90-0.86 (m, 2H).

Example 394

{3-(4-Ethylphenyl)-5-[3-(2-methoxyethyl)-1,2,4-oxadiazol-5-yl]piperidin-1-yl}(3-hydroxyazetidin-1-yl)methanone [racemic cis isomer]

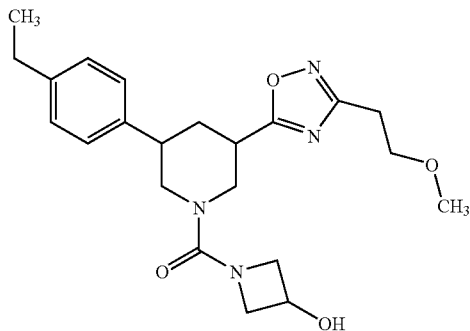

60 mg (0.18 mmol) of the compound from Example 138A and 43 mg (0.27 mmol) of N'-hydroxy-3-methoxypropanimidamide were reacted according to the General Method 2. Yield: 25 mg (33% of theory)

LC-MS (Method 1B): $R_t$=2.08 min; MS (ESIpos): m/z=415 [M+H]$^+$;

$^1$H-NMR (400 MHz, DMSO-d$_6$): δ=7.22 (d, 2H), 7.17 (d, 2H), 5.58 (d, OH), 4.41-4.35 (m, 1H), 4.16 (br d, 1H), 4.08 (q, 2H), 3.72-3.66 (m, 5H), 3.23 (s, 3H), 3.02-2.87 (m, 4H), 2.82-2.76 (m, 1H), 2.57 (q, 2H), 2.27 (br d, 1H), 1.96 (q, 1H), 1.17 (t, 3H).

Example 395

(4-Hydroxypiperidin-1-yl){3-{3-[2-(propan-2-yloxy)ethyl]-1,2,4-oxadiazol-5-yl}-5-[4-(trifluoromethyl)phenyl]piperidin-1-yl}methanone [racemic cis isomer]

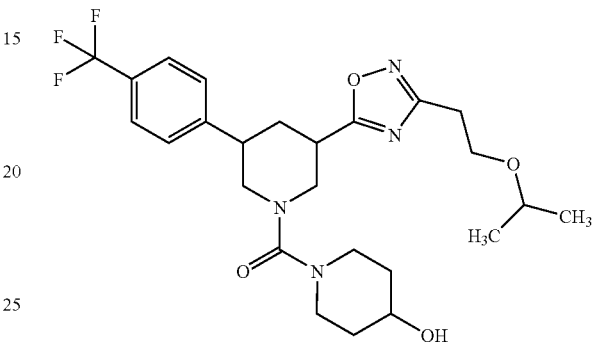

100 mg (0.25 mmol) of the compound from Example 99A and 61 mg (0.38 mmol) of the compound from Example 65A were reacted according to the General Method 2. Yield: 82 mg (61% of theory)

HPLC (Method 2A): $R_t$=2.29 min; MS (ESIpos): m/z=511 [M+H]$^+$;

$^1$H-NMR (400 MHz, DMSO-d$_6$): δ=7.70 (d, 2H), 7.56 (d, 2H), 4.68 (d, OH), 3.94 (br d, 1H), 3.71 (t, 2H), 3.63-3.38 (m, 6H), 3.07-3.00 (m, 3H), 2.96-2.84 (m, 4H), 2.33 (br d, 1H), 2.00 (q, 1H), 1.73-1.70 (m, 2H), 1.34-1.27 (m, 2H), 1.04 (d, 6H).

Example 396

{3-(3-{[1-(Hydroxymethyl)cyclopropyl]methyl}-1,2,4-oxadiazol-5-yl)-5-[4-(trifluoromethyl)-phenyl]piperidin-1-yl}(4-hydroxypiperidin-1-yl)methanone [racemic cis isomer]

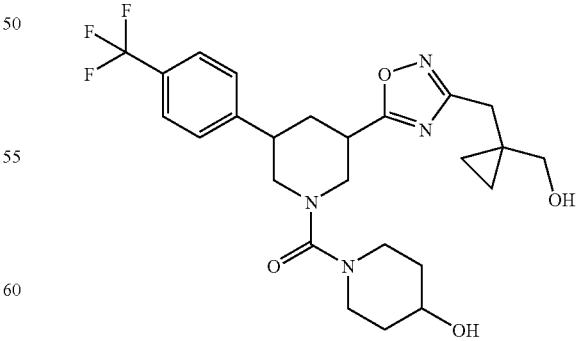

100 mg (0.25 mmol) of the compound from Example 99A and 62 mg (0.38 mmol) of the compound from Example 67A were reacted according to the General Method 2. Yield: 66 mg (52% of theory)

HPLC (Method 2A): $R_t$=4.19 min; MS (ESIpos): m/z=509 [M+H]$^+$;

$^1$H-NMR (400 MHz, DMSO-d$_6$): δ=7.70 (d, 2H), 7.57 (d, 2H), 4.68 (d, OH), 4.57 (t, OH), 3.95 (br d, 1H), 3.62-3.57 (m, 2H), 3.54-3.37 (m, 3H), 3.26 (d, 2H), 3.07-2.99 (m, 3H), 2.91 (br t, 2H), 2.78 (s, 2H), 2.35 (br d, 1H), 2.00 (q, 1H), 1.73-1.70 (m, 2H), 1.34-1.24 (m, 2H), 0.45-0.41 (m, 4H).

Example 397

{3-{3-[(Methylsulphonyl)methyl]-1,2,4-oxadiazol-5-yl}-5-[4-methyl-3-(trifluoromethyl)phenyl]-piperidin-1-yl}(morpholin-4-yl)methanone [racemic cis isomer]

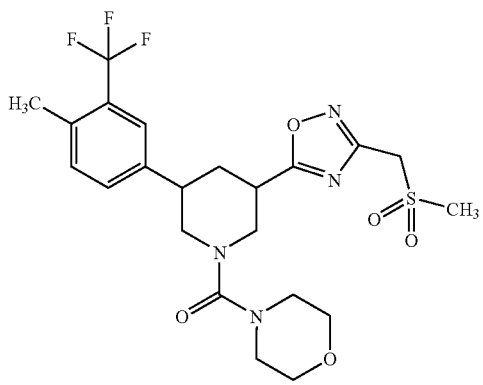

100 mg (0.23 mmol) of the compound from Example 160A and 53 mg (0.35 mmol) of N'-hydroxy-2-(methylsulphonyl)ethanimidamide were reacted according to the General Method 2. Yield: 65 mg (54% of theory)

LC-MS (Method 5B): $R_t$=2.16 min; MS (ESIpos): m/z=517 [M+H]$^+$;

$^1$H-NMR (400 MHz, DMSO-d$_6$): δ=7.60 (s, 1H), 7.53 (d, 1H), 7.40 (d, 1H), 4.85 (s, 2H), 4.02 (br d, 1H), 3.60-3.55 (m, 5H), 3.49-3.44 (m, 1H), 3.21-3.19 (m, 4H), 3.17 (s, 3H), 3.10 (t, 1H), 3.04-3.01 (m, 2H), 2.42 (s, 3H), 2.34 (br d, 1H), 2.03 (q, 1H).

Example 398

(4-Hydroxypiperidin-1-yl) {3-{3-[(methylsulphonyl)methyl]-1,2,4-oxadiazol-5-yl}-5-[4-methyl-3-(trifluoromethyl)phenyl]piperidin-1-yl}methanone [racemic cis isomer]

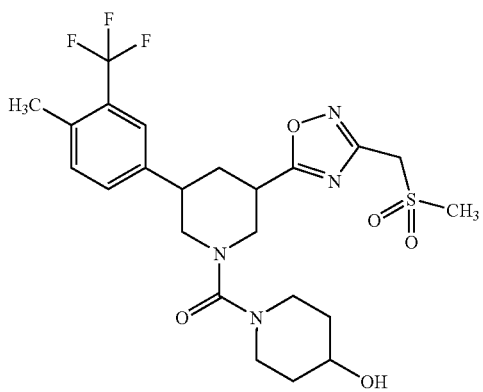

100 mg (0.24 mmol) of the compound from Example 163A and 55 mg (0.36 mmol) of N'-hydroxy-2-(methylsulphonyl)ethanimidamide were reacted according to the General Method 2. Yield: 72 mg (56% of theory)

LC-MS (Method 2B): $R_t$=1.11 min; MS (ESIpos): m/z=531 [M+H]$^+$;

$^1$H-NMR (400 MHz, DMSO-d$_6$): δ=7.61 (s, 1H), 7.52 (d, 1H), 7.40 (d, 1H), 4.85 (s, 2H), 4.66 (d, OH), 3.97 (br d, 1H), 3.64-3.61 (m, 1H), 3.57 (br d, 1H), 3.58-3.46 (m, 3H), 3.17 (s, 3H), 3.09-3.00 (m, 3H), 2.89 (br t, 2H), 2.41 (s, 3H), 2.32 (br d, 1H), 2.02 (q, 1H), 1.73-1.70 (m, 2H), 1.34-1.27 (m, 2H).

Example 399

{3-[3-(2-Methoxyethyl)-1,2,4-oxadiazol-5-yl]-5-[3-methyl-4-(trifluoromethoxy)phenyl]piperidin-1-yl}(morpholin-4-yl)methanone [racemic cis isomer]

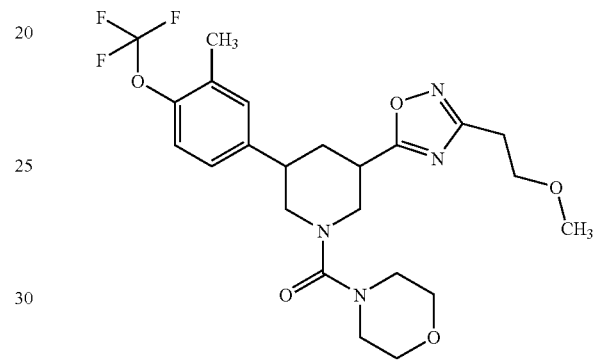

100 mg (0.240 mmol) of the compound from Example 167A and 57 mg (0.360 mmol) of 1-hydroxy-3-methoxypropanimidamide were reacted according to the General Method 2. Yield: 58 mg (48% of theory).

LC-MS (Method 2B): $R_t$=1.33 min; MS (ESIpos): m/z=499 [M+H]$^+$;

$^1$H-NMR (400 MHz, DMSO-d$_6$): δ=7.37 (s, 1H), 7.27 (s, 2H), 3.98 (br d, 1H), 3.67 (t, 2H), 3.60 (br d, 1H), 3.58-3.53 (m, 4H), 3.39 (tt, 1H), 3.23 (s, 3H), 3.22-3.17 (m, 4H), 3.05-2.89 (m, 5H), 2.30 (br d, 1H), 2.27 (s, 3H), 1.97 (dd, 1H).

Example 400

{3-[3-(3-Fluorophenyl)-1,2,4-oxadiazol-5-yl]-5-[3-methyl-4-trifluoromethoxy)phenyl]piperidin-1-yl}(morpholin-4-yl)methanone [racemic cis isomer]

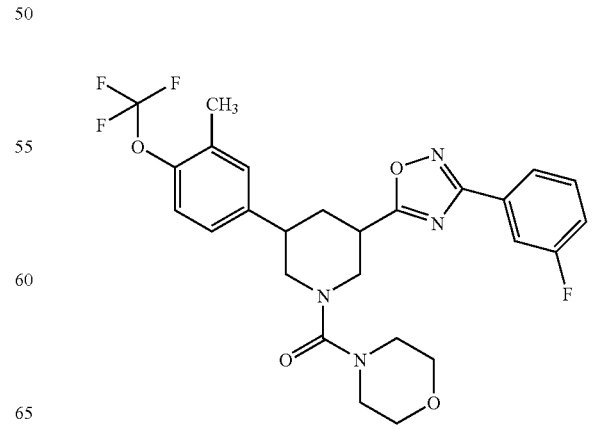

100 mg (0.240 mmol) of the compound from Example 167A and 55 mg (0.360 mmol) of 3-fluoro-N'-hydroxybenzenecarboximidamide were reacted according to the General Method 2. Yield: 95 mg (74% of theory).

LC-MS (Method 1B): $R_t$=3.00 min; MS (ESIpos): m/z=535 [M+H]$^+$;

$^1$H-NMR (400 MHz, DMSO-d$_6$): δ=7.87 (br d, 1H), 7.51 (d, 1H), 7.63 (dd, 1H), 7.46 (dd, 1H), 7.39 (s, 1H), 7.29 (s, 2H), 4.08 (br d, 1H), 3.63 (br d, 1H), 3.61-3.54 (m, 4H), 3.51 (tt, 1H), 3.25-3.18 (m, 4H), 3.15-2.93 (m, 3H), 2.38 (br d, 1H), 2.28 (s, 3H), 2.06 (dd, 1H).

Example 401

{3-(3-Cyclopropyl-1,2,4-oxadiazol-5-yl)-5-[3-methyl-4-(trifluoromethoxy)phenyl]piperidin-1-yl}-(morpholin-4-yl)methanone [racemic cis isomer]

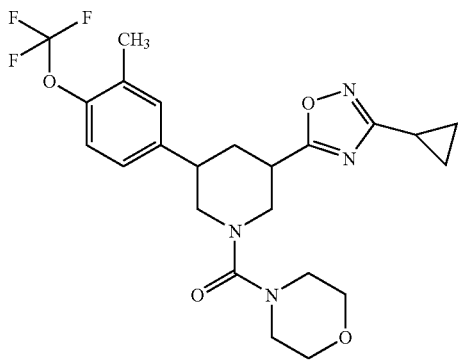

100 mg (0.24 mmol) of the compound from Example 167A and 36 mg (0.36 mmol) of N'-hydroxycyclopropanecarboximidamide were reacted according to the General Method 2. Yield: 72 mg (62% of theory).

LC-MS (Method 2B): $R_t$=1.43 min; MS (ESIpos): m/z=481 [M+H]$^+$;

$^1$H-NMR (400 MHz, DMSO-d$_6$): δ=7.36 (s, 1H), 7.26 (s, 2H), 3.99 (br d, 1H), 3.58 (br d, 1H), 3.58-3.52 (m, 4H), 3.22-3.15 (m, 4H), 3.01-2.87 (m, 3H), 2.27 (s, 3H), 2.25 (d, 1H), 2.14-2.07 (m, 1H), 1.92 (dd, 1H), 1.08-1.03 (m, 2H), 0.90-0.86 (m, 2H).

Example 402

3-[3-(Propan-2-yl)-1,2,4-oxadiazol-5-yl]-5-[4-(trifluoromethyl)phenyl]piperidin-1-yl}methanone [racemic cis isomer]

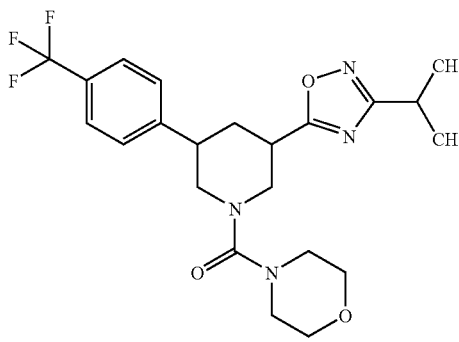

200 mg (0.518 mmol) of the compound from Example 49A and 79 mg (0.78 mmol) of N'-hydroxy-2-methylpropanimidamide were reacted according to the General Method 2. Yield: 82 mg (35% of theory).

LC-MS (Method 1B): $R_t$=2.53 min; MS (ESIpos): m/z=453 [M+H]$^+$;

$^1$H-NMR (400 MHz, DMSO-d$_6$): δ=7.70 (d, 2H), 7.57 (d, 2H), 3.99 (br d, 1H), 3.62 (d, 1H), 3.60-3.55 (m, 4H), 3.41-3.37 (1H), 3.24-3.18 (m, 4H), 3.10-3.01 (4H), 2.34 (br d, 1H), 2.03 (q, 1H), 1.26 (s, 3H), 1.25 (s, 3H).

Example 403

{3-[3-Methyl-4-(trifluoromethoxy)phenyl]-5-[3-(propan-2-yl)-1,2,4-oxadiazol-5-yl]piperidin-1-yl}-(morpholin-4-yl)methanone [racemic cis isomer]

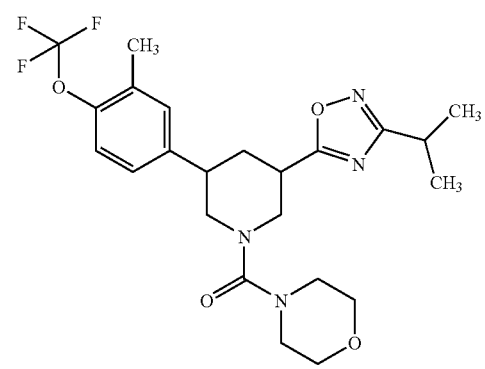

500 mg (1.15 mmol) of the compound from Example 167A and 130 mg (1.27 mmol) of N'-hydroxy-2-methylpropanimidamide were reacted according to the General Method 1. Yield: 286 mg (51% of theory)

LC-MS (Method 9B): $R_t$=1.29 min; MS (ESIpos): m/z=482 [M+H]$^+$.

Example 404

(4-Hydroxypiperidin-1-yl) {3-[3-methyl-4-(trifluoromethoxy)phenyl]-5-[3-(propan-2-yl)-1,2,4-oxadiazol-5-yl]piperidin-1-yl}methanone [racemic cis isomer]

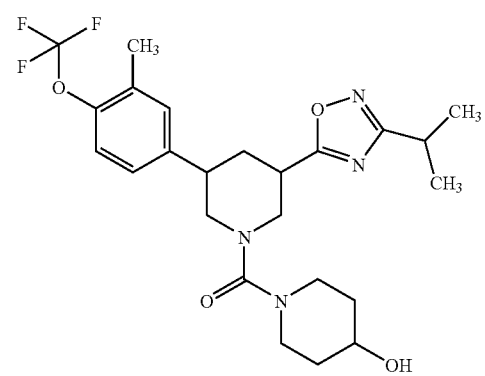

500 mg (1.12 mmol) of the compound from Example 169A and 125 mg (1.23 mmol) of N'-hydroxy-2-methylpropanimidamide were reacted according to the General Method 1. Yield: 373 mg (67% of theory).

LC-MS (Method 2B): $R_t$=1.39 min; MS (ESIpos): m/z=496 [M+H]$^+$;

Example 405

{3-(4-Ethylphenyl)-5-[3-(2-methoxyethyl)-1,2,4-oxadiazol-5-yl]piperidin-1-yl}(morpholin-4-yl)methanone [enantiomerically pure cis isomer]

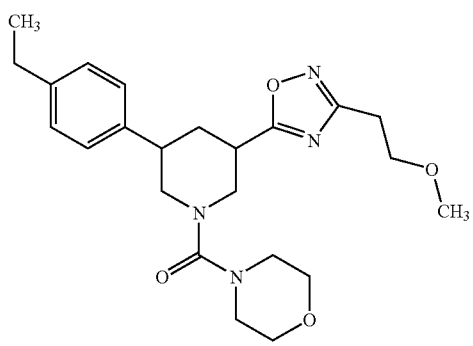

The enantiomer separation of 315 mg (0.7 mmol) of the compound from Example 150 according to Method 14D gave 198 mg of the title compound from Example 405 (Enantiomer 1) and 216 mg of the title compound from Example 406 (Enantiomer 2).

HPLC (Method 11E): $R_t$=5.17 min, >98.5% ee; LC-MS (Method 9B): $R_t$=1.11 min; MS (ESIpos): m/z=429 [M+H]$^+$;

$^1$H-NMR (400 MHz, DMSO-d$_6$): δ=7.22 (d, 2H), 7.17 (d, 1H), 3.99 (br d, 1H), 3.68 (t, 2H), 3.58 (br d, 1H), 3.57-3.55 (m, 4H), 3.42-3.35 (m, 1H), 3.23 (s, 3H), 3.20-3.18 (m, 4H), 3.05-3.01 (m, 1H), 2.98-2.82 (m, 4H), 2.57 (q, 2H), 2.29 (br d, 1H) 1.94 (q, 1H), 1.16 (t, 3H).

[α]$_{365}^{20}$=−31.9, methanol

Example 406

{3-(4-Ethylphenyl)-5-[3-(2-methoxyethyl)-1,2,4-oxadiazol-5-yl]piperidin-1-yl}(morpholin-4-yl)methanone [enantiomerically pure cis isomer]

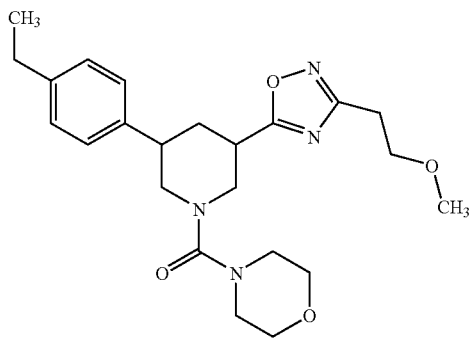

The enantiomer separation of 315 mg (0.7 mmol) of the compound from Example 150 according to Method 14D gave 198 mg of the title compound from Example 405 (Enantiomer 1) and 216 mg of the title compound from Example 406 (Enantiomer 2).

HPLC (Method 11E): $R_t$=7.39 min, >98.5% ee; LC-MS (Method 9B): $R_t$=1.11 min; MS (ESIpos): m/z=429 [M+H]$^+$;

$^1$H-NMR (400 MHz, DMSO-d$_6$): δ=7.22 (d, 2H), 7.17 (d, 1H), 3.98 (br d, 1H), 3.67 (t, 2H), 3.58 (br d, 1H), 3.56-3.52 (m, 4H), 3.42-3.36 (m, 1H), 3.23 (s, 3H), 3.20-3.18 (m, 4H), 3.04-3.00 (m, 1H), 2.98-2.82 (m, 4H), 2.57 (q, 2H), 2.30 (br d, 1H) 1.94 (q, 1H), 1.16 (t, 3H).

[α]$_{365}^{20}$=+24.0, methanol

Example 407

{3-(3,4-Dimethylphenyl)-5-[3-(2-methoxyethyl)-1,2,4-oxadiazol-5-yl]piperidin-1-yl}(4-hydroxypiperidin-1-yl)methanone [enantiomerically pure cis isomer]

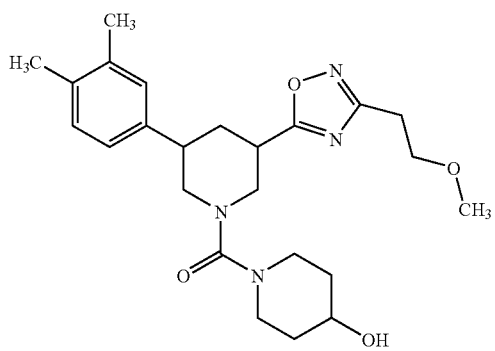

The enantiomer separation of 138 mg of the racemate from Example 186 according to Method 6D gave 44 mg of the title compound from Example 407 and 25 mg of the title compound from Example 408.

HPLC (Method 5E): $R_t$=4.67 min, >99.5% ee; LC-MS (Method 2B): $R_t$=1.15 min; MS (ESIpos): m/z=443 [M+H]$^+$.

Example 408

{3-(3,4-Dimethylphenyl)-5-[3-(2-methoxyethyl)-1,2,4-oxadiazol-5-yl]piperidin-1-yl}(4-hydroxypiperidin-1-yl)methanone [enantiomerically pure cis isomer]

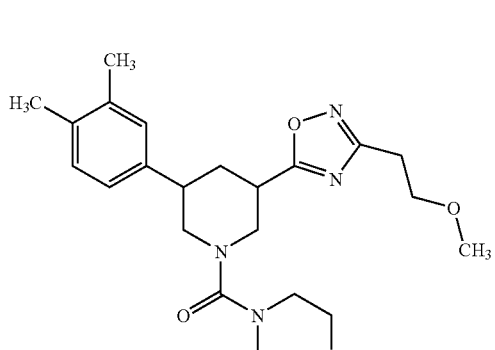

The enantiomer separation of 138 mg of the racemate from Example 186 according to Method 6D gave 44 mg of the title compound from Example 407 and 25 mg of the title compound from Example 408.

HPLC (Method 5E): R$_t$=6.27 min, >99.5% ee; LC-MS (Method 2B): R$_t$=1.15 min; MS (ESIpos): m/z=443[M+H]$^+$.

Example 409

{3-(3,4-Dimethylphenyl)-5-[3-(2-methoxyethyl)-1,2,4-oxadiazol-5-yl]piperidin-1-yl}(3-hydroxy-azetidin-1-yl)methanone [enantiomerically pure cis isomer]

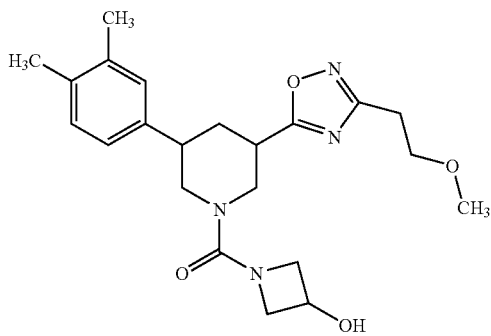

The enantiomer separation of 99 mg of the racemate from Example 216 according to Method 19D gave 28 mg of the title compound from Example 409 (Enantiomer 1) and 28 mg of the title compound from Example 410 (Enantiomer 2).

HPLC (Method 15E): R$_t$=7.99 min, >99.5% ee; LC-MS (Method 2B): R$_t$=1.09 min; MS (ESIpos): m/z=415[M+H]$^+$.

Example 410

{3-(3,4-Dimethylphenyl)-5-[3-(2-methoxyethyl)-1,2,4-oxadiazol-5-yl]piperidin-1-yl}(3-hydroxyazetidin-1-yl)methanone [enantiomerically pure cis isomer]

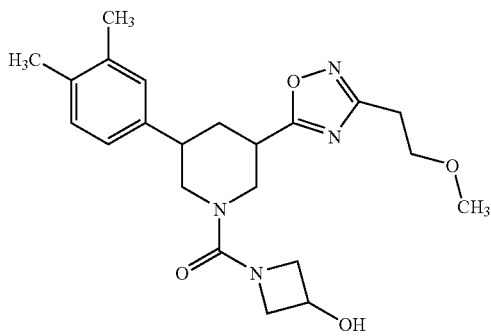

The enantiomer separation of 99 mg of the racemate from Example 216 according to Method 19D gave 28 mg of the title compound from Example 409 and 28 mg of the title compound from Example 410.

HPLC (Method 15E): R$_t$=15.89 min, >99.5% ee; LC-MS (Method 2B): R$_t$=1.09 min;

MS (ESIpos): m/z=415[M+H]$^+$.

Example 411

{3-[3-(3-Fluorophenyl)-1,2,4-oxadiazol-5-yl]-5-[4-methyl-3-(trifluoromethyl)phenyl]piperidin-1-yl}(morpholin-4-yl)methanone [racemic cis isomer]

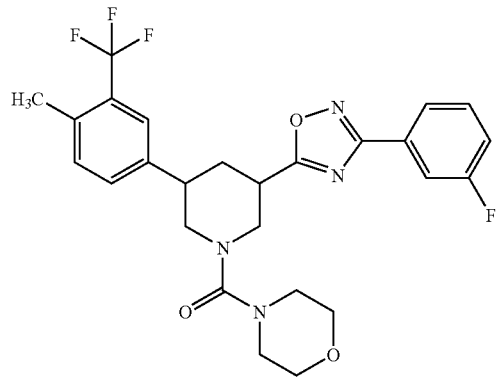

100 mg (about 0.24 mmol) of the compound from Example 160A and 55 mg (0.36 mmol) of 3-fluoro-N'-hydroxybenzenecarboximidamide were reacted according to the General Method 2. Yield: 67 mg (54% of theory).

LC-MS (Method 2B): R$_t$=1.54 min; MS (ESIpos): m/z=519 [M+H]$^+$;

$^1$H-NMR (400 MHz, DMSO-d$_6$): δ=7.87 (d, 1H), 7.75 (d, 1H), 7.64 (dd, 2H), 7.55 (d, 1H), 7.46 (dd, 1H), 7.41 (d, 1H), 4.07 (br d, 1H), 3.59-3.55 (m, 4H), 3.50 (tt, 1H); 3.23-3.18 (m, 4H), 3.16-3.00 (m, 3H), 2.41 (s, 3H), 2.38 (br d, 1H), 2.09 (dd, 1H).

Example 412

1-({3-[3-(3-Fluorophenyl)-1,2,4-oxadiazol-5-yl]-5-[3-(trifluoromethyl)phenyl]piperidin-1-yl}-carbonyl)piperidine-4-carbonitrile [racemic cis isomer]

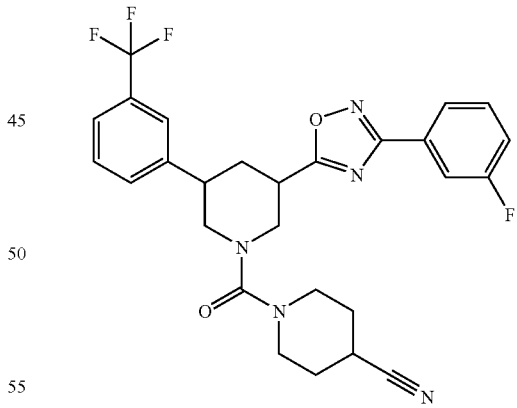

100 mg (0.24 mmol) of the compound from Example 152A and 56 mg (0.37 mmol) of 3-fluoro-N'-hydroxybenzenecarboximidamide were reacted according to the General Method 2. Yield: 87 mg (68% of theory).

LC-MS (Method 5B): R$_t$=2.70 min; MS (ESIpos): m/z=528 [M+H]$^+$;

$^1$H-NMR (400 MHz, DMSO-d$_6$): δ=7.87 (d, 1H), 7.74 (d, 2H), 7.70-7.57 (m, 4H), 7.45 (dd, 1H), 4.05 (br d, 1H), 3.60 (d, 1H), 3.51 (tt, 1H); 3.39 (br d, 1H), 3.19-3.03 (m, 6H), 2.40 (br d, 1H), 2.13 (dd, 1H), 1.92-1.83 (m, 2H), 1.75-1.63 (m, 2H).

Example 413

{3-[3-(3-Fluorophenyl)-1,2,4-oxadiazol-5-yl]-5-[4-methyl-3-(trifluoromethyl)phenyl]piperidin-1-yl}(4-hydroxypiperidin-1-yl)methanone [racemic cis isomer]

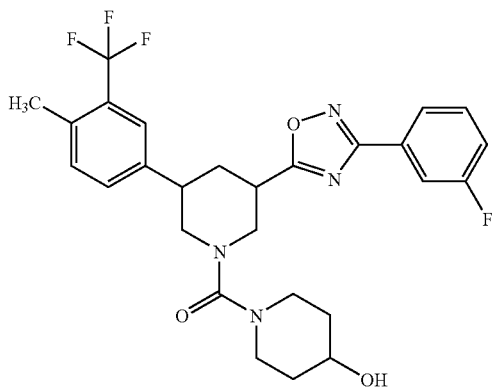

100 mg (0.24 mmol) of the compound from Example 163A and 55 mg (0.36 mmol) of 3-fluoro-N'-hydroxybenzenecarboximidamide were reacted according to the General Method 2. Yield: 71 mg (55% of theory).

LC-MS (Method 9B): $R_t$=1.29 min; MS (ESIpos): m/z=533 [M+H]$^+$;

$^1$H-NMR (400 MHz, DMSO-d$_6$): δ=7.86 (d, 1H), 7.75 (d, 1H), 7.67-7.61 (m, 2H), 7.54 (d, 1H), 7.46 (dd, 1H), 7.41 (d, 1H), 4.69 (d, 1H), 4.03 (br d, 1H), 3.65-3.60 (m, 1H), 3.56 (d, 1H), 3.52-3.46 (m, 3H), 3.13 (t, 1H), 3.02 (dd, 2H), 2.92 (dd, 2H), 2.42 (s, 3H), 2.39 (br d, 1H), 2.08 (dd, 1H), 1.74 (br d, 2H), 1.37-1.27 (m, 2H).

Example 414

{3-(3-Cyclopropyl-1,2,4-oxadiazol-5-yl)-5-[4-methyl-3-(trifluoromethyl)phenyl]piperidin-1-yl}-(morpholin-4-yl)methanone [racemic cis isomer]

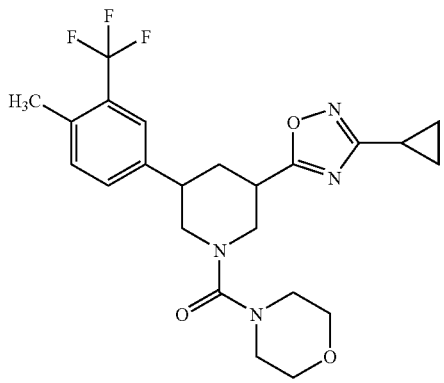

100 mg (0.25 mmol) of the compound from Example 160A and 37 mg (0.38 mmol) of t-hydroxycyclopropanecarboximidamide were reacted according to the General Method 2. Yield: 43 mg (37% of theory).

LC-MS (Method 2B): $R_t$=1.39 min; MS (ESIpos): m/z=465 [M+H]$^+$;

$^1$H-NMR (400 MHz, DMSO-d$_6$): δ=7.61 (s, 1H), 7.51 (d, 1H), 7.40 (d, 1H), 3.94 (br d, 1H), 3.57 (d, 1H), 3.57-3.53 (m, 4H), 3.21-3.16 (m, 4H), 3.06-2.94 (m, 3H), 2.41 (s, 3H); 2.25 (br d, 1H), 2.14-2.07 (m, 1H), 1.95 (dd, 1H), 1.08-1.03 (m, 2H), 0.90-0.86 (m, 2H).

Example 415

{3-(3-Cyclopropyl-1,2,4-oxadiazol-5-yl)-5-[4-methyl-3-(trifluoromethyl)phenyl]piperidin-1-yl}(4-hydroxypiperidin-1-yl)methanone [racemic cis isomer]

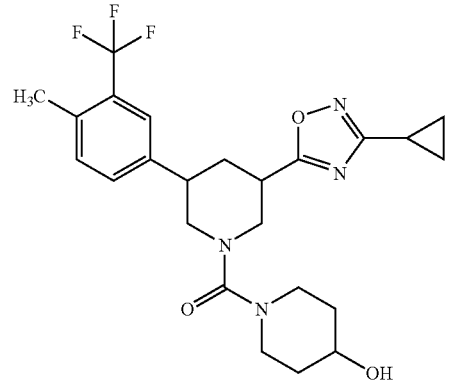

100 mg (0.24 mmol) of the compound from Example 163A and 36 mg (0.36 mmol) of N'-hydroxycyclopropanecarboximidamide were reacted according to the General Method 2. Yield: 60 mg (51% of theory).

LC-MS (Method 9B): $R_t$=1.15 min; MS (ESIpos): m/z=479 [M+H]$^+$;

$^1$H-NMR (400 MHz, DMSO-d$_6$): δ=7.60 (s, 1H), 7.51 (d, 1H), 7.39 (d, 1H), 4.68 (d, 1H), 3.89 (br d, 1H), 3.64-3.57 (m, 2H), 3.53-3.45 (m, 3H), 3.02-2.96 (m, 3H), 2.89 (dd, 2H), 2.43-2.39 (s, 3H), 2.25 (d, 1H), 2.14-2.07 (m, 1H), 1.95 (dd, 1H), 1.70 (br d, 1H), 1.29 (dd, 2H), 1.07-1.03 (m, 2H), 0.90-0.86 (m, 2H).

Example 416

{3-(3-Methyl-1,2,4-oxadiazol-5-yl)-5-[4-(trifluoromethyl)phenyl]piperidin-1-yl}(morpholin-4-yl)methanone [racemic cis isomer]

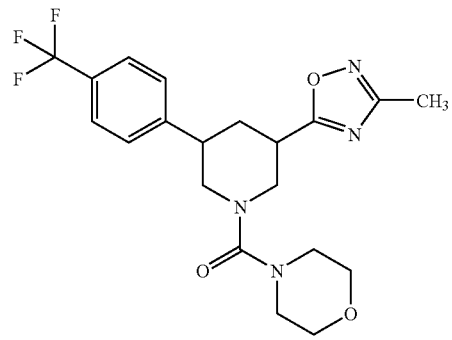

200 mg (0.518 mmol) of the compound from Example 81A and 57 mg (0.78 mmol) of t-hydroxyethanimidamide were reacted according to the General Method 2. Yield: 94 mg (41% of theory).

LC-MS (Method 1B): $R_t$=2.26 min; MS (ESIpos): m/z=425 [M+H]$^+$;

$^1$H-NMR (400 MHz, DMSO-d$_6$): δ=7.70 (d, 2H), 7.57 (d, 2H), 3.98 (br d, 1H), 3.63 (d, 1H), 3.62-3.52 (m, 4H), 3.39 (t, 1H), 3.23-3.18 (m, 4H), 3.08-2.96 (m, 3H), 2.35 (s, 3H), 2.02 (q, 1H).

Example 417

(4-Hydroxypiperidin-1-yl) {3-[3-(2-methoxyethyl)-1,2,4-oxadiazol-5-yl]-5-[4-methyl-3-(trifluoromethyl)phenyl]piperidin-1-yl}methanone [racemic cis isomer]

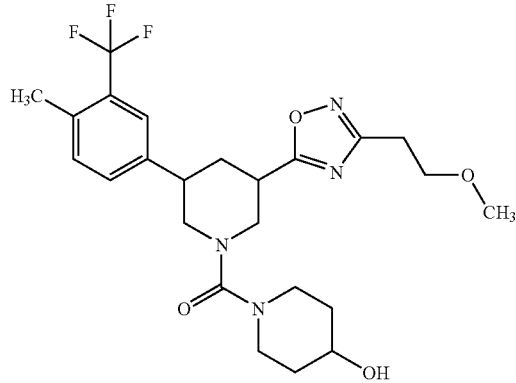

200 mg (0.48 mmol) of the compound from Example 163A and 114 mg (0.72 mmol) of t-hydroxy-3-methoxypropanimidamide (Example 64A) were reacted according to the General Method 2. Yield: 105 mg (44% of theory).

LC-MS (Method 9B): $R_t$=1.07 min; MS (ESIpos): m/z=497 [M+H]$^+$;

$^1$H-NMR (400 MHz, DMSO-d$_6$): δ=7.61 (s, 1H), 7.52 (d, 1H), 7.40 (d, 1H), 4.68 (d, 1H), 3.92 (br d, 1H), 3.67 (t, 2H), 3.64-3.56 (m, 1H), 3.53 (br d, 1H), 3.51-3.43 (m, 2H), 3.38 (tt, 1H), 3.23 (s, 3H), 3.06-2.98 (m, 3H), 2.93 (t, 2H), 2.88 (br d, 1H), 2.41 (s, 3H), 2.30 (br d, 1H), 2.00 (dd, 1H), 1.71 (br d, 2H), 1.35-1.24 (m, 2H).

Example 418

(3-Hydroxypyrrolidin-1-yl) {3-[3-(propan-2-yl)-1,2,4-oxadiazol-5-yl]-5-[4-(trifluoromethoxy)-phenyl]piperidin-1-yl}methanone [mixture of diastereomers]

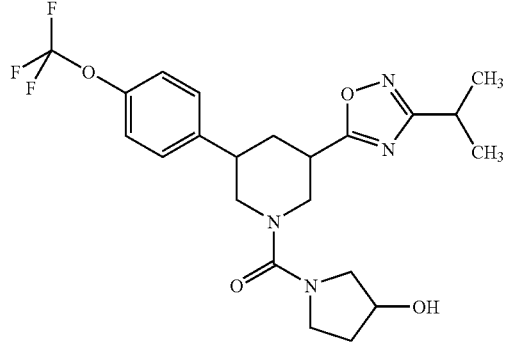

200 mg (0.50 mmol) of the compound from Example 112A and 76 mg (0.75 mmol) of N'-hydroxy-2-methylpropanimidamide were reacted according to the General Method 2. Yield: 125 mg (54% of theory).

LC-MS (Method 2B): $R_t$=1.28 min; MS (ESIpos): m/z=469 [M+H]$^+$;

$^1$H-NMR (400 MHz, DMSO-d$_6$): δ=7.47 (d, 2H), 7.32 (d, 2H), 4.88 (d, 1H), 4.25-4.18 (m, 1H), 4.09-4.00 (m, 1H), 3.72-3.64 (m, 1H), 3.52-3.37 (m, 3H), 3.15-2.84 (m, 5H), 2.35-2.28 (m, 1H), 1.96 (dd, 1H), 1.84-1.78 (m, 1H), 1.75-1.68 (m, 1H), 1.25 (d, 6H).

Example 419

{3-(3-Cyclopropyl-1,2,4-oxadiazol-5-yl)-5-[4-(trifluoromethoxy)phenyl]piperidin-1-yl}(3-hydroxypyrrolidin-1-yl)methanone [mixture of diastereomers]

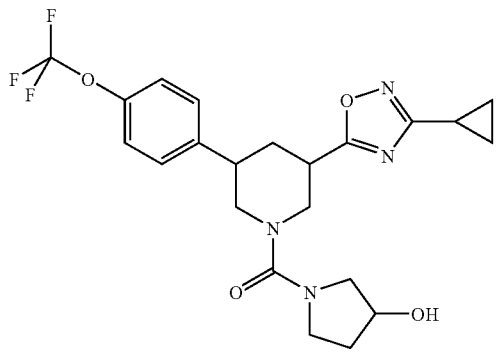

200 mg (0.50 mmol) of the compound from Example 112A and 75 mg (0.75 mmol) of N'-hydroxycyclopropanecarboximidamide were reacted according to the General Method 2. Yield: 127 mg (55% of theory).

LC-MS (Method 2B): $R_t$=1.24 min; MS (ESIpos): m/z=467 [M+H]$^+$;

$^1$H-NMR (400 MHz, DMSO-d$_6$): δ=7.46 (d, 2H), 7.32 (d, 2H), 4.87 (d, 1H), 4.24-4.18 (m, 1H), 4.06-3.96 (m, 1H), 3.73-3.63 (m, 1H), 3.52-3.42 (m, 4H), 3.14-3.05 (m, 1H), 3.00-2.83 (m, 3H), 2.35-2.25 (m, 1H), 2.16-2.07 (m, 1H), 1.93 (dd, 1H), 1.87-1.77 (m, 1H), 1.75-1.65 (m, 1H), 1.08-1.02 (m, 2H), 0.92-0.85 (m, 2H).

Example 420

(3-Hydroxypyrrolidin-1-yl) {3-[3-(2-methoxyethyl)-1,2,4-oxadiazol-5-yl]-5-[4-(trifluoromethoxy)-phenyl]piperidin-1-yl}methanone [mixture of diastereomers]

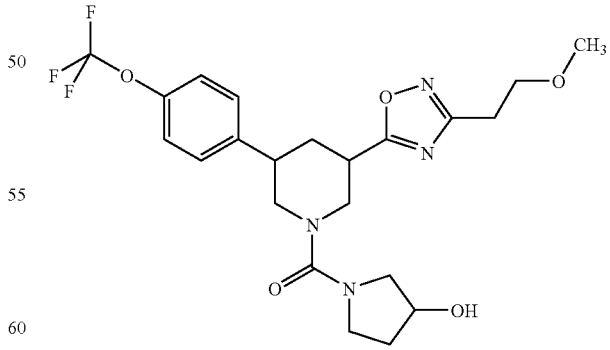

200 mg (0.50 mmol) of the compound from Example 112A and 88 mg (0.75 mmol) of N'-hydroxy-3-methoxypropanimidamide were reacted according to the General Method 2. Yield: 67 mg (27% of theory).

LC-MS (Method 3B): $R_t$=1.81 min; MS (ESIpos): m/z=485 [M+H]$^+$;

¹H-NMR (400 MHz, DMSO-d₆): δ=7.47 (d, 2H), 7.32 (d, 2H), 4.88 (d, 1H), 4.25-4.18 (m, 1H), 4.09-4.00 (m, 1H), 3.73-3.65 (m, 3H), 3.52-3.40 (m, 3H), 3.23 (s, 3H), 3.10 (dd, 1H), 3.03-2.84 (m, 5H), 2.36-2.29 (m, 1H), 1.98 (dd, 1H), 1.87-1.77 (m, 1H), 1.76-1.68 (m, 1H).

Example 421

{3-(3-Ethyl-1,2,4-oxadiazol-5-yl)-5-[4-(trifluoromethoxy)phenyl]piperidin-1-yl}(3-hydroxypyrrolidin-1-yl)methanone [mixture of diastereomers]

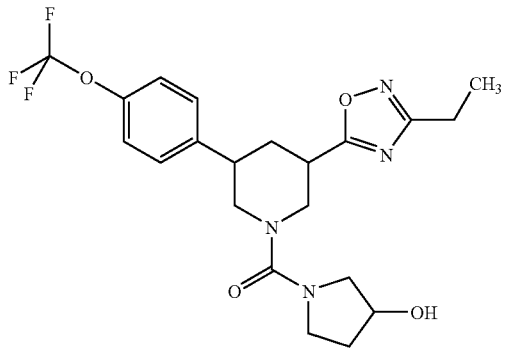

200 mg (0.50 mmol) of the compound from Example 112A and 67 mg (0.75 mmol) of N'-hydroxypropanimidamide were reacted according to the General Method 2. Yield: 17 mg (7% of theory).

LC-MS (Method 3B): $R_t$=1.92 min; MS (ESIpos): m/z=455 [M+H]⁺;

¹H-NMR (400 MHz, DMSO-d₆): δ=7.46 (d, 2H), 7.32 (d, 2H), 4.88 (d, 1H), 4.25-4.18 (m, 1H), 4.09-4.00 (m, 1H), 3.69 (dd, 1H), 3.52-3.41 (m, 3H), 3.10 (dd, 1H), 3.04-2.86 (m, 3H), 2.74-2.67 (m, 3H), 2.37-2.28 (m, 1H), 1.97 (dd, 1H), 1.86-1.77 (m, 1H), 1.76-1.68 (m, 1H), 1.22 (t, 3H).

Example 422

(3-Hydroxypyrrolidin-1-yl) {3-(3-methyl-1,2,4-oxadiazol-5-yl)-5-[4-(trifluoromethoxy)phenyl]-piperidin-1-yl}methanone [mixture of diastereomers]

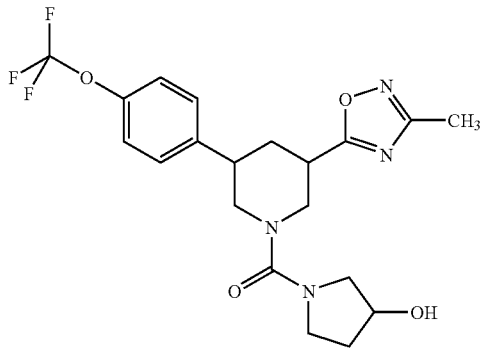

200 mg (0.50 mmol) of the compound from Example 112A and 55 mg (0.75 mmol) of N'-hydroxyethanimidamide were reacted according to the General Method 2. Yield: 15 mg (6% of theory).

LC-MS (Method 2B): $R_t$=1.14 min; MS (ESIpos): m/z=441 [M+H]⁺;

¹H-NMR (400 MHz, DMSO-d₆): δ=7.46 (d, 2H), 7.33 (d, 2H), 4.88 (d, 1H), 4.25-4.18 (m, 1H), 4.09-4.00 (m, 1H), 3.69 (dd, 1H), 3.52-3.37 (m, 3H), 3.10 (dd, 1H), 3.03-2.82 (m, 4H), 2.32 (s, 3H), 2.30 (br d, 1H), 1.97 (dd, 1H), 1.87-1.77 (m, 1H), 1.77-1.68 (m, 1H).

Example 423

1-({3-[5-(2-Methoxyethyl)-1,3,4-oxadiazol-2-yl]-5-[4-(trifluoromethoxy)phenyl]piperidin-1-yl}-carbonyl)piperidine-4-carbonitrile [racemic cis isomer]

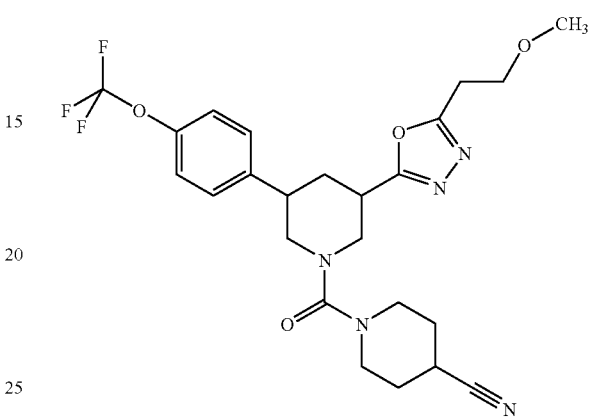

100 mg (0.15 mmol) of the compound from Example 108A and 36 mg (0.31 mmol) of 3-methoxypropanehydrazide were reacted according to the General Method 4. Yield: 5 mg (7% of theory).

LC-MS (Method 2B): $R_t$=1.20 min; MS (ESIpos): m/z=508 [M+H]⁺;

¹H-NMR (400 MHz, DMSO-d₆): δ=7.46 (d, 2H), 7.33 (d, 2H), 3.95 (br d, 1H), 3.68 (t, 2H), 3.57 (br d, 1H), 3.24 (s, 3H), 3.12-2.96 (m, 7H), 2.28 (br d, 1H), 1.93 (q, 1H), 1.90-1.82 (m, 2H), 1.73-1.62 (m, 2H).

Example 424

[3-(4-Ethylphenyl)-5-(5-methyl-1,3-oxazol-2-yl)piperidin-1-yl] (morpholin-4-yl)methanone [racemic cis isomer]

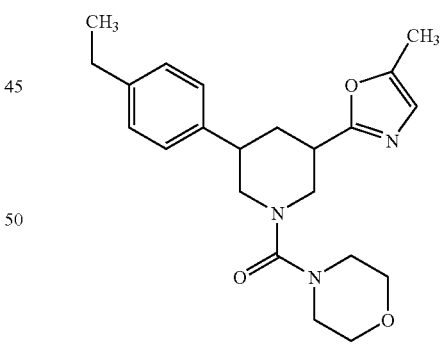

50 mg (0.13 mmol) of the compound from Example 199A were initially charged in 0.5 ml of acetonitrile, and 2 mg (0.01 mmol) of gold trichloride were added. The reaction mixture was stirred at 50° C. for 16 h, concentrated and purified by preparative HPLC. Yield: 10 mg (15% of theory).

HPLC (Method 2A): $R_t$=1.28 min; MS (ESIpos): m/z=384 [M+H]⁺;

¹H-NMR (400 MHz, DMSO-d₆): δ=7.22 (d, 2H), 7.16 (d, 2H), 6.74 (s, 1H), 3.95 (br d, 1H), 3.60 (br d, 1H), 3.58-3.55 (m, 4H), 3.23-3.17 (m, 4H), 3.11-3.07 (m, 1H), 2.98-2.79 (m, 3H), 2.58 (q, 2H), 2.26 (s, 3H), 2.25 (br d, 1H), 1.89 (q, 1H), 1.16 (t, 3H).

Example 425

{3-[5-(Furan-2-yl)-1,2,4-oxadiazol-3-yl]-5-[4-(trifluoromethyl)phenyl]piperidin-1-yl}(morpholin-4-yl)methanone

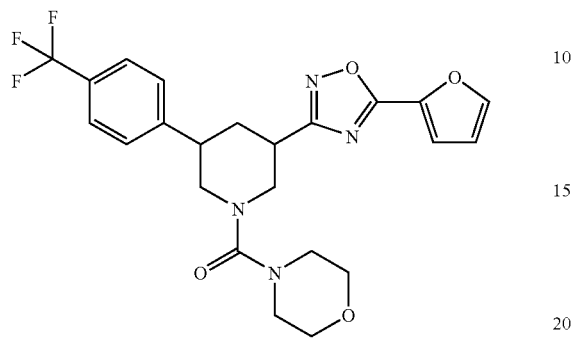

The title compound was prepared according to the General Method 8. Yield: 0.48 mg (12% of theory)

LC-MS (Method 10B): $R_t$=2.25 min; MS (ESIpos): m/z=477 [M+H]$^+$.

The compounds listed in Table 5 were prepared from 0.1 mmol the compound from Example 84A and the appropriate carboxylic acid according to the General Method 8.

TABLE 5

| Example No. | Structure | Yield (% of theory) | LC-MS: $R_t$ (Method 10B) |
|---|---|---|---|
| 426 | 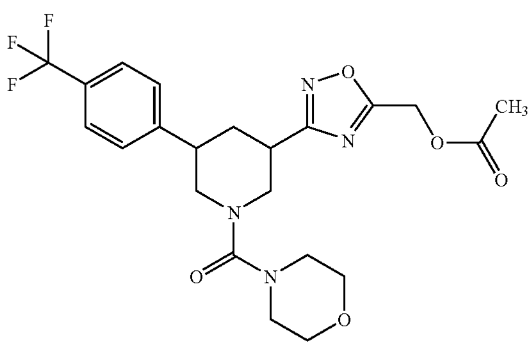 | 3 | m/z = 482; 2.10 min |
| 427 | 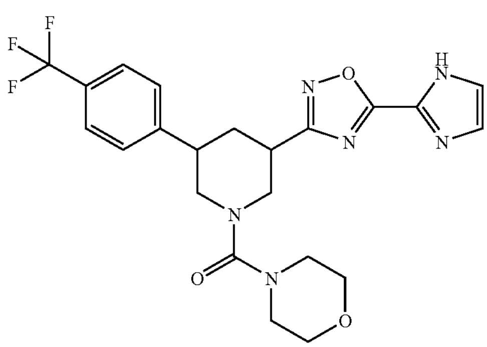 | 5 | m/z = 476; 1.91 min |

TABLE 5-continued

| Example No. | Structure | Yield (% of theory) | LC-MS: R$_t$ (Method 10B) |
|---|---|---|---|
| 428 | 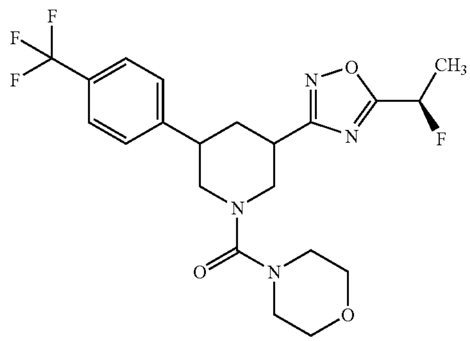 | 9 | m/z = 456; 2.19 min |
| 429 | 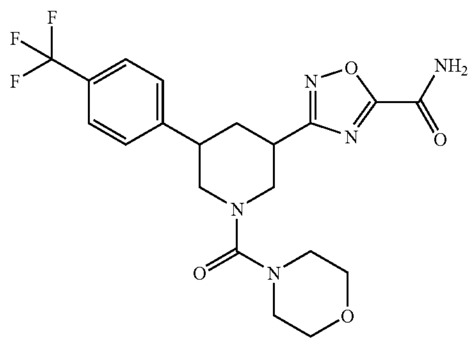 | 2 | m/z = 453; 1.90 min |
| 430 | 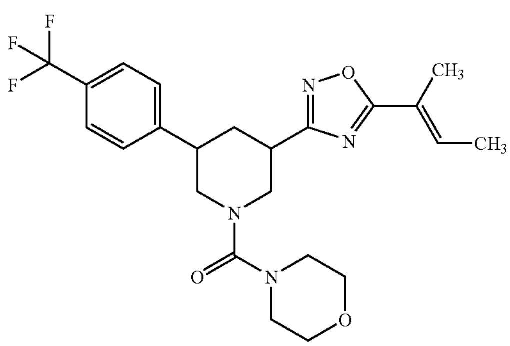 | 15 | m/z = 464; 2.36 min |
| 431 | 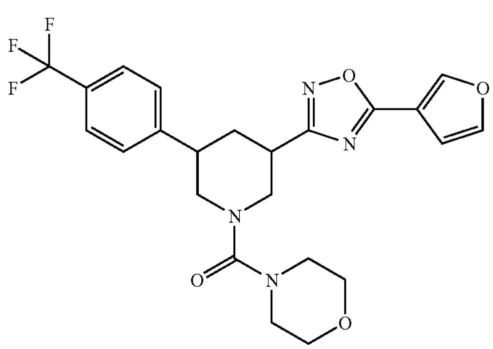 | 15 | m/z = 476; 2.25 min |

TABLE 5-continued
| Example No. | Structure | Yield (% of theory) | LC-MS: $R_t$ (Method 10B) |
|---|---|---|---|
| 432 | 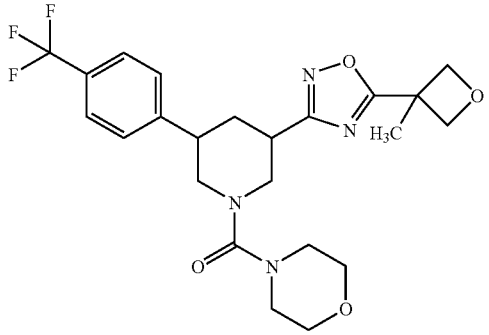 | 40 | m/z = 480; 2.12 min |
| 433 | 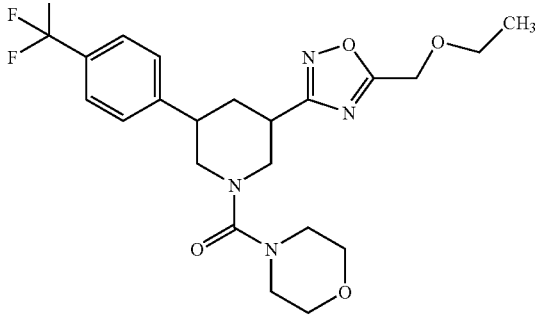 | 8 | m/z = 468; 2.17 min |
| 434 | 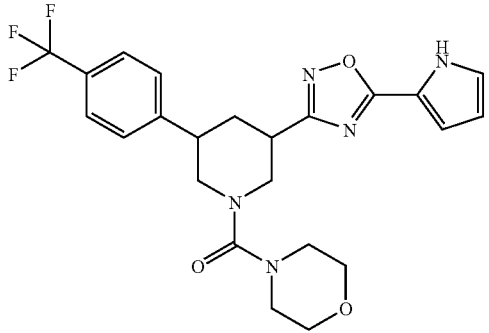 | 6 | m/z = 475; 2.19 min |
| 435 | 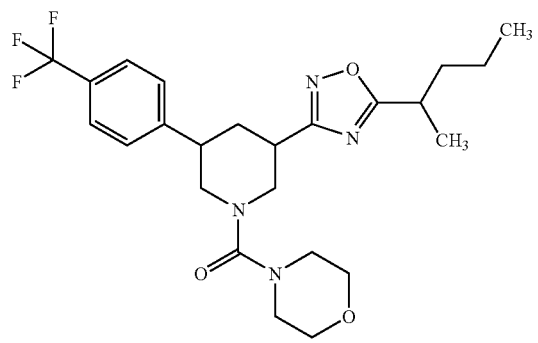 | 18 | m/z = 480; 2.41 min |

TABLE 5-continued

| Example No. | Structure | Yield (% of theory) | LC-MS: R$_t$ (Method 10B) |
|---|---|---|---|
| 436 | 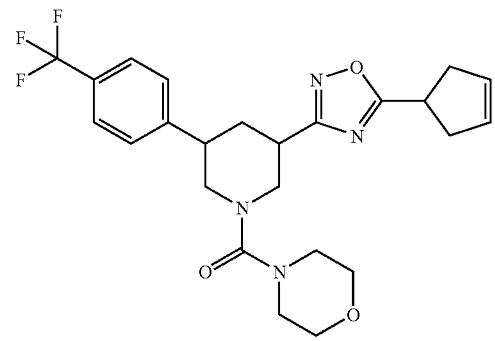 | 47 | m/z = 476; 2.32 min |
| 437 | 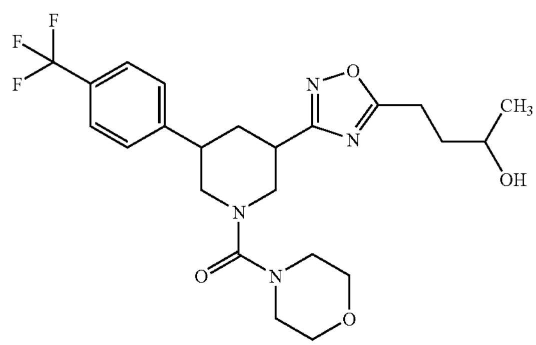 | 11 | m/z = 468; 2.01 min |
| 438 | 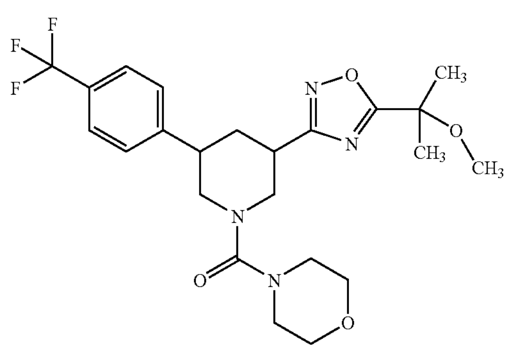 | 19 | m/z = 482; 2.25 min |
| 439 | 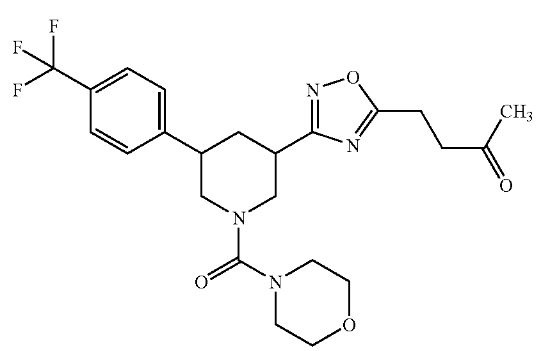 | 15 | m/z = 480; 2.04 min |

TABLE 5-continued

| Example No. | Structure | Yield (% of theory) | LC-MS: $R_t$ (Method 10B) |
|---|---|---|---|
| 440 | 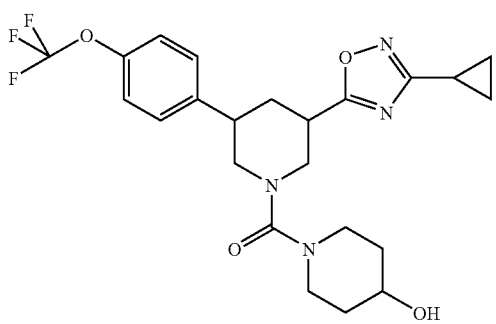 | 18 | m/z = 182; 2.04 min |

Example 441

{3-(3-Cyclopropyl-1,2,4-oxadiazol-5-yl)-5-[4-(trifluoromethoxy)phenyl]piperidin-1-yl}(4-hydroxypiperidin-1-yl)methanone [racemic cis isomer]

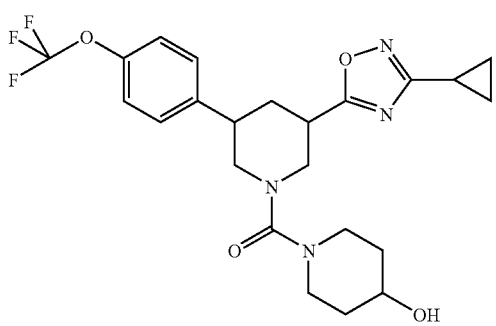

200 mg (0.480 mmol) of the compound from Example 63A and 96 mg (0.961 mmol) of N'-hydroxycyclopropanecarboximidamide were reacted according to the General Method 2. Yield: 130 mg (56% of theory).

LC-MS (Method 2B): $R_t$=1.30 min; MS (ESIpos): m/z=481 [M+H]$^+$;

$^1$H-NMR (400 MHz, DMSO-d$_6$): δ=7.45 (d, 2H), 7.32 (d, 2H), 4.66 (d, 1H), 3.91 (br d, 1H), 3.64-3.57 (m, 1H), 3.54 (d, 1H), 3.50-3.42 (m, 2H), 2.99-2.86 (m, 5H), 2.27 (br d, 1H), 2.14-2.07 (m, 1H), 1.92 (dd, 1H), 1.71 (br d, 1H), 1.33-1.24 (m, 2H), 1.07-1.03 (m, 2H), 0.90-0.86 (m, 2H).

Example 442

{3-(3-Cyclopropyl-1,2,4-oxadiazol-5-yl)-5-[4-(trifluoromethoxy)phenyl]piperidin-1-yl}(4-hydroxypiperidin-1-yl)methanone [enantiomerically pure cis isomer]

The enantiomer separation of 130 mg of the racemate from Example 441 according to Method 11D gave 48 mg of the title compound from Example 442 and 48 mg of the title compound from Example 443.

HPLC (Method 9E): $R_t$=4.14 min, >99.0% ee; LC-MS (Method 2B): $R_t$=1.26 min; MS (ESIpos): m/z=481 [M+H]$^+$.

$[α]_{365}^{20}$=+2.4, c=0.63, methanol

Example 443

{3-(3-Cyclopropyl-1,2,4-oxadiazol-5-yl)-5-[4-(trifluoromethoxy)phenyl]piperidin-1-yl}(4-hydroxypiperidin-1-yl)methanone [enantiomerically pure cis isomer]

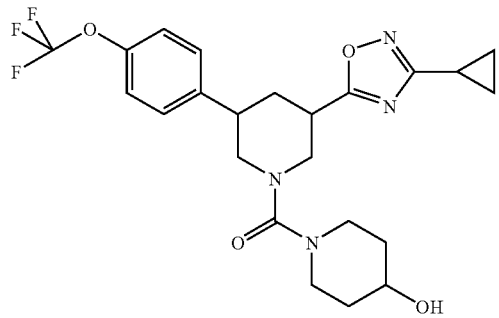

The enantiomer separation of 130 mg of the racemate from Example 441 according to Method 11D gave 48 mg of the title compound from Example 442 and 48 mg of the title compound from Example 443.

HPLC (Method 9E): $R_t$=6.35 min, >99.0% ee; LC-MS (Method 2B): $R_t$=1.26 min; MS (ESIpos): m/z=481 [M+H]$^+$.

$[α]_{365}^{20}$=+0.3, c=0.61, methanol

Example 444

Ethyl 5-{1-(morpholin-4-ylcarbonyl)-5-[4-(trifluoromethyl)phenyl]piperidin-3-yl}-1,2,4-oxadiazole-3-carboxylate [racemic cis isomer]

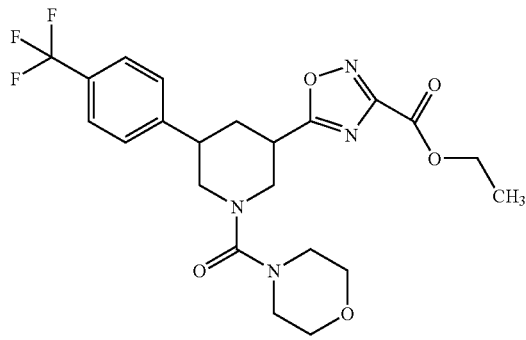

200 mg (about 0.47 mmol) of the compound from Example 49A and 54 mg (0.41 mmol) of ethyl amino(hydroxyimino)ethanoate were reacted according to the General Method 1. Yield: 17 mg (8% of theory).

LC-MS (Method 2B): $R_t$=1.30 min; MS (ESIpos): m/z=483 [M+H]$^+$;

$^1$H-NMR (400 MHz, DMSO-d$_6$): δ=7.71 (d, 2H), 7.58 (d, 2H), 4.41 (q, 2H), 4.03 (br d, 1H), 3.63 (d, 1H), 3.60-3.51 (m, 5H), 3.22-3.10 (m, 4H), 3.15-3.00 (m, 3H), 2.36 (d, 1H), 2.07 (q, 1H), 1.32 (t, 3H).

Example 445

{3-[3-(3-Fluorophenyl)-1,2,4-oxadiazol-5-yl]-5-[4-(trifluoromethoxy)phenyl]piperidin-1-yl}(4-hydroxypiperidin-1-yl)methanone [enantiomerically pure cis isomer]

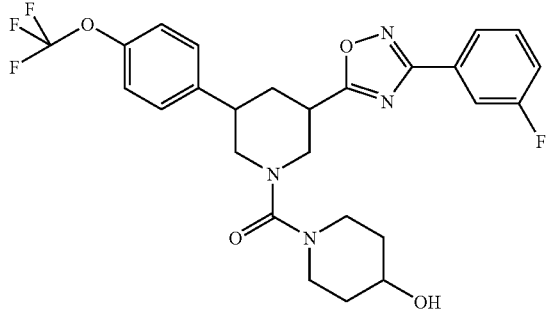

Enantiomer separation of 130 mg of the racemate from Example 444 according to Method 12D gave 31 mg of the title compound from Example 445 and 32 mg of the title compound from Example 446.

HPLC (Method 9E): $R_t$=5.25 min, >99.0% ee; LC-MS (Method 2B): $R_t$=1.41 min; MS (ESIpos): m/z=534 [M+H]$^+$.

$[α]_{365}^{20}$=3.0, c=0.62, methanol

Example 446

{3-[3-(3-Fluorophenyl)-1,2,4-oxadiazol-5-yl]-5-[4-(trifluoromethoxy)phenyl]piperidin-1-yl}(4-hydroxypiperidin-1-yl)methanone [enantiomerically pure cis isomer]

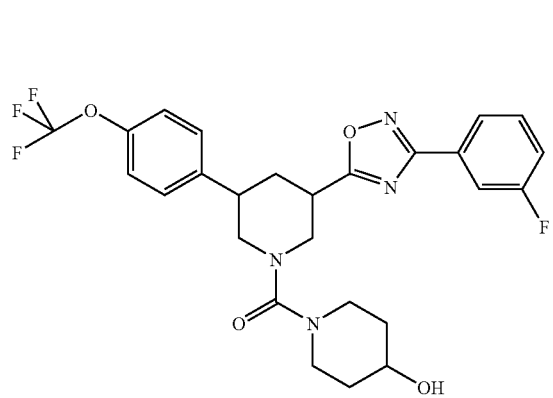

Enantiomer separation of 130 mg of the racemate from Example 444 according to Method 12D gave 31 mg of the title compound from Example 445 and 32 mg of the title compound from Example 446.

HPLC (Method 9E): $R_t$=9.33 min, >99.0% ee; LC-MS (Method 2B): $R_t$=1.41 min; MS (ESIpos): m/z=534 [M+H]$^+$.

$[α]_{365}^{20}$=−3.0, c=0.61, methanol

Example 447

(4-Hydroxypiperidin-1-yl){3-[3-(2-methoxyethyl)-1,2,4-oxadiazol-5-yl]-5-[4-(trifluoromethoxy)phenyl]piperidin-1-yl}methanone [racemic cis isomer]

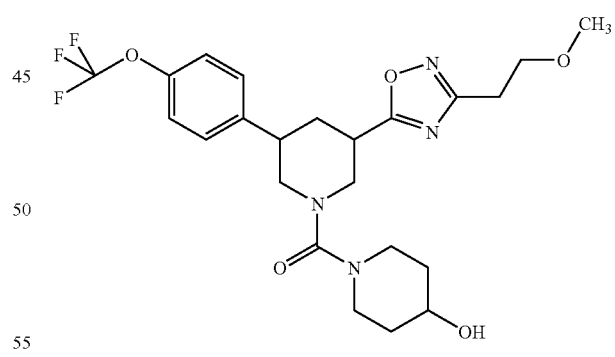

200 mg (about 0.432 mmol) of the compound from Example 63A and 102 mg (0.865 mmol) of N'-hydroxy-3-methoxypropanimidamide were reacted according to the General Method 2. Yield: 92 mg (36% of theory)

LC-MS (Method 2B): $R_t$=1.20 min; MS (ESIpos): m/z=499 [M+H]$^+$;

$^1$H-NMR (400 MHz, DMSO-d$_6$): δ=7.46 (d, 2H), 7.33 (d, 2H), 4.68 (d, 1H), 3.94 (br d, 1H), 3.67 (t, 2H), 3.63-3.57 (m,

1H), 3.55 (d, 1H), 3.51-3.35 (m, 3H), 3.23 (s, 3H), 3.03-2.90 (m, 7H), 2.31 (br d, 1H), 1.96 (dd, 1H), 1.71 (br d, 2H), 1.35-1.26 (m, 2H).

Example 448

(4-Hydroxypiperidin-1-yl) {3-[3-(2-methoxyethyl)-1,2,4-oxadiazol-5-yl]-5-[4-(trifluoromethoxy)-phenyl]piperidin-1-yl}methanone [enantiomerically pure cis isomer]

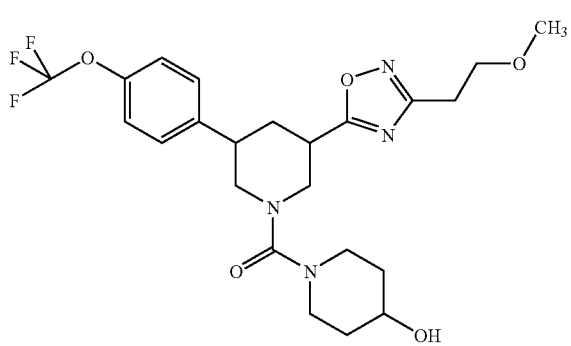

Enantiomer separation of 91 mg of the racemate from Example 447 according to Method 12D gave 33 mg of the title compound from Example 448 and 33 mg of the title compound from Example 449.

HPLC (Method 9E): $R_t$=5.11 min, >99.0% ee; LC-MS (Method 9B): $R_t$=1.04 min; MS (ESIpos): m/z=499 [M+H]$^+$.

$^1$H-NMR (400 MHz, DMSO-d$_6$): δ=7.48 (d, 2H), 7.33 (d, 2H), 4.68 (d, 1H), 3.94 (br d, 1H), 3.67 (t, 2H), 3.61-3.37 (m, 5H), 3.23 (s, 3H), 3.03-2.88 (m, 7H), 2.32 (br d, 1H), 1.96 (dd, 1H), 1.73 (br d, 2H), 1.37-1.25 (m, 2H).

Example 449

(4-Hydroxypiperidin-1-yl) {3-[3-(2-methoxyethyl)-1,2,4-oxadiazol-5-yl]-5-[4-(trifluoromethoxy)-phenyl]piperidin-1-yl}methanone [enantiomerically pure cis isomer]

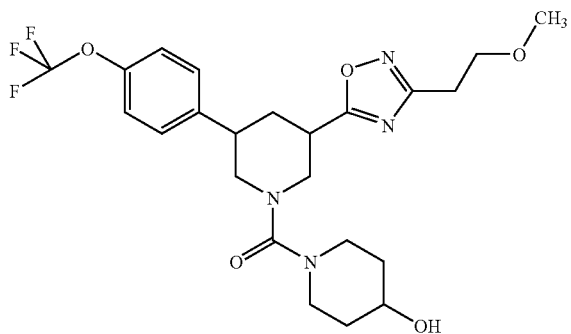

Enantiomer separation of 91 mg of the racemate from Example 447 according to Method 12D gave 33 mg of the title compound from Example 448 and 33 mg of the title compound from Example 449.

HPLC (Method 9E): $R_t$=11.94 min, >99.0% ee; LC-MS (Method 9B): $R_t$=1.04 min; MS (ESIpos): m/z=499 [M+H]$^+$.

$^1$H-NMR (400 MHz, DMSO-d$_6$): δ=7.48 (d, 2H), 7.33 (d, 2H), 4.68 (d, 1H), 3.94 (br d, 1H), 3.67 (t, 2H), 3.61-3.37 (m, 5H), 3.23 (s, 3H), 3.03-2.88 (m, 7H), 2.32 (br d, 1H), 1.96 (dd, 1H), 1.73 (br d, 2H), 1.37-1.25 (m, 2H).

Example 450

(4-Hydroxypiperidin-1-yl) {3-[3-(propan-2-yl)-1,2,4-oxadiazol-5-yl]-5-[4-(trifluoromethoxy)-phenyl]piperidin-1-yl}methanone [racemic cis isomer]

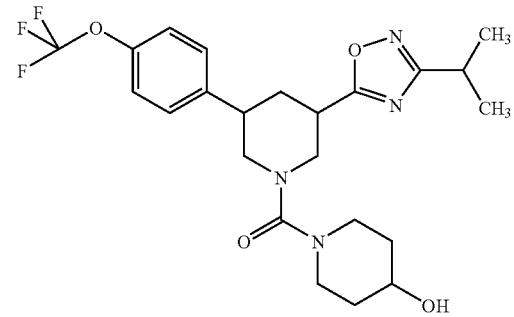

200 mg (0.480 mmol) of the compound from Example 63A and 98 mg (0.961 mmol) of N'-hydroxy-2-methylpropanimidamide were reacted according to the General Method 2. Yield: 62 mg (27% of theory)

LC-MS (Method 9B): $R_t$=1.16 min; MS (ESIpos): m/z=483 [M+H]$^+$;

$^1$H-NMR (400 MHz, DMSO-d$_6$): δ=7.46 (d, 2H), 7.32 (d, 2H), 4.67 (d, 1H), 3.94 (br d, 1H), 3.64-3.57 (m, 1H), 3.55 (br d, 1H), 3.52-3.47 (m, 2H), 3.42-3.34 (m, 1H), 3.08-2.85 (m, 6H), 2.31 (br d, 1H), 1.96 (dd, 1H), 7.71 (br d, 1H), 1.37-1.28 (m, 2H), 1.26 (s, 3H), 1.24 (s, 3H).

Example 451

(4-Hydroxypiperidin-1-yl){3-[3-(propan-2-yl)-1,2,4-oxadiazol-5-yl]-5-[4-(trifluoromethoxy)phenyl]piperidin-1-yl}methanone [enantiomerically pure cis isomer]

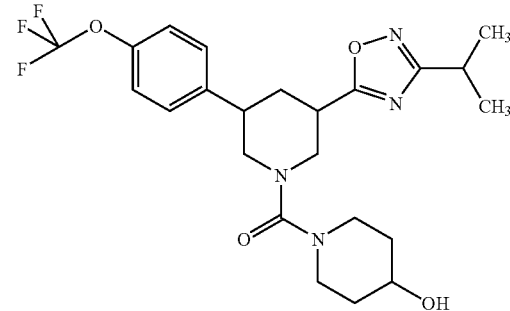

The enantiomer separation of 60 mg of the racemate from Example 450 according to Method 13D gave 25 mg of the title compound from Example 451 and 24 mg of the title compound from Example 452.

HPLC (Method 10E): $R_t$=4.04 min, >99.0% ee; LC-MS (Method 9B): $R_t$=1.15 min;

MS (ESIpos): m/z=483 [M+H]$^+$.

Example 452

(4-Hydroxypiperidin-1-yl){3-[3-(propan-2-yl)-1,2,4-oxadiazol-5-yl]-5-[4-(trifluoromethoxy)phenyl]piperidin-1-yl}methanone [enantiomerically pure cis isomer]

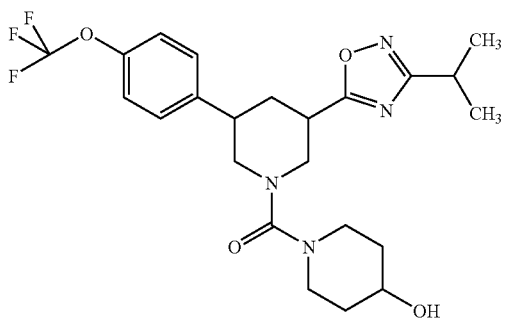

The enantiomer separation of 60 mg of the racemate from Example 450 according to Method 13D gave 25 mg of the title compound from Example 451 and 24 mg of the title compound from Example 452.

HPLC (Method 10E): $R_t$=6.14 min, >99.0% ee; LC-MS (Method 9B): $R_t$=1.15 min;

MS (ESIpos): m/z=483 [M+H]$^+$.

Example 453

(4-Hydroxypiperidin-1-yl){3-(3-methyl-1,2,4-oxadiazol-5-yl)-5-[4-(trifluoromethoxy)phenyl]-piperidin-1-yl}methanone [racemic cis isomer]

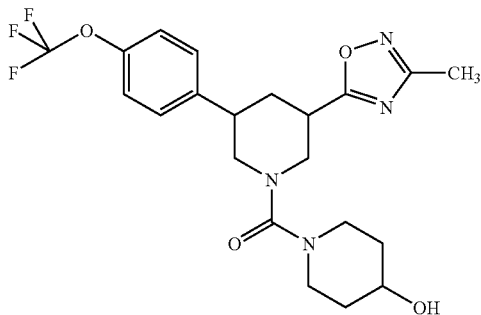

200 mg (0.480 mmol) of the compound from Example 63A and 71 mg (0.961 mmol) of N'-hydroxyethanimidamide were reacted according to the General Method 2. Yield: 144 mg (62% of theory)

LC-MS (Method 2B): $R_t$=1.19 min; MS (ESIpos): m/z=455 [M+H]$^+$;

$^1$H-NMR (400 MHz, DMSO-d$_6$): δ=7.45 (d, 2H), 7.33 (d, 2H), 4.68 (d, 1H), 3.93 (br d, 1H), 3.65-3.54 (m, 2H), 3.51-3.44 (m, 2H), 3.37 (tt, 1H), 3.03-2.85 (m, 5H), 2.33 (s, 3H), 2.30 (br d, 1H), 1.96 (dd, 1H), 1.71 (br d, 1H), 1.35-1.25 (m, 2H).

Example 454

(4-Hydroxypiperidin-1-yl){3-(3-methyl-1,2,4-oxadiazol-5-yl)-5-[4-(trifluoromethoxy)phenyl]piperidin-1-yl}methanone [enantiomerically pure cis isomer]

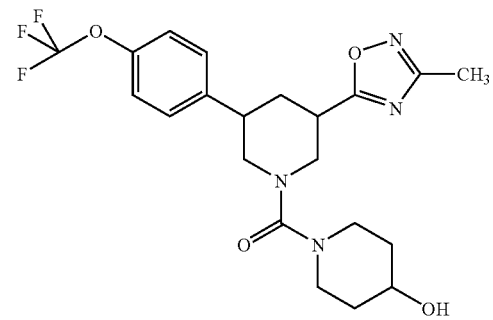

Enantiomer separation of 140 mg of the racemate from Example 453 according to Method 12D gave 54 mg of the title compound from Example 454 and 54 mg of the title compound from Example 455.

HPLC (Method 9E): $R_t$=4.48 min, >99.0% ee; LC-MS (Method 2B): $R_t$=1.16 min; MS (ESIpos): m/z=455 [M+H]$^+$.

Example 455

(4-Hydroxypiperidin-1-yl){3-(3-methyl-1,2,4-oxadiazol-5-yl)-5-[4-(trifluoromethoxy)phenyl]-piperidin-1-yl}methanone [enantiomerically pure cis isomer]

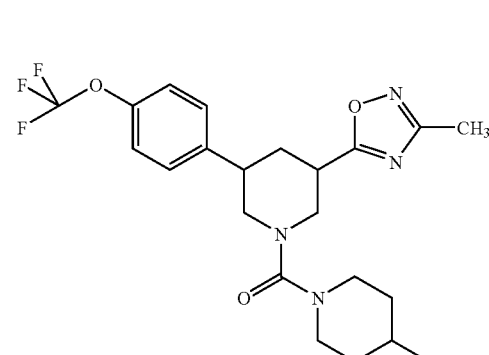

Enantiomer separation of 140 mg of the racemate from Example 453 according to Method 12D gave 54 mg of the title compound from Example 454 and 54 mg of the title compound from Example 455.

HPLC (Method 9E): $R_t$=12.43 min, >99.0% ee; LC-MS (Method 2B): $R_t$=1.16 min; MS (ESIpos): m/z=455 [M+H]$^+$.

Example 456

[3-(3,4-Dimethylphenyl)-5-(3-methyl-1,2,4-oxadiazol-5-yl)piperidin-1-yl] (4-hydroxypiperidin-1-yl)methanone [enantiomerically pure cis isomer]

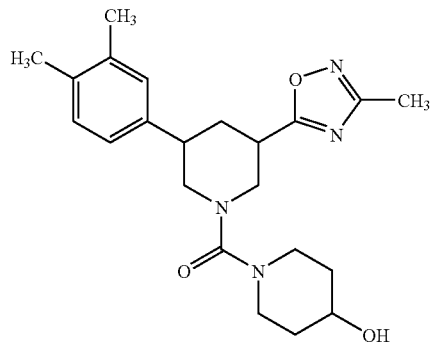

The enantiomer separation of 150 mg of the racemate from Example 198 according to Method 6D gave 75 mg of the title compound from Example 456 and 66 mg of the title compound from Example 457.

HPLC (Method 5E): $R_t$=4.42 min, >99.0% ee; LC-MS (Method 2B): $R_t$=1.16 min; MS (ESIpos): m/z=455 [M+H]$^+$.

$[\alpha]_{365}^{20}$=−28.9, methanol

Example 457

[3-(3,4-Dimethylphenyl)-5-(3-methyl-1,2,4-oxadiazol-5-yl)piperidin-1-yl] (4-hydroxypiperidin-1-yl)methanone [enantiomerically pure cis isomer]

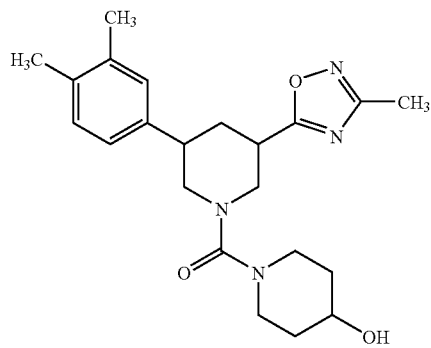

The enantiomer separation of 150 mg of the racemate from Example 198 according to Method 6D gave 75 mg of the title compound from Example 456 and 66 mg of the title compound from Example 457.

HPLC (Method 5E): $R_t$=6.86 min, >99.0% ee; LC-MS (Method 2B): $R_t$=1.16 min; MS (ESIpos): m/z=455 [M+H]$^+$.

$[\alpha]_{365}^{20}$=+25.0, methanol

Example 458

{3-[3-(2-Methoxyethyl)-1,2,4-oxadiazol-5-yl]-5-[4-methyl-3-(trifluoromethyl)phenyl]piperidin-1-yl} (morpholin-4-yl)methanone [enantiomerically pure cis isomer]

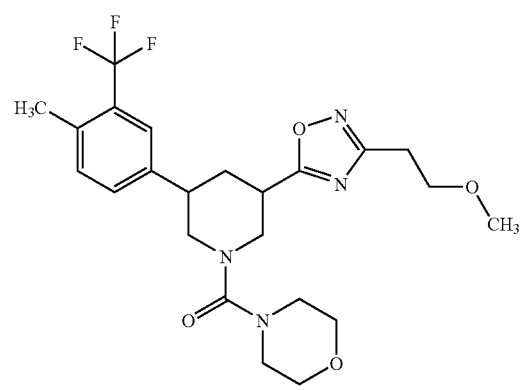

The enantiomer separation of 100 mg of the racemate from Example 416 according to Method 13D gave 41 mg of the title compound from Example 458 and 41 mg of the title compound from Example 459.

HPLC (Method 10E): $R_t$=7.21 min, >99.0% ee; LC-MS (Method 2B): $R_t$=1.16 min; MS (ESIpos): m/z=455 [M+H]$^+$.

$[\alpha]_{365}^{20}$=−18.4, methanol

Example 459

{3-[3-(2-Methoxyethyl)-1,2,4-oxadiazol-5-yl]-5-[4-methyl-3-(trifluoromethyl)phenyl]piperidin-1-yl} (morpholin-4-yl)methanone [enantiomerically pure cis isomer]

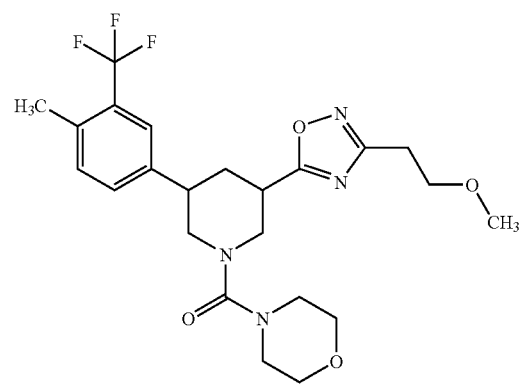

The enantiomer separation of 100 mg of the racemate from Example 416 according to Method 13D gave 41 mg of the title compound from Example 458 and 41 mg of the title compound from Example 459.

HPLC (Method 10E): $R_t$=9.83 min, >99.0% ee; LC-MS (Method 2B): $R_t$=1.16 min; MS (ESIpos): m/z=455 [M+H]$^+$.

$[\alpha]_{365}^{20}$=+16.7, methanol

Example 460

(4-Hydroxypiperidin-1-yl){3-[3-(2-methoxyethyl)-1,2,4-oxadiazol-5-yl]-5-[4-methyl-3-(trifluoro-methyl)phenyl]piperidin-1-yl}methanone [enantiomerically pure cis isomer]

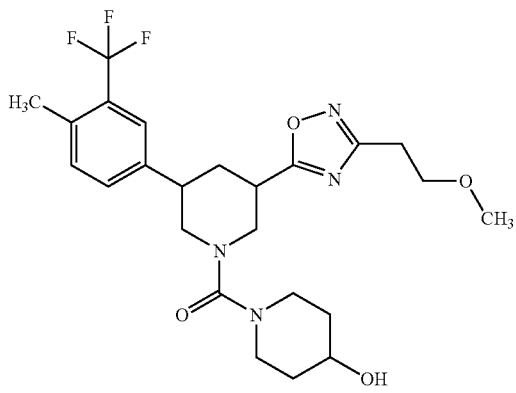

The enantiomer separation of 100 mg (0.20 mmol) of the racemate from Example 417 according to Method 11D gave 47 mg of the title compound from Example 460 (Enantiomer 1) and 46 mg of the title compound from Example 461 (Enantiomer 2).

HPLC (Method 10E): $R_t$=6.89 min, >99.0% ee; LC-MS (Method 2B): $R_t$=1.16 min; MS (ESIpos): m/z=455 [M+H]$^+$.

Example 461

(4-Hydroxypiperidin-1-yl){3-[3-(2-methoxyethyl)-1,2,4-oxadiazol-5-yl]-5-[4-methyl-3-(trifluoro-methyl)phenyl]piperidin-1-yl}methanone [enantiomerically pure cis isomer]

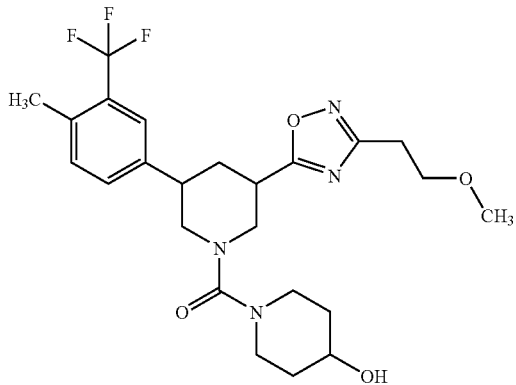

The enantiomer separation of 100 mg (0.20 mmol) of the racemate from Example 417 according to Method 11D gave 47 mg of the title compound from Example 460 (Enantiomer 1) and 46 mg of the title compound from Example 461 (Enantiomer 2).

HPLC (Method 10E): $R_t$=24.50 min, >99.0% ee; LC-MS (Method 2B): $R_t$=1.16 min; MS (ESIpos): m/z=455 [M+H]$^+$.

Example 462

(2,2-Dimethylmorpholin-4-yl){3-(3-methyl-1,2,4-oxadiazol-5-yl)-5-[4-(trifluoromethyl)phenyl]-piperidin-1-yl}methanone [racemic cis isomer]

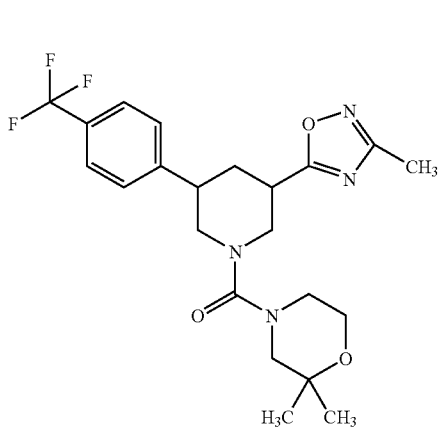

250 mg (0.410 mmol, 68% pure) of 1-[(2,2-dimethylmorpholin-4-yl)carbonyl]-5-[4-(trifluoromethyl)phenyl]piperidine-3-carboxylic acid and 33.4 mg (0.451 mmol) of N'-hydroxyethanimidamide were reacted according to the General Method 2. Yield: 117 mg (62% of theory).

LC-MS (Method 2B): $R_t$=1.31 min; MS (ESIpos): m/z=453 [M+H]$^+$;

$^1$H-NMR (400 MHz, DMSO-$d_6$): δ=7.71 (d, 2H), 7.57 (d, 2H), 3.99 (br d, 1H), 3.68-3.57 (m, 3H), 3.41 (tt, 1H), 3.19-3.11 (m, 2H), 3.10-2.96 (m, 5H), 2.38-2.30 (m, 4H), 2.04 (dd, 1H), 1.14 (s, 6H).

Example 463

Morpholin-4-yl{3-[5-(pyrrolidin-2-yl)-1,2,4-oxadiazol-3-yl]-5-[4-(trifluoromethyl)phenyl]-piperidin-1-yl}methanone hydrochloride [racemic cis isomer]

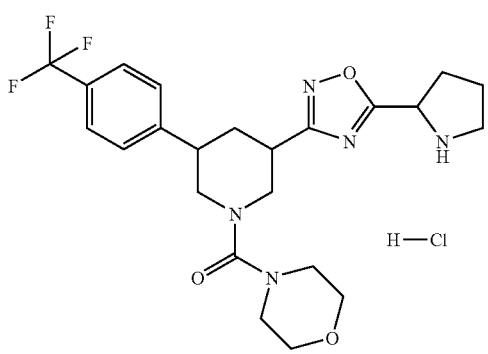

0.36 ml (1.46 mmol) of a 4N solution of hydrogen chloride in dioxane was added to a solution of 84 mg (0.146 mmol) of the compound from Example 91A in 0.7 ml of dioxane, and the mixture was stirred at room temperature for 20 hours. The reaction mixture was then concentrated under reduced pres-

Example 464

{3-[5-(Azetidin-3-yl)-1,2,4-oxadiazol-3-yl]-5-[4-(trifluoromethyl)phenyl]piperidin-1-yl}-(morpholin-4-yl)methanone hydrochloride [racemic cis isomer]

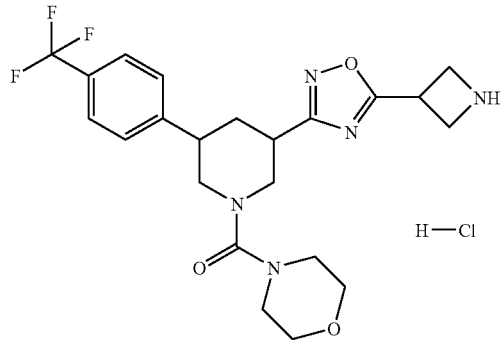

0.30 ml (1.16 mmol) of a 4N solution of hydrogen chloride in dioxane was added to a solution of 67 mg (0.117 mmol) of the compound from Example 92A in 0.6 ml of dioxane. The reaction mixture was stirred at room temperature for 20 hours. The mixture was concentrated using a rotary evaporator and once more taken up in 0.6 ml of dioxane, and 0.3 ml (1.16 mmol) of a 4N solution of hydrogen chloride in dioxane was added. The reaction mixture was stirred at room temperature overnight and then concentrated to dryness under reduced pressure and dried until the weight remained constant. Yield: 58 mg (100% of theory).

LC-MS (Method 1B): $R_t$=1.44 min; MS (ESIpos): m/z=466 [M+H—HCl]$^+$.

Example 465

{3-[5-(Methoxymethyl)-1,2,4-oxadiazol-3-yl]-5-[4-(trifluoromethyl)phenyl]piperidin-1-yl}-(morpholin-4-yl)methanone

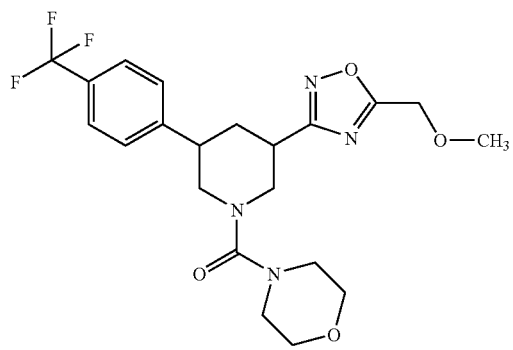

38 mg (0.425 mmol) of 2-methoxyethanoic acid and 100 mg (about 0.212 mmol) of the compound from Example 84A were reacted according to the General Method 2. Yield: 16 mg (17% of theory).

LC-MS (Method 2B): $R_t$=1.22 min; MS (ESIpos): m/z=455 [M+H]$^+$;

$^1$H-NMR (400 MHz, DMSO-d$_6$): δ=7.70 (d, 2H), 7.57 (d, 2H), 4.74 (s, 2H), 3.96 (brd, 1H), 3.66 (d, 1H), 3.58-3.54 (m, 4H), 3.28 (s, 3H), 3.27-3.16 (m, 5H), 3.09-2.97 (m, 3H), 2.27 (br d, 1H), 1.96 (q, 1H).

Example 466

Morpholin-4-yl{3-[5-(pyrazin-2-yl)-1,2,4-oxadiazol-3-yl]-5-[4-(trifluoromethyl)phenyl]piperidin-1-yl}methanone [enantiomerically pure cis isomer]

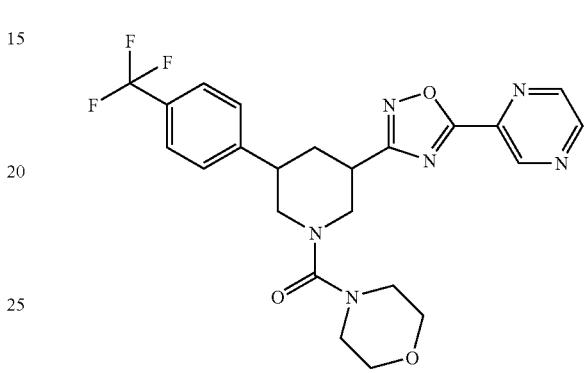

63 mg (0.509 mmol) of pyrazine-2-carboxylic acid and 200 mg (about 0.425 mmol) of the compound from Example 84A were reacted according to the General Method 1. Enantiomer separation of 38 mg of the racemate according to Method 14D gave 10 mg of the title compound from Example 466 and 10 mg of the title compound from Example 467.

HPLC (Method 11E): $R_t$=5.48 min, >99% ee; LC-MS (Method 1B): $R_t$=2.32 min; MS (ESIpos): m/z=489 [M+H]$^+$;

$^1$H-NMR (400 MHz, DMSO-d$_6$): δ=9.41 (d, 1H), 8.95 (d, 1H), 8.91 (dd, 1H), 7.71 (d, 2H), 7.60 (d, 2H), 4.06 (br d, 1H), 3.66 (d, 1H), 3.60-3.56 (m, 4H), 3.35 (tt, 1H), 3.24-3.19 (m, 4H), 3.14-2.99 (m, 3H), 2.38 (br d, 1H), 2.06 (q, 1H).

Example 467

Morpholin-4-yl{3-[5-(pyrazin-2-yl)-1,2,4-oxadiazol-3-yl]-5-[4-(trifluoromethyl)phenyl]piperidin-1-yl}methanone [enantiomerically pure cis isomer]

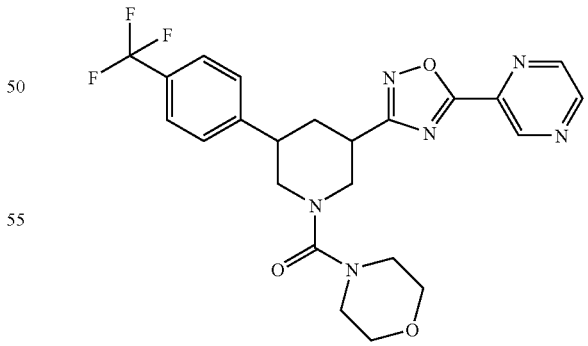

63 mg (0.509 mmol) of pyrazine-2-carboxylic acid and 200 mg (about 0.425 mmol) of the compound from Example 84A were reacted according to the General Method 1.

Enantiomer separation of 38 mg of the racemate according to Method 14D gave 10 mg of the title compound from Example 466 and 10 mg of the title compound from Example 467.

HPLC (Method 11E): $R_t$=10.62 min, >99% ee; LC-MS (Method 1B): $R_t$=2.32 min; MS (ESIpos): m/z=489 [M+H]$^+$;
$^1$H-NMR (400 MHz, DMSO-$d_6$): δ=9.41 (d, 1H), 8.95 (d, 1H), 8.91 (dd, 1H), 7.71 (d, 2H), 7.60 (d, 2H), 4.06 (br d, 1H), 3.66 (d, 1H), 3.60-3.56 (m, 4H), 3.35 (tt, 1H), 3.24-3.19 (m, 4H), 3.14-2.99 (m, 3H), 2.38 (br d, 1H), 2.06 (q, 1H).

Example 468

Morpholin-4-yl{3-[5-(propan-2-yl)-1,3,4-oxadiazol-2-yl]-5-[4-(trifluoromethoxy)phenyl]piperidin-1-yl}methanone [racemic cis isomer]

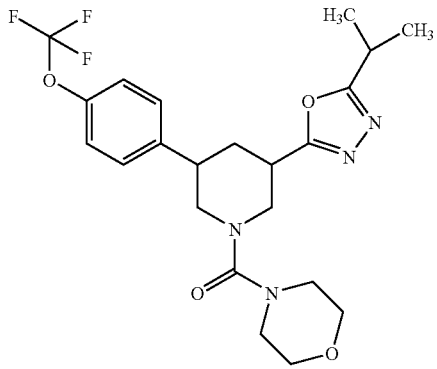

100 mg the compound from Example 44A and 28 mg (0.273 mmol) of 2-methylpropanehydrazide were reacted according to the General Method 4. Yield: 45 mg (39% of theory).
LC-MS (Method 1B): $R_t$=2.34 min; MS (ESIpos): m/z=469 [M+H]$^+$;
$^1$H-NMR (400 MHz, DMSO-$d_6$): δ=7.47 (d, 2H), 7.33 (d, 2H), 4.98 (br d, 1H), 3.61 (d, 1H), 3.60-3.53 (m, 4H), 3.22-3.13 (m, 5H), 3.03-2.96 (m, 3H), 2.28 (br d, 1H), 1.92 (q, 1H), 1.28 (d, 6H).

Example 469

Ethyl (5-{1-(morpholin-4-ylcarbonyl)-5-[4-(trifluoromethoxy)phenyl]piperidin-3-yl}-1,3,4-oxadiazol-2-yl)acetate [racemic cis isomer]

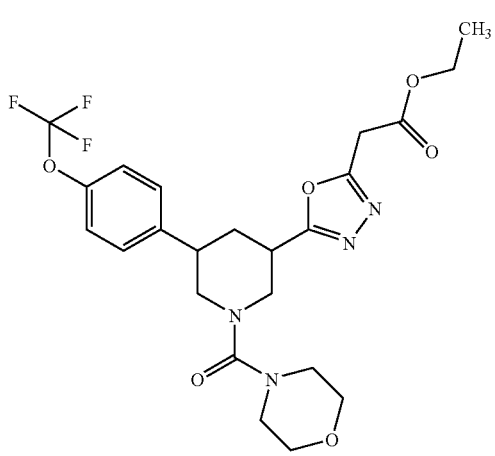

100 mg (0.249 mmol) of the compound from Example 44A and 40 mg (0.273 mmol) of ethyl 3-hydrazinyl-3-oxopropanoate were reacted according to the General Method 4. Yield: 9 mg (6% of theory).

LC-MS (Method 3B): $R_t$=1.95 min; MS (ESIpos): m/z=513 [M+H]$^+$;
$^1$H-NMR (400 MHz, DMSO-$d_6$): δ=7.47 (d, 2H), 7.33 (d, 2H), 4.16 (s, 2H), 4.13 (q, 2H), 3.98 (br d, 1H), 3.61 (d, 1H), 3.58-3.54 (m, 4H), 3.21-3.15 (m, 4H), 3.04-2.94 (m, 3H), 2.29 (br d, 1H), 1.94 (q, 1H), 1.19 (t, 3H).

Example 470

{3-{5-[(Dimethylamino)methyl]-1,3,4-oxadiazol-2-yl}-5-[4-(trifluoromethoxy)phenyl]piperidin-1-yl}(morpholin-4-yl)methanone [racemic cis isomer]

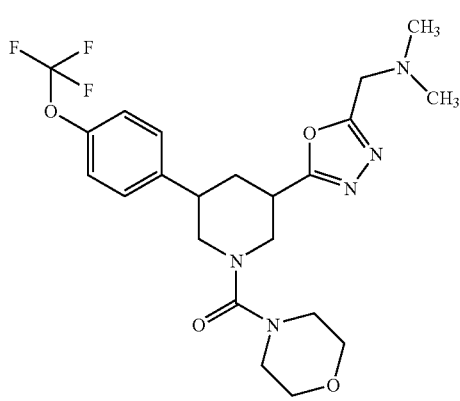

100 mg (0.249 mmol) of the compound from Example 44A and 42 mg (0.275 mmol) of 2-(dimethylamino)acetohydrazide were reacted according to the General Method 4. Yield: 13 mg (11% of theory).
LC-MS (Method 2B): $R_t$=0.93 min; MS (ESIpos): m/z=484 [M+H]$^+$.

Example 471

{3-[5-(4-Fluorophenyl)-1,3,4-oxadiazol-2-yl]-5-[4-(trifluoromethyl)phenyl]piperidin-1-yl}-(morpholin-4-yl)methanone [racemic cis isomer]

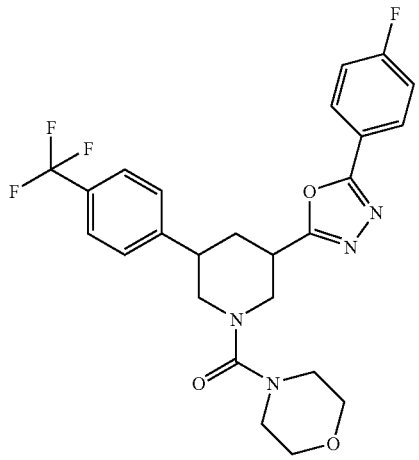

200 mg (0.518 mmol) of the compound from Example 49A and 87 mg (0.569 mmol) of 4-fluorobenzylhydrazide were reacted according to the General Method 4. Yield: 9 mg (3% of theory).

LC-MS (Method 2B): $R_t$=1.34 min; MS (ESIpos): m/z=505 [M+H]$^+$;
$^1$H-NMR (400 MHz, DMSO-d$_6$): δ=8.07 (dd, 2H), 7.73 (d, 2H), 7.60 (d, 2H), 7.45 (dd, 2H), 4.09 (br d, 1H), 3.67 (d, 1H), 3.60-3.56 (m, 4H), 3.43 (tt, 1H), 3.24-3.19 (m, 4H), 3.12 (t, 1H), 3.10-2.99 (m, 2H), 2.42 (br d, 1H), 2.07 (q, 1H).

Example 472

{3-[5-(3-Chlorophenyl)-1,3,4-oxadiazol-2-yl]-5-[4-(trifluoromethyl)phenyl]piperidin-1-yl}-(morpholin-4-yl)methanone [racemic cis isomer]

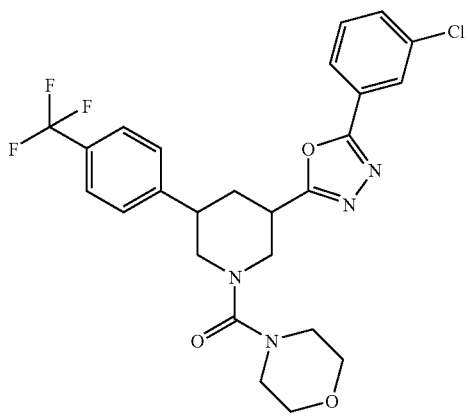

200 mg (0.518 mmol) of the compound from Example 49A and 97 mg (0.569 mmol) of 3-chlorobenzenecarbohydrazide were reacted according to the General Method 4. Yield: 13 mg (11% of theory).
LC-MS (Method 2B): $R_t$=1.42 min; MS (ESIpos): m/z=521 [M+H]$^+$.

Example 473

{3-[5-(3-Fluorophenyl)-1,3,4-oxadiazol-2-yl]-5-[4-(trifluoromethyl)phenyl]piperidin-1-yl}-(morpholin-4-yl)methanone [racemic cis isomer]

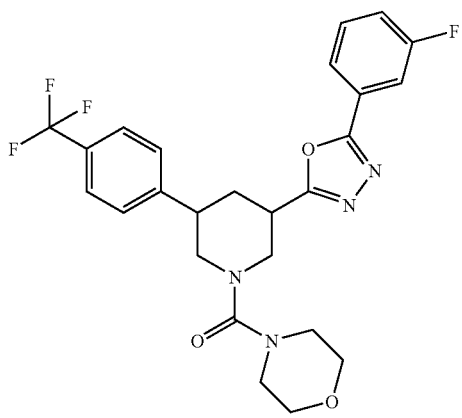

200 mg (0.518 mmol) of the compound from Example 49A and 87 mg (0.569 mmol) of 3-fluorobenzylhydrazide were reacted according to the General Method 4. Yield: 14 mg (5% of theory).

LC-MS (Method 5B): $R_t$=2.41 min; MS (ESIpos): m/z=505 [M+H]$^+$;
$^1$H-NMR (400 MHz, DMSO-d$_6$): δ=7.87 (d, 1H), 7.81 (d, 1H), 7.71 (d, 2H), 7.66 (dd, 1H), 7.60 (d, 2H), 7.50 (td, 1H), 4.09 (br d, 1H), 3.67 (d, 1H), 3.62-3.56 (m, 4H), 3.44 (tt, 1H), 3.28-3.20 (m, 4H), 3.13 (t, 1H), 3.10-3.01 (m, 2H), 2.43 (br d, 1H), 2.08 (q, 1H).

Example 474

{3-[5-(2-Methylpropyl)-1,3,4-oxadiazol-2-yl]-5-[4-(trifluoromethoxy)phenyl]piperidin-1-yl}-(morpholin-4-yl)methanone [racemic cis isomer]

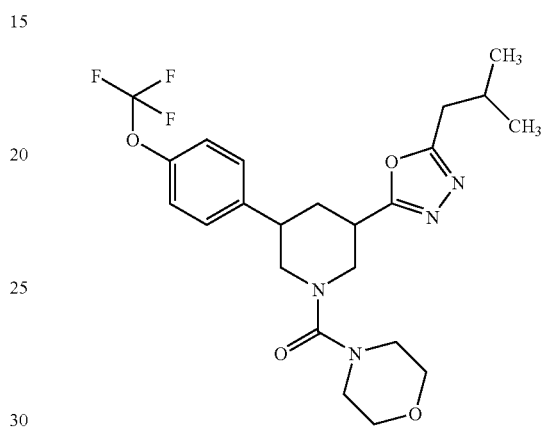

100 mg (0.249 mmol) of the compound from Example 44A and 32 mg (0.273 mmol) of 3-methylbutanehydrazide were reacted according to the General Method 4. Diastereomer separation of the cis/trans isomer mixture according to Method 14C gave 44 mg of the title compound (cis isomer) and 12 mg of the trans isomer.
LC-MS (Method 1B): $R_t$=2.48 min; MS (ESIpos): m/z=483 [M+H]$^+$;
$^1$H-NMR (400 MHz, DMSO-d$_6$): δ=7.47 (d, 2H), 7.33 (d, 2H), 3.98 (br d, 1H), 3.61 (d, 1H), 3.59-3.53 (m, 4H), 3.21-3.18 (m, 4H), 3.03-2.96 (m, 3H), 2.71 (d, 2H), 2.28 (br d, 1H), 2.08-1.98 (m, 1H), 1.93 (q, 1H), 0.93 (d, 6H).

Example 475

Morpholin-4-yl{3-{4-[(propan-2-ylsulphanyl)methyl]-1,3-thiazol-2-yl}-5-[4-(trifluoromethyl)-phenyl]piperidin-1-yl}methanone [racemic cis isomer]

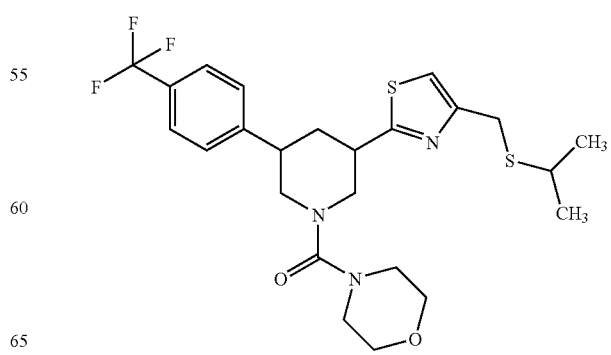

115 mg (0.352 mmol) of caesium carbonate and 34 μl (0.352 mmol) of propane-2-thiol were added to a solution of 138 mg (about 0.293 mmol) of the compound from Example 214A in 2.6 ml of dioxane. The reaction mixture was stirred at 70° C. overnight. Without any further work-up, the mixture was purified by preparative HPLC. Yield: 43 mg (28% of theory).

LC-MS (Method 2B): $R_t$=1.48 min; MS (ESIpos): m/z=514 [M+H]$^+$;

$^1$H-NMR (400 MHz, DMSO-d$_6$): δ=7.70 (d, 2H), 7.58 (d, 2H), 7.39 (s, 1H), 3.98 (brd, 1H), 3.84 (s, 2H), 3.65 (d, 1H), 3.58-3.54 (m, 4H), 3.40-3.33 (m, 1H), 3.24-3.16 (m, 4H), 3.08-2.89 (m, 4H), 2.31 (brd, 1H), 1.97 (q, 1H), 1.20 (d, 6H).

Example 476

Morpholin-4-yl{3-{4-[(pyridin-4-ylsulphanyl)methyl]-1,3-thiazol-2-yl}-5-[4-(trifluoromethyl)-phenyl]piperidin-1-yl}methanone [racemic cis isomer]

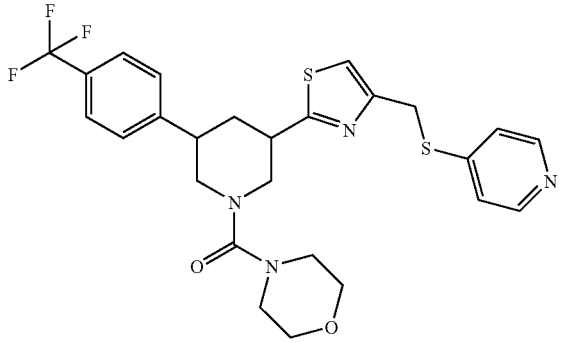

114 mg (0.349 mmol) of caesium carbonate and 39 mg (0.349 mmol) of 4-mercaptopyridine were added to a solution of 138 mg (0.291 mmol) of the compound from Example 214A in 2.4 ml of dioxane. The reaction mixture was stirred at 70° C. overnight. Without any further work-up, the mixture was purified by preparative HPLC. Yield: 20 mg (13% of theory).

LC-MS (Method 2B): $R_t$=1.79 min; MS (ESIpos): m/z=549 [M+H]$^+$;

$^1$H-NMR (400 MHz, DMSO-d$_6$): δ=8.36 (dd, 2H), 7.70 (d, 2H), 7.58 (d, 2H), 7.55 (s, 1H), 7.37 (d, 2H), 4.45 (s, 2H), 3.96 (brd, 1H), 3.65 (d, 1H), 3.57-3.53 (m, 4H), 3.36 (tt, 1H), 3.21-3.16 (m, 4H), 3.06-2.95 (m, 3H), 2.30 (brd, 1H), 1.97 (q, 1H).

Example 477

{3-[4-(3-Fluorophenyl)-1,3-thiazol-2-yl]-5-[4-(trifluoromethyl)phenyl]piperidin-1-yl}(morpholin-4-yl)methanone [racemic cis isomer]

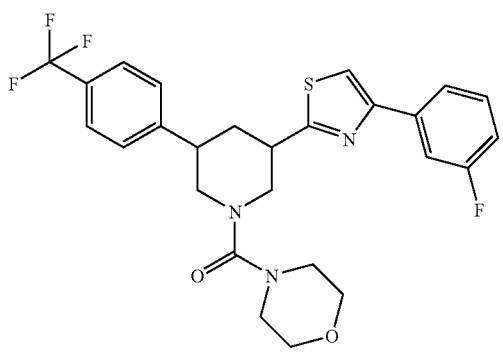

250 mg (about 0.211 mmol) of the compound from Example 53A and 154 mg (0.710 mmol) of 1-bromo-3,3-dimethylbutan-2-one were reacted according to the General Method 3. Yield: 88 mg (29% of theory).

LC-MS (Method 3B): $R_t$=2.58 min; MS (ESIpos): m/z=520 [M+H]$^+$;

$^1$H-NMR (400 MHz, DMSO-d$_6$): δ=8.18 (s, 1H), 7.82 (d, 1H), 7.77 (d, 1H), 7.72 (d, 2H), 7.61 (d, 2H), 7.49 (dd, 1H), 7.18 (td, 1H), 4.07 (br d, 1H), 3.68 (d, 1H), 3.61-3.56 (m, 4H), 3.44 (tt, 1H), 3.23-3.19 (m, 4H), 3.11-3.03 (m, 3H), 2.38 (br d, 1H), 2.06 (q, 1H).

Example 478

{3-{4-[(1H-Imidazol-2-ylsulphanyl)methyl]-1,3-thiazol-2-yl}-5-[4-(trifluoromethyl)phenyl]piperidin-1-yl}(morpholin-4-yl)methanone [racemic cis isomer]

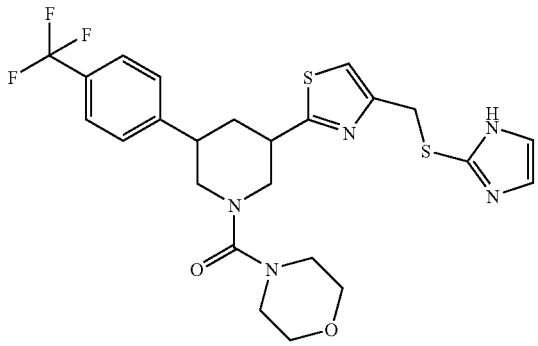

115 mg (0.352 mmol) of caesium carbonate and 42 μl (0.442 mmol) of 1-H-imidazole-2-thiol were added to a solution of 139 mg (0.293 mmol) of the compound from Example 214A in 2.4 ml of dioxane. The reaction mixture was stirred at 70° C. for 4 hours. Diastereomer separation of 123 mg of the cis/trans isomer mixture according to Method 13C gave 40 mg of the title compound (cis isomer) and 21 mg of the trans isomer.

LC-MS (Method 2B): $R_t$=1.01 min; MS (ESIpos): m/z=538 [M+H]$^+$;

$^1$H-NMR (400 MHz, DMSO-d$_6$): δ=7.71 (d, 2H), 7.57 (d, 2H), 7.33 (s, 1H), 7.23 (br s, 2H), 4.37 (s, 2H), 3.93 (brd, 1H), 3.65 (d, 1H), 3.57-3.54 (m, 4H), 3.21-3.18 (m, 4H), 3.08-2.91 (m, 3H), 2.28 (brd, 1H), 1.93 (q, 1H).

Example 479

{3-[4-(2-Methylpropyl)-1,3-thiazol-2-yl]-5-[4-(trifluoromethyl)phenyl]piperidin-1-yl}(morpholin-4-yl)methanone [racemic cis isomer]

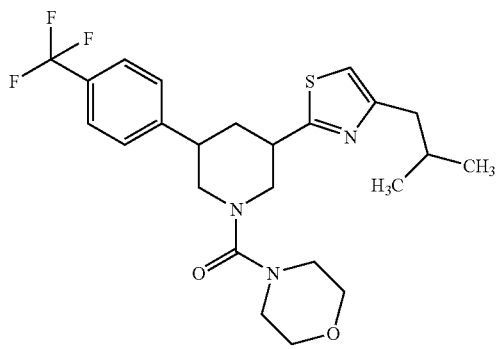

150 mg (about 0.315 mmol) of the compound from Example 53A and 76 mg (0.426 mmol) of 1-bromo-4-methylpentan-2-one (J. Org. Chem., 19, 2005, 4141-4153) were reacted according to the General Method 3. Yield: 68 mg (40% of theory).

LC-MS (Method 2B): R$_t$=1.52 min; MS (ESIpos): m/z=482 [M+H]$^+$;

$^1$H-NMR (400 MHz, DMSO-d$_6$): δ=7.70 (d, 2H), 7.58 (d, 2H), 7.17 (s, 1H), 3.97 (brd, 1H), 3.65 (d, 1H), 3.59-3.53 (m, 4H), 3.22-3.17 (m, 4H), 3.05-2.94 (m, 3H), 2.30 (brd, 1H), 2.06-1.87 (m, 2H), 0.88 (6H).

Example 480

{3-(4-Ethyl-1,3-thiazol-2-yl)-5-[4-(trifluoromethyl)phenyl]piperidin-1-yl}(morpholin-4-yl)methanone [racemic cis isomer]

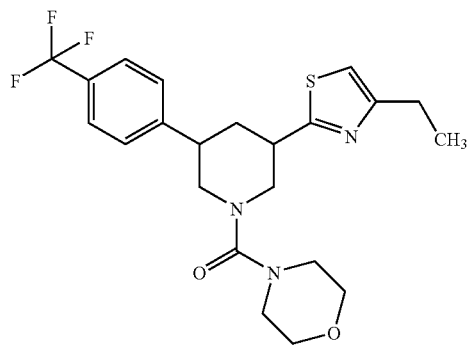

220 mg (about 0.384 mmol) of the compound from Example 53A and 70 mg (0.460 mmol) of 1-bromobutan-2-one were reacted according to the General Method 3. Yield: 63 mg (36% of theory).

LC-MS (Method 2B): R$_t$=1.39 min; MS (ESIpos): m/z=454 [M+H]$^+$;

$^1$H-NMR (400 MHz, DMSO-d$_6$): δ=7.70 (d, 2H), 7.58 (d, 2H), 7.17 (s, 1H), 3.96 (brd, 1H), 3.65 (d, 1H), 3.58-3.54 (m, 4H), 3.21-3.17 (m, 4H), 3.12-2.95 (m, 4H), 2.70 (q, 2H), 2.30 (brd, 1H), 1.97 (q, 1H), 1.21 (t, 3H).

Example 481

[3-{4-[(Cyclopropylamino)methyl]-1,3-thiazol-2-yl}-5-(4-ethylphenyl)piperidin-1-yl](morpholin-4-yl)methanone [racemic cis isomer]

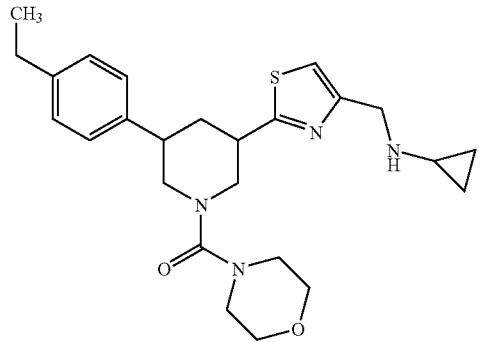

24 mg (0.411 mmol) of cyclopropylamine and 70 mg (0.685 mmol) of triethylamine were added to a solution of 119 mg (0.274 mmol) of the compound from Example 141A in 2 ml of N-methylpyrrolidone. The reaction mixture was stirred at 80° C. overnight. Diastereomer separation of 13 mg of the cis/trans isomer mixture according to Method 15C gave 5 mg of the title compound.

LC-MS (Method 1B): R$_t$=1.51 min; MS (ESIpos): m/z=455 [M+H]$^+$;

$^1$H-NMR (400 MHz, DMSO-d$_6$): δ=7.74 (s, 1H), 7.23 (d, 2H), 7.18 (d, 2H), 4.36 (br s, 2H), 4.02 (br d, 1H), 3.62 (d, 1H), 3.58-3.53 (m, 4H), 3.40 (tt, 1H), 3.23-3.18 (m, 4H), 3.02-2.87 (m, 3H), 2.74 (br s, 1H), 2.57 (q, 2H), 2.28 (br d, 1H), 1.95 (q, 1H), 1.16 (t, 3H), 0.80-0.72 (m, 4H).

Example 482

[3-(4-Ethylphenyl)-5-{4-[(propan-2-ylamino)methyl]-1,3-thiazol-2-yl}piperidin-1-yl](morpholin-4-yl)methanone [racemic cis isomer]

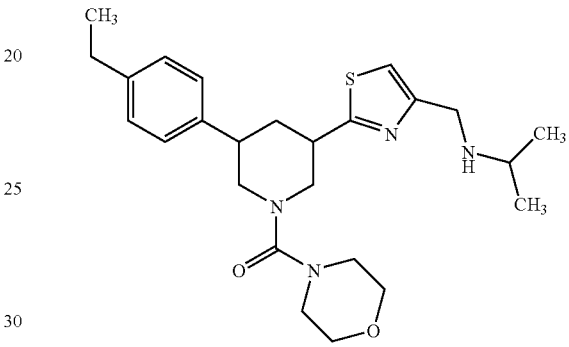

24 mg (0.411 mmol) of isopropylamine and 70 mg (0.685 mmol) of triethylamine were added to a solution of 119 mg (0.274 mmol) of the compound from Example 141A in 2 ml of N-methylpyrrolidone. The reaction mixture was stirred at 80° C. overnight and, without any further work-up, purified by preparative HPLC. Yield: 10 mg (8% of theory)

LC-MS (Method 3B): R$_t$=1.27 min; MS (ESIpos): m/z=457 [M+H]$^+$;

$^1$H-NMR (400 MHz, DMSO-d$_6$): δ=7.30 (s, 1H), 7.23 (d, 2H), 7.17 (d, 2H), 3.97 (br d, 1H), 3.75 (s, 2H), 3.61 (d, 1H), 3.59-3.52 (m, 4H), 3.22-3.13 (m, 4H), 2.97-2.85 (m, 3H), 2.75-2.71 (m, 1H), 2.57 (q, 2H), 2.25 (d, 1H), 1.92 (q, 1H), 1.16 (t, 3H), 1.00 (d, 6H).

Example 483

2-[5-(4-Ethylphenyl)-1-(morpholin-4-ylcarbonyl)piperidin-3-yl]-N-(pyridin-4-yl)-1,3-thiazole-4-carboxamide [racemic cis isomer]

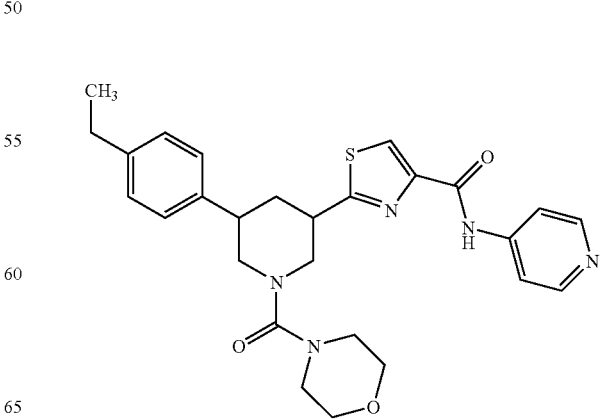

145 mg (0.279 mmol) of PYBOP and 169 mg (1.304 mmol) of N,N-diisopropylethylamine were added to a mixture of 80 mg (0.186 mmol) of the compound from Example 143A in 0.5 ml of THF. The reaction mixture was stirred at room temperature for 40 minutes. 21 mg (0.223 mmol) of 4-aminopyridine were then added, and stirring of the mixture at RT was continued overnight. For work-up, the solvent was evaporated and the residue was taken up in ethyl acetate. The organic phase was washed successively with water and saturated aqueous sodium chloride solution, dried over magnesium sulphate and concentrated. Diastereomer separation of the cis/trans isomer mixture according to Method 12C gave 14 mg of the title compound (cis isomer) and 23 mg of the trans isomer.

LC-MS (Method 3B): $R_t$=1.42 min; MS (ESIpos): m/z=506 [M+H]$^+$;

$^1$H-NMR (400 MHz, DMSO-d$_6$): δ=10.45 (s, 1H), 8.48 (d, 2H), 7.86 (d, 2H), 7.26 (d, 2H), 7.18 (d, 2H), 4.09 (br d, 1H), 3.63 (d, 1H), 3.59-3.55 (m, 4H), 3.48 (tt, 1H), 3.22-3.16 (m, 4H), 3.06 (t, 1H), 3.00 (t, 1H), 2.90 (t, 1H), 2.58 (q, 2H), 2.36 (br d, 1H), 2.03 (q, 1H), 1.17 (t, 3H).

Example 484

[3-(4-Ethylphenyl)-5-{4-[(ethylsulphanyl)methyl]-1,3-thiazol-2-yl}piperidin-1-yl](morpholin-4-yl)methanone [racemic cis isomer]

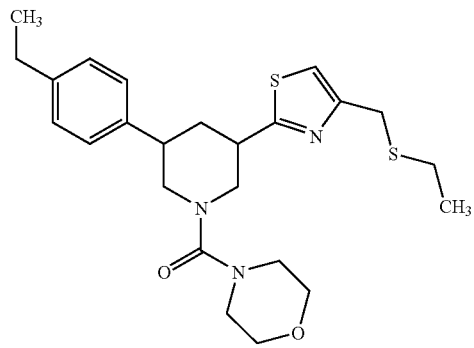

73 mg (0.221 mmol) of caesium carbonate and 36 μl (0.442 mmol) of ethanethiol were added to a solution of 100 mg (about 0.184 mmol) of the compound from Example 141A in 1.5 ml of dioxane. The reaction mixture was stirred at 70° C. for 4 hours. Without any further work-up, the mixture was purified by preparative HPLC. Yield: 40 mg (47% of theory).

LC-MS (Method 1B): $R_t$=2.71 min; MS (ESIpos): m/z=460 [M+H]$^+$;

$^1$H-NMR (400 MHz, DMSO-d$_6$): δ=7.38 (s, 1H), 7.23 (d, 2H), 7.17 (d, 2H), 4.98 (br d, 1H), 3.81 (s, 2H), 3.61 (d, 2H), 3.58-3.54 (m, 4H), 3.20-3.15 (m, 4H), 2.97-2.84 (m, 3H), 2.57 (q, 2H), 2.26 (br d, 1H), 1.91 (q, 1H), 1.17 (t, 3H), 1.16 (t, 3H).

Example 485

{3-[4-(2-Methylpropyl)-1,3-thiazol-2-yl]-5-[4-(trifluoromethoxy)phenyl]piperidin-1-yl}-(morpholin-4-yl)methanone [racemic cis isomer]

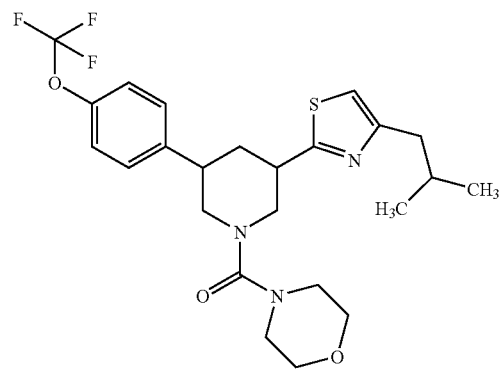

100 mg (about 0.182 mmol) of the compound from Example 115A and 49 mg (0.273 mmol) of 1-bromo-4-methylpentan-2-one (J. Org. Chem., 19, 2005, 4141-4153) were reacted according to the General Method 3. Yield: 50 mg (55% of theory).

LC-MS (Method 1B): $R_t$=2.92 min; MS (ESIpos): m/z=498 [M+H]$^+$;

$^1$H-NMR (400 MHz, DMSO-d$_6$): δ=7.48 (d, 2H), 7.32 (d, 2H), 7.17 (s, 1H), 3.97 (br d, 1H), 3.63 (d, 1H), 3.58-3.54 (m, 4H), 3.20-3.16 (m, 4H), 3.02-2.92 (m, 3H), 2.29 (br d, 1H), 2.02-1.87 (m, 2H), 0.88 (d, 6H).

Example 486

{3-(4-Cyclopropyl-1,3-thiazol-2-yl)-5-[4-(trifluoromethoxy)phenyl]piperidin-1-yl}(morpholin-4-yl)methanone [racemic cis isomer]

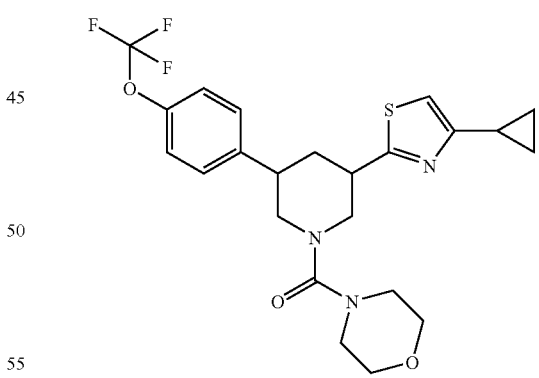

100 mg (about 0.182 mmol) of the compound from Example 115A and 44 mg (0.273 mmol) of 2-bromo-1-cyclopropylethanone (Tetrahedron, 43, 20 1987, 4609-4619) were reacted according to the General Method 3. Yield: 49 mg (56% of theory).

LC-MS (Method 1B): $R_t$=2.73 min; MS (ESIpos): m/z=482 [M+H]$^+$;

$^1$H-NMR (400 MHz, DMSO-d$_6$): δ=7.47 (d, 2H), 7.32 (d, 2H), 7.15 (s, 1H), 3.94 (br d, 1H), 3.63 (d, 1H), 3.58-3.54 (m, 4H), 3.28 (tt, 1H), 3.20-3.16 (m, 4H), 2.99-2.89 (m, 3H), 2.26 (br d, 1H), 2.08-2.01 (m, 1H), 1.90 (q, 1H), 0.90-0.85 (m, 2H), 0.79-0.76 (m, 2H).

Example 487

{3-(4-tert-Butyl-1,3-thiazol-2-yl)-5-[4-(trifluoromethoxy)phenyl]piperidin-1-yl}(morpholin-4-yl)-methanone [racemic cis isomer]

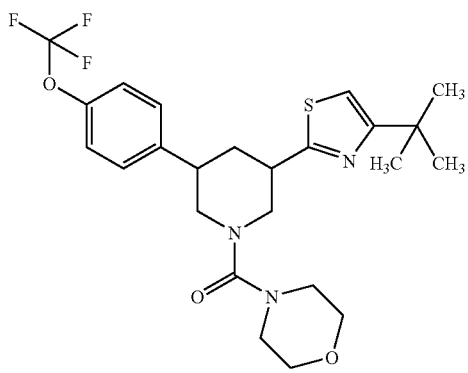

100 mg (about 0.182 mmol) of the compound from Example 115A and 49 mg (0.273 mmol) of 1-bromo-3,3-dimethylbutan-2-one were reacted according to the General Method 3. Yield: 56 mg (59% of theory).

LC-MS (Method 1B): $R_t$=3.0 min; MS (ESIpos): m/z=498 [M+H]$^+$;

$^1$H-NMR (400 MHz, DMSO-d$_6$): δ=7.48 (d, 2H), 7.33 (d, 2H), 7.16 (s, 1H), 4.00 (br d, 1H), 3.63 (d, 1H), 3.58-3.54 (m, 4H), 3.20-3.18 (m, 4H), 3.01-2.91 (m, 3H), 2.31 (br d, 1H), 1.91 (q, 1H), 1.28 (s, 9H).

Example 488

{3-[4-(3-Fluorophenyl)-1,3-thiazol-2-yl]-5-[4-(trifluoromethoxy)phenyl]piperidin-1-yl}-(morpholin-4-yl)methanone [racemic cis isomer]

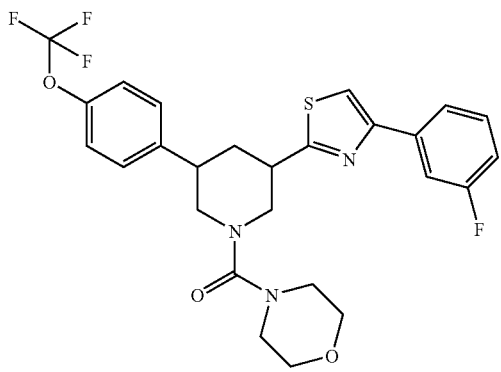

100 mg (about 0.211 mmol) of the compound from Example 115A and 55 mg (0.253 mmol) of 2-bromo-1-(3-fluorophenyl)ethanone were reacted according to the General Method 3. Yield: 78 mg (69% of theory).

LC-MS (Method 2B): $R_t$=1.57 min; MS (ESIpos): m/z=536 [M+H]$^+$;

$^1$H-NMR (400 MHz, DMSO-d$_6$): δ=8.17 (s, 1H), 7.82 (d, 1H), 7.75 (d, 1H), 7.52-7.46 (m, 3H), 7.35-7.33 (d, 2H), 7.17 (td, 1H), 4.06 (br d, 1H), 3.65 (d, 1H), 3.60-3.56 (m, 4H), 3.43 (tt, 1H), 3.23-3.20 (m, 4H), 3.08-3.00 (m 3H), 2.36 (br d, 1H), 2.03 (q, 1H).

Example 489

{3-(4-Methyl-1,3-thiazol-2-yl)-5-[4-(trifluoromethoxy)phenyl]piperidin-1-yl}(morpholin-4-yl)-methanone [racemic cis isomer]

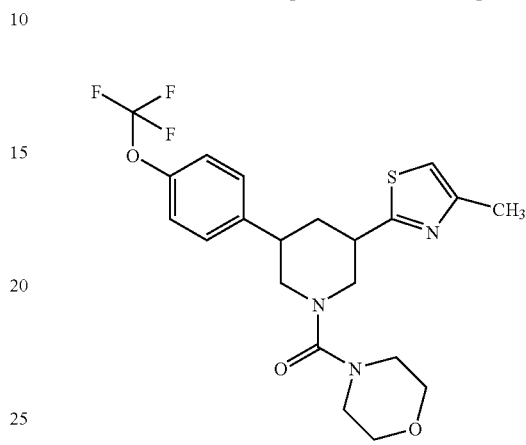

100 mg (about 0.182 mmol) of the compound from Example 115A and 25 mg (0.273 mmol) of 1-chloropropan-2-one were reacted according to the General Method 3. Yield: 40 mg (44% of theory).

LC-MS (Method 2B): $R_t$=2.48 min; MS (ESIpos): m/z=455 [M+H]$^+$;

$^1$H-NMR (400 MHz, DMSO-d$_6$): δ=7.47 (d, 2H), 7.32 (d, 2H), 7.17 (s, 1H), 3.95 (br d, 1H), 3.63 (d, 1H), 3.58-3.54 (m, 4H), 3.20-3.16 (m, 4H), 2.99-2.93 (m 3H), 2.37 (s, 3H), 2.27 (br d, 1H), 1.95 (q, 1H).

Example 490

{3-(4-Ethyl-1,3-thiazol-2-yl)-5-[4-(trifluoromethoxy)phenyl]piperidin-1-yl}(morpholin-4-yl)-methanone [racemic cis isomer]

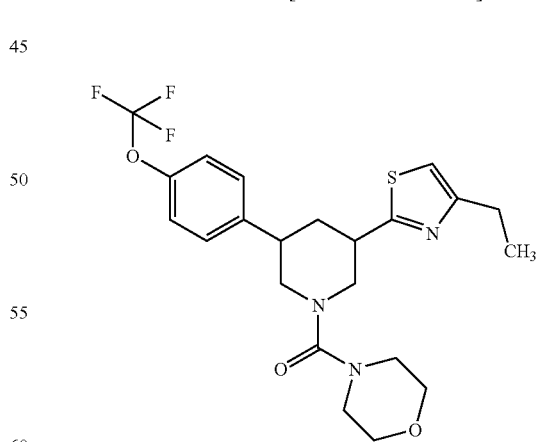

100 mg (about 0.211 mmol) of the compound from Example 115A and 38 mg (0.253 mmol) of 1-bromobutan-2-one were reacted according to the General Method 3. Yield: 49 mg (47% of theory).

LC-MS (Method 2B): $R_t$=1.42 min; MS (ESIpos): m/z=470 [M+H]$^+$;

¹H-NMR (400 MHz, DMSO-d₆): δ=7.48 (d, 2H), 7.32 (d, 2H), 7.17 (s, 1H), 3.63 (br d, 1H), 3.57-3.53 (m, 4H), 3.21-3.15 (m, 4H), 2.99-2.93 (m, 3H), 2.70 (q, 2H), 2.27 (br d, 1H), 1.93 (q, 1H), 1.21 (t, 3H).

Example 491

1-({3-(4-tert-Butyl-1,3-thiazol-2-yl)-5-[4-(trifluoromethoxy)phenyl]piperidin-1-yl}carbonyl)-piperidine-4-carbonitrile [racemic cis isomer]

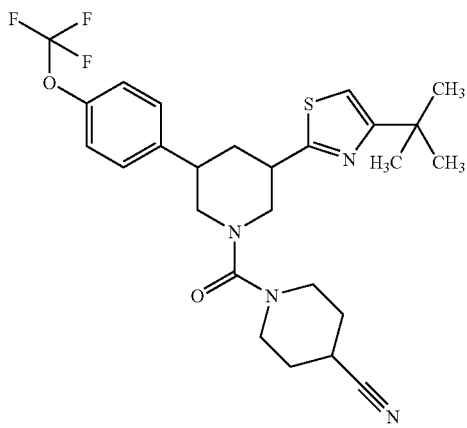

200 mg (about 0.204 mmol) of the compound from Example 117A and 55 mg (0.300 mmol) of 1-bromo-3,3-dimethylbutan-2-one were reacted according to the General Method 3. Yield: 43 mg (40% of theory).

LC-MS (Method 2B): R$_t$=1.64 min; MS (ESIpos): m/z=521 [M+H]⁺;

¹H-NMR (400 MHz, DMSO-d₆): δ=7.48 (d, 2H), 7.33 (d, 2H), 7.15 (s, 1H), 3.97 (br d, 1H), 3.60 (d, 1H), 3.09-2.87 (m, 5H), 2.71 (s, 1H), 2.33 (br d, 1H), 1.98-1.87 (m, 2H), 1.72-1.64 (m, 1H), 1.28 (s, 9H).

Example 492

{3-[5-(2-Methoxyethyl)-1,3,4-thiadiazol-2-yl]-5-[4-(trifluoromethoxy)phenyl]piperidin-1-yl}-(morpholin-4-yl)methanone [racemic cis isomer]

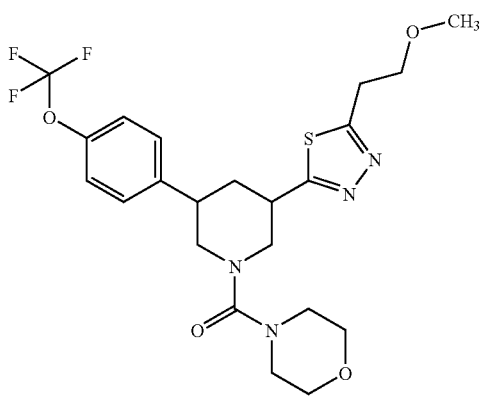

93 mg (0.185 mmol) of the compound from Example 120A and 150 mg (0.371 mmol) of Lawesson reagent were reacted according to the General Method 9. Yield: 9 mg (10% of theory)

LC-MS (Method 2B): R$_t$=1.21 min; MS (ESIpos): m/z=501 [M+H]⁺;

¹H-NMR (400 MHz, DMSO-d₆): δ=7.48 (d, 2H), 7.33 (d, 2H), 3.97 (br d, 1H); 3.66-3.47 (m, 8H), 3.27 (s, 3H), 3.20-3.18 8 (m, 4H), 3.08-2.99 (m, 3H), 2.30 (br d, 1H), 1.98 (q, 1H).

Example 493

{3-(5-Methyl-1,3,4-thiadiazol-2-yl)-5-[4-(trifluoromethoxy)phenyl]piperidin-1-yl}(morpholin-4-yl)methanone [racemic cis isomer]

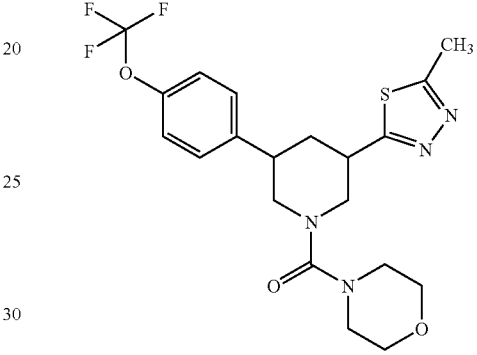

106 mg (0.231 mmol) of the compound from Example 121A and 187 mg (0.462 mmol) of Lawesson reagent were reacted according to the General Method 9. Yield: 10 mg (10% of theory)

LC-MS (Method 2B): R$_t$=1.18 min; MS (ESIpos): m/z=457 [M+H]⁺;

¹H-NMR (400 MHz, DMSO-d₆): δ=7.47 (d, 2H), 7.33 (d, 2H), 3.97 (br d, 1H); 3.67-3.45 (m, 6H), 3.20-3.18 (m, 4H), 3.09-2.96 (m, 3H), 2.70 (s, 3H), 2.28 (br d, 1H), 1.97 (q, 1H).

Example 494

Morpholin-4-yl{3-[5-(propan-2-yl)-1,3,4-thiadiazol-2-yl]-5-[4-(trifluoromethoxy)phenyl]piperidin-1-yl}methanone [racemic cis isomer]

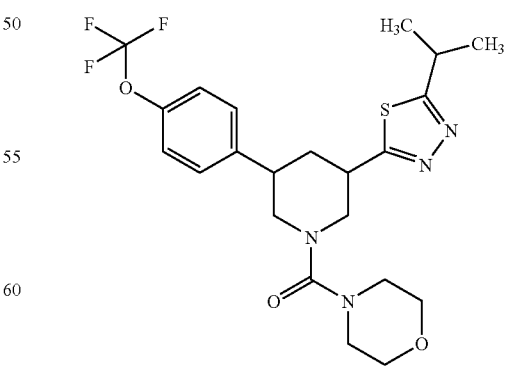

79 mg (0.155 mmol) of the compound from Example 122A and 126 mg (0.310 mmol) of Lawesson reagent were reacted according to the General Method 9. Yield: 17 mg (22% of theory)

LC-MS (Method 2B): $R_t$=1.32 min; MS (ESIpos): m/z=485 [M+H]$^+$;

$^1$H-NMR (400 MHz, DMSO-d$_6$): δ=7.47 (d, 2H), 7.33 (d, 2H), 3.98 (br d, 1H); 3.64 (d, 2H), 3.58-3.54 (m, 3H), 3.50 (tt, 1H), 3.45-3.38 (m, 1H), 3.20-3.18 (m, 4H), 3.07-2.95 (m, 3H), 2.30 (d, 1H), 1.98 (q, 1H), 1.34 (d, 6H).

Example 495

Morpholin-4-yl{3-(5-phenyl-1,3,4-thiadiazol-2-yl)-5-[4-(trifluoromethoxy)phenyl]piperidin-1-yl}-methanone [racemic cis isomer]

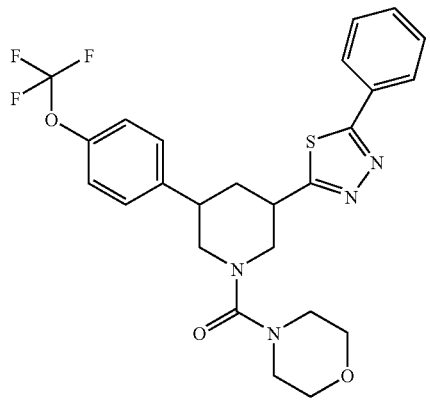

132 mg (0.239 mmol) of the compound from Example 123A and 193 mg (0.478 mmol) of Lawesson reagent were reacted according to the General Method 9. Yield: 40 mg (32% of theory)

LC-MS (Method 2B): $R_t$=1.40 min; MS (ESIpos): m/z=519 [M+H]$^+$;

$^1$H-NMR (400 MHz, DMSO-d$_6$): δ=7.95 (dd, 2H), 7.59-7.53 (m, 3H), 7.50 (d, 2H), 7.34 (d, 2H), 4.07 (br d, 1H), 3.75-3.57 (m, 6H), 3.23-3.20 (m, 4H), 3.13 (t, 1H), 3.07-3.00 (m, 2H), 2.38 (br d, 1H), 2.06 (q, 1H).

Example 496

(3-Methoxyazetidin-1-yl){(3-[3-(propan-2-yl)-1,2,4-oxadiazol-5-yl]-5-[4-(trifluoromethyl)phenyl]piperidin-1-yl}methanone [racemic cis isomer]

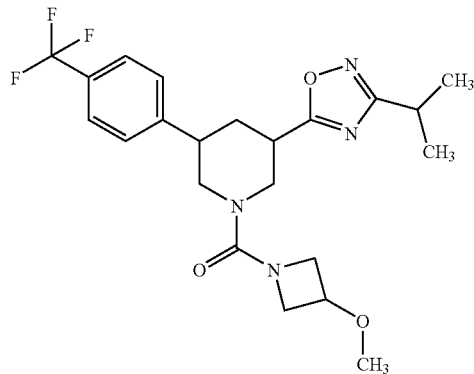

250 mg (0.647 mmol) of 1-[(3-methoxyazetidin-1-yl)carbonyl]-5-[4-(trifluoromethyl)phenyl]piperidine-3-carboxylic acid (Example 103A) and 72.7 mg (0.712 mmol) of N'-hydroxy-2-methylpropanimidamide were reacted according to the General Method 1. Yield: 207 mg (69% of theory).

LC-MS (Method 9B): $R_t$=1.21 min; MS (ESIpos): m/z=453 [M+H]$^+$;

$^1$H-NMR (400 MHz, DMSO-d$_6$): δ=7.70 (d, 2H), 7.57 (d, 2H), 4.20-4.05 (m, 4H), 3.81-3.71 (m, 3H), 3.36-3.27 (obscured, 1H), 3.18 (s, 3H), 3.10-2.93 (m, 3H), 2.31 (s, 3H), 2.31 (br d, 1H), 2.03 (dd, 1H), 1.26 (d, 6H).

Example 497

{3-(3-Ethyl-1,2,4-oxadiazol-5-yl)-5-[4-(trifluoromethyl)phenyl]piperidin-1-yl}(3-methoxyazetidin-1-yl)methanone [racemic cis isomer]

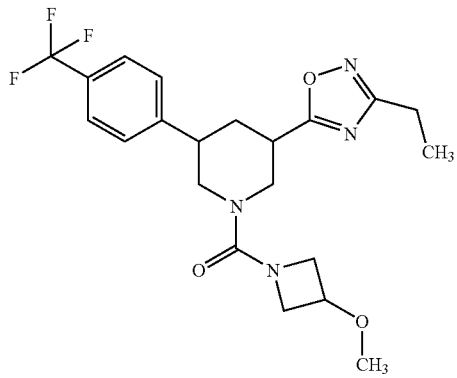

250 mg (0.647 mmol) of 1-[(3-methoxyazetidin-1-yl)carbonyl]-5-[4-(trifluoromethyl)phenyl]piperidine-3-carboxylic acid (Example 103A) and 88.7 mg (0.712 mmol) of N'-hydroxypropanimidamide hydrochloride were reacted according to the General Method 1. Yield: 151 mg (52% of theory).

LC-MS (Method 9B): $R_t$=1.15 min; MS (ESIpos): m/z=439 [M+H]$^+$.

$^1$H-NMR (400 MHz, DMSO-d$_6$): δ=7.70 (d, 2H), 7.57 (d, 2H), 4.20-4.05 (m, 4H), 3.81-3.71 (m, 3H), 3.37-3.28 (obscured, 1H), 3.19 (s, 3H), 3.08-2.94 (m, 3H), 2.71 (q, 2H), 2.32 (br d, 1H), 2.03 (dd, 1H), 1.22 (t, 3H).

Example 498

3-Methoxypiperidin-1-yl){3-[3-(propan-2-yl)-1,2,4-oxadiazol-5-yl]-5-[4-(trifluoromethyl)phenyl]-piperidin-1-yl}methanone [mixture of diastereomers]

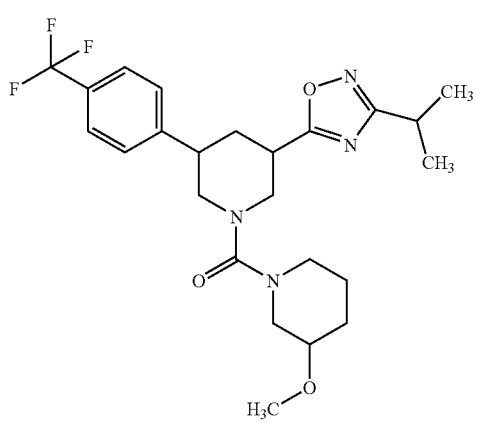

250 mg (0.434 mmol, 72% pure) of 1-[(3-methoxypiperidin-1-yl)carbonyl]-5-[4-(trifluoromethyl)phenyl]piperidine-3-carboxylic acid (Example 207A) and 48.8 mg (0.712 mmol) of N'-hydroxy-2-methylpropanimidamide were reacted according to the General Method 1. Yield: 120 mg (57% of theory).

LC-MS (Method 2B): $R_t$=1.44 min; MS (ESIpos): m/z=481 [M+H]$^+$;

$^1$H-NMR (400 MHz, DMSO-d$_6$): δ=7.71 (d, 2H), 7.57 (d, 2H), 3.96 (br d, 1H), 3.67-3.56 (m, 1H), 3.52-3.32 (m, 2H), 3.27-3.17 (m, 5H), 3.12-2.91 (m, 6H), 2.34 (br d, 1H), 2.01 (dd, 1H), 1.90-1.78 (m, 1H), 1.51-1.30 (m, 2H), 1.25 (d, 6H).

Example 499

{3-(3-Ethyl-1,2,4-oxadiazol-5-yl)-5-[4-(trifluoromethyl)phenyl]piperidin-1-yl}(3-methoxy-piperidin-1-yl)methanone [mixture of diastereomers]

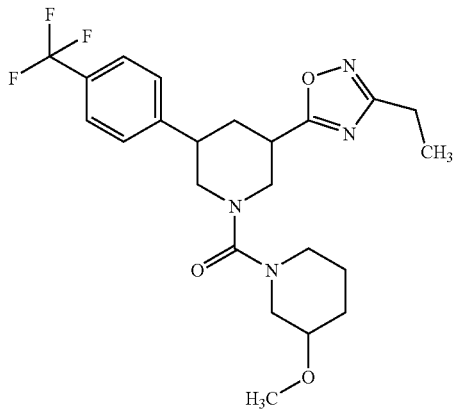

250 mg (0.434 mmol, 72% pure) of 1-[(3-methoxypiperidin-1-yl)carbonyl]-5-[4-(trifluoromethyl)phenyl]piperidine-3-carboxylic acid (Example 207A) and 59.5 mg (0.712 mmol) of N'-hydroxypropanimidamide hydrochloride were reacted according to the General Method 1. Yield: 93.9 mg (46% of theory).

LC-MS (Method 2B): $R_t$=1.44 min; MS (ESIpos): m/z=481 [M+H]$^+$;

$^1$H-NMR (400 MHz, DMSO-d$_6$): δ=7.70 (d, 2H), 7.57 (d, 2H), 3.96 (br d, 1H), 3.66-3.58 (m, 1H), 3.52-3.30 (m, 3H), 3.27-3.18 (m, 5H), 3.11-2.91 (m, 5H), 2.71 (q, 2H), 2.34 (br d, 1H), 2.09-1.96 (m, 1H), 1.94-1.79 (m, 1H), 1.71-1.62 (m, 1H), 1.50-1.32 (m, 1H), 1.22 (t, 6H).

Example 500

{3-[3-(2-Methoxyethyl)-1,2,4-oxadiazol-5-yl]-5-[4-(trifluoromethyl)phenyl]piperidin-1-yl}(3-methoxypiperidin-1-yl)methanone [mixture of diastereomers]

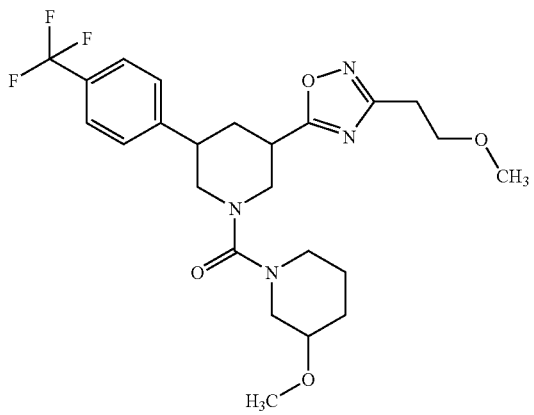

250 mg (0.434 mmol, 72% pure) of 1-[(3-methoxypiperidin-1-yl)carbonyl]-5-[4-(trifluoromethyl)phenyl]piperidine-3-carboxylic acid (Example 207A) and 75.3 mg (0.478 mmol, 75% pure) of N'-hydroxy-3-methoxypropanimidamide were reacted according to the General Method 1. Yield: 105 mg (48% of theory).

LC-MS (Method 2B): $R_t$=1.30 min; MS (ESIpos): m/z=497 [M+H]$^+$;

$^1$H-NMR (400 MHz, DMSO-d$_6$): δ=7.71 (d, 2H), 7.57 (d, 2H), 3.96 (br d, 1H), 3.68 (t, 2H), 3.65-3.58 (m, 1H), 3.53-3.35 (m, 2H), 3.27-3.17 (m, 8H), 3.12-2.95 (m, 5H), 2.93 (t, 2H), 2.35 (br d, 1H), 2.01 (dd, 1H), 1.90-1.78 (m, 1H), 1.72-1.63 (m, 1H), 1.51-1.30 (m, 2H).

Example 501

4-({3-[3-(2-Methoxyethyl)-1,2,4-oxadiazol-5-yl]-5-[4-(trifluoromethyl)phenyl]piperidin-1-yl}carbonyl)piperazin-2-one [racemic cis isomer]

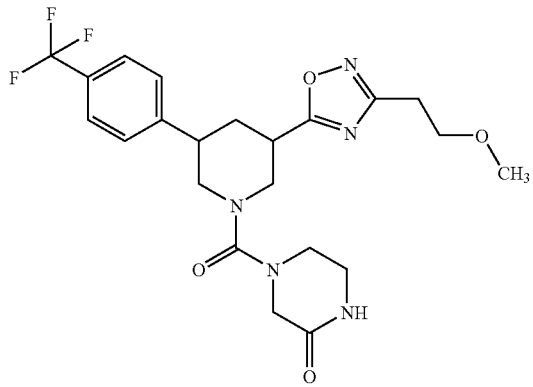

250 mg (0.626 mmol) of 1-[(3-oxopiperazin-1-yl)carbonyl]-5-[4-(trifluoromethyl)phenyl]-piperidine-3-carboxylic acid (Example 206A) and 108 mg (0.689 mmol, 75% pure) of N'-hydroxy-3-methoxypropanimidamide were reacted according to the General Method 1. Yield: 72.0 mg (23% of theory).

LC-MS (Method 3B): $R_t$=1.68 min; MS (ESIpos): m/z=482 [M+H]$^+$;

$^1$H-NMR (400 MHz, DMSO-d$_6$): δ=7.98 (s, 1H), 7.70 (d, 2H), 7.58 (d, 2H), 4.00 (br d, 1H), 3.78 (s, 2H), 3.71-3.60 (m, 3H), 3.49-3.38 (m, 3H), 3.26-3.18 (m, 5H), 3.13-3.00 (m, 3H), 2.93 (t, 2H), 2.34 (br d, 1H), 2.02 (dd, 1H).

Example 502

4-({3-(3-Ethyl-1,2,4-oxadiazol-5-yl)-5-[4-(trifluoromethyl)phenyl]piperidin-1-yl}carbonyl)-piperazin-2-one [racemic cis isomer]

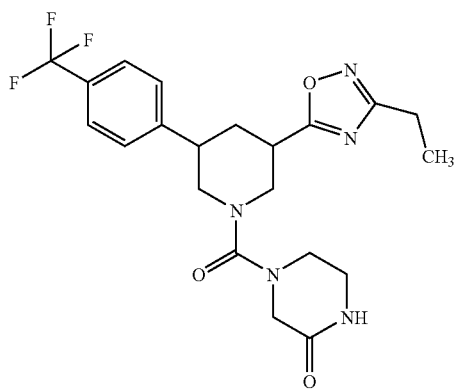

250 mg (0.626 mmol) of 1-[(3-oxopiperazin-1-yl)carbonyl]-5-[4-(trifluoromethyl)phenyl]-piperidine-3-carboxylic acid (Example 206A) and 85.8 mg (0.689 mmol) of N'-hydroxy-propanimidamide hydrochloride were reacted according to the General Method 1. Yield: 127 mg (44% of theory).

LC-MS (Method 2B): $R_t$=1.14 min; MS (ESIpos): m/z=452 [M+H]$^+$;

$^1$H-NMR (400 MHz, DMSO-d$_6$): δ=7.97 (s, 1H), 7.70 (d, 2H), 7.58 (d, 2H), 4.00 (br d, 1H), 3.78 (s, 2H), 3.65 (br d, 1H), 3.48-3.38 (m, 3H), 3.24-3.17 (m, 2H), 3.13-3.00 (m, 3H), 2.71 (q, 2H), 2.34 (br d, 1H), 2.02 (dd, 1H), 1.22 (t, 3H).

Example 503

4-({3-[3-(Propan-2-yl)-1,2,4-oxadiazol-5-yl]-5-[4-(trifluoromethyl)phenyl]piperidin-1-yl}-carbonyl)piperazin-2-one [racemic cis isomer]

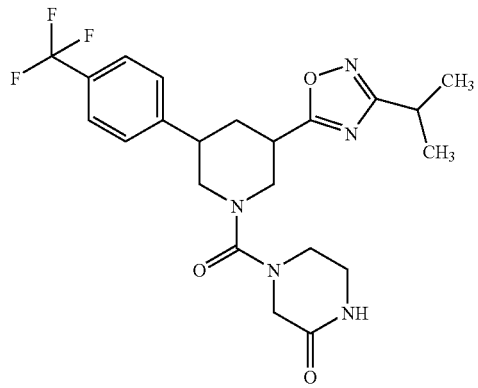

250 mg (0.626 mmol) of 1-[(3-oxopiperazin-1-yl)carbonyl]-5-[4-(trifluoromethyl)phenyl]-piperidine-3-carboxylic acid (Example 206A) and 70.3 mg (0.689 mmol) of N'-hydroxy-2-methylpropanimidamide were reacted according to the General Method 1. Yield: 190 mg (62% of theory).

LC-MS (Method 9B): $R_t$=1.07 min; MS (ESIpos): m/z=466 [M+H]$^+$;

$^1$H-NMR (400 MHz, DMSO-d$_6$): δ=7.97 (s, 1H), 7.70 (d, 2H), 7.57 (d, 2H), 4.00 (br d, 1H), 3.77 (s, 2H), 3.64 (br d, 1H), 3.47-3.35 (m, 3H), 3.24-3.17 (m, 2H), 3.13-3.00 (m, 4H), 2.34 (br d, 1H), 2.02 (dd, 1H), 1.25 (d, 6H).

Example 504

(2,2-Dimethylmorpholin-4-yl){3-[3-(propan-2-yl)-1,2,4-oxadiazol-5-yl]-5-[4-(trifluoromethyl)phenyl]piperidin-1-yl}methanone [racemic cis isomer]

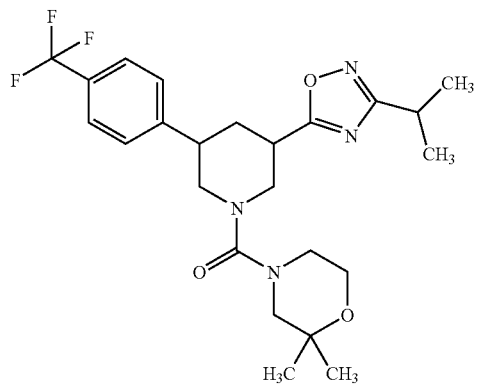

250 mg (0.410 mmol, 68% pure) of 1-[(2,2-dimethylmorpholin-4-yl)carbonyl]-5-[4-(trifluoromethyl)phenyl]piperidine-3-carboxylic acid (Example 208A) and 46.1 mg (0.451 mmol) of N'-hydroxy-2-methylpropanimidamide were reacted according to the General Method 1. Yield: 118 mg (59% of theory).

LC-MS (Method 2B): $R_t$=1.44 min; MS (ESIpos): m/z=481 [M+H]$^+$;

$^1$H-NMR (400 MHz, DMSO-d$_6$): δ=7.71 (d, 2H), 7.57 (d, 2H), 4.00 (br d, 1H), 3.66-3.57 (m, 3H), 3.41 (tt, 1H), 3.18-3.12 (m, 2H), 3.10-3.00 (m, 6H), 2.34 (br d, 1H), 2.04 (dd, 1H), 1.25 (d, 6H), 1.14 (s, 6H).

Example 505

(2,2-Dimethylmorpholin-4-yl){3-[3-(2-methoxyethyl)-1,2,4-oxadiazol-5-yl]-5-[4-(trifluoromethyl)phenyl]piperidin-1-yl}methanone [racemic cis isomer]

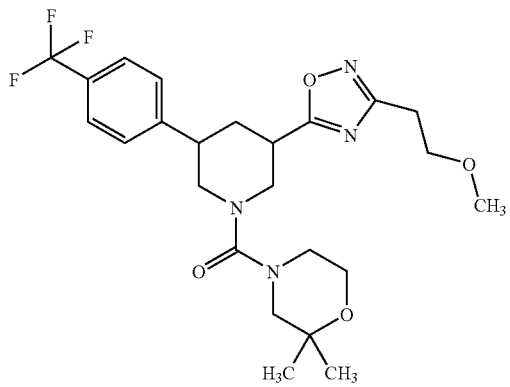

250 mg (0.410 mmol, 68% pure) of 1-[(2,2-dimethylmorpholin-4-yl)carbonyl]-5-[4-(trifluoromethyl)phenyl]piperidine-3-carboxylic acid (Example 208A) and 71.1 mg (0.451 mmol, 75% pure) of N'-hydroxy-3-methoxypropanimidamide were reacted according to the General Method 1. Yield: 103 mg (50% of theory).

LC-MS (Method 2B): $R_t$=1.31 min; MS (ESIpos): m/z=497 [M+H]$^+$;

$^1$H-NMR (400 MHz, DMSO-d$_6$): δ=7.71 (d, 2H), 7.57 (d, 2H), 4.00 (br d, 1H), 3.67 (t, 2H), 3.65-3.57 (m, 3H), 3.43 (tt, 1H), 3.23 (s, 3H), 3.18-3.12 (m, 2H), 3.10-2.98 (m, 5H), 2.93 (t, 2H), 2.35 (br d, 1H), 2.04 (dd, 1H), 1.14 (s, 6H).

Example 506

(2,2-Dimethylmorpholin-4-yl){3-(3-ethyl-1,2,4-oxadiazol-5-yl)-5-[4-(trifluoromethyl)phenyl]piperidin-1-yl}methanone [racemic cis isomer]

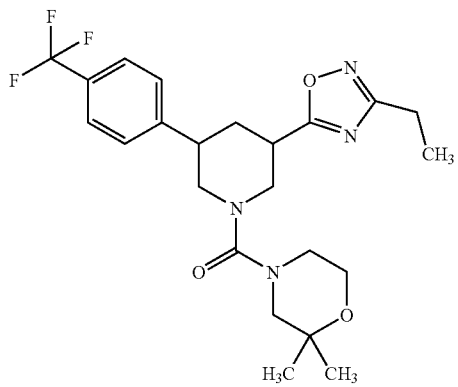

250 mg (0.410 mmol, 68% pure) of 1-[(2,2-dimethylmorpholin-4-yl)carbonyl]-5-[4-(trifluoromethyl)phenyl]piperidine-3-carboxylic acid (Example 208A) and 56.2 mg (0.451 mmol) of N'-hydroxypropanimidamide hydrochloride were reacted according to the General Method 1. Yield: 80.6 mg (42% of theory).

LC-MS (Method 2B): $R_t$=1.36 min; MS (ESIpos): m/z=467 [M+H]$^+$;

$^1$H-NMR (400 MHz, DMSO-d$_6$): δ=7.71 (d, 2H), 7.57 (d, 2H), 4.00 (br d, 1H), 3.68-3.57 (m, 3H), 3.41 (tt, 1H), 3.19-3.12 (m, 2H), 3.10-2.96 (m, 5H), 2.71 (q, 2H), 2.34 (br d, 1H), 2.04 (dd, 1H), 1.22 (t, 3H), 1.14 (s, 6H).

Example 507

4-({3-(3-Ethyl-1,2,4-oxadiazol-5-yl)-5-[4-(trifluoromethyl)phenyl]piperidin-1-yl}carbonyl)-1-methylpiperazin-2-one [racemic cis isomer]

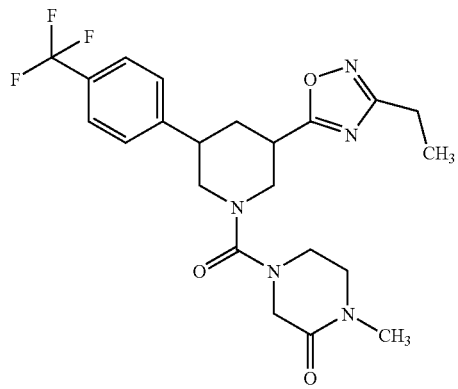

250 mg (0.605 mmol) of 1-[(4-methyl-3-oxopiperazin-1-yl)carbonyl]-5-[4-(trifluoromethyl)phenyl]piperidine-3-carboxylic acid (Example 209A) and 82.9 mg (0.665 mmol) of N'-hydroxypropanimidamide hydrochloride were reacted according to the General Method 1. Yield: 110 mg (39% of theory).

LC-MS (Method 9B): $R_t$=1.05 min; MS (ESIpos): m/z=466 [M+H]$^+$;

$^1$H-NMR (400 MHz, DMSO-d$_6$): δ=7.70 (d, 2H), 7.57 (d, 2H), 4.01 (br d, 1H), 3.81 (s, 2H), 3.65 (br d, 1H), 3.50-3.37 (m, 3H), 3.14-3.03 (m, 3H), 2.84 (s, 3H), 2.71 (q, 2H), 2.36-2.30 (m, 1H), 2.01 (dd, 1H), 1.22 (t, 3H).

Example 508

(4-Aminopiperidin-1-yl){3-[3-(propan-2-yl)-1,2,4-oxadiazol-5-yl]-5-[4-(trifluoromethoxy)-phenyl]piperidin-1-yl}methanone hydrochloride [racemic cis isomer]

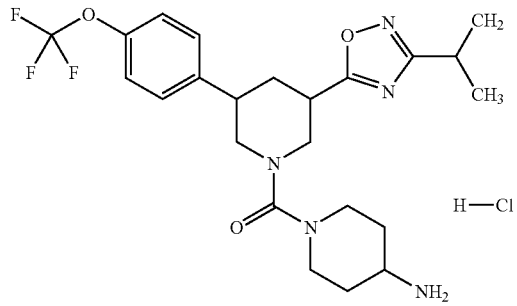

0.31 ml (1.27 mmol) of a 4N solution of hydrogen chloride in dioxane was added to a solution of 50 mg (0.087 mmol) of the compound from Example 210 A in 1.13 ml of dioxane. The reaction mixture was stirred at room temperature for 20 hours. The mixture was then concentrated to dryness under reduced pressure and dried until the weight remained constant. Yield: 18 mg (36% of theory).

LC-MS (Method 2B): $R_t$=1.10 min; MS (ESIpos): m/z=482 [M+H—HCl]$^+$;

$^1$H-NMR (400 MHz, DMSO-d$_6$): δ=7.94 (bs, 2H), 7.47 (d, 2H), 7.33 (d, 2H), 3.94 (br d, 1H), 3.65 (d, 2H), 3.55 (d, 1H), 3.23-3.10 (m, 1H), 3.10-2.94 (m, 4H), 2.84 (dd, 2H), 2.31 (d, 1H), 1.98 (dd, 1H), 1.88 (br d, 2H), 1.43 (dd, 2H), 1.25 (d, 6H).

Example 509

(4-Aminopiperidin-1-yl){3-[3-(2-methoxyethyl)-1,2,4-oxadiazol-5-yl]-5-[4-(trifluoromethoxy)-phenyl]piperidin-1-yl}methanone [racemic cis isomer]

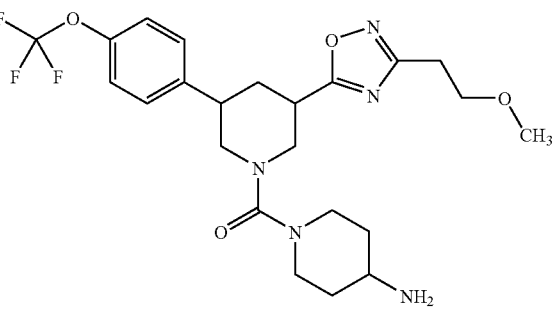

0.255 ml (1.022 mmol) of a 4N solution of hydrogen chloride in dioxane was added to a solution of 50 mg (0.082 mmol) of the compound from Example 211A in 0.4 ml of dioxane. The reaction mixture was stirred at room temperature for 20 hours. The mixture was then concentrated to dryness under reduced pressure and dried until the weight remained constant. Yield: 43 mg (97% of theory).

LC-MS (Method 9B): $R_t$=0.85 min; MS (ESIpos): m/z=499 [M+H—HCl]$^+$;

$^1$H-NMR (400 MHz, DMSO-d$_6$): δ=7.95 (bs, 1H), 7.93 (bs, 1H), 7.47 (d, 2H), 7.33 (d, 2H), 3.95 (br d, 1H), 3.65-3.64 (m, 4H), 3.55 (d, 1H), 3.45-3.36 (m, 1H), 3.23 (s, 3H), 3.21-3.13 (br s, 1H), 3.07-2.92 (m, 5H), 2.84 (dd, 2H), 2.33 (br d, 1H), 1.98 (dd, 1H), 1.88 (br d, 2H), 1.43 (dd, 2H).

Example 510

(4-Aminopiperidin-1-yl){3-(3-methyl-1,2,4-oxadiazol-5-yl)-5-[4-(trifluoromethoxy)phenyl]-piperidin-1-yl}methanone hydrochloride [racemic cis isomer]

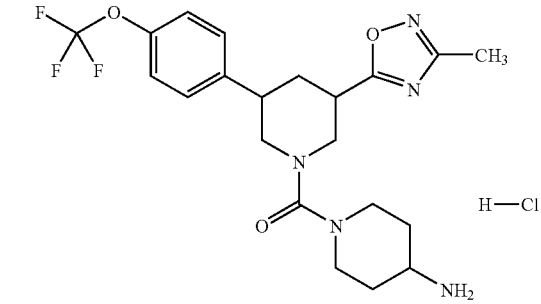

0.365 ml (1.463 mmol) of a 4N solution of hydrogen chloride in dioxane were added to a solution of 70 mg (0.126 mmol) of the compound from Example 212A in 0.6 ml of dioxane. The reaction mixture was stirred at room temperature for 20 hours. The mixture was then concentrated to dryness under reduced pressure and dried until the weight remained constant. Yield: 60 mg (97% of theory).

LC-MS (Method 9B): $R_t$=0.83 min; MS (ESIpos): m/z=454 [M+H—HCl]$^+$;

$^1$H-NMR (400 MHz, DMSO-d$_6$): δ=7.86 (bs, 2H), 7.46 (d, 2H), 7.33 (d, 2H), 3.96 (br d, 1H), 3.64 (d, 2H), 3.56 (d, 1H), 3.18 (bs, 1H), 3.09-2.97 (m, 3H), 2.84 (dd, 2H), 2.33 (s, 3H), 2.31 (d, 1H), 1.98 (dd, 1H), 1.87 (br d, 2H), 1.42 (dd, 2H).

Example 511

(3-Hydroxyazetidin-1-yl){3-[3-(2-methoxyethyl)-1,2,4-oxadiazol-5-yl]-5-[4-(trifluoromethoxy)-phenyl]piperidin-1-yl}methanone [racemic cis isomer]

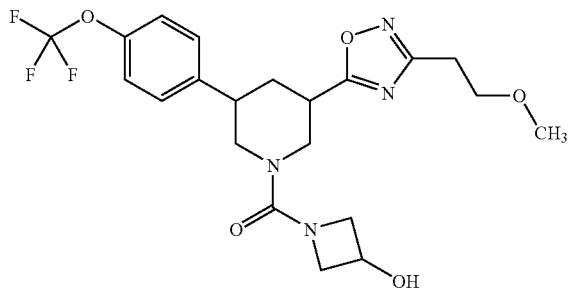

150 mg (0.324 mmol) of the compound from Example 110A and 77 mg (0.649 mmol) of N'-hydroxy-3-methoxypropanimidamide were reacted according to the General Method 2. Yield: 23 mg (15% of theory).

LC-MS (Method 5B): $R_t$=2.06 min; MS (ESIpos): m/z=471 [M+H]$^+$;

$^1$H-NMR (400 MHz, DMSO-d$_6$): δ=7.46 (d, 2H), 7.33 (d, 2H), 5.58 (d, 1H), 4.42-4.35 (m, 1H), 4.16 (br d, 1H), 4.09 (dd, 2H), 3.75-3.66 (m, 5H), 3.23 (s, 3H), 3.04-2.89 (m, 5H), 2.30 (br d, 1H), 1.99 (dd, 1H).

Example 512

(3-Hydroxypyrrolidin-1-yl){3-[3-(methoxymethyl)-1,2,4-oxadiazol-5-yl]-5-[4-(trifluoromethoxy)-phenyl]piperidin-1-yl}methanone [mixture of diastereomers]

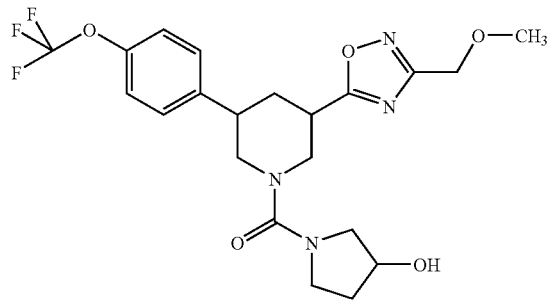

200 mg (0.497 mmol) of the compound from Example 112A and 77 mg (0.746 mmol) of N'-hydroxy-2-methoxyethanimidamide were reacted according to the General Method 2. Yield: 55 mg (24% of theory).

LC-MS (Method 2B): $R_t$=1.14 min; MS (ESIpos): m/z=471 [M+H]$^+$;

$^1$H-NMR (400 MHz, DMSO-d$_6$): δ=7.47 (d, 2H), 7.32 (d, 2H), 4.86 (d, 1H), 4.53 (s, 2H), 4.24-4.19 (m, 1H), 4.10-4.04 (m, 1H), 3.70 (dd, 1H), 3.51-3.44 (m, 3H), 3.33 (s, 3H), 3.11 (d, 1H), 3.05-2.84 (m, 3H), 2.34 (br d, 1H), 2.04-1.94 (m, 1H), 1.86-1.78 (m, 1H), 1.75-1.66 (m, 1H).

Example 513

{3-(3-Cyclobutyl-1,2,4-oxadiazol-5-yl)-5-[4-(trifluoromethoxy)phenyl]piperidin-1-yl}(morpholin-4-yl)methanone [racemic cis isomer]

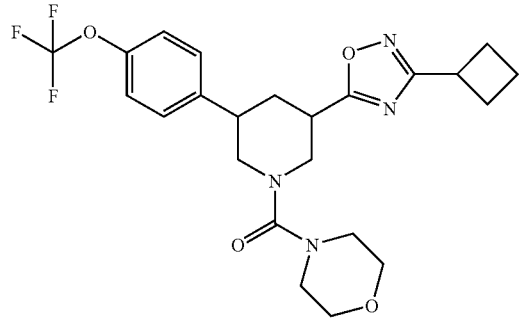

150 mg (0.373 mmol) of the compound from Example 44A and 85 mg (0.746 mmol) of N'-hydroxycyclobutanecarboximidamide were reacted according to the General Method 2. Yield: 58 mg (48% of theory)

LC-MS (Method 2B): $R_t$=1.42 min; MS (ESIpos): m/z=481 [M+H]$^+$;

$^1$H-NMR (400 MHz, DMSO-d$_6$): δ=7.47 (d, 2H), 7.33 (d, 2H), 3.99 (br d, 1H), 3.69-3.60 (m, 2H), 3.59-3.53 (m, 4H), 3.41 (tt, 1H), 3.23-3.16 (m, 4H), 3.08-2.97 (m, 3H), 2.37-2.20 (m, 5H), 2.11-1.88 (m, 3H).

Example 514

{3-(3-Cyclobutyl-1,2,4-oxadiazol-5-yl)-5-[4-(trifluoromethyl)phenyl]piperidin-1-yl}(morpholin-4-yl)methanone [racemic cis isomer]

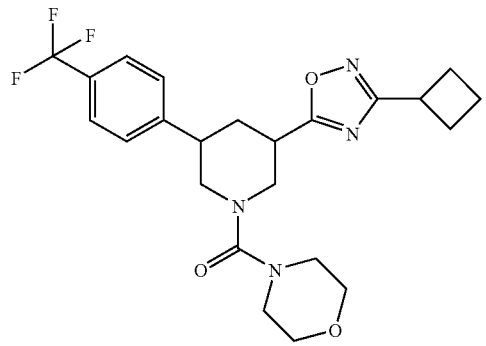

150 mg (0.388 mmol) of the compound from Example 81A and 88 mg (0.776 mmol) of N'-hydroxycyclobutanecarboximidamide were reacted according to the General Method 2. Yield: 124 mg (65% of theory)

LC-MS (Method 2B): $R_t$=1.39 min; MS (ESIpos): m/z=465 [M+H]$^+$;

$^1$H-NMR (400 MHz, DMSO-d$_6$): δ=7.70 (d, 2H), 7.58 (d, 2H), 3.99 (br d, 1H), 3.68-3.60 (m, 2H), 3.58-3.53 (m, 4H), 3.40 (tt, 1H), 3.23-3.17 (m, 4H), 3.10-2.99 (m, 3H), 2.37-2.23 (m, 5H), 2.09-1.92 (m, 3H).

Example 515

{3-[3-(3-Fluorophenyl)-1,2,4-oxadiazol-5-yl]-5-[4-(trifluoromethyl)phenyl]piperidin-1-yl}-(morpholin-4-yl)methanone [racemic cis isomer]

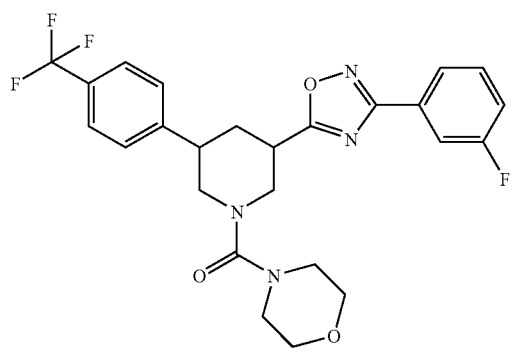

250 mg (about 0.52 mmol) of the compound from Example 49A and 89 mg (0.58 mmol) of 3-fluoro-N'-hydroxybenzenecarboximidamide were reacted according to the General Method 1. Yield: 26 mg (10% of theory).

LC-MS (Method 1B): $R_t$=2.81 min; MS (ESIpos): m/z=505 [M+H]$^+$;

$^1$H-NMR (400 MHz, DMSO-d$_6$): δ=7.87 (d, 1H), 7.76 (d, 1H), 7.71 (d, 2H), 7.64 (d, 1H), 7.60 (d, 2H), 7.47 (td, 1H), 4.10 (br d, 1H), 3.65 (d, 1H), 3.60-3.50 (m, 5H), 3.25-3.20 (m, 4H), 3.16 (t, 1H), 3.10-3.06 (m, 2H), 2.42 (br d, 1H), 2.10 (q, 1H).

Example 516

1-({3-(3-Cyclopropyl-1,2,4-oxadiazol-5-yl)-5-[4-(trifluoromethoxy)phenyl]piperidin-1-yl}-carbonyl)piperidine-4-carbonitrile [racemic cis isomer]

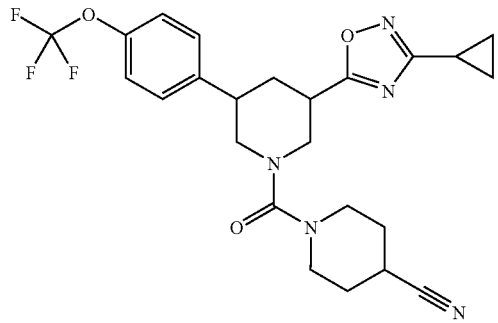

100 mg (about 0.153 mmol) of the compound from Example 108A and 30 mg (0.306 mmol) of N'-hydroxycyclopropanecarboximidamide were reacted according to the General Method 2. Yield: 312 mg (41% of theory)

LC-MS (Method 3B): $R_t$=2.29 min; MS (ESIpos): m/z=490 [M+H]$^+$;

$^1$H-NMR (400 MHz, DMSO-d$_6$): δ=7.47 (d, 2H), 7.32 (d, 2H), 3.92 (br d, 1H), 3.58 (d, 1H), 3.39-3.33 (m, 3H), 3.10-2.91 (m, 6H), 2.27 (br d, 1H), 2.07-2.14 (m, 1H), 1.92 (dd, 1H), 1.90-1.80 (m, 2H), 1.71-1.63 (m, 2H), 1.08-1.03 (m, 2H), 0.90-0.86 (m, 2H).

Example 517

1-({3-[3-(2-Methoxyethyl)-1,2,4-oxadiazol-5-yl]-5-[4-(trifluoromethoxy)phenyl]piperidin-1-yl}-carbonyl)piperidine-4-carbonitrile [racemic cis isomer]

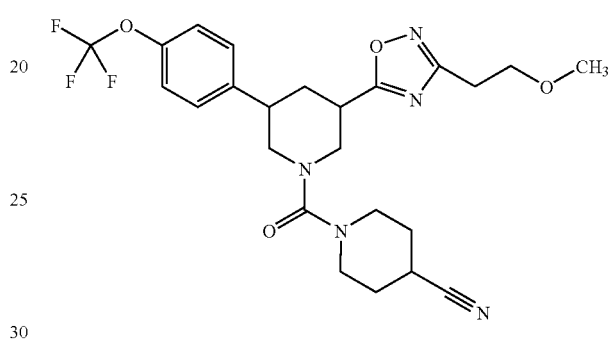

100 mg (about 0.153 mmol) of the compound from Example 108A and 36 mg (0.306 mmol) of N'-hydroxy-3-methoxypropanimidamide were reacted according to the General Method 2. Yield: 14 mg (18% of theory)

LC-MS (Method 3B): $R_t$=2.11 min; MS (ESIpos): m/z=508 [M+H]$^+$;

$^1$H-NMR (400 MHz, DMSO-d$_6$): δ=7.47 (d, 2H), 7.33 (d, 2H), 3.96 (br d, 1H), 3.67 (t, 2H), 3.57 (d, 1H), 3.41-3.35 (m, 2H), 3.23 (s, 3H), 3.10-2.96 (m, 6H), 2.95 (t, 2H), 2.31 (br d, 1H), 1.96 (dd, 1H), 1.90-1.80 (m, 2H), 1.74-1.63 (m, 2H).

Example 518

1-({3-(3-Methyl-1,2,4-oxadiazol-5-yl)-5-[4-(trifluoromethoxy)phenyl]piperidin-1-yl}carbonyl)-piperidine-4-carbonitrile [racemic cis isomer]

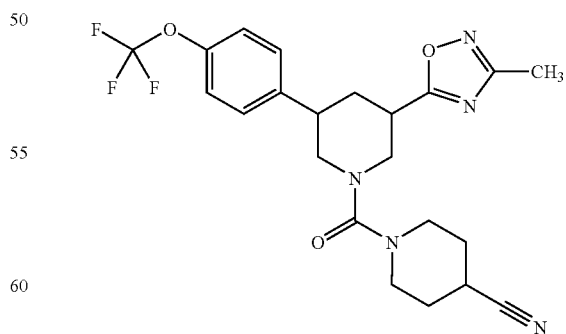

100 mg (about 0.153 mmol) of the compound from Example 108A and 22 mg (0.306 mmol) of N'-hydroxyethanimidamide were reacted according to the General Method 2. Yield: 12 mg (17% of theory)

LC-MS (Method 3B): $R_t$=2.11 min; MS (ESIpos): m/z=464 [M+H]$^+$;

$^1$H-NMR (400 MHz, DMSO-d$_6$): δ=7.46 (d, 2H), 7.33 (d, 2H), 3.95 (br d, 1H), 3.58 (d, 1H), 3.41-3.35 (m, 3H), 3.10-2.91 (m, 6H), 2.31 (s, 3H), 2.30 (br d, 1H), 1.96 (q, 1H), 1.90-1.82 (m, 2H), 1.73-1.63 (m, 2H).

Example 519

1-({3-(3-Ethyl-1,2,4-oxadiazol-5-yl)-5-[4-(trifluoromethoxy)phenyl]piperidin-1-yl}carbonyl)-piperidine-4-carbonitrile [racemic cis isomer]

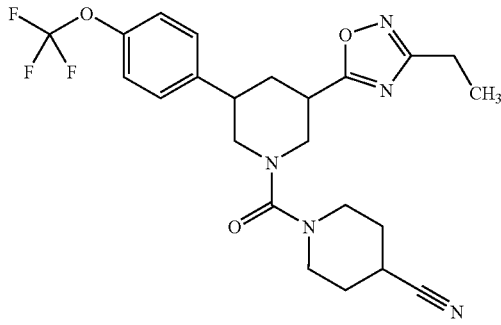

100 mg (about 0.153 mmol) of the compound from Example 108A and 27 mg (0.306 mmol) of N'-hydroxypropanimidamide were reacted according to the General Method 2. Yield: 7 mg (10% of theory)

LC-MS (Method 3B): $R_t$=2.24 min; MS (ESIpos): m/z=478 [M+H]$^+$;

$^1$H-NMR (400 MHz, DMSO-d$_6$): δ=7.46 (d, 2H), 7.33 (d, 2H), 3.95 (br d, 1H), 3.57 (d, 1H), 3.39-3.34 (m, 3H), 3.10-2.93 (m, 6H), 2.71 (q, 2H), 2.30 (br d, 1H), 1.96 (q, 1H), 1.90-1.83 (m, 2H), 1.73-1.63 (m, 2H); 1.22 (t, 3H).

Example 520

1-({3-[3-(Propan-2-yl)-1,2,4-oxadiazol-5-yl]-5-[4-(trifluoromethoxy)phenyl]piperidin-1-yl}-carbonyl)piperidine-4-carbonitrile [racemic cis isomer]

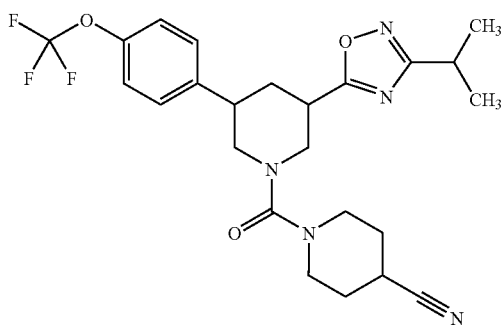

100 mg (about 0.153 mmol) of the compound from Example 108A and 31 mg (0.306 mmol) of N'-hydroxy-2-methylpropanimidamide were reacted according to the General Method 2. Yield: 60 mg (80% of theory)

LC-MS (Method 3B): $R_t$=2.38 min; MS (ESIpos): m/z=492 [M+H]$^+$;

$^1$H-NMR (400 MHz, DMSO-d$_6$): δ=7.47 (d, 2H), 7.32 (d, 2H), 3.96 (br d, 1H), 3.57 (d, 1H), 3.42-3.35 (m, 4H), 3.11-2.94 (m, 6H), 2.31 (br d, 1H), 2.01-1.91 (m, 1H), 1.90-1.80 (m, 1H), 1.67 (q, 1H), 1.25 (d, 6H).

Example 521

3-[3-(3-Fluorophenyl)-1,2,4-oxadiazol-5-yl]-N-(2-methoxyethyl)-5-[4-(trifluoromethyl)phenyl]-piperidine-1-carboxamide [racemic cis isomer]

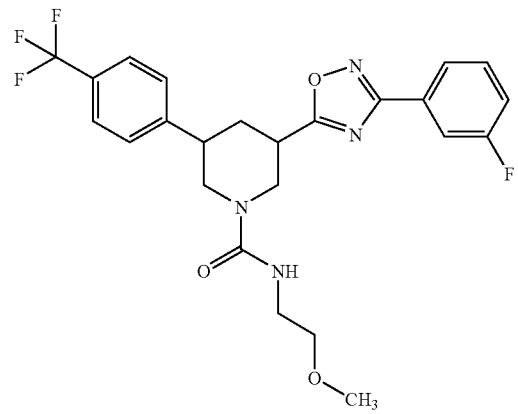

100 mg (0.267 mmol) of the compound from Example 105A and 77 mg (0.497 mmol) of 3-fluoro-N'-hydroxybenzenecarboximidamide were reacted according to the General Method 2. Yield: 64 mg (55% of theory)

LC-MS (Method 3B): $R_t$=2.39 min; MS (ESIpos): m/z=493 [M+H]$^+$;

$^1$H-NMR (400 MHz, DMSO-d$_6$): δ=7.87 (d, 1H), 7.76 (dd, 1H), 7.72 (d, 2H), 7.64 (dd, 1H), 7.59 (d, 2H), 7.46 (dd, 1H), 6.84 (dd, 1H), 4.53 (br d, 1H), 4.11 (dd, 1H), 3.36 (t, 3H), 3.25 (s, 3H), 3.27-3.20 (m, 2H), 3.11-2.99 (m, 1H), 2.95 (dd, 2H), 2.42 (br d, 1H), 2.08 (dd, 1H).

Example 522

N-(2-Methoxyethyl)-3-[3-(2-methoxyethyl)-1,2,4-oxadiazol-5-yl]-5-[4-(trifluoromethyl)phenyl]-piperidine-1-carboxamide [racemic cis isomer]

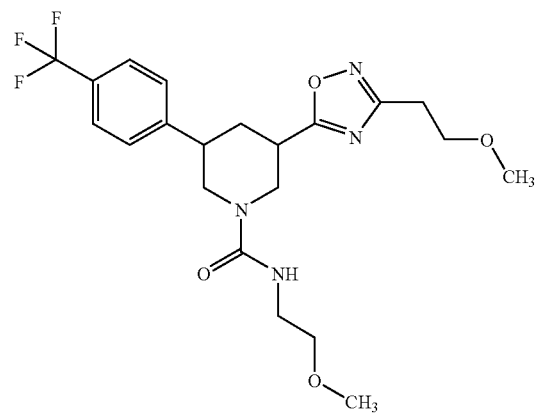

100 mg (0.267 mmol) of the compound from Example 105A and 78 mg (0.497 mmol) of N'-hydroxy-3-methoxypropanimidamide were reacted according to the General Method 2. Yield: 22 mg (17% of theory)

LC-MS (Method 3B): $R_t$=1.87 min; MS (ESIpos): m/z=456 [M+H]$^+$;

$^1$H-NMR (400 MHz, DMSO-d$_6$): δ=7.70 (d, 2H), 7.57 (d, 2H), 6.82 (dd, 1H), 4.43 (br d, 1H), 4.08 (d, 1H), 3.68 (t, 2H), 3.24 (s, 3H), 3.23 (s, 3H), 3.26-3.18 (m, 3H), 2.98-2.89 (m, 5H), 2.32 (br d, 1H), 1.98 (dd, 1H).

Example 523

N-(2-Methoxyethyl)-3-[3-(propan-2-yl)-1,2,4-oxadiazol-5-yl]-5-[4-(trifluoromethyl)phenyl]-piperidine-1-carboxamide [racemic cis isomer]

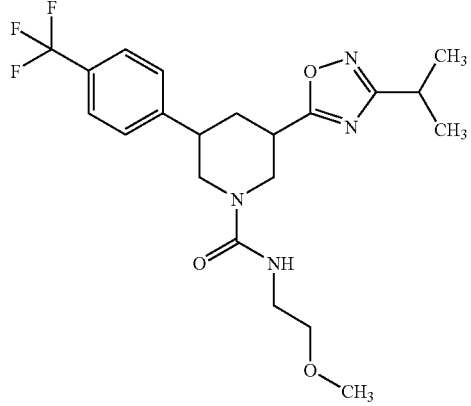

100 mg (0.267 mmol) of the compound from Example 105A and 51 mg (0.497 mmol) of N'-hydroxy-2-methylpropanimidamide were reacted according to the General Method 2. Diastereomer separation of 83 mg of the cis/trans isomer mixture according to Method 14C gave 60.5 mg of the title compound and 6.7 mg of the trans isomer.

LC-MS (Method 2B): $R_t$=1.34 min; MS (ESIpos): m/z=441 [M+H]$^+$;

$^1$H-NMR (400 MHz, DMSO-d$_6$): δ=7.70 (d, 2H), 7.57 (d, 2H), 6.80 (dd, 1H), 4.42 (br d, 1H), 4.08 (dd, 1H), 3.24 (s, 3H), 3.27-3.18 (m, 3H), 3.09-3.02 (m, 1H), 2.97 (br d, 1H), 2.91 (br d, 2H), 2.31 (br d, 1H), 1.98 (dd, 1H), 1.25 (d, 6H).

Example 524

3-(3-Cyclopropyl-1,2,4-oxadiazol-5-yl)-N-(2-methoxyethyl)-5-[4-(trifluoromethyl)phenyl]-piperidine-1-carboxamide [racemic cis isomer]

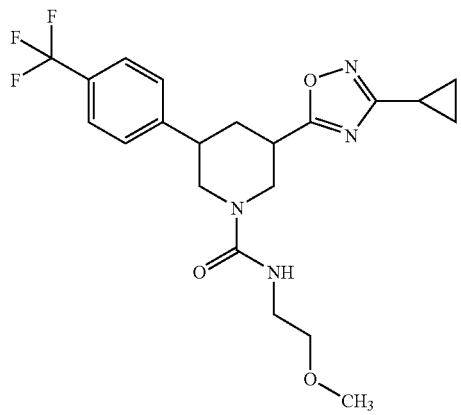

100 mg (0.267 mmol) of the compound from Example 105A and 54 mg (0.534 mmol) of N'-hydroxycyclopropanecarboximidamide were reacted according to the General Method 2. Diastereomer separation of 64 mg of the cis/trans isomer mixture according to Method 14C gave 45.4 mg of the title compound and 5.5 mg of the trans isomer.

LC-MS (Method 2B): $R_t$=1.30 min; MS (ESIpos): m/z=439 [M+H]$^+$;

$^1$H-NMR (400 MHz, DMSO-d$_6$): δ=7.70 (d, 2H), 7.56 (d, 2H), 6.79 (dd, 1H), 4.40 (br d, 1H), 4.07 (dd, 1H), 3.24 (s, 3H), 3.22-3.15 (m, 3H), 2.94-2.86 (m, 3H), 2.38 (br d, 1H), 2.14-2.08 (m, 1H), 1.94 (dd, 1H), 1.08-1.03 (m, 2H), 0.90-0.86 (m, 2H).

Example 525

Morpholin-4-yl {3-[3-(pyridin-2-yl)-1,2,4-oxadiazol-5-yl]-5-[4(trifluoromethyl)phenyl]piperidin-1-yl}methanone [racemic cis isomer]

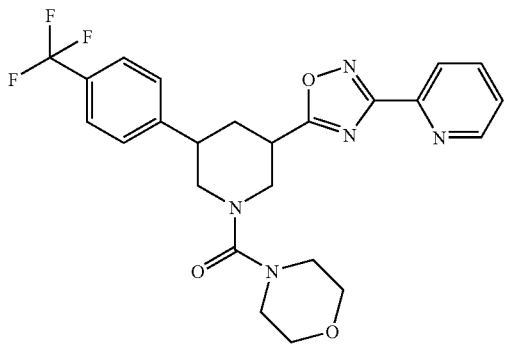

250 mg (about 0.520 mmol) of the compound from Example 49A and 79 mg (0.580 mmol) of N'-hydroxypyridine-2-carboximidamide (Example 69A) were reacted according to the General Method 1. Yield: 49 mg (19% of theory).

LC-MS (Method 3B): $R_t$=1:99 min; MS (ESIpos): m/z=488 [M+H]$^+$;

$^1$H-NMR (400 MHz, DMSO-d$_6$): δ=8.76 (dm, 1H), 8.08 (d, 1H), 8.02 (td, 1H), 7.73 (d, 2H), 7.62-7.59 (m, 3H), 4.10 (br d, 1H), 3.66 (d, 1H), 3.60-3.50 (m, 5H), 3.25-3.21 (m, 4H), 3.16-3.02 (m, 3H), 2.43 (br d, 1H), 2.12 (q, 1H).

Example 526

{3-(3-Ethyl-1,2,4-oxadiazol-5-yl)-5-[4-(trifluoromethoxy)phenyl]piperidin-1-yl}(4-hydroxy-piperidin-1-yl)methanone

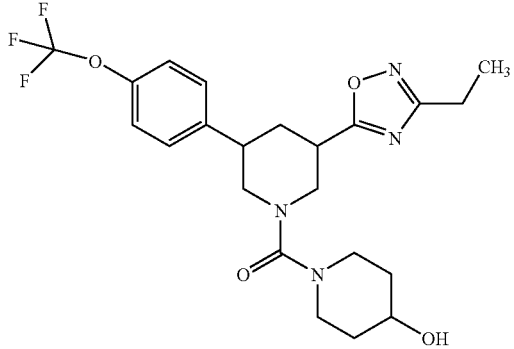

200 mg (0.480 mmol) of the compound from Example 63A and 85 mg (0.960 mmol) of N'-hydroxyethanimidamide were reacted according to the General Method 2. Yield: 101 mg (43% of theory)

LC-MS (Method 9B): $R_t$=1.09 min; MS (ESIpos): m/z=469 [M+H]$^+$;

$^1$H-NMR (400 MHz, DMSO-$d_6$): δ=7.46 (d, 2H), 7.33 (d, 2H), 4.69 (d, 1H), 3.93 (br d, 1H), 3.66-3.59 (m, 1H), 3.56 (d, 1H), 3.52-3.44 (m, 2H), 3.38 (tt, 1H), 3.03-2.88 (m, 5H), 2.70 (dd, 2H), 2.31 (d, 1H), 1.97 (dd, 1H), 1.71 (d, 2H), 1.36-1.25 (dd, 2H), 1.22 (t, 3H).

Example 527

1-({3-[3-(Methoxymethyl)-1,2,4-oxadiazol-5-yl]-5-[4-(trifluoromethoxy)phenyl]piperidin-1-yl}-carbonyl)piperidine-4-carbonitrile [enantiomerically pure cis isomer]

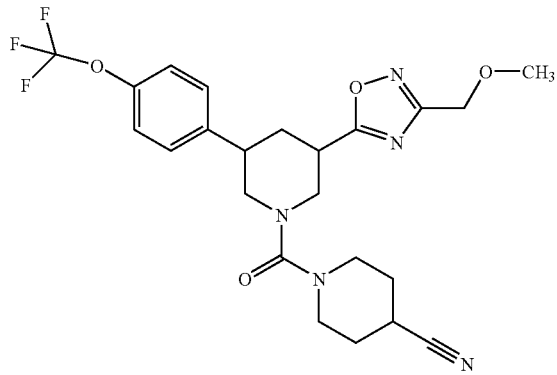

100 mg (about 0.153 mmol) of the compound from Example 108A and 79 mg (0.306 mmol) of N'-hydroxymethylmethoxycarboxamidine were reacted according to the General Method 2. Enantiomer separation of 21 mg of the racemate according to Method 15D gave 4 mg of the title compound from Example 527 and 4 mg of the title compound from Example 528.

HPLC (Method 12E): $R_t$=7.81 min, >99.0% ee;

LC-MS (Method 9B): $R_t$=1.13 min; MS (ESIpos): m/z=494 [M+H]$^+$.

Example 528

1-({3-[3-(Methoxymethyl)-1,2,4-oxadiazol-5-yl]-5-[4-(trifluoromethoxy)phenyl]piperidin-1-yl}-carbonyl)piperidine-4-carbonitrile [enantiomerically pure cis isomer]

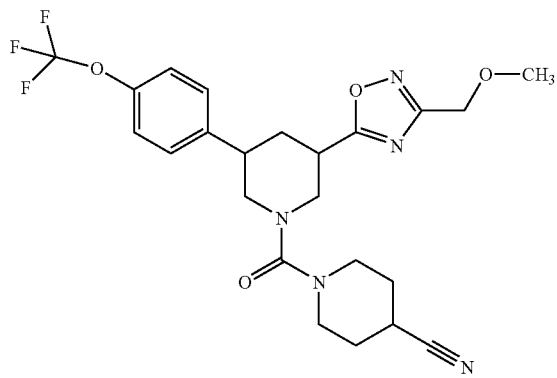

100 mg (about 0.153 mmol) of the compound from Example 108A and 79 mg (0.306 mmol) of N'-hydroxymethylmethoxycarboxamidine were reacted according to the General Method 2. Enantiomer separation of 21 mg of the racemate according to Method 15D gave 4 mg of the title compound from Example 527 and 4 mg of the title compound from Example 528.

HPLC (Method 12E): $R_t$=9.75 min, >99.0% ee;

LC-MS (Method 9B): $R_t$=1.13 min; MS (ESIpos): m/z=494 [M+H]$^+$.

Example 529

(3-Hydroxyazetidin-1-yl){3-[3-(propan-2-yl)-1,2,4-oxadiazol-5-yl]-5-[4-(trifluoromethoxy)phenyl]piperidin-1-yl}methanone [racemic cis isomer]

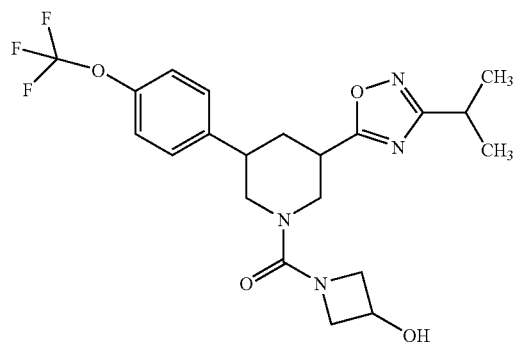

185 mg (about 0.400 mmol) of the compound from Example 110A and 55 mg (0.600 mmol) of N'-hydroxy-2-methylpropanimidamide were reacted according to the General Method 2. Yield: 28 mg (16% of theory)

LC-MS (Method 9B): $R_t$=1.12 min; MS (ESIpos): m/z=455 [M+H]$^+$;

$^1$H-NMR (400 MHz, DMSO-$d_6$): δ=7.46 (d, 2H), 7.33 (d, 2H), 5.58 (d, 1H), 4.46-4.35 (m, 1H), 4.15 (br d, 1H), 4.08 (dd, 2H), 3.75-3.66 (m, 3H), 3.08-2.87 (m, 4H), 2.29 (br d, 1H), 1.99 (dd, 1H), 1.25 (d, 6H).

Example 530

(3-Hydroxyazetidin-1-yl){3-(3-methyl-1,2,4-oxadiazol-5-yl)-5-[4-(trifluoromethoxy)phenyl]piperidin-1-yl}methanone [racemic cis isomer]

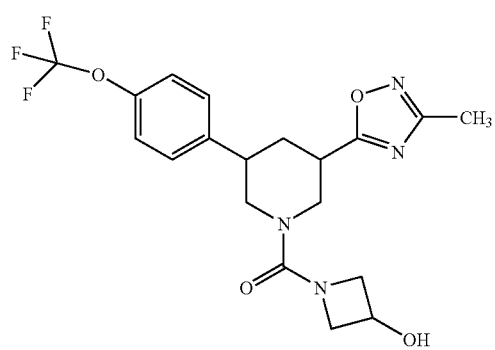

185 mg (about 0.400 mmol) of the compound from Example 110A and 55 mg (0.600 mmol) of N'-hydroxyethanimidamide were reacted according to the General Method 2. Yield: 16 mg (9% of theory)

LC-MS (Method 9B): $R_t$=0.99 min; MS (ESIpos): m/z=427 [M+H]$^+$;

$^1$H-NMR (400 MHz, DMSO-d$_6$): δ=7.45 (d, 2H), 7.33 (d, 2H), 5.58 (d, 1H), 4.42-4.35 (m, 1H), 4.13 (br d, 1H), 4.09 (dd, 2H), 3.76-3.67 (m, 3H), 3.03-2.91 (m, 3H), 2.33 (s, 3H), 2.29 (br d, 1H), 1.98 (dd, 1H).

Example 531

(3-Hydroxypyrrolidin-1-yl){3-(3-methyl-1,2,4-oxadiazol-5-yl)-5-[4-(trifluoromethoxy)phenyl]-piperidin-1-yl}methanone [enantiomerically pure cis isomer]

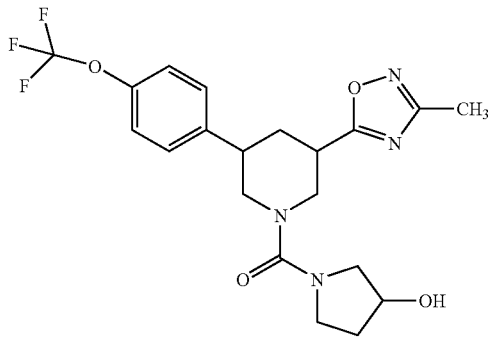

Enantiomer separation of 62 mg of the racemate from Example 422 according to Method 13D gave 12 mg of the title compound from Example 531, 13 mg of the title compound from Example 532, 13 mg of the title compound from Example 533 and 13 mg of the title compound from Example 534.

HPLC (Method 10E): $R_t$=9.45 min, >98.0% ee;
LC-MS (Method 9B): $R_t$=1.01 min; MS (ESIpos): m/z=441 [M+H]$^+$.

Example 532

(3-Hydroxypyrrolidin-1-yl){3-(3-methyl-1,2,4-oxadiazol-5-yl)-5-[4-(trifluoromethoxy)phenyl]-piperidin-1-yl}methanone [enantiomerically pure cis isomer]

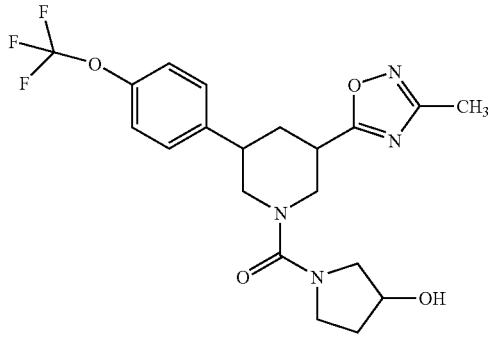

Enantiomer separation of 62 mg of the racemate from Example 422 according to Method 13D gave 12 mg of the title compound from Example 531, 13 mg of the title compound from Example 532, 13 mg of the title compound from Example 533 and 13 mg of the title compound from Example 534.

HPLC (Method 10E): $R_t$=17.75 min, >98.0% ee;
LC-MS (Method 9B): $R_t$=1.01 min; MS (ESIpos): m/z=441 [M+H]$^+$.

Example 533

(3-Hydroxypyrrolidin-1-yl){3-(3-methyl-1,2,4-oxadiazol-5-yl)-5-[4-(trifluoromethoxy)phenyl]-piperidin-1-yl}methanone [enantiomerically pure cis isomer]

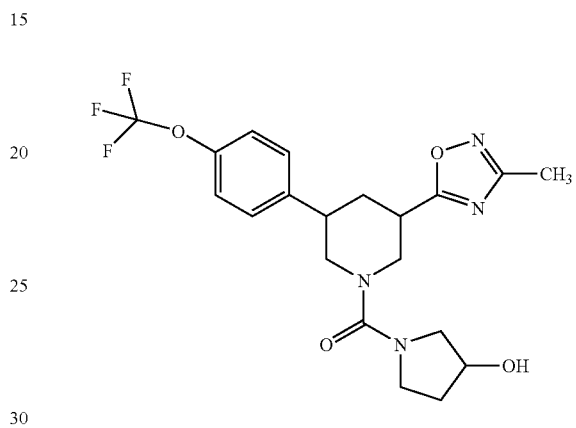

Enantiomer separation of 62 mg of the racemate from Example 422 according to Method 13D gave 12 mg of the title compound from Example 531, 13 mg of the title compound from Example 532, 13 mg of the title compound from Example 533 and 13 mg of the title compound from Example 534.

HPLC (Method 10E): $R_t$=22.22 min, >98.0% ee;
LC-MS (Method 9B): $R_t$=1.01 min; MS (ESIpos): m/z=441 [M+H]$^+$.

Example 534

(3-Hydroxypyrrolidin-1-yl){3-(3-methyl-1,2,4-oxadiazol-5-yl)-5-[4-(trifluoromethoxy)phenyl]-piperidin-1-yl}methanone [enantiomerically pure cis isomer]

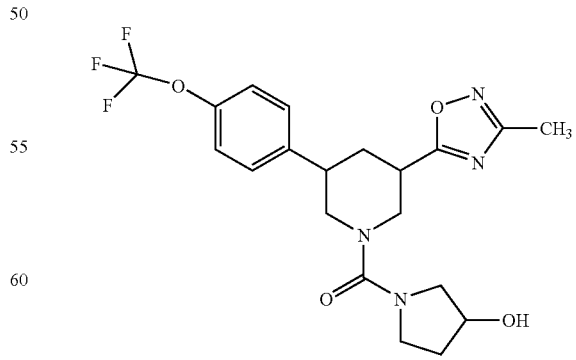

Enantiomer separation of 62 mg of the racemate from Example 422 according to Method 13D gave 12 mg of the title compound from Example 531, 13 mg of the title compound from Example 532, 13 mg of the title compound from Example 533 and 13 mg of the title compound from Example 534.

HPLC (Method 10E): $R_t$=42.69 min, >98.0% ee;
LC-MS (Method 9B): $R_t$=1.01 min; MS (ESIpos): m/z=441 [M+H]$^+$.

Example 535

{3-(3-Ethyl-1,2,4-oxadiazol-5-yl)-5-[4-(trifluoromethoxy)phenyl]piperidin-1-yl}(3-hydroxy-pyrrolidin-1-yl)methanone [enantiomerically pure cis isomer]

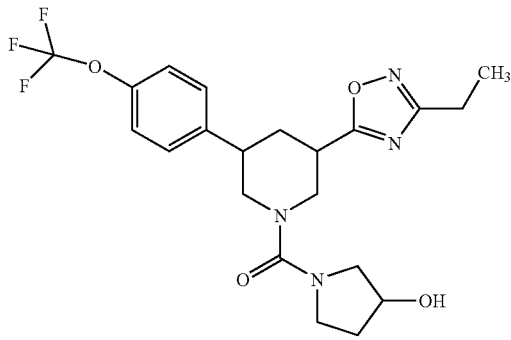

Enantiomer separation of 61 mg of the racemate from Example 421 according to Method 13D gave 13 mg of the title compound from Example 535, 13 mg of the title compound from Example 536, 13 mg of the title compound from Example 537 and 13 mg of the title compound from Example 538.

HPLC (Method 10E): $R_t$=7.49 min, >98.0% ee;
LC-MS (Method 9B): $R_t$=1.07 min; MS (ESIpos): m/z=455 [M+H]$^+$.

Example 536

{3-(3-Ethyl-1,2,4-oxadiazol-5-yl)-5-[4-(trifluoromethoxy)phenyl]piperidin-1-yl}(3-hydroxy-pyrrolidin-1-yl)methanone [enantiomerically pure cis isomer]

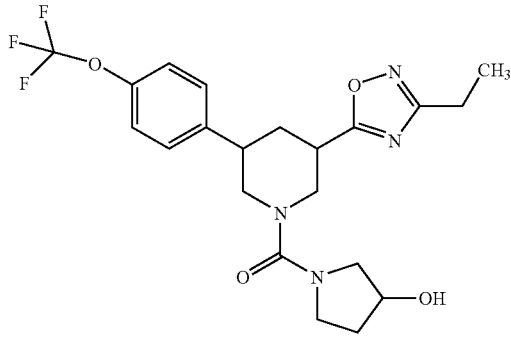

Enantiomer separation of 61 mg of the racemate from Example 421 according to Method 13D gave 13 mg of the title compound from Example 535, 13 mg of the title compound from Example 536, 13 mg of the title compound from Example 537 and 13 mg of the title compound from Example 538.

HPLC (Method 10E): $R_t$=13.79 min, >98.0% ee;
LC-MS (Method 9B): $R_t$=1.07 min; MS (ESIpos): m/z=455 [M+H]$^+$.

Example 537

{3-(3-Ethyl-1,2,4-oxadiazol-5-yl)-5-[4-(trifluoromethoxy)phenyl]piperidin-1-yl}(3-hydroxy-pyrrolidin-1-yl)methanone [enantiomerically pure cis isomer]

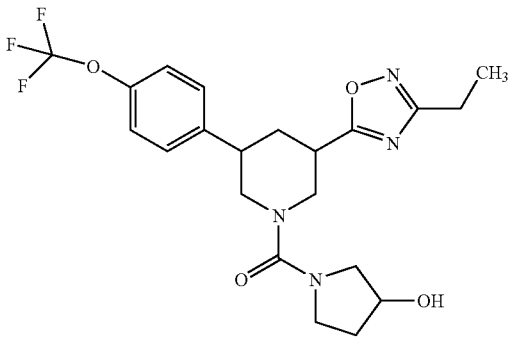

Enantiomer separation of 61 mg of the racemate from Example 421 according to Method 13D gave 13 mg of the title compound from Example 535, 13 mg of the title compound from Example 536, 13 mg of the title compound from Example 537 and 13 mg of the title compound from Example 538.

HPLC (Method 10E): $R_t$=17.99 min, >98.0% ee;
LC-MS (Method 9B): $R_t$=1.07 min; MS (ESIpos): m/z=455 [M+H]$^+$.

Example 538

{3-(3-Ethyl-1,2,4-oxadiazol-5-yl)-5-[4-(trifluoromethoxy)phenyl]piperidin-1-yl}(3-hydroxy-pyrrolidin-1-yl)methanone [enantiomerically pure cis isomer]

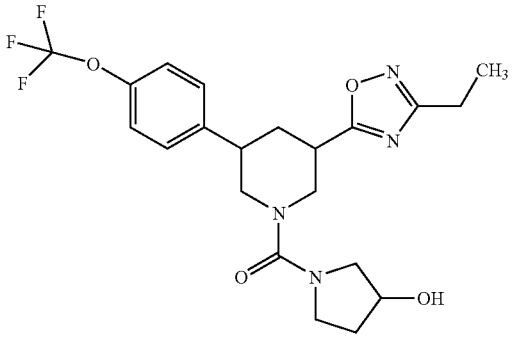

Enantiomer separation of 61 mg of the racemate from Example 421 according to Method 13D gave 13 mg of the title compound from Example 535, 13 mg of the title compound from Example 536, 13 mg of the title compound from Example 537 and 13 mg of the title compound from Example 538.

HPLC (Method 10E): $R_t$=23.43 min, >98.0% ee;
LC-MS (Method 9B): $R_t$=1.07 min; MS (ESIpos): m/z=455 [M+H]$^+$.

Example 539

(3-Hydroxypyrrolidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

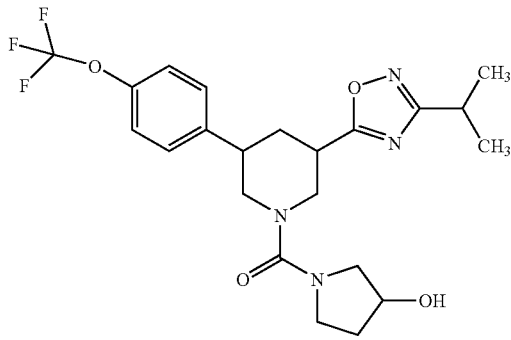

Enantiomer separation of 117 mg of the racemate from Example 418 according to Method 13D gave 26 mg of the title compound from Example 539, 26 mg of the title compound from Example 540, 25 mg of the title compound from Example 541 and 24 mg of the title compound from Example 542.

HPLC (Method 10E): $R_t$=5.64 min, >99.0% ee;
LC-MS (Method 9B): $R_t$=1.13 min; MS (ESIpos): m/z=469 [M+H]$^+$.
$^1$H-NMR (400 MHz, DMSO-d$_6$): δ=7.47 (d, 2H), 7.32 (d, 2H), 4.88 (d, 1H), 4.25-4.18 (m, 1H), 4.04 (br d, 1H), 3.70 (br d, 1H), 3.45-3.88 (m, 2H), 3.13-2.98 (m, 4H), 2.88 (dd, 1H), 1.95 (dd, 1H), 1.88-1.78 (m, 1H), 1.76-1.68 (m, 1H), 1.25 (d, 6H).

Example 540

(3-Hydroxypyrrolidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

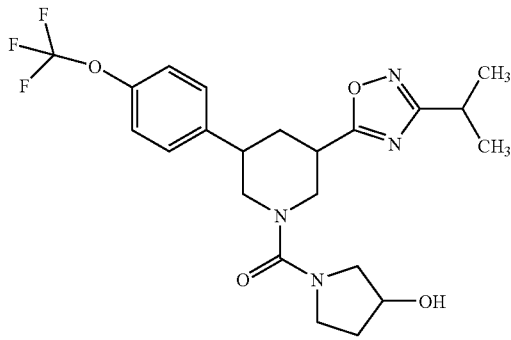

Enantiomer separation of 117 mg of the racemate from Example 418 according to Method 13D gave 26 mg of the title compound from Example 539, 26 mg of the title compound from Example 540, 25 mg of the title compound from Example 541 and 24 mg of the title compound from Example 542.

HPLC (Method 10E): $R_t$=8.47 min, >99.0% ee;
LC-MS (Method 9B): $R_t$=1.13 min; MS (ESIpos): m/z=469 [M+H]$^+$.
$^1$H-NMR (400 MHz, DMSO-d$_6$): δ=7.47 (d, 2H), 7.32 (d, 2H), 4.88 (d, 1H), 4.24-4.18 (m, 1H), 4.05 (br d, 1H), 3.67 (br d, 1H), 3.52-3.37 (m, 4H), 3.12-2.89 (m, 5H), 2.32 (br d, 1H), 1.97 (dd, 1H), 1.87-1.77 (m, 1H), 1.76.1.67 (m, 1H), 1.26 (d, 6H).

Example 541

(3-Hydroxypyrrolidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

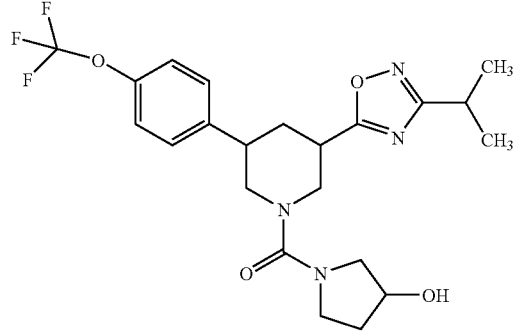

Enantiomer separation of 117 mg of the racemate from Example 418 according to Method 13D gave 26 mg of the title compound from Example 539, 26 mg of the title compound from Example 540, 25 mg of the title compound from Example 541 and 24 mg of the title compound from Example 542.

HPLC (Method 10E): $R_t$=12.34 min, >99.0% ee;
LC-MS (Method 9B): $R_t$=1.13 min; MS (ESIpos): m/z=469 [M+H]$^+$.
$^1$H-NMR (400 MHz, DMSO-d$_6$): δ=7.47 (d, 2H), 7.32 (d, 2H), 4.88 (d, 1H), 4.24-4.18 (m, 1H), 4.05 (br d, 1H), 3.67 (br d, 1H), 3.52-3.37 (m, 4H), 3.12-2.89 (m, 5H), 2.32 (br d, 1H), 1.97 (dd, 1H), 1.87-1.77 (m, 1H), 1.76.1.67 (m, 1H), 1.26 (d, 6H).

Example 542

(3-Hydroxypyrrolidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

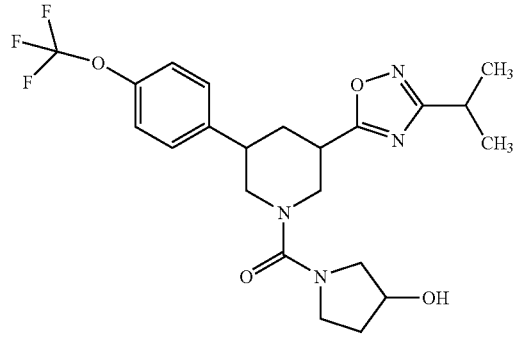

Enantiomer separation of 117 mg of the racemate from Example 418 according to Method 13D gave 26 mg of the title compound from Example 539, 26 mg of the title compound from Example 540, 25 mg of the title compound from Example 541 and 24 mg of the title compound from Example 542.

HPLC (Method 10E): $R_t$=13.96 min, >99.0% ee;
LC-MS (Method 9B): $R_t$=1.13 min; MS (ESIpos): m/z=469 [M+H]$^+$.

$^1$H-NMR (400 MHz, DMSO-d$_6$): δ=7.47 (d, 2H), 7.32 (d, 2H), 4.88 (d, 1H), 4.25-4.18 (m, 1H), 4.04 (br d, 1H), 3.70 (br d, 1H), 3.45-3.88 (m, 2H), 3.13-2.98 (m, 4H), 2.88 (dd, 1H), 1.95 (dd, 1H), 1.88-1.78 (m, 1H), 1.76-1.68 (m, 1H), 1.25 (d, 6H).

Example 543

{3-(3-Ethyl-1,2,4-oxadiazol-5-yl)-5-[4-(trifluoromethoxy)phenyl]piperidin-1-yl}(4-hydroxy-piperidin-1-yl)methanone [enantiomerically pure cis isomer]

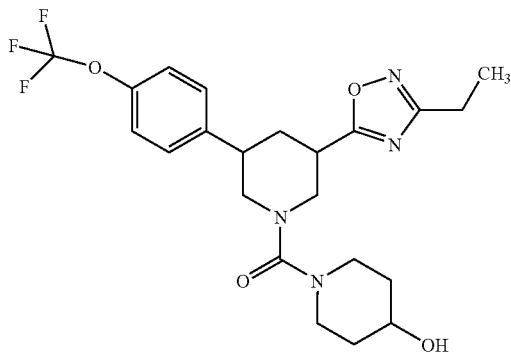

Enantiomer separation of 100 mg of the racemate from Example 526 according to Method 16D gave 35 mg of the title compound from Example 543 and 36 mg of the title compound from Example 544.

HPLC (Method 16E): $R_t$=5.02 min, >99.0% ee;
LC-MS (Method 9B): $R_t$=1.09 min; MS (ESIpos): m/z=469 [M+H]$^+$.

Example 544

{3-(3-Ethyl-1,2,4-oxadiazol-5-yl)-5-[4-(trifluoromethoxy)phenyl]piperidin-1-yl}(4-hydroxy-piperidin-1-yl)methanone [enantiomerically pure cis isomer]

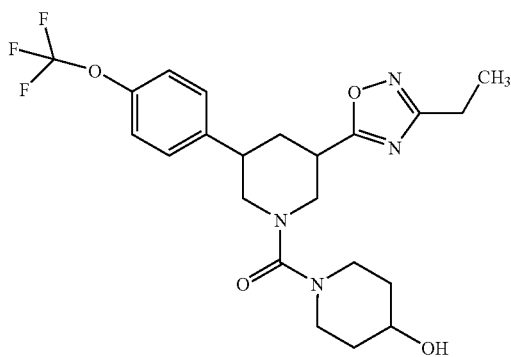

Enantiomer separation of 100 mg of the racemate from Example 526 according to Method 16D gave 35 mg of the title compound from Example 543 and 36 mg of the title compound from Example 544.

HPLC (Method 16E): $R_t$=11.23 min, >99.0% ee;
LC-MS (Method 9B): $R_t$=1.09 min; MS (ESIpos): m/z=469 [M+H]$^+$.

Example 545

(3-Hydroxypyrrolidin-1-yl){3-[3-(2-methoxyethyl)-1,2,4-oxadiazol-5-yl]-5-[4-(trifluoromethoxy)-phenyl]piperidin-1-yl}methanone [enantiomerically pure cis isomer]

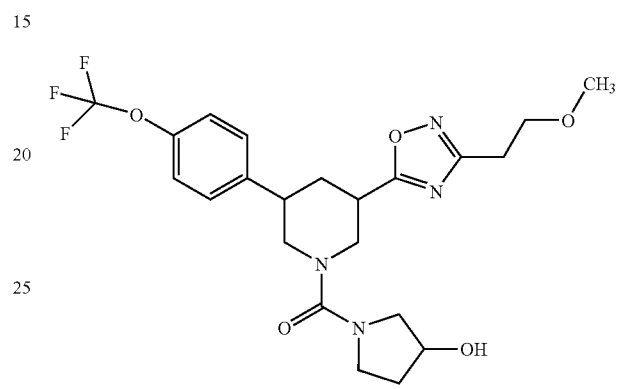

Enantiomer separation of 53 mg of the racemate from Example 420 according to Method 13D gave 13 mg of the title compound from Example 545, 13 mg of the title compound from Example 546, 11 mg of the title compound from Example 547 and 11 mg of the title compound from Example 548.

HPLC (Method 16E): $R_t$=6.45 min, >99.0% ee;
LC-MS (Method 9B): $R_t$=1.02 min; MS (ESIpos): m/z=485 [M+H]$^+$.

$^1$H-NMR (400 MHz, DMSO-d$_6$): δ=7.46 (d, 2H), 7.32 (d, 2H), 4.88 (d, 1H), 4.18-4.25 (m, 1H), 4.04 (br d, 1H), 3.72 (br d, 1H), 3.67 (t, 2H), 3.56-3.43 (m, 2H), 3.23 (s, 3H), 3.11 (br d, 1H), 3.05-2.97 (m, 2H), 2.93 (t, 2H), 2.87 (dd, 1H), 2.35 (br d, 1H), 1.97 (dd, 1H), 1.88-1.77 (m, 1H), 1.75-1.68 (m, 1H).

Example 546

(3-Hydroxypyrrolidin-1-yl){3-[3-(2-methoxyethyl)-1,2,4-oxadiazol-5-yl]-5-[4-(trifluoromethoxy)-phenyl]piperidin-1-yl}methanone [enantiomerically pure cis isomer]

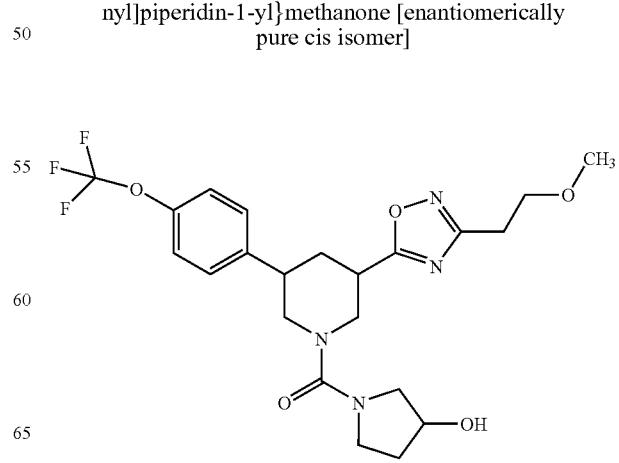

Enantiomer separation of 53 mg of the racemate from Example 420 according to Method 13D gave 13 mg of the title compound from Example 545, 13 mg of the title compound from Example 546, 11 mg of the title compound from Example 547 and 11 mg of the title compound from Example 548.

HPLC (Method 16E): $R_t$=5.76 min, >99.0% ee;

LC-MS (Method 9B): $R_t$=1.02 min; MS (ESIpos): m/z=485 [M+H]$^+$.

$^1$H-NMR (400 MHz, DMSO-$d_6$): δ=7.47 (d, 2H), 7.33 (d, 2H), 4.87 (d, 1H), 4.24-4.17 (m, 1H), 4.06 (d, 1H), 3.69-3.65 (m, 3H), 3.52-3.40 (m, 3H), 3.23 (s, 3H), 3.09 (br d, 1H), 3.00-2.92 (m, 5H), 2.31 (br d, 1H), 1.97 (dd, 1H), 1.87-1.76 (m, 1H), 1.75-1.67 (m, 1H).

Example 547

(3-Hydroxypyrrolidin-1-yl){3-[3-(2-methoxyethyl)-1,2,4-oxadiazol-5-yl]-5-[4-(trifluoromethoxy)-phenyl]piperidin-1-yl}methanone [enantiomerically pure cis isomer]

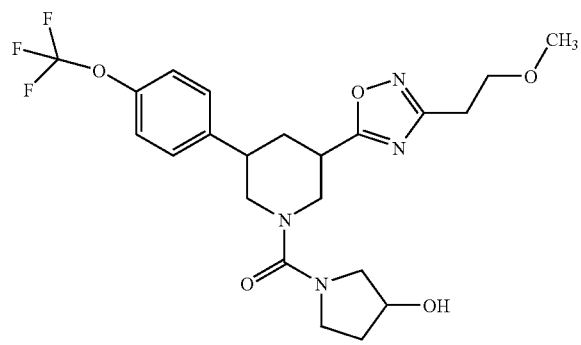

Enantiomer separation of 53 mg of the racemate from Example 420 according to Method 13D gave 13 mg of the title compound from Example 545, 13 mg of the title compound from Example 546, 11 mg of the title compound from Example 547 and 11 mg of the title compound from Example 548.

HPLC (Method 16E): $R_t$=8.94 min, >99.0% ee;

LC-MS (Method 9B): $R_t$=1.02 min; MS (ESIpos): m/z=485 [M+H]$^+$.

$^1$H-NMR (400 MHz, DMSO-$d_6$): δ=7.46 (d, 2H), 7.32 (d, 2H), 4.88 (d, 1H), 4.18-4.25 (m, 1H), 4.04 (br d, 1H), 3.72 (br d, 1H), 3.67 (t, 2H), 3.56-3.43 (m, 2H), 3.23 (s, 3H), 3.11 (br d, 1H), 3.05-2.97 (m, 2H), 2.93 (t, 2H), 2.87 (dd, 1H), 2.35 (brd, 1H), 1.97 (dd, 1H), 1.88-1.77 (m, 1H), 1.75-1.68 (m, 1H).

Example 548

(3-Hydroxypyrrolidin-1-yl){3-[3-(2-methoxyethyl)-1,2,4-oxadiazol-5-yl]-5-[4-(trifluoromethoxy)-phenyl]piperidin-1-yl}methanone [enantiomerically pure cis isomer]

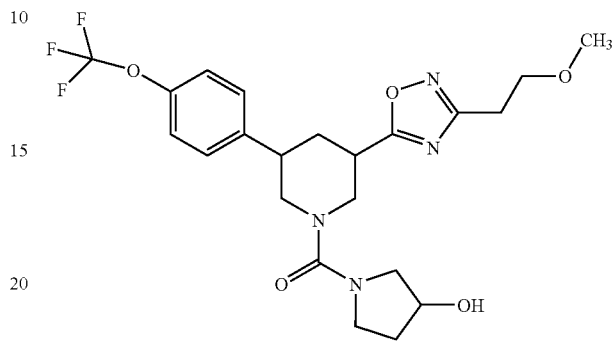

Enantiomer separation of 53 mg of the racemate from Example 420 according to Method 13D gave 13 mg of the title compound from Example 545, 13 mg of the title compound from Example 546, 11 mg of the title compound from Example 547 and 11 mg of the title compound from Example 548.

HPLC (Method 16E): $R_t$=11.45 min, >99.0% ee;

LC-MS (Method 9B): $R_t$=1.02 min; MS (ESIpos): m/z=485 [M+H]$^+$.

$^1$H-NMR (400 MHz, DMSO-$d_6$): δ=7.47 (d, 2H), 7.33 (d, 2H), 4.87 (d, 1H), 4.24-4.17 (m, 1H), 4.06 (d, 1H), 3.69-3.65 (m, 3H), 3.52-3.40 (m, 3H), 3.23 (s, 3H), 3.09 (br d, 1H), 3.00-2.92 (m, 5H), 2.31 (br d, 1H), 1.97 (dd, 1H), 1.87-1.76 (m, 1H), 1.75-1.67 (m, 1H).

Example 549

{3-(4-Ethylphenyl)-5-[3-(2-methoxyethyl)-1,2,4-oxadiazol-5-yl]piperidin-1-yl}(4-hydroxy-piperidin-1-yl)methanone [enantiomerically pure cis isomer]

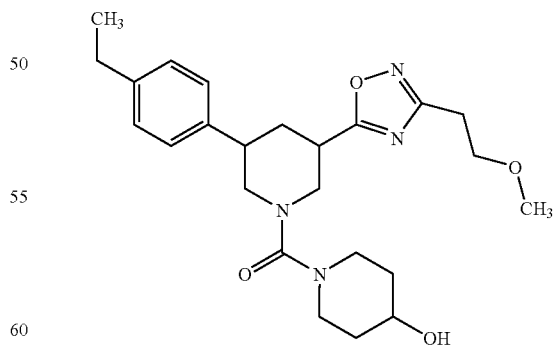

The enantiomer separation of 394 mg (0.9 mmol) of the compound from Example 183 according to Method 22D gave 190 mg of the title compound from Example 549 (Enantiomer 1) and 183 mg of the title compound from Example 550 (Enantiomer 2).

HPLC (Method 15E): R$_t$=5.12 min, >99.0% ee;
LC-MS (Method 9B): R$_t$=1.04 min; MS (ESIpos): m/z=443 [M+H]$^+$;
$^1$H-NMR (400 MHz, DMSO-d$_6$): δ=7.21 (d, 2H), 7.16 (d, 2H), 4.68 (d, OH), 3.95 (br d, 1H), 3.68 (t, 2H), 3.66-3.59 (m, 1H), 3.55 (br d, 1H), 3.49-3.46 (m, 2H), 3.42-3.34 (m, 1H), 3.23 (s, 3H), 3.01-2.85 (m, 7H), 2.57 (q, 2H), 2.29 (br d, 1H), 1.94 (q, 1H), 1.73-1.70 (m, 2H), 1.35-1.25 (m, 2H), 1.16 (t, 3H).

Example 550

{3-(4-Ethylphenyl)-5-[3-(2-methoxyethyl)-1,2,4-oxadiazol-5-yl]piperidin-1-yl}(4-hydroxy-piperidin-1-yl)methanone [enantiomerically pure cis isomer]

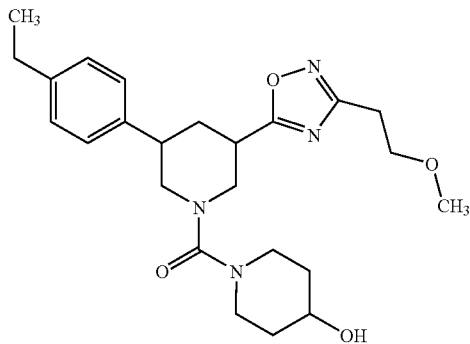

The enantiomer separation of 394 mg (0.9 mmol) of the compound from Example 183 according to Method 22D gave 190 mg of the title compound from Example 549 (Enantiomer 1) and 183 mg of the title compound from Example 550 (Enantiomer 2).

HPLC (Method 15E): R$_t$=7.47 min, >99.0% ee;
LC-MS (Method 9B): R$_t$=1.04 min; MS (ESIpos): m/z=443 [M+H]$^+$;
$^1$H-NMR (400 MHz, DMSO-d$_6$): δ=7.21 (d, 2H), 7.17 (d, 2H), 4.68 (d, OH), 3.94 (br d, 1H), 3.68 (t, 2H), 3.63-3.58 (m, 1H), 3.55 (br d, 1H), 3.49-3.46 (m, 2H), 3.41-3.35 (m, 1H), 3.23 (s, 3H), 3.01-2.85 (m, 7H), 2.57 (q, 2H), 2.28 (br d, 1H), 1.95 (q, 1H), 1.73-1.70 (m, 2H), 1.35-1.26 (m, 2H), 1.16 (t, 3H).

Example 551

(3-Hydroxypyrrolidin-1-yl){3-[3-(methoxymethyl)-1,2,4-oxadiazol-5-yl]-5-[4-(trifluoromethoxy)-phenyl]piperidin-1-yl}methanone [enantiomerically pure cis isomer]

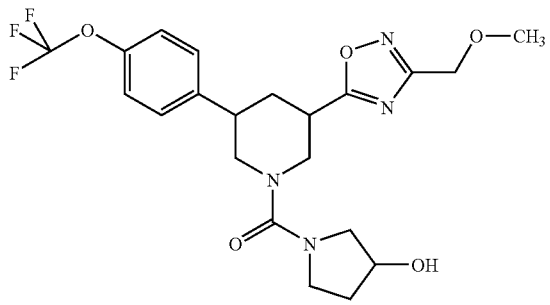

Enantiomer separation of 34 mg of the racemate from Example 512 according to Method 21D gave 17 mg of the title compound from Example 551, 16 mg of the title compound from Example 552, 17 mg of the title compound from Example 553 and 17 mg of the title compound from Example 554.

HPLC (Method 18E): R$_t$=5.07 min, >99.0% ee;
LC-MS (Method 9B): R$_t$=1.02 min; MS (ESIpos): m/z=471 [M+H]$^+$.
$^1$H-NMR (400 MHz, DMSO-d$_6$): δ=7.47 (d, 2H), 7.32 (d, 2H), 4.88 (d, 1H), 4.53 (d, 2H), 4.24-4.18 (m, 1H), 4.07 (br d, 1H), 3.68 (br d, 1H), 3.34 (s, 3H), 3.55-3.40 (m, 3H), 3.09 (br d, 1H), 3.00-2.85 (m, 3H), 2.33 (br d, 1H), 1.99 (dd, 1H), 1.87-1.77 (m, 1H), 1.76-1.68 (m, 1H).

Example 552

(3-Hydroxypyrrolidin-1-yl){3-[3-(methoxymethyl)-1,2,4-oxadiazol-5-yl]-5-[4-(trifluoromethoxy)-phenyl]piperidin-1-yl}methanone [enantiomerically pure cis isomer]

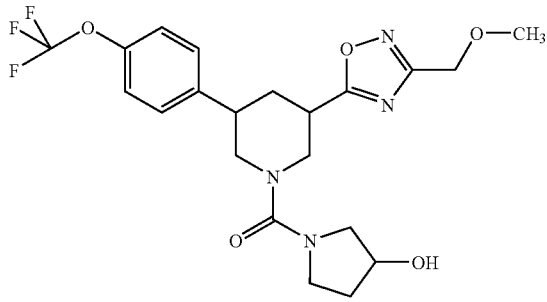

Enantiomer separation of 34 mg of the racemate from Example 512 according to Method 21D gave 17 mg of the title compound from Example 551, 16 mg of the title compound from Example 552, 17 mg of the title compound from Example 553 and 17 mg of the title compound from Example 554.

HPLC (Method 18E): R$_t$=5.78 min, >99.0% ee;
LC-MS (Method 9B): R$_t$=1.02 min; MS (ESIpos): m/z=471 [M+H]$^+$.
$^1$H-NMR (400 MHz, DMSO-d$_6$): δ=7.47 (d, 2H), 7.33 (d, 2H), 4.88 (d, 1H), 4.53 (d, 2H), 4.25-4.19 (m, 1H), 4.05 (br d, 1H), 3.70 (br d, 1H), 3.52-3.45 (m, 2H), 3.42-3.35 (m, 1H), 3.34 (s, 3H), 3.11 (br d, 1H), 3.03 (dd, 2H), 2.86 (dd, 1H), 2.35 (br d, 1H), 1.98 (dd, 1H), 1.88-1.78 (m, 1H), 1.78-1.68 (m, 1H).

Example 553

(3-Hydroxypyrrolidin-1-yl){3-[3-(methoxymethyl)-1,2,4-oxadiazol-5-yl]-5-[4-(trifluoromethoxy)-phenyl]piperidin-1-yl}methanone [enantiomerically pure cis isomer]

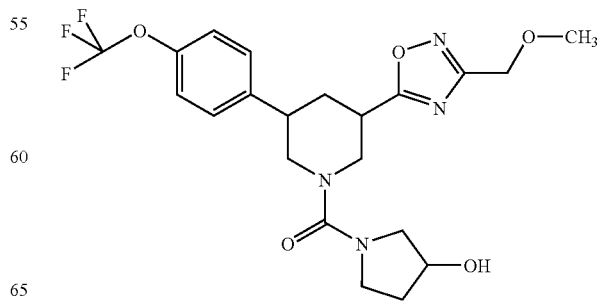

Enantiomer separation of 34 mg of the racemate from Example 512 according to Method 21D gave 17 mg of the title compound from Example 551, 16 mg of the title compound from Example 552, 17 mg of the title compound from Example 553 and 17 mg of the title compound from Example 554.

HPLC (Method 18E): $R_t$=8.62 min, >99.0% ee;

LC-MS (Method 9B): $R_t$=1.02 min; MS (ESIpos): m/z=471 [M+H]$^+$.

$^1$H-NMR (400 MHz, DMSO-d$_6$): δ=7.47 (d, 2H), 7.33 (d, 2H), 4.88 (d, 1H), 4.53 (d, 2H), 4.25-4.19 (m, 1H), 4.05 (br d, 1H), 3.70 (br d, 1H), 3.52-3.45 (m, 2H), 3.42-3.35 (m, 1H), 3.34 (s, 3H), 3.11 (br d, 1H), 3.03 (dd, 2H), 2.86 (dd, 1H), 2.35 (br d, 1H), 1.98 (dd, 1H), 1.88-1.78 (m, 1H), 1.78-1.68 (m, 1H).

Example 554

(3-Hydroxypyrrolidin-1-yl){3-[3-(methoxymethyl)-1,2,4-oxadiazol-5-yl]-5-[4-(trifluoromethoxy)-phenyl]piperidin-1-yl}methanone [enantiomerically pure cis isomer]

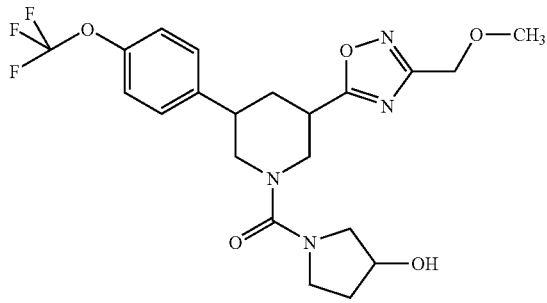

Enantiomer separation of 34 mg of the racemate from Example 512 according to Method 21D gave 17 mg of the title compound from Example 551, 16 mg of the title compound from Example 552, 17 mg of the title compound from Example 553 and 17 mg of the title compound from Example 554.

HPLC (Method 18E): $R_t$=12.78 min, >99.0% ee;

LC-MS (Method 9B): $R_t$=1.02 min; MS (ESIpos): m/z=471 [M+H]$^+$.

$^1$H-NMR (400 MHz, DMSO-d$_6$): δ=7.47 (d, 2H), 7.32 (d, 2H), 4.88 (d, 1H), 4.53 (d, 2H), 4.24-4.18 (m, 1H), 4.07 (br d, 1H), 3.68 (br d, 1H), 3.34 (s, 3H), 3.55-3.40 (m, 3H), 3.09 (br d, 1H), 3.00-2.85 (m, 3H), 2.33 (br d, 1H), 1.99 (dd, 1H), 1.87-1.77 (m, 1H), 1.76-1.68 (m, 1H).

Example 555

(3-Hydroxyazetidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

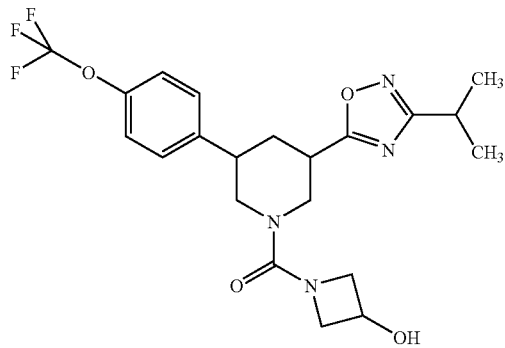

Enantiomer separation of 28 mg of the racemate from Example 529 according to Method 20D gave 10 mg of the title compound from Example 555 and 9 mg of the title compound from Example 556.

HPLC (Method 17E): $R_t$=4.14 min, >99.0% ee;

LC-MS (Method 9B): $R_t$=1.12 min; MS (ESIpos): m/z=455 [M+H]$^+$.

Example 556

(3-Hydroxyazetidin-1-yl){3-[3-(propan-2-yl)-1,2,4-oxadiazol-5-yl]-5-[4-(trifluoromethoxy)-phenyl]piperidin-1-yl}methanone [enantiomerically pure cis isomer]

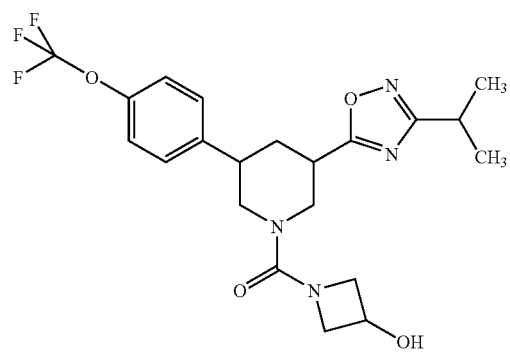

Enantiomer separation of 28 mg of the racemate from Example 529 according to Method 20D gave 10 mg of the title compound from Example 555 and 9 mg of the title compound from Example 556.

HPLC (Method 17E): $R_t$=4.96 min, >99.0% ee;

LC-MS (Method 9B): $R_t$=1.12 min; MS (ESIpos): m/z=455 [M+H]$^+$.

B) Assessment of the Physiological Activity

Abbreviations:

BSA bovine serum albumin

DMEM Dulbecco's Modified Eagle Medium

EGTA ethylene glycol-bis-(2-aminoethylether)-N,N,N',N'-tetraacetic acid

FCS fetal calf serum

HEPES 4-(2-hydroxyethyl)-1-piperazineethanesulphonic acid

[3H]haTRAP tritiated high affinity thrombin receptor activating peptide

PRP platelet-rich plasma

The suitability of the compounds according to the invention for treating thromboembolic disorders can be demonstrated using the following assay systems:

1.) In Vitro Assays
1.a) Cellular Functional In vitro Test

A recombinant cell line is used to identify agonists of the human protease activated receptor 1 (PAR1) and to quantify the activity of the substances described herein. The cell is originally derived from a human embryonal kidney cell (HEK293; ATCC: American Type Culture Collection, Manassas, Va. 20108, USA). The test cell line constitutively expresses a modified form of the calcium-sensitive photoprotein aequorin which, after reconstitution with the cofactor coelenterazine, emits light when the free calcium concentration in the inner mitochondrial compartment is increased (Rizzuto R, Simpson A W, Brini M, Pozzan T.; *Nature* 1992, 358, 325-327). Additionally, the cell stably expresses the endogenous human PAR1 receptor and the endogenous purinergic receptor P2Y2. The resulting PAR1 test cell responds to stimulation of the endogenous PAR1 or P2Y2 receptor with an intracellular release of calcium ions, which can be quantified through resulting aequorin luminescence with a suitable luminometer (Milligan G, Marshall F, Rees S, *Trends in Pharmacological Sciences* 1996, 17, 235-237).

For testing the substance specificity, its effect after activation of the endogenous PAR1 receptor is compared to the effect after activation of the endogenous purinergic P2Y2 receptor which utilizes the same intracellular signal path.

Test procedure: The cells are plated out two days (48 hours) before the test in culture medium (DMEM F12, supplemented with 10% FCS, 2 mM glutamine, 20 mM HEPES, 1.4 mM pyruvate, 0.1 mg/ml gentamycin, 0.15% Na bicarbonate; BioWhittaker Cat.# BE04-687Q; B-4800 Verviers, Belgium) in 384-well microtitre plates and kept in a cell incubator (96% atmospheric humidity, 5% V/V $CO_2$, 37° C.). On the day of the test, the culture medium is replaced by a tyrode solution (in mM: 140NaCl, 5l KCl, 1$MgCl_2$, 2$CaCl_2$, 20 glucose, 20 HEPES), which additionally contains the cofactor coelenterazine (25 µM) and glutathione (4 mM), and the microtitre plate is then incubated for a further 3-4 hours. The test substances are then pipetted onto the microtitre plate, and 5 minutes after the transfer of the test substances into the wells of the microtitre plate the plate is transferred into the luminometer, a PAR1 agonist concentration which corresponds to the $EC_{50}$ is added and the resulting light signal is immediately measured in the luminometer. To distinguish an antagonist substance action from a toxic action, the endogenous purinergic receptor is immediately subsequently activated with agonist (ATP, final concentration 10 µM) and the resulting light signal is measured. The results are shown in Table A:

TABLE A

| Example No. | $IC_{50}$ [nM] |
|---|---|
| 28 | 28 |
| 37 | 21 |
| 38 | 31 |
| 39 | 6.8 |
| 60 | 10 |
| 113 | 47 |
| 119 | 68 |
| 144 | 8.51 |
| 146 | 9.39 |
| 148 | 14 |
| 150 | 19 |
| 152 | 48.1 |
| 159 | 4.61 |
| 160 | 5.4 |
| 169 | 6.74 |
| 170 | 18.8 |
| 178 | 17.05 |
| 181 | 28.8 |
| 183 | 31.5 |
| 187 | 53.4 |
| 194 | 66.1 |
| 197 | 77.5 |
| 212 | 142 |
| 229 | 1.72 |
| 230 | 2.81 |
| 232 | 6.44 |
| 234 | 15.4 |
| 239 | 5.74 |
| 249 | 13.1 |
| 260 | 11.4 |
| 275 | 10.3 |
| 276 | 25.3 |
| 279 | 14.7 |
| 283 | 14.9 |
| 284 | 9.73 |
| 322 | 3.01 |
| 329 | 24 |
| 330 | 87.8 |
| 335 | 25.1 |
| 352 | 4.77 |
| 356 | 2.73 |
| 368 | 11.7 |
| 420 | 23.8 |
| 449 | 86.3 |
| 451 | 19.6 |
| 454 | 47.5 |
| 459 | 84.2 |
| 465 | 24.4 |
| 470 | 4.16 |
| 474 | 23.4 |
| 484 | 76.6 |
| 487 | 107 |
| 490 | 25.1 |
| 494 | 5.67 |
| 495 | 3.51 |
| 513 | 5.16 |
| 519 | 20.8 |
| 520 | 11 |
| 549 | 12.5 |
| 559 | 49.8 |
| 561 | 5.76 |

1.b) PAR-1 Receptor Binding Assay

Platelet membranes are incubated with 12 nM [3H]ha-TRAP and test substance in various concentrations in a buffer (50 mM Tris pH 7.5, 10 mM magnesium chloride, 1 mM EGTA, 0.1% BSA) at room temperature for 80 min. The reaction mixture is then transferred onto a filter plate and washed twice with buffer. After addition of scintillation liquid, the radioactivity on the filter is measured in a beta counter.

1.c) Platelet Aggregation in Plasma

To determine the platelet aggregation, blood of healthy volunteers of both sexes who had not received any thrombocyte aggregation-influencing medication for the last ten days is used. The blood is drawn into monovettes (Sarstedt, Nümbrecht, Germany) which contain, as anticoagulant, sodium citrate 3.8% (1 part of citrate+9 parts of blood). To obtain platelet-rich plasma, the citrated whole blood is centrifuged at 140 g for 20 min.

For the aggregation measurements, aliquots of the platelet-rich plasma are incubated with increasing concentrations of test substance at 37° C. for 10 min. Aggregation is then triggered by addition of a thrombin receptor agonist (TRAP6, SFLLRN) in an aggregometer and determined at 37° C. using the turbidimetric method according Born (Born, G. V. R., Cross M. J., The Aggregation of Blood Platelets; *J. Physiol.* 1963, 168, 178-195). The SFLLRN concentration giving maximum aggregation is individually determined for each donor.

To calculate the inhibitory effect, the increase of light transmission (amplitude of the aggregation curve in %) is determined 5 minutes after addition of the agonist in the presence and absence of test substance, and the inhibition is calculated. The concentration at which the aggregation is 50% inhibited is calculated from the inhibition curves. The results are shown in Table B:

TABLE B

| Ex. No. | IC$_{50}$ [μM] |
|---|---|
| 38 | 93 |
| 39 | 5.6 |
| 60 | 19.6 |

1.d) Platelet Aggregation in Buffer

To determine the platelet aggregation, blood of healthy volunteers of both sexes who had not received any thrombocyte aggregation-influencing medication for the last ten days is used. The blood is drawn into monovettes (Sarstedt, Nümbrecht, Germany) which contain, as anticoagulant, sodium citrate 3.8% (1 part of citrate+9 parts of blood). To obtain platelet-rich plasma, the citrated whole blood is centrifuged 140 g for 20 min. A quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. The platelets are resuspended in incubation buffer and adjusted to 200 000 cells/μl. Prior to the start of the test, calcium chloride and magnesium chloride, final concentration in each case 2 mM (2M stock solution, dilution 1:1000), are added. Note: in the case of ADP-induced aggregation, only calcium chloride is added. The following agonists can be used: TRAP6-trifluoroacetate salt, collagen, human α-thrombin and U-46619. For each donor, the concentration of the agonist is tested.

Test procedure: 96-well microtitre plates are used. The test substance is diluted in DMSO, and 2 μl per well is initially charged. 178 μl of platelet suspension are added, and the mixture is preincubated at room temperature for 10 minutes. 20 μl of agonist are added, and the measurement in the Spectramax, OD 405 nm, is started immediately. Kinetics are determined in 11 measurements of 1 minute each. Inbetween measurements, the mixture is shaken for 55 seconds.

1.e) Platelet Aggregation in Fibrinogen-depleted Plasma

To determine the platelet aggregation, blood of healthy volunteers of both sexes who had not received any platelet aggregation-influencing medication for the last ten days is used. The blood is drawn into monovettes (Sarstedt, Nümbrecht, Germany) which contain, as anticoagulant, sodium citrate 3.8% (1 part of citrate+9 parts of blood).

Preparation of fibrinogen-deleted plasma: To obtain platelet-poor plasma, the citrated whole blood is centrifuged at 140 g for 20 min. In a ratio of 1:25, reptilase (Roche Diagnostic, Germany) is added to the platelet-poor plasma, and the mixture is inverted carefully. This is followed by 10 min of incubation at 37° C. in a water bath, followed directly by 10 min of incubation on ice. The plasma/reptilase mixture is centrifuged at 1300 g for 15 min, and the supernatant (fibrinogen-depleted plasma) is obtained.

Platelet isolation: To obtain platelet-rich plasma, the citrated whole blood is centrifuged at 140 g for 20 min. A quarter of the volume of ACD buffer (44.8 mM sodium citrate, 20.9 mM citric acid, 74.1 mM glucose and 4 mM potassium chloride) is added to the PRP, and the mixture is centrifuged at 1300 g for 10 minutes. The platelet pellet is resuspended in wash buffer and centrifuged at 1300 g for 10 minutes. The platelets are resuspended in incubation buffer and adjusted to 400 000 cells/μl, and calcium chloride solution is added to a final concentration of 5 mM (dilution 1/200).

For the aggregation measurements, aliquots (98 μl of fibrinogen-depleted plasma and 80 μl of platelet suspension) with increasing concentrations of test substance are incubated at RT for 10 min. Aggregation is then triggered by addition of human alpha thrombin in an aggregometer and determined using the turbidimetric method according to Born (Born, G. V. R., Cross M. J., The Aggregation of Blood Platelets; *J. Physiol.* 1963, 168, 178-195) at 37° C. The alpha thrombin concentration just sufficient to cause maximum aggregation is determined individually for each donor.

To calculate the inhibitory activity, the increase of the maximum light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%.

1.f) Stimulation of Washed Platelets and Analysis in Flow Cytometry

Isolation of washed platelets: Human whole blood is obtained by venipuncture from voluntary donors and transfered into monovettes (Sarstedt, Nümbrecht, Germany) containing sodium citrate as anticoagulant (1 part of sodium citrate 3.8%+9 parts of whole blood). At 90° rotations per minute and 4° C., the monovettes are centrifuged for a period of 20 minutes (Heraeus Instruments, Germany; Megafuge 1.0RS). The platelet-rich plasma is carefully removed and transferred into a 50 ml Falcon tube. ACD buffer (44 mM sodium citrate, 20.9 mM citric acid, 74.1 mM glucose) is then added to the plasma. The volume of the ACD buffer corresponds to a quarter of the plasma volume. The platelets are sedimen-ted by ten minutes of centrifugation at 2500 rotations and 4° C. The supernatant is then carefully decanted and discarded. The precipitated platelets are initially carefully resuspended in one milliliter of wash buffer (113 mM sodium chloride, 4 mM disodium hydrogen phosphate, 24 mM sodium dihydrogen phosphate, 4 mM potassium chloride, 0.2 mM ethylene glycol-bis(2-aminoethyl)-N,N,N'N'-tetraacetic acid, 0.1% glucose) and then made up with wash buffer to a volume which corresponds to that of the amount of plasma. The wash procedure is repeated. The platelets are precipitated by another ten-minute centrifugation at 2500 rotations and 4° C. and then carefully resuspended in a milliliter of incubation buffer (134 mM sodium chloride, 12 mM sodium hydrogen carbonate, 2.9 mM potassium chloride, 0.34 mM sodium dihydrogen carbonate, 5 mM HEPES, 5 mM glucose, 2 mM calcium chloride and 2 mM magnesium chloride) and adjusted with incubation buffer to a concentration of 300 000 platelets per μl.

Staining and stimulation of the human platelets with human α-thrombin in the presence or absence of a PAR-1 antagonist: The platelets suspension is preincubated in the substance to be tested or the appropriate solvent at 37° C. for 10 minutens (Eppendorf, Germany; Thermomixer Comfort). Platelet activation is triggered by addition of the agonist (0.5 μM or 1 μM α-thrombin; Kordia, The Netherlands, 3281 NIH units/mg; or 30 μg/ml of thrombin receptor activating peptide (TRAP6); Bachem, Switzerland) at 37° and with shaking at 500 rotations per minute. At the time points 0, 1, 2.5, 5, 10 and 15 minutes, in each case one aliquot of 50 μl is removed and transferred into one milliliter of singly-concentrated Cell-FiX™ solution (Becton Dickinson Immunocytometry Systems, USA). To fixate the cells, they are incubated in the dark at 4° C. for 30 minutes. The platelets are precipitated by ten minutes of centrifugation at 600 g and 4° C. The supernatant is discarded, and the platelets are resuspended in 400 µl of CellWash™ (Becton Dickinson Immunocytometry Systems, USA). One aliquot of 100 µl is transferred into a new FACS tube. 1 µl of the platelet-identifying antibody and 1 µl of the activation state-detecting antibody are made up with Cell-Wash™ to a volume of 100 µl. This antibody solution is then added to the platelet suspension and incubated in the dark at 4° C. for 20 minutes. After staining, the reaction volume is increased by addition of a further 400 µl of CellWash™.

A fluorescein isothiocyanate-conjugated antibody directed against the human glycoprotein IIb (CD41) (Immunotech Coulter, France; Cat. No. 0649) is used to identify the platelets. With the aid of the phycoerythrin-conjugated antibody directed against the human glycoprotein P-selectin (Immunotech Coulter, France; Cat. No. 1759), it is possible to determine the activation state of the platelets. P-Selectin (CD62P) is localized in the α-granules of resting platelets. However, following in vitro or in vivo stimulation, it is translocated to the external plasma membrane.

Flow cytometry and data evaluation: The samples are measured in the FACSCalibur™ Flow Cytometry System instrument from Becton Dickinson Immunocytometry Systems, USA, and evaluation and graphic representation is carried out with the aid of the CellQuest software, Version 3.3 (Becton Dickinson Immunocytometry Systems, USA). The extent of platelet activation is determined via the percentage of CD62P-positive platelets (CD41-positive events). From each sample, 10 000 CD41-positive events are counted. The inhibitory activity of the substances to be tested is calculated via the reduction of platelet activation, which refers to the activation by the agonist.

1.g) Platelet Aggregation Measurement Using the Parallel-Plate Flow Chamber

To determine the platelet aggregation, blood of healthy volunteers of both sexes who had not received any thrombocyte aggregation-influencing medication for the last ten days is used. The blood is drawn into monovettes (Sarstedt, Nümbrecht, Germany) which contain, as anticoagulant, sodium citrate 3.8% (1 part of citrate+9 parts of blood). To obtain platelet-rich plasma, the citrated whole blood is centrifuged at 140 g for 20 min. A quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. For the perfusion study, a mixture of 40% erythrocytes and 60% washed platelets (200 000 µl) is prepared and suspended in HEPES-tyrode buffer. Platelet aggregation under flow conditions is measured using the parallel-plate flow chamber (B. Nieswandt et al., *EMBO J.* 2001, 20, 2120-2130; C. Weeterings, *Arterioscler Thromb. Vasc. Biol.* 2006, 26, 670-675; JJ Sixma, *Thromb. Res.* 1998, 92, 43-46). Glass slides are wetted with 100 µl of a solution of human α-thrombin (dissolved in Tris buffer) at 4° C. overnight α-thrombin in various concentrations, for example 10 to 50 µg/ml) and then blocked using 2% BSA.

Reconstituted blood is passed over the thrombin-wetted glass slides at a constant flow rate (for example a shear rate of 300/second) for 5 minutes and observed and recorded using a microscope video system. The inhibitory activity of the substances to be tested is determined morphometrically via the reduction of platelet aggregate formation. Alternatively, the inhibition of the platelet activation can be determined by flow cytometry, for example via p-selectin expression (CD62p) (see Method 1.f).

2.) Ex vivo assay 2.a) Platelet Aggregation (Primates, Guinea Pigs)

Awake or anaesthetized guinea pigs or primates are treated orally, intravenously or intraperitoneally with test substances in suitable formulations. As a control, other guinea pigs or primates are treated in an identical manner with the corresponding vehicle. Depending on the mode of application, blood of the deeply anaesthetized animals is obtained by puncture of the heart or of the aorta for different periods of time. The blood is transferred into monovettes (Sarstedt, Nümbrecht, Germany) which, as anticoagulant, contain sodium citrate 3.8% (1 part of citrate solution+9 parts of blood). To obtain platelet-rich plasma, the citrated whole blood is centrifuged at 140 g for 20 min.

Aggregation is triggered by addition of a thrombin receptor agonist (TRAP6, SFLLRN, 50 µg/ml; in each experiment, the concentration is determined for each animal species) in an aggregometer and determined using the turbidimetric method according to Born (Born, G. V. R., Cross M. J., The Aggregation of Blood Platelets; *J. Physiol.* 1963, 168, 178-195) at 37° C.

For measuring the aggregation, the increase of the light transmission (amplitude of the aggregation curve in %) is determined 5 minutes after addition of the agonist. The inhibitory activity of the administered test substances in the treated animals is calculated via the reduction of aggregation, based on the mean of the control animals.

3.) In vivo Assays 3.a) Thrombosis Models

The compounds according to the invention can be studied in thrombosis models in suitable animal species where the thrombin-induced platelet aggregation is mediated via the PAR-1 receptor. Suitable animal species are guinea pigs and, in particular, primates (compare: Lindahl, A. K., Scarborough, R. M., Naughton, M. A., Harker, L. A., Hanson, S. R., *Thromb Haemost* 1993, 69, 1196; Cook JJ, Sitko G R, Bednar B, Condra C, Mellott M J, Feng D-M, Nutt R F, Shager J A, Gould R J, Connolly T M, *Circulation* 1995, 91, 2961-2971; Kogushi M, Kobayashi H, Matsuoka T, Suzuki S, Kawahara T, Kajiwara A, Hishinuma I, *Circulation* 2003, 108 *Suppl.* 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b) Impaired Coagulation and Organ Dysfunction in Disseminated Intravasal Coagulation (DIC)

The compounds according to the invention can be studied in models of DIC and/or sepsis in suitable animal species. Suitable animal species are guinea pigs and, in particular, primates, and for the study of endothelium-mediated effects also mice and rats (compare: Kogushi M, Kobayashi H, Matsuoka T, Suzuki S, Kawahara T, Kajiwara A, Hishinuma I, *Circulation* 2003, 108 *Suppl.* 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861; Kaneider N C et al., *Nat Immunol,* 2007, 8, 1303-12; Camerer E et al., *Blood,* 2006, 107, 3912-21; Riewald M et al., *J Biol Chem,* 2005, 280, 19808-14.). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b.1) Thrombin-antithrombin Complexes

Thrombin/antithrombin complexes (hereinbelow referred to as "TAT") are a measure of the thrombin formed endogenously by coagulation activation. TATs are determined via an ELISA assay (Enzygnost TAT micro, Dade-Behring). Plasma is obtained from citrated blood by centrifugation. 50 μl of TAT sample buffer are added to 50 μl of plasma, and the mixture is briefly shaken and incubated at room temperature for 15 min. The samples are aspirated, and the well is washed three times with wash buffer (300 μl/well). Inbetween the wash steps, the plates are tapped to remove any residual wash buffer. Conjugate solution (100 μl) is added, and the sample is incubated at room temperature for 15 min. The samples are aspirated, and the well is washed three times with wash buffer (300 μl/well). The chromogenic substrate (100 μl/well) is then added, the mixture is incubated in the dark at room temperature for 30 min, stop solution (100 μl/well) is added, and the formation of colour at 492 nm is measured (Saphire Plate reader).

3.b.2) Parameters of Organ Dysfunction

Various parameters are determined, which allow conclusions to be drawn with respect to the functional restriction of various internal organs owing to the administration of LPS, and the therapeutic effect of test substances can be assessed. Citrated blood or, if appropriate, lithium heparin blood, is centrifuged, and the plasma is used to determine the parameters. Typically, the following parameters are determined: creatinine, urea, aspartate aminotransferase (AST), alanine aminotransferase (ALT), total bilirubin, lactate dehydrogenase (LDH), total protein, total albumin and fibrinogen. The values give indications regarding kidney function, liver function, cardiovascular function and vascular function.

3.b.3) Parameters of Inflammation

The extent of the inflammatory reaction triggered by endotoxin can be demonstrated by the increase of inflammation mediators, for example interleukins (1, 6, 8 and 10), tumour necrosis factor alpha or monocyte chemoattractant protein-1, in the plasma. ELISAs or the Luminex system may be used for this purpose.

3.c) Antitumour Activity

The compounds according to the invention can be tested in models of cancer, for example in the human breast cancer model in immundeficient mice (compare: S. Even-Ram et. al., *Nature Medicine*, 1988, 4, 909-914).

3.d) Antiangiogenetic Activity

The compounds according to the invention can be tested in in vitro and in vivo models of angiogenesis (compare: Caunt et al., *Journal of Thrombosis and Haemostasis*, 2003, 10, 2097-2102; Haralabopoulos et al., *Am J Physiol*, 1997, C239-C245; Tsopanoglou et al., *JBC*, 1999, 274, 23969-23976; Zania et al., *JPET*, 2006, 318, 246-254).

3.e) Blood Pressure- and Pulse-modulating Activity

The compounds according to the invention can be tested in in vivo models for their action on arterial blood pressure and heart rate. To this end, rats (for example Wistar) are provided with implantable radiotelemetry units, and an electronic data aquisition and storage system (Data Sciences, MN, USA) consisting of a chronically implantable transducer/transmitter unit in combination with a liquid-filled catheter is employed. The transmitter is implanted into the peritoneal cavity, and the sensor catheter is positioned in the descending aorta. The compounds according to the invention can be administered (for example orally or intravenously). Prior to the treatment, the mean arterial blood pressure and the heart rate of the untreated and treated animals are measured, and it is made sure that they are in the range of about 131-142 mmHg and 279-321 beats/minute. PAR-1-activating peptide (SFLLRN; for example doses between 0.1 and 5 mg/kg) is administered intravenously. Blood pressure and heart rate are measured at various time intervals and time spans with and without PAR-1-activating peptide and with and without a compound according to the invention (compare: Cicala C et al., *The FASEB Journal*, 2001, 15, 1433-5; Stasch J P et al., *British Journal of Pharmacology* 2002, 135, 344-355).

4.) Determination of the Solubility

Preparation of the Starting Solution (Original Solution):

At least 1.5 mg of the test substance are weighed out accurately into a wide-mouth 10 mm screw V-vial (from Glastechnik Grädfenroda GmbH, Art. No. 8004-WM-H/V15μ) with fitting screw cap and septum, DMSO is added to a concentration of 50 mg/ml and the vial is vortexed for 30 minutes.

Preparation of the Calibration Solutions:

The required pipetting steps are carried out in 1.2 ml 96-deep well plates (DWP) with the aid of a liquid-handling robot. The solvent used is a mixture of acetonitrile/water 8:2.

Preparation of the starting solution of calibration solutions (stock solution): 833 μl of the solvent mixture are added to 10 μl of the original solution (concentration=600 μg/ml), and the mixture is homogenized. 1:100 dilutions in separate DWPs are prepared from each test substance, and these are homogenized in turn.

Calibration solution 5 (600 ng/ml): 270 μl of the solvent mixture are added to 30 μl of the stock solution, and the mixture is homogenized.

Calibration solution 4 (60 ng/ml): 270 μl of the solvent mixture are added to 30 μl of the calibration solution 5, and the mixture is homogenized.

Calibration solution 3 (12 ng/ml): 400 μl of the solvent mixture are added to 100 μl of the calibration solution 4, and the mixture is homogenized.

Calibration solution 2 (1.2 ng/ml): 270 μl of the solvent mixture are added to 30 μl of the calibration solution 3, and the mixture is homogenized.

Calibration solution 1 (0.6 ng/ml): 150 μl of the solvent mixture are added to 150 μl of the calibration solution 2, and the mixture is homogenized.

Preparation of the Sample Solutions:

The required pipetting steps are carried out in 1.2 ml 96-well DWPs with the aid of a liquid-handling robot. 1000 μl of PBS buffer pH 6.5 are added to 10.1 μl of the stock solution. (PBS buffer pH 6.5: 61.86 g sodium chloride, 39.54 g sodium dihydrogen phosphate and 83.35 g 1 N aqueous sodium hydroxide solution are weighed out into a 1 liter measuring flask and made up with water, and the mixture is stirred for about 1 hour. 500 ml of this solution are added into a 5 liter measuring flask and made up with water. The pH is adjusted to 6.5 using 1 N aqueous sodium hydroxide solution.)

Procedure:

The required pipetting steps are carried out in 1.2 ml 96-well DWPs with the aid of a liquid-handling robot. The sample solutions prepared in this manner are shaken at 1400 rpm and at 20° C. using a variable temperature shaker for 24 hours. In each case 180 μl are removed from these solutions and transferred into Beckman Polyallomer centrifuge tubes. These solutions are centrifuged at about 223 000×g for 1 hour. From each sample solution, 100 μl of the supernatant are removed and diluted 1:10 and 1:1000 with PBS buffer 6.5.

Analysis:

The samples are analysed by HPLC/MS-MS. Quantification is carried out using a five-point calibration curve of the test compound. The solubility is expressed in mg/l. Analysis-sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 9) sample solution 1:10.

HPLC/MS-MS Method:

HPLC: Agilent 1100, quat. pump (G1311A), autosampler CTC HTS PAL, degaser (G1322A) and column thermostat (G1316A); column: Oasis HLB 20 mm×2.1 mm, 25µ; temperature: 40° C.; mobile phase A: water+0.5 ml of formic acid/l; mobile phase B: acetonitrile+0.5 ml of formic acid/l; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API-Interface; HPLC-MS inlet splitter 1:20; measurement in the ESI mode.

C) Exemplary Embodiments of Pharmaceutical Compositions

The substances of the invention can be converted into pharmaceutical preparations in the following way:

Tablet:
Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. The granules are dried and then mixed with the magnesium stearate for 5 min. This mixture is compressed in a conventional tablet press (see above for tablet format).

Oral Suspension:
Composition:

1000 mg of the compound of Example 1, 1000 mg of ethanol (96%), 400 mg of Rhodigel (xanthan gum) (from FMC, USA) and 99 g of water.

A single dose of 100 mg of the compound according to the invention corresponds to 10 ml of oral suspension.

Production:

The Rhodigel is suspended in ethanol, and the compound of Example 1 is added to the suspension. The water is added while stirring. The mixture is stirred for about 6 h until the Rhodigel has finished swelling.

Solution which can be Administered Intravenously:
Composition:

1 mg of the compound of Example 1, 15 g of polyethylene glycol 400 and 250 g of water for injections.

Production:

The compound of Example 1 is dissolved together with polyethylene glycol 400 by stirring in the water. The solution is sterilized by filtration (pore diameter 0.22 µm) and dispensed under aseptic conditions into heat-sterilized infusion bottles. The latter are closed with infusion stoppers and crimped caps.

The invention claimed is:
1. A compound of the formula

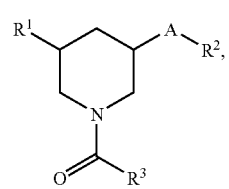

(I)

in which
A represents a group of the formula

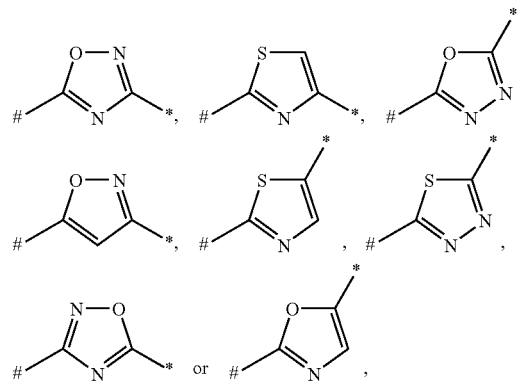

where
# is the point of attachment to the piperidine ring, and
* is the point of attachment to $R^2$,
$R^1$ represents phenyl,
where phenyl may be substituted by 1 to 3 substituents independently of one another selected from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy, $C_1$-$C_4$-alkoxycarbonyl and $C_3$-$C_6$-cycloalkyl,
where $C_2$-$C_4$-alkoxy may be substituted by a substituent selected from the group consisting of methoxy and ethoxy, and
where cycloalkyl may be substituted by 1 to 3 substituents independently of one another selected from the group consisting of halogen and $C_1$-$C_4$-alkyl,
$R^2$ represents hydrogen, trifluoromethyl, aminomethyl, $C_1$-$C_6$-alkyl, $C_2$-$C_6$-alkenyl, $C_1$-$C_4$-alkoxycarbonyl, $C_3$-$C_6$-cycloalkyl, cyclopentenyl, 4- to 6-membered heterocyclyl, phenyl, 1,3-benzodioxolyl, 5- or 6-membered heteroaryl or pyridylaminocarbonyl,
where cycloalkyl, heterocyclyl, phenyl and heteroaryl may be substituted by 1 to 3 substituents independently of one another selected from the group consisting of halogen, cyano, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino, $C_1$-$C_4$-alkoxycarbonylamino, $C_3$-$C_6$- cycloalkyl, 4- to 6-membered heterocyclyl, phenyl and 5- or 6-membered heteroaryl,
where alkylamino may be substituted by a substituent selected from the group consisting of $C_1$-$C_4$-alkoxy and $C_1$-$C_6$-alkylamino, and
where $C_1$-$C_4$-alkyl may be substituted by a substituent selected from the group consisting of halogen, hydroxyl, amino, aminocarbonyl, $C_1$-$C_4$-alkoxy, $C_1$-$C_6$-alkylamino, $C_1$-$C_4$-alkylthio, $C_1$-$C_4$-alkylcarbonyl, $C_1$-$C_4$-alkylcarbonyloxy, $C_1$-$C_4$-alkylsulphonyl, $C_1$-$C_4$-alkoxycarbonyl, $C_1$-$C_4$-alkoxycarbonylamino, $C_3$-$C_6$-cycloalkyl, $C_3$-$C_6$-cycloalkylamino, 4- to 6-membered heterocyclyl, phenyl, phenoxy, 5- or 6-membered heteroaryl and 5- or 6-membered heteroarylthio,
where cycloalkyl, heterocyclyl, phenyl, phenoxy, heteroaryl and heteroarylthio may be substituted by 1 to 3 substituents independently of one another selected from the group consisting of halogen, cyano, hydroxymethyl, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_3$-$C_6$-cycloalkyl, 4- to 6-membered heterocyclyl, phenyl and 5- or 6-membered heteroaryl,
$R^3$ represents $C_1$-$C_6$-alkyl, $C_1$-$C_6$-alkoxy, $C_1$-$C_6$-alkylamino, $C_3$-$C_7$-cycloalkyl, 4- to 6-membered heterocyclyl, phenyl or 5- or 6-membered heteroaryl,
where alkyl, $C_2$-$C_6$-alkoxy and alkylamino may be substituted by a substituent selected from the group consisting of hydroxyl, amino, cyano and $C_1$-$C_4$-alkoxy, and
where cycloalkyl, heterocyclyl, phenyl and heteroaryl may be substituted by 1 to 3 substituents independently of one another selected from the group consisting of halogen, cyano, nitro, oxo, hydroxyl, amino, aminomethyl, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl and $C_1$-$C_4$-alkylaminocarbonyl,
or one of its salts.

2. A compound according to claim 1, wherein
A represents a group of the formula

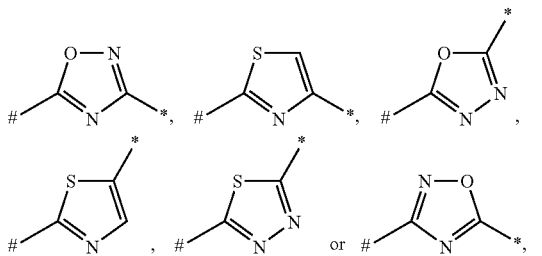

where
# is the point of attachment to the piperidine ring, and
* is the point of attachment to $R^2$,
$R^1$ represents phenyl,
where phenyl is substituted by 1 or 2 substituents independently of one another selected from the group consisting of trifluoromethyl, trifluoromethoxy, methyl, ethyl, isopropyl and methoxy,
$R^2$ represents methyl, ethyl, isopropyl, n-propyl, tert-butyl, methoxycarbonyl, ethoxycarbonyl, cyclopropyl, cyclobutyl, azetidinyl, oxetanyl, pyrrolidinyl, tetrahydropyridinyl, phenyl, 1,3-benzodioxolyl, thienyl, furanyl, pyrrolyl, thiazolyl, isoxazolyl, imidazolyl, triazolyl, pyridyl, pyrimidinyl or pyrazinyl, where azetidinyl, oxetanyl, pyrrolidinyl, tetrahydropyridinyl, phenyl, thienyl, furanyl, pyrrolyl, thiazolyl, isoxazolyl, imidazolyl, triazolyl, pyridyl, pyrimidinyl and pyrazinyl may be substituted by 1 to 2 substituents independently of one another selected from the group consisting of halogen, trifluoromethyl, trifluoromethoxy, methyl, ethyl, methoxy, ethoxy and ethylamino,
where ethylamino may be substituted by a substituent selected from the group consisting of methoxy and dimethylamino, and
where methyl and ethyl may be substituted by a substituent selected from the group consisting of hydroxyl, amino, methoxy, ethoxy, isopropoxy, dialkylamino, methylsulphonyl, cyclopropylamino, morpholinyl, phenyl and phenoxy,
where phenyl may be substituted by 1 or 2 substituents independently of one another selected from the group consisting of halogen, hydroxymethyl, trifluoromethyl, trifluoromethoxy, methyl, ethyl, methoxy and ethoxy,
$R^3$ represents tert-butyl, N-methyl-N-ethylamino, methoxyalkylamino, cyclopropyl, cyclopentyl, azetidinyl, 3,3-difluoroazetidinyl, 3-hydroxyazetidinyl, 3-methylazetidinyl, 3-methoxyazetidinyl, 3-dimethylaminoazetidinyl, pyrroldinyl, 3,3-difluoropyrroldin-1-yl, 3-hydroxypyrroldin-1-yl, 3-aminopyrroldin-1-yl, 4,4-difluoropiperidin-1-yl, 4-hydroxypiperidin-1-yl, 4-aminopiperidin-1-yl, 4-cyanopiperidin-1-yl, 3-methoxypiperidin-1-yl, thiazolidinyl, morpholin-4-yl, 2,2-dimethylmorpholin-4-yl, 2-oxopiperazin-1-yl or 3-oxo-4-methylpiperazin-1-yl,
or one of its salts.

3. A compound according to claim 1, wherein
A represents a group of the formula

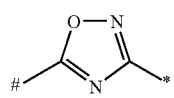

where
# is the point of attachment to the piperidine ring, and
* is the point of attachment to $R^2$,
$R^1$ represents phenyl,
where phenyl is substituted by 1 or 2 substituents independently of one another selected from the group consisting of trifluoromethyl, trifluoromethoxy, methyl and ethyl,
$R^2$ represents methyl, ethyl or isopropyl,
where methyl and ethyl may be substituted by a substituent methoxy,
$R^3$ represents 3-hydroxyazetidinyl, 3-hydroxypyrroldin-1-yl, 4-hydroxypiperidin-1-yl, 4-cyanopiperidin-1-yl or morpholin-4-yl,
or one of its salts.

4. A compound according to claim 1, wherein the substituents -$R^1$ and -A-$R^2$ are in the cis-position to one another.

5. A process for preparing a compound of the formula (I) or one of its salts according to claim 1, wherein either

[A] a compound of the formula

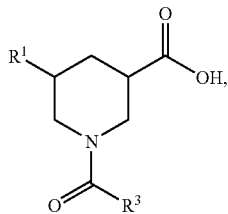

(II)

in which
R¹ and R³ have the meaning given in claim 1,
is reacted with a compound of the formula

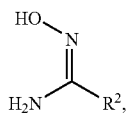

(III)

in which
R² has the meaning given in claim 1,
or

[B] a compound of the formula

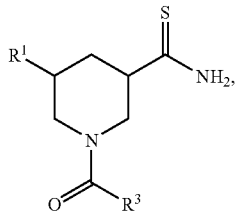

(X)

in which
R¹ and R³ have the meaning given in claim 1,
is reacted with a compound of the formula

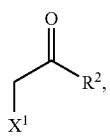

(XI)

in which
R² has the meaning given in claim 1, and
X¹ represents bromine or chlorine,
or

[C] a compound of the formula (II) is reacted with a compound of the formula

R²CONHNH₂ (XVI), in which
R² has the meaning given in claim 1,
in the presence of phosphoryl chloride or thionyl chloride
or

[D] a compound of the formula (II) is, in the first step, reacted with a compound of the formula

R²COCH₂NH₂ (XVII), in which
R² has the meaning given in claim 1,
in the presence of thionyl chloride or phosphoryl chloride, and, in the second step, reacted with Lawesson reagent
or

[E] a compound of the formula (II) is reacted with a compound of the formula (XVII) in the presence of thionyl chloride or phosphoryl chloride
or

[F] a compound of the formula (II) is, in the first step, reacted with a compound of the formula (XVI) in the presence of thionyl chloride or phosphoryl chloride and, in the second step, reacted with Lawesson reagent
or

[G] a compound of the formula

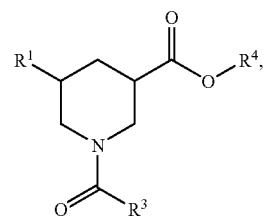

(IV)

in which
R¹ and R³ have the meaning given in claim 1, and
R⁴ represents methyl or ethyl,
is reacted with a compound of the formula

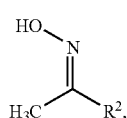

(XVIII)

in which
R² has the meaning given in claim 1,
in the presence of butyllithium
or

[H] a compound of the formula

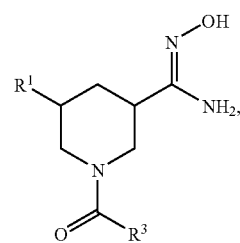

(XIX)

in which
R¹ and R³ have the meaning given in claim 1,
is reacted with a compound of the formula

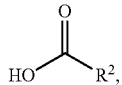     (XX)

in which
R² has the meaning given in claim 1,
or
[J] a compound of the formula

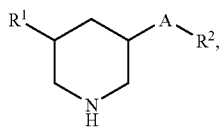     (XXI)

in which
A, R¹ and R² have the meaning given in claim 1,
is, in the first step, reacted with 4-nitrophenyl chloroformate and, in the second step, reacted with a compound of the formula

     (XXII), in which
R³ has the meaning given in claim 1.

6. A pharmaceutical composition, comprising a compound according to claim 1 in combination with an inert non-toxic pharmaceutically acceptable auxiliary.

7. The pharmaceutical composition of claim 6, further comprising an active compound selected from the group consisting of calcium channel blockers, statins, cholesterol resorption inhibitors, cholesterol ester transfer protein inhibitors, low-molecular weight heparins, other anticoagulants, antiarrhythmics, alpha-adrenergic agonists, beta-adrenergic blockers, aldosterone antagonists, angiotensin-converting enzyme inhibitors, angiotensin II receptor blockers, endothelin antagonists, inhibitors of neutral endopeptidase, phosphodiesterase inhibitors, fibrinolytics, GP IIb/IIIa antagonists, direct thrombin inhibitors, indirect thrombin inhibitors, direct and indirect factor Xa inhibitors, direct and indirect factor Xa/IIa inhibitors, lipoprotein-associated phospholipase A2 modulators, diuretics, nitrates, thromboxane antagonists, platelet aggregation inhibitors, cyclooxygenase inhibitors, B-type natriuretic peptides, NV1FGF modulators, HT1B/5-HT2A antagonists, guanylate cyclase activators, e-NOS transcription enhancers, antiatherogenic substances, CPU inhibitors, renin inhibitors, inhibitors of adenosine diphosphate-induced platelet aggregation, NHE-1 inhibitors, antibiotic therapies, and medicaments for proliferative disorders.

8. A method for the treatment of a thromboembolic disorder, comprising administering to a human or animal in need thereof an anticoagulatory amount of at least one compound according to claim 1, wherein the thromboembolic disorder is selected from ST-segment elevation myocardial infraction (STEMI) and non-ST-segment elevation myocardial infraction (non-STEMI); stable angina pectoris; unstable angina pectoris; reocclusions and restenoses after coronary interventions, angioplasty, stent implantations or aortocoronary bypass; peripheral arterial occlusion diseases; pulmonary embolisms; deep venous thromboses and renal vein thromboses; transitory ischaemic attacks; and thrombotic and thromboembolic stroke.

\* \* \* \* \*